(12) United States Patent
Cotta-Ramusino et al.

(10) Patent No.: US 11,866,726 B2
(45) Date of Patent: Jan. 9, 2024

(54) SYSTEMS AND METHODS FOR TARGETED INTEGRATION AND GENOME EDITING AND DETECTION THEREOF USING INTEGRATED PRIMING SITES

(71) Applicant: Editas Medicine, Inc., Cambridge, MA (US)

(72) Inventors: Cecilia Cotta-Ramusino, Cambridge, MA (US); Carrie M. Margulies, Waban, MA (US)

(73) Assignee: Editas Medicine, Inc., Cambridge, MA (US)

( * ) Notice: Subject to any disclaimer, the term of this patent is extended or adjusted under 35 U.S.C. 154(b) by 782 days.

(21) Appl. No.: 16/630,510

(22) PCT Filed: Jul. 13, 2018

(86) PCT No.: PCT/US2018/042040
§ 371 (c)(1),
(2) Date: Jan. 13, 2020

(87) PCT Pub. No.: WO2019/014564
PCT Pub. Date: Jan. 17, 2019

(65) Prior Publication Data
US 2020/0165636 A1  May 28, 2020

Related U.S. Application Data

(60) Provisional application No. 62/582,563, filed on Nov. 7, 2017, provisional application No. 62/532,509, filed on Jul. 14, 2017.

(51) Int. Cl.
| | |
|---|---|
| *C12N 15/90* | (2006.01) |
| *C12N 9/22* | (2006.01) |
| *C12N 15/10* | (2006.01) |
| *C12N 5/0735* | (2010.01) |
| *C12N 5/0789* | (2010.01) |
| *C12N 5/074* | (2010.01) |
| *C12N 15/113* | (2010.01) |
| *C12N 15/86* | (2006.01) |

(52) U.S. Cl.
CPC ......... *C12N 15/902* (2013.01); *C12N 5/0606* (2013.01); *C12N 5/0647* (2013.01); *C12N 5/0696* (2013.01); *C12N 9/22* (2013.01); *C12N 15/102* (2013.01); *C12N 15/113* (2013.01); *C12N 15/86* (2013.01); *C12N 2310/20* (2017.05)

(58) Field of Classification Search
None
See application file for complete search history.

(56) References Cited

U.S. PATENT DOCUMENTS

| | | |
|---|---|---|
| 8,546,553 B2 | 10/2013 | Terns et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,074,199 B1 | 7/2015 | Chavez et al. |
| 9,228,207 B2 | 1/2016 | Liu et al. |
| 9,228,208 B2 | 1/2016 | Frendewey et al. |
| 9,234,213 B2 | 1/2016 | Wu |
| 9,260,723 B2 | 2/2016 | Mali et al. |
| 9,260,752 B1 | 2/2016 | May et al. |
| 9,267,135 B2 | 2/2016 | Church et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,388,430 B2 | 7/2016 | Liu et al. |
| 9,404,098 B2 | 8/2016 | Terns et al. |
| 9,410,198 B2 | 8/2016 | May et al. |
| 9,422,553 B2 | 8/2016 | Terns et al. |

(Continued)

FOREIGN PATENT DOCUMENTS

| | | |
|---|---|---|
| WO | WO-2020/003006 A2 | 1/2000 |
| WO | WO-2020/005980 A1 | 2/2000 |

(Continued)

OTHER PUBLICATIONS

US 10,077,445 B2, 09/2018, Doudna et al. (withdrawn)
Dimitrov et al., Germline Gene Editing in Chickens by Efficient CRISPR-Mediated Homologous Recombination in Primordial Germ Cells. PLOS ONE (2016), DOI:10.1371/journal.pone.0154303, 1-10 (Year: 2016).*
Lanza et al., Employing single-stranded DNA donors for the high-throughput production of conditional knockout alleles in mice. BioRxiv preprint doi: https://doi.org/10.1101/195651, posted Sep. 29, 2017 (Year: 2017).*
Bak and Porteus, CRISPR-Mediated Integration of Large Gene Cassettes Using AAV Donor Vectors. Cell Reports (2017), 20: 750-756 (Year: 2017).*

(Continued)

*Primary Examiner* — Samuel C Woolwine
*Assistant Examiner* — Catherine Konopka
(74) *Attorney, Agent, or Firm* — McCarter & English, LLP; Maria Laccotripe Zacharakis; Marcie B. Clarke

(57) ABSTRACT

Disclosed herein are genome editing systems and related methods which allow for the detection and quantitative measurement of all possible on-target gene editing outcomes, including targeted integration. The compositions and methods described herein rely on the use of donor templates comprising a 5' homology arm, a cargo, a one or more priming sites, a 3' homology arm, and optionally stuffer sequence.

12 Claims, 17 Drawing Sheets

Specification includes a Sequence Listing.

(56) References Cited

U.S. PATENT DOCUMENTS

| | | |
|---|---|---|
| 9,476,065 B2 | 10/2016 | Horwitz et al. |
| 9,493,844 B2 | 11/2016 | Sastry-Dent et al. |
| 9,512,444 B2 | 12/2016 | Chen et al. |
| 9,512,446 B1 | 12/2016 | Joung et al. |
| 9,528,124 B2 | 12/2016 | Fahrenkrug et al. |
| 9,546,384 B2 | 1/2017 | Frendewey et al. |
| 9,567,603 B2 | 2/2017 | Joung et al. |
| 9,567,604 B2 | 2/2017 | Joung et al. |
| 9,580,701 B2 | 2/2017 | May et al. |
| 9,580,727 B1 | 2/2017 | Donohoue et al. |
| 9,587,252 B2 | 3/2017 | Church et al. |
| 9,616,090 B2 | 4/2017 | Conway et al. |
| 9,637,739 B2 | 5/2017 | Siksnys et al. |
| 9,650,617 B2 | 5/2017 | May et al. |
| 9,663,782 B2 | 5/2017 | Yu et al. |
| 9,677,090 B2 | 6/2017 | Donohoue et al. |
| 9,688,971 B2 | 6/2017 | Doudna et al. |
| 9,688,972 B2 | 6/2017 | May et al. |
| 9,725,714 B2 | 8/2017 | May et al. |
| 9,738,908 B2 | 8/2017 | Wu |
| 9,745,562 B2 | 8/2017 | Donohoue et al. |
| 9,745,600 B2 | 8/2017 | Donohoue et al. |
| 9,752,132 B2 | 9/2017 | Joung et al. |
| 9,771,600 B2 | 9/2017 | Donohoue et al. |
| 9,771,601 B2 | 9/2017 | May et al. |
| 9,790,490 B2 | 10/2017 | Zhang et al. |
| 9,803,194 B2 | 10/2017 | May et al. |
| 9,809,814 B1 | 11/2017 | May et al. |
| 9,816,074 B2 | 11/2017 | Conway et al. |
| 9,816,081 B1 | 11/2017 | Donohoue et al. |
| 9,816,093 B1 | 11/2017 | Donohoue et al. |
| 9,822,370 B2 | 11/2017 | Musunuru et al. |
| 9,822,372 B2 | 11/2017 | Zhang et al. |
| 9,833,479 B2 | 12/2017 | Conway et al. |
| 9,840,702 B2 | 12/2017 | Collingwood et al. |
| 9,840,713 B2 | 12/2017 | Zhang |
| 9,868,962 B2 | 1/2018 | May et al. |
| 9,873,894 B2 | 1/2018 | Conway et al. |
| 9,879,269 B2 | 1/2018 | Barrangou et al. |
| 9,879,283 B2 | 1/2018 | Ravinder et al. |
| 9,885,026 B2 | 2/2018 | Brouns et al. |
| 9,885,033 B2 | 2/2018 | Joung et al. |
| 9,902,974 B2 | 2/2018 | Conway et al. |
| 9,909,122 B2 | 3/2018 | May et al. |
| 9,926,545 B2 | 3/2018 | Joung et al. |
| 9,926,546 B2 | 3/2018 | Joung et al. |
| 9,932,566 B2 | 4/2018 | Kennedy et al. |
| 9,944,912 B2 | 4/2018 | Joung et al. |
| 9,957,490 B1 | 5/2018 | Donohoue et al. |
| 9,957,501 B2 | 5/2018 | Reik et al. |
| 9,957,526 B2 | 5/2018 | Holmes et al. |
| 9,963,689 B2 | 5/2018 | Doudna et al. |
| 9,963,719 B1 | 5/2018 | Friedland et al. |
| 9,970,001 B2 | 5/2018 | Miller |
| 9,970,024 B2 | 5/2018 | Church et al. |
| 9,970,026 B2 | 5/2018 | Donohoue et al. |
| 9,970,027 B2 | 5/2018 | Donohoue et al. |
| 9,970,028 B2 | 5/2018 | Cost et al. |
| 9,970,029 B1 | 5/2018 | Donohoue et al. |
| 10,023,853 B1 | 7/2018 | Donohoue et al. |
| 10,041,092 B2 | 8/2018 | Horwitz et al. |
| 10,059,940 B2 | 8/2018 | Zhong |
| 10,066,233 B2 | 9/2018 | Barrangou et al. |
| 10,077,453 B2 | 9/2018 | Liu et al. |
| 10,093,910 B2 | 10/2018 | Joung et al. |
| 10,100,291 B2 | 10/2018 | Chavez et al. |
| 10,100,333 B2 | 10/2018 | Donohoue et al. |
| 10,113,167 B2 | 10/2018 | Doudna et al. |
| 10,113,179 B2 | 10/2018 | Begemann et al. |
| 10,113,207 B2 | 10/2018 | Wang |
| 10,119,133 B2 | 11/2018 | Joung et al. |
| 10,125,354 B1 | 11/2018 | Donohoue et al. |
| 10,125,361 B2 | 11/2018 | May et al. |
| 10,138,472 B2 | 11/2018 | Donohoue et al. |
| 10,155,938 B2 | 12/2018 | Stark et al. |
| 10,190,137 B2 | 1/2019 | Zhang et al. |
| 10,196,619 B1 | 2/2019 | Donohoue et al. |
| 10,196,651 B2 | 2/2019 | Conway et al. |
| 10,202,589 B2 | 2/2019 | Joung et al. |
| 10,202,619 B2 | 2/2019 | Wu |
| 10,208,319 B2 | 2/2019 | Musunuru et al. |
| 10,227,611 B2 | 3/2019 | Doudna et al. |
| 10,266,850 B2 | 4/2019 | Doudna et al. |
| 10,301,651 B2 | 5/2019 | Doudna et al. |
| 10,308,961 B2 | 6/2019 | Doudna et al. |
| 10,329,587 B2 | 6/2019 | Church et al. |
| 10,337,001 B2 | 7/2019 | Ryan et al. |
| 10,351,878 B2 | 7/2019 | Doudna et al. |
| 10,358,658 B2 | 7/2019 | Doudna et al. |
| 10,358,659 B2 | 7/2019 | Doudna et al. |
| 10,369,232 B2 | 8/2019 | Chivukula et al. |
| 10,377,998 B2 | 8/2019 | Zhang et al. |
| 10,378,027 B2 | 8/2019 | Joung et al. |
| 10,385,360 B2 | 8/2019 | Doudna et al. |
| 10,392,607 B2 | 8/2019 | Sternberg et al. |
| 10,400,253 B2 | 9/2019 | Doudna et al. |
| 10,407,697 B2 | 9/2019 | Doudna et al. |
| 10,415,059 B2 | 9/2019 | Joung et al. |
| 10,415,061 B2 | 9/2019 | Doudna et al. |
| 10,421,980 B2 | 9/2019 | Doudna et al. |
| 10,428,319 B2 | 10/2019 | Steinberg et al. |
| 10,428,352 B2 | 10/2019 | Doudna et al. |
| 10,435,679 B2 | 10/2019 | Chavez et al. |
| 10,435,708 B2 | 10/2019 | Mali et al. |
| 10,443,076 B2 | 10/2019 | Doudna et al. |
| 10,450,585 B2 | 10/2019 | Lee et al. |
| 10,479,982 B2 | 11/2019 | Joung et al. |
| 10,487,341 B2 | 11/2019 | Doudna et al. |
| 10,494,621 B2 | 12/2019 | Zhang et al. |
| 10,513,712 B2 | 12/2019 | Doudna et al. |
| 10,519,467 B2 | 12/2019 | Jinek et al. |
| 10,526,590 B2 | 1/2020 | Kennedy et al. |
| 10,526,591 B2 | 1/2020 | Joung et al. |
| 10,526,619 B2 | 1/2020 | Doudna et al. |
| 10,544,405 B2 | 1/2020 | Weiss et al. |
| 10,550,363 B1 | 2/2020 | Garst et al. |
| 10,550,372 B2 | 2/2020 | Konermann et al. |
| 10,550,407 B2 | 2/2020 | Doudna et al. |
| 10,563,225 B2 | 2/2020 | Church et al. |
| 10,563,227 B2 | 2/2020 | Doudna et al. |
| 10,570,415 B2 | 2/2020 | Doudna et al. |
| 10,570,418 B2 | 2/2020 | Doudna et al. |
| 10,577,631 B2 | 3/2020 | Doudna et al. |
| 10,597,679 B2 | 3/2020 | Liu et al. |
| 10,597,680 B2 | 3/2020 | Doudna et al. |
| 10,604,752 B2 | 3/2020 | Chen et al. |
| 10,612,045 B2 | 4/2020 | Doudna et al. |
| 2010/0076057 A1 | 3/2010 | Sontheimer et al. |
| 2010/0093617 A1 | 4/2010 | Barrangou et al. |
| 2013/0011828 A1 | 1/2013 | Barrangou et al. |
| 2014/0068797 A1 | 3/2014 | Doudna et al. |
| 2014/0093941 A1 | 4/2014 | Terns et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0242664 A1 | 8/2014 | Zhang et al. |
| 2014/0242699 A1 | 8/2014 | Zhang |
| 2014/0256046 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273233 A1 | 9/2014 | Chen et al. |
| 2014/0287938 A1 | 9/2014 | Zhang et al. |
| 2014/0294773 A1 | 10/2014 | Brouns et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0356956 A1 | 12/2014 | Church et al. |

(56) References Cited

U.S. PATENT DOCUMENTS

| | | |
|---|---|---|
| 2014/0357523 A1 | 12/2014 | Zeiner et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031132 A1 | 1/2015 | Church et al. |
| 2015/0031133 A1 | 1/2015 | Church et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056705 A1 | 2/2015 | Conway et al. |
| 2015/0059010 A1 | 2/2015 | Cigan et al. |
| 2015/0071889 A1 | 3/2015 | Musunuru et al. |
| 2015/0071898 A1 | 3/2015 | Liu et al. |
| 2015/0071899 A1 | 3/2015 | Liu et al. |
| 2015/0071901 A1 | 3/2015 | Liu et al. |
| 2015/0071902 A1 | 3/2015 | Liu et al. |
| 2015/0079680 A1 | 3/2015 | Bradley et al. |
| 2015/0079681 A1 | 3/2015 | Zhang |
| 2015/0082478 A1 | 3/2015 | Cigan et al. |
| 2015/0128300 A1* | 5/2015 | Warming .......... A01K 67/0276 435/325 |
| 2015/0140664 A1 | 5/2015 | Byrne et al. |
| 2015/0152436 A1 | 6/2015 | Musunuru et al. |
| 2015/0159174 A1 | 6/2015 | Frendewey et al. |
| 2015/0159175 A1 | 6/2015 | Frendewey et al. |
| 2015/0166969 A1 | 6/2015 | Takeuchi et al. |
| 2015/0176013 A1 | 6/2015 | Musunuru et al. |
| 2015/0184139 A1 | 7/2015 | Zhang et al. |
| 2015/0184199 A1 | 7/2015 | Horwitz et al. |
| 2015/0203872 A1 | 7/2015 | Zhang |
| 2015/0218253 A1 | 8/2015 | Liu et al. |
| 2015/0232833 A1 | 8/2015 | Mali et al. |
| 2015/0232882 A1 | 8/2015 | Zhang et al. |
| 2015/0240261 A1 | 8/2015 | Siksnys et al. |
| 2015/0240263 A1 | 8/2015 | Holmes et al. |
| 2015/0247150 A1 | 9/2015 | Zhang et al. |
| 2015/0259684 A1 | 9/2015 | Church et al. |
| 2015/0259704 A1 | 9/2015 | Church et al. |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0307867 A1 | 10/2015 | Orkin et al. |
| 2015/0322457 A1 | 11/2015 | Kim et al. |
| 2015/0344912 A1 | 12/2015 | Kim et al. |
| 2015/0353905 A1 | 12/2015 | Weiss et al. |
| 2015/0353917 A1 | 12/2015 | Miller |
| 2015/0356239 A1 | 12/2015 | Zhang et al. |
| 2015/0376586 A1 | 12/2015 | May et al. |
| 2015/0376587 A1 | 12/2015 | May et al. |
| 2015/0376645 A1 | 12/2015 | Zechiedrich et al. |
| 2016/0002670 A1 | 1/2016 | Church et al. |
| 2016/0010076 A1 | 1/2016 | Joung et al. |
| 2016/0010154 A1 | 1/2016 | Laganiere et al. |
| 2016/0017366 A1 | 1/2016 | Chen et al. |
| 2016/0024474 A1 | 1/2016 | Conway et al. |
| 2016/0024523 A1 | 1/2016 | Joung et al. |
| 2016/0024524 A1 | 1/2016 | Joung et al. |
| 2016/0024529 A1 | 1/2016 | Carstens |
| 2016/0029604 A1 | 2/2016 | Fahrenkrug et al. |
| 2016/0030477 A1 | 2/2016 | Conway et al. |
| 2016/0032274 A1 | 2/2016 | Church et al. |
| 2016/0032292 A1 | 2/2016 | Storici et al. |
| 2016/0040155 A1 | 2/2016 | Maizels et al. |
| 2016/0040189 A1 | 2/2016 | Kennedy et al. |
| 2016/0046949 A1 | 2/2016 | May et al. |
| 2016/0046961 A1 | 2/2016 | Jinek et al. |
| 2016/0046962 A1 | 2/2016 | May et al. |
| 2016/0046963 A1 | 2/2016 | May et al. |
| 2016/0046978 A1 | 2/2016 | May et al. |
| 2016/0060653 A1 | 3/2016 | Doudna et al. |
| 2016/0060654 A1 | 3/2016 | Doudna et al. |
| 2016/0060657 A1 | 3/2016 | Frendewey et al. |
| 2016/0068864 A1 | 3/2016 | Doudna et al. |
| 2016/0068887 A1 | 3/2016 | May et al. |
| 2016/0076020 A1 | 3/2016 | May et al. |
| 2016/0090607 A1 | 3/2016 | Conway et al. |
| 2016/0102322 A1 | 4/2016 | Ravinder et al. |
| 2016/0102324 A1 | 4/2016 | Duchateau et al. |
| 2016/0108470 A1 | 4/2016 | May et al. |
| 2016/0115488 A1 | 4/2016 | Zhang et al. |
| 2016/0115489 A1 | 4/2016 | Zhang et al. |
| 2016/0122774 A1 | 5/2016 | Duchateau et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0138046 A1 | 5/2016 | Wu |
| 2016/0145644 A1 | 5/2016 | Cost et al. |
| 2016/0145646 A1 | 5/2016 | Frendewey et al. |
| 2016/0153003 A1 | 6/2016 | Joung et al. |
| 2016/0153004 A1 | 6/2016 | Zhang et al. |
| 2016/0153006 A1 | 6/2016 | Zhang et al. |
| 2016/0160210 A1 | 6/2016 | Mali et al. |
| 2016/0160291 A1 | 6/2016 | Scully et al. |
| 2016/0168592 A1 | 6/2016 | Church et al. |
| 2016/0175462 A1 | 6/2016 | Zhang et al. |
| 2016/0177304 A1 | 6/2016 | Collingwood et al. |
| 2016/0177340 A1 | 6/2016 | Bradley et al. |
| 2016/0184362 A1 | 6/2016 | Duchateau et al. |
| 2016/0186152 A1 | 6/2016 | Brouns et al. |
| 2016/0186213 A1 | 6/2016 | Zhang et al. |
| 2016/0186214 A1 | 6/2016 | Brouns et al. |
| 2016/0201072 A1 | 7/2016 | Cigan et al. |
| 2016/0201089 A1 | 7/2016 | Gersbach et al. |
| 2016/0207983 A1 | 7/2016 | Bradley et al. |
| 2016/0208243 A1 | 7/2016 | Zhang et al. |
| 2016/0208288 A1 | 7/2016 | Liu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0222416 A1 | 8/2016 | Church et al. |
| 2016/0237455 A1 | 8/2016 | Glucksmann et al. |
| 2016/0237456 A1 | 8/2016 | Church et al. |
| 2016/0251640 A1 | 9/2016 | May et al. |
| 2016/0257948 A1 | 9/2016 | Bradley et al. |
| 2016/0257974 A1 | 9/2016 | Bradley et al. |
| 2016/0264995 A1 | 9/2016 | Yamamoto et al. |
| 2016/0272965 A1 | 9/2016 | Zhang et al. |
| 2016/0281072 A1 | 9/2016 | Zhang |
| 2016/0281111 A1 | 9/2016 | Cotta-Ramusino et al. |
| 2016/0289673 A1 | 10/2016 | Huang et al. |
| 2016/0289675 A1 | 10/2016 | Ryan et al. |
| 2016/0298097 A1 | 10/2016 | Chavez et al. |
| 2016/0298125 A1 | 10/2016 | Chen et al. |
| 2016/0298132 A1 | 10/2016 | Chen et al. |
| 2016/0298133 A1 | 10/2016 | Chen et al. |
| 2016/0298134 A1 | 10/2016 | Chen et al. |
| 2016/0298135 A1 | 10/2016 | Chen et al. |
| 2016/0298136 A1 | 10/2016 | Chen et al. |
| 2016/0298137 A1 | 10/2016 | Chen et al. |
| 2016/0298138 A1 | 10/2016 | Chen et al. |
| 2016/0304855 A1 | 10/2016 | Stark et al. |
| 2016/0304907 A1 | 10/2016 | Mali et al. |
| 2016/0312198 A1 | 10/2016 | Joung et al. |
| 2016/0312199 A1 | 10/2016 | Joung et al. |
| 2016/0312280 A1 | 10/2016 | May et al. |
| 2016/0319260 A1 | 11/2016 | Joung et al. |
| 2016/0319261 A1 | 11/2016 | Joung et al. |
| 2016/0319281 A1 | 11/2016 | Tsai et al. |
| 2016/0319349 A1 | 11/2016 | May et al. |
| 2016/0340662 A1 | 11/2016 | Zhang et al. |
| 2016/0354487 A1 | 12/2016 | Zhang et al. |
| 2016/0355795 A1 | 12/2016 | Ran et al. |
| 2016/0355796 A1 | 12/2016 | Davidson et al. |
| 2016/0355797 A1 | 12/2016 | Konermann et al. |
| 2016/0355816 A1 | 12/2016 | Terns et al. |
| 2016/0362667 A1 | 12/2016 | Donohoue et al. |
| 2016/0362668 A1 | 12/2016 | May et al. |
| 2016/0369258 A1 | 12/2016 | Maizels et al. |
| 2016/0369262 A1 | 12/2016 | Reik et al. |
| 2016/0376610 A1 | 12/2016 | Davis et al. |

(56) References Cited

U.S. PATENT DOCUMENTS

| | | |
|---|---|---|
| 2017/0002339 A1 | 1/2017 | Barrangou et al. |
| 2017/0002380 A1 | 1/2017 | Buerckstuemmer |
| 2017/0009256 A1 | 1/2017 | Buerckstuemmer |
| 2017/0016027 A1 | 1/2017 | Lee et al. |
| 2017/0029805 A1 | 2/2017 | Li et al. |
| 2017/0037416 A1 | 2/2017 | Barrangou et al. |
| 2017/0037432 A1 | 2/2017 | Donohoue et al. |
| 2017/0044508 A1 | 2/2017 | Donohoue et al. |
| 2017/0044535 A1 | 2/2017 | Collingwood et al. |
| 2017/0044536 A1 | 2/2017 | Collingwood et al. |
| 2017/0044537 A1 | 2/2017 | Collingwood et al. |
| 2017/0044569 A9 | 2/2017 | Church et al. |
| 2017/0051276 A1 | 2/2017 | May et al. |
| 2017/0051310 A1 | 2/2017 | Doudna et al. |
| 2017/0051312 A1 | 2/2017 | Jinek et al. |
| 2017/0058271 A1 | 3/2017 | Joung et al. |
| 2017/0058272 A1 | 3/2017 | Carter et al. |
| 2017/0058298 A1 | 3/2017 | Kennedy et al. |
| 2017/0058299 A1 | 3/2017 | Horwitz et al. |
| 2017/0067078 A1 | 3/2017 | Frendewey et al. |
| 2017/0073705 A1 | 3/2017 | Chen et al. |
| 2017/0080107 A1 | 3/2017 | Chivukula et al. |
| 2017/0081650 A1 | 3/2017 | Joung et al. |
| 2017/0107536 A1 | 4/2017 | Zhang et al. |
| 2017/0107539 A1 | 4/2017 | Yu et al. |
| 2017/0114334 A1 | 4/2017 | May et al. |
| 2017/0114369 A1 | 4/2017 | Donohoue et al. |
| 2017/0121694 A1 | 5/2017 | May et al. |
| 2017/0137845 A1 | 5/2017 | Tan et al. |
| 2017/0152508 A1 | 6/2017 | Joung et al. |
| 2017/0152528 A1 | 6/2017 | Zhang |
| 2017/0159073 A1 | 6/2017 | Donohoue et al. |
| 2017/0166875 A1 | 6/2017 | Maizels et al. |
| 2017/0166893 A1 | 6/2017 | Doudna et al. |
| 2017/0166903 A1 | 6/2017 | Zhang et al. |
| 2017/0175140 A1 | 6/2017 | Hummel et al. |
| 2017/0175142 A1 | 6/2017 | Zhang et al. |
| 2017/0175143 A1 | 6/2017 | Tolar et al. |
| 2017/0175144 A1 | 6/2017 | Zhang et al. |
| 2017/0189450 A1 | 7/2017 | Conway et al. |
| 2017/0191078 A1 | 7/2017 | Zhang et al. |
| 2017/0191082 A1 | 7/2017 | Chen et al. |
| 2017/0198269 A1 | 7/2017 | Zhang et al. |
| 2017/0198277 A1 | 7/2017 | Kmiec et al. |
| 2017/0198302 A1 | 7/2017 | Feng et al. |
| 2017/0204388 A1 | 7/2017 | Donohoue et al. |
| 2017/0211142 A1 | 7/2017 | Smargon et al. |
| 2017/0215392 A1 | 8/2017 | Haining et al. |
| 2017/0226534 A1 | 8/2017 | May et al. |
| 2017/0233703 A1 | 8/2017 | Xie et al. |
| 2017/0233762 A1 | 8/2017 | Zalatan et al. |
| 2017/0251647 A1 | 9/2017 | Mashimo et al. |
| 2017/0260547 A1 | 9/2017 | Dombrowski et al. |
| 2017/0268022 A1 | 9/2017 | Liu et al. |
| 2017/0273284 A1 | 9/2017 | Shen |
| 2017/0275611 A1 | 9/2017 | Bradley et al. |
| 2017/0283831 A1 | 10/2017 | Zhang et al. |
| 2017/0298330 A1 | 10/2017 | Sato et al. |
| 2017/0306306 A1 | 10/2017 | Potter et al. |
| 2017/0306307 A1 | 10/2017 | Zhang et al. |
| 2017/0306335 A1 | 10/2017 | Zhang et al. |
| 2017/0314002 A1 | 11/2017 | Gong |
| 2017/0314015 A1 | 11/2017 | Friedland et al. |
| 2017/0314016 A1 | 11/2017 | Kim et al. |
| 2017/0321214 A1 | 11/2017 | Zhang et al. |
| 2017/0327805 A1 | 11/2017 | Joung et al. |
| 2017/0327806 A1 | 11/2017 | Joung et al. |
| 2017/0327820 A1 | 11/2017 | May et al. |
| 2017/0335300 A1 | 11/2017 | Frisch et al. |
| 2017/0335346 A1 | 11/2017 | Donohoue et al. |
| 2017/0335347 A1 | 11/2017 | Donohoue et al. |
| 2017/0349894 A1 | 12/2017 | Dahlman et al. |
| 2017/0349914 A1 | 12/2017 | Cox et al. |
| 2017/0349915 A1 | 12/2017 | May et al. |
| 2017/0355985 A1 | 12/2017 | Dellinger et al. |
| 2017/0362611 A1 | 12/2017 | Tsai |
| 2018/0002682 A1 | 1/2018 | Sternberg et al. |
| 2018/0016601 A1 | 1/2018 | Qi et al. |
| 2018/0021413 A1 | 1/2018 | Porteus |
| 2018/0021457 A1 | 1/2018 | Kim et al. |
| 2018/0030425 A1 | 2/2018 | Joung et al. |
| 2018/0030438 A1 | 2/2018 | Porteus et al. |
| 2018/0044700 A1 | 2/2018 | Doudna et al. |
| 2018/0049412 A1 | 2/2018 | Shen |
| 2018/0051281 A1 | 2/2018 | Ryan et al. |
| 2018/0051298 A1 | 2/2018 | Fahrenkrug et al. |
| 2018/0057810 A1 | 3/2018 | Zhang et al. |
| 2018/0066242 A1 | 3/2018 | Zhang et al. |
| 2018/0066258 A1 | 3/2018 | Powell |
| 2018/0071405 A1 | 3/2018 | Kim et al. |
| 2018/0073002 A1 | 3/2018 | Deiters et al. |
| 2018/0073039 A1 | 3/2018 | Durocher et al. |
| 2018/0080051 A1 | 3/2018 | Sheikh et al. |
| 2018/0094257 A1 | 4/2018 | Wang et al. |
| 2018/0100148 A1 | 4/2018 | Vakulskas et al. |
| 2018/0105564 A1 | 4/2018 | Davis et al. |
| 2018/0112213 A1 | 4/2018 | Welstead et al. |
| 2018/0112235 A1 | 4/2018 | Li et al. |
| 2018/0119121 A1 | 5/2018 | Brouns et al. |
| 2018/0119140 A1 | 5/2018 | Porteus et al. |
| 2018/0119173 A1 | 5/2018 | Donohoue et al. |
| 2018/0119175 A1 | 5/2018 | Conway et al. |
| 2018/0127780 A1 | 5/2018 | Liu et al. |
| 2018/0127783 A1 | 5/2018 | Zhang et al. |
| 2018/0127785 A1 | 5/2018 | Junge et al. |
| 2018/0127787 A1 | 5/2018 | Gurumurthy et al. |
| 2018/0135073 A1 | 5/2018 | Chen et al. |
| 2018/0135109 A1 | 5/2018 | Jayaram et al. |
| 2018/0142236 A1 | 5/2018 | He et al. |
| 2018/0142262 A1 | 5/2018 | Webber et al. |
| 2018/0142263 A1 | 5/2018 | May et al. |
| 2018/0148735 A1 | 5/2018 | Begemann et al. |
| 2018/0155708 A1 | 6/2018 | Church et al. |
| 2018/0155716 A1 | 6/2018 | Zhang et al. |
| 2018/0155720 A1 | 6/2018 | Donohoue et al. |
| 2018/0163188 A1 | 6/2018 | Xie et al. |
| 2018/0163213 A1 | 6/2018 | Aneja et al. |
| 2018/0179521 A1 | 6/2018 | Rahdar et al. |
| 2018/0179523 A1 | 6/2018 | Collingwood et al. |
| 2018/0187176 A1 | 7/2018 | Behlke et al. |
| 2018/0187186 A1 | 7/2018 | Yin et al. |
| 2018/0187195 A1 | 7/2018 | Siksnys et al. |
| 2018/0195089 A1 | 7/2018 | Ravinder et al. |
| 2018/0200387 A1 | 7/2018 | Porteus |
| 2018/0201956 A1 | 7/2018 | Friedland et al. |
| 2018/0208921 A1 | 7/2018 | Joung et al. |
| 2018/0208931 A1 | 7/2018 | Doudna et al. |
| 2018/0216088 A1 | 8/2018 | Joung et al. |
| 2018/0216135 A1 | 8/2018 | Tsai et al. |
| 2018/0230494 A1 | 8/2018 | Joung et al. |
| 2018/0230495 A1 | 8/2018 | Doudna et al. |
| 2018/0230496 A1 | 8/2018 | Doudna et al. |
| 2018/0230497 A1 | 8/2018 | Doudna et al. |
| 2018/0235194 A1 | 8/2018 | Fahrenkrug et al. |
| 2018/0237801 A1 | 8/2018 | Doudna et al. |
| 2018/0245099 A1 | 8/2018 | Donohoue et al. |
| 2018/0245100 A1 | 8/2018 | Doudna et al. |
| 2018/0245101 A1 | 8/2018 | Doudna et al. |
| 2018/0250424 A1 | 9/2018 | Cotta-Ramusino |
| 2018/0251791 A1 | 9/2018 | Doudna et al. |
| 2018/0251793 A1 | 9/2018 | Doudna et al. |
| 2018/0251794 A1 | 9/2018 | Doudna et al. |
| 2018/0251795 A1 | 9/2018 | Charpentier et al. |
| 2018/0265864 A1 | 9/2018 | Li et al. |
| 2018/0273609 A1 | 9/2018 | Porteus et al. |
| 2018/0273932 A1 | 9/2018 | Bothmer et al. |
| 2018/0273938 A1 | 9/2018 | Turk et al. |
| 2018/0273981 A1 | 9/2018 | Doudna et al. |
| 2018/0282713 A1 | 10/2018 | Van Der Oost |
| 2018/0282714 A1 | 10/2018 | Joung et al. |
| 2018/0282722 A1 | 10/2018 | Jakimo et al. |
| 2018/0282764 A1 | 10/2018 | Jinek et al. |
| 2018/0291383 A1 | 10/2018 | Musunuru et al. |
| 2018/0296603 A1 | 10/2018 | Gori et al. |

(56) References Cited

U.S. PATENT DOCUMENTS

| | | |
|---|---|---|
| 2018/0298360 A1 | 10/2018 | Sternberg et al. |
| 2018/0298392 A1 | 10/2018 | Cotta-Ramusino |
| 2018/0298406 A1 | 10/2018 | Doudna et al. |
| 2018/0298407 A1 | 10/2018 | Doudna et al. |
| 2018/0305697 A1 | 10/2018 | Sfeir et al. |
| 2018/0305718 A1 | 10/2018 | Nelson et al. |
| 2018/0305719 A1 | 10/2018 | Perez-Pinera et al. |
| 2018/0312824 A1 | 11/2018 | Zhang et al. |
| 2018/0312827 A1 | 11/2018 | Donohoue et al. |
| 2018/0312874 A1 | 11/2018 | Doudna et al. |
| 2018/0312875 A1 | 11/2018 | Doudna et al. |
| 2018/0312876 A1 | 11/2018 | Doudna et al. |
| 2018/0320163 A1 | 11/2018 | Koonin et al. |
| 2018/0320197 A1 | 11/2018 | Gersbach et al. |
| 2018/0320201 A1 | 11/2018 | Vakulskas et al. |
| 2018/0327761 A1 | 11/2018 | Duchateau et al. |
| 2018/0346927 A1 | 12/2018 | Doudna et al. |
| 2018/0355332 A1 | 12/2018 | Steinberg et al. |
| 2018/0363009 A1 | 12/2018 | Doudna et al. |
| 2019/0002889 A1 | 1/2019 | Cheng et al. |
| 2019/0002921 A1 | 1/2019 | Doudna et al. |
| 2019/0002922 A1 | 1/2019 | Doudna et al. |
| 2019/0002923 A1 | 1/2019 | Doudna et al. |
| 2019/0010471 A1 | 1/2019 | Zhang et al. |
| 2019/0010481 A1 | 1/2019 | Joung et al. |
| 2019/0010495 A1 | 1/2019 | Boitano et al. |
| 2019/0010520 A1 | 1/2019 | Doudna et al. |
| 2019/0032091 A1 | 1/2019 | Dever et al. |
| 2019/0040416 A1 | 2/2019 | Chavez et al. |
| 2019/0048338 A1 | 2/2019 | Yin et al. |
| 2019/0048340 A1 | 2/2019 | Charpentier et al. |
| 2019/0062734 A1 | 2/2019 | Cotta-Ramusino et al. |
| 2019/0062790 A1 | 2/2019 | Doudna et al. |
| 2019/0071688 A1 | 3/2019 | Begemann et al. |
| 2019/0083656 A1 | 3/2019 | Khalili et al. |
| 2019/0085329 A1 | 3/2019 | Siksnys |
| 2019/0093129 A1 | 3/2019 | Doudna et al. |
| 2019/0106687 A1 | 4/2019 | Joung et al. |
| 2019/0106688 A1 | 4/2019 | Oh et al. |
| 2019/0106693 A1 | 4/2019 | Rinn et al. |
| 2019/0106711 A1 | 4/2019 | Doudna et al. |
| 2019/0106712 A1 | 4/2019 | Doudna et al. |
| 2019/0106713 A1 | 4/2019 | Doudna et al. |
| 2019/0106714 A1 | 4/2019 | Doudna et al. |
| 2019/0106715 A1 | 4/2019 | Doudna et al. |
| 2019/0136210 A1 | 5/2019 | Cotta-Ramusino et al. |
| 2019/0169639 A1 | 6/2019 | Zhang et al. |
| 2019/0185819 A1 | 6/2019 | Soto-Gutierrez et al. |
| 2019/0218547 A1 | 7/2019 | Lee et al. |
| 2019/0218602 A1 | 7/2019 | Zhang et al. |
| 2019/0225961 A1 | 7/2019 | Robb et al. |
| 2019/0241911 A1 | 8/2019 | Dong et al. |
| 2019/0249172 A1 | 8/2019 | Kohn et al. |
| 2019/0256829 A1 | 8/2019 | Chakraborty et al. |
| 2019/0264186 A1 | 8/2019 | Yamano et al. |
| 2019/0284583 A1 | 9/2019 | Doudna et al. |
| 2019/0316121 A1 | 10/2019 | Smith et al. |
| 2019/0367949 A1 | 12/2019 | Crawley et al. |
| 2019/0374576 A1 | 12/2019 | Henley et al. |
| 2019/0376045 A1 | 12/2019 | Schrepfer et al. |
| 2019/0382751 A1 | 12/2019 | Radhar et al. |
| 2019/0382799 A1 | 12/2019 | Henley et al. |
| 2019/0388469 A1 | 12/2019 | Marson et al. |
| 2019/0390195 A1 | 12/2019 | Tondera et al. |
| 2019/0390229 A1 | 12/2019 | Potter et al. |
| 2020/0010817 A1 | 1/2020 | Van Der Oost |
| 2020/0056164 A1 | 2/2020 | Steinberg et al. |
| 2020/0056209 A1 | 2/2020 | May et al. |
| 2020/0069734 A1 | 3/2020 | Valamehr et al. |
| 2020/0080107 A1 | 3/2020 | Rezania |
| 2020/0080114 A1 | 3/2020 | Rezania |
| 2020/0102561 A1 | 4/2020 | Mickanin et al. |
| 2020/0109382 A1 | 4/2020 | Zhang et al. |
| 2020/0131539 A1* | 4/2020 | Bak .................. C12N 15/8616 |

FOREIGN PATENT DOCUMENTS

| | | |
|---|---|---|
| WO | WO-2020/006423 A1 | 2/2000 |
| WO | WO-2020/014577 A1 | 1/2001 |
| WO | WO-2020/022803 A1 | 1/2002 |
| WO | WO-2020/030984 A2 | 1/2003 |
| WO | WO-2020/032711 A1 | 1/2003 |
| WO | WO-2020/033601 A1 | 1/2003 |
| WO | WO-2020/033774 A1 | 1/2003 |
| WO | WO-2007/025097 A2 | 3/2007 |
| WO | WO-2010/011961 A2 | 1/2010 |
| WO | WO-2013/098244 A1 | 7/2013 |
| WO | WO-2013/126794 A1 | 8/2013 |
| WO | WO-2013/141680 A1 | 9/2013 |
| WO | WO-2013/142578 A1 | 9/2013 |
| WO | WO-2013/176772 A1 | 11/2013 |
| WO | WO-2013/188522 A2 | 12/2013 |
| WO | WO-2014/018423 A2 | 1/2014 |
| WO | WO-2014/065596 A1 | 5/2014 |
| WO | WO-2014/085593 A1 | 6/2014 |
| WO | WO-2014/089290 A1 | 6/2014 |
| WO | WO-2014/093479 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/099744 A1 | 6/2014 |
| WO | WO-2014/099750 A2 | 6/2014 |
| WO | WO-2014/113493 A1 | 7/2014 |
| WO | WO-2014/127287 A1 | 8/2014 |
| WO | WO-2014/143381 A1 | 9/2014 |
| WO | WO-2014/144288 A1 | 9/2014 |
| WO | WO-2014/144592 A2 | 9/2014 |
| WO | WO-2014/144761 A2 | 9/2014 |
| WO | WO-2014/145599 A2 | 9/2014 |
| WO | WO-2014/150624 A1 | 9/2014 |
| WO | WO-2014/152432 A2 | 9/2014 |
| WO | WO-2014/165825 A2 | 10/2014 |
| WO | WO-2014/172458 A1 | 10/2014 |
| WO | WO-2014/186585 A2 | 11/2014 |
| WO | WO-2014/191518 A1 | 12/2014 |
| WO | WO-2014/191521 A2 | 12/2014 |
| WO | WO-2014/197568 A2 | 12/2014 |
| WO | WO-2014/197748 A2 | 12/2014 |
| WO | WO-2014/204578 A1 | 12/2014 |
| WO | WO-2014/204724 A1 | 12/2014 |
| WO | WO-2014/204725 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO-2015/006290 A1 | 1/2015 |
| WO | WO-2015/006294 A2 | 1/2015 |
| WO | WO-2015/006498 A2 | 1/2015 |
| WO | WO-2015/010114 A1 | 1/2015 |
| WO | WO-2015/013583 A2 | 1/2015 |
| WO | WO-2015/021426 A1 | 2/2015 |
| WO | WO-2015/026885 A1 | 2/2015 |
| WO | WO-2015/035139 A2 | 3/2015 |
| WO | WO-2015/035162 A2 | 3/2015 |
| WO | WO-2015/040402 A1 | 3/2015 |
| WO | WO-2015/048577 A2 | 4/2015 |
| WO | WO-2015/048690 A1 | 4/2015 |
| WO | WO-2015/077290 A2 | 5/2015 |
| WO | WO-2015/077318 A1 | 5/2015 |
| WO | WO-2015/079056 A1 | 6/2015 |
| WO | WO-2015/088643 A1 | 6/2015 |
| WO | WO-2015/089351 A1 | 6/2015 |
| WO | WO-2015/089354 A1 | 6/2015 |
| WO | WO-2015/089419 A2 | 6/2015 |
| WO | WO-2015/089427 A1 | 6/2015 |
| WO | WO-2015/089473 A1 | 6/2015 |
| WO | WO-2015/089486 A2 | 6/2015 |
| WO | WO-2015/095804 A1 | 6/2015 |

(56) References Cited

FOREIGN PATENT DOCUMENTS

| | | |
|---|---|---|
| WO | WO-2015/112896 A2 | 7/2015 |
| WO | WO-2015/117081 A2 | 8/2015 |
| WO | WO-2015/127439 A1 | 8/2015 |
| WO | WO-2015/138620 A1 | 9/2015 |
| WO | WO-2015/148716 A1 | 10/2015 |
| WO | WO-2015/148860 A1 | 10/2015 |
| WO | WO-2015/148863 A2 | 10/2015 |
| WO | WO-2015/160683 A1 | 10/2015 |
| WO | WO-2015/166272 A2 | 11/2015 |
| WO | WO-2015/168125 A1 | 11/2015 |
| WO | WO-2015/168547 A2 | 11/2015 |
| WO | WO-2015/179540 A1 | 11/2015 |
| WO | WO-2015/183885 A1 | 12/2015 |
| WO | WO-2015/188056 A1 | 12/2015 |
| WO | WO-2015/188065 A1 | 12/2015 |
| WO | WO-2015/200555 A2 | 12/2015 |
| WO | WO-2016/011080 A2 | 1/2016 |
| WO | WO-2016/014794 A1 | 1/2016 |
| WO | WO-2016/019144 A2 | 2/2016 |
| WO | WO-2016/022363 A2 | 2/2016 |
| WO | WO-2016/022866 A1 | 2/2016 |
| WO | WO-2016/025759 A1 | 2/2016 |
| WO | WO-2016/028682 A1 | 2/2016 |
| WO | WO-2016/036754 A1 | 3/2016 |
| WO | WO-2016/044416 A1 | 3/2016 |
| WO | WO-2016/049258 A2 | 3/2016 |
| WO | WO-2016/054106 A1 | 4/2016 |
| WO | WO-2016/054326 A1 | 4/2016 |
| WO | WO-2016/057821 A2 | 4/2016 |
| WO | WO-2016/057835 A2 | 4/2016 |
| WO | WO-2016/057951 A2 | 4/2016 |
| WO | WO-2016/057961 A1 | 4/2016 |
| WO | WO-2016/065364 A1 | 4/2016 |
| WO | WO-2016/073433 A1 | 5/2016 |
| WO | WO-2016/073990 A2 | 5/2016 |
| WO | WO-2016/081923 A2 | 5/2016 |
| WO | WO-2016/089433 A1 | 6/2016 |
| WO | WO-2016/090385 A1 | 6/2016 |
| WO | WO-2016/094867 A1 | 6/2016 |
| WO | WO-2016/094872 A1 | 6/2016 |
| WO | WO-2016/094874 A1 | 6/2016 |
| WO | WO-2016/094880 A1 | 6/2016 |
| WO | WO-2016/100819 A1 | 6/2016 |
| WO | WO-2016/100951 A2 | 6/2016 |
| WO | WO-2016/106236 A1 | 6/2016 |
| WO | WO-2016/106244 A1 | 6/2016 |
| WO | WO-2016/111546 A2 | 7/2016 |
| WO | WO-2016/112242 A1 | 7/2016 |
| WO | WO-2016/114972 A1 | 7/2016 |
| WO | WO-2016/115326 A1 | 7/2016 |
| WO | WO-2016/118726 A2 | 7/2016 |
| WO | WO-2016/123230 A1 | 8/2016 |
| WO | WO-2016/123578 A1 | 8/2016 |
| WO | WO-2016/124765 A1 | 8/2016 |
| WO | WO-2016/135557 A2 | 9/2016 |
| WO | WO-2016/135558 A2 | 9/2016 |
| WO | WO-2016/135559 A2 | 9/2016 |
| WO | WO-2016/138574 A1 | 9/2016 |
| WO | WO-2016/141224 A1 | 9/2016 |
| WO | WO-2016/142719 A1 | 9/2016 |
| WO | WO-2016/148994 A1 | 9/2016 |
| WO | WO-2016/154579 A2 | 9/2016 |
| WO | WO-2016/154596 A1 | 9/2016 |
| WO | WO-2016/161207 A1 | 10/2016 |
| WO | WO-2016/164356 A1 | 10/2016 |
| WO | WO-2016/164797 A1 | 10/2016 |
| WO | WO-2016/166340 A1 | 10/2016 |
| WO | WO-2016/167300 A1 | 10/2016 |
| WO | WO-2016/172727 A1 | 10/2016 |
| WO | WO-2016/182917 A1 | 11/2016 |
| WO | WO-2016/182959 A1 | 11/2016 |
| WO | WO-2016/183448 A1 | 11/2016 |
| WO | WO-2016/186745 A1 | 11/2016 |
| WO | WO-2016/195598 A1 | 12/2016 |
| WO | WO-2016/196655 A1 | 12/2016 |
| WO | WO-2016/196887 A1 | 12/2016 |
| WO | WO-2016/201047 A1 | 12/2016 |
| WO | WO-2016/201155 A1 | 12/2016 |
| WO | WO-2016/205613 A1 | 12/2016 |
| WO | WO-2016/205680 A1 | 12/2016 |
| WO | WO-2016/205703 A1 | 12/2016 |
| WO | WO-2016/205711 A1 | 12/2016 |
| WO | WO-2016/205749 A1 | 12/2016 |
| WO | WO-2016/205759 A1 | 12/2016 |
| WO | WO-2016/210271 A1 | 12/2016 |
| WO | WO-2017/004261 A1 | 1/2017 |
| WO | WO-2017/004279 A2 | 1/2017 |
| WO | WO-2017/011519 A1 | 1/2017 |
| WO | WO-2017/015015 A1 | 1/2017 |
| WO | WO-2017/015101 A1 | 1/2017 |
| WO | WO-2017/019867 A1 | 2/2017 |
| WO | WO-2017/023801 A1 | 2/2017 |
| WO | WO-2017/027423 A1 | 2/2017 |
| WO | WO-2017/031483 A1 | 2/2017 |
| WO | WO-2017/040348 A1 | 3/2017 |
| WO | WO-2017/040511 A1 | 3/2017 |
| WO | WO-2017/040709 A1 | 3/2017 |
| WO | WO-2017/044776 A1 | 3/2017 |
| WO | WO-2017/048969 A1 | 3/2017 |
| WO | WO-2017/053431 A2 | 3/2017 |
| WO | WO-2017/053729 A1 | 3/2017 |
| WO | WO-2017/053879 A1 | 3/2017 |
| WO | WO-2017/062754 A1 | 4/2017 |
| WO | WO-2017/064546 A1 | 4/2017 |
| WO | WO-2017/066588 A2 | 4/2017 |
| WO | WO-2017/066707 A1 | 4/2017 |
| WO | WO-2017/068377 A1 | 4/2017 |
| WO | WO-2017/070598 A1 | 4/2017 |
| WO | WO-2017/070633 A2 | 4/2017 |
| WO | WO-2017/074962 A1 | 5/2017 |
| WO | WO-2017/077394 A2 | 5/2017 |
| WO | WO-2017/096041 A1 | 6/2017 |
| WO | WO-2017/096328 A1 | 6/2017 |
| WO | WO-2017/099494 A1 | 6/2017 |
| WO | WO-2017/106251 A1 | 6/2017 |
| WO | WO-2017/106569 A1 | 6/2017 |
| WO | WO-2017/106657 A1 | 6/2017 |
| WO | WO-2017/115268 A1 | 7/2017 |
| WO | WO-2017/123609 A1 | 7/2017 |
| WO | WO-2017/127807 A1 | 7/2017 |
| WO | WO-2017/129811 A1 | 8/2017 |
| WO | WO-2017/131150 A1 | 8/2017 |
| WO | WO-2017/131237 A1 | 8/2017 |
| WO | WO-2017/134529 A1 | 8/2017 |
| WO | WO-2017/136335 A1 | 8/2017 |
| WO | WO-2017/136794 A1 | 8/2017 |
| WO | WO-2017/141109 A1 | 8/2017 |
| WO | WO-2017/142923 A1 | 8/2017 |
| WO | WO-2017/147056 A1 | 8/2017 |
| WO | WO-2017/155407 A1 | 9/2017 |
| WO | WO-2017/155408 A1 | 9/2017 |
| WO | WO-2017/160752 A1 | 9/2017 |
| WO | WO-2017/160890 A1 | 9/2017 |
| WO | WO-2017/161068 A1 | 9/2017 |
| WO | WO-2017/165655 A1 | 9/2017 |
| WO | WO-2017/165826 A1 | 9/2017 |
| WO | WO-2017/172775 A1 | 10/2017 |
| WO | WO-2017/180694 A1 | 10/2017 |
| WO | WO-2017/180711 A1 | 10/2017 |
| WO | WO-2017/181107 A2 | 10/2017 |
| WO | WO-2017/182881 A2 | 10/2017 |
| WO | WO-2017/184768 A1 | 10/2017 |
| WO | WO-2017/184786 A1 | 10/2017 |
| WO | WO-2017/184799 A1 | 10/2017 |
| WO | WO-2017/186550 A1 | 11/2017 |
| WO | WO-2017/186718 A1 | 11/2017 |
| WO | WO-2017/189308 A1 | 11/2017 |
| WO | WO-2017/189336 A1 | 11/2017 |
| WO | WO-2017/189821 A1 | 11/2017 |
| WO | WO-2017/190664 A1 | 11/2017 |
| WO | WO-2017/191503 A1 | 11/2017 |
| WO | WO-2017/197238 A1 | 11/2017 |
| WO | WO-2017/201311 A2 | 11/2017 |
| WO | WO-2017/205290 A1 | 11/2017 |

(56) References Cited

FOREIGN PATENT DOCUMENTS

| | | |
|---|---|---|
| WO | WO-2017/205650 A1 | 11/2017 |
| WO | WO-2017/207589 A1 | 12/2017 |
| WO | WO-2017/212264 A1 | 12/2017 |
| WO | WO-2017/214460 A1 | 12/2017 |
| WO | WO-2017/215648 A1 | 12/2017 |
| WO | WO-2017/216771 A2 | 12/2017 |
| WO | WO-2017/219027 A1 | 12/2017 |
| WO | WO-2017/219033 A1 | 12/2017 |
| WO | WO-2017/220527 A1 | 12/2017 |
| WO | WO-2017/222773 A1 | 12/2017 |
| WO | WO-2017/222834 A1 | 12/2017 |
| WO | WO-2017/223449 A1 | 12/2017 |
| WO | WO-2018/005691 A1 | 1/2018 |
| WO | WO-2018/009822 A1 | 1/2018 |
| WO | WO-2018/013840 A1 | 1/2018 |
| WO | WO-2018/013932 A1 | 1/2018 |
| WO | WO-2018/015936 A2 | 1/2018 |
| WO | WO-2018/022634 A1 | 2/2018 |
| WO | WO-2018/025206 A1 | 2/2018 |
| WO | WO-2018/030208 A1 | 2/2018 |
| WO | WO-2018/030457 A1 | 2/2018 |
| WO | WO-2018/031686 A1 | 2/2018 |
| WO | WO-2018/033110 A1 | 2/2018 |
| WO | WO-2018/035387 A1 | 2/2018 |
| WO | WO-2018/035388 A1 | 2/2018 |
| WO | WO-2018/035423 A1 | 2/2018 |
| WO | WO-2018/049073 A1 | 3/2018 |
| WO | WO-2018/049077 A1 | 3/2018 |
| WO | WO-2018/049079 A1 | 3/2018 |
| WO | WO-2018/049168 A1 | 3/2018 |
| WO | WO-2018/052247 A1 | 3/2018 |
| WO | WO-2018/053053 A1 | 3/2018 |
| WO | WO-2018/057946 A2 | 3/2018 |
| WO | WO-2018/058064 A1 | 3/2018 |
| WO | WO-2018/062866 A2 | 4/2018 |
| WO | WO-2018/064352 A1 | 4/2018 |
| WO | WO-2018/064371 A1 | 4/2018 |
| WO | WO-2018/064387 A1 | 4/2018 |
| WO | WO-2018/068053 A2 | 4/2018 |
| WO | WO-2018/069474 A1 | 4/2018 |
| WO | WO-2018/071572 A1 | 4/2018 |
| WO | WO-2018/071663 A1 | 4/2018 |
| WO | WO-2018/071868 A1 | 4/2018 |
| WO | WO-2018/071892 A1 | 4/2018 |
| WO | WO-2018/074979 A1 | 4/2018 |
| WO | WO-2018/081470 A1 | 5/2018 |
| WO | WO-2018/081476 A2 | 5/2018 |
| WO | WO-2018/085414 A1 | 5/2018 |
| WO | WO-2018/089437 A1 | 5/2018 |
| WO | WO-2018/089664 A1 | 5/2018 |
| WO | WO-2018/093954 A1 | 5/2018 |
| WO | WO-2018/094356 A2 | 5/2018 |
| WO | WO-2018/096356 A1 | 5/2018 |
| WO | WO-2018/097257 A1 | 5/2018 |
| WO | WO-2018/098383 A1 | 5/2018 |
| WO | WO-2018/106693 A1 | 6/2018 |
| WO | WO-2018/106727 A1 | 6/2018 |
| WO | WO-2018/107028 A1 | 6/2018 |
| WO | WO-2018/108272 A1 | 6/2018 |
| WO | WO-2018/108338 A1 | 6/2018 |
| WO | WO-2018/108339 A1 | 6/2018 |
| WO | WO-2018/109101 A1 | 6/2018 |
| WO | WO-2018/111947 A1 | 6/2018 |
| WO | WO-2018/112451 A1 | 6/2018 |
| WO | WO-2018/119060 A1 | 6/2018 |
| WO | WO-2018/125964 A1 | 7/2018 |
| WO | WO-2018/126176 A1 | 7/2018 |
| WO | WO-2018/130830 A1 | 7/2018 |
| WO | WO-2018/138385 A1 | 8/2018 |
| WO | WO-2018/142364 A1 | 8/2018 |
| WO | WO-2018/144546 A1 | 8/2018 |
| WO | WO-2018/149418 A1 | 8/2018 |
| WO | WO-2018/149888 A1 | 8/2018 |
| WO | WO-2018/152325 A1 | 8/2018 |
| WO | WO-2018/162702 A1 | 9/2018 |
| WO | WO-2018/170015 A1 | 9/2018 |
| WO | WO-2018/170184 A1 | 9/2018 |
| WO | WO-2018/172556 A1 | 9/2018 |
| WO | WO-2018/175872 A1 | 9/2018 |
| WO | WO-2018/188571 A1 | 10/2018 |
| WO | WO-2018/191440 A1 | 10/2018 |
| WO | WO-2018/191715 A2 | 10/2018 |
| WO | WO-2018/192961 A1 | 10/2018 |
| WO | WO-2018/195313 A1 | 10/2018 |
| WO | WO-2018/195418 A1 | 10/2018 |
| WO | WO-2018/195540 A1 | 10/2018 |
| WO | WO-2018/195545 A2 | 10/2018 |
| WO | WO-2018/195555 A1 | 10/2018 |
| WO | WO-2018/197020 A1 | 11/2018 |
| WO | WO-2018/197495 A1 | 11/2018 |
| WO | WO-2018/209158 A2 | 11/2018 |
| WO | WO-2018/209320 A1 | 11/2018 |
| WO | WO-2018/209712 A1 | 11/2018 |
| WO | WO-2018/213351 A1 | 11/2018 |
| WO | WO-2018/217981 A1 | 11/2018 |
| WO | WO-2018/218135 A1 | 11/2018 |
| WO | WO-2018/220210 A1 | 12/2018 |
| WO | WO-2018/221685 A1 | 12/2018 |
| WO | WO-2018/226762 A1 | 12/2018 |
| WO | WO-2018/226853 A1 | 12/2018 |
| WO | WO-2018/226855 A1 | 12/2018 |
| WO | WO-2018/227114 A1 | 12/2018 |
| WO | WO-2019/006471 A2 | 1/2019 |
| WO | WO-2019/009682 A2 | 1/2019 |
| WO | WO-2019/014564 A1 | 1/2019 |
| WO | WO-2019/018041 A1 | 1/2019 |
| WO | WO-2019/036185 A1 | 2/2019 |
| WO | WO-2019/036513 A1 | 2/2019 |
| WO | WO-2019/040650 A1 | 2/2019 |
| WO | WO-2019/046540 A1 | 3/2019 |
| WO | WO-2019/048881 A1 | 3/2019 |
| WO | WO-2019/048882 A1 | 3/2019 |
| WO | WO-2019/049913 A1 | 3/2019 |
| WO | WO-2019/051419 A1 | 3/2019 |
| WO | WO-2019/051428 A1 | 3/2019 |
| WO | WO-2019/060469 A2 | 3/2019 |
| WO | WO-2019/062522 A1 | 4/2019 |
| WO | WO-2019/067322 A1 | 4/2019 |
| WO | WO-2019/070762 A1 | 4/2019 |
| WO | WO-2019/072596 A1 | 4/2019 |
| WO | WO-2019/074542 A1 | 4/2019 |
| WO | WO-2019/079527 A1 | 4/2019 |
| WO | WO-2019/081982 A1 | 5/2019 |
| WO | WO-2019/084168 A1 | 5/2019 |
| WO | WO-2019/084664 A1 | 5/2019 |
| WO | WO-2019/089796 A1 | 5/2019 |
| WO | WO-2019/089804 A1 | 5/2019 |
| WO | WO-2019/089808 A1 | 5/2019 |
| WO | WO-2019/089820 A1 | 5/2019 |
| WO | WO-2019/090173 A1 | 5/2019 |
| WO | WO-2019/090174 A1 | 5/2019 |
| WO | WO-2019/090175 A1 | 5/2019 |
| WO | WO-2019/092042 A1 | 5/2019 |
| WO | WO-2019/094518 A1 | 5/2019 |
| WO | WO-2019/099943 A1 | 5/2019 |
| WO | WO-2019/103442 A2 | 5/2019 |
| WO | WO-2019/106163 A1 | 6/2019 |
| WO | WO-2019/106522 A1 | 6/2019 |
| WO | WO-2019/113149 A1 | 6/2019 |
| WO | WO-2019/118516 A1 | 6/2019 |
| WO | WO-2019/126709 A1 | 6/2019 |
| WO | WO-2019/126716 A1 | 6/2019 |
| WO | WO-2019/126748 A1 | 6/2019 |
| WO | WO-2019/126762 A2 | 6/2019 |
| WO | WO-2019/126774 A1 | 6/2019 |
| WO | WO-2019/133714 A1 | 7/2019 |
| WO | WO-2019/147014 A1 | 8/2019 |
| WO | WO-2019/150203 A1 | 8/2019 |
| WO | WO-2019/152519 A1 | 8/2019 |
| WO | WO-2019/168953 A1 | 9/2019 |
| WO | WO-2019/173654 A2 | 9/2019 |
| WO | WO-2019/178416 A1 | 9/2019 |
| WO | WO-2019/178426 A1 | 9/2019 |
| WO | WO-2019/178427 A1 | 9/2019 |

(56) References Cited

FOREIGN PATENT DOCUMENTS

| WO | WO-2019/178428 A1 | 9/2019 |
|----|-------------------|--------|
| WO | WO-2019/183000 A1 | 9/2019 |
| WO | WO-2019/183150 A1 | 9/2019 |
| WO | WO-2019/191495 A1 | 10/2019 |
| WO | WO-2019/199984 A1 | 10/2019 |
| WO | WO-2019/209912 A2 | 10/2019 |
| WO | WO-2019/209914 A2 | 10/2019 |
| WO | WO-2019/233990 A1 | 12/2019 |
| WO | WO-2019/237069 A1 | 12/2019 |
| WO | WO-2019/238772 A1 | 12/2019 |
| WO | WO-2019/239361 A1 | 12/2019 |
| WO | WO-2020/041751 A1 | 2/2020 |
| WO | WO-2020/047353 A1 | 3/2020 |
| WO | WO-2020/049535 A1 | 3/2020 |
| WO | WO-2020/053224 A1 | 3/2020 |
| WO | WO-2020/065062 A1 | 4/2020 |
| WO | WO-2020/067993 A1 | 4/2020 |
| WO | WO-2020/069029 A1 | 4/2020 |
| WO | WO-2020/072390 A1 | 4/2020 |
| WO | WO-2020/077360 A1 | 4/2020 |

OTHER PUBLICATIONS

GenBank: HI203079.1 https://www.ncbi.nlm.nih.gov/nuccore/HI203079.1 [retrieved Oct. 27, 2022] (Year: 2022).*
Stults et al., Genomic architecture and inheritance of human ribosomal RNA gene clusters Genome Research (2008), 18:13-18. (Year: 2008).*
Mali et al., RNA-Guided Human Genome Engineering via Cas9. Science (2013) 339: 825-826 (Year: 2013).*
International Preliminary Report on Patentability for Application No. PCT/US2018/042040, dated Jan. 23, 2020, 11 pages.
International Search Report and Written Opinion for Application No. PCT/US2018/042040, dated Oct. 26, 2018, 14 pages.

\* cited by examiner

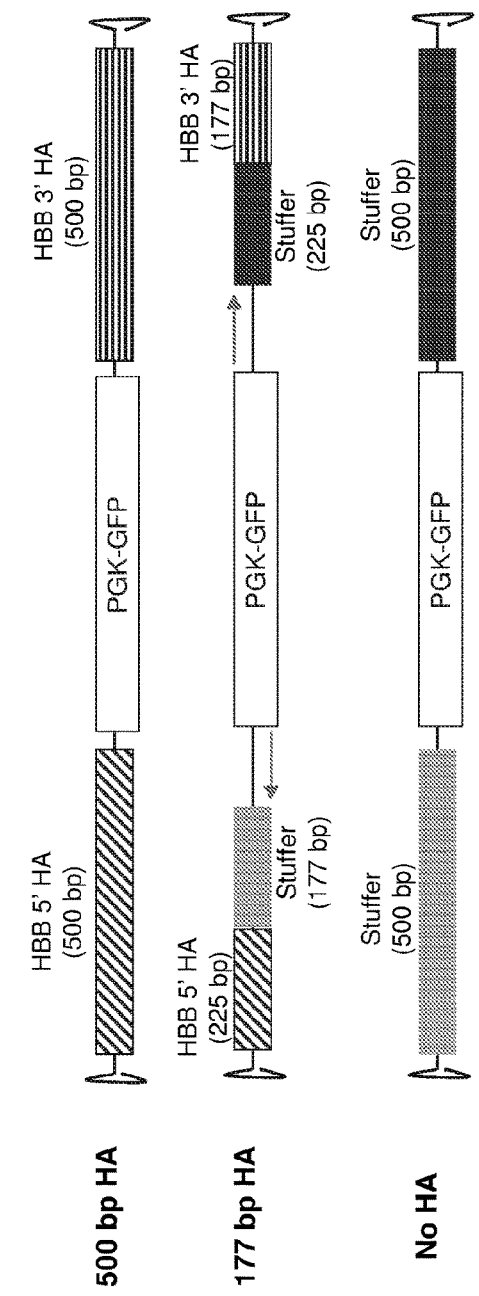
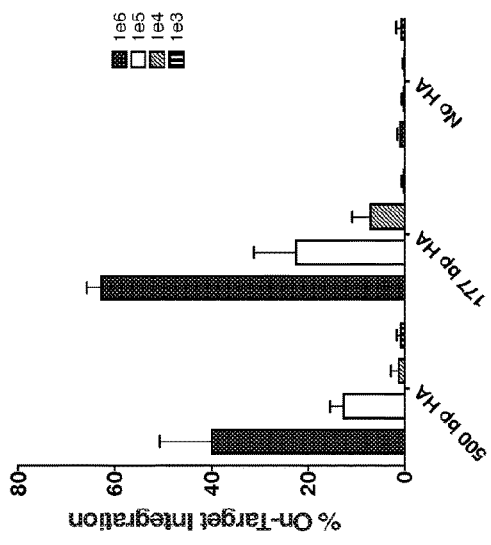
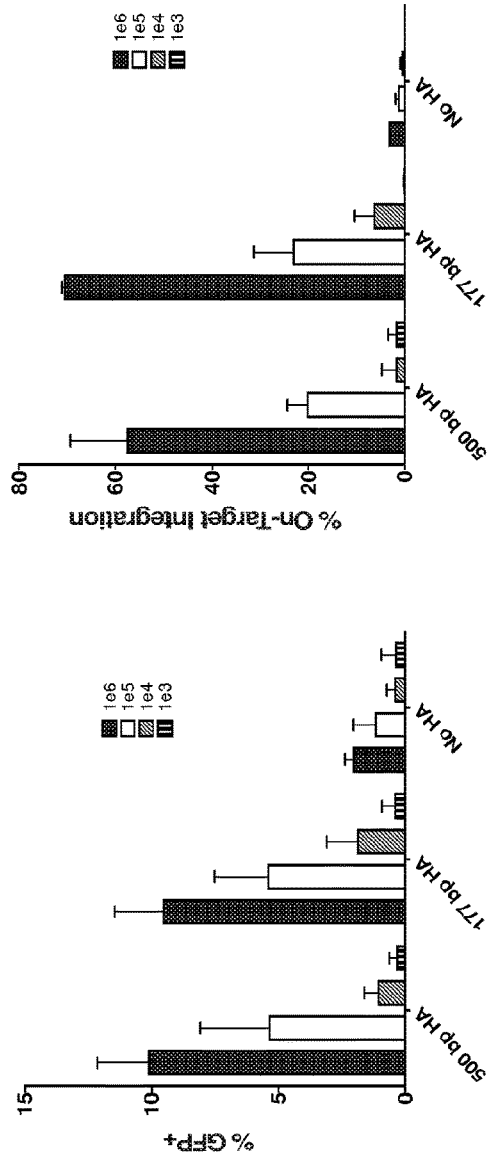
Fig. 2A
Fig. 2B
Fig. 2C
Fig. 2D

SEQUENCE LISTING

```
<160> NUMBER OF SEQ ID NOS: 118

<210> SEQ ID NO 1
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
tcaatagccc agtcggtttt gttagataca ttttatcgaa tctgtaaaga tattttataa    60
```

```
taagataata tcagcgccta gctgcggaat tccactcaga gaatacctct cctgaatatc    120
agccttagtg gcgttatacg atatttcaca ctctcaaaat cccgagtcag actatacccg    180
cgcatgttta gtaaaggttg attctgagat ctcgagtcca aaaaagatac ccactacttt    240
aaagatttgc attcagttgt tccatcggcc tgggtagtaa aggggggtatg ctcgctccga    300 gtcgatggaa ctgtaaatgt tagccctgat acgcggaaca tatcagtaac aatctttacc    360
taatatggag tgggattaag cttcatagag gatatgaaac gctcgtagta tggcttccta    420
cataagtaga attattagca actaagatat taccactgcc caataaaaga gattccactt    480
agattcatag gtagtcccaa caatcatgtc tgaatactaa attgatcaat tggactatgt    540
caaaattatt ttgaagaagt aatcatcaac ttaggcgctt tttagtgtta agagcgcgtt    600
attgccaacc gggctaaacc tgtgtaactc ttcaatattg tatataatta taggcagaat    660
aagctatgag tgcattatga gataaacata gattttttgtc cactcgaaat atttgaattt    720
cttgatcctg ggctagttca gccataagtt ttcactaata gttaggacta ccaattacac    780
tacattcagt tgctgaaatt cacatcactg ccgcaatatt tatgaagcta ttattgcatt    840
aagacttagg agataaatac gaagttgata tattttttcag aatcagcgaa aagacccccct    900 attgacatta cgaattcgag tttaacgagc acataaatca aacactacga ggttaccaag    960
attgtatctt acattaatgc tatccagcca gccgtcatgt ttaactggat agtcataatt   1020
aatatccaat gatcgtttca cgtagctgca tatcgaggaa gttgtataat tgaaaaccca   1080
cacattagaa tgcatggtgc atcgctaggg tttatcttat cttgctcgtg ccaagagtgt   1140
agaaagccac atattgatac ggaagctgcc taggaggttg gtatatgttg attgtgctca   1200
ccatctccct tcctaatctc ctagtgttaa gtccaatcag tgggctggct ctggttaaaa   1260
gtaatataca cgctagatct ctctactata atacaggcta agcctacgcg ctttcaatgc   1320
actgattacc aacttagcta cggccagccc catttaatga attatctcag atgaattcag   1380
acattattct ctacaaggac actttagagt gtcctgcgga ggcataatta ttatctaaga   1440
tggggtaagt ccgatggaag acacagatac atcggactat tcctattagc cgagagtcaa   1500
ccgttagaac tcggaaaaag acatcgaagc cggtaaccta cgcactataa atttccgcag   1560
agacatatgt aaagttttat tagaactggt atcttgatta cgattcttaa ctctcatacg   1620
ccggtccgga atttgtgact cgagaaaatg taatgacatg ctccaattga tttcaaaatt   1680
agatttaagg tcagcgaact atgtttattc aaccgtttac aacgctatta tgcgcgatgg   1740
atggggcctt gtatctagaa accgaataat aacatacctg ttaaatggca aacttagatt   1800
attgcgatta attctcactt cagagggtta tcgtgccgaa ttcctgactt tggaataata   1860
aagttgatat tgaggtgcaa tatcaactac actggtttaa cctttaaaca catggagtca   1920
agttttcgct atgccagccg gttatgcagc taggattaat attagagctc ttttctaatt   1980
cgtcctaata atctcttcac                                              2000
```

<210> SEQ ID NO 2
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2

-continued

| | | | | | |
|---|---|---|---|---|---|
| aaaacgtact | acgtccacta | atatagtgct | cagggccttt | aaagttatga | acaggaatac | 60 |
| ggcgatgacg | atagagatgt | acaactcagt | gcgaacccca | gtgtatgtac | aaaaagttac | 120 |
| taattcactt | tactgttttg | aggatgtacc | tgccaaaaag | attcagatta | tcaaagtcag | 180 |
| atctttatat | gacggaacgc | gcaaaggatc | ctattaggat | gcgcctcaaa | aagccatcta | 240 |
| aaaagttcat | gtattgagct | tattagtaaa | ggtatcaaca | aaaatgattc | caccttatat | 300 |
| aaataagctt | gatcccatta | attgaataat | aaagaccgag | taatcacttt | tatgcatgta | 360 |
| acaaaaatcc | cgtttgcggc | tatgctacaa | cggtcatccc | atagaatatt | atcatcgtac | 420 |
| aagcccaaga | cccgatgctc | aacattagag | ccaaataacg | tgcacactcc | taatatgaga | 480 |
| tgactgccgc | ttttaacacc | agatctgtta | gttaggccac | gcacttccaa | gtttatctag | 540 |
| agtgcatgtc | tttatatatg | ttggtcccct | gtaatgactt | ataatatttc | cttcgactgt | 600 |
| gttgaacatc | tgtaacaata | aagactaaag | ctctgggtat | ataaggttgc | agtggtacct | 660 |
| tattaggtcc | attatcgcag | aatactgcgg | atggacaatc | ttgccaattt | aattgactat | 720 |
| ctattagttt | gcacaatata | acgattcgtc | ttggacaaat | ttggcgagtg | agccccttac | 780 |
| tcgctcaaaa | tgttacaatt | gccgagctcg | gagttgaatg | attagttaca | tattatagaa | 840 |
| cacaatgcag | atgtagttag | acaagatgtg | ttgatgaatg | tcaagtctga | ctggagtaaa | 900 |
| ggaacaagag | cacccaccta | cgtatattgc | gcattttaaa | tgtagcctcg | actctaacac | 960 |
| gtgcgacgtg | agtcataatt | gtgcatgtta | ttagatctat | ggaatgttgt | ttttttaatt | 1020 |
| atcaaacgta | cgtcaaaccg | ccaaactccg | tgtgccatag | agtatactcc | tgaagttcga | 1080 |
| aattaggcca | taaagtctttt | cttgctggtt | gtgaaatgaa | ggggtgtttc | ataatttaac | 1140 |
| tttgactgct | tctgttggga | cgacgtaccc | gttcgtttgt | ttgtcctact | atttagtatc | 1200 |
| ttaaaacagt | ccatttaccg | ttaatgttct | taacccttaa | agatacaaac | ttagctctgt | 1260 |
| aatcaacttc | aagacgtctt | tgacagaacg | tctaagaccc | agatctgtgt | tagccaactc | 1320 |
| gtattcaatt | tcgtaccggt | ggacttcggc | ccctcacact | gccattagtt | gatgctgaac | 1380 |
| tttgtatttg | ctgggtagga | tatataacga | ttttgcagat | gtgtgtgcta | agtatattgt | 1440 |
| cttagtgacg | gtccagcata | taaaacacct | acacaagaag | gttattctta | atggttgatt | 1500 |
| gaatattatt | aaattgttgc | ttttactttt | tcctcctaca | aattgtcatg | agctcaaatt | 1560 |
| tgttgaccta | aggtattaat | attgtatcct | acacggattg | tgaacggtag | ggtcgtaaca | 1620 |
| atcgtacttt | acggcttaaa | aattgtaagc | accttgccag | gtagatgaaa | acttaaagga | 1680 |
| tagaagtata | gtaactcaca | tgcttgcggc | agcatcgtag | ggcagaggtg | tgatcttggt | 1740 |
| gattgaaatt | aaggggtagg | atgatcggcc | gcatatatcg | gctactagga | ttagatagat | 1800 |
| gcaacgcttt | actttaatca | agtgacgtcc | gtataagtaa | gacatctaat | ggctgtatttt | 1860 |
| ttgtatacaa | gtataaggaa | ccggggagtc | tttatagcga | cgcgtaatta | tatattccaa | 1920 |
| atcagttaag | tggcgtcggt | tacgaaacta | aagagagtgt | tcaagacgca | atgaagaatc | 1980 |
| gtgagcgtaa | ttgttcgcgc | | | | | 2000 |

<210> SEQ ID NO 3
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3

```
aaccctcgtg tccggtaaaa cacgcttcga atacaaaaga ttatataggt acggaaggct      60
gggaatcttt cttcgatgga actgagatta tattccactg taaccttatt atgactatag     120
atttccaaca tacggataga ttaataccga ctgtagattc catacttgaa ctatgaagcc     180
gtacgagtac ccatactata actaagacta tgacacgtgt gaattcgtgt ttatcatagt     240
gcaaactctt gctattccac atgggagttt agaactcagc tgttcctata caattagcac     300
tacaaaccca ctaatatgga tagcatgata ccatctgagg aggatttggt gttaccatgt     360
tgtaatctaa gaagtttcac aaaatcaacg ttagataaac ggcaatatac gcgcactaat     420
aatgaacccc aagatatcag ttgaaaaatt ttcgatctcc tctttaaatt aacaaatatt     480
gcagagtaag taccgaaatt gtgacacaag tgccgtttgc ccgtcttttt cacagcctat     540
aaagttcaga tctatatggg ctcccactta accttcagat agataacaag ttactggaag     600
tgattctatc ataatacaat caactataac acatccaatg atatatctcg agaaagtcgt     660
agtctagagc tccttctatt atccggtctt acctaaatag ttatatttag ttgcccattt     720
aaaattggat aggaggaggg gtgctcatga tttaaaaacc aactgtgcat gcggttcttt     780
gatgtggatc caccttgcaa agcgctaaag ataaaagtag tcactacagg aattcaactt     840
ccgtcgttgt cagctggcgc gggaacccat cttgtgtaaa aaactgtata accagacacg     900
tggactcgac cgagaaacag tcagaacctg tcacaagaaa taatcttgat taaaggcttt     960
cacggcaaac ggacctcttc cctgctgaag tgtacgattg aatatccaca tcgaaggtca    1020
attaccctca tcttttacat ggtcataaga caataatctc ctatttggat taaaatccgc    1080
gcacgaaaga taagagtgga atcgattgca ttatcgagtt tttaagcccc atacccgaca    1140
gatgtgtaaa aagtgtagtg gtaatggcgt caccaagacc tatgcttctc ataataatag    1200
gacgtatgcc ctagctactg ctaacggtcg ctcttacaat actagctaaa agaaacaaat    1260
ttgaaaagtt atgtaggaag tcattggcgg tgaaaaagtg agaaaaaagg tccccggaga    1320
ctgtgctttc atgttatcaa agtacatgcc gagtgaagag tttgttttga tcaacttttta    1380 ttatctggag tcattatacg atattgccat ggttccttgg ctgtccaacc aggggtcttt    1440
tacaccagat aatcttctac tacactcac ctcaggtacg attctttcgt tatcaatcga    1500
ctacaagatt atagtgtctc taaggcgtga tgtaggtttt ccctcaatga caaagacttt    1560
acagcaatcc ggttcaatac gagaattaag tgtgcgagta acagcaaagt aaaatctaac    1620
agaaaggaga ctcagaaaac aacctattga ggactgtaat atcaactcag cattattgtt    1680
tactttaaaa tctaataatc gtttcgagga tatgagcacg gtatcctaac atcaagacaa    1740
ataccacatc atctaaatac aactggttgc aatgagtcga atcgcgaaca aataaagcaa    1800
ctataagcac gataaaccac tgttatggga atgataaaca gtcttatgac gtggtctatc    1860
tgtcgtaggt ggtaaagcct tctgaagatc actatccagt tctggcctca agaaccattt    1920
agacagcctt ttctaaacat gatcgttgct ataaggaccg gggacaccta gacaaactca    1980
cggaagggat aacttacatc                                                 2000
```

<210> SEQ ID NO 4
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4

```
actgcttata taggaggtac aaacagatac aatccttagt taactagaga gaatgctttt      60
tttcgaccga cacgcttata acttcactgg gcatggtcac catatttagg taaaacaaac     120
tgctgcgcta tatgtcgtac acatcctgag tgtaccaata tgtaggtgga aggcaagttc     180
aatgagacgt cagttaccaa gcaaatttac attctagcag ttataaatgt attatgacgc     240
agttcttgtg gtgagcgatc atttacatta aaactttatt caagagcgta tattagcata     300
tattttccgg agagtgcact acgggccgaa atttaggctg gaactccgca aattggttac     360
gaccctgtat acatagttct tattattaag taaaatgtgt gaataaaacc tacacgacgc     420
gtcatatacg taaaagttta tctcttgtag taatcaacta aattaactta ctactatctg     480
gtcgtccgta tgaccctgtg agcagattat tttcgactcg acatctatga attctacggc     540
acgaaaagtt ggtaacttgt actgggttaa acaatgtgta ttcgggagtc tgcggaagaa     600
cgttttttaat gtaacttcct ttgcaaacca aaatttggtc tattcaaact gacactagcg    660
taatctatac cgcatgagat cctgacatga tcctatatct atgcgcatag gtactcgcac     720
caataagtgg gtcgtagaat ttcacgtaac tcaatgttgt ctcctttcat tttttgttaa     780
ttcgagaaaa ctacaaaaat agttagtaaa atgctcaagg agtcaggtgc tacctgtgga     840
atacatctat gtccaatgga acttgctccc tcggatgtgc gatttcgttg ttcagttggg     900
cctttaagga atacagcaac tccaactctt tgattttagg taagtatttg attcgcggaa     960
agtacagtgt ataatctgtt atttgccaag acgtcatcga aatcgagtgt atcgagatca    1020
gaccatcgcg ctatcgcaag atatgaagag catagacaga tcacgatgcc aatcagtgtc    1080
gatggtgcga agacgcagcc cctgtgatca aatcgtccgt ttctcgattt actagcggaa    1140
aacaaaaacg aagcggtgaa taccctgcga gctaatgtct ttacccggtt atacgagctg    1200
ataactcgga aaatgctaat atcgaggctg cgcacttaaa aaaatacttt aataatatta    1260
ataagcatag ctgtatcata acttaaaatt ctactgtatg atttagaatc taacagtgtt    1320
aacgatctac agaccgcact aagatgaaga cggactaatc tcctccctaa ttttccttgt    1380
tgattagcaa agggagatcc ttttgttatt tgaggtttac gagaaagatg taagagtcga    1440
aataattacg taaacctcat agtcgtcacc tagagcaact ataacatgaa ccactcgcct    1500
tggttaaata taaataaact tcttctctgt aacattgttg cacacaagcg agcgacaaaa    1560
tttcacaaca tttgttgcgt agataatatt actgcatcat ttttgcgtca gagtgaatgt    1620
cacttatata actaggaaaa attagtagga tagctcttgc ggttgagagt aatgtcgact    1680
gaatcgaccg ccatagatgg tagagggagt gattcaaata gattaatgta tgcgctccat    1740
ctataaggac ggacaaggat caatgttccc ttatacttag ctaacaggac cctctccgaa    1800
ggtctgataa tgcactcata taagcatcga tgcgtcctga gtagaaaaat ctttacaaac    1860
ttttaataga taagttatct tggaggtgct atctattcaa atctctgaac agatctgcgg    1920
catgataatg tctttgtacc ggtgtgaata atgtgagtca gacgtctgtg cgaagtggga    1980
accgaaatct tttaatcatt                                                2000
```

<210> SEQ ID NO 5
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 5

```
gattcggtcg cgttccataa tcgaacccct aagcccatct tccagctgtt aacgttatgt      60
accatcttac ctcaatgtca gcgatctatg aggttcatgt ttttggtgga ttaaaaaact     120
tctttatagt ggtttagaca gaacgtttag cgctgcgctc gaagtgtctt atctaacgga     180
ggactaaaat tacctggtca ctccttagac ttttcgtagt acttaattgc cggacatccg     240
ttgggctaca ccagcaagaa cacaaagtgg tatgtgtgaa gctagactga cctcatgatt     300
cgtactacat tataagaatc aagcttcccg gatttgtgtt ctgagatatt accacgtaca     360
ttttttaaggg ggttcttgac atcgtaacgc taaggctgat taaagaggag ggtgctatgc    420
agagtttatt ggtgtttcat caatgtatca cacaaaatta gctactatag gaagtagctt     480
tggtgcgagc aggggcggt atggttaaga aagctatggt aagaaaggcc caggtgatac      540
tacgtgtaag gttgtgaaga gccacaagag ccaagttttg atattcgact tcctccgaat     600
ctacagctta tcgagggtta aacgttacgc atattacgag attacatgat agcttctcag     660
ttctagcaca tttatgagac cctttgaatg gtgtcaataa ataggaggtc cccatatgac     720
aagtagaata ctaactataa gagatttgta acgctggata ccatttgcag aggattggcc     780
caaagaatga ttgcccaacg cttatattgt cagaccttgc attagaagaa taacgcagaa     840
tacgactgca gtttgatata attttggctc tgggttgcct tagtatcatt actaatagac     900
ttgtggtcta tatccatttg tttaatggaa tagactgggg aaaacacacc tcttccaggc    960
tgtagttctt catgttgtaa ggatccgtca tggcgtgcaa actaggggag gtattttttg    1020
ctaattgcgg taacggctcc agttgggata tcgtcaatat gtgccactcg gcccttttctc   1080
tgagacgcta agatttccgt aaggtatagc gataagagtc tctaatgcca gaggaattgt    1140
taccgcgagc aagattcatg tctatatata aaatatcatc cactttgaat tactggttgg    1200
aatcatcgtt cgcgttataa caaaaaacct tttaattatg ttaccacaga tctcgaagtc    1260
ccttttgagg cagaagttta aatataagct ctaattgtcg catctaacgg gtatatcgtc    1320
tcaacggtag gtcaaaaaca tttgttaact tcagactgta cattcgcatt taactcgcca    1380
tgtaaaccgc aatacatctc gtgcctatct ctcctagtaa cgtattatcg ctgggtgaaa    1440
gcgcaactaa gtaataagtg aatgtcattc acaataccta actctatccg acgcgtaaga    1500
gcgacccagc agtttaatga catgataaat caaattctat gcaaggcagt acttgctttg    1560
tggacgatag cgattttcca ccgtattgcg aagtcagtta tgctgaaatt ttattccatt    1620
cgcataacac caaggcttac tcttaggaaa aaatgtaata ccgatttttgg tatgaagtat   1680
gttacagtac agaatgaaat gcccggcggc gtggtcaaac tgtttcctga ggttcatata    1740
gggaaaggtc atccctcaga attggccccg taatcgcaaa gcctacggga gctttcttaa    1800
gtccaaccgg taaagccaaa tctcaattca tatgaggaaa tgtttgaccg ataaagaata    1860
gattgtcgaa ctaacagtca cagagaaaat acgagtagca tcacctaaac aaagcaggta    1920
ataaaataga ctaatggaga tcatcgtatc ggcttatgac ctgcgtccat ttaaaggcaa    1980
tgaatacatt accgactaga                                                2000
```

<210> SEQ ID NO 6
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 6

```
agttatgagg ttcacttctc atataacact atcaacaatg atcatctctt gcgaaacaag      60
cgccctacac agcttcaatg gaaccaagag ccataatgag gtaagggacg gctagttact     120
aataaaggaa tcgattttac aaacactaaa tgaaaaactt gcgctggttg caatgctata     180
aaaaaatgaa atgcaaacca gtgaagatcc cgatcaaccg ttcgctgatt tttattgatg     240
ctgtacgttg tgttagttta atgatatata ggccatctcc aggttactta ggacgccaaa     300
attactattt tgaagctcaa ccgtggtata atagctacaa taattaattg atgcctgcag     360
gtcgtatctc gaacgattgt acgcattacc tatgatatga acagaatctg tatcccatac     420
ttaaaatctt gaccttgtaa agatttcgca tacgcattaa gaaatttcgt tctacccgca     480
cggattgtcc aagtatatct ggccattcac agaagttact aatcttcatc tctaagttta     540
aggccgacaa agggtccaaa acctgcgtag gttacaacgc agcttacact cagtgactaa     600
ccaacgctca gtagggtaac tggacttgtt ctcgctattc agctggtact gtaatgatca     660
acttagaacg gccctatggc taagcaagga gtacgcaatg ttttagaata cgtgtttgct     720
cacacaggta gtagtttaat atacccctg acaagatatg ttaacataga tgaagtttgg     780
tattacttat agccagacta ttcttcaaca tatacactgg gttttaggag tgtgcaattt     840
ataaggacag ttatattcct acaatcgttg tatgatcctt ttgggtttgg tagaactacg     900
tttgggccgc gcctttggtc aaccacggac tttctgtcta gatgccaatt cctacaagct     960
tagtcctatc aatttagtag agaacaaatt ttgtcatcac tgaattgtcg tcttactatc    1020
ggatcattct ccgctaatta taggattatt agtaacgcgt atataggagc gattaatgac    1080
tcatcaatga atagcatcac taggtgtatt atatgaacct ctctctattc tattaactgc    1140
ccactgtggg taatttgagt tatacctgac cggtccctcg gatccttaat cctttgatgt    1200
cgataggtaa ctgaagtgta agatcctgat atatgaagcc ggtaaggaga cggagatttt    1260
atattagtgt tcttggatac tgtgctagaa ggttctactc taactcaaac aggttataaa    1320
gtaggaagga aaaagttgat agtggtaaac taattatgag ttggcttgct tattccaagt    1380
tagcgaggtt ttcatgacgt aagtctgata aggtttgctg gaagctgaaa agttttacaa    1440
aaacgttgtt ttagaatggt ttgtccccga aaatcgaacc tggcatagcc ctcaggagac    1500
gaacaagccc aggcaaaccg ggggtttctc gcttattgct ataatcacct ctagtgttgt    1560
agaagcaatt acggtgggga ggcgtcaatg tggcctgagt tccgttgagg acttttcacg    1620
tgtaggaccc attaatagag gagatatatg tctttcagct gcggaattca taatagtgga    1680
aagaagaaaa gggattacta gattaatatt actcatccca gacttaagtt gaaagctaca    1740
tcttcacacc caggaaaccg gaccgccttt gttcaggtct aagtagtctg gaacagaacc    1800
gtatcaactg ccccaattca taggtgttag cgtgacagcg atcgcggatt tttagtccag    1860
actggctggg ccatccgctt caataagtta gaggactaca tacaacgatg gacccaattg    1920
gcaatagtcg tggtaaactt cgaaggggcg gtgtaagatt caagctgtag tcgtgatgaa    1980
ggagatcatc gtataaacag                                                2000
```

<210> SEQ ID NO 7
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

```
atacatctag actactaaga gggattatcc cagcgcagtc ccacccaaac atcaatctgt      60
ccctttgttc taatatatct ctggtcgcga atgagtaaac ggggctaaag gtccattatt     120
tttatgtagg agcatgttgc ttattatggc atagcagtcg ccatccccct gtcactcgat     180
ctagatacat ctcacattga ttggaaactt ctacaaaacg ttagtactta agatgagtga     240
tttagtgcat ttctcgtttt cacaaacttt gctaaacaaa cgtattgagt ggcgcgtttt     300
ttgatttgtc gcataaccgt ttactccctg ttcgaaggaa atcgatctcc ttataaataa     360
tgagtacatt atacagctag cataatctgc gtgtggcaaa agtgaacgtt taatctacaa     420
ttgatggaaa aatagcccgt tagtcctttt aaagacgtct tggaaaaata ttgagacaac     480
cttcgtccaa aatatgtcaa agcttcgtca catcttttca cctattacta actccgtagt     540
tcaactgact ttagagggca agttttgaga caatatctta gggctgacta ataagacggt     600
tatatttcaa gaaggaaaga tcttaagagt caaaaaaacg tcagggctat cgttacgata     660
ttggtatgaa cagtaatgat atattttgca gatcttaata taacgacatt cgaacacaat     720
agcgtcagac aaaggttacc actcctctat aattactgca gcttcaattg atgagcgtca     780
tttaattttg gccggacatt tacatcgtga gctggcagca cgctcagctt tattgttctt     840
gccagaacat tacgaatagc cgttcaatgc caattagtat gataaaagta gtgagtgtaa     900
aacatggcct gggtttaaag aatgagtaac tattattttg taggaataac tgattccctt     960
gagttctatc ttaagttgta cagaatcaca ctcctacagc gaataagcaa cgacatagaa    1020
tccgttattt cgtatgtctc ggcgggacat gtataagtag catacgttat atcggttgtc    1080
gcacgaaccg ccttcattcc aaaggcgctt acaaatctgc agtaaaaagc ttagcattta    1140
ctatagagta tcggcgttga ccgttaagcc cgtcccgtcc attcaatcac tcaattgatc    1200
atcttttggc aatagtcgtc atatgagaaa atagctctgt cgttgttatt attggctaga    1260
gtataagctg ttaaactaca gaatgacgtt ttgtggaaag tggacgtaag atccttgttc    1320
gcgaagactc gcacggtggg gaacaattcc tgggaatatt tgatctacgt acggttattc    1380
tgcatgtgat tacaatattt ccaacgcagt ccttttgaca ttatatgaaa ccagacccga    1440
tgcatatgtt ttctgactgg tggtttgagt cagagtcaac aaaagtatca gtctttcgtt    1500
actaaatctt cctaagtaaa tggtgggcga ccattccttg taacctgttc tgttataggt    1560
actattccag cctggaaatc gtggaacaca tcgatctagt tgtctatcta taagagaaca    1620
ctcggttcca aatatgtaat ccgcacgtaa gagaggagtc tcgtacatga tatataacgt    1680
tgggtacatt tcttagacat tccggtgata cataatgtac aagtcacatg attacaccag    1740
ctggtagata gaatacctga gactgggtcc tagatgatta taacaagtgt tacatggacg    1800
ctctcgtttt gttgttggct taacaccagg gcttgctcca tgttctcatg tcgttattac    1860
tgaattatct tccattatga tcctggacgg atgaacgaag cagaagataa caaagatgac    1920
tgaatgccgg aaaaggaatt aggccctgat atatcgcgct tctttatgca tgtttacgct    1980
gtaccaataa acgcaagagg                                                2000
```

<210> SEQ ID NO 8
<211> LENGTH: 2000
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 8

```
gtacccgtat atcgtcactt catttgaagc tattattaat gtaaaatcct tccgtcacac      60
actcttttca aaagggaag tctaaattaa cattcagatg aaaagcgctg acccacatgg      120
gaatatcctt tctacgctat cagccgaaaa gctccagcga ttagctaaat atctaagcct     180
ccagaacaga gttattatat attggttcga atatgctaat attacagtag aaagtaaggt     240
accggcactt ttaacgccga agtcgaccgg tgtagctgtg aaaatatatt tagtacacgt     300
aatattaatt ggaaattgat gagatcgaat cttcaggaga atctgacgag cattactaat     360
cgcgcgtgac gggaacgtta atatacaagc gtctattcta ggttataata aactcctatc    420
tggcaagttg aatggttttt tcaaaacttt aacgttctgg ctatacaaag ctagttgctt    480
taacttatcg catactatga tccttcccat caatcaatct cagtgactat aaacgcaagt    540
gacacaattg tctgcgttcc acatttctaa atctcttatc gctcattccc tctacacaaa    600
gttcgattac caaacgcggg tctacacaca agcttacaag gattacaata tccaattttt    660
tgttatcaaa ggcgaactca acgaatttaa tcgttggtca ttggtatgga atggcgatta    720
taagaaaact cttttagtca tagtagctcg agatgaagtg aaccgggcca gtcggtagtt    780
tcactatcgc gcagtagtca cgatcagttc ttagaatcta tctcctaatc aagtccaaca    840
agcaatccga aatgttgctt tctataaagg gtatgtgtac ctgccaatat taaacttgat    900
tcactcaata gtgattttaa atatgtccat atttatgcaa gaatcattga cattagtaaa    960
ttcagccgtg catttgacac aataaaggta gatttagact gcatatttcc cgcatattta   1020
ttattgtcaa cgcacaaagt tgatggaccg accacgatcg catcgaagac cgtctaaacg   1080
acgatattct tcggagatcc atatttgttt tcaattaccg accattgttc atcaagtgta   1140
gttcagtcgg aaattttcg tgtgcttttt aaaataccaa atctgaggaa aaagctcgct    1200
agatgttgag tcaatccgta agaatatgcc ccaggagaca tatgtaagtc acagccgtag    1260
actctcggtt accccacgat atgttccata tgcaacgttt gttgagtaat atgcagttca    1320
gtcgggcgta ttatcaacag acagactggc acagtaaatt ttatcatcgg gtttaaaata   1380
tctagatacc tcagtttcaa gggggagttg aactttaaca cgagatcaaa ctacatacac   1440
aagattatca gtgggtacgc tgagacttat ccttagcctg gagagagtcc agctacagga   1500
actgctagta cttagcgtgc gacctcaaat cgagagaact aattaccctg atcgacagat    1560
cgggcaagtt aagcaaacgc ggctcgcgtg tagaaccata acaattggag atgctcctgc   1620
ttaagagatt atagaaccgc aacccatcaa tcgtcagtta cccgagggct cacgcacgcg   1680
gtgatggaag ttagttcctt tgtacgcacg agctgcaata cgtggtgatt ataatcggcg   1740
cacactaaag gggtggatac aatagtagaa gcatatacgt cgcataggcg tacgcgggcg   1800
aaaattttaa tcgttaacgt ggcactaaca gcgttttgtc tccccactcg tgggttgcgg    1860
tgcatcgcac atattcccac aacacctctt aatgctttat tatttgtatt aatggcgcga   1920
atctgcctga tattagtatt cgcactagtg ggtaacgaaa tcttagtcgc tggctactgc   1980
agaactaatt gcgttgcgat                                                2000
```

<210> SEQ ID NO 9
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9

```
actagctaca gatctgtaat agaaaaatgc agatgcttgt tctgcgtcga ctcgctcatc     60
aacatcctgt ctcacaagtt atgcatcctg tgcattttat tgaagctttg atggggatta    120
gatcgtgtat ggaaatgttt attcgcctgg ataagatctg tcggcttatt cgtggccaat    180
aataggtcaa tttgcggaaa cataaagact cgcataccaa tactcgctta tcctgaggtt    240
aaatttagtg tatgtagacg aacaacagta tttagtagta tgacgttccc ccgtattgcc    300
agaactcctg aatatttgga tatgaggtat gactacgaaa aaaatactac gttgctcata    360
accattggtg cagggatacc gaactcattg ttaagggacg ccacagtcca gtctcttttc    420
gttcagagcg tgttttcaa agtgcttgta ttagtgtgga cagagtttac tgatctctcc    480
gcacttggac tgattgtgat cccgatcatc tcttttcata attgtaacac gctttcatag    540
tacacttctg tacattgaag agtgcttgca gccggacagt cctatagaat ttggcgtttg    600
ttcggccaat gtgtgcattt aactttagg cgccatctct tgagattact cctttgaaaa     660
attttggcgg aggttaactc tggtctttaa cataggcgtg cttaacacga gctttacggt    720
caggtacagg taacaaaaca ggtctaaatt tatttaagca gcttctgata cttttccaagg   780
gtcacagttg gggagccttc cgaggtatga caatcagttt tcaaaggtg tagaatatca     840
tatattctat ctaggccaga gcattctaag ctgttaaaag agtgctatgc tcagaagttg    900
actgttctaa tcgaaaatcg gacatagata acccgcatac cacaagtccc gttgtaacgt    960
acccatcgtt tttgattcta tgtctttgct aatgattggc gattgagaca tcctacttct   1020
gtagcttggc tgttatgcga tccaaaatgg tatccagtgg tggatgtccg ccgcaaactg   1080
aaactcccta tcagttcttt gaattaatt tgcgggctat ccgactcatt ctttaggaat    1140
taacagaaga acacgcgtct gtaccaaggt tcttctttgt tatatcacat aacaatgaat   1200
cacgttctat gatgaatcca ggtatagaag ttgtaggtaa gcacttgtat aaggggggcgc  1260
tcctctcaga ttgattcatt atttactaaa aaaggagcgt gttattactt ctaacaactc   1320
ctcgccatta tatattattt aactaccatt cccactagaa atggatatcg tgttctaaga   1380
ccctaattgt gctcattaaa ctaactaccg caccaaccgc cttgaatcac cggaccacac   1440
tagttaagct gccgataccc aatatggtat tttagtgtat accggatatg accttattta   1500
cgaatggatt gagctcaccc catagatcag taccagcgtt attatgaaaa tcttgttatt   1560
ttaacagaga gacatgcttg gtcattacta cgaatttgag tttacgttat acaaggcgat   1620
ccaaacggac aatagcgcga tacgagatta tagtaccaat agcacgaatc agttttagcg   1680
atctcgtccg atctgtcaag ccgaatgact ctgaaacgtt agtatctgaa acgtttcatt   1740
cagcctaaga tatgtatagt atcattatac cgtgtgggta gaacaatcaa atgcagataa   1800
agctatttaa tgcacttcac ataacctctc cgttggaaat ccatgtattc tctaatcaat   1860
tgaattgtac cttagaaagc acaggggac acctgaagac ctcccatctc ttaaggttac    1920
cggcacgtga aacttcaaaa gtcagacaat caaacggcaa cgtgaatgtc ttcggaagtg   1980
gtggtatgca catcgcgtca                                               2000
```

<210> SEQ ID NO 10
<211> LENGTH: 2000
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10

```
ttaatagaag taataagtgc tattggacta aaatcgcgtc aattagctat agaacagctc      60
tgtgacgaac tatcaatggg gcattcgttc actagtggat accgtacaag ctcgccgtga    120
tcgtgcgtca aggatagtgc cagagcgccg cgctatatgt gtaacgacgc ataagtagat    180
gtttatgtta ttgggcaaag tcattcttat ccataataag cgctgccgat aaagattcat    240
cagagatatt gagattctcc atacttgact aatctctgag taattaaaat atatttctaa    300
tcggataagt tagggatcac cgaacccaat gaacttagtt taatgtgttc tcgcgaatat    360
ccccatgata taaagatccg aatacctcag ctccgtgcgt gctcgtgcag tcgtgcgttt    420
tctatgaatc aaccatcagt aacgagtagc ggtaactact tctcgagttt aaccaaagcc    480
tatgtatact agcgtgcaat cacgtgcgga aggtccgacc tacagcagca ttttcgttcg    540
aaaaacgaaa actaatgtgc actatgttga atgggcattc aggccttaac ttctaacgtt    600
aaactagatt tgcgattatt aggtatgaga tcgaccaggc cgccacagat aattaaagat    660
agccctagca aagtgataag gtccggatgt tagaacttgc aagagtgtgt aagattattt    720
actctcggtg cgtcgacagg cgaaacccat aacttttatc ggtcaagatt acgaccttca    780
gctagtatct tgagatttga aagggcctaa aagcaattta gtgtacttgt gtaacataac    840
cttaattatt gatggttcta tcgactccca gcggtaataa tcttgtaata ttgtcggatt    900
tagttgaagg gcaggttgac ataccgaaca atagctagta tcaatgtata actagcaggc    960
atctaatttc gtaaacactc ctgacacttg tcgtgtctaa gcatgttagg acaaaagacc   1020
agtttttta aacctgactg taccggcaac gccacagatt ttatgtctcg catacgtacg   1080
aactgaattt gaggggggctc aggtttggac ttacaccgca cgtgactata ctgagatcga   1140
ggctccatta acggcaacat aagactagca ctgtatgatc tgaagccagg ctctggtgaa   1200
attgcgggta gttaacgaca tttatcgacg aacccttgat aaaaagtgat tatgttgtat   1260
ctgcgtgata tattcttttc gtgttcagtc tctagaactt cgtgcgtaat aaagattata   1320
gaggaacggt taacctcatt acaagacgga gaccgttcat agacgccgat ggattacagg   1380
gtctactata gctacctaga acactggtga acatagggat aacatacaat taacaatatt   1440
ccgagccaaa ttatgtcttg agtcttggtt gttatctata tcgttattat gttagaaact   1500
aataaatgcg ataagaacta gattttacag tagatccaaa taccggaatc tatcgggacg   1560
attgattaag acttactcaa acctaacttt agcccgattt tgcaattaga gatacgtcga   1620
tttcgagaca agagtagcgt ccccatggca aatatccacg gacagataat gacacgtgag   1680
ggatggcaag agtagttgct caggatgtag gcgttgatgg tctggcgcta atgtcgtggc   1740
tacctgttga gtctcgcgta atgactagta gtgttcgaac gtatgaccaa gttccttcct   1800
agtgttacca ctttgacaca tacccagggg tttgccgcat gtcgctacta tagtataggt   1860
gctgctatga agcttctgaa tcagcggcta acaagtacct aagaaaattg gacatctttt   1920
ggatgacagt gcacaggagc ctatactgaa ttatcggtga tcgatgcttc atgtaatcaa   1980
aaccagcgcg tacacacttt                                              2000
```

<210> SEQ ID NO 11
<211> LENGTH: 2000

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
tactcttaat tcattacata ttgtgcggtc gaattcaggg agccgataat gcggttacaa      60
taattcctat acttaaatat acaaagattt aaaatttcaa aaaatggtta ccagcatcgt     120
tagtgcgtat acatcaagag gcacgtgccc cggagacagc aagtaagctc tttaaacatg     180
ctttgacata cgattttaa taaaacatga gcatttgaat aaaaacgact tcctcatact      240
gtaaacatca cgcatgcaca ttagacaata atccagtaac gaaacggctt cagtcgtaat     300
cgcccatata gttggctaca gaatgttgga tagagaactt aagtacgcta aggcggcgta     360
ttttcttaat atttaggggt attgccgcag tcattacaga taaccgccta tgcggccatg     420
ccaggattat agataacttt ttaacattag ccgcagaggt gggactagca cgtaatatca     480
gcacataacg tgtcagtcag catattacgg aataatccta tcgttatcag atctcccctg     540
tcatatcaca acatgtttcg atgttccaaa accgggaaca ttttggatcg gttaaatgat     600
tgtacatcat ttgttgcaga ccttaggaac atccatcatc cgccgccctt catctctcaa     660
agttatcgct tgtaaatgta tcacaactag tatggtgtaa aatatagtac ccgatagact     720
cgatttaggc tgtgaggtta gtaactctaa cttgtgcttt cgacacagat cctcgtttca     780
tgcaaattta attttgctgg ctagatatat caatcgttcg attattcaga gttttggtga     840
ggagccccct cagatgggag catttttcact actttaaaga ataacgtatt tttcgccctg    900
tcccttagtg acttaaaaag aatgggggct agtgcttaga gctggtaggg cttttttggtt    960
ctatctgtta agcgaataag ctgtcaccta agcaaattaa tgctttcatt gtaccccgga   1020
actttaaatc tatgaacaat cgcaacaaat tgtccaaagg caacaatacg acacagttag   1080
aggccatcgg cgcaggtaca ctctatccac gcctatcaga atgtcacctg gttaatggtc   1140
aatttaggtg gctggaggca catgtgaagc aatatggtct agggaaagat atcggtttac   1200
ttagatttta tagttccgga tccaacttaa ataatatagg tattaaagag cagtatcaag   1260
agggtttctt cccaaggaat cttgcgattt tcatacacag ctttaacaaa tttcactaga   1320
cgcaccttca ttttgtcgtc tcgttgtata tgagtccggg gtaagaattt tttaccgtat   1380
ttaacatgat caacgggtac taaagcaatg tcatttctaa acacagtagg taaaggacac   1440
gtcatcttat tttaaagaat gtcagaaatc agggagacta gatcgatatt acgtgttttt   1500
tgagtcaaag acggccgtaa aataatcaag cagtctttct acctgtactt gtcgctacct   1560
agaatcttta atttatccat gtcaaggagg atgcccatct gaaacaatac ctgttgctag   1620
atcgtctaac aacggcatct tgtcgtccat gcggggttgt tcttgtacgt atcagcgtcg   1680
gttatatgta aaaataatgt tttactacta tgccatctgt cccgtattct taagcatgac   1740
taatattaaa agccgcctat atatcgagaa cgactaccat tggaatttaa aattgcttcc   1800
aagctatgat gatgtgacct ctcacattgt ggtagtataa actatggtta gccacgactc   1860
gttcggacaa gtagtaatat ctgttggtaa tagtcgggtt accgcgaaat atttgaaatt   1920
gatattaaga agcaatgatt tgtacataag tatacctgta atgaattcct gcgttagcag   1980
cttagtatcc attattagag                                               2000

<210> SEQ ID NO 12
```

<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

| | | | | | |
|---|---|---|---|---|---|
| ggccctatag | attttaacct | aagctctagc | ttgtgtgtgc | tcagagtact | gctcataaat | 60 |
| atgctcgata | aaggaggtaa | ggcatatcgt | aatttggaag | ataataccac | acttattggt | 120 |
| aacacgttgg | aatcacatat | taattatgag | ccagccttgg | cattcgagca | gggatatgtg | 180 |
| ggagtatcag | ttgagtttgg | ctccttgcta | ctgccctctg | atgctctgct | tgctctagct | 240 |
| taggtcatta | atgataaaaa | agagccagag | tgtgggctaa | acaggcaacg | gtaccgttgt | 300 |
| agagcgaggt | attgctatcg | ggagacgtcg | ggtcaaagtg | ggattcatgc | agtaagtttg | 360 |
| ccaaagggtc | tgcttaaaga | gaccgattcc | ggaaggctat | atgccatagc | aaggtatgca | 420 |
| ctgcattgag | ctgaaaactc | ttgagcatag | tatttactaa | ataaagaatc | tgatatcttc | 480 |
| tagcgtgttc | actggactat | tatttagatg | gtcgccaaca | acaagcgtgc | gaatcatata | 540 |
| gacccaaccc | agggtggtat | tgaattctat | attaaaatgt | ctcgcccctta | taactctcta | 600 |
| ggtttccata | gtacaaacct | aggtgtcgtc | aactgcatgc | actgcttttt | gtatcggtaa | 660 |
| tgttgatcga | cccgatgggc | ttttttttaat | aaaggtcttg | tttagttgat | catactacca | 720 |
| attttggtgg | tcgatggctc | aatgaccaat | ggaatcttta | tagtaaaaga | gcccttggca | 780 |
| ccaacgaatc | atgaaattta | ggacgatgtc | tcatttacca | tattttgcat | tcagactatg | 840 |
| actttcaata | atagaatatc | atcgtcaaac | accgtggata | tggcatcgac | aagtgttggg | 900 |
| atgcccactg | aataacgtct | cttcgtcatc | tttagggcgg | ctatccatta | aggaggattt | 960 |
| tatttttata | gcagtcttag | tccgaggcat | tggcgccaaa | catcggctca | acactagaca | 1020 |
| cgtctttaat | ggaaagtatc | tagtgttact | gcggtacgga | aagcaagttc | agtactttta | 1080 |
| tccaatctaa | gtatcaccca | gcttatattt | aaaagctagg | taatagggaa | gttactaata | 1140 |
| actcatgcgc | gtgtagtgta | gtcttgctgt | cgcttaaagc | aactgaatga | atgtacggct | 1200 |
| gacaaaggct | tacccaagaa | aactctcttg | tacgctacaa | gaaacctgta | acaagagaaa | 1260 |
| aatattttag | cccacgtata | gtgaggccaa | acttgatgcc | cgtaaaagca | aacaagtaat | 1320 |
| attcagcaga | atttgcggtc | attcaagtgt | ttaggtacgt | aacttttaca | gaattagctg | 1380 |
| ttgattaggt | aatactaaat | caaaatgtcg | taataccgaa | gcagaagtat | atgatctaat | 1440 |
| ttgtcgcctc | gcttcatgct | acgaatgtta | cttcgtttat | tacagctgca | aacttgcagt | 1500 |
| gacttgcatt | tgataggatt | cttcctaggg | aaccatactg | ggccgcggac | agggagtcag | 1560 |
| gaactcataa | cggatgaaga | tgtaatctct | ataggggtga | ataacaggat | tgaagatagt | 1620 |
| aatctaagta | ctctcatctc | gtggacgact | ttaagcgcac | tgacagcgac | tcgcgattcg | 1680 |
| acgaacaccc | gtgatcgatt | tacacgttca | ttctgaaaga | tatacaggta | ataattctaa | 1740 |
| aagataattg | agtaccaata | tataggtttt | atgatcttag | gcgcatgtca | ctgacgagag | 1800 |
| aaaagatagt | cttgccgcct | ctaagtgttc | tatttctgga | cgtgcctggg | cattaagggc | 1860 |
| gacgttgact | tttatacaca | tttcatgtcc | actaacaatt | ttatatcacg | tagcaggaca | 1920 |
| taaagggagg | actctataaa | aagtttcgct | atatacgtac | agtacgttca | aaatctccag | 1980 |
| aggaaagctt | gtaaaaaaag | | | | | 2000 |

<210> SEQ ID NO 13
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
cgctcgacac gagtataaca aatatcgata gatgctatag tgataaggta taagtaaaat      60
agtactgcga atacaaatag cttggagaaa tacgttcatc ctttaacttc aaaaattttt     120
ggacctcagg cacgttgtca ttattactgg caggtgatac cacccaaaaa tcgtacccgc     180
aatatatctt cggtaattct tgccaagttg ggattttaca tacttagtat taatagtggg     240
atcagcttcg atcgaagacc ataactcagt atgtgtattc ctcatacaag atttctgaag     300
gacgaaggct catcaatgct gaggtgttat caggtcaata acaagccgca ttaacgccgt     360
aaccctaatg ccataattct tgacgaaat gccaaatagt ttcatcagga atcacattat      420
ttggataagg aagcacaaca aacgctttaa tctataccc tagaattaag aggacagcat      480
gataggcttt gcaatgaacc agtctcctaa gcgtaccacc actccggagc cttatggcgc     540
gccggtatta tggcgatgca ctgcctgggc gaaactcgag tgaatcattt ttcccgatat     600
acacagcagt acgccgacgg tctggtaaaa aaacgttat aggctttgac cgcatggtga      660
tcgtggttaa gtgcctttac ctagagtgct gctagatgta acacaattga tctgacagtt     720
tacgaccttg taatccaaga accatataga tgacccgctg agttagtaag ataatgcacg     780
ctccggggct aaatctagtg cggttcatga ataccgaatc aactacggtt attggctgcg     840
gtagaatatt tagttgtgtt aaatatactc taagatgaac atgtatcact ataatcactc     900
accccctctg cgttcataag taagtggcta gtgtgatagt aacttgtatc agcgaccact     960
actatatgtg gaagcttttg aatgagaatc tccgcacatg atgatgtatt gatacaattc    1020
ttttgttcga aaaagcttcg gtgttttta ggacaggaga ttaacgcttt agagtcatac     1080
atatatgtca agaaaccggg gaaaaatgc cagcccagag tgttctaaac gataggttgt    1140
tcagttttta ataacccgcg acgcgtcaag taacgtcacg ggtcagctac gattaccaat    1200
ttgctataaa cttttccccg acgagccaaa tccctcaaag ctgccagata aaggatagc    1260
aacctgtact ccccgtcaaa tctaatgcat tcttgttttt taagtctcgt gtaacatgcg   1320
ttggctaatc ttctctaccg ggtccagtgc cctttcagct tatgcctcac ctttgattag    1380
taatggacat cagcttttag tcacatcgga gtgccaatta taccgttata tctttctctg    1440
atgcagaccg acctgtcgtg taccgattca tcctagggta actagccgtg gcaaaatatc    1500
tttatcgtgt tgtcaggact tggttgttat atactctagc ccgtagattt aaaataaatt    1560
aagtgtagat cgtccaaata tctaaagcaa tcgcagtttt tatcacatca tgtgttaaaa    1620
tgcgatcaaa agaaaaatac tgttatttcg agagtcaagg ctgtgaggaa atatgatgaa    1680
gactgccatc ctggtggact ggcggcccca acgttgaagt ttctatttga tcggttatta    1740
aaggatactc gagaacaaca tcgaaggaat aaacttttat agaaagtctc cgaaatgaat    1800
aacttaagat ataaatttat cgcgcgatag ttctggtgga tgatagcttt attcctctta    1860
atgcagtata gctattgcac ctattaattt gtataataac gtatcatgtt agacggtcag    1920
catgatattc cggatagtgg aagcaaatta cgacatctaa atatgtcgct agtatttgag    1980
tcattatagc ttcgaggctt                                                 2000
```

<210> SEQ ID NO 14
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

| | | | | | |
|---|---|---|---|---|---|
| ctctaacgtg | catttcttcg | tcgcctttgt | aagacccccac | aaaaacatga | cgctttaggg | 60 |
| atatggtcca | agactccgaa | ttgaaagtat | gctggtatga | tatgggacgt | ttttgaaacc | 120 |
| cccctctcac | gcgggtaatt | gggttttttag | ttagtgtatc | atagtaggta | tatctacgaa | 180 |
| ctacgtctga | ctgagagaga | ctttgtgcct | ctcaaccgct | atggtgtcag | cgactgatat | 240 |
| tggagttatt | tacccgtcgt | tatacgtggg | taatctttac | tacggttcaa | ggtaactaat | 300 |
| ctagtgtagg | tagaatgctg | aagaattacc | cgttggaccc | ggtagtccgt | ccgctccacg | 360 |
| catggaatgc | atgagtaacg | tctaggtgaa | tatccggagt | gcataacttt | ttggtatcta | 420 |
| gtccgctact | ggatgcagaa | tgacatattt | ttttcgagtg | cttactatta | ctcttctcaa | 480 |
| acagaacgat | cattatgttg | cttaaattca | cgctatgttc | tcgatgtaaa | acaattttcg | 540 |
| tagagaaaga | tgcgtaaaac | gcagagttag | catataaaaa | gtacaatcaa | gcccgaagca | 600 |
| ctcacaagaa | acataggggc | taaatgttac | cgtccaagtg | agtaggattt | aatatcaagc | 660 |
| cgggcttatt | gggtacagta | cgtggacgga | ctacgacgca | tgtgtgttat | agaatgaagt | 720 |
| gcctacaact | gaagcacaat | tactaaagga | atgtacctgg | gtttacacta | agcatcccat | 780 |
| cctcttcgcg | gttcagcctg | atgtaaacgt | aaatctcgtc | ttcccattat | taagacgcct | 840 |
| cgatctacga | taggtgatac | gtgtacatcg | gtggaccatg | tgttttgata | ttcaacgatg | 900 |
| taagtatggt | tccctgcagt | gaacccctct | tcaagtcgtc | gatgtacctg | caagtgtaca | 960 |
| atcggaagac | catgggtcca | tatgtaaaaa | taagttaggg | gtcttttggt | ctgtgttggt | 1020 |
| tataatcgat | attgccaaaa | tattatggac | agttagttcg | aattttgtgt | atggtagccg | 1080 |
| tcgaaaaggg | tggacgttaa | gtatatccat | cccagcggct | gggagatatg | tagaccgacg | 1140 |
| agtgttaagt | tattccactt | actttaggac | gaaatcaata | cgattatttt | acatcggagg | 1200 |
| acatgacaac | aaaaaactac | tcggtttcga | caggtggaag | atgtcgctgc | gcaccagtag | 1260 |
| agcttaggag | agcgacggta | ctcatttgca | gcatgggtac | gtaatcacgt | tagtaaataa | 1320 |
| gtaagtatgc | cttctcttat | gtcattttat | aagctataat | ggtgttgtgc | caacttaaag | 1380 |
| attgacacat | gatatgctac | cagataagcc | tcgagtcgcc | tatattttgc | tactaaacct | 1440 |
| gattaactag | agaataggta | taatccctgg | taaccagtaa | ttttaatact | atgttgccac | 1500 |
| ttgatgtaga | cctggctgtg | gttactaagg | tgctttgaaa | ccattgacca | cccgtttctg | 1560 |
| ctcgggttgt | gcatctaacg | taaatattca | gagataacgt | ggctctgcta | ttattttat | 1620 |
| attgcctgct | gacatatcat | catccttgaa | tggccagcaa | cagttcttga | tcggcagagg | 1680 |
| ccccatgaac | tagggtaata | tagcagatta | actatcggtt | aactgtatta | aacttgtgta | 1740 |
| atacttatat | tgactaattg | ggattgcctt | tgtcgttatc | tcgtttatct | tgaaaacggt | 1800 |
| gatgttttta | gaggcgatag | tattgaatag | ctcgaatgat | caccagccat | caagaatgta | 1860 |
| gctaactccg | aaactccttg | acgagagctc | aagcgaatac | taggtcggcg | ctgctatccg | 1920 |
| cagagttcag | ggttctaccc | ggggtataaa | atcccattga | tcattcagat | attatggact | 1980 |
| tggcgtttat | gcgacgagtc | | | | | 2000 |

<210> SEQ ID NO 15
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
aagaagcagc tagtgctact tcggaatagt tgtcgtttaa gtccgttcaa acatgacgct    60
ctagtcattt tgaaacctaa accagtaata atagactgac tcagaatgat tatactgcta   120
tctctagttt aaggagatcc agcgaaataa cttggtgaac tatgccgaga tactataaaa   180
agatcaagga cgggtcgctc acggttttgg tttattttac tacttcttcg tggctgtatt   240
agtcgatgca agttctaata aatagcaaac gttttaagtg ggattagtac atattgatgg   300
acgtccacca cgtcaaatct cgcagcgtca tagaaggagc tataaccatt cactgcgact   360
acgacatgtg tttgggtagt gccaactacc cgcttccgcg tccctgccgt tctgtacact   420
tataaaattg atattttaat cagtggatgt gctgatacgg ggcactgaga tgatgaatag   480
tattaggctg tagtacctta tgtacgcaag aaattttaga gtaaagatta gtctgtgggt   540
aaggaaaaag ctaagttatg attatccatg gccatggcat ctacaagctg atgaacgtac   600
caacattatc taatttaaga acttaacttg tcttatcctc tcttaaagtc ttaatttgca   660
ctattaagct tagggaagtc gcaaccaaac tcgtgtagta ttgagataaa ttattaaact   720
ttcttagtat ctactgatat ccgtatcaag tatgcttata aattcttgtt ctgcctgaca   780
ggctagtgaa tcctgcaccc gggacgattg caggtgtata caggccctca cgctagcaat   840
caataccaat acgaaataag ggctaacatt tttcgtaaca gattagaagc agtcccgttc   900
agaacttacc actgcaccaa cggaggtact gaattcggac tcatagaatc ctcgagtagt   960
aagaccgtag aagagacagt gcatattaat gtcatagatc aatttatatt ttatatggtt  1020
gcccatttca tgatacccct ttaaatttat aacttagaaa aggagccgca ctaataatga  1080
gcggcatgct gtaaaaaagt aggccaaaac gcaagataag gtacctttgt tgtccaatca  1140
aattaattga tttattcttc gatcgatcga ccgtcatagt tgaagtaact atttagttac  1200
ggcagataca gcgtatcaat tcattcggtg actttgctta gataactgct cgataatccg  1260
gaattatcat cgttcaaagt ccttccctta ctaaggctct tggattcaga tgatcggtca  1320
tccctaacaa acagcccact gccatgctgc tatggtgaca ttcgttacta cattgatttc  1380
tgcagacctt catccataat acgatggtaa cgtctcgctt actatgcacg gtgtgcccct  1440
gcctatatct tcacgatata ccaagtggag aaccgtaggc atgtagtcat tcaggtggcc  1500
actctccttc acattatgtt tagaggtcat gaataaccct aatcgtgtga cctcaaacag  1560
catcgtattc cgaataagta acaagtaggg gtgtttcaag ttgcatgaca caataggata  1620
tgattctcaa ccaaacttgg caataaacgc ataggtttag cagtactaac aagccattat  1680
gtttaatata gagcatggct tactctgtca tgttcaaggt ggctaaaccc aacgcgttaa  1740
tacactcatc ggttacagtg tttttagaag agcaattgat atctcttcag gtgatacctg  1800
gttcattatc ctaattcagt tggttcagga agccttataa ctaccaattc gatattttta  1860
agcatataga ttaggtgata ccacaccgta ggaaattgtg cagaatttgg tgtctagaaa  1920
tttaacatta agtgatcaga aaattctctg tgttaaacga ctgttgcgaa tctgtgtctt  1980
```

```
tcaacctcaa gtacgatctc                                                 2000

<210> SEQ ID NO 16
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
taacaacctg taactgtcaa ctaatgacct ccttaccaaa attgagggta gttggttcaa     60
agagaatgca gcatgacgca gagcttgtag tcacatcgtt cttctagtac gcagagtgta    120
gagttaagat tattaaactc agagcacgtt gtggacaaac caataccagt ccattcaatt    180
acatggtatc taacagtatc gtacaacttt aatatggtct agggctagtg aagtgtacca    240
actacttgat acgcagtaaa taatttcatc ctatctttac gtcgccatcg aaaagcaaag    300
ttatggcgcg tggaaattca gatgaaccat aaccaaacag ataaattggc agcagttttt    360
tgtagacatt tatataagaa gagctcgagg cgtaggttaa ttctatacaa cgctatgata    420
gtcaagttct acttgaccaa ctcgctggga aatgtttatt aaattcaact gggggcaaac    480
tagcatatac tgtctgagtg tccttcgatg gttctataca aacggggtgt cgaggtacta    540
gtggaatgga gaaactaccg acaaacgcat atcttatctt ctactcggga tttatgaaat    600
tttttgcgta tactattcct gtgagcaatg ttcaacagcg tagtgagcct cataacgtca    660
catcaattgt ttcacgtctg tggctatcga gtattcctta acttaactag agtatagaca    720
ttagagtcta attctatgca agttagataa ctactactac tgtcgtactt cattcagttc    780
ctgctcgtac tcggcgacgc tataaccggc ctagtttgtg cgtcgccaga taactgttcc    840
ttttaaacgt ataaaaagta cgaaagatta acccagcgga agttgggccc cataaatgtc    900
atatagggac tcagactact gttaaaaaact cctagtatac attgtagata atcaactaaa    960
gttggactat caagaatcaa actgtaatca ggtcacagaa caaatggact aatagagcta   1020
tctaatcatc atacagattt atacccagtg gaaacaaaac tttacccctt gaggatttac   1080
tggagttgtg tcaagttaga aatcggtcaa cataaattag aaaatgcctt ggaacgctgt   1140
ataactgatc acatatagct gtgcctaatg cttcaatcgt caatgctgac cacaatctac   1200
ctgacttgga aatccgctac acccatatcc atatacttaa agaatccgta ctttatatcc   1260
tattcaccga tgtccgatgt ggcgctatgt gtgtctagta gtatatcagt tcaaggcgag   1320
aatgaagaag aatacagggt ctctttagag cactgtgtca ctgtttctta ggccagttaa   1380
ttctagaaat caaataaatg aataactcgc gacggctcaa aagaaatcta tggtttacgc   1440
ataagctgta ggtacttcta agcttgattt gcttccgggg gatcctaatc taaatgtgaa   1500
ggggcagatt tagatctctg ctcattgagt gggaggttgg acattgaaca tagaactacc   1560
ttccctgcgt gctgtaagat tatgagaatc tatgctcggt cgttgtctaa aaatcagact   1620
acaagggtaa gaataataac agaccgaaat agatgtctcc ttcaagatag tcagtttgcg   1680
caagtctggc aggaacgtta agtaatcctg agttataata gcgcccttttt aagctttcct   1740 ggcgaaaacc gaaccaagcc cccgtaacac aatgtcacta tccgtacgaa agttagtgta   1800
ataacgactg tacctattat aagcacattt ggttggctat cttctcccta gattcctggc   1860
ggaaaagaag catgtctacg ttcgatagga ctcattttg aggaaaacta ttataacggc   1920
tataacgcgc gattaatccc tgtcggtcca tcattcacgt gagtgtaaaa ttgtgattag   1980
```
tacttaaacg ggttcgtgga                                              2000

<210> SEQ ID NO 17
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17
ttgacgattt atatagctac tacttagcct tactacatat tccggcgtgc cggtagatat    60
gactaagtta atacttacag acattcaata ttaggatttc ggtgacctcg atctctcttg   120
attgaataaa aaatggatat taatgcgtcg atagttgtga taagttatgt atgatgtcct   180
gagggacata tgataatctt ctaatagtta ccttaaaccg aattgtgttt atgatgaaaa   240
ataggtga agttagcacc tatcaccaga ctttgggata gttagtccgt accaagcagc    300
agttcaactg acaggaacgt caattctgtc tctcattact ttggccatgg attgaaaatc   360
gacttcagtc tgactcacaa cagtgtataga aggattttgg ctcaccactc ttcgaaatag  420
gtcatttaat gcgtactgct ttttttgacg gccctttatt cattctattg agggaatccc   480
taactttagc cacacgcaaa ctggtttata tggatactct caagattgtt acatatcca    540
gaagcttata cttcctcaat gtgatgcaca caaggtggga tcatcttgtt tctacaatgc   600
agaatgaatt aaaaatcgcc cttcctggca catcttgctg tacggctaca gagtaaaatt   660
agctcgttat ttatgagtgt ttacacaacc caaatctaag tcgaatgtac tttaaacttg   720
gcgtggattc atagacatgc aatcagtgtt aaattgtcac tcaaacacgt gcctgacttc   780
agacaaattc atggattcaa gctgctaata ttcacaatag acgagatagg ggcgtagctt   840
tttctgtacg atgggggaat atacgagcat ttctatgaac caaaacaggc aaaatgagca   900
aataccttgt gcatcatata gtttccatca actggagaaa gcctcttgat cggctacaac   960
ttttcaagtc cttgcggcgt tggccctgaa gtactatagc cttttgttct cactaatcta  1020
gccaatcact tgttgactat tcttgcctca cccatagagt ggtaatggaa ttccaaaaac  1080
ctattcccga gtttaacccg tattgtttga gaggagttcc tagtgtcttc attaaattgc  1140
acatggactc tacggaaatt acttttaatt aaatcataga atctctgtca tcagtccatg  1200
cgtcctcagt caataacggt cgccgtgtct acggaaaggt tcattctatg cctgtaaagt  1260
acatctaaca caatttagtg tgggtcttct actacagttc acccgggaaa cgttttatgt  1320
acgagtgttg gtaaagcgtc ctcatcaagt cgatccattg taaggaatcg actatatact  1380
ccagcttaac taggaccccg ttacatctta atggtaggtc taagaggtga taagactgga  1440
acctacatca tgagttgagt gagcaatgag agccagcaaa tggtgggaag actagaccaa  1500
cacaggatct catgcttcct gtagcagtgc aactcagttc gctgcgaaaa taattaacat  1560
atcccctatt ggcaaaaccc tgcatacgta tttagcaaat atctgtaggg gtcgtccaat  1620
agcagtgccg ttttataaat tgggttgata cataacactg aatcaagtga atcgaacgg   1680
tggtaaaatg gcttgaaagg ggaagttgtt taacattcgc tagcgacaca tgttgcatgg  1740
ttagggttgc tatttcgcct cattctcgtt acgacattct caaccagtag cccaccaacc  1800
caattaaggt cacgcacgaa cctatcatcc acttacctct tacaacataa aatagtcaat  1860
acaccttcct caattagcct taatcaaata aagctagtta ttttttgtctc ctggggatca  1920

```
gggcgcttac ttcgtactcg cttcccccgc taggaaggcc actggttccc gaagaaacgt      1980
gaataattgc acatgcttta                                                  2000

<210> SEQ ID NO 18
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
agtatggaag gtgcctcggt aattacggaa agagcttatc tgccggaaac ttttattttg        60
tttcatcaaa aggttatacg ataataccgc atctacctttt tcgtatcaaa attggtccac      120
aaatccaact tattgtcatc ttgaatcaca cattcatctt tccgtctaat gaaggagcgt      180
cattacttgt tgtatgaaac gcaaattctc tacactagta agtgagacat taactacagc      240
ctattaaata attcaggtag actgatgagt aatatttctt ctatatatat gtgatactca      300
ctctctactg agttgactag tggactcttt gttcttgtac acacacaaca gagaaatgcc      360
tagaacaaag tcaaagaaag cgcctagatg actttgtaaa ttgcaccaga tctgaagtcg      420
agtcgtgaat agaactttgc ataagactct aggacttccg atggcgtatt atacttagga      480
aaccaagccg gtagtaagaa tcaggataaa tactctggga agtcttccgt atttgcgtca      540
acaaccagct tctggatcaa gcatttctta actagattaa gcttcctctt tcgttttaaa      600
gcgttttact tcagcaattg taatccctac atttgtatta gccgaataga acgatgctcc      660
tacaacacca ggccgacctc atgttacgat ggccgagacc ataactcttc gatgaatcat      720
tagtggaaga gttatctact gacggcatga tcctgggaca tgaaattgga aagcatttgc      780
acacgttaat tcgccttta cttcaacgct cggacccggt ataagataaa attagaccgt      840
tatcttcgta gatcgtaata cgtatcatct cgtatatgcc gcttgtattc aacgttttcc      900
tttttagact ggagcgatct acgctggctt ggtttaagga ctatgctagg gtttgtacgt      960 aatccctta ataattaacg accgagctga caaactgaat aagtacagca tcaacaggac     1020
ggttcgattg acagctggaa acctattagg catcttggcc cttagcataa gtcccagtat     1080
tatttgttcc tccagtaaaa atctccccgg aattagagca gcggtgaaat ttatggactt     1140 gaccttttg gtttagtcgt agagggacaa atatcatctc atctgaacgc tcatcaccag     1200
ttagttcatc caaattcaat taggaggcgt catattgtcg ggcgtctgta acggagccag     1260
atctagaagt tcattgctat aaagaattag tgtgcttggc acatcaccta atcaaatttt     1320
gggaagcagc atagctattc aggtgttggt caaccagata aagtctatga agaaaaaaac     1380
ctgtgttagt tctgcgtatt agtattgtag tataatgtac gacatcccga aagttaaatt     1440
caggtcgcag agtccctagt ccaccgttct aactcacaaa tcgatgttcg gacatagcta     1500
tttaacagtc catatttacc ttaagtgttt cgacttatgt atgctagtta ggtgtgtggc     1560
tcgccttccc actgttagac cacatctaga cggacatcgt taataatatc tgatatacac     1620
aaaaacgttt accatagaaa acactatatt catggacact ttatcatatt cctcgcccat     1680
cctcacgacc cagataatag ggagttgtag ttttttctaaa cggttttaat atgcaggtcc     1740
ataaagcatg cagtcacatta ctgtttaaaa ctttaattca gatatatcct ggagaagaaa     1800
atctcgattg gttaatcact tcattgttaa attcgatttc gctatacgtt tctgtactag     1860
gaaatttttc atattaggca cgcggtgttg gttccgtaac actattaatt tcctcccggt     1920
```
tcgatcatgg cttgcggtaa gtcctcaatt taacataatt gagataccga aatcaaccca   1980
gcgtcgcagt attttgagtt                                                2000

<210> SEQ ID NO 19
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
ggttaaatgc atgctcacgc ctcgccaggt tgttaaacca tgtacttact caatttgaca     60
actgatgtcc actctccacc tcgcgcgatg ctactttctt aatactaacg ccaccttgtc    120
aaacacctag atcgttctaa gtgtagcacc agacagagta gacaccgtaa aaggtgaaaa    180
ggggattaat ttctcctcct tttgcacaaa aaagttaagg ggtaggccgg aggaaggtta    240
acgcgaagca cctgcgtaat cggtttcgtg ctatatcgga gatataccgt aatgactcgt    300
cgacgaaagt cgaaggcttt aagctccatg ccccatgttg gtgcgttagg actttggtaa    360
agtggtaaaa tttagatctc tttgtgtcct ttatatcaag ttagtgtgaa tgctgagttt    420
tctcattttt taatgtaagt gattaatatg aagatgtgta gtctaatttg gagaaccaac    480
ttaaaacgga ataggatcgg tgtatcaatg catatgaaac cggtaaattt agtcctgttg    540
acctgaaact gatgggaaca aaccctcaaa cgctatcgca acaccgtcct aggttccatg    600
cactattaac ctgttattgc ccgtgcggag atctggtttt tattgtttta tactctagat    660
atattagcgg ttatgttttt ctgttaattt aagatgcata gtctactttg acctccggca    720
acgtgatttg tagaaaatat ttcccacaca cactatatgt gctactcagg ttacccatag    780
tttatgtaat aagtatcact ttaaaccctc cacccgccca tacaatagaa gcccttcaat    840
tatacgagga ggtattgacc tgactagttt accaaagcca aagatacctg acaagttgg     900 acaaatacta aaggactact gtagcatagt gtttgcgggc cagtatacgc ttatttaaac    960
gatactactg ataagaaaca ctggggtcaa cgtgctttca tcacctgtcc attactccaa   1020
cagtcccaat tttttaaaga aggaattttc gggacagtga acgcggaatc gctaataata   1080
ttcagataga tagctcgaca caatataact aatcagacaa aaactattca aaactttctc   1140
ctaggtagtg cgcggctctt ttacgtgggg tttattcacc tgcgaattat cctgatgccc   1200
aggagcaaac tcattataat accaccaggt gacagcctac aagtttcatg gcatggctgc   1260
aacctgcaca cgaacgctta tgcagcatgt gctcttgagt tataccagct acttgattcg   1320
atatatggtt tttgtgaaga atttgatacc attgacacgg gatgttgcaa atatttaata   1380
agtccatgca tactaatacc aacgccagag atagattgtc agtagaactc ttgaagtcaa   1440
tatggaccga gtgacttggg tggtttatcc cactgttaga aagttatcgt aaaataaatt   1500
cttggtcaaa tctaatcctt ataaacactc tgttattact ctgcttcgaa tatgttgtta   1560
ttgaccatgc tgataactac atcctttatg ttaattcaag gcattctctg aaagtcaaca   1620
attaacttca tatcagacat ttgacctatt cctcactttt ctataacatg acaatcacgg   1680
tgattaaaaa catgacgcgt atcggcagca aaccactgta ctgatatgta agagcgcccg   1740
tcgcatagat attttagact ctgtccaaat cactctacgc caacttgagg tcagaatgca   1800
taccgtggta agctgaatag ttcttataca cttttctaatt tacccagatg acgatttttt   1860

```
gttatatgaa tgacgatctt ggcattatac tgccaagact gcaatcaaat cctaaattca    1920
taatttagta agtcaatagc agatctgaat cccataaatg aattctatcg aagtacctac    1980
actatgtcac gtagaacaag                                                2000
```

<210> SEQ ID NO 20
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20

```
ctaggtaaat tcttaggtag ccgagttgaa ctattaataa gtctcgtctg tgagtatgtc      60
ttccgttagg tattttcata tagcttcatg tgcctgtaaa gacagaagta taattggata     120
catcagactt tttatccctt ttacagtcta gaaagaccta cttgaaacat gtttcttaat     180
gggtaacgta gtgaattatg ctcgttttc ctttggtaga atgatattta ctccatatg      240 ctctgagttg gataatttgt aaagaattat acacgttaat tcaacctctt tatcaatgaa     300
ctacgcgggc ttgatcagag taaactcaca atagtatctt gatcttcaca atctgatgga     360
tattgatgcg agttatacga cctgtggcat atcaacaatg aagtgaagtg tctgtcctta     420
tgattcgaaa caaataagt gtccttgcta gctacaccca caccgcggtg tgcatcccat      480
aaaggctcag gtatagtctt gtcataagcg ctacactgcc attcgtttag aatcattgtt     540
tagcaatctc aaaagtaata acatccgact ttcgaatagg ttcagtttcc tgatctactg     600
gagcctatat atatgcacag acgaatctcg tacatggcat aagcaagtca tgagaagagg     660
ctgtaccacg taaatataag cctctgatta cgctgaagct taataatcat cacccatcta     720
cgaatccgat tgagggcata ggctttcatg tcttttttcgc tgtaggtcta tgcgattgtg    780
agactattga gtttttccaca atatggtggt aggtactgag tagggtacat ttcactgtcc    840
tattgcgctg tcgtatgtct atccgccgtt gccgtcgtcg atgttatacc atttgactaa    900
cagtgttatg agtcactccc ttggatgcga tgtaccttct gttgtgaggg atgtaagttg    960
cagttaagca ctattagcga ataacgctag gattctggaa gaagaaaaca cagggtcgct   1020
tcaggtctcg agaatcttac ggttagaaaa tttggatctg aataaagaga tgtctagcca   1080
gtgtgggggt tgaataagct aaatgtctgc aatgtgtatg cttctgcaca gatattaaca   1140
aatccgccat atttaggcac atttggtaat ggctgacaat cggatctcaa gaattctata   1200
ctgagttatc ggactacaac taaaaagatg ctatataaaa ttgtcataat tcatgaaaag   1260
ccagtaggcc gaccatcatc gctctaagtt gagttgtttg acgcgaggca acattacgtg   1320
catggacgat atacacgtta ctagttgtat ggtatttcgg ctaagtttcc tagctaattt   1380
cattaaaagc tgcgcattgg tgttttttcag cctatatact gacgtagtaa acttacatac   1440
ttaattatac taggtaatga tatagaaaat ggctgtacat cctttctgaa atgcttccat   1500
gcaatggtgc tacaagtctt agatttacat tataatcgga aaaacatcaa cagtatgatt   1560
acctaggagg agctagcata tccagaaagt agaatagcag aagccaccaa cagactgggt   1620
gagagtgacg ttatgacgga tggatcatac cccatcttag gagggtcagg tcatttctca   1680
atcatatgtt tccagatgcg atgcaaagac aaggcccaga aatttcaatt gtaggccaat   1740
cgtccggtcg tattaatctc aaccaagtaa ataaaaagca tgtgggctgg gcgcagtcaa   1800
agtcgctttt cttggtcctt actaatctga agaatataca gtaaacagag gatagtgggg   1860
```

| | |
|---|---|
| ctagttcaga gtaataggca acaaaccctt tcatgcatta ctgtagaatt tgatactatt | 1920 |
| gcgtgtatcg cttttaactt tataaagagt cgatacagcg caggctcata atgtttggag | 1980 |
| tctgtctaat aaacatctaa | 2000 |

<210> SEQ ID NO 21
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

| | |
|---|---|
| tttatctatt tcatatattg ctagataaag ttgactgact tattacgatt attgtcccag | 60 |
| acagccgagc tgggccgtgc gtcaatgcac gggctcagcc tcctaatgtt agcatttgtt | 120 |
| actcttggaa catttggata tagttgattt tttgatagtg caaaggttct cggtcatccg | 180 |
| gtataacgat actccctacc ctagacattc aatcggtgcg atggtaagtc cgtttcgcac | 240 |
| tgaaagcctg tagagtctat ttgatgttta cttaatgcga tttgactcaa atgtaggtta | 300 |
| ggagtccgtt cgcatcctat gcagtgataa actatctagt gtgtttaaaa agacgcaacc | 360 |
| actaccaatc agaccagcaa atttacatca atttatgtca aaacgccctt acttcgtcta | 420 |
| aatatagata tatcaccaca tcaagcctgc acttctcaca ctatgttcta tgtcatgtcg | 480 |
| ttgtaccgaa caattgatat ttaaccggag ttgaagatca gctaaagaga gaagttatat | 540 |
| aaccaacaaa tacagcccac ccatcaatga tcgtgaaaac aaactgtact aacagttca | 600 |
| agaacagtca ccatttctcg acgtacaaaa gattcttcca ttatggttcg atacaaattg | 660 |
| ttcaaacgcc tgtctatagc agggctccgc catatttcga gcatactaaa tcattgggtg | 720 |
| gtcaaacagt ctcacaaaca ggtctgttgc gattcatacg agacgaccat acttaggcgt | 780 |
| tgaaatgtcg ttgcatttaa gtaacaaata ctatagaccg ctggtagtcg ccatataact | 840 |
| ctggctccag attatacatg acctgtttag aaaggcaatg ggaagagggc aaaaccccaa | 900 |
| gattgttcct aatagttgta gataaatgga tgatatctgc atcatcactg tttagagaat | 960 |
| cccgctttcc tttattcggt tatactcacc gtttctcggc gggttgagac atgcataact | 1020 |
| tctatctatc gttgagaatt atcaacttca attcccgaga ctgtcattat ctatagttga | 1080 |
| ggaaccttcg tcgctgctat tgaatagtaa gaacccctct agtccagctg atgcttgtgg | 1140 |
| taactgcact agtaattcat ctgccatccg tgcttaattg gcatgctttt gttgcatccc | 1200 |
| actcccgaac ttgaaggttg gaactctcgt tttgccagca cagttaacag ggagtaagac | 1260 |
| ctattggtgt gacataacag ttaggtaaat ccatctaaac acgtgtgttt actaatattc | 1320 |
| agtcggtgga ctaacagaca ggagcttacc catccgtgga tgttttctta agggtgtcgt | 1380 |
| tagaatgaat agtacatgta tagtactgtc cgaggtgtag atagaataaa tgtgaccgtg | 1440 |
| atctcagatt tatggttcaa acgttctaat tttccgagga gtagtacatg ttggtacctt | 1500 |
| ttcacattat ggtgctaatt aggcatgtat aatatcatat catagctttg cccatactga | 1560 |
| ctatactaaa attgctattt tggaaagttt ataaggccgt ttctcattgt atctaagacc | 1620 |
| taagcttcgc gtcaagaaat acccttacaa tcggcctatt taaaattatt catttgtcta | 1680 |
| gggcgcgatg atccttccg aatatttat cgattactac ttatggatac ccgttagacg | 1740 |
| cttatcctcc tactacaccg tactaattac gtacttttt cgaagtacga tctgattagt | 1800 |

```
gtcgaccacc ttgcccttaa atctgatcgc tcccaccagt acgcaggaca cacgtaacgg      1860
tttcgatacc cagcgagatc agccttacca gtgcttgtgt ggtataacca cactatttca      1920
atgcacaatg acaagagtac tatgttaatt cacatgccta tctagttcaa ttacgttcag      1980
actcataaaa tgccattgct                                                  2000

<210> SEQ ID NO 22
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
tcgaaattgg atcgacggag ctaatacgca aattatttgt ttgtgatttc tatcgcgctt        60
caaaacctac aaaaaataac agcctttggt gtaattcgtc gtggccataa atatggctta       120
ttctatatat ccgaggccca ggcataaca aattctccaa gatttactaa attagtacgg        180
ccttcattcc gacgggaagt ttaaactcaa gccatggagt ccggtagtct ttcaactttg       240
tcgtatgacg gtatgctaca tgcccccaat ccgctattga acaatggcaa acactacagc       300
agttagccag agaattacgc tctttcactt tcctagaagt acacaagtcc tgaacctacc       360
aactgactgt acacaccctc tatggtactt ttgctgttta gttgccgaat gatgcatcat       420
gtctgatttt tcgggctagc cttagctgag tgtcagcttc accctgataa gacaggagtc       480
agaaacggaa tttcattaat accgcctaag gcgaaagaga ggctgtcatg taagccggca       540
ggtttccccc ttacggggcc cacactctcc cctcgctatg aaatgacact tcacaaacag       600
tcgctactca ggatttattc caagttccaa cgatgttgag tacattgaga atgtattata       660
ttaagctaat aggcagtttt ctccaactat cgattattcg gctgatatag ccccatcct       720 gagacgttat tacgtcactg aggatgatct attcacacaa cacttgggtt accatagttc       780
ggaatgcgat ctaacgtctc acaatggttt ttggtggaag tatagtctta ttccccgggc       840
tatcgcaagc acccaggagt agtttcgttg gtgtcatgct tatccctacg acccaccaga       900
gtgtccaatc aatttacacc taaactggaa cctaatatat taatcaaact ttaaatctct       960
atatattcag actactttac tcactttgat gttagatgcg taacaagcat ataaacccgt      1020
ttgtgatcgt actcaatcgc acccttctcg ttattgattg atccttgcgc gaggtaacct      1080
gggtaatctc taagttatcg atgcaccgta tcaacattca tgatcgaaaa aagtttagtg      1140
agaaggagtt aatggatcgt tccgactaaa ctaatggaat tatgtatggg atgtatttcg      1200
tttgagccaa ttaactagga actaactcat acatcttgca atagtggtag cgtaaaatgg      1260
ttgaacgtag ttgaaatagt agggatacga catgtcccct aagcctcacc cttggtagtt      1320
ctcgtaagcg acaacgcgt tatcatcacg ctttggagtg tactagttta tgtctactgc       1380
gttcgctgac aataagaaca gcaatatccc aattctcagt actgacgtag gaccattagc      1440
gctataaaaa aagtagcgtg aactgtcatt tattaagcat tccattttat ccagtgtccg      1500
ctaggcggct aaattataca aacagaacgg tgttcttata ctgttactac ctccacaagt      1560
gggatttacg aacgcagaaa gagataagct cactctcgct atgtgcaccg atgagtcata      1620
cagaggtcat cagtaaagga actcaatcta gagttacagt ccagcaatcc aatccggatg      1680
ccaacaggcg taacgattat attcaaccac taagccgcat aaagtatcga tgattagcgg      1740
gggaatacct cctaaacagt ttgaccggaa cgtctacaat actttgccgg ttatcaatga      1800
```

```
aatatgcggg gacgaaccat gcatcgttac tcagcctttg gtgtacgcca gtaggagtac    1860
tacttgttct tcttacacga cacgtagcta cttctatgta tagtaatgta gttgactata    1920
gaatgacgaa tagagaaggg aaccagagct cacttattcc gtcaactcga tttatcatgt    1980
tgttaaaaaa gataaaatgt                                                2000

<210> SEQ ID NO 23
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
gctactattt tagatatgca tcaaagaaaa acaaggacat ctcctgtata cgtataggta      60
ataagaagag gatccaacgg aaaaagccac cggtggagat aataactatt gttagcaagt     120
ccagttttct gtcaggggca acgttaagat agaggccagg gtaattattt aactactagc     180
tgcacttcga cttcattttc tgagctctgt aaataccaat ggagcgagta gctacggtta     240
aacagatatc ggctggatgt cggtggtagg aaaatgtgcc tgttgcggct gataagcatt     300
aacttaccta aacatagatt gttggttttc ctaaggtttt ataagaacgt atataaagat     360
ttcttaaatg acaagcttag cctgcatagg ctacatgtga gtgtggatgg cttcgacagt     420
gatcccgcag tggaccagat tccattacct gaatgaaaac gttcaattaa accacttacc     480
gtatcactct gtccttgtag ccctgtaaaa tgagacttgc ggataccaaa ttagccaaat     540
tattcatcta actataatac ttcttccatg aaacattaat acggccaccg ggaagccacc     600
gattctgtcg ccttatattt tttgctctat gtctttcttt tagtccgaca actaatgtga     660
acaaatttcg acctaacaaa atagagacaa ataaccctat attaatacaa cgctacgaag     720
atcttcaata ggattggtcc gattatagac caattatact tttacataat atgtacaaaa     780
catctcggca ttcgatggca ttggcgtgga tattcgattg taaaagcaat ggatttttct     840
tgcgctgaaa atgatgatcg ccctcgatca tctgtatagc acgggtcgaa gtttcagaaa     900
tgatagttgc tcaatttggt tcacttcgaa tttacgctga tgtcccaagc gacatgtccc     960
cgatcaacat ggttgttgga tatcaaaaag ctgataaaaa atgtgaaagg acacgcctcc    1020
aacgcgtaac tgtttcacct acttccattt cgaggaactg ggtcgattta acgacatcaa    1080
agttgtttgc tcagacagtc ttcctatgaa aatgaaaagt gatctaggag tagaacccga    1140
tggctattaa taaacacact cttactaaat aatttggcga gcatcagagc gtaggtactc    1200
ggaacctgat tgccgttccg cttctctatac actgtgaata acaaagtcat tgaggtgaca    1260
accttgccgc gtgcacggtc taaagcatga aatttaaag caacaatcaa atctctaacg    1320
gcctatctca agttacgcag ctggcggtag gtgggttttc gcactgactc tttaaccaag    1380
ctgctgctaa aatactctta cctcactgtt gatataatgg tcgcgattac agataatccc    1440
gcacatctgt caaatagaag atccagtaaa gagtccaaat cagagagacc caataaagta    1500
accaaggcat taccgtttca cgaggtggac tttcatgaaa gcataagtat ggcgtataat    1560
ataatgttat ttggaaaaaa gatctccaca acctgtttta ccgctgaaaa acctaaatac    1620
cgtaccagac gaaccacttg atagtcgaat gcgccattga aggaaacatt ctccgttaat    1680
ctgattttaa gctcatcagg cttttatctt tgcgttatct acatttgacg attaccaagg    1740
```

| | |
|---|---|
| atcaattacg tgattggact atacttaata tcaatgtacg aaatcgtcta cgatactaca | 1800 |
| aggtaaccac tgataattcc tcattgctct atgttcacac tgaccttgct aatcgacgtg | 1860 |
| gacttgcgtc cttgtctagc ttataatagt gagatttaat gacaatgctg gtataatacc | 1920 |
| gtgcaactac acgcatagaa attactcagc gctcgagaaa agtagattac ttcgctcctt | 1980 |
| cggagttttg cgtattttca | 2000 |

<210> SEQ ID NO 24
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24

| | |
|---|---|
| cctcatttgc cctttatat ttacccgagt tagttcacga atgtgccata attctggtcg | 60 |
| cagcaaactg cggtgtttag aaataatctt ccgttattcg tttatcaaga cctcgttgtt | 120 |
| tagtagttct agctgaatgc ggtctattaa gttggagaag atctgggttc attacattag | 180 |
| aacccaaact aattattaag ttctgctcat tagcattagg tagaatctat tcttgtccgg | 240 |
| cgctgttgct actgggttta gtctaagtag tactttaact gttcctaagg gatgctgcaa | 300 |
| aatgagatat actcctccga taatgatcaa tttggatttt gggcagcggt aaatgtttta | 360 |
| tagtgtgaat tgtgttacta aatttcatga cgtaagctga ccttctaacc gtcgtgcttg | 420 |
| gaggatttac gcggcgccaa aaagaaatat actagtccca atcgcactag gatttgttta | 480 |
| aaaaaagacg gaaaacctgc aaccaaaggt gtcttgtact gactctatct gcaaaatttg | 540 |
| gatgttctag ctccgtttat ggtcgctaca tggaaacgct attggttaaa gattcactat | 600 |
| aggccagttc aagtttcccg aaaaatcgtg acggacgtta tactctaaca ttgataagaa | 660 |
| ccatgtatca agcgatccgc aatataggga aacacggcga agatcaaatt tatagatggg | 720 |
| aggaagcaca cacaatatga gtattagtgt gctgaaatca gcagcgtaaa gtgcttctgt | 780 |
| tccacctata ctttacgag tctcgtaata gcgtattacc atgtaagatg cattaaagct | 840 |
| ataactttat ggcaaaaaag gtaatttatt cgctcattac tattatttgt cgttttgcat | 900 |
| aaataaagtg ttgttacttc aggaagcttt aattctctgt ctgccttaac ccgaattcta | 960 |
| cgcgatctcc gtatagcaga tgagaaccgg tgacacgaga cccgcactcg caagtcgttt | 1020 |
| cttgaggcta acgacaaaat gaagccatca gcgaaatctc atccgttagg ctacccaaag | 1080 |
| ttaagacttt ccctgtatcc cgctaatgcg tcaattggta gacgtatcgg gattagatat | 1140 |
| tcaagaccaa gtcaggtaga gttggcgcta gttgaacatg gacctggcct tacaaacaag | 1200 |
| aagaccacga gagccctagt acaggaattt atcggaaaaa ataagaaaat taaaatcccc | 1260 |
| gatctgtgtg gtgctcaaat aaggcaaggg cgcttagcct cacagtcgtt actaagtcaa | 1320 |
| ggttctaaaa gcacgtgttt tagcttgatg gatcatgact tcgctacggt cactactcca | 1380 |
| ccgtgtttct ggaggtatgc aagggaaaat cgagggatgt gctcaaatct gtggcaaccg | 1440 |
| gagcaccatt ctaggtaact tccattaact tttgatttag agtatatggt taagctatta | 1500 |
| aacgtttcct aaggacaagt gggatagtga tatactttt tcggcgacat caatccagga | 1560 |
| ttatccgcta acagatcgcc tagcgctacc gcatatgatg atatccttag gaagagatcc | 1620 |
| accccggcca agaaactcca cactcaatag gcggtgacct atttgtgagt tatgcagatg | 1680 |
| tgtttcaaga ctcaacgccg acaaagttca ccaccagaga gtgtaaggct tatcaaattt | 1740 |

| | |
|---|---:|
| ctgattttat cgacttataa atttgacacg tctaacagat tcggcctttg attgtaaaca | 1800 |
| tcgccgctat gatattttcg tgatcctttg ggatacgaga tgcatcagta ctggccccga | 1860 |
| atatttccat tttaattact gtgtaatgct taggttcaca atcaacaagt agttcgtgaa | 1920 |
| aatgttacta taatatccac acaaagattt acgcactcta atggtggacg ttggacctct | 1980 |
| gttaacccgc tttcgttatt | 2000 |

<210> SEQ ID NO 25
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

| | |
|---|---:|
| actaaagtcc tggagagtat gcttggcctc gtgcggtaac atttgaacag catgctaggt | 60 |
| gctagtagac cctttcttga cagcggaatt tgctgttatt caaaccacct gtcaggccaa | 120 |
| ttctggagcg caacccacag tgatagaaga tagtcgttac aatcaaatcc cacaacttga | 180 |
| gactagccct cagactgcaa cagtacacag ttatgctgtg gagacaaata aaatacgtta | 240 |
| tgtattggtc attagatttg gctttcttat acgtcgtgta gtaatgcttg tgatcggttg | 300 |
| ccgacatggt tacgaatagc tgtttattaa tttaaaattc aattctgtcg atttagagga | 360 |
| tggataatat ccgctatgta gacatgagtg agttccttat ccttcaattc ccttttttct | 420 |
| gttatttttgg atctacgaat gaggtattaa gttcgtagca ctcgtccgtt tcgtggaatg | 480 |
| acttattcga gatggcttga taaggaattg tacctcaaag gtttcattgt taagaagatg | 540 |
| aattttcacg cccatggcat aagcatatga ttacgtccac taggtcatag acacatgata | 600 |
| actcgtcgct caaaataatc gaaagaacgt ctatcggcca aattattact ttgatcccaa | 660 |
| aggagaaatc atattggggc gcgggacttc atgtgtatta ccatccagca agcatttgat | 720 |
| aaaagtaact cctatattat tatgaatagc ggtaagtttc tttgaccaac ctgacaataa | 780 |
| caccaagtga ctcactgagc ccgttatcta ctaggtattc gcgaataccg taaaagcttg | 840 |
| atgcaggtga caatgagaat tatcattagc gtactgtatg ctcaacctag cctccttgca | 900 |
| agatttcgtt ctatctattt tgtattcatt tctttccgcg acatgcattc ttttgctaga | 960 |
| tcctgggtcc tgcaatcatt tataagcacg caacttagct taaaagtgtg gagacgagac | 1020 |
| gtacaatcac tacttcccat cacttcttct cttataagcg taccgaaaga cctcgtatt | 1080 |
| tattaaacaa taacgtgcag ttggcctaac ataattcgat gtctttcagt gttctaggaa | 1140 |
| aggtgcggtg tgtctagcaa gcatgtcagc cctacagatt cttaacatac ctatgtgtct | 1200 |
| aaatcgagta tactataatg atgtaccata agcccttgcc aaaggatcat attcggacta | 1260 |
| gttattgcct tctggatggg gtacttagac taacatttta aacctcttgc gatacgacct | 1320 |
| ggtgctaata cactattcct tctttttctca cgcgaacttt cagtatcgta caaaagtatg | 1380 |
| ggatttaaac cttttgaagt ttggtcgtga ttatttgttt ttagggcctc ctcgacgcct | 1440 |
| caaataggga tttcttcagc actacatatt ttgagccgta tgcgaaccct tcttaggacc | 1500 |
| gcggtagttt gttcacgagc acgttggcca caccccaatt atccagaaag ccggacttaa | 1560 |
| gacatattga gtttgttagt gcataaatag ggtcgcatat tgatctgcga ctcgagtaaa | 1620 |
| tgtcgtactg gtgatatatt ctcccgtttt cgaaggcccc aatcaattac taattaccct | 1680 |

| | |
|---|---|
| atttacgaat gtcgagagat gttcaaacga aacatgaggg cgcatcccaa cgcccatttt | 1740 |
| gaaacttgat tgttgtataa ttcttaattt ttgtagattc agcgttcttg acacatttta | 1800 |
| aagacgtcag ttcaccgtac ctaccccttc ggttacgcga aaaagattag gttaacgatt | 1860 |
| tctatcgttc gttggttgtt atttctgcag tacattaatt ttataacttg atatatcaaa | 1920 |
| tctgttttg attaatgttt gaaagcaaat cgtaacacca aggaatgcaa ataatcatac | 1980 |
| gtggcggacc agctactata | 2000 |

<210> SEQ ID NO 26
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

| | |
|---|---|
| tacatcccca tcagtcaaga cgattcgtta acaaatatcg ctgactggga gaatcccagc | 60 |
| atgtcttggc tggctaaata gaagctacta tgttacgcac ttccattttg aattacaggc | 120 |
| gacaacatta ccagacttag ttaattatta acaagatca ctttgcgaca gtcctctgag | 180 |
| gatcagttag agtgcaatca cttaagtaat acaaaaatac agaaggattc tctggcgaac | 240 |
| aggtttatta gcgcatggcc aaatttctaa tcaaccccctt tagttagtac ccatttctag | 300 |
| ccaatatcaa atgtactcca agccggcgta tagttgtcag tgtgtgattt aacgaatagg | 360 |
| atcccccccc ataacaaata ctaataagag tggagcaatt atagtttaga tcgtaaaggt | 420 |
| ttaaataaat aaacgtcaag cacaattatg gactcgtatg gggacaaatt gagcctacta | 480 |
| gcagttctag cgaaataagt tgacctaacc agtccatgga ctgccggttc gttgaagtcg | 540 |
| gtccaacgga ttgcagatca ttgctaggca gttggtagat aaatttctag tacttatagt | 600 |
| cacgtaattg tcaaaagtcc tacgagcgtg gtcaccgtat tactacgacc tccatagttt | 660 |
| tctaccgtgc attctgaaag aaatatggct ggagtgtcct agctcatgat agaaaacgcc | 720 |
| tacacttagc caatcagaca ttaatgcggt aacggatcaa gcattacagg gcggattggt | 780 |
| cgcatatcat tgcacggaaa gcgttgcctt aagttcggta cattccactt tcaacttcat | 840 |
| attgactcaa atagtgggac agtgatttac gcggagtttt aatctaaaaa ttcttgagtt | 900 |
| tatgatagaa cagatctaaa ttacggtttt tatatgtagt ggtattaata atgttcataa | 960 |
| ccctagatat ttccgagatt agcactcgtt cggcgcattg ccggtataga acaatatgtg | 1020 |
| aagaaatttg cacctaagaa gttgatattc tcctctacat gcgtataata tatagtacca | 1080 |
| taagtggatc attattaaaa taaatctgag tgggtggact tatcttctgt caccctaact | 1140 |
| ggatcagcag tgggctagta gccattaagg aacaaccact tggcccgaaa ctatttgaaa | 1200 |
| agtgataaat acatacacga tttactacat aaccactcct cttgttgata ggcatgccca | 1260 |
| aggattcgta tgggcgattt tccataaacc tacagggtga ttcgcgcata taaataacac | 1320 |
| caaagcagtc aggcttttttg tatgaagtgt agcttcccta acagtatgat agttgtgtag | 1380 |
| agtcgcttct gaactggctg accctagtta taattagttc ggcggaggat gggccgcgag | 1440 |
| acaaagtata ctcgaacctt agggccgcat tccaaaggtt atttagataa agtacgcaa | 1500 |
| acccgcacat gagttgaaat aatgaagtac aatgttattt attgtgcgtg gtaatagtct | 1560 |
| cgtgactgaa aattttttacc tttagggttc tctatccgga ggagcgtcat gagctcaaat | 1620 |
| acaaaatcgg agcattgact caattactac tttatgacaa attctacgtc taagcgattt | 1680 |

```
ttctaaatcg ccgtgatcaa caaactagat ctacaccagt gatgcatgct cacggcgaat    1740
gtcctgaagt cagatctaat tcttaagggt tggattagct ggctatagca agccatatta    1800
atatgattag tcgtgtatgg tttacgctac ctctccatag atatttctaa cttacatttg    1860
taaatgtttc caagcatacc gtcagtataa atacccaatg atgtggctct ccttcaagtg    1920
tttagataat agctatttcc ataaggtgcc tcccctatcc gctcatcctc gggtttcata    1980
tgttgtaagt ggcacttaga                                                2000

<210> SEQ ID NO 27
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
ttgtttcttg gagggttact tacgattatt caatgtcaag ctggtaccaa ataatatgtt      60
aacatcgaca accttgctga ttctttaact gtacgattta ctcaatcctt acaacagtct     120 ttcccccga tgcttccgat aatccggatg gaatgtaaaa gctttaattt agccataatg     180
gagctactct gcaacagtaa ggcaaaattt tcttaaatgg aggccaggca agatttgtcc     240
ccgccagaat agcctactcc acaatattct ctttaaatat tcgccatgct atctcacgca     300
tccatgaaca ggttatgaaa gcgtagagtc aaacgtacac tttaggttag gtgccttgtg     360
gggatttcac gccacaaagt agagtagaag cagtgtatca aactatgtgt aaaagtaatt     420
tcatatagta atagccacca agaatgcgaa cataggtgtc ggcctgaaga tctaaaatta     480
tacttattaa caatcatgtg agtaggttgg attttaacac gttcataagt atcgatcgct     540
tcgcttaaat agaataaagt acacatcatg tgacgacgcg cttcgattat tgtgctgcgt     600
taagagtagt aggataattt ttgatagacc tgtctataac acggtattta atccgaagtt     660
cactatacaa tcataatagg atatcgtgtt ctgtctcgat gatctattcg tcgcttcggg     720
tgcaatatag gattcctata tgaaactcac ttccctgagc attgggattt cttgatagct     780
agatcgcgtt agagtcgggc ggtgtatagt ctcggataca agaacataag agtaattatg     840
tggaaccttt tcatgtgatt gtgctaactg tgtgatattc gcaataattc ctacatctta     900 gttttttagac tggactttt tttcccaagc tctaagcata cattattcgc tgcgtatgtc     960
actgacctag aggaataagt gttctgctgt caaaactaac tctctctagc agccttttg     1020 accatattat caattacgcg ccatcccata ataacttcaa aatttgcaac catcggaatt    1080
agaaatcccg acgtaatcaa gacgaatctt cgccgattat cgagcttaca taatcgaagg    1140
tgcatttctg aaccttggct acgctaaccc tctagtcggg gcaagatgac ttggttatct    1200
ggttaactag gaactcctag cctcatattg tatcaatctg atctaataca gcgtctacca    1260
attatttgat taggtttgct tgccctcata gcatcgcagc gagtatctca caatgtgtat    1320
gggtattctt ctagttacga gtttagacgg agaataagcc gcttgtggtt aacctctgta    1380
aatacctcta gttgaataag tgtgcaaccc aattcacatt cgtcatgtta acaaatcggc    1440 aatcttttcca ctaatgagaa aaaacaaatc attaatatat gtgaaagtaa ttattgtgtc    1500
ctcataacgg taaagactta cgagtaggta acaatctcaa cttcaccaat taccacctag    1560
attccagcac cgccaacgta atcagtgttc cgtgcgtctt acacaagaga actccttaag    1620
```

```
cggctagcgt atacttttaa gagcagtggg tatgtggccc ggggcatcta ttgtttaccg    1680
taatataagc gcactagtct attttttacac taaatatcat tccatatccg gttctttcag   1740
taacaaaagt aaacacagtg ttttggaagc agtgtatcaa gaattgtgaa cttctttcac    1800
cggcgcaggg atccactgtc tagagagaat cttaattcta tcaaccgacc ctccatgtct    1860
tatagattgt gtcaacggag cacctaaccg tatccttaaa aatttagagg aaatagaact    1920
ctcattcttc agcctgttaa gccaattaaa tcgaaaccgt tgctattagg tgtaacggta    1980
gatgtgataa aagggtcaca                                                2000
```

<210> SEQ ID NO 28
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28

```
aggacgagct ctaggggtgc ccctgctgtt gttggttatt taaaagccgc gatgaagaga     60
acgctagggg gaaaaaacga tttgcctaga atagtggatc ggcgttttga tgtaagtgta    120
attgggtaga aggacttgtt ttacatttgc gaaatcttgc tcggggacgt tataatatgg    180
ccttgaaatg gatgatgaca atatagtttt aatgttatta taattagagt atcgtattat    240
taaaaaggat gtccactgtg gatccaagtt aagcattagg cgcgttgaag agattgtacc    300
gcccgaacca atgcaattga catgcctaac tagcaagaca aacgtgttaa gactaaagtc    360
cctcctatca acgtacacct catacgcttg actaggtaga atactaaaat actctcgtaa    420
tgaataccta ttatctaagt gactgctgcg ttctttttagg tggtgaactg gctccggaaa   480
gtgtgctaat agtctatatg tccgcgcctg ccacgtaacc acgaggcgga tcagctagaa    540
acataaagcc gtttgagcaa taagtgacta tacttaacgg tctgtaaatt cgcgcttcaa    600
tacctcttac tctctgcgtt ctatcccgtc tttttataaa ttcaactata cgctccattg    660
gttatcgcca tatgagtcct tatctactta aactggctac caattccttg ctctaagcta    720
atgaaagtcc attcgcagga ttacaacatc aatgctaact ttctcttgca tacagtatat    780
cgtctaataa atgtataggc tcccggaggt cggaacagca gtactcccgg ccacgtatcc    840
cgaatacaaa ccttattagt aaaggaaaca ctagtgagag cgtacgggga ttactcgaaa    900
tatcgcagga aggtggttaa tatgccaagg aaatacgaat aattctctcc gcattccgaa    960
actgttagca catagacaag acaaagagtt tactgacaca tcttttgaca acccgcactc   1020
tacaacgacc tactctttat acaagtacgg attattgtaa cgctccagcc tagagagagt   1080
aacccggagt tatatggagt cgcttgagga gaaatattaa agctgaattc tgttacgact   1140
agtaacatta ccagccgagg tctgaataac gtgcctatgg cgatcaggac aatacgagag   1200
aatttcttct accacactat gtgcagcagc tcactcaaga gtcctatgta gactgtttaa   1260
ccagtaagga ttgttgtgcg gaagtgtaat atggtcgaga ataccgcta atatggataa     1320 gttaattgaa cttcggacgt cacattctcc tataatgagg atctattcaa atcgttttga    1380
agtaacctcc tcatttgagt aaactaggct tgcctggaga tggggccccc aactgtaatg   1440
tgttatgttt agtttgaact cagttggctc aaagtatccc gcagtactaa tattaaatct    1500
tgttattgta cagctggcga agaaagttaa gaaatgtgac tcctatacta ttactggatt   1560
tacaaagtaa gcgtctttga cattaattat ggtattgaca aatcaaatga gagacagtaa    1620
```

-continued

```
gatgatgaca ttcgctcata ttgtatggct cgttgactga tgcaaatagt accaaaccct    1680
ttttttagaa ttccagatga ggaattagat ttttcagtca atagttactt gttatgccac    1740
gtaggcttat gtcccctaaa tcgcatataa taagatagag tgcgaatgcg tgcacgtgta    1800
cactaatcag ggcaaactaa acatttaacc tttggagaaa ttccgtggcg ctgaacttag    1860
tgatgatata tgattaaggg atccgttttg ttttcgataa tctaagaact gacgaaggca    1920
ctaatatcgg agttacacag gaaatagaat gtcgcaagat gtgccttagg agtcagaaat    1980
caacgagtgt tgatcccaca                                                2000
```

<210> SEQ ID NO 29
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 29

```
acaacgactt tcgaaggtgg ctgaagaaaa ccacatgata aaatcgcgag tatggtaaaa      60
ttagctacct gagtatattt aatcgaggtt atatcttttg tgagtcggac acaaattcta     120
tatttgacgg agcatagggc agacggacat ataaaattat aaacagtctg tacggcgggg     180
cctccaattg gattcccgcg atcatatcag tcagttggga accataaatt gcgaaactca     240
gtactatgct tcaatgcccc tttctaacac gtttatcgct tcaacctaac ggtatttgca     300
ctccgactat cgtcttatgc ctcacaatca gatgtaataa tgcgggattt ataaagattt     360
tgaaccattg acaactgac ggcttctcat ctcaccttga cgagagtatt tcctattaac     420
ctgaatttcg ctaaatactt atctttatcg ccaataattc ctttatgata cacagggctt     480
ctccaattca tccacgcaga aactgcccaa atgaggagaa taaaaaactt tataattaaa     540 tgaatttat agcctatgcg tatccccta cttcaaatct gtgcagtgat gataaactat     600
tgtaatgaag tcatttaat tcgcgagatt aaacagattc atgttctaat gcgattattc     660
tggtgtgata tcgtgcatgg ataatagaaa gctgatccat ttagaaacca agcttatgcc     720
tatccgcacc tttaacacac gcatagatta gcgctctgcg cgaatcctgc gcgttgcaac     780
tgtactgata caatgcgcac caaaacaact tatactctag caatgtacac acatattgcg     840
agccaatctg ttcagtttcc ctttgatatt tcaggataat cagatggacg ccaaatagat     900
tactcttata ctgaggaaaa tatgaagttc aggttcagcg ttacacgcaa atcagcgatt     960
aggtctgcct aatatgattt acgtaaataa atctaccaac tagaaatccg gatattttac    1020
aataatcatg gcaacgggta tgaccactgg gttcgatcca tatacctgat gggctcggca    1080
aaagtctgta agaattctct acatcccgat cgatgcttct ttatttattt tacttcataa    1140
actcgtattt aagctatgca ttgccaacag ggcttaaata agaaaagtg ttgcacacag    1200 aagttgctat gccgcaatgg aaagagtact ttcatgaaaa tacgtagata tttaggagct    1260
ttcatttagt aggtcatctg gttgaccata tactaatcgg atacttgcga attattgtcc    1320
tttcagcagt gaatcctgag actgataagc cagcaggcgg gaatcgtatt agtaaaattt    1380
aaggacatct gagtacgggc gaaatctaca acacgacgaa atcatcaatc tattatgaca    1440
taagtattgg acagtacgtc tgactggaa acatagcttt atgttggata tgtacattag    1500
tgcaaatctg tgttacgtgt taaatcatcg cgttctagaa ctcttaatca catagcgagc    1560
```

| | | | |
|---|---|---|---|
| taccttggcg | aacactcgtt actgttctcg ttttgctatc atgtcctaaa agcggcaaaa | 1620 |
| gttattactg | caggaccgaa aaatatgaaa aacttatttt ttcatgggac tacacaaatc | 1680 |
| gagttgagcc | tttaagcggt tctatgttac ttgagtatct tgaacttgga gggggttat | 1740 |
| aatgataata | gcaatacata ggttatgata aactgtcctg ttttagatac acgggagcct | 1800 |
| tagtaggctt | attttaatag tgtagttgtt gatatgaata atatagaaag gccatggagg | 1860 |
| agaagtgcta | tgttaagagg gcagtcgcgg tcacgtgtgc cattgacgct cacttatatg | 1920 |
| ctgcgttttc | gcagtgtctc aaagattaaa ttagccatat ggtgtctatt gttttcgtaa | 1980 |
| acgcctagca | tgcgttcgtc | 2000 |

<210> SEQ ID NO 30
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

| | | |
|---|---|---|
| cttgtgcgtc gaaatcgaaa ctcaaatagt atgtacgctg aaaataataa agcctagcta | 60 |
| acaatccatc cgcgtttaga tcgtaattca cattttaccg ataaaaagtt aagtacaaca | 120 |
| ttggaattgt tattacttag ccagccaata acgcgtccta attaccaaaa aaaacagact | 180 |
| ctgaatcatg gtagattaat tgggtatcga taacattatc caaattcagg gggccattcg | 240 |
| cttaagaaaa gagatgttaa cgtactccag cgatctgcgg tgttctgact gtaaaaatac | 300 |
| gcatacattt cacccatagc agaagacgta ggacgtcttt tctaccaggt gtctgtatta | 360 |
| catacccccat gcatatctaa aaggattctg gacgtatttt gatttttacc agttgagata | 420 |
| gtgtcaaatt ctgactttca aatgacaatc gcaaaaatgt atgcgaaggc tgatgatctt | 480 |
| gtaatcaata ctggtgctag tcacatactg ttgtagatac gccagattta cactatacac | 540 |
| agtgaacaag gtcatgtcaa taacaactat ttttgtttat aatcactaac cctgcatatg | 600 |
| agggtcttga tccaagttcg aatggttgag aattccgagt ttattggtaa gggaagatgt | 660 |
| atcaaatata atccttgctt acttcccaac agtcacaaga agcagagtta acgactgatt | 720 |
| acggctggac caataaatat tgaaacatcg caataaaact tgaagaaatt tgactacaaa | 780 |
| gtttaagtgt atacagtaga tcggttaggg tatactcaat tagggcggaa cccgcattcc | 840 |
| tgtcgataag ctagtagtag gtggttttca ggttggtatc aaccatcaat attcgacata | 900 |
| cattaatcca gtgaataggg gcgtccggat tttgtaaagc attaaccttc tgtataaata | 960 |
| ctgccaatca tatggcttga gtaaccgttt ttgtcagtgg aatcgtcccc tcgctagaag | 1020 |
| catctgtacg atatctaatg gctgtagttg ccttaaatcg gaaaggtaag tcggaacctg | 1080 |
| ggctctcatt cgaataagac caatcctaaa cggcgaattc ctttatcttg ttaactgctg | 1140 |
| tgtcaagtcc tcttatcgaa aattcttaca tgtttactct tgcgattaac tatggtgaac | 1200 |
| taatcccaac aatgactgtt cgtaatagat gtgtttgtaa aattagtatt tggtgacat | 1260 |
| ctctagtcat ttcatgcctt catagatcat cggtatttcg caataatctg ctcatactat | 1320 |
| gtacagaaat accactacct tctgacaccc ttgctagcac tctggaacta aataactcat | 1380 |
| agacgaaaat acaatgcaaa gctcatcttc ttttgaatat tgagcgaagt agattgttga | 1440 |
| cgttaagaaa tgagtagttt cattcgagaa catccgtaat caactacaat tataatctca | 1500 |
| caagatcggt ctattaaatc gctcatactc ctaggactag aaccaacgat cgaatttgtg | 1560 |

```
ctttgggctt aggtaaagac gtataatcct acctagaagt tatccattta tccacttgat      1620
aacatatgtc tattccccaa tcataataag acgtagaaga aaacgactct cacaacgaca      1680
gtatgcccta atatgcgatg gcgactgaaa atcttacggc gcccgcctca atcacgttca      1740
cgtgacccag cacattagat ccaggactga ctcaagatca ttactcggcg atcaacgcac      1800
tatcctcaat tggctatgtg cgaactcctc gtataggata aggatattcc ggtctccgta      1860
tacgctaggc tcagtaacgc gtcttactct gggtcaaggg tttaaagatc atagcggtat      1920
catacaaaaa atcatatggc ctactttgtc gttttaagcg aagatcaacg acgtaatagc      1980
taacttaatg agcaagattt                                                  2000

<210> SEQ ID NO 31
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
tcgataggac agataagtga ccgcttgttg agtcttatat gtattggact taacatcgag        60
caacagtctg taacatatgt cactacgtga ttgaaggccg tcgtcagtaa ttaaggataa       120
ggcggtaaga cataagatac cgtacaagga tatttatcgt tatctcaagg tcaaatctaa       180
ctataggtaa caattacctt ctactagtag gggaattccg ttggatagct agtaaaagat       240
tgcttcaact aatccaacaa agtattacat caaaacagat tggttatcaa gattggagct       300
tcagaactag agtggtgagc aaagcactct catgcctttt gtaagaaccg ggaatgaacc       360
gcaagaatca cttgacaaag gtattgggtg gttatgttgc cgggaagcta cgattatatc       420
caataggcta cggtcgttgt acaaccggtt gtctatctgg tacttggttg atgacctagg       480
tgcgagccat tctgccaaat ttatatggag attaagagtg gtctttgcct gatgaaaggg       540
ccaactgccg aagtactttg gagcagtgtt gactgcagct ccaaacatct tgtattttaa       600
tatttcggaa tagacatcta tcgttagtga ggaaagaatt tgatcccgcg ctattttccc       660
gacattctca acacttggat tacttaactc atagaatttt ctacctatta tattataaca       720
aaaaggtcag tattggtcct gacgtatctg attcacgtat tacggggcgg ggtggaaaaa       780 cttggttttcc tagagcctta gacgagcgtt aatatacaac aaactagttt cacataatat       840
tacgtatgga gtagactcaa acaatggatc gcggcgacgt ggatggtatt atcgcatgat       900
gcaattctaa cgatgaattt gtgtccgcgc tgttgtcgtt ttaacaacga ttttgaggtt       960
atgatagtta taatcattag aacatgtccg aaattcaagt ggttcacctt agctttgtca      1020
attttgtcac acttcaggga gggtccagga ggaactgcaa tcgtcagtct gaatcgttcg      1080
agcagtagaa atgacctaat ttgctcgtga cgtactgacg ataccaaatc aatgattgag      1140
ttcgaggatc tgatgtttgg agcttgcgtt ggacgatctg atactcaaaa gtcgacactc      1200
aacatttttt gccacgacag atattctcca gacttaagaa atccttgctg aatatcaaac      1260
atgcagctta gattagttat tatgtaaatt gtgagatact atgctaactc gatagtgagg      1320
tgttggtctg acaccgtgaa ttaataggtc gtccttaaca agtaccactt agattcctcg      1380
cttttgagtc tttgacgcct ttggccggat gcatgtataa atccttttca aaaggctgtt      1440
cattcccatc caagttctgt aataggtcta tctttacttc tggtaacaag agggagttgg      1500
```

| | | | | |
|---|---|---|---|---|
| gttacgacga | gtaattgttg | tagcaaggat | aaactgctat | ttttgattaa cagcctcaca | 1560 |
| tataatacgg | gcagccaagt | cagcctgccg | gcaaatttag | cagtgtttct gctcgccaat | 1620 |
| gtctcgagac | tcctagctct | ctcgtccatt | gctgactaga | actagccaat tcggcgagca | 1680 |
| ttagagtgct | aaaaaaatcg | gtacaggagc | ctaagggtat | ccgggcagaa gcaagtggtg | 1740 |
| ccaaagacag | ttagtttatg | agcttacgtc | caatgataga | atttgcaaac ggtatggtta | 1800 |
| ccttcttttc | tgtatcttct | caatgtaata | tgttaatgaa | cacattgtta atgtggtttc | 1860 |
| atatagtaaa | gtagaaaact | agccgacaac | caaagtaaga | ggagcagttt tagaatcaaa | 1920 |
| tacaccaact | taaaaatttg | catctatgtt | tttgacaatt | gacatacgac ataataaaag | 1980 |
| taggatagtt | gtagatcgtc | | | | 2000 |

<210> SEQ ID NO 32
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 32

| | | | | |
|---|---|---|---|---|
| acaacaatcc | agaattaaag | agtcaatgat | taaagtctct | ataattcttg gtggttaagg | 60 |
| tgcaactttt | gtcaagccaa | tgcttctcta | gcttacgaaa | ggaactagta ttacaatttg | 120 |
| ttaccgcata | tactaatgat | caaacattgt | acaggtacgg | ttaataggcg cactagtaac | 180 |
| accgtcaatt | attatcctcg | tccgacctga | gaaaggatga | tagatcgtgc atagagggac | 240 |
| ttgtggaacg | aagaacattt | cctacgcagc | tacaaaagat | atattgcacc agggacgtca | 300 |
| cactaaagat | gtatactaca | gcattgtttc | tcataacctc | taggtaggtc tgtagattca | 360 |
| gcgtatatcg | actacctaca | tctcgtctga | tattcatcta | tcgccttaaa attgtgtaaa | 420 |
| ataatctgag | gtcatcaatg | gttttgtttt | tacattatgt | aaggtccgta atggtaactt | 480 |
| gtgaaccgac | atagttcccc | gtcgcttagg | tgtgcagata | attagatcca atggatcaat | 540 |
| tctcggagat | agtcttctac | ggcattctat | ctgtacacgt | attggtacgg gggtcgtagg | 600 |
| cagggagaca | tctacaaaag | ttagcggttg | ctgaattatt | aatatacagc tttacgctta | 660 |
| tacggttgac | tacaaaaaaa | ttacaagatt | cttcatgaga | ttgtacctgt caacttaatt | 720 |
| cgtatcaaaa | attctaaagt | gcgcatctaa | cttcatacaa | cggagaaaag tacatataag | 780 |
| tagggtgtga | acgcagataa | cgttcaaaat | gatttaaact | atgattgaga tgtccaagtt | 840 |
| aaggacggta | gggttgctac | cgtggactat | aaaccctaat | gcctaaatct ttatattcgg | 900 |
| gaattgtttc | gggttagggg | gaatacgcac | gaggctaaca | caatatgcat agtgcgtatc | 960 |
| attagcgtat | ggaggacgaa | aagagatata | cccaattata | gcctgaatgt cttaatcaga | 1020 |
| cccttatcgt | catctcattt | ttgactacaa | tcggtaataa | ctactcgggt ttactagatc | 1080 |
| ctaacgggat | gactcataat | agaacgaata | gtgtaaaagc | aacctacgcg taagaccttc | 1140 |
| ccggtcatga | ggatgtcatc | ctatgcaagc | gttcctcccg | cgaacgccac gtgatctctc | 1200 |
| gattccattc | tataggattc | attaaagctc | tactattacc | ccaattgctg ggtgttctaa | 1260 |
| gatctataat | gttattgtcc | agattaagtt | ctcctgcact | actcgcgatt gtgtctttcg | 1320 |
| cccgcttgtc | cccccgtaat | tggatcgggc | cttcgcgttc | tgctaatatt tgttacgtca | 1380 |
| cgtcggataa | cccctacttg | tgcaacatcc | tgacgaatgt | tgtaaaaagt ttttctttgg | 1440 |
| aaatttgtac | agttaaaaga | caagataata | tgattggatg | gcaagtgact gtaaagttct | 1500 |

-continued

| | |
|---|---|
| atccagtgtt tcgtatacga ttaatgaaac taaacgagaa actttgctga cctccaccca | 1560 |
| agatagcctt cactctttca ctaactccac ggtgaatttt ttttagtaat tttcataaag | 1620 |
| gcaaagacta agtttaccta gtaacgccaa tccccccacc atagtacact gtgattcgaa | 1680 |
| aaaaggatat ttttgagctt ctatgcttta gggatattta gttaacgga aagcaccgtc | 1740 |
| agcttggaat attaaacacg cacatgattt atggacccat agttgacatc aaggtctttg | 1800 |
| ataccgacgg ttttcgtatt ttccagtgaa agccgaagct ttacaaagga gagtaatt | 1860 |
| gagcaaattt ctcactgcat gtcacaggga ctgataaatt agtccaaaaa ctttattacg | 1920 |
| tttgacctta gaggtaccct aatgcggctt attatttgga ggccagacta ttgcgcgtaa | 1980 |
| caggctgttt gagcatcggt | 2000 |

<210> SEQ ID NO 33
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 33

| | |
|---|---|
| ctcctcgagc ttatagaaaa gtcaacgaat gtgtagaacc aagaaagtga ccagctatca | 60 |
| aataaataac aagtgagagg tacagcgtat ctaataggcg aaagtctagc tccaggtatc | 120 |
| ggtgaagtct aactatgaat taaacgcatt gcgtagctac atggttttac acgcaccatt | 180 |
| aacaggcgca taactactgc ctgaatcgct ctgatattaa agtcaaagga agctaaagac | 240 |
| ttgctatatc gttgcatggt gttaagtaaa tacgactcga gtattttaaa aaatcctctg | 300 |
| aatcgaccaa ctatttattc gttcattctc tgtcattgag tagcgctaat caatgtagta | 360 |
| tttggatcaa taaccctctg ggttaggcga ctacatgagt acccttggaa aaactctggt | 420 |
| cgagcaaaac aagacacatg gggttaaata aagtctatac agtttataat tatgcaaatt | 480 |
| tgacgaattt tgtacagaat tttatctata atcttacggg ggtatacata tgacagcttt | 540 |
| ccggtgttac aatactcctt gtgctttgta cacttggcgg aaaattcacc acaatgtatg | 600 |
| gggttccgcg caagctctct tttcggtaa tctgggattc ctttttttgtg ccctttaca | 660 |
| taacaagacg aattggtctc cttttactc agaaagaatt ataatacttt tcttacttgt | 720 |
| ccgtttcccc tcatcttttt ttacctccaa atccgattca tcgccttaag tccagtgtct | 780 |
| tccaatgtag tggtttaacg cgagctacat aaccatcccg gatgtatacg attctacagc | 840 |
| gtcttgaaaa tattatgttt aggtttcggg tgaaacgcac ctagaaatta tagcaataat | 900 |
| aatcttaaat ctcctcatca taatagatag gttattgata ggcgacatga aacccagcgg | 960 |
| attcacctat caccaatcaa accacagttc cttttgatgc agtcattcct acaggcatcc | 1020 |
| tattaacaaa caagcgtgtg ccgatgaaga attcgtatct gttaagcatc cgacggcaca | 1080 |
| tgtgcaagag tcgatctcct gataccaatt ttagtacttc tcctctgatt aaaacaactt | 1140 |
| ccaaagttcc aacagatgga gtatagataa tcagtttcc agaattaatc agtaatttga | 1200 |
| caagtggaag cgctagagga ctattcccgg taatactata acaagtaata gtgaccttgt | 1260 |
| gtataaatag acgttgatag atatatatac acttcttgat agctgaggta gacgttgata | 1320 |
| caacccgcaa gtgagtccat taccttaggc cctacgaaca tgctcaaacc cttttatgct | 1380 |
| ttcccagact caaaatcaat acgtagatat attgtaaccg tatagaaaag agcttctgtt | 1440 |

| | | |
|---|---|---|
| ggatacagtg gtataacagc tcatgttcaa ggtttatacg gtatgacaaa tgtgattttc | | 1500 |
| ttttatgtga gataaccgaa ccaatttcga aagattacta ctagttgaaa taccaatttt | | 1560 |
| aaaggtatcc tttccattag accccttata ttattctact gtattagcaa attttagaaa | | 1620 |
| gttcgtgtgg tactcaaatc cgatgaaact attcaccgtg accattaaat aagtttgatg | | 1680 |
| atcaccgaga attcacacct cgtaaataac acctatctta atagaattcg tgcgcagctc | | 1740 |
| taagagagag catcttccaa aacgaagagc tgtttacaat tgctgccacg tctttgatat | | 1800 |
| acactctttt attgtccaat ccgatgtttc acaataggat ccatggttcc ggttacttcc | | 1860 |
| tagctaaaag ggtttgccca cgcggtgagg aagtctgtc ggtatattag acgtagtgtt | | 1920 |
| cacgaataag taagattttt aatttggaat ggtttgcaac aattacataa ggataagtaa | | 1980 |
| acgcgccgta taatgctcta | | 2000 |

<210> SEQ ID NO 34
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 34

| | | |
|---|---|---|
| atctcataga taactctatg aggagttaac gcctagaaat tttggtctgc atggtacagt | | 60 |
| tacatatcgt atgaattcgt ctaacatttg aacggaccac accatctgat ccgcactcaa | | 120 |
| tggacagtag gcattcggtt acactttcgt ctggaagaac agtccgaata tgaaaatatg | | 180 |
| cttagatgat tccaagttaa tttcgtctat aaataagtag cttttgctct ataagataa | | 240 |
| cctcctacag tcgtaacaga gctcatatac gataagaaga gtatactttt agttttttcgc | | 300 |
| acatttagcc attcaatcga gaacatagac gcctcgagcc gaattgctta gcacattttc | | 360 |
| ctaataaatg tattcgaata tccaaaatga acttgcatga ctccgtagca cgcactagat | | 420 |
| ttagtgtgcc taaagattaa tatcccaagg ttgggctaga actaaaaacg ctgttgccaa | | 480 |
| taggttagat tgtaaactgg cccttaacaa gctgattatc aggtgctttg gatacttagc | | 540 |
| acatacttaa cacatcggcg tgaataagtg ggaaaatgtg cacaaactca ttagaaattc | | 600 |
| tgtgattggg tctttacgtt atgttaaagt tggtattgct taataactt attctcgca | | 660 |
| gcgtactcga gaacgtttga attcgtgaga gcccttaaat caacgacccc cggcgtttag | | 720 |
| aaacggcaat ccatatacct gtcataaatt atcttagaat tattattata ccctagcctt | | 780 |
| agccattttg tttaccagaa cacggatgga tctagttacg attcatataa agtgagagag | | 840 |
| gctagtgttg taagggagtg agagagcttg catcttacga gctcttagct cctcttatca | | 900 |
| aaatatcatt tgggcccaac aacgcgtaag tcagatgatc tattagcagt ttggatatgt | | 960 |
| tcaagaagtc ctccagcggg tttgcgagat tctctgtatc gttgacttgt gacatatgat | | 1020 |
| ttgtattcca agacggtcag ttgcaatctt gcctgaacta gttggattat cagccacccc | | 1080 |
| aggctgttgc atctaattaa gttttcctat ctgtaaaacc tttcacttag caatggctta | | 1140 |
| atgctcttac cgatcagctg gaagccggta gtactgtcac ttggttttct taacctatca | | 1200 |
| aaacggaaac aagccgtatt tttgatggta gcacttcaaa tggtgggcaa ccgactaaag | | 1260 |
| aacgtcactc tttaaattct cataagttaa aatcggatgt cgagtcaata ttttgtcggg | | 1320 |
| ccatgggaaa gagagcagta tgctaccttc ttaatctcta ccttacttta gacaagcata | | 1380 |
| cgtcaacaac tgtgactctt caaggacggg tattccctga ctcaatgctt tggaagaaca | | 1440 |

```
tttaactggg ttccattata gtggtcggac tctttatgct tatgtcgcac caggtccatc   1500
tatcgaattc ctgtattcta taaacaccgg ctgcactcta agaaagatcg agcttctgat   1560
tccaaaagtc tataaatgat cagttagcct agcgccgaca cattgctccg ttagaagctt   1620
gacgtttgtt attatgaggg atcacagatt accgtgtgtc gattggtggc tcacttatct   1680
atgagccagt ttcgttatgg tcataccttt aattaaggga acatcgtgct aaaatttta    1740 gaatggggta ctgtctagac tgtctcgagg attcatgccg atgaagacct gaaatttgaa   1800
tcggaacttt tgtggcaccg ccgtatcgca aaatgagaaa aagatatcgt taaccccta    1860 taaaccgcaa ctaactaagt caaaataagt cgacgtgact taagtactg attaagaaat   1920 ggtatcacgg ctcttttgca ataccattac caaaattgcc aatgaaactg ttttggccta   1980
tcttaagcca cgaataatat                                               2000
```

<210> SEQ ID NO 35
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 35

```
attcttaaag tcgattcggt gtcataatag ggttatctaa catatgtaca aacgccctat   60
aaagttatta tcggactggt gcataagtaa cagttcgcta taaagttaaa tgctatcaag   120
agaaataagg catactgtga tgaaaacgag gtcgtacaga aacacctgca ggaattaatc   180
tgccgtatca tacaaggaat atcgttggag tcaagatgac tgcccatttg cagttgtcat   240
cttaactgat gatggtttct tgcttgatag cacccgcctc agtaaaaaca gatggaacac   300
tccaatgcta gccaactgaa atttaacgtt agtaccaaag gcatccaagc agtcccctgg   360
ctaagttgga gtgtggcatc gatataaaat agttaaaaaa acggtctgat gtttcatgca   420
gtcgcaacca cgcatacggt tccggttcgc aacgattgat gtggcggtct cagtatttta   480
caagttttaa catgtcggca gccgctaggt agatacctgc accctgtggt ttcgtatata   540
gggaatttcg gtgctttaag ataaggatta ctcatagggg atattactcg attgcctcga   600
aaaatgcgat gagtctctat attcaacggt ctattacagg cttctatttt tctcgggacg   660
cctaggagtt gaatgatgca catcattaag ctacttatgc ggtcttccat accattccaa   720
tgtcgtcgaa agaggatgca gtgacaactc aggatactaa taattccttg agaactgtct   780
atttcaagcc tattctaaca taattagttg ctagccatat aagaaaatat catcaaacag   840
atagggttga taacagaggg tgctgcccgt atagtgaaca tcgtaaccgg gtttcacatc   900
ctagattggt ggcctcctac tatgtaagat gtagttatac tgaatgtggt gttgtgatca   960
agacgtagga aaatttatca gatatgccaa ctagtatcat cctgagttat aaagggggta   1020
atttcggaca aaggtgttgt ttcaaaaggt tcaagccgac gtacccgcac atcaacttat   1080
cttgtaatga ttcaaggttt atgtagcttg atcaccaagc aacccaagcg agctgtacca   1140
gatacgatta tgttaataaa ggtttggcgt actagactta acgctaaggt ttcgtaatgt   1200
aacgcctgca ttcacgtcaa taatagctca gtatgtgaga agtccgatgc tgttaattct   1260
aataacgctc ccacttgaag gagaaagcgg gagtaggtgc gtttgttcag aaaccactta   1320
agcggtttgt ttgtacgtac aaaatttgct tttagatgta tagttgtata cataaccatc   1380
```

| | |
|---|---|
| gtccgaaagt aaccttcata tgaaactcaa aggcattagt tgggaagcag tatgtggcgt | 1440 |
| ttgtgacaca tcgggattat aaaattccaa tatatattct aagtagcagt taaatgaact | 1500 |
| ccactatggt taaatacttg tacctatcgt tattcgcaat tgtgccactt ttacatagat | 1560 |
| tgtgaaccgg tatatcgcgt ggtcaagacc aggcttcaaa gctgtagaga actgtttatt | 1620 |
| ctttgagtga catagtatcg agacttgtat aaacatggat ggtacacaac gttggaaaag | 1680 |
| ccgaaagcca ataagatatt taagcattat gcttttatgt caacactgac tttctaaacc | 1740 |
| acacaccttta atcagtaga acagcatttt gaaggagtgg ctaaaccatg ttgcgtgcaa | 1800 |
| ttctccgggc tcgtaaaaac gtgtcgtgct aaaggctcta atctcgcag taaaggaggc | 1860 |
| cctccaaact aacttaactc attttgacga actcaagtag cttctattaa attcgtccga | 1920 |
| ataccatgaa gaacgggatt cgcatactgc gttcgccgta gtggagctcg ttacaaatca | 1980 |
| aatggatcga taaacaaacg | 2000 |

<210> SEQ ID NO 36
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 36

| | |
|---|---|
| ttagtatagt taagataatg cgtcgctaaa caacataaag attctttacc gatgagttct | 60 |
| cgctggtatt cgcttttta gtcttactcg ctcaagttat cttgagagat gtggaactga | 120 |
| accacttgag gtagccccat caattataag gaaattgaaa taggatcgaa atattctgaa | 180 |
| ctatttccat ctagtctact gaaattaaca ttgacacctt tcacaaacga atggcaaaaa | 240 |
| aggacggatc catccccaca gacaacttcg tttatttcag cacatttgtc cctggacaac | 300 |
| agccgtatgt ggttcgacat actacctgat agtgagcgt tatcgaaatg tccttgacta | 360 |
| gctactaaga ggctttatac aatattccta cacacataga cccagtagat atgagttcta | 420 |
| gttggagatt tttcaacaca attacgccac gaggtccgac aacgtatcct ccacagttag | 480 |
| gaacatttat tacaaggagg ttagctccgt gctacagcaa cacgaattac tccaccgtgt | 540 |
| tgagcaggta aacgagggca aaatacaccc caaagcgtaa ctgcatacga ctttccgctc | 600 |
| gaagattgtt aaaacaagac tgcaatttct gtggcaaaag acactaaaga tgacagtaca | 660 |
| gcacccatgg agagtttgta cccggttcga cctaagtatc tgttgtccag aatcgtgaaa | 720 |
| tttgaagtgg cctaaaagct gagacgagta tagtagggtg gaggtttcct atatgttggt | 780 |
| cggtcagtaa atatttaaac cacggggagtt aaacttatct taaatgtatc tatacattag | 840 |
| tatataggct gagattcgat atatatagac gccaccccga gaaatagaaa gatagtgatt | 900 |
| caaattccta acagttcgga gtggtatacg catttctgag taatttggcg tacaaagttt | 960 |
| gagtagagca cagagttgat aactagagca atgtctgaga gtggattaac ttggtgtgct | 1020 |
| ctgctagaaa tccccagtga tgatctctca taaaaagtga ctgcaagact aggatacaat | 1080 |
| ttattatcga agtatcaaga tcgtgggttc cttttttcct ggtcaaagat gaatctgtct | 1140 |
| tacttaacga aacacaggaa cttttcttgc ataggcaccg atcttgctat gtattgaagc | 1200 |
| tacttcaaag gacctatcag cgggtgtaca caatgtcgga acatgcataa atggcagaag | 1260 |
| gcgatgagtc atttcgcaca ccaacaggcc gacgagcgta ggagcgactc agaacactac | 1320 |
| caactatagc ataacgataa acggagaacg tccatgccgt tatgtgacca ttcggttcgg | 1380 |

```
agtcgtgggt taccgaccac gatagaacat ggcacactgc tttctcactt ccccaataag    1440
aaacaccctg gacgtatacc tcgattggat ctggagacag tactcggatc cacacctaag    1500
tagtacctca ctgtgggcga tggccaagac gcgaggttga ctatctgcgt ggtggaaaag    1560
gccgacagat ctttatcaat tgtagtgagc tgatgagtcc tttatccgtt ataagctact    1620
tttattgggt aatagatggt gctcttactc cttcgagtta atatatagaa atcaccgcaa    1680
agttaaacgc aacatgagtg gtttggatta acaacttctg gaatcattat aaccttagga    1740
gcgttctagt gatgctgaaa ttgagacagt aaaaagtgcc catgatgtag gaaagtcact    1800
ataaagtgaa tctcttgtcc ttaaacataa agcgcggtaa acactcacgt taagatggtt    1860
gtggccacaa catgactctt gtggttcttg acgtgttaac gcggtggcac tagcagggat    1920
gatacaagtt gatgcttacc catatgatta ttgttccccg gagccaccac taagccacta    1980
aatgaagatt tttgcggcga                                                2000

<210> SEQ ID NO 37
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
gatgttctga agttccttag cgtacaaaca caaaacgtgc attggaaaat ggagagggaa      60
ccctctatgt ctgatgattt tttcggttga gctaattcca gtgcaatcga caataagggc     120
atgtccgaaa ttcgcttttt aatggtagta ggtccggcat cattatgttg tcggcctaaa     180
taccataatc attgctcaac cttcaactct ttgctggaac aattagtact tttcgtttgc     240
gcttaaccat gcgtataatg taataaaagc accagtttat agatatcgga aaatttagag     300
ttcatgccat agtttgaacc gacggtaggt acctataacg tcttttgatt tccgcaacct     360
atgtattgta agcagttgtc ctaaggagta ttttcactgt ctaagtggta accagcggcg     420
agaacatagt cggcggaacg gttctgattt cgactagcat cggcgacatt gccttgtcaa     480
tctccataat gatataaaca tggtctttta actctcacaa cctaaattat taacaggtcg     540
atacttctct ggcgaggttg ttttaaaact tccactccgg ataggaattt cattgaaaat     600
ataaaaggtt gatgtgtcaa tcgaagtcta aaaagaatga agattagtgt cgcctaggac     660
atctatttgt tttaaagtgc aaggaacgtg ttcacgtaga attgtgaaat tggatacatg     720
tttagtgtca tgcattgttt atgggattga ctataactta gatagagaac tagttaccct     780
tattactttg cagtatatga acgactgatt gtcaagactg agcctaaatt aaagtaatca     840
gcacattttg gatatggata ggagctcagt ttctggtttc actctcatcg acttctttgt     900
ccaaatacgg caatcacgta atgcataaaa attcaaacat aatgtgatga agaacatat     960 cacccgtcta aaaaattaaa tatatactat agtgctgcaa tacatcctta aattgtccta    1020
tattggtaag tcaaacgata caacctgcat tcttggggga taactgatgt ttactgdacg    1080
gcggaaatac tttaatttat aggctactcc agtgcatagt aagaatcata atttggtagc    1140
gcctagtaaa aagaaatcct caaaaactaa acgctattct gatcgctatc atcaagaaat    1200
gaattgtaag tgagggctgt attctaactc atcctagcag gatttattgc ctgcatcatc    1260
gacattctgt tcgaagcggt gatccccatt tggacaaatt caaggtttgg attatctagc    1320
```

```
gcccttggag tctctttacg tgtttaggtg ttcctgtagg aaaatcatct tattgtcgcg 1380
aatagaaggt acaaaaagac ctcaaagtta ccatatgcac catggagatg aaacggtaaa 1440
agtaactggg accaaagctg tccttccggg attcattatt accataatca ttaggcatca 1500
ataatattct gtgcgatatg ttgctcggct tattaacctc aatgaaacaa tatgaccgca 1560
tatcgctaca gtaaatctac gacgtttta ctgattgatt gaatcgcact ttttaataat 1620
tgtatgcccc gatacataaa atgtcataat cgagaagcat atagtagtat tgtagtatcc 1680
tcaggatcgg ttggtagctt taatacgtgt aaatttttct cgtaattatc gagagtgtgg 1740
agacgtccgt gtactggatt cgtaagaatt caataccctg atgtccgtcc gagtagatcg 1800
```

```
ataaagtaag tagggatatt cagatattta atgtatttcc tgtacactgt gacatctctg 1860
caacgagatt gttatactgg cggcgcgtag gaaaaattca accagtctgt ttgcagggat 1920
agttaaaatt cattagagac cagagcaaat aatgagcatc cgaaatgtat ccaaagcgat 1980
atacgcgctt acaaactctg 2000
```

<210> SEQ ID NO 38
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 38

```
ttgatgtgcg aatataacat tgatcatcag aggcaaggtg ataggtatta aaacgttagc 60
gtccacgctc ctggttctat aaaacttctt tagatgctgc taagtccatt gatttactgt 120
tttatagata cgagagtaaa tatagtttaa attttttaag tttgaaatac gtgtagctat 180
cgttgcgcta aggagagttg tctatgtact agtgatttca gtcggaaata gcagaaacat 240
gaacctatca catgactgtc gaatggaaaa tttggagtct ggaacattca gtatgagata 300
tacattaatc catgactcag aggaattgac ccactaatgt tattcttagt tgcaattcca 360
ggtatgtcta gaatttgcaa tcggttagcc gttgtgtact tcgtatcaat tttcaaacag 420
aatacaaaac cacgctagtt agccgaaatt actcctaatt gtcgtcacta tgtaagagat 480
ttagaaaaaa tagtatttgg tactactaag ataatcgctg tccactataa acttgtaggt 540
agttagtcga gtgttctgca agggtacatt catggaattc gcgagcaacg ttcgcttctc 600
cccaaatatt gatataaaga cgatccattc tatgtatttt cgcactagta aaatacctat 660
ctactcgact tacgctatag ctcagggatc tatttgtagg catccacagc tcagacgaaa 720
taatagattt acgaactgat agcggccctc catgcctgct aatcatgttc atacatccaa 780
acaaatcgtt ttgttggtag acaacaacat agcgataatt tcaactggtt gaaatggttg 840
tatagctgaa tataaacgat cccaaaaaat tcaagatggt ggctgcaccg gaacgacgtt 900
aatagcgtga ggaggtgtta aaagcaacaa aatcacaccc gccgtcttct agggtaagcg 960
ggtgccagcc gggtctactg gataagtaga tatttagcaa agaacctcag ttatccattt 1020
tctggttacg tgcacaatta gttttgcatc tgccggcttt tgtctctggc acttgacaaa 1080
cctagcaaaa ctcaactgag gggttaacac gctctaagat tcctcttact agatgaggta 1140
ttcatctgcg tatctgattc tacgttatag gctttttctc tcgaatacta atgtctggac 1200
tgatcaataa gaattggcta attgcggaag tcaaaataga accaattata ttcatacttc 1260
tattattagt tctaggatga ttttcccgac catcggtagt aggaggaggt gatgtaactc 1320
```

| | |
|---|---|
| agtagtatta tgctgagtga ttgcacctct gattctatta atatgggggg atgctgcttg | 1380 |
| cctcgtgggt tagtgtccgg atgaaaaccc ccctaaccta ttcacgtata gtatcccagt | 1440 |
| caattgagtc agtgacctta atcctaacaa aaaatacaga atgctgtgaa tgacctcgtt | 1500 |
| cttcttattg tgcacgatct gattcgaaaa tgaacggtat agagtctgag catcacgata | 1560 |
| taagagattc attctgtatt atttacgaaa ggcgtagcac cattcgatca gcgagcagaa | 1620 |
| ccacggggca gtattgaatt tccgtttttc cgatttcaaa acggctagaa atggctgctg | 1680 |
| gatgatagat gcccaactca cacggttgaa cttgcttatc aattgtgcgg ttcatatcag | 1740 |
| acatagcagt ctgcttggaa gatattgagt aacttcagca ttcaaacgcg caaagctatt | 1800 |
| gagttgcccc tgatgctgtc tatcgtgtat taagtgatcg tgggaattag acatacaact | 1860 |
| ttacctcttc tagcttgttt atagagcctc accgaggtat aaatcattaa ttacccagga | 1920 |
| gaccggtttt gctattacct tgtaatgttc aaaaaagaag tggaacacag tgaaagcctc | 1980 |
| atttctcaag caagtgagta | 2000 |

<210> SEQ ID NO 39
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
   Synthetic polynucleotide"

<400> SEQUENCE: 39

| | |
|---|---|
| tgtagacatt tgtcttcaat ctaacctctt tctcacgaaa taagggcttg tattgttcct | 60 |
| tcgtttgttt accgcacaga aacagcttca cttaacatac attgtaagtg tgtatttctc | 120 |
| ggggtacgta acataacgaa acttaaagca atcagacata cagtgccatt ccctacggta | 180 |
| ctgtctcagt atgttaatac tactcatttg caaaaggatg tacgcacttc atactacagc | 240 |
| tgctgacggt gtatatcaaa caattatatt aacgctcgta ggatagttca cgtccgccat | 300 |
| atctttgatt taggcttcaa aattcagaat aatacgaaat agtctgtcta ctaggccaaa | 360 |
| gtcacttaag ggctaagagt gtaatgagta atcaaaataa taatcgttga gtcgtcaatt | 420 |
| ggagcatcag ttatggcatt aaaacatcta gtgggtcgaa aggatcagga aattatgtat | 480 |
| gggtgagagt cgctgctacg gtatcgcttt tggattgagg gctactacac tcagtaccca | 540 |
| cagtgtgtgt attaataaga atcgcaatat gcgtcctttt aagttttaag gtaccctacc | 600 |
| tttcatatct agtggaaatc atttacgcct atgcgacaaa ttagagactt ttatttgtaa | 660 |
| aacattggat gttggaatga ccctagatgc atgttaaata gcacgttcat tagtggtaca | 720 |
| cgcctatcac taacgctatg gaaaaataga agaagccaga acaagtaaac ctatggtgac | 780 |
| aaataattac ataaggaaat ccctcataat tagaatacca taaaacgtta gttgtactat | 840 |
| ccgtaatcta ccttctagcg tggaatagtt gagtgtattc tagtcacgcc ccgttccata | 900 |
| acgatacatg taaaatttac agcgacgttt aggaacccta caaggggagc agcagcgagg | 960 |
| atagctgact agccttacaa taagcaccca tacttatgat tgacatgatg gtcatgcggc | 1020 |
| gttaccactc cgctagcgtt acttctttcg tcttgtaccg gttggcaat gcgatgcagc | 1080 |
| ccaggtaccg tagagaaagt agcgatgtgt gaggtcgagt actttgtcag aaagcaagtc | 1140 |
| ggattgcggt cccatttacc gcgacgtgca tttgtacagt atgaccgttt tttaccactt | 1200 |
| actgatgagg ccagactaat aaacgatatt tggtcacagg acaatattac ggccaattat | 1260 |

```
gaaataactg actggcctat tgaatgacta ggaatgtcaa gtccagactc tagctatttg    1320
ggaggtttat atgtttggac cgacttgtgg gagtttgaca ctacgagtaa caagattatc    1380
cctttttatg ctgcgctagt tgacatggat tgacgaggtt attaatatcc atgactaact    1440
catcacagct tcccgagccg agacggatta ttttaatctc gttgatcgat atattaggtg    1500
acgtgagaag aagatgtgtc gtaatcagta atagttagga tcaagaggtt aaaagaagcg    1560
ccttcttcac agattctcag tatctaccag cacagagttc tcagtttcta acgtgttccg    1620
tatggatttg cgccactttc tgaataagtc ttatgagata tacttacctg gtccagatgt    1680
agcagcgagt taagattata actgcggttt agcacgcagc gtttaaatac aaatactctt    1740
gactgttata acgttcagga ttaggaacag gttcctcacg gatatagaac ccaattcacg    1800
tgcatgaggt attctatctt aggggagga actgcgctgg agcttgaaac tgaccctcta    1860
ggcgcttgct ttcactgaga tctattcaaa ctgacgttta gtaagaaatc ataagactta    1920
tctacgccgc cttataattt atgttattaa aacatgatca tgcgatcaat taggtaaatt    1980
tctttgtgcc ttgcaatatg                                                2000

<210> SEQ ID NO 40
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
cgaatattta ttttcctac gcacctacac tatcgtgaag ttcatggtat caattatatg      60
tcactagagc cacaaatacg tacttaaatc atttacctcg actgaaggtt gtaggcttgg    120
acatactctt gccaccattg taacaaaggt agatcggttg gacccgaaat ttggtacttt    180
taatctagaa tcagcaatat cctacggaaa ggcccaagag atgtctcaat ggatgagagt    240
gtaattacct aatttcagaa aagagagttt aacacaaata agaacagacg aatatcaata    300
aagtgcacgt cgggcctaaa tgagcccaca gcctggatag attaagtgcg atacgtcgct    360
accaacgaac aaaagtattt ggtattatga catcggctcc gacggtatag dataggaata    420
actcccaaac aatataatct tggatacgat taagtttgag tttgattgat cccatcaaac    480
atttgttggt ataaagttaa tgtgtgatcc agttagaatt atatgaacat agtgttgtca    540
cgattttgag acgaccgtta aacattatac tgcggtggca tagcaagttc atctcctgac    600
attagtcagc atttaatagt aagcaggagt actattaaca cgctcctata atcggttgcc    660
tgttggggat aatcagaaca tgaaaaactc catattagaa aattacataa tatagatcac    720
gtgtatgaaa cctaataccg cgaatataat tacattatga ttgcaataca tagggtagac    780
tcctagttaa cgtaaaccaa ataaccgact cgagaaacac aggactaaca attataattt    840
ataaactaag agtgctatac tagttactgc ctgataccta tgtttatttg caagtcaaaa    900
gtttcaaata gcccttggca agctacatga tgggtgattg gaggtgggac taggagttcc    960
gtccttagtc tgaataaaga acatgatgtg caccgatttg tcgtctactc ggacgttgtg   1020
gcaagaataa aagtgaggta tagtaccgct agccgcagag atactgcctt catatgcgcc   1080
gatactctat tgttcataaa cagcaatgag gcagagcaca taatcttaat tattaattta   1140
gttaacggct tccaattta gcaatgaata aattttttga ggtgcatctg tgattaattc   1200
acccagaaac gctttcgcga attacctgtc actatagatc cttaatgaat tatcttcgtc   1260
```

```
gtcggaacaa ttatcggact ttattttgcc tgttttatgt atcgagttaa ataacgggaa    1320
tcataatttt atattacatc tgttttgtat agcggatctc agtaggttac atcactgtcg    1380
tcggattcaa cagcaacaac accgttaatg aatatagcta cactgcatga gtcccaacag    1440
cactggtcca ctagaaatat ataattatac gaatactttg ctatgttcat gacctgtcaa    1500
aggagaaatc tagtaaagac ccacggatat cgaagaacat tgtagttctg actcggtttg    1560
aatgtccggt aactgcaggt tcccgttata ctgagcggtc cgaaaatggc agtctaagtc    1620
cccctacatg acgattgcta tttattaggt ctcagaatat aacattagac acaagagcac    1680
aatagtcgga gtatgcgtta tcgagaccgt atatgagtca atcgaacgta gatcgatcat    1740
agctaactag gtggtgtatc actgacgact tgacgatgtt ttatcgctga ttagtttatg    1800
atcttgtaaa gattggatgc tacatattat ggtaattttg ctacttcccc caactatacc    1860
aaatgactca ctgtttatca aaggtgactg gataggcgct aggtatatcc cggtgcgcaa    1920
ttattgccct ggcgagccga acatctcgaa tatgtaaaga cgaatactcc ctaattacct    1980
tttcgaggta acaatgaata                                                2000

<210> SEQ ID NO 41
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
atcgagttgg tttctacgag tagctggcaa gcgcacatag aacacacatt gcatgtgagt      60
ggagcgattg cgagacgaaa caaccttcca aaagcccaac gattacagtg ctagttatct     120
atgggaactt attcccttag ggccaaagtc cctaggttat tctatacgac tcacaccgaa     180
gaggctgtaa attaacccga atatagatga ttagtccttt gtttgtctta gggatggcac     240
cataataaaa ttgtcaaatt agggtacagg actagttcga tttcttctat ccgtcgtcct     300
aggtttatat gtggccgtca ccactgtatc acatgccagc tagcaacagt atgatgtata     360
gcggcaaatc attcgtcggg ggcatgcaga acgtcagtta actttaaaga tgagactacg     420
ttttggtcac aatacaatga cttagactca tctcttaact cagacaatca cttttatact     480
tagtgcaatg tgtcacagcc acttaatggc ctagctaatc cttatagtcg gtagctagcg     540
agttatagaa tcttgttgtg gataatcctg ctcaaccttg cctggaagtc taagaccagt     600
actagaagtt aggcgtcgga gtctgtgatg ctaaagttgt tcggccaact aattaggggt     660
gtacctcctt gtctaatcct cttagaaatt attcgagaag ggtacagtac ccctcacaaa     720
gagaatctaa gttaccgtct gaagtctgag tgatccgttt tgaggtaaac agctgttata     780
catacttaca gcttagtcta catgacctac taagcgcttc gtgctcctta ccgtcccaga     840 ataccatgg ctcgcgtctc ctgccgtaca atacgtagat ttaatactcg taatgtttac     900
aaaaaatggc tcagcgaata tgaatacgat atacagtacc atatttatgg atacaaaatt     960
tgtggcatcc gcctaatagg gctttcctca gggcttactc cacatactgt tcaaccttct    1020
aggttcagta aaagtggaga ccacgatgca gtgtccttct taatctggcc ttatttgtcg    1080
atcccttatc tcgctaagat tagtcacacg acaaagaggt cgttaatgac gtatctagcc    1140
acaatcgaca gtcttctggc gaagatatct acaagagtcg ttgattcgtc acttttagcc    1200
```

```
ttgtaaaatt gcccttttgaa taggtgacac ccgaatggat tggtactttc gtaattaacc   1260
gagactttgg agaattgtct ccggcgtttc atgtggcgaa gaatagaggt gactttgatg   1320
gcaccagaat ctcactgaca attgctatag acctaatatc ggatatttct gcaacttcct   1380
aatcgaaaaa atttctacaa accagtcgca gccttgagta ttcgcccttg acatagattc   1440
acaagattga gtcgcaaatg gtcctatgat aatggatgtg ttattgctgg aactttatca   1500
tgatgcaaag aggttataat attttgtgtt agtagcacac ttaatgcacg cagaatcctt   1560
aatcaatcat tagctgctaa tgagaatcaa ccgaccgtgt tggtgttact ggaattatat   1620
tcagtatcgc tctgatctta aggccctcag cacctgaggt ctaacgaaaa tttttttaag   1680
cccattctcg caaggccaca accatcagtc tctcgagaac gacattggac ctcatatcca   1740
agcctccggt tattcaccga tgtatttctt cgagtatcta aaatctgcca atacgattca   1800
agagaagtta gtatgcggga tcatgtagcg tacctttata tgaataaaac atacctggta   1860
gatggaaact tggtgacccg ggagtacgtc attctggtac tgatacttga gggtgaacat   1920
ggtgcgtgat tccagtatag cggtgaacct acgacaatat gtgcatggca ttgcttattt   1980
ggtgtatcgt tttttgagaa                                                2000

<210> SEQ ID NO 42
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42
taactatatg gtgtctgttt actacgattg cattaagatt tctagcaatc ttctccagta    60
actgcacttc cccatattgt agaagcgact tatggagcta atctttcact tggtttaatg   120
ctaactggga tttgagcacg taaaacttaa ctcggaccac tttgttgaca taattccgct   180
gcttatatac ccatattcat gtctacgatt ataaagttct tcgtatttgg ctaagcgtct   240
ctacctaggc tcaagccttt ttagccaatc tgaacgctaa acgggtgcta gcctagtgat   300
tatttaatga cgatttgagt tcatggacga aattacatta ttactgtcta accggacaac   360
gggcacgtca caataagaag ggtacagttg ggatcgcagt ttattcatgc tgtatgccaa   420
ttctactacc tctcgtcatc ttaattcata tatagctgaa gggctagcaa gtagtggatg   480
actataatcg ggatttagaa gagttttttc ctcgaacatt agccttatgt gtctattttg   540
ttaaaattga catgctaaac gatagctatt agctggagga ataacataat gttgtaaaag   600
gtaaccagct catcacttca ggaatcttac ttcctacgat ggctgtcttt tagtcgacgt   660
aaagaaaccc aaccaaggaa tacttagaca gacaggagat catcctacaa agatagtcga   720
tcttttattt agtccaacgc ttaccaatga atagggctgt ctgagactca aaatattgga   780
ccatgggttt cgcaaagcgc aaacggagaa ctatgatttc ttgttgtggc agcgtatggt   840
ccccacgggt gactgtacaa tcacggagac ttttatcata taacgatagt acatttatct   900
ggataccgga tccttcattt ctcggaactc tatacttact ttaatttaat ggcccgaaat   960
ctattatcct taaattacac cgccgtggac tcggaatgaa gatgagtccg caaggcatac  1020
tgttagatcg gctgagatat tgcctagtgc aatcgatctt ttgatggtat ttgtgtacat  1080
tctaattcga ggcgaaactg tcaataaact aatgggaaaa gcaagcatat cacgagaaat  1140
attctagggg ataacattac gttttcggaa cacaacaggt tcgacataaa tcttttatca  1200
```

```
tattatttgc ttacaattat ttagggcttc cgcccatact cagtagttca aatgatgcaa    1260
aggatgtggt gtctagtaga tctcttaaat ttctatcgaa tggcgtagtt acattgcagt    1320 tattttaca tggcaaaatg atcaaatttg tacgcaatag cagtaacata ttctctgtag    1380
tctatatctt tatgattgga gactgttaaa agctgatatg actaatcaag aaaatatcga    1440
aatttgatct acgacttaac attttaacta agcagacatc ataacgttta ttcttcaacg    1500
ggccgttact gctaaacatt aatctaacgt aaatcggaac tctgcagagt gcccgtctct    1560 tatttgtct gaattttaga atttacaagg agatgctcaa gccgagttag aagaagagaa    1620
atataatgaa tccaccgagt gtatgtttat acataaagaa ctatctttag gcgacgtgct    1680
agatcccact atgttcatgt gtaacgcatt tattggtgga actctcgcaa aatcttacat    1740
tatttcgcca ttacgtctat acaaaagcta gatccgtgaa gggtcataac ctcctttaaa    1800
ggcatgaaag aggttatcta acttatgatt ctataacatc gtcactggtg gagtaaaaac    1860
atctgtgata aatacttgtg atactctcta acatccctgt aatatgatga tcataacgct    1920
tgcacctatt aacttaaaag aaagttgtct tatggtgatt cttaaataaa agtgcctgag    1980
ccaccttgtg taattttaa                                                2000
```

<210> SEQ ID NO 43
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43

```
cacaatagta tagggacgtc tattattgaa aattatacca tgtggacata ttctggattt      60
gaatttattt tttacgaact tactcgtctc tttgtcgaac tgatcgaacc atgataggcg     120
gtccatacgt gtagtgtgtg ctagaagcat ctgtacttgt attgaaagga acaaagtcaa     180
ccatgctgtt caccaatttg atacgaagga atgtcctatc taaccgggct tattttacag     240
gctaagtagg tgaataatga caggaaaaat tcgaataaat cagaagagtt ttaagtaagg     300
ctcactggtc gaacggtgat aatactggcg gcaagttcta tgtagcttat tagataactc     360
ttcgggtgag agaaagagct tataaatgtg gcgctgaaat ccgatgccag ctgtagccga     420
gtcgcgtcat ctcctaacgg atcagttaac attatgctta ctggacgtaa agtggcttgt     480
ctagctctca tgcgccttgt aaagcttttt ctcactgtgt tcgattatag tgctctcagc     540
ctaccgttgc aaacaatgac tagcgactga gatgacaaca cgccacacat atcgagtggt     600
accgtattgg gagggtagtg gagagaccac ccgatatgga taacacgtac aagatgtggt     660
taaagagcca atcacaaatt gagcggcgat cgtgtcgaca ttttttcatt gtgtaagcat     720
gcatgtatac tagaaataga gtaatactta gcatatacga ttaactcttg gtgagatgag     780
attctagctt taaaagaggg gataccgata gagtaataca tgttctttg agcaaatggg     840 ttgttcgccc tgatccatga taacgactat ttcatagctc taatttagat gcttgaccca     900
gtgtaaagat ccgttttaac taacttagat gataatgaga ataaagtaa ttgactactt     960 agtacacttt aaatcctcca gtcgatgtgt attgtcgcta tatcgcaacc cgatgttcac    1020
atacagggtc ctgactttgg gtatacctta gtacgtaaca atctcactca caatcaatcc    1080
aagcgcggtt actatgttac gacggggaag caatacacag ctaggcgtgc agtactgctc    1140
```

```
ttagctctcc gaaatctgat ctagatgccc aaataatttt gtttccaaag ctagcgaggt    1200
tttacgacca gtcatgacag attctgcagt tgaagcatgt cacaggtaag caaaagcgtg    1260
gaacggatgg agcgagtaat caatagaact tactttacga gcggtgttac aaaattgggt    1320
ataatgcact agccgacatc gatggtgtag tgaattggac tggcaccctc aaggcctcgc    1380
ccaactcagt ctcgctagtt tgctacctgc atcctatgaa gctgttttta aaaatatcga    1440
tttctagcgg tagttaaact attaggaagg gctaaaacaa agttaattat acttatgtga    1500
acttacaatt tatatattag aaagtgagta agcatatctg aacaagcatc atcgtaatga    1560
ggtcggttcg aagtataaac ttaagttaac gacatcttcc aataccatcg aagtctacta    1620
agtaagttag gtgcttaatg atcattcata gtgtagcaag tccccgcaac tagataaagt    1680
caacgactta ggagtttaga tagaattgtg taccactagc tcgctacaat tggtttgtct    1740
agacttaatc ccttacctgt tgagaccgac tctatttcgg taaaaatcgg caaaatacgg    1800
taacattgtc tgcagtctga acacagacta gcttatatac atggatcaac catcaggtgt    1860
gactatgttt tattatatga actgttacca tggcgcctac gacaatagta tatttccatt    1920
tcggttacca gtttttgtct actttatcca ttaagtgata tatatacatg tgtccaacgt    1980
tatatggaca gcgttgtgca                                                2000

<210> SEQ ID NO 44
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44
taaaagaacg gacatggcgc acaaaatgac tatgaggcgg ttacttctga tgatcacacc      60
ctagttctta ctcaggctat tgtacaccct gccctctcaa tatcccgga aatatgcatt     120 tatacggcaa tcgatcttga atcccagttc gagtctttac aaaattccatc gtttactacg     180 caacgtcatg ctaaataaca ccttcccata tatgtagcgt gggcgggact attagagtca     240
ctttgtgcta aacagccggt aagtataata gtttactccg gaaggtgtca atatgtttag     300
cgactgtatt ttggtacttt atccctaaac ttagctaatt tacacatata gcagctggag     360
gagcaaggta tcatttaatc ttgcttaaga ccctagtttg taccctgtc gcacactaaa     420 cccaaaattg cgacattgag ccacttaggc cacattcgtt aatctggtag ttacagcaca     480
atggctataa tatacagata cgtctagaaa aaagttattt aatgcatagc ttgcataatc     540
gattctttaa aacagggtgg ggagctacgt atctaggatt ttattctacg tcatgataac     600
gaatcttcct gaacgtacta gatggcgact atcggagaat gatttagaac gccgggtgtg     660
tcttgatgat ataacaataa gtaccacgaa aagaatgtaa ataacttgat atcgactgtc     720
acaatttgtt tgtatcattg ttcgtatcat tatgctcctg ctcgtgtcgc aattcccctt     780
tcaccttttg gttctttata cacaatcata ttatagactt atacggaata ttggttgtaa     840
cttagagtaa taccgattga acccacatgt cgctgactgc gacgctacgg catcttaagc     900
cgatatatcg tcgtgacgta actaggagtc cgtaagcgaa gagtagcata gcgatgatcg     960
tttcagactc ggagtattag agttaccatg ctagccacat agaacggcct tccgtaaccg    1020
gtggcactcg ttcgcagtgg gaagcccaag ttagaataaa ttgctaaatc tgattctccc    1080
gtctggactt cgatcttcga gctagagtgc cactacgggc actaacacat tcaacgagtt    1140
```

```
tcgtcgggtg gctcgactat cggcacgagt gttgctctac gagaatacct gccttcctta    1200
ctgcgatttc tctttacgct cttccactgg tgccaagtgg ctgtatatta ctggtcgagt    1260
agggctcgct gattgtcgtg attcaaaaac gcaactctaa aatccatacc tttgttgaat    1320
acctttattc tcgttatcat agaggtgttc gggccctcac tatcgatggc agatatagct    1380
tctccgctcg tactttcata tagatgttcc ccaacagctt taaagttaga atgatccact    1440
ttcagggcat ccagtaactc gagcaattat gtatgtaacc gatctttcga tgataggga    1500 tagtacacct taaccttgt ccccggtgaa ttgcggcgac accatgcggt aggcgtatgt    1560
acggtgtgcc cttaattaac atcgctactg tactacacgg ttaggtcgtt tgaaaaggca    1620
gccatgaatg ttaagatctt attttaaaat tgatcattta catttagctg ctttgggggt    1680
aaatctactg atccaggtat taatctcttt tgtataatgt accaattgta gtaggttctc    1740
tatgttctta agtttcattg tcgataataa actaatcggc aaaggaagaa aactcaataa    1800
cttgtattgt accaaaaaag cggggctat agttagatcg gtgactcact ttcttcgata    1860
taagggaaac ccaccgtata acgacggtga tcttaagcct ctcccaggt taacgtatag    1920 cctacaaatg aatgcattca aaatgtcgta agccttttac ctggaaagca caaacgatag    1980
cgcatttcct taaagtacct                                                2000

<210> SEQ ID NO 45
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
acttgcacag aaatgacaaa gacgtcgatt cacgataagg cattccaata agtataacat      60
aatcgtgttt cggggcgcac aaaatagata cccaaaagag tgtcctttcc actcgacagt     120
agagctcata gttccgtgag attcttgcct cgtaactagt agactgtcta tcgcaagaat     180
atcacaccca atatttaaca acgctctgac gtagtagtgg ctacttgtgc gaataatcta     240
gtttctcata tttgcgattc aacttacggc taaacggcct catagttttt ccctattttg     300
aacataagtc gctgttaagc agagtgatac ttcccttatt taagtgtaag atgttaaaca     360
ctaagctaga acacagtaag ccccgtatc ttagacgtaa tagccctgtt agattaaagg     420
attgcgatcg acataccaac agatgacatt aaagcaagta tagcttcaat tcccgccacg     480
gtaaacacct atcacgatac aaaggataga cttaccgagt accgtagtta gtaacctcta     540
agctagtaaa tcaagttttt cgctagttat tcataagaac aaaattacaa aatgcgtatt     600
tacaactcat ttacagtgat gagaccgatt ctaatccaat cggtgttagt tttgcttatc     660
tgaaaatact gttagaaatg acgtggctgt taatcaatgt ataacgtgca tgcgctgaat     720
atcaatcatc agtatcgagg agttggcata cgcggggggct gttgttaaaa attgatccga     780
atcatctggt ttactccact aatggattaa gcctcctcaa ggcagctgat gtgaaaccca     840
aagatgtcaa tttgatttcg gtaattaatt gaaatccctg tcctgagcag actataaaca     900
gataaccgta tggaaatctg attccttaga cgttttcaaa tctattcaag taaatttta     960 cgggaatctt aaacgatatc gttccgtgaa gtaattcaaa aaacggtctt gatcttataa    1020
ttcacgtttg atactaattt agtcctccgc tccctaatga tttttacga aatggtccag    1080
```

```
tttattgttt ttaaaactct ttggaaaatt cgtgtatgag gatgataaat tgttcgatca    1140
acgtttgtat acttagatct caagcaagaa ctgtcagcga cctgtcgtta ggtagtttgt    1200
tgcctgccac ctcgcgacct taggaaagga aggtaatcta ttccttaata cgtactatgt    1260
acaagagatg caagaaaagg gcaacatgag aacggttagt ctctttgacc ctcttactgg    1320
ttagtgaata tttttaccag ctgctacgat gcaggatatc tggccctttg actgttccat    1380
ggacacgagc ccgaaggata tttatttaat cgagagctgt atttagtatc ttcataggac    1440
ttgaaatcgg ataccgctgt aattgtggaa cctcatgaga cctcctaaca aaacaagtat    1500
cgacctgccc tatctccgac atttactcaa ctctacccccc aggttgacaa tttaggatgg    1560
tgtctatggg aaatatgatt cgtaacgtgc tgcctcaaga ataggttatg aaaatatata    1620
tataaaattc tatgatagtt ccttcgtctc actcaatact aagtcgttaa gccaactagc    1680
tcgggcgggc tattagttgc catatgagga tccatgaatc aaacaaataa tgcaattctg    1740
ctaaaaagtg tgtatataga gcgtacacac aagaaacaaa actgaccgat ccgacttaac    1800
catttcaata taatgctgca cccttgtcct caatagcttg caggggggcaa ttacgtttgg    1860 agtctggttg tggtaatact cgactgtcct cggcgatata gaataattat agagtgtatt    1920
atagcacaaa ttattaatag attccatagc ctggcgttac atgaatattc tcagttaaag    1980
catttgaacg atcaagtggt                                                2000
```

<210> SEQ ID NO 46
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 46

```
aggaacaatg ttaatatcaa gtcgggtcca aaaagatgtg taaagtttgc gaaccgttgc      60
gatctgtttc tgtatcgtct tacactgtca gggcactagg actcactacg actcatatgt     120
acattgttta gctcactccg agacgcttag tgaatcgtta ataggttgat ttgttattga     180
agctgtctga cttattatct tcttaaacga cttttttacgt attgggagtc ataggcgttt    240
tacagatatc cgcgtcagtc cacgacgtgg tgctctatcg gataggtaca atcaacaaga    300
atgattattg ctcatcttaa tttactatgt gcgccgtttc accccaaatt cgctcaagct    360
cagaccattg agggcggaat aggattgagg ggtagtgagg cgctgctgta ttaggcaacc    420
ccggtggttc atttgaaaaa acaatcgcgg aaacaactct aggcctaagg ggaacaatcg    480
ctttgactat gagcttctat acctttgaat atacactttg cgtggagctt ggcgcgactc    540
cttttgaggt aatgcgatcc tacccatttt gggttccctc ttaattatat tatcggcttt    600
tgtcaccatg atctcataat actgataagt taccccctgat gttacgaccc cgcagccgtt    660
agatatttta tttaggagga cctacccaag gcctatgatc ctttctctat atcacgagga    720
ttacagacaa gagatgtgta atccgcccaa gttactctac tcaaggttgc gcatattagg    780
ggagggcgtt tgacagttgc agtatgccat cttggaaggc aacaataaac ggtacacaac    840
tttacaaata ttccataatt gtttctactt ttcattcatt cattatgtat ccctctatac    900
ttataaaaca tgtacgacat gtcctgtaga gcgggacctg ttcccgctca tgacagacga    960
gttatttgtc tccgacgtat catccatctt taaatattga atagcagcag catcaagtgt   1020
ggataagtgc aagcactatt aaatccgcgt gaactttcat atgacatgag aatcggactg   1080
```

```
tctgttatcg taaataaacc cgagataatg ttaaaactat tctaatgact tcatgaagca    1140
ggatcatcta aagttatcac aagaggtggt cttgagtctt gcaaacttca gaaaacattt    1200
acaaacgatt caaattagcc taaaccactt acttaaccac tcatattcca caagttacgg    1260
ttctttagaa tattaaggtg taatgaccca tcgagcctta tagctcgaat caagattaaa    1320
agaatattct aaatgaccat accggttaca tgtgtgggcg gagtcaaaag ttttctgac     1380 tattaggtgc acaaaggtgt tcagaactta accaaactct tagcacattt gattagctag    1440
tcagattaag gtctccactt tcttttctgt ggtagttcgg taaattgatg ggcattaaca    1500
aacttaaggt tgattacaat gggggggttat cggatggtta ttgtaattga cccgtccata   1560
gatttgctta aaaatcgcat tttgaataca tatcctaact tccaagcatt acacagcgct    1620
gcactataga gctaggatga ctgtacaacc tcggattata gcttctacgt aaggcgtggc    1680
cgtggctggt ataatagtgg ggtggaggga gaattgacaa aaaaagttta tcatttaaat    1740
attagtaatg gggttgtcgt tctaggaccg tatttcgcgt actaagtcac atacccttat    1800
atattttcca cagcaagtct atcattgcaa gctgttaact tcattccggc ggctgctgaa    1860
ccagtatcag ttggtccaca gaagctaaag ttagcaaagt aatacacgcc aacctactta    1920
tatatgtata tcgtatagct taattgagat gtcgtagcca ttacatgctg agccttattt    1980
ttgaccgaga ccaggtacac                                                2000
```

<210> SEQ ID NO 47
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47

```
ttggacgtcg aaattatttt tgatatacgt gtaatgatag actaaaggca aaagaagga      60 gtataagtct aagttcgaag aggcggattt ggttatacgt cctgcacctc ttgccagaca    120 ttctttaat tcttgtgacc tggacttgaa gttccttttt gcgaccattt gtgggttag     180 tacgaaaccc ccataagcag ttagcattaa accatcaggt ttgactcgcc acattcgcta    240
tcgcaaatgc tactaattca tcttaatctg accccccgg gaaggaagcc atttaataga     300
taatctgagt cgttccagag atgtacttct cagataaacc gtgaacacta ttacgacata    360
tgctgaataa ccagtatgta tggctgttgt cgactctcat tcctatagtg gagagaactg    420
atacatacat attccctaca cggatgttaa agagtcgcag gacctggtga ggcactggat    480
caacaagttg ccaaactgag tgccagtgga gctaatcaca ccttcggctc tgcgttacat    540
gcgttagtga aggtccttga ggtgtgccag caaagattgt taacatataa tctaagggat   600
tatatggtgt atatgggact gaaaacctag aggtctgtgg ggaagaccg tacagtccct    660 gaccatcaca ataaaaaata gccaaaatag cgtgccattc taaaatttta attttaatc    720 aatcgcgact cctttggttt catgctagtt gattctattt aagaatccaa gtgagtttta   780
atcttaaccc taatgattta aggttccagt aagcaaataa acgactcgcc gtaaagcgaa   840
attgatcgat acgtttcttg ctttatttt gggtacagca atccttcgaa atgttggctt    900
cgtaattccc tccagtaact taatcagtt aatttgcatt gtaagaaaac agcaagtgaa   960
tcatgtcgcc gcttcagtaa cttactgcaa aatgaaagcc taataaatag ttacccatct  1020
```

| | |
|---|---|
| atctaagtat aaacgacttt tgcttatgtc cacccatgct aggctgtgaa tcctcttacg | 1080 |
| tataacgtgc tttgcgtgta ctttcgaact ttctaagtat caatcgcaaa tcgaagtaac | 1140 |
| ttaccaccgc tcgtaggaat tgcatgttaa aaagggttaa ctcccttcgc tttgtcgttt | 1200 |
| cccaacctga tgaaggaagg tgaaatacaa catatggaat gatatatatc acaaatacac | 1260 |
| acgactctgg accagtgcaa agtagttata aactcaaaac gcccccgaca tacattaatt | 1320 |
| ctacttcgaa aaatatgttg ccctaacgaa atggtttgcc taacagcggc aaaagatatg | 1380 |
| tcgactcgat tgtatttaaa tcgattatta agattgggat gagggccacg tagccgaaac | 1440 |
| tgcaacatac cgaaatgggc gttacaatgc attaattata atttattggc gctcagcctt | 1500 |
| aattaacaat ctaggcgtgc tcatactgtg tactttaaag caccatttac atgtcataac | 1560 |
| agattattga tgttacgtaa aattcatagt atacagtatc acctcgatca aattcatatg | 1620 |
| tttttatttt aaacaagagt actcctgtgt cgttctgaat tactattagt caggtgcgtt | 1680 |
| aagctctgca gaacgatacc gactatctgt gcatctacct gattcgaaaa tgaaggcgat | 1740 |
| tgggactctc cactagttct gagttgtcct cctcgattta caaaagataa cttcagctgg | 1800 |
| atgtttatcg aacgcacaaa tcttaacaat ggtttaagta gccgaatcag attcgccatt | 1860 |
| caaatctttg ctctagtttc atcagtccga gttactctca aaataacaac ctaactcgtc | 1920 |
| ttgcctacac tggttctggg ttttatattt agagacataa tcacgaaact tcatgcacta | 1980 |
| tagaaggcac catgctgttc | 2000 |

<210> SEQ ID NO 48
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 48

| | |
|---|---|
| tgagcttcgc ttttttccaga gtcgctgact aaagtgaagt gtctagtcgt tgtccatgcg | 60 |
| atatcggggt ccatcaacta gaattcattt acggtacgcg ttgtcatgcc ttatatttag | 120 |
| caataagact aacggaagct cctctggagg gaaagtaaga acgtcccccc gggaacatac | 180 |
| ctaaaataaa ggtgcatgaa ccatcacgga gtggagacgc aaaagatcaa ttagtacaaa | 240 |
| tcagcaggag acatgcaaag accgcgcccc tttctttta taccatctta atagccttta | 300 |
| ctgatcgtgt atgttttcat cgtgcaccta attatgaaa ttctatgaag cttttgctcc | 360 |
| taatcgttta gtaatgctct cggatgccac gttatcttac tgagaagccc gtgaccaaag | 420 |
| catggtgaca atagaaccaa tatatatgaa aataccgggt tcgtctgaag actgtgtagt | 480 |
| aacaaaggta ttcttgtgaa ttcacgtttt taatctcatc tactatcgga tatgacaaca | 540 |
| aactctgatt agggtaatat aaaatttacc gttcggccta attaaaggac aaccggtatg | 600 |
| taaaacagca acatcaccta gcacgaaatt tacctatgag tgtggaattc gttagcgctg | 660 |
| tcgacgtgca taacctacgg gttgttgcat acgggtcagt gggataatgt tgactcggtc | 720 |
| cttagtaaag actagctctt cttattcttg cgcttgtaac tgacaagtcg agttcacgtg | 780 |
| ggcgcagtaa agtcgggaag acggtaatcg caaaagttcg gtaaaactaa cagttttaa | 840 |
| cgagtccgta agttcaaggg cctaaatagc tggaggattt taacgtctaa acattcggga | 900 |
| cacagtgtat gacccgcata aaaggttcaa agaaataata cttagagccg tcgttcggat | 960 |
| cttatatgtt tgaatgaacc cttaatcacc ctataacatg aagctacgac acattaatca | 1020 |

-continued

```
gatcaaaacc tacttagagc tcgtccgata ctacaacttg aaatcttcca ccaaaactaa    1080
agggtccatt atgtcaaaat accatttcta tttatatttt aaccatcaat tcgcctatac    1140
ccctaatcag cattaatctc gcttaaagat ggtagagtta aatacaacgc agagctttta    1200
tactaccagt gatggatcac aggattgcgt ttcaaaaggt gatagcaatt accaatgacc    1260
tttgacagta atgttacatc ctaaccggat tatttggaat accctctatt tgctttctgt    1320
ttagccgacg cctgtaattg tctacctgcg tgcgttgtga tgccggtccg ctcgatttaa    1380
gcactccgat atctcatgta ggtgtggact ttggacaagg ggaaataact ctcaatgaca    1440
atcgtactgc ttatgttagg caatgctggc atatgcaact ctgaggctaa ctaagttagt    1500
cttgtccgtg atctcagaac agtaactatt tagttgcttg cgagtatatt tcggtagaga    1560
cgtatcttct actaaacacg gttaaatatt ttttggttat ctctcgcccg gtctagtagt    1620
gccataacgt ttacgaggtc ataaactgt catacattgc aaggcgcttt atctcaattg    1680
tgaacaagta attatagcca tgatacaatt tttggacgga acttgtttta tctaaatcga    1740
aagaacctac attgcctcgg catagacctc ggaagcagct agttcactag ctgcttcatg    1800
atggtccaag cttgtgaaag attcacataa aatcaacctc cgtgggagtc tccgatggac    1860
gaagctgtgt gactggatat tatctcatga ttgcgtcacc cttaacatgt gtgaggtaga    1920
gctaactata gaaataccag tcgagttagc gacataatgc gaattgatcc gcctgtcaat    1980
tcctccttat acgcgccgtt                                                2000
```

<210> SEQ ID NO 49
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49

```
attgtccatt cttgtatttg aatcactccc taatgaacca aactctctaa gcccattctt      60
gtagtattta acacacatga caacggtcca attttcatgt atagtcggag taacgcgata     120
tactgaatct tctgacttat cagacatata agatgtaaaa acagcggatc aaaagtgttc     180
tctgctgggt gaaaaatgac aattaagcgt ggtattatct ctgtaaataa cacagggatt     240
tatatgtaag gatcgcgccc tcatacattc attaattctc actcagactt ccctccttcg     300
ggctacgtta gattgaaatg aaaataacat gttgtaatca ttaaatagta catactgagt     360
ttttaaagtc gaatactaca aaaaatatca tactttttt accagttcag tattggagtc      420
gacacatgat ctaacataac agaagacata gcgatgggga ttatcgacct ttttatgggt     480
agtaacaggt ggttgccgga tgcactagca tgatcaggtc tcctactcac acagtccttc     540
tgactgttag gttgtctttg cttataaaaa tactcggatt attgcgccac aattatttga     600
tcaacgagct tcttggagag aataaaaata ttacacttcg gatagataat acaggttagg     660
ttctcctatg aatttgaaga tcccatgttc gttaccgtcc aagagccacg gcttgcttgc     720
tcgaaattaa agtgggcatt cgcgcgggat gggaagtacc ctcagtcttg acaattccca     780
tcgtcaatat tagaacggtg gattcgccat caccaggaaa cgtattgctg atgatgattt     840
caatactgaa gtcgtacact tctcacccgg aaacgttaaa aggacgataa tgacttaatt     900
gagatcatcg aggtacgagc ccatgcctta ggtcgcttcg taggggtcct ccttaaagga     960
```

```
gactgtttct tacatgattt gttacttcgt tgaaaataaa tcatggatcg acgtcaccaa   1020
ttactggggt acctgagtat atagcgtaga acgtgaaagt gattacacct gtataggaaa   1080
tgatgagctc ggggaaccat aatgaattat agtgtaaaga taaaaaactt gccccgtgcc   1140
acgagaagga atgtagcaga caatcatggg gacattgtaa cttacccaga ctttaatttc   1200
gttttcacta taccactcaa ttatgatgtg acattctgga attgatagcg tatgttgcag   1260
ccttctaaac tcaacactga gctccttaag ggttattatg gttatatttg agactataat   1320
ataatccgag ttcggtcgaa gtgagtaatc tttggagggt ttagggggggc agaattcact   1380 ataagcagca gagattttct tagaaagagc cgggtcccgt tccaataagc cctaccggac   1440
gtttataatc attggtgcat cagtgaggcc ttctgttcat cttctattct gctgtaccct   1500
tcttgcacca acgcgttgga tccttgtatc gagtcactgc caggtttgtg gattttttgc   1560
agcccaccct acgttatatc ttaacaatcg gataattaaa ccaagctatc gaatgctatg   1620
agctaccaca gattatcatc gattgttttc cctatcatta cgatccctga cggactactt   1680
agtatgtcct tttcttaata ttcgttaaga actggagtac aggctgatta cacaaccagt   1740
aggattagga ttaaatagag aaatgtatcc ggaaaagcgg agttactgtt tgggtcttta   1800
accgcgaatc gcggttttt ttctaatatg cagtgatcct ttatttggtt actgtacatc   1860
tgctgaacac gctatgtgga tctcccacag ttgcaagtgc aaaatattaa taaattaatc   1920
acaatacagt acagctagat ttcatactaa atgctgattt tgaccgcac cctcgagagt   1980 aattcaatga cggccatgta                                               2000
```

<210> SEQ ID NO 50
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 50

```
aatcagaatg agcagatgta aaacatattt atgtaagcag gttatcccgt atggcactcg     60
ttgctctaag tagatgtttt tgtctcgggt aacttatgtc cccatcctca gagtgtattt    120
acttttattt aacccgacgg tgagaacata caacgggtca acaagacaat acgaccatta    180
tactgctaaa ctctcttcct caggtgctat atgagttacg acacaatttt tgatgttaaa    240
gtcgacccta gctgctaact gaacttctgg gacttaaaac taccagaaag gatgaagaat    300
tagtttggtc aataactata tacgaaacgc cctgaaggaa gtcgtattaa atttggagtg    360
cataagacat ggtgagcgaa aactaacacc tacctcttag atacagatta cttttagtta    420
tcttctggtc tatcgttgat cattctaagt ttattcagca ctagagactt ttggaatacg    480
actgccaaag ctagtatagg attatctaaa gatcattatt attaacggat aatgcgaaat    540
ttgctagatc gtatatacta ttaatgcagc aacttaacta agatatatt tacagtgggg    600 cttatgcaac cggtgagccc tcggttcttt atgattcgtc aagtaaagtt gcacaacgtt    660
cacgatttaa tcttattctt tgatcttggg ctgatgtatc ctcattattt atgatagaaa    720
attgattggt gcatttgatt cgcccgatac tagacccaca gctgttgttc gatcccgtat    780
acaatgagag catgttcaga tcaacagtag gtgtaacatc ttatgttccg agccttctag    840
taaccaacga acacctggca aatgaatttg ccatcttttcc gctgtacgaa tagggggtaat    900 gtgcccttga tttaaaatgt tatcgatagg ggaactacag atactgagaa ctcctgaaac    960
```

```
gacgttaaca aacctcctgc aaaacttgca ctctttgaac gaggttgcct agtttccaga   1020
agtaggttct tgtcacttga atttcgatgg aattctcctt atctatccag tgacgaggaa   1080
gaagaaatgg gttttacaa ggactaagtg tttagacaga aaaactaatc tttcagtaaa   1140
ggtgagaagt gattttgcag agggagattg tgttacgagg atagtactga cgtttatatg   1200
agaaatagtt atcgataatg tgcgtgtctt taccaaggga ctgaccaact gatgtggaaa   1260
tttaactctt catgatcaca taatttcaat acgttaacag ttagaagcgg tgatctttac   1320
aaagtagaca atgagttatt gtcccatagc aatgcctaat gtcgagcgtg cttcaaacaa   1380
ttgaatggcg ttatttttg atccttagga aacaaaaacc agcaacgtaa cttattcttg    1440
tatcttcatg taatcacatt accggtatag agatggtttt acatatacgc acgttacttt   1500
gagatagcga agcatacgaa tatacacgat acaatgtcag aaggataaaa tcactatggc   1560
ctcactcggt gcatttgatt tcaaaggctt aatgtagctc tgttcgcact cgtggatata   1620
gttggagcca gatagactag gaagatgttt gtttagatag tatcctcgtt cgtgcataat   1680
atccttgaga tagtataggt cgaatctcca cagcagcaag attctccgtg agcattgcca   1740
ctctttcagt agtaagccta agtaattcat taagcgtaat tagagactta ttttccatat   1800
ctgcgcgtcg agtttcttct gcagccctag ttaggagaca tacgggacgc ttgcgttttt   1860
atcgtagatt cacttagtac agggaagata aacatgagag gaaatccgac acctaacaat   1920
actttcaaac tgagggggctg gattgtactt accttcacat catcgaagtc aattcttcac   1980
cttcacaagc tctttcttcg                                              2000
```

<210> SEQ ID NO 51
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51

```
atttacaccc atgccgaaca taaataaaca aacacaaaag gatgagagga ataatgggtt     60
aactaagggg agtcgaatcg tattgatact tatgaatggc tatgttacac tcaggttgta   120
ctggatttcg tttgcgctac agcttagacc tttcgctaaa gatacacgcc gcagtgtctg   180
aaacagacgc acatttaaac cgctgggctg ttaacgctca ttctcgctga actagtctgt   240
catttatcag tgacatcagc ttatctccaa tcctcataag accgtcgaca ggaaccctca   300
attccactcg taacagtccc acgctgggtt gcgtagtctg ttgtaagaat tcattcatgg   360
ttgaaatggg gctgatgact atgaggcggc atcattggt atggtttagt agacgatcag    420
aggaagtctg tatagtcagg gctcaatatg tatccacgta gtaatgttgc ctgctaccga   480
cacgatttag acaacgtcag cgtaattacg aacacgacct cggttccacg tgtcatcgtc   540
tagatggtcc ctttgttcgt aggcctccaa gacctcagta atatctaatt cgagcttcaa   600
gtttgctaga cgttgacttg acgtagcaga taaatcgcac tgtaatggaa tgatacctga   660
atcccgttaa cttccagcat ggcacatacg attttttaaat tacgcttaag ataaagaagc   720
agtgcggtct aatccaaagt gcacaagcat atcaaaactc aggtctggtt tgtacgatta   780
tttggagcag attttcaaga tagttatgcc aatctctcca taaccatata cagtgacggg   840
gaccctctat gatacgtcat ctccgggacc tactttgacg ctggagtctt acagatggtg   900
```

```
ggaccatttg tgcttaagct actttagtg cggtaggagc cctccacaat atgattcaaa    960
cctaaagaag ctaggagccc tctcgaccct ggtacttggc attggcttaa atttcacgta   1020
tacgccatag cagattagtt taatctccga ttttcaaaat actagatagg gagagttcta   1080
taccacatta actcgccccg atgggagaac gcacaagagt tagttttcga cgccgcgtaa   1140
aacaattcaa catggccctc gagtctgcta ctgtagtgca tgaaagcttt cctagttggg   1200
ctagtagccc aagattctgg aaaaattcaa gttagtcgac agatgttcc gccttacgag    1260 taatttaaag aggttacccc gagaccgcaa agagtttagt gcatcttatg tgcattgtgt   1320
tgttcgtcag ggggctttgc acctaaacgg tcttacgtac aagctcagtt cgtggataca   1380
tgaaagtctt ggagtcaaga cctacaaatc gacgcgattc taagtctaat gtatccttac   1440
ttcgggcgta ttgtgatagt atcataacgg ttaagacagt ttaggataaa ccgcagagac   1500
aaaaaatctc gttcgtgtaa ctgagtatat agtgtacact tgtgcccgca aatgcatatt   1560
attgatcgag taatttaacg tgtgcctcct tggtagaggg tttccctaac atactccttt   1620
tcctgattac ctcagtctcc tgcttcaacc ggtctcccata agtgagaggt tgtgtgtacc   1680
gcactttaga agagtagagg tttggcaaat tttgggagca ttagactagt cgaatttcat   1740
acttcttagt cgtctgggag aacgtaagac ctgattaaac gcatgataca cgaagtcatt   1800
cagttcttca gttaagaggt tgcatcaaat agcactagct taaatgtaaa tcgtcttaag   1860
tccaactatt atgcggcact tgatcaccat ttcactcacc tcatcactac gcttgatagt   1920
atgatctcat cgtgatggta cccagttgag atcagcgagg atctcctcat aaatttacac   1980
attgttaaaa ggtcccgcgc                                              2000

<210> SEQ ID NO 52
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52
tagatctgct ttgtgaatgc cgaatttcag attgactgtc cgcgcgctag ctcattatga     60
cccggcagtt gaaatcgtat agggttggac ccaactacta acggaactca accactcgcc    120
ctgtacgaga tcacagggaa cgtcggctaa ggaggttatg gtggccttac cttagcacta    180
tataaagtgc gttcgaaacc tcagtgattc cccgatagta tgatttttaa gttctaagat    240
taaatttgat acatcagttg gtcctagagt tagtgctact aagcttaaat caaccaaaat    300
tttacccgtt ctattcagaa ggaaactata gtggtagcaa gtgtgacagt aggtatagac    360
ttaaatagtt acggcgaaat agaaagatta cgacgttcag ccttgtgtat cgaatttgtg    420
actttagagg cacacagagt aatggaccta tcatctacgt cctgtcagag tatcatgtgc    480
atgattcgac agaaatctca ataataaccc aaatcgggct ctcttgcatt gaataattca    540
tcatcaacat gaggtaatag caaaatgcct ttacttcagt tgattagggt gatggccgat    600
cacctatgta tttgaacata tattgtatat ccggtcggaa tatggcatcc ttagccgtcg    660
tgcgccggct ttcggaattt gatctgtctc tgtttagacg cgtaacctca attcgccgca    720
aactagatca ctattctaat aatctcacta ggaatctatt cgacatgcga tctttgatta    780
taggattcag aatctaagaa attgctacga tggggtgtca tagcgatgtc tatttgagtt    840
tctatagtga attggccatt tgttttggca tcatagatcg ctgacacaat cattgtgtct    900
```

```
ttcatcgatc tggagtacag ttagaagaga agcgagggct ggtaacatgc ttatagattc    960
ttatacttac taccttaggg tacactaaca atatttgaca ttataggtcg accaaaaaga   1020
tttctctatc aggtttagag acaaagtcgt cgacatattt ctgtttgaac tcttgaggat   1080
gcacgaaagt gtctatcggg gtatcagtga aaggcgtgg caagcattct ctaggtgaat    1140
tccacccttt ttagtcctcg ttagtacccc gtagaccgcg aacatcgag aagttattcg    1200 taaacgtgtc tatctgttct atgttaggag taggtcattg aacaaattga gctttcaaat   1260
agattctaga atgtagcgcg taagtatgtc ccgatagcgg ttttcagtgt attagttgca   1320
tctaatgtaa ttgagatgaa gaaaaccttg gtcgaagaga catgcctaaa gaagaaggct   1380
aagtgaaggc ctttatatca cgtggttcat agcccattat ataaaattt atattggaga    1440 tgtcccattg gtattgatag atggttggta gctgtcagca gtgcgcccta ggtaaaccag   1500
aagactcctt aacagatcgg tataattatt cgaggtttcc ggctctagca ttcagacatg   1560
gaaggttctt tctaagcgga tatattgctc gaagcccgtg aacctttaga atcaaccttt   1620
attatctcta accatctttt ttacgtttca cctttaactt acgcgaatcg attcacgact   1680
gccgaagtac aaacgatgac tcagtgttgg ttttcgctac aacattgagc tcagctctat   1740
agcgcggact acaagttctg cgtagatttt gccaaaaaaa gttgcgggta gccttattca   1800
tttaacgtat gactgggagg cgctcaaatc tctcactgca cctattcgca gacgcaaatt   1860
atggcgtcga ccccaaactt tcaggtaaat agctcacaag attgaccatt ggcaagtttg   1920
aactagtgtc gtaacgtcct gaacaaatgt ttttctagcc gctcctgcta accttatgga   1980
cattttcctc ttcacccctg                                               2000

<210> SEQ ID NO 53
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
aaactacaga agaacccaaa ggctactcac tcccttgct gtgttcagct cgctggctcg     60
tcaagataac ggactcatgt ctgtgggcaa agcaattat tacagctata ccttgtgga    120 aaagtctcct tgtaaaattg ttagcaatat tgtttcgagt tatatcgaat ttaaggttta   180
ttgttattcg tgaccataag gagctaacat gatgcggttt aatgcgtatg aaaagcgat    240 agtgttttta gtgagggaat gtagaagacc tcgtttcaac ccttaccata cccgagggtg   300
tcttaatctg ttattaaata aagagcagca aaataaaaaa aaatgcagt gtctatcaaa    360 ttcccaaatt tggctacgtc gttcactacc aattttcaaa ataataagaa gaagtatatg   420
gatccagtct gattgtcttt ccgatcagca atataaagca ccaacgtctt ataagagcta   480
aatagtgatg attccatgca gtataattca attccctaa agctactgtc gataaacttc    540
atataacata tgtacttgga ccgtttggtt tggacttgac aggctttaag cagtctgcat    600
catgagcctc cttctagatg tgcaagcatt ccccagaggc ggttcgcttc agcgtggtaa   660
ggaatgatct ctgggtcgga ggtagtgcag aatgaccact tatcctatct agtggtttac    720
tttatctaaa acaacagggg actagatctt attatacggc caaaactgaa atgaagatca   780
tctcatgaat attctcttaa catgagaaat ttccgttgtc aattttttaaa tggattaatg   840
```

```
tcataaaatc tgggatatgg cgagcttaac acaatgcccc tagtttacgt taagaaacat        900
ttgatacatc aacaaaacgt aggatccgcc ccggttttt ggaatccact tctagaagca         960
ggagcgggtc gctgtattta agtcataaag gacgtcgttt tacgaacaag accgtgtatg       1020
aatctggact gttacaacgg cccatcccca ccactagtta tactagtcac cgaataatct       1080
gaactatttt actagaaagt ctagaaattc atcctttgac ataaatggat tggaattaaa       1140
aaaagaattt caaatataat catataaaag tggatgcacc agagctcatg cgacgtcatt       1200
ctacgagcga tttatagctt ataccaataa accccgcgtg tattaacggt ccagtcaaaa       1260
atactatgat accgaacaag gtttatcgac ttgtcccgtt gaaatcctag atgaagttta       1320
taaccaaatg gcgccccttt agtgacgctg taaacgcaga tttatcaaac aggaaacatt       1380
tctgattaac cagaagtatg cgtagtgaag gtatatcgcg cagtaacatt caggtgcttc       1440
ggggattcaa aaacgtgttg ctggtatagc tcgcctgttt tatcgaatgt agtctcaaaa       1500
tctagccgag tttatcaact ggtcgacgct ggaagtctgc acttgaacat cgttcacatg       1560
taagccagag ataatggcct cagcatcgtc ttattgctaa tctcacgctg ctttgtcgcg       1620
acgtactctc tgcattacca aatgggatta gtttaatttc gttctctggg tgaccttgtg       1680
cacgctatgt gggtttgtat tagttgatta aagagtccct ttgaagatgg cttcactcac       1740
cacatgacta cacttcctat cgaggtaagg aaacgttttc ttgtgcaaac accccagact       1800
taccaagttt aaagttttgt ataatattaa gaatttatct aacactgaga caccatacac       1860
agcttccgta ccctattggt ccacaatata agacgttaga tattgccaat aaatgcttca       1920
ttcggttttt tgttagacaa ttggaaaatc ttatacataa catataaacg tttcgcatcc       1980
ctggttcctt ccgataggtc                                                   2000

<210> SEQ ID NO 54
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
tcgttttatc acgttttaac attgaatctt tagtgcaacc aagagccact tctcctgggt         60
tataatcatc atctatttag cataccaacg cgtttggctg cctcggtttg tatatagtcg        120
taaaagcctc cggtttatga ggtgatgaa attagttgga tacttgaata gataatatcc         180
catgcggtat tcacccactg aatcacatcg cctgatgatc cttgctgttt gcgggagagc        240
tcttctaatg attttgcaa atgctgtgca tccctaatag tcttttacag ggcaaagtac         300
agggattgac agcccccgaa tgtctacagc cgacaaaccg aaagtcttct accccgaggt        360
agctgaaggt gcatagacgt agacatgttg actaatctca tcttgtctac tatcttgtac        420
acaaaatcaa aattacaatt atatggaagg catgggatga gtgatcgtta attagacagg        480
ggcgtctttg gcaatgcatt ctcttatgat aaaaggttga ccagattact gctcatgact        540
tagtgtccac cggcccaaca attaataatt aagagactca accgacatac gttaataccc        600
aataatgccc caatacccag actttacag ggttattcgt gaacatgagt ccctcgacat         660
cttcccagat ttaatcccc atattactag tttgtaacag attggttatg ggactgatta        720
gaacagggaa tttcagctgg aaatcactac taacttattg ctagtttgcc gatctaagaa       780
gagtctttgc taattgattt taaagagata ttctgaacac gtcaatatcc aaattttatc       840
```

```
cgcaccattc tgacgtaatg acgcctagag aacgagttgg tggcagtcta tcgcttctgt    900 ttatttaac cttcaaaata tgataaggcc ccagttataa actatttttt acggcaactt    960
cggattaagt gttctatacg ccaaaactat tgatttactt aacatttcat cccgagaagc   1020
tccgtcttat caagtacgag atgatcccct attagaaaaa ccacggctag tatcaacgac   1080
atgcgttaca cacacgcctc agtggggggcc gtcacacata gttcaaatat tgatactgct   1140
cgtctcgata tgtgttcaat gtcggcaatc aagcagtgtc ggaactgaac ccgcactacg   1200
ggctcgtaaa cgacccaaaa tcccctaatc aatcattgta gtaatggtag caacttgtat   1260
gtcctgtcaa cgcaacaccc tcctggtgaa ttattctatt agaactacta aaaataaac    1320 ccgaggtcca gctctatcgt acacgacacg aaaacgtatc aaggtacagt tcgatagccg   1380
tacttattat ggtgactagc gccatataca aggtcataag ggaccttgtt agcggtgtgt   1440
tcacttcatc gtcagcgact cgttcgactg tcatttcaat gaaatcttta atgagtttaa   1500
tagagtagga agggacagta agatatttta tgaataatgt cgtacgtagg atttttttca   1560
aatgatgact atcacagtac ggcatacgga aaattcagta gggaattaga tcaagtgtaa   1620
aattactggt atactagcgt atacctagta cgatgataat taacaatcac ccccagcatg   1680
atgtgagaat agtaaagtat ccatatttac aactaaaaag ctcggaagct gaaatcccaa   1740
accgcttgaa cagctctcga ataataccgg tgtttatcat cggaaggaca gcgcctcagg   1800
attttcggca aatcatagct cttatcttcg atctaagcgt ttgatgaata ttagaatcgg   1860
actgagatat aaagaatagt gatatatgtc ggaaaacgac gatgtcattt tagactatga   1920
tcttaagacg gagaaagcta ccatcataac accgacttgt cctgccattg tattactggc   1980
tttccatcgt gagggatagc                                              2000
```

<210> SEQ ID NO 55
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55

```
attatgatcc caggcttcgt tgagtctaat agctatccga ctaatcaact tctcaggcat     60
gtctcgactc cgatcctggt ggccttaaat ttcttaggtg cacggaattg tgtgtacctg    120
gtatgtagag actataacga ctcacttctt gccaattagg attcaaaact ccctacttga    180
gcaacgtgtt cccccgcatt atccatatca caacagttga atttttctaa cgtcttctcc    240
tcaaaccgga gggaagtgtg aatgtactgt tgtccggcca tgcctgaggt attttgattc    300
tagttagtaa ttacattagg aactcacttc gtcaactcaa acacgttgac aaatgtgcag    360
ttgggtaata catgccgtgc aaagcatgta tgaccgtggt ctactagatg gcttcgcgat    420
ttactgtttt gcgatatagg cgtcggaata aacttcagca ggtgcggatg ctgatctggc    480
gccgtcattt ataagatat ggctacgact tagctcgtga gatcgagaca aaatcaagat    540
cttatcgtct tccacaaaaa gtaccctcaa tcggatattc ggaccgtaaa aaagagcatg    600
gcgcttgatt atcgtagcta gcgcccaagg aacaattgta ttattcagat taaaccccgg    660
attggaccta ttttcatcct agtagaaacg gtgacgacgc gacttccgaa aactccagga    720
acagtgcggt ctacccaggt tgtagtagat gcccgttttc tcagggcaac cagggcatca    780
```

| | |
|---|---|
| tacgttaact taatcggttt taaccgcgaa gttcgatacg gactgattta ataataaacg | 840 |
| cgaacaacct agtaatatca taaattgcgg cgtgtacttc agaaatggta actaaatgtc | 900 |
| agacttcttg aaaaggaaca agcgcgcttt ctcaagtttg ttgagtctca tcataatggg | 960 |
| ggaactccgt acatggtccg atggactcga tatccgaagg cgataataat tatccccgtg | 1020 |
| ttctacgcta tttacgaact attaataatg atcggtcatg tcggtggttt attccattcc | 1080 |
| tttatctccg ataagtacgt taccatggga ttacgcaaca gctagatttt caaatgatcg | 1140 |
| ggtcgaatcc ggcctaaacg aaacgtcgct agcgattgag aacggatgta cagatctctc | 1200 |
| gaatacatga gatgcgcgta atcatagtgt acgatagaac ctcatgttat caacaggtgc | 1260 |
| tatcttagta aaatacatag tcatattctt tacacgcgta aagattcttt gagccagcga | 1320 |
| acatggaaat gggcgttggt gtgtttctcc ccggctttcg taatagtcgc caccatccgc | 1380 |
| ttgggtgctg attcgatcag ttctaaccaa ggagcctgac agtcttcgat ttttgtgtat | 1440 |
| tcctgtagaa tatggcacca taattcagcg ggaaaaaatt gtcaactcag cagtgtctat | 1500 |
| taagagatta ctctcgcttt tggactggta cagcctttac ctagtaatat agacggacaa | 1560 |
| aaattttgtg agtcagacgg catatcctga aaacaaatac aagtgtagtc tacgttttag | 1620 |
| aatagactga gtggcgtcgg tagaagttac tgctcgagtt attgtaaaat tcttgccaag | 1680 |
| aacgaagtta ctccatatgg aaaagatgac tcaatcgagt cttactagat tatttccgaa | 1740 |
| gtcttaaacg tttagaccta acttagtcga agttgagcc ccagaagtca tctctcccag | 1800 |
| tttatcaata gtgggtggaa caaattcatc ggctgttgac cttattgcat ccacctcgtt | 1860 |
| ggagttatct tgccatgtat cctcaagtgt tccgacctgg aagtatgtag aaaccccttt | 1920 |
| gaaatatcta tcacaaagca atatcttata ttatcttcgt agtttttaga attatatcta | 1980 |
| tttaagggca caaagtctag | 2000 |

<210> SEQ ID NO 56
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 56

| | |
|---|---|
| ttaacaataa atgattaggt tgtgcttgcc tcctaatttt gtttaaaaag ttgttcttct | 60 |
| gctgactagt ttgattctac tcatttctgt agtaccggtt cggcgtactt tttttagagg | 120 |
| aaaatactaa tgtgcggagg agggcttaag aaaactgcag atcactggat gagcaggaaa | 180 |
| accgaaggac gtgcacgaaa atcggacttg ctgttgtgac tatacgcagg ctagaatcaa | 240 |
| taccgtcggt gctcgtgcct cagccgtatc agatatgatt cttgagcgat gttatcgttg | 300 |
| gatcaaatag ttcttttcgt ggaaaggtat ggttagatat ccggggcctc ttaatattgg | 360 |
| tttcgactag atctgacaga gtcgggtcaa agctaacgct gtcgctaatg atgacagtgt | 420 |
| caatctggtt aagtatactc tggagttatt agtcgatctc tctcagtgtt tcttaaggtg | 480 |
| ttctcagctg gccgggttgt gcgcttgtga gggagcgata gcagtttgtg ctcggtctac | 540 |
| gcagtagatc gttcacaact tagtcagacc aatttatatt cctatgccta agaaatagta | 600 |
| gatcatctaa atgtagttgc cgatcaactc aaaaatcatg agcagtgata aacgctagta | 660 |
| cggagctagc atatgcgcct gccgatagat tgcatagaac cacagaatct ctaaatttct | 720 |
| ggcactgact ttaccttact tgtctactga tcatttagtt ctaaggcggg tcccagcata | 780 |

-continued

| | |
|---|---|
| tactgagtaa aggaaattgc aacggtccaa caaagaatca ataagtaaat agaactcatc | 840 |
| aatctccatg gttttttacc ctgtggtatg agagcttcga gacagtacaa atacattcta | 900 |
| cgagtgcatt tattaaacac acggacccta tacaaattaa tagcatcact agctcgaaac | 960 |
| ctattacagc ctgaacgttt cgaacgcact tcggtataca gtgtactcgc gcgcgtgttg | 1020 |
| aaccgaaggt gctagccgaa ttagttggat tcgtatatat gtgggatccc gatttccaag | 1080 |
| tccttgctgg tttaacacac ggatattagt tgctattatt agcgtgtttg aaaaccatgt | 1140 |
| cagagttaac gaccggctaa aaagccgact tataaaaagc cgagtggttt ggcaaccttc | 1200 |
| tactggtctt ggaattaact tctgaataaa tacaaacatg aaaagagtga actgctagac | 1260 |
| tgcacctgtg aatgatcca taacagttaa attactccgc cgagtccatt ttgctgacgg | 1320 |
| tggattatcc taactgaaga gcgtacagcg attctgtcca accgttgaaa tcagtaattt | 1380 |
| tctataccta ctatcgtttg accaaactca gggaagcata cctaaatatc atcaaggcga | 1440 |
| gaaactttta gacccatagt tgtattatag tctaatttca atgcacattc tgttcaggca | 1500 |
| cagactgata ttgaaagagg cccgcgactt tgaaggtggg ctaaatttat gcaataatgg | 1560 |
| cacaccaatc aacacagtct agaacttacc aaaccaagcc tagattcacc tatctatttt | 1620 |
| tgatccgact gtataacgta ttgtaatacc tcaagacata agacactcat aacaatttaa | 1680 |
| ctttctctta ttaggaggct cctctatggg attcgtcgtc gagttaaatg atttgaggtt | 1740 |
| ttatgtggac tccgagcacg cccggtaaga atttctagga cttaggatac aatgcaactc | 1800 |
| agtggagtat gttcccccgt gtgatctata tgatagctga gtacgacaat aggcatgcga | 1860 |
| ttcagactat ccgcttttaa ttaccaatga atgtcacgac ggagaacgtt atgaaaggtt | 1920 |
| ttctctagca cgccctatcg ctcttatatg cgaaatacat tcctgcttgt gaatggccgg | 1980 |
| gattgcttac acattagcct | 2000 |

<210> SEQ ID NO 57
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

| | |
|---|---|
| cttaagattt cagctagaat ggttctggcg cgcctaagaa actaggttaa gtcttctttt | 60 |
| gcgcgttaaa taaaaatttt gtcggtagtt cttaaatggt gcacgaagtt gactgcatat | 120 |
| atatatgaag cacctaagag ctctatcccc ccttaaatgt caagattggc taatatacca | 180 |
| ccccatacac atgattaacc cggttacctt cgacaggttt ggatctttaa atacaattag | 240 |
| ttgatcttcg ctctggcaga gctcgggttc gttcgtagtg tataaaatat ctctacttgc | 300 |
| aattatcgtt taacccctgc aagagcgtct attggtcttg ctgttttctt acagttgtat | 360 |
| gctcgccatg tataggcagg taaacagact ttgacaaggg tgggcgagtc gcgtagaacc | 420 |
| tttccatgaa ggcatttatt tttgattatc tctgatacct gggtgtgtat aattggatgc | 480 |
| aacgtcgctt gctaagacat tcgagctcga aattctagga ttttgtctat acccttagga | 540 |
| atcttcactt ctataaatga ctaaaaacat gggaaatgac aaattagcaa gcggcgcttt | 600 |
| tttgaatcaa tcactagata tatttctaaa acttagcaat gctttcatga aaaccactaa | 660 |
| ttttaattac atatttgtaa ataacccgca tcaaacgcaa gttgatgtcg catcatatat | 720 |

| | |
|---|---|
| atctccatag tcatttctat tcaactggca tgttcggtta atcaaacaaa cctgacaaca | 780 |
| ttattggtct catcaaaatt tgctctattg gcatccagaa gattgaattt tgagtgacca | 840 |
| gtaatattac cctctgggac tacttgtatc ttttgtaaaa gacgtataat tgtagggaaa | 900 |
| atttgaagtt gtaaactaga acaatgaaat aaatcacaag cctcttaaat ttccgagtgt | 960 |
| gtttaatagc tgtccgaaga ataaatatcc agggaggatc tgatctctaa aaaggaaact | 1020 |
| ttcctaggtg caattcatgg gacaatagtc tttaccatca tttggatcgg aatctttaaa | 1080 |
| gatttaacgt aaaactgtag atgggtgaag caaccactgg tgtcaggatt gttgtaataa | 1140 |
| cctacaatac gaaaacacat ggaaatattt ttttcacgag ctatacacgt agttatacgt | 1200 |
| atgaaaacaa acaggactca aataatctat agaggaattt ataggttctt cgtgaacgtt | 1260 |
| tcgagagcat agacatgatt acaggctgca gatgattgct ctagggacac tggatacgtc | 1320 |
| tgtctcagta tattaagagg cattaactta tagagctggt ttgagttcct catgagagag | 1380 |
| aatatatatt tgcacaatga tactcaaaaa cttaccgctc tgcacaatcc gcacatcgcg | 1440 |
| atcatacgcg ccgttaaagt tatcatccaa tatactcata aatggtgtaa cctagctcct | 1500 |
| accacaaact gagtaccggg atcgctatcc acatcgctga acaatggga aagaaaggt | 1560 |
| ttccttcgag tcacgcactg actagatcta caatacttat gctctagaac gcgtgatatt | 1620 |
| tctatgtaaa gtaaagcatg ctactaaggt acatctaatt ttacgaaacc gtatactact | 1680 |
| actcgccatt ggtatacttt agactttgta agtaaaaaac gagtagggcc tcaaggacat | 1740 |
| agtcactgct tatacagcga aacgaagctg ctaacaaagc tcagaccggt attgctgtta | 1800 |
| gtatattctt gttagaagcg tacatcggtt gggccgtatg gtccgattac cttaagaata | 1860 |
| gttgactagg atcgtctcta aggtcgtact tacccaccta gcagctgata tcttcgatgc | 1920 |
| ctatatctgt ataggtagag attcattctc agcgcattgc cgcggtagat cctatgtaga | 1980 |
| ttatttagca tagttaatta | 2000 |

<210> SEQ ID NO 58
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58

| | |
|---|---|
| gaaccttggg tccttatcct gaaataaaaa gaaagtgcac gtctccgtaa tatatggatg | 60 |
| tctcagtgat atccacgatt acatcaagct gagttatttt taatgatagt tgactgtatt | 120 |
| gcctaaaacg tatctgtagt aatgaataca taaaggtact ggtgattgag aagttctcat | 180 |
| taaacgttaa aatccgcatc atctgtaaaa ggtgggtaat tgcactatag agggtagacc | 240 |
| acgcctgtag cccgcttaga acaattcttg tactatcatt tttaagtcct tcaatgtcta | 300 |
| tcataagtat tggacattgc acgagaaaac acgggacaaa atgctcgtcg tttgagacta | 360 |
| tggatcgcta ttcgggtcga gcaatctgaa acagatattg tcatgtttgg aaggtgagcc | 420 |
| cattagtagt aagcgcttta taccactatt caggagtaat aatttaagga gtgtaacagt | 480 |
| atgatgtcta ccggtacacg ggagattgta atacagtagt agctccttat ggcttgggaa | 540 |
| taaattacaa actgaacgct ttctttagag ctctagtgtc ctgatttatg ggtaaggcgt | 600 |
| attatctgca agtctcagtt cgggataggt attccgtcat ctaatattac ctctaggtg | 660 |
| tatactacca tcctttgcag actataaata ctatctatcg tcggcactga tagatggagg | 720 |

```
attccttgca agacctgata tctccgtctc catgtctagt ttatagattt gccttacaag      780
ttcatttatg catgtgtaat agaatgattt atatgaaccg tcatagttcc attttagcat      840
ccgagcgtgt gtcctctctc gtaattaggc gtacgtcgaa tcattttgct ttcactgtaa      900
ataggcaaag caaatgtag caaaggaagg aatgaaatga tcattctcat gctacatgtg      960
tccttataca taaaaatata tatacttgat taattgcaca tgaatcactt acattcgatt     1020
atcataatac atcccccact cggattgctc cacgaccaga tggttaaaaa gttgaatctg     1080
tgctttgatt tttaagtgag cactcacgta gtatgaaacc gctagctcag gttttttttg     1140
gggatcgttc agtattcacg aaagaagaat gcggcgggt ggttccacac catatcaact      1200
agtgtttata gttgcttata taacggcaac cggctagtaa atggtaactt aacagtaaaa     1260
tgtctaggat tagtaaacat atattatgga ggcgttaagg ctgtacgcct tgatagtaca     1320 cacctttta caatcacaat cctaggttga tctaaaaccg ttgacgtcaa gtccattata      1380
aaatcttaat cgcctgattt ccctgtccta aaatgaagag attaaagaag tgaaatatat     1440
ccctaagcca gaagtgggag aataccattt ggatatatgc gagcttctgc caaatcttag     1500
agatttctgg acttttcaat tatccaatat gaggcttgag gattaccaac tctggactac     1560
atgacagttc cacagaaact atttagttag acgcagagcc aattagaacc tcgacaatta     1620
ggtaaagtaa agtttacaat actgttaagt cgcgtaaaaa aggttgattc aactatgacg     1680
ggtatagagg aggaaataga ggctctcgtt agctgtgtcg ttggacatag taacttttta     1740
caaagaatgt tagagctgtt gaatatttac gcttatacaa agtatctgct gtatcacgac     1800
ggattttatc catgcagggc agtaatccat caggcttttg gagaggacag ccttgggaag     1860
gatatcgtca cgaggcgttt cgcactcaga cacccgaaaa aattacgagg aaatgataat     1920
cgtaacgtgg cgcctagcgc tggataatta ccataattta acagaggcca caacaggttt     1980
tcacccttca atgagtgtaa                                                 2000
```

<210> SEQ ID NO 59
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59

```
gattctgtac aattgtttca aaatatagct taacacattt gatggaataa taagggttcc       60
aactagatat agttagttag gagttacggg agtggtgctc gggtacaccg aagcgtttat      120
gtctaagctc tcttctgagg gggctcagac agctggtaca ataattcatc cgagccgcgg      180
tgaatgcggc atcaggcccc ttctatactt ataaagagc atatctaatt tattggcata       240
ttcctgcagg ctacataaag tcactcggtc gaggcatccc tattcgggct aaatttcaac      300
acgtctggtt tgaatagcga ctgttttta cagatggctt ggataaccaa tcaaccttca       360
agaagcacag ttcttatgtt aggaaccgta tgcaaccgta gactcctatt ttcacttgcg      420
tgagcattca acgaaattgg gaagacagat ggacttacat taacgtatcg gactacgatc     480
gtaatatccg tgatgtgagt attatagtat acaagagtga ggagatggaa atcatgacgg     540
ttatcccacg tagcagcaca cgcagatgca gaccagacat atacgaataa acttttttgt    600
acggttgccc ggtaaactag cctgggatcc cgcgaacaaa tgttagaata aaaacgcgag    660
```

| | |
|---|---:|
| agacttgctt tagtagcttt tcatcaggat tccttgcaaa agttaacac aaagtaagcg | 720 |
| tgttgttagt aatgtaatgt ttgtgaggta acactgtggg ttaagtagta ctaatgatct | 780 |
| ttctttgctg tttgactttc aaaatgcgtg gagttcagtg gtggcaaaga ttgtttaagt | 840 |
| cttacgtatt ggtagtactc gttaagcttg aaagtttcga ttatctcttt ttattccgat | 900 |
| ctgaaatgag cttgttctat ccgaagctga ggtagtccac ttagaccgat ctatcgctaa | 960 |
| cgagaataat acttattatt taaatccttt ctcatgccaa tagaggagac tgtcatggta | 1020 |
| accggtatgc ttgtgttcat attaattcta agatttgcta caggattaag tctagttcaa | 1080 |
| gtcctattcc aaataccaca atctctaagg cctcacacgc cttaacagaa aggggattat | 1140 |
| acgcgtcggt tgttcgttat gccttatagt actcaaccca taaatagatc gcacataaga | 1200 |
| gtatgaatcg gttgatgaaa aagtacataa ctcactacag tgccggatga gagattcccg | 1260 |
| tgaattaact agtggctaca aaacgtaacg tgcgaagagc aaaggtggcc gcgatattac | 1320 |
| ctttactttc ggtgccttag taaaagagga taatggcaaa atgaacgtcc tgggcaatca | 1380 |
| gaccagaggg aatatgctta gctattggct ttgtaattgt tgtagttttt aatggttcta | 1440 |
| aatatcaaca aataccatca tgatagttac cgatcagatg agcttgagcc gttgaaaaga | 1500 |
| atgcaaatac aaaatcttgt tcattaatcc gatgcaacgt gccggcttga aattcatttt | 1560 |
| cgaagtagtg cgtccccgcg tatagacgct acagtagctc cgaaggtcta ttgttagaac | 1620 |
| aacatttttag aaacgggcct aataggagtt cctcggaaaa aagaggaagg gacaagttga | 1680 |
| ttgtctatta agatagatga tcctattata gcgatgtcaa tactacgccc agtgacacca | 1740 |
| tcaaaataga ctggaaatga tggtacgatt ggatgagaag atcattagct gccttttacct | 1800 |
| tcgacgactt cgtcgtagtg agggttctga ccaatgtcca tagcagttga aagcgcgaca | 1860 |
| ttactcgaac aacgctgtgg tcactcttta atgattcgta taatgaatct tcctctgcaa | 1920 |
| cagttggaca gaaaagtggc ttcttgctta ggacctagct agactttgtt gcctttctat | 1980 |
| gtaatacgta cgcaaattcc | 2000 |

<210> SEQ ID NO 60
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60

| | |
|---|---:|
| cagtagatga ggataagccc aagtatcgat tccaggaagc cgccatatgg agatatagag | 60 |
| gtatctctgg cttcgcgaac tcacaaagga gtgtctcgat ggacctccat aggtaacaaa | 120 |
| gatcaaggcc ccttaccaac tcatgttcta taaactgaca tctatgcaat aaagttaaca | 180 |
| ccagaaggtg ggtcagacca caaccacaa ccccgctcaa ttttagaaca aagtctacta | 240 |
| agaggtgcga atcaagccga aaacgggagt ttattgtcca tatgatgctg gatcggatta | 300 |
| ttgtattata atagcctaag atcgtgtctc cgatccaaat gcgtgtacgc atcaatcctg | 360 |
| agagatccgg gatggttgct ggggttaata acttctcctt tatatccgga tgactgctaa | 420 |
| ttcctcaaat gcaatcattc tggaattatg aggcctatta aacgaattta acagtaccta | 480 |
| gtcggtagaa acaattctac cccgcatcct taagtctact ttcagagcta ctggcgcctt | 540 |
| tgacgcatag gtaaaccgg cgactagagg aatgtcgtat caagataagc cctaatttac | 600 |
| ttatgctagc ctgtgttcga taaataagat gtctgaattg aattcgcgca gaaaccagtg | 660 |

```
ctgccacggt gaagagtgat cggggcggct atcaactacg cggtgaacta ccccaaaaca   720
tttaggacat gcgaatatat caaagagaaa tcaattccat tagttcgaag atgagcacga   780
tcgttactaa ctgcagacaa agaaggcact attgatagaa ccgattgaca acccgaacgt   840
gtaccggagt ttggatcaga tcttgagact gcgcttaaaa gcaagaaccc atcacaaaaa   900
ggcaatagca ttaggaggaa tcgcgcacaa gtacaataac ttttccgta ttttaataat    960 attaattgtc cttctcacca cgaggccgtt ccttcgtgg aaccagtcgt cctactttct   1020
ctccgtaatt tcattttatt tagaataaag gtatatacgg acgactatcg ttcggaacaa   1080
ctaataacag tgcttggagg tgaatagaag taagttgaac tgagctaaag tgaacaacta   1140
caattcgtag ccctgatttc attgtcattt ttttctgac tcaacacccc aaagatcgcg    1200
caaagaataa ggccatagct caaacccgaa aaaatcttct aaggcctgat aacttagtta   1260
ttatatgaac accggtaatc cctgcatgca gcatatga aataaaatgc cgtcgttttc     1320
attgtttcgt ataagtaggg aacgaggtcc atgtgctatt tgctctttt atgtgtgccc    1380 aagggggtact ggaatgtcga gtaatactca gtccttcaat gctcatcttg tgaccaaatt  1440
cattggggaa ctccattggg aaaggaatct gtgagagtga atccagacta ggatctaccc   1500
acattgtagt ctgaatttta ccttctagaa agtaccgctc aagttgacta tatttacac    1560 aatgtgggct gatggctggt ctccggttga ggaaggatca atcatactca tcatgcatac   1620
atgaagatat actagtatga ttaacaatag gttttcaaaa cagacactcg acttattgag   1680
caccctattg gctaagcaac tgcatctgca ctagcaatgg atcttaaggc atcatataac   1740
cggttaggta cttctcttgtt aggtagaaca acacggttga tcaggccaat cgctactgaa   1800
gtaatgaaat caataaacac tgagtcttat gaagtactat tacaatctcc tagggtcgta   1860
tcagaccttt gttatgtttt aaggacaatg cgggatctct catccaaaaa gcgaaattga   1920
taccaggcat tggtagtcaa gattaccgaa ttattttacg taggtcatta tatgcctgca   1980
attttggcgc tttacgctca                                                2000
```

<210> SEQ ID NO 61  
<211> LENGTH: 2000  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 61

```
gtttaatctc cttgactaac aggagtctct tgccaacgga tgtacgtaac cgtatgttaa    60
gacattatga agagttaata ttacatgcaa ccattcgatt tgccataaat gtaccgaacg   120
ccgttatatt tacttactgg atgaaagatt caagaatcaa tataagttaa atcttaaaa    180 agatcaatca tacgtataaa gtctatttgc tattagagac gactgtctga tttgatgatg   240
cagcgcgttg ttataaacct cataaataag aggcggtggc tttcttacta ttagcacaag   300
tctcactgag tagtagaata actcttactc tatatgtttc atcaggtacg accccacgtg   360
gcaaaattac attttgcaca cgaggcacat taagaccgaa gagaacattt ggccgagagg   420
tatgtcaaag ccggcttaat gatatcgaca caactcataa atggtgaaag ttataaccag   480
gtaatcttat gggattctgt ggagtaaagc ccattggact tcggaataaa taagcaagct   540
aatcagttat aatagcatat atgttaatac caagcgtgga atgagcacat tttggcagtt   600
```

| | |
|---|---|
| taacactaag cttgataaaa ctcgtagagt agcgattgga cactacaaga cgcgtgtttc | 660 |
| gctagagacg aaccaccttg tgccaacaga ttactctgaa gctcgcctat ttgtggaagt | 720 |
| aaatattacg taacggttat agcattgtta acgatgattt tgtcgagtaa cggtatgaat | 780 |
| ttatgaaaaa cgtcaaacaa gcgtgatcag tttcgcatga tcgaattgag tttttgcccg | 840 |
| cgcagggttc gcgtcaaaac accttagagt aaatacttaa gaggaatcgc tacgtctatt | 900 |
| tgtaaaagtc cgagtaccca ccttggaatc cccattttt tttttccagt cagctcaacg | 960 |
| gttgaatcca cgtgtccgaa gaagctctga gcaaactatg gtgtcgccgt tctaagccca | 1020 |
| tttcaaacgt tatggagcgt tgtgcctctt tgttggcact tgttattcac cgcggcgaag | 1080 |
| taacgcgctc gtcaagcgaa tcattttatg cctactcggg ctatagttaa cggagttaaa | 1140 |
| atgcttcaag tgtaggtcga caaaagatca ggaattcgag ataaactctc catgtgaaat | 1200 |
| agcaagttta cgtcctcgtt tttgattata gactaagatt acgaattctt tagcgctggc | 1260 |
| tcatttgaat ccaaaaccgt agaataagaa ccccagactt atgtcctcga aattatcagg | 1320 |
| taagagaaca aataattcac gagtactgac agtataagcg cttatgtgag acgaccacgt | 1380 |
| aactacaatt tataaacttg accgttatta tgtagtattt agtggctcat aaaaccagct | 1440 |
| tagcttagat ctgtgagact gaccagctga cccacaagac ttttacattg aagttgcagc | 1500 |
| tatatggaaa cgtactttat aatttcttaa tgtaagaata aatttgctgt atcgctttgt | 1560 |
| tcgtttgaac tcttttctat gtaaaaggct gactaaccca ggaagagggg agcatatttt | 1620 |
| acaaattagt aagcgctctc tcattcattt aatgatcacc ttataccgac ttcagcctat | 1680 |
| ggaagatctt gcgctgttgc gtacctacag cgggtaaacg gatgtgttaa acacgatagt | 1740 |
| aatagtaagt ttccgttagg ctgtagttta aacagtaac ataagtgcta acgagatcaa | 1800 |
| cacaattcaa gttgcgaaag caagaaaatc ttgctacata tatcttagat aagtatgaaa | 1860 |
| acatagattg cgttttaca aaaagtacga aaacattata ttctcaagct cacgctccat | 1920 |
| gaacatgcca tggatgcgag agctacttaa tattatccgg taattattaa agtaactacc | 1980 |
| ggttgcgcac aacggcttaa | 2000 |

<210> SEQ ID NO 62
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62

| | |
|---|---|
| gactcttctt ctcagtccac gtttgaaaat cagacaacta catattcaat ggaagcgctg | 60 |
| agtcggagtg gctttccgat tgactgcagg tgtctggcga tagattatta aaataaccga | 120 |
| ggacctcatc tgtgattact tatgttaaca cgtcgttaca agcaaaatgt acagatcgtg | 180 |
| tgtgggttag gggttcacta gaatcggtgg ggcaaatttg ccgcaaccga tatcgtatct | 240 |
| gtcgccattt agtgggagct gggcgtgcta tcagaattta tttaaacggt ttggggacaa | 300 |
| aagaggacct tatactggta gtataccttc tttagtcttt gctccgattg aatacaccgg | 360 |
| aacctaattt gtaaagaggc ccagatgttg gacagagtgg ttatgagtgc aggtttatag | 420 |
| ttcaagcatc agaatagtat taagataaaa ctgagggctt tcaggccttg atttaaatgt | 480 |
| gagagtattg tcaggccatt tggaaatatc ataaatcct tgtgccaga tagttatgaa | 540 |
| gctgcttaga tccacttgcc ttcatttgag tctgctgact gccaattaga gtcctcctcg | 600 |

```
gtacgtatga atagaaaact tcaaatacga ttctccccaa tttgctctgt gcagccttgc    660
cgatagtcct ttatgtcata cactaggtgt gagctccaag ggtcttggtt ccagccccgc    720
aattcagata aacataagcc ccagtagcgg aggagatttt gaataccaaa ctaactttat    780
aacccgcgca tggccagtgc catagcgaat gcgcggggag aagtcatttt agaagcctat    840
caggcgatcc cggatcatta ccctcgtata ataaatagcc ttagctgcaa gttcgtgtcg    900
ccgccaacgt attcggtatc agactctgat gtcctttaat agtgattatg acgactgtca    960
taaactttgt agtagtgtat attatcgatt gcgttttatt catcttgatg atgggataca   1020
tctgcacttt tgagctaatc taagatcaaa tatctatttt cacgatcccg ctactacggc   1080
tcgagaaagt tactttaccg gaccgggctt aacacaagac ttacgacgtc ctggatagaa   1140 ttttagggggt ttctaaattg atccggtttg agaacttctt acttatattc cagtttcgag   1200
```

```
gtacgtatga atagaaaact tcaaatacga ttctccccaa tttgctctgt gcagccttgc    660
cgatagtcct ttatgtcata cactaggtgt gagctccaag ggtcttggtt ccagccccgc    720
aattcagata aacataagcc ccagtagcgg aggagatttt gaataccaaa ctaactttat    780
aacccgcgca tggccagtgc catagcgaat gcgcggggag aagtcatttt agaagcctat    840
caggcgatcc cggatcatta ccctcgtata ataaatagcc ttagctgcaa gttcgtgtcg    900
ccgccaacgt attcggtatc agactctgat gtcctttaat agtgattatg acgactgtca    960
taaactttgt agtagtgtat attatcgatt gcgttttatt catcttgatg atgggataca   1020
tctgcacttt tgagctaatc taagatcaaa tatctatttt cacgatcccg ctactacggc   1080
tcgagaaagt tactttaccg gaccgggctt aacacaagac ttacgacgtc ctggatagaa   1140
ttttagggggt tctaaattg atccggtttg agaacttctt acttatattc cagtttcgag   1200
gactaggcat tcttcatta agaccgaggc atgggttatt tttatattgt gatgcaaatc   1260
ggtttgcccc gccggagaga ctacatgcca gttggtaacg tgacaaggca tgtgcaacgt   1320
tctttagtgt cgctacggga ttctgaagtc tactgcttac ctgattatac cacggttcaa   1380
cttcggttac aaaggatatt cgctattgca cgggatggaa attattcat gtcccaaaaa   1440
acaaactcga caaggtgcc cacatgcggc ctcattttac agtgcactta tgagctattg   1500
cgagctccct ccaaatattg gtgggacagt aataaaaac gatctgataa aaatagtagg   1560
tatcgagacc taagattgga atgatcacat tcgcgtgtta taagattgga gatgttctaa   1620
cttggatgaa aatgttagtt acaataacca tatcctggtt cgaagagtat tgagatggac   1680
tttcgacatt ataatatgat ttcagaaagg tcgcacatga ctgatccttt cctctgcagg   1740
tggtcctgtc atcgggtatg ttttttttcct ctagataaat ggatattgta agcaaatagt   1800
aattcctgca tgctggatac catacatgat gtgaccgcca aagctaacc agcttctaaa   1860
aaaatacact ccttgctagt atggtgatta gttacggtgc atgaaaatag taggaacgct   1920
gattctcgtt cattttgtgt gcgttccacg acgaatttct gttcaaagtc ctgcagatct   1980
tattgagacc tttacagcac                                               2000
```

<210> SEQ ID NO 63
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63

```
tcgtaggcta atagaaacag aattatcaat tccttattta atacatcact ggactgagtc     60
attctctcag agcaaaaggt aatcgcttca ttaaggtatt gtctatcctg taagaacacc    120
cacgccgtgg atatatctca acatgtaatt aggggggtaca tgcagtgtcg caaaattcaa    180
gcgcgaactg gggcatttct agttatgcta gctaatctac tcttgtaaag gagctttcga    240
ctaaaaactg ccactataat ctgattcaat ggtggtaata agcggtaatc tttaaccgtg    300
tttttgctgt ccgacttagt gaattgatac gtttataggg aaaaaatagg tcgctcaata    360
taccttaaag ataatatcac cggcatgcgc ctatgaggta tcgatcctgt gtctatgagg    420
taaaaaacga gactaaagtt tgactgtatt aataattatg aagggaacc ttgtagtcaa     480
aagattaaga gcaaacccgt ctttcaatga caagacatac attggatgcc tcgaaattga    540
```

```
ttattaagta accagaacca atgattatac taagagctta ttcctttctc cgcagactct    600
taagaaacaa ggacaactgc ccctgagcaa ccagcctgct gatacgtcca acaacccgt     660
tatcattagc ctgtattgag ctaaaagcac gtttattact tacatggcaa gtattattta    720
ttatgtggct cgtataggtc gggtatagaa atgttgcaca ttacaagaaa gttcaatcat    780
aaagcgaatc gtttatgtta gcagacttta tctacagtta acacgaggct agcgagatgt    840
gctactttc aagtgtttgg aatgcatccg aggtcactat aggcaattct ttaccgcgat     900
caattcgtat ttgaaacgcc cggctagcct cccatagatt cccagtcaaa ggaatcaagg    960
ctgcgccatt ctgtgattta ctccctcttt ggacaaccaa cgtactagcc tgcaggatac    1020
gatgccaaca ttaattttta taaccgtgag atcaacgcgg tcaaggaaaa agttaggcat    1080
aatatcgcgg acaccctggc gtgaacgatt aacatctgcg ggatatgaac atttctcgat    1140
ttactttaat gatacttggc ttcataataa acataataca tcccctgag gttgataaac     1200
gttagaaact taggcgagtc cataagcgct ttaaggatc ttttatcaca cacgcgaaac     1260
attaccattc gataaaactc ttatcactca tcccgaaatg ccagtttcgc acatgcaaaa    1320
ataagccttc gagattggtc acgcccgatc agtcgtcttt cgctacctaa cctatgataa    1380
aatagttctt aggagtcagg caattgactt gcctgtgtct ctttggaggc ttccaagttc    1440
ggatttaagg gtatatgcct gttgtagtcg acaaataga taggataagc gctttccagg    1500
cggactacac tattagtaac tatcagcgaa tataaatgta ctcggcagct taagcgtaga    1560
cttagtactc gcaggacctc ttgctcgttc tagcatatat cctggtcgtt tttaacattt    1620
taagctcgaa aaagttgtcg gaagatgact ccattagatg gacgattaac gaacaaaggt    1680
ctgtgaatga catacacatc tgatcagtat tggccgcatt cgcaggatag tacatcgcgg    1740
ggcagacgta ttaaatcaac ctctccacac ccgggtttcg ttttgccatt gttgccctcg    1800
acagcagcgt ttcattaata ggaggcttta taatacgtcc agaaggtgtc agaggcctac    1860
gagctcacga acgtatcctc ataaactat tgtgtcacca gtcaagtcgt attttatctc     1920
ctaaaacgac ttacccacac cttatggagg cttagcgatc gtgtatatat gcttcttatt    1980
atagtgcacc ctgggttcta                                                 2000
```

<210> SEQ ID NO 64
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64

```
attgggcatt tcgtcggaca ctaaatgaac attaaaggat tgatcttaga gtgctatatt     60
gaatcactca gcccagtcct tcggacttcc ttgtatttca ctgggcgtat actacattct    120
caaaataatt ttgcgagtca attaaactag ataccaccta tgggggttt cgtcttggtt     180
tcaaattaga tggtagtaag tttacgtgaa caccgttgag acgtagacgg cttttatggg    240
ttgtctgtgt tagactcatt gagctgctca tccgaattat tcattcagta ctatttagca    300
cttggacatc cctgctagag ctctgcgaaa tgcggtatta ggtctggggt gacctccagc    360
tcaattaatt tacaccggta gtaaccaaag gttagttaaa ctcacgaaaa tgatactcac    420
tgttttgtgt atccttagtt atatgtcggc ggattcaacc ttcggataat aagtaaatgg    480
tctcagatcg tagctgcaaa aaatcgtaaa gcaactgttg ttaagattgg ctactcctaa    540
```

```
caaattccgc ctccctcaag caggacactt cggaatacaa tccgaaaata tggcgtgaac    600
cctctatgat cgactgattc caatcacggt tcagtccact ctatctaatt aacttatcgg    660
gtagatacta gaaactcact caaaccgtat tcgtgaaata attattcgga gtcagtaagc    720
aaagcccagt gtgtatttta cacttaattg gctctctgtc aacttcttgc aaattaatcc    780
attacttgat aataatatat cgcgttcaat ggcaagaaat ccaccgcaga atcgcaaatg    840
gactccctct catctaggtt aaagcaaaaa tgttgagatt ccacctaaaa gtggatatag    900
aagacaaaat tatttgtacc aacagtaaac agggacggaa ggtgcctctc aggtagttac    960
tgaatacctg ttagacgggt tctgcccggc ttctatgact tgagattatg tggttctaca   1020
gtatatcatc cgtctaggag tgaacctaat gaaaaatact ctaggttggt acgtattcat   1080
tcacataaac ggatgcgatg agttggcggg ttggaagttc tgttaatgtc gtaagtactt   1140
ataggctgac aagaggtaac tgtcatacga aaggattcgg tctcgacggc cgaactctaa   1200
aaggtctcct tttccggaga acacaagact cttctgcttc tgaccgtatt tggatagatc   1260
catcggcggt accttttgttt gttggatcgt aacatctctt ttgatcctac tatgtgccaa   1320
ctcagttagt tcgcgctgaa ttaagattca agatcctgtt catatctttt ataaaacatg   1380
tggatgtctt aaaactcatc tcttcaaacg ccattgctcg tttctggagt gttacgggtt   1440
cggagtagag tggtattgga tgtcaatatg tgaatttatc cactctgaca tacacaacga   1500
gtccgagaat tttagatcgt gcctccaaac agcgctcaaa tcttacaaat attaatgtag   1560
agccatggcc ccatgcagag atgttacatt cgcatggatc aatctaagtt tgtacaaaag   1620
aaaggcactt cttaatctga acttcatatc gtgtttccct agcgattact atgattctag   1680
tgtagcgtta gttgcttatg ctctttatac actcgaggta tcatgtacca acaacctagc   1740
gaaactgata ctgagaggtt gcagatagtc ttcgacgatt tagctactgt catttaacat   1800
tcctgcctaa aatagcttcc gtccactcac gtactggatc tcattctccg cgagccttat   1860
agagactgga ttacgtatat tcaataataa tctactctag accaccgacc tcatcccttg   1920
tttattgata gtggtgtccc tagctgacca gtcttgttgg gaagaagcat gtaacattcc   1980
tattagcgcc aacaacgcgt                                              2000
```

<210> SEQ ID NO 65
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 65

```
agagaacgtg tcacgtacta agtgcaaaag aggctgggtt tttttgtta gcttaaaaca     60 ccaatagaca caaatccatg gagatttaaa tgcaattatt aatcttgatc gaattgtctt    120
ttagccgaca acctgttggt cccgacaata aatttaacga ttgtttttat cctaagatca    180
accgttgacg aacaaattag gcgaaagtta tattagtagc cagacgcgtt tggaaacagg    240
caaaaactgc tagaataccc gtagaaacct actggaataa atgaaccgat acgttaccgt    300
ctcaggaact acttaggttt gatagacagt ggaatgccat atgtctttta gcgtaacaac    360
cctaaaacct tattattgga aatttaccag gtaggatgtc atgtaacacg ccaatccaat    420
tcatgtcaca aagtgattag gtatactagc atttataact tgggtaagtg catctcatgt    480
```

```
aagtaccgat gggcgtacct cttcgatgta ttaaccagca cccacttcat acaagttcat    540
cggtaagtgg tttacaagaa acatcataaa tagaaataac acctcttcag tgataagcgg    600
aaccccgtgc cacttgaaac aatctctcgc agatgaccct tggaacaggg ctgacagttt    660
gaagtgacag ggtgaagtca ttcctttaca atttaagccg ggaaatttat caacactaaa    720
cgtaaaataa aattggcgta ctgcctggac attggtcgca atgtaatctt ctttgttctc    780
gtaaaccaaa caataatatt ttgaatcgta ttatattgca caggtaagcc actgcaatta    840
aattagagcc catcacttcc cgggctaatt gagactaagt caaattatcc tttcagactt    900 cttttaaccta aacatgaaga gggttttgga attgttaaag acattccatg gggtactgac    960
gtagtaccag ccagagttcg attcttacaa ttcacacgta taggtagagg gtcccacagc   1020
tacatatcct atcctgagcc gaattctcgc cattgttagc tttaaatatt tcgagccaga   1080
cctgtggaat ttagtgagtt gaagactatg ggagccatac cgaagttgct aataaaattg   1140
tttctaatta ctcttcgtac atcagaggca cgccatgtgt gtgattaatt catcttgttt   1200
cccgtacaag caatagcaat attgctcgca tcacgtccac caagtaatta ttgtatagtt   1260
actttgaact atatctctgt agcatttcga gtggtgctca gaggcgcgga tcttgcctgt   1320
cggggattgt gaaagttggt cagaaagtta aacggtatg gtattttaga aatcgcgaac   1380
ctgattgcgt cctaacgcga tgttattagt attcaacggt tggtcagagt tatataccccc   1440 tagagaggcc tatggagata gacagtctcg cgtatctcat cataactctt gatcaatcta   1500
gtcaagtagt tcacgggact agccgtacac aataaggaac ctaagtgcaa aaccactctt   1560
tagataagga tcctgcgcca tgctttgagc cgcagcattc tctcgatgag tccagcgtgg   1620
tttgcaacac ttagtacata agatagttaa atacagagcg gtcctatttt gaaaagaaa    1680 tcctatggac cgcaccagcc ggaggttacc taagacttcg gacgaacatc cttgtttaaa   1740
tgtatgactg gatgactgat tttcaacaga gcgaggtcca agaaaaacta caagccactt   1800
attaaagaca tgagtaagga cgagttattg aaactaagac atacgtggga tagctaggtg   1860
gcataataca agcagataac cccgtacgat tcaaacgatc ttaacaagta ttttattaca   1920
aacgggcctg gttttaagag aaaaacgtgc agtaccctca atatgagtaa taagggaagt   1980
gacagggagc actcggcgat                                                2000
```

<210> SEQ ID NO 66
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66

```
agggcttgca tatccacaaa aatgaattta tctaggttca attacgtgtt atccactcca     60
gcgaaaactt gacactagga ttattgtctt ttgtcgacac gttaatacag caacgttccaa   120 gagatctctt gctttggctt gaacttgcaa tattcacggg ttgtttccat tcttacctcg    180
actggctagc tgaatgacct ttcacctggg ttacgatgta cgcggggcac tgtggcatta    240
aacgaagtca ttatctgcac caacccttga taacaaaata aatatggtct gcgacacctt    300
gtgctgggag acaaaaatct tctgtaattg gttctgtacg acaggattag ttcctcttta    360
tttcttacca tgtttcctct tccagcatta agatggtaaa ttgaatgtat agtgcgcgat    420
acggagcacg tgtcagttgt cgctcggtcg tcgcgattat tgcttggagg atcctaataa    480
```

-continued

```
agctaaatga gtggagtagt agtatgcgtg tgtgccggcc gtaatatctc attcacgtgc      540
atcatagcgc atatattcga cacttgtaat cccgtctttc gaagaatcta ggttaaatgg      600
atactacttt ttacacacgc atcctgcctc tcggcgggaa atatgttatt agaaacttct      660
gaagttgtct ggattaaagt actcatcatg gctaaaacac tctattttg gtgtgaatat       720 agctctattt acttctatcg aggcctcgtt ctagaggtta ttagtgacag tccgtccgta      780
aattttcctg tatactcgtc ttccttatta gggttgaggt gtactgcatg tcttatgcta      840
tacaatcagc gtacgatcaa gactgtaata tgtgtatacg accacattat gaatgagggt      900
aaggtgcgat agtcagtagc tgcttgctat tatccttaaa tcgaataatg cagcgcttca      960
acaatagatc atatgtattt caagcaacaa ttaggggatt caactagaga tgctaatgta     1020
ggtttgtgaa tattttggtc gtacattggt agggcatctg attgcatgta tacagtcata     1080
attcagagcg acgctctttt taaccttggg aaaggccgtg aacgaatgcg attaggccaa     1140
tctagcgcat atagttaatt attttactct ttatctcttg agcaacagcg gcaaggaaac     1200
ctgggagttg ctagacaccg agtagaaatc ccttacttcg ccagcggatc gatctgtact     1260
acatgcatct tctactaatg gttgaaagtg aagctagtac ttatttgcat ggtgcaccca     1320
ttcttacaac caggttgttc taatgtcttt tcatcaattc ttagcggagt gggcataatg     1380
aaagtataag aatggaagtg ttctattttg caaccggaga ccacatgaaa ggatcgacac     1440
agagatgcaa acagtgcata cattcgatgt ggcatagacc aactcttgta cgatttaatg     1500
tgatctctgt cacaattcgt ttaggtgtct atggtaaaac ctcagccaca acatgtatag     1560
tcttacaggc atggctatcg tgatttaacc gtgaataact tgtcggtaac agaaactctg     1620
gcacaggtga gcgtaatcaa atcaacttca gtaatgagga cttctaagat agttccgaat     1680
ctgttcacag tattagcacg gtgattgagt tctcttctaa tattcctatc tttacattgc     1740
gtactgtcac agaatgctgt tgcctctatg attttacaac ggcaatctaa atcgtcgtat     1800
catatgttca gaatattaaa tagctcaact ccgtgttgag tcctaagata aagatagaaa     1860
cattgactat aaaatctatc cattgtaaac cagactaatc atgcaagcac aaattagagg     1920
gcagaccgcg gccattggaa tcatttatat ctttatcgtt taattcacaa gaatggctaa     1980
atgccggatt ttgaccgggc                                                 2000
```

<210> SEQ ID NO 67
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67

```
ttacataacg actccgtcga agccgtcccg gacatcgagt ctgacactta caaccctgag       60
agccgcttcc ctatatgtct atagattgcg agtgtatgcc actgtcattg cagatttagg      120
gtcaccccaa aaacacgagt attattagag actacgaatc atttagcaaa caatttcgcg      180 aagcccctaat tgaaaaggca accgattcac ccctggatag ataagctaaa atagtgttat     240
gcggagcaat gttctcattt ggacccatac actctattcc ttctgaatga ccttcgaaat      300
acgaataaga acatggcgtt cccaatcatc catataccccg ttcaggctga gtagccaaca    360
tttcgtattc aaagatacag ttgacaagct gacattcatt gatgacttag gggctaacat      420
```

```
atcaggcctt ttcttaatgt ttaaatactt gcctattatg tggccatgag gagtgcgatg    480
ataccaatgt tattggagta tcgttaaaaa aattcggtag tgttataatt acgaactata    540
gcttacgggt catctatttt aacatagtga gggcttcttc acacttccag tcgtcggtct    600
gcatgaaaca aaaatgagtt acatttagag gaatgcgggg taggcacaac taaacacaag    660
gattaaattc gtcgcgacag gagtacacta aacgtaatta aaaagctacc aggcgaaact    720
tctatttacg ggcaattacg aatcctatga cacttcaagg acctctcatt ctaaaataga    780
gacagcctcc actcgagctc cgattgagct ctgctctctt ccaaacaaga acctccgtgc    840
gagcagcata tagcgagcat tcttcggaag gacctatata gatcggtcag ttgggaaatc    900
ttacaaaacg tcgagcatat attatttgcc gtccgcaacc tatgcacagg ggcctttaaa    960
tcagtttatt taaaaaatct aatttcaaac agtcttgcaa taggttaggt gggtatagag   1020
tatcaaaaat acgtgactaa aaacaacaga agttgataaa caacagtgat tttcgggatt   1080
tatgctacac cttagcgaga aacttctgtt aacattgtct atgctttgaa actatgtaaa   1140
ggaattcgtg atatggtata cctaataggc ccataccatt aaactgaatc atagtggacg   1200
agaagcttta tcgccctcta atgcgtagtg acgaatgaaa atcagacaac cattatagaa   1260
gtccgagtca gccacggatg ttcggaattg ctatatatac gcatgacttg ccaaagttgt   1320
ggtttactgt atatttcgta ttccacaatt acatatagct aaatctacga tcgcggcgcg   1380
gtataagatt tcaaactcgg taaacttgaa tgatttaaat catccaattg ttttatggat   1440
cgtggcctgg agtttggcaa ttaattaaag gatatttagc tgaatgtgta aaataatttt   1500
taacccaaat gtgtctataa tatgtgctcg gataaagctc aggcataacc acagatctac   1560
gcgaccttgt gatcgtcctt gtatgtgtat atagagcaac taccaacagt tgttcagacg   1620
caatcaaacg atagctttac gataggatgt tcatttatta ccaagtacta ttattcactc   1680
tatagggtta ttatatcctc tactactccg gggtgcgcaa ctttccttac gccattatta   1740
acggaatgag cggtaagcgg caccttctat atcatcgtca taagagtgag atgtaatgtt   1800
actatgcctt atgcttgcca tggtaagccg aaaataagaa gatcacaaaa tagcaccatc   1860
ttttccatag attctcataa acattgatgt ttgagcaaaa taacagctat tacaatgatg   1920
taaattatta taaatgtcta atcataagcc agtaatttcg ttaagcaatc tagagaagta   1980
tcttaagagc gttaagaacc                                               2000
```

<210> SEQ ID NO 68
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68

```
cctcactgag accaattatg acttttctct tgcaattaca caatagtgcg ttaagtactg     60
aaaaccatcc tcaaggctaa atgttataag attttttcata cgagtggcga aaaccaagtc   120
aaactggtta atgatgtct actacaagtt tgggcttggc tgacaaattt ttctatgagc    180
tactgtaata atgcgtcttc atacgaacgc actctgccca taaataggcg atggacctaa   240
tacgtcaagc ccatcttcaa atagtttttc ttgtaaattt ttgtcttgac agacatgata   300
cgttaacgtt gtctttgacc attatatctt cgcgataggg tcgagttcgt atttattaaa   360
ttgatgaaat tgcgacacat atcacgtgac ttaatcccga aaaattagag ttcttgcgct   420
```

```
tgtcataggc atgaaaagct cccctcataa tacgtttgac ctttaacgta tgtctttaac    480
atatgttcct ggtaaccagg atttaaagtc atggtcagcc ttcgaaaaat gtgagaagat    540
cgcgaataca tcacgaactc tctcaggcaa acatctcatc caccatttat atagtagatg    600
cgctacccac tgttaacctg tttgagatgt cgatttaaac gttagaaggt ggttccatcg    660
ctggattgca acctttactt aaggtcgatg atacgtacaa tcgctttact ttaagctaag    720
ttattggcat actactgaaa ttcacttcct ggcagacttg cgttgctctc gcaatcccgc    780
agtcctttat gatgtctagg cgttttacaa atcgacagtc attgtattaa agtcattgga    840
ttgtacggtg taagtcgaca gggaacgtgt tgagttaata gtaaaaggtt cagattcttg    900
caagcgcgct tttctatcgc ctggtttatc aaactcatgg tgattatata ttttgcaatt    960
catcagccct catatgttgg taagactcgg attgggtcga cgccagacta acgtcataaa   1020
tgttagaatt attaaagacg caattgttta tgatactcac taatgggtcg ttagatactt   1080
attgttttaa ggcaccagcc tccatttgtc cgagtccagg cccgagcttg ggcgcaaaac   1140
ttttagtatc taactgtgag tgacaacctt tagagttctc tcgtatagaa ggtccgacgt   1200
cagagtatca taacctactg gaattggccg ggttcgcgtg cactctcact tcctgccaga   1260
acgcaattaa gcatgctggt agtctcgacc cggtacctca ctctatcaaa tgaaactata   1320
gtatacctat cgatcttaag atgtgggttc tagctgtgac tgcccgaaga aatagtattt   1380
caacgacccg atcgtctagg agcgttgtgg gagggttcaa tgctctcgta tcgattccca   1440
agacgttgtg gacatactag ctggcgaata atactatgtg tagtgaagtt tgcggtaatc   1500
tgcgtagtgg ctaattaaga aacaccgagc cgtgtctttt gcaaactcat cgaggcgttg   1560
actaaaatgt ctaacggtta gggcgatatt ttattttac ccgcggttta ttatctatga   1620
gtactcccca ttcccatata gcgtgcatag tttacttttc catatgttat tagcaggctg   1680
tccgcccaaa cgttgcgcta gccaccgtta gatcacagtc atattatcat aacgattacc   1740
aggttatagt ttcactgact aaggagccca taaatgttca ttttcactag acatgctatg   1800
ggtttggccc gaccaagatt gataaactgc ggtaatggcg atatgattaa acgattaaac   1860
ttttaactac catggggaga caagacttct taactagtcg gtatggattg ctgcttgtaa   1920
agctaaacaa gctgaatgta agaacaggct ggccggttca taacactatc acgagtggct   1980
gacagagttt tacttatagt                                              2000
```

<210> SEQ ID NO 69
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

```
attcgcattg tttgagtagc cgagcactag tgggatcatt taccttctcg cggaagagtt     60
acaaaagtac tgaggaaata tgtgaattgt tatagctttt aggaaagtaa acatgaaaca    120
aggtagaaca gatgacgacg tgatacaatt atttacacaa ctggaaaatt ccgtcaaagt    180
tttaaagtat attccttgag tcctattatt gaatattcga aaggtagtca cctgagttgt    240
cccgtaataa ttcataaagt atccgtatgg caacaaatat ctcctagatc cgggccgcgg    300
atagttttcg ctaaagtatc taaatcgaac ttcttagcat acgattacta gactatcacc    360
```

| | |
|---|---|
| ttgagtagtc tatatctctg cgagtgtaaa atgcacacgc cgttaaatcg cctaaatgcc | 420 |
| tttccgtggc cattatatgc cccacttgct ttcaattcat tccataaact atgatcatgg | 480 |
| acccggttgc gagatgttac agataaagtc gaaactttca agagcagctg acgacaggta | 540 |
| aaattacgat gcactgcggt gtaaggaaat aatctccagg ttgcaataga catttaaatt | 600 |
| gtagaggaat agagttacgc aaaccaagcc caaggatcta ccgaaccccct ctaccttata | 660 |
| caaactcgtc agccgaaata taccaaatag cacgttgcct agaggtttac attaatcatt | 720 |
| ttacacgatc cctttactat aatatatcg attccgatct aaaaggcgtt tcaaggatag | 780 |
| caatagtcct atcaaaatca ttcagttact ggcaatccaa ccaattcgct gtacacgacg | 840 |
| gggtgaggtc gtaaaatatt atatgtcata gatgcactgt ttgcgaccat gtctagcatt | 900 |
| tttcaatagc tccacccacg cgttggcgac ccattgttat tcaaaaatgg gccgcatgaa | 960 |
| gagttaattc gtcttgttct gacataagtg ttgaccatca gacaatagac gtataccgct | 1020 |
| ggttacctct aatcgaagat ccagagctcc ttatgcaacg tatagtaaac ctggctcgga | 1080 |
| aaggggttac tcttattttt agcacctaca ttcgggatca aatcatatgc actttcaaga | 1140 |
| tggtgctcac tataacacaa taacttgggt ttccagttag gatgaggaat ccgccaggtt | 1200 |
| actctatgaa gtcaagctct tccgtagttt aggcgacgct tgacccgcgt tcctcacaag | 1260 |
| taacgcgaca gattggagca atagcgactg cttcaccata tagggactta catacagatc | 1320 |
| gaatgatttg cagctttaac aacccataac gatctgcact agatgcgatg agatctctgt | 1380 |
| aaaacgaaac ttggaattac ccagagcagt tctaattaag cttttcgat aatattacac | 1440 |
| agcaactaaa tgagcacgta tgctcaagtg tcgcaaaatc cttattgtat aggaataggt | 1500 |
| cgttgtcaca acataggtct gtcaccaaac tcagacatta tagtacttta cggagcatgt | 1560 |
| ttagacataa tctgcacaat gctgattagt ctcagtgtgg tcaaattctt taacgtctct | 1620 |
| gttccaatca aagtgagcag actgattgca tcacaactcc atcacttaac caattattaa | 1680 |
| tagtccacac aattcattca ctcttcactg ttcagcactc agtcatgctc tggatattcc | 1740 |
| atatttcccc gccacatata ctgagtttgg tcactcatat gttcgctaaa atcgattttt | 1800 |
| aagccattct tgcctattaa cgacggtcct aatcgtttcc cttcaccatg gatatacggt | 1860 |
| acgggcccta ttatctgcgt tacgcaatgt caataaaaga tattctaaga agaaaaaaag | 1920 |
| ataagttgcg taagcgtgct gcaagagaca ctctctcttc gcagtaaact aattttttcct | 1980 |
| ttaagaatac aaagcgaaca | 2000 |

<210> SEQ ID NO 70
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70

| | |
|---|---|
| ggattagatt gtgccataac gcaacaggta aaattattag accagcaaaa gaatcctaac | 60 |
| gtatacaatt ttatcgtaca taacccgtga atcttattaa acccagccag gccgccttac | 120 |
| tttgctccaa gtaggagcat aatgcataga agtttcagta tcctgtctaa agctattaag | 180 |
| tcgaaatgag acaaaagtga cgagttatta acgatcagaa actagtctaa agggaaccct | 240 |
| cctgcggcca tttcttgagg acttacgtgc accatatcat gaggtcctac tgtgggaaag | 300 |
| gaaatcctca gtttacatga tttgaaatac tgtagtgacc tgtcaattta ctgatttcta | 360 |

```
tgcataaaat gacaatctca ccgagtacgc ataaatcagc gcagatctca tatattcata    420
ataatctccg ggacgttatt aaattaattt ttttctagac agatattcag aagtccgacg    480
ttatacaagt gcccagtaac atgttctgag caaatagatt gtcgacagcc ccaattaacc    540
acctactagt ctttaggcac tgtgtgaatg aagctattaa gtactagaca taatgtcatt    600
gctggctcta gctgaagagt atacctagct ttttttccag attttgagt acgggatctg     660 ttcttgttga acaaataatc tggatggcgc atacaggcg tcgcctggag cgtcaagctc     720
acatacccta tcgtcaaagt atgttccgtc aaaggtgtct cagcacttaa atacttaaac    780
aatccgagtt tcgagttcta aatggttgca caatatgcct ggtagattga tataatcttg    840
aagcaacgat ggatgaacaa aaattattga tacttacttt tacccacaca aaccgtctga    900
gtgtcttttt aagagggtta cgaatatata aaagcggatc acgatattcc accgggaata    960
gcgcaattag tcatatggaa catggtgtga aaccacaact atgaaatcta tccgtacacc   1020
aaccaagaga cctaaaagtt ttacataatc cgtttgcttt cgtattgccc tctatctaat   1080
gaaaacccat tgacaattat aaagaacaaa ggttatcaca cgctgcgtat ttagagaaga   1140
gaggacatgt gggatcaatg tggtcgcaaa aattatcact ttaatcaaca ccgattctaa   1200
gaagaaataa acgtcgtatt caagggtact gtataggtac gttaagcgtt gtcgtacact   1260
cagcgattta actaacagcc gggagaatgc ataattatga taaagtgaat ccacttagcg   1320
tctcgaatag aggctatttc gcttgcaatc aaatgcttaa gagtatccta accaatttta   1380
gacaaatatc agtatgttta tcgattaagc tggacaattc ctctacacag atgtttaagc   1440
gaactagcat tttcatcctc ccgactcata ggagtccttc gttgcacagt agatagtcag   1500
cgtgtgttct cttctccaat tgatatgctg aaaaactata ggttacccgt ttcggtcgga   1560
taaagaattt gacttaattt tcttgccgat agtaggtata ctgtaaggca gccaatataa   1620
ccgttagagc ttgattagta tgatattcgc tccttttaat gtatctacat ctagctctgg   1680
aaaacccggt gtagaagtaa tgtattaagt ctgcgaagcg ggaatctgct tgtgacaaag   1740
attctgtcgc ccgcaaacgt caagtaataa atcgcagata cggtcagaaa ttccttctgc   1800
atttcaagat tagtaatcta ttcgattcca aacatcctgc tcctaacaga atgcgcacgg   1860
gacctaatga acttttcata tacgtttcat caagcagtag tgttcggaaa cgagacataa   1920
cagggtacat gtgcatcaac ctttaaaaac caatctctat ttggtatagt cgtattcgaa   1980
atccagtagt gaggtgaaaa                                                2000
```

<210> SEQ ID NO 71
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71

```
aattggagcc aaccataaat tggatggtag ttccaaaatt ttataaccta ttctagtgtc     60
tgcaagtatt taggagatag gtgaattaca cgtcgtacac ataaatatga taatgcgatc    120
aagagtgaat ggggtctata gtaatatgat gtaaaactta aggatattgt ggactgattt    180
aacgttacgt agtcctgaca agagtttaga tgccaggtcg tagaagttgt gtatccccct    240
attctcccaa tggtagatac cgtgataaaa gataaattcc tgttaaggaa gtcgaggatg    300
```

```
ttctgtggag tgcagagttc tacatgtgat gagataacct aagagaaaaa gtaatttata    360
gattgccccc gttaggagct acacccgact atttgtttcg ttaagatatt tgttcgtacc    420
atgctgttat aacgacactc cctcgaatct tattttatgg caattaaaga tgttacaggt    480
ggcgttggca attctggtaa actccgcact ttacaaattg ttgtttgcaa ctctctcata    540
ttgtatgcaa tcgaccccaa accctcatcc tcgaccctat gaatgaaggt tttctgtgcc    600
aaaagccatt ttactcaaaa attagctttt aatttgggga gcttaatagc gaattccaga    660
atcgtttcat ggggattagg agatatatta taggagtcca ccaatagtct attgacttag    720
tggttttggc tcatgcacgg tggacaaaac ttcaggcgtg ttatctaatt caacccgta     780
ttcatacata tcagggtgt tgatttcaga gaatagatta ggaaactacg agcaatacca     840
attttgaaga tatggtctac tagtagctca cttactcaac attgctactt tattcgaagg    900
cccatattga ggaatactgt cttgttgagt aaaacgatac ccgtaacttt aaactataaa    960
ggcataccag aaaaagtgtc accgcaggaa aatataagaa cgtccatcaa tatatgatgc   1020
aaactagaga aagagcttga taaattatca aactagcact tctgggaata ctccgtggtt   1080
gcaaggttac agggttcagt caaagagtta ttaaatcgat tgatatactt attcaagtga   1140
ttgattctat atagctacgc atatctgctg acttttcga aacgttgcct ggttgtccag    1200
agcatgtttt ggacgagaaa tttcgcgcag atatcatgat tacgattggc aactaaggat   1260
gactagcgta atgagaacct ggctaatttt gtgtttctta ttcaaattgt ataactaggt   1320
aaggaacgac tcgttcagaa tgagttctaa tcataatctt ctaaaatact gacagaaata   1380
ataatatata ttatgactat tcagaaaacc tataaaaagc actccgtaga agctcttcaa   1440
tcttagaatc ctcacctagg aacctgaaga ttattgtatt gacttatttt gtagttatta   1500
aagaaatcca acgacgggga cgactgcttg tatgtaatat ttccgttcca caagccggga   1560
gtaataataa gcaaccgtag aggagcaatg ggttttatc tcacgcacag gatgtcggag    1620
tagcgagccg tctgagtatg ttatcaccaa agatatatgt aatatggtta atcagctgat   1680
ttaaagagaa cttcatccca acctcgaccg acgatccgat tactgtttat cgtcatacct   1740
tacgagatgt caggtcctcg cacaaaccgc cacaaattcc ttgtcactgc aagaataagt   1800
ttgtccgcaa actgtctacg cgctaggtcg ttgtatgtat tgatgagccc tatccttatg   1860
acactcggac tgctagcctt ctgagattta cgacaggcag tctagtatta aacccttact   1920
acttttgct gtatattgca ttgcaagttc caacaagtta atgaaacaca accgtgatc    1980
gcctcacccc acaaaaggct                                               2000
```

<210> SEQ ID NO 72
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 72

```
gtaagggtcg aacctctgat catattcgat tactaataac tccagatata tagaattgag     60
aaaggcaaat gtatttaaa cagcaagaaa ctgtttcaat tcggcttatc tgatgtacat     120
ttaataaata gaatgaagat cgagtattag aactgatatg aaagttcgta acatcaggac    180
gattagagtt tatgcatgct aacaggaact gacctgctga cattatatca tacaatttcc    240
tgcgtcccgc ttatggatgg cgtcaatagg ctagtaacct aattgcagct tagaataagg    300
```

```
agaaccaagt aacgacaaca aaatgaaaag caatagatgg cggactgcgc tttaattgca    360
ttgaaatact ctgggcttca agtgttagtt cattaaagct gtctcgcgat acacaaacgc    420
tgcgaagtgg ttccggagta aatgtgacca atgttagaca gtgggcccgc catgaatgtg    480
aagttagtta ctaggaagag tattctcagt ttggtgttta ctagaggtgt gcttggcgtt    540
tatctgggat aataattgta actcaattct attcttttc gttttttctg ctcatatcga    600
agttttgctc gcctcaatca acgttgtttg tatagcactt aggatcactc tgcgcatagg    660
gaatgcttaa atcagggagt tcatcggtgt ccatcctgca gggacatgaa agctgtcata    720
cacggactcg taccggtctg acaatccgct ttgcctcata gcaactattg agccgcattc    780
gcgtggagct gaactatcag aatggctaga aaggataaac ctgtggtggg tccacgagat    840
tggtcttctt atgttaatat tagctcacaa agtccagagt tagtatccat ctcttccagt    900
cacatggaat tttactaatt attgtggtat cattattata aaaatgacat tatctagcat    960
gactccctac cactagtgca gagctactat gtacataact cgctgtttat gcgatactcc   1020
aacaagtaga tacggtaatt tcgatatagg atgaaaaaac cttcataaca gcttaagttt   1080
aacttcgagg gtccgtgtaa tcggacaacg cacatacgaa gtggcacgac ctttcatttg   1140
ggctcccttt tgcaggctag taaacctagt atacatgaaa gccgtcttgc ttgtgcctac   1200
ggcttatttc gttgaacgta cgtctaatag tgccaaggaa cgaacacacg gctagatcat   1260
aatattactc caggtgatgg tttcggtatt tgcaaagtaa agataagtta tctgattcac   1320
aacaatcgag aatttgtcct gtttgaacgc cgaaatatta tcttactatt gctttactca   1380
gatacctcca ataaattata aaatggcttg tttgaatgtg tatcgaaacc gaaagctata   1440
tcttttgacc gaattaacca aatgctacgc gtttgctgtt tattatgtcc atcatcgctt   1500
taggttaagc ttaataggtt agggaaaact accagcattc acataatatc ctatctagga   1560
agttaaattc acccatgtat actatactac ttagtctaca atatttctgc tttattcttt   1620
atttccatta tcaaagtatt tcggctctta aatggggcaa ttacgaaaga tatgattcta   1680
gctcatgctc aattgagatg aatttatgac tttaatgggg tgtaccattt aataatgcag   1740
cgctaacata acgtgcgacg ctaatatcat ttactaatag attttcattc actataataa   1800
ttaataatct tctggcccca tggcacaggc aattttaaat ccgtacccgt cagccctaaa   1860
atgccaagat tagtgaatct ggtgtcatac aggactaaca ggtgcaaaaa ccggttgcgt   1920
catcaaaacg caggatttac tcaggatctt aagaaatcta aattttcgca gaatcgctca   1980
tcgccaaaat tttaggcgtc                                               2000

<210> SEQ ID NO 73
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
cacgtggttt tcagcggtta acgcaatctg cattattggt agaattttac acttaacaaa     60
atatcaccac gcggacaact gatttagcaa atgccgtccg tgacgcggga cccgcagcac    120
attattagac atagtacatc agcctgtaac cgatcagtca tcacatatcc cggaaagatt    180
tcaatccagt tgtaatcaac gcgtaaagtt atataatcac ttcaatcacc ttactaactt    240
```

```
cagaatggca gcctaaaaat ctgatgctac gaaccgcatg gtgttgaata aattcaatag    300
aatggagctc ctggatattt cacgacgccg ggacagaaat agtgttatag agaagaaggc    360
atgccgtttt actcgattcg taagtagttt gacgaagcaa aaacttgggg aagaacttat    420
gagttagcca cgacaactac cgggaggatt tgcttttctt cctccatgcc aatcttggag    480
ggagtacctc aatcacacga tgaatcagcc ttaatgggcg cccaaaacat tcttggtgcc    540
agaaaagcgg atgcttcctc gaatgtgtaa tcagaaaagt ggtagatgaa tctccggctc    600
catcatggat agagctgcag gtattggtgc agcaggaacg aaggttctac cagtaagtaa    660
agtttgacgt tagttacgag tctagaaggc ccaaagggca accaaaacgt cggcaccata    720
acatctacag gtggtaggct aatgtaaaag tggttataat tgctaggcag aaataaggcc    780
gttcattggg catgtgtaca ctccattgat ggagcttaat tcctctcaaa ataattacat    840
tctgttaaca agaaataact tattggtcga tctacgagct agcaataaat aatcatgacc    900
aaagagctgt gctgtgatca gaagttatga cgcttataca gagagcattg taaagggcag    960
gccgaagcaa attcacagag tacctgaagc gaacaaagga agagacttct ttataattta   1020
catcgcttgg caattaaaga agcgaaacac agttgctcga atcacatcct tacgtgtcgt   1080
cgacaatatc ataagcatta ctagtttaga gaggtgagat atcggtagta ggtattagaa   1140
cattctaata cctaaagctc attactatta gcacctttcc tcaccttatt tggatttccc   1200
gcacgccgtt cgcaccgagc taagtgcaat aagccatggc gatgacttag atgtcacatt   1260
gccccatgaa ttcaccccag tgagttgaga cgatttgaag tttaatacgt cgttcgtgga   1320
cagcttgaat gtttcacacg tggtaagttg catatgaaca tataggaggg ccacaaagc    1380 ttatgcgtga agcaaatatg attcctccct cgatccgtta attagagttg ctgaagggca   1440
taaactttag cgagtttgta ttaacatagt catatgaagt aacagagacc cgtcataacg   1500
cttgaaaacc tgaactcaga atgcgctttg tgtaccatag gcatataccc cacattacgg   1560
agatgataat cgacaaatgc tccaagaagt agacctctag ccatcatcac gtgtctctac   1620
tgtattctcc gaagttccgg aggccagttc ttaagtaggc acagaacaca cgatggattt   1680
cctagggacg tacgtatgtt cgacttctcg tcagtaatcg cgacagaaat gggaaggtga   1740
gcttaaccta acccacattt ttgtcatggg actctgtgaa tggtgttttct tatgaagcta   1800 tcacggtgta aagatatcta gacacgctat gtgctactcc gataacccta cgtttaggtt   1860
tacgagattg gagaaatata ctttattaat tcttccctgg aatcgtacca acaagttcca   1920
aaatggctct gcggtctgtc aaaatatgaa gggctcaact tgacaggacg actgaccgga   1980
aatgatttaa gtgaacctcc                                                2000
```

<210> SEQ ID NO 74
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 74

```
ataattatcg acatagatgt gcttcactcg atttgacagc tggatagtaa gaattagtgt     60
ataacccaat acgtatgcta atacaaaccc tggactgatt tgaatgtaat cctattcata    120
atattttagc taccgtaaat gtattctgca attgaatttc gtgtgaatgt aaaaggttta    180
gaagtttcct aagttatcgg gtgacgtttt taatgggtct taccgtagat tcagacaatc    240
```

| | |
|---|---|
| ttttggaaac caactgaaga aggaaatcac acgacctggc ggataagggt ttgtaattcg | 300 |
| cgttaaaaaa ctgacgtttg ctataagaga cgttaatgta aatgtaacgc tttaaattct | 360 |
| ctgtgcgaga gttttttaaa tgagatcaag gattgttaat ttcaggaagc tccgttattg | 420 |
| gattttgcct tctcattcgt cactatccct ctccgatcaa tccgattgag tcctagtgta | 480 |
| gaaagttcac atagaaagca gttttccgat tagtctagcg gggtactaag tgaacactag | 540 |
| tcagttggtg atatactata gctaggctgt gataatgtta atcggtttgt gcctactgga | 600 |
| atgcttaatt tcatcttgag gacttgcgct aggaatcggt atgtcttcgt taagtccaaa | 660 |
| gtgccttttc gacagatgtt ggattgatgc actcctccga aaaggaatca aattgggttt | 720 |
| ataaattttg tctttgtgac acctgccgaa tttagatctc accattatcc acaataaccc | 780 |
| tattatcttt acctacttcc gtcggagctt gattatgaat attggcagaa ttatgtaata | 840 |
| gtcattaata tgttgaataa agatatcaat acattcagac aattgaatta atcctgcgta | 900 |
| aaaacctact taggacgagt tgctggtatt tgtttttata atggtagaca tgagggacat | 960 |
| attacgaacc tctgtaagcc tgttctgatg tggccggcga tcacgttacc tgatgagatt | 1020 |
| tatagatctc aagtcggatg tcctctttaa taaactgaaa aattgacgac taagtgggct | 1080 |
| aattatgcca tcagaaataa gctaaccaaa cctctaaagt cgaccctgta gtataactgg | 1140 |
| cagtgctaga tatcacaggg tgtttgtcta ctgaaatttc ggcattctgg tcacacttat | 1200 |
| tgccgatagg ttctagtagc tagtttatct agactccaat tgaaagctta cttcggccta | 1260 |
| tcaggttgaa tgatagacgg tctgtcttaa gaaactacag gacatatact gcatcgaatg | 1320 |
| cgtttaaatc ctaacgcaga agggttgtta tctgatcatc agtaagcacc aatctgcatg | 1380 |
| attacgacg taccaacaac tgaatacatc ctgcctcctg agaactagaa cctattgtat | 1440 |
| tgcggatgag ggtaagatag gtagaaacct gctgccaact tatcgataat aattatgaac | 1500 |
| catgcgtggg tgttgatata gacttaatat gacctcctgt ctggttcata taccagtttt | 1560 |
| caatgcttaa gagaactagc ttgtacggag ttttttttaat acaagtgcta aattaacaat | 1620 |
| tgttcaaaaa cagtttatag tagtaaggta ttgtaccaat cgtatagcaa taaatcatac | 1680 |
| ctgtgtttac tccatacttt cttgattatc gggcacgaga agaggacaac tcccaaacat | 1740 |
| caatgtagcc atagtgaatg aaaaaagtcg gttatgaatc gttagctaaa tcgtttgctc | 1800 |
| caattaacaa aactataacc taaactggtg aacacataga taaatgccaa ctcgttatcg | 1860 |
| tgttatgcta tagatccgaa tttggtggtt ctccgagtct gtatcgtttt taatcgagat | 1920 |
| cttaccttat tcctaaccac atttcgtaag cctattgaaa cgggtattgc cggttcgccc | 1980 |
| atctggtagt acgtaaacga | 2000 |

<210> SEQ ID NO 75
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75

| | |
|---|---|
| gaggttagtg atcaagcgca ttagcttttt actgcggaac gcatacagga tatttacgct | 60 |
| taaaaaggtg gatttcgtat ttattaagta ttctctttac tgaattattg tccatcagta | 120 |
| atcgctggct ttatgaacta tcaacattcg gtgttgtgtt aagttattaa tgacacatgc | 180 |

| | |
|---|---|
| tcgacgttcc ccaattcccg tgcgtgatat attatcatat gaccattaaa tgattaaagg | 240 |
| ggcataatat tttgaaataa cactattaat ttgaaacttt tgtccttttc gcactacatg | 300 |
| ttggtaacat cgcacgcact aaatactgac atatcgtgca ccatgctttc taatagcact | 360 |
| ccgttccagt ccatagctga gactgtcttt tcggacaaca caatagataa gagtctatct | 420 |
| ctcatcaaaa ctgtaagaaa agctctacca taattgggc cgaaacgtaa tacgattatt | 480 |
| atgatatcgc tcctgccgag gtcaaacacc atagcactca aaaatggtat ccaatttaga | 540 |
| ggggctatga gtagttaaaa aataggaatt aaggtggcaa caggacagaa gtcaataggt | 600 |
| tcccttgaag gctagattaa cagaactgta atgtgactgc ctgtaagcgc actggagaca | 660 |
| tcaagtattg tacgagtata attgcacttt ggaggtacaa catcgcactc gactctttca | 720 |
| tcgatatttt ttcgtgggtg aacttgagtt aaagttgatg gtcccattca caacgagcgg | 780 |
| ttttcgcgat gtaaacgccg gccaaagaca acctaacgcc gaattattct acttcatatg | 840 |
| cctaagtaag cccgttctt ggagaagtct catcctctat tattatacat agttatcata | 900 |
| ttagtctagt cgccaaagtg tggtttctaa ttgataaata taataagtta aaaaatgaga | 960 |
| gctcaaagtt tttccttacc gtgccgcaca agtaagtagt ctcaaaagga ccgcgtaggg | 1020 |
| agggaaaatt taatgagttc taatataata tgcaggcttg tgaaagctga cattgactac | 1080 |
| tctggactgg tcggatagtt gctagacata cctattgtga caaactgacc cattatcgag | 1140 |
| tctagtagaa ccggtccgta caattacaca ttcttcgtaa actagttcta taaagactaa | 1200 |
| aaaaatctat atcacttgga gaattatgga agatgagtca actccgaagt gtggtcaaaa | 1260 |
| atattacaga ttgtatcaaa tcgaataggc cgtaaacaag gggtatacgt tcacagtaca | 1320 |
| aaataaatca aagccttcaa ttatatcgag agattattac actaccgctg ctcttgacta | 1380 |
| gtcaaacgta cctctcattg acaacattca gcatgattat tgctccatgt caaagactcc | 1440 |
| gtgttcccat tagttttaaa ggcataattt atctcttttc ctcttggata acgagagata | 1500 |
| attagacaat gctagtttca ccaagcccga ctcgataagt ggcggttta gcctacccaa | 1560 |
| tcgcctaaat atatcaaaaa tgacttgtac gcgataatac tgctcgggta gttaacggcc | 1620 |
| aagtacacgc tcacagaaca acggttgtac cgcttatcta attagggaat gtacggctct | 1680 |
| ctcactaata tgcgattaat ctatttgat ttttatgcag agcatcctaa gtgaaactct | 1740 |
| agatgccgcc aattttgtt tatcatttcg ccaaccgtga attccaagat ggcccgccaa | 1800 |
| agggcgtata aatcgagtat ttacgaagta ataagttaat tctaaaattc tttaaatatg | 1860 |
| aagacaaaca atgaattgat tatgatttcc agatatttac tttggtaccg gattaaaccc | 1920 |
| atttgaacgt cattcgatat caaagtccgc taataagggt ttcaattaca attcttcagg | 1980 |
| agaacacatc ggtaaccttc | 2000 |

<210> SEQ ID NO 76
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 76

| | |
|---|---|
| gcgcaaacca gcaaattagg tttgaccttc aacaactgta actcgatctg cagacgagtg | 60 |
| agtaacaaca gctactggta caattttttt gtaccgcagc attcaggtat tacccccttca | 120 |
| cgctcagtac agaggtatcg ggcatccgta taaaaaattg acttcttttt acgatagtcc | 180 |

```
aatagaccgt tagcttctac ttcatagtac taataataac ctaatgcaat agtctggata      240
acattcacgg gacactgata ctagaatcaa ctacgctgat gagcatgtcc agactgacaa      300
tcggtcgaca tgagaaggaa tagaaaaaat cctaccctgt taattctggt catgtttgct      360
ggtctctttc ctactcggtg cttctcaaat gccacatatt cgagcataat acctagttat      420
aggcataaac ttattgttgc tgcccatgtt gagcattttt tatatttagg cctttttacga     480 atttctgttt ctattactaa agatgtcaga gtaataccac cttcagacag aatcacatga     540
ttaaaactat agaatcggcg gtacaaagat gtatctcacc tatagagtat gctgataaaa     600
tcatagaccc tagacatact attcttatcg ccccttagaa attattgtag gggttgcgat     660
tacaacgcat acggtatttg ctatatgagc actcatggct tatgtgtaca atttattgat     720
atatatattt agagctccgg atcgggttac agaatcactt cacgacccag caaatgctaa     780
tgatttaagc gtagtatatt ggctttgtgt ccagttttca ctacgggttc ctttctatgt     840
cctgataatc tgtacaaccg acatacctg aattcatgcc gcatatgtcg tgttaacagt     900
gatctagggt ccagtgatag ggtcattttc gtatcgtcgc atctgtatcg attggaaaag     960
aattatacag tccgattatc acttagaact acacgagggg acctcttatc tgccctacct     1020
attggagtta aagttctaac tgctcaatct caagacggcc gaagatggtt ttaaaatgac     1080
ggtccacaca tttacagaca aattggaatg cttagatata tcctactgtt gattttgtc     1140 caaaattaga ggcgatgtaa ccccactgaa agattgagca gtacagtaat tctaacttga     1200
aaaaataaat ttttgggtat gctcaatctt taaggtgacc tactaacaat atcctagatc     1260
ccatacggta gttcgacaga gatccaatac attctaatcg aacattagta agttaaataa     1320
tatagagcta catttctaag taaatcgatg cttgaagata ttggtagttc gcagaatttg     1380
catccatcac aaacactagt ctttacgttt gccaattgct aggtagagta gattacgagt     1440
caatcagaag accaaatttt ttgacccata ggatacaaca cgtagtcatg acaatcgcat     1500
atcgctagta tgttagatct aagaaaatag tctacttaac cgggtcatac atctcagcta     1560
ttaacgatat tatgttgcct tatgttagac acgtcaataa gtagagcatg catttctgcc     1620
tcaaataaca aatttgttaa tatgcaatga ataccctgagt tgaatgaacc caaactaaac     1680
tcagggtcct tccatagcga gagcgctagg ctaacatgag attctgacgt cttcgtgagt     1740
tgacaggatc ttgccaacaa attacatatt tgaataggca tgtacgatcc attatactat     1800
gagtgccaga gaaaactctg ctggccgacc gttttacggg gggaaagtca aatatgtagt     1860
aagtacgaat tttcctggga gactatagtt gctgaacgtt cttattctca tttcttgaa     1920 gttaaggatg gtaaaacata ctatacctat gtagatattc tttggtagta taactattat     1980
agtagcgtag acgttatgtg                                                 2000
```

<210> SEQ ID NO 77
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77

```
gcctaaagac ctctatattt taagctagca taaaggcagg agacgttcta acatcgcacc       60
gagttcgact atgaagagag gtattatcaa ccctgtctcc cagttcacac cggttgcatt      120
```

| | |
|---|---|
| atcatgacgt ttttgatttg ttttttttga gtaacgggtt cattgtacgt tcgatagagt | 180 |
| actcgataaa cgactcattc cacgcaagcc tattttgtaa cttataacta gacattagtc | 240 |
| tatggctact ttcacacccg aacttacgaa caacgagtat ttttttttg gcaaaaacgt | 300 |
| aacgttcgta tgtggcctaa gtcattaaaa gacaaatatt gaagaaaaac ccatgattta | 360 |
| ataccgatag gacattacaa gggtcattag agataacaaa taaattaggc ttcttccaag | 420 |
| agttatccga ctagttgtgc tccagatctg cgatactgat cgaatttata cctcattaga | 480 |
| cattcgtagt cattggtgtt ggacttgaag ttctgtacaa tcctcggtga tcactcttgg | 540 |
| acaacctgct gataaaacat gtctatcgtc agtccagttt gtataataaa ctaatgagac | 600 |
| aatatacaaa acaatccgtg gcactacatg ttgtatacca acataaattc tgaagaccta | 660 |
| tgattcttgt ggccgaatag tcaacagatt ttacgatcac taataaccat atatctgtta | 720 |
| cttgtcttct cagataggag cggactagaa atactcactt atgttattct tacgttactg | 780 |
| tgccagacga gaggttttg cagactctat ggtttgccgg atcttgctag gaaaagggta | 840 |
| actggtgcct gattgcatga actatgtggt atgactatag atgaagcatc cgtcactgag | 900 |
| ctcttcgaag tcttttatga gacaagaata ttctttgata gaatcatcta tgtctcaatt | 960 |
| taatcaaggg aacggttggg tactaaatcg agttatcatg aggtcctatc ggaatgcatt | 1020 |
| gtatttgagc aatatctata actgtaggta ctatggcgga tatttatttt ccttgctgcg | 1080 |
| acttcatgta gcaagtcggc aattccccgc ggttttacat tttctgcttc gaggtattaa | 1140 |
| ggccctaaag ttgtatatat tataaattaa agatctggat tattaactca gtgcagaggg | 1200 |
| cgtaatctga cgtggcgaca tgtagatgaa gcttgcccaa aagatatgag atcttaatat | 1260 |
| ctataagaag tatgcctact gttaattttg gggagaaatg ctaccccgga caattatgcg | 1320 |
| attgtcaagc gaatatcttg attttatcct tggaataggt atattacttc ggttacacca | 1380 |
| gatatgaacc tatctattac ttcatatttt actcaggctt ggtcgggacc tgtgttactt | 1440 |
| taaaggcatt aaaacataca gcgtcgacaa tcctcctaat caatatcctc agaaggaatt | 1500 |
| tactcgcaat agcgaactga gttttttgcc tgtacaacgg tcgtgcctac tcaatcattg | 1560 |
| ccgcatacta atctctatca tattgccttt acggggcgac caaggaggaa tcctatctaa | 1620 |
| tcccagggca cctggaacac ctgcggaaca tgcttcaata ataacatcgt ataagtctat | 1680 |
| gtctgcgctt gtgacgtcat agtacttctt ctagtgatat attacgccgt tggattggga | 1740 |
| tcacgtttag aacgacactg tgaacttcta tatgtactct tttctcacga tatgccgtcg | 1800 |
| agttttttat cgataatagg cagtgttgga gcgggacgtg tcattagtaa taagttttc | 1860 |
| ctatcaattt cctgcgatac ttgactcctt tggggcaaac atagacgacg gttggagtca | 1920 |
| aggtgaacca aaatagaagt acctgggtaa atgcttcata ggcacttgga caagacatta | 1980 |
| agtcgacaca ctatgccttt | 2000 |

<210> SEQ ID NO 78
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 78

| | |
|---|---|
| aatgttcggt cccgggtaag ctatcattct ataaagtcc cacccccgctt atttaagatt | 60 |
| cacagcgccg caatgacgcg gaacagggtt gtctatgatg acctaactac ggcactttag | 120 |

-continued

```
gtatcatata ttgagttgag cgaatggatc tgctaggctt cccgtctatc ggatgcttta    180
atgcaggtta atggcccgat tgaagtttat agtatatata tacactgtga tggtgtaact    240
acgttacttc gttactgatc aattttcaaa ttatctcatt tgttaggcta caactaggac    300
taaagctcaa gtaaccgatg cgaagaggcc gagatggtat aatcaacggg ggtgtaatct    360
aatatacgaa tcatgctagg agagcagctt atcgtcaaaa ctctgttggc cagattctaa    420
ttactcttta ttgtatcttt tttcatgtag attaaccgtg aagacagtag ttcatgtacg    480
ttagtcaatt attgagaaca ttagcttgaa tggacgcgtg ctcaaataat accccagtaa    540
tctaaaccat attgttaatc ttttacaaga cccaccaatg acctaatgag ttcacctcca    600
catacctgtc attaggtgac cttatttcca catttgtatt aaatactaat aactgaccat    660
attgtgctgt ggttctgtac acttgtatac ctgttcggct aatactagtc agtgatttca    720
tagcgaatat aacatttgac aagactgtag caacaagttt ttggtatagg gtttgttaaa    780
gcataccgcg caggacgacc gtctcttaca ttaatttact cgttttaatc tataattatc    840
catataatca actagtcctg agccaaatct tcaatttccc ccgcgtttga gattgcttga    900
tgaggcgaaa taagaggcga acggaactcc aaaaaagagc gatcttttat cacgtccctc    960
cataacgctt tataagtcat tagtcggcat cgttacaaat taatgataga ccagaaagta   1020
cacagacgtg tcttttatcc tgtaacgacc ctaattcggc accgtctact aaatgctttg   1080
ccgtacgctc tgatgattct atccagcgat tacgtatatg ttccggggta actacctaaa   1140
tctaatgcgg ccataggccc atactgatcc gccgatttcg cgcactgctt tacttatata   1200
catcagtact actcgggcaa ccggtaaata atttacaata gaagtttaag tgcagttaca   1260
tgcttaagat atcgagagaa cttgtgaaat acgtacacta ggattttctc aaattcgtga   1320
cattacaagg tctggtttcg cgattctctt ggactgatat aatatgattg aaaaatgtag   1380
tagatatgat cctggataac attttttaaac aagtcttggg tgagctcggt accttaaatc   1440
cgatcataga atacaacatg gcacctacat tcatattaaa tagtctatta catgataaga   1500
ctccttcatg tctgaaacat tggttagaca attcgcggtt tcagtgggta gcgtgttcta   1560
ttgacttcga aatgagaaag tgtttcggcg cgtacggtat atcttccccc atgattatac   1620
ataacatcct tctaaaaatc gcgccactgc agggtcctct tttcttatat attattgagg   1680
atttggaccg atcaaactta atattaaata tgattctaca tacaaaggta atgatggcaa   1740
tctacttgcg ggctcgactc gtagtctgtt caatgaaaaa tacatttctc aagaaataat   1800
cttcgagcta tttcactctg tagttaaagt ttcaatcttg ttacatactg cttatacaaa   1860
tttaatttaa aagcatgtgt caatttaagg ctaaatgctc agtgtaaatt gtattggtaa   1920
actccctaag actaatgaat aacttgataa tgtggataga ttaaatccgt gcaagcctat   1980
cctaaaatca atttgaagtg                                                2000
```

<210> SEQ ID NO 79
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 79

```
tacaaattgt ccacgggcgt gaaaacaagc ccattcttct tcaattgcaa gatttgcgat     60
```

```
acttaaacct tactgattta ataatcgatt caaaacgcaa gagtcatgaa cagaacgaga    120
ccccgccata tttaaatgca cattcgtgca gcgatgggta tattgaggct gtgagaggct    180
caattaaaca ttttaccagg agatgggcaa ataatgcgt ggggatcgcg ggactataat    240
ctaatcagtc atactctaaa gtgagcttcg tgatatcttg aggataaaaa agggcctaag    300
cgcacagggt tattgagttc cagctaatga tgctcgataa taatcggccg taacttcaat    360
gcgaagagaa tatacgattc tgaacagtta cagataaggc ctattaggcg cgaaaatagt    420
cgtctaaaag aggagaactg ctggtcgaga atgagtgggg gttattctaa caaaggtagc    480
taggtgtggt tataaacgag aaggactaca cccaattgat ctcgataata gggcgggatt    540
gtttattgac agtagtgagg tgttctaata acagaaattt agttaaggtg cgtattcttg    600
gagtagagca caaacccgc taatgagcat tgtatgaatc cgcgacaaaa gagcaaagat    660
cacagcaacg aaagtctaat tgaaatagtc ctcgattatg ccggtgagtt gaaaaaagtt    720
gtacgttcgt ttatgccgtt ctagataatt tacacatcac attcctcacg taactacatg    780
atttacctac tatcacttcc aatcaccaac tcggatttag gaatactgta acttatttcc    840
gattatccga ttgagaccta agcagaaaaa cataagatgc ccatccgaat tgtgatgtgg    900
ataccagttg tgataattcg tcggattgaa ctcagcctgc ttaccgcttt tgatcgcagt    960
cgccgcgggt agatgtagtt agcctcaccg gctggataca tatctccagg aaatcgcgga   1020
gtatcaatct ctagagtaaa tccctgcct tccgttgatc gtcttgctca cctaaatgtc   1080
tgaactaggc tgagaacaca accatactcc ggccacgtag acgatgctga atattacgca   1140
gctatactca aagttaaact cttctcagtg atttatgatg tagcttagtg atctttacag   1200
atttggtatc gattgggaat ccagtttaaa actgaaacga catatagaaa tatgtaccaa   1260
tctaccagcg caaaccgagt cgaagtcata ttatacggta aatcaccatc gtgtgatata   1320
ttgcaatttg aactgatttt taatccctag cttaaatact tcattgattt ctcgccttta   1380
attctctgaa cgttacaatt tttctgccca acgtcctcc tctagaatac ctcgagagcc   1440
gacacaaata cagttagaga attttttggtg atttgtgcga cttattagaa ccacggggtc   1500
atgaccttag cccgaatagg tagtatccgg atatctgaaa ctccaggcag taataataca   1560
ttgccggaac gacaatcgga tctagtgaat gcgacataga cggtaatatg ttaagcacct   1620
catagatgat tactatcagg aaatatcaat ttaaagctgc gatgaaaggg tcaggaccca   1680
gccctttcaa gtctacgtaa ctccactagc cacattgtct aagggtgcca atcatagatc   1740
atgcatcaac accggcgata cgcttgttca ggcattcata tcttatagtt ataaaatttg   1800
tttatcgtgt gcaggggtcg atttttctca ctttcggcaa ccaggaaaag tagtaattac   1860
tatataaaat gaaggcgaat ttcggattac tctgcaaaaa atcattagaa tacacatcta   1920
ggatccggag gtatctgcct ccatgaagtt aactccattg tggatatgat gcgagtaaca   1980
tatttaggtc cgaagaaagg                                               2000
```

<210> SEQ ID NO 80
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 80

```
atcatctacc taagacagag ctgaccgtat ccattgtcaa tagaacagca acgattttt     60
```

```
ccatcgctgg aagagtgatg cgcactagtt catttcggac aagtaacttg gacgcgatac    120
aagatacaat cgatgtcaca gcctctttag tacataccat ggaattatga atcgactaaa    180
aacgcagacg tataattcag ctgatcgaat gatttcgatt atataccgaa gtcagtgacg    240
agaaccttca ctttgcggga taccgaactc tgtcacaaga aataagtata ggttagaatc    300
cagagaaaac attgaatatt atgttttttc gcaccaaaat aatccaacga tgttacgctt    360
agttagtgga tatcatgact tcactaaaca cttggattgt tatctaaagt ttttatcttc    420
ctggctgcga cattgtttat ttaagacgta gttaaaaaag tcgaccacgg aggaggaatt    480
acatcgtcgc tgatgagccc attttcgcta aatgcagtcg actacgaaga gtttttcgcg    540
tatcgtcaac ataagttgat cttttagat aacaaacaaa actcttcgca tcgacgtaaa    600
acatttttca taggcgcttt ttacaccgaa gaatctcagc ttcagaattg tacgatgtct    660
tgtcacagat atcctttaaa caaataacta atagcgttga ttgtttgaca tctactcctt    720
attgttatga atgtatacca tattgttata tgctattaaa tcccacatat tgcggttcgc    780
actaaaatga acatctatat aacttgactg ttacttgaat tagttatggt ccagctaatt    840
tttcattcta ggcatttaat cctttatgtt ccatagtttc cttcgacgcc ttgaacgatg    900
ggtgcgagtc cgacggacta acatttataa acacatttgt gggtttgggt ttgctacaga    960
tatctggacg caggatgttt agagtaacat ctgttgtcat ttggctagca aaatttgagt    1020
tacctgatag accttcctca ttcccttaat attaaactgt ctttctcgaa taccgttcgc    1080
acagggtcca ggaaatgtga tgttatgacg gcgtgcaatg gttagtcctt atgcaggagt    1140
ttctccgcac ccatcaatgc cattatttta cagtcaaaaa aacataaact tgtatgacga    1200
atgcagacct ttgaactttt gttaacctac ttttgtaaaa ccagcgaacc ctaacagtta    1260
tgtaacgaga tccgttaacc aaaagcggtt atccgaggat aagcttccta cgacgtcaca    1320
tttgtcatct tccttaccgg tatgaattgt atgcaggtcc ctattcgaaa tgtggttata    1380
actgatgggt atcagcaggt tatttataac gcgtacttta tccttgtagg ttagttgctc    1440
agtacgccca aatcaaagag gaggccgagg tgcaggaagg acctgactga caatcgtaac    1500
taaattatcc aacaggattg ttaattgaca atgtttacac tgactatggc aaaaattgtc    1560
tcccaaacgg ctgcggacag cgttcttttt atcgatctga ggtagcactt gcatatggat    1620
atagcaataa gaaatagga gataccagcg aagaacggag tagatgcctg tgacgtgtgc    1680
cgacctgaca ttgattatcg agcatgcgga ttaaaattca acaactattc ccgtgaagag    1740
tgccagcctg tagtcaatta ttgtggatat tatctaagtt cagatcatac ctctcgtcgg    1800
tgaaaacaga tagaggccaa agggcaaatc tattgaatga ttgacaattt gatcatatac    1860
gtgtctaaga attaattgta acggatgcga attcgttaat cttcctgggg tactcttctc    1920
cacgtcacga gagataacaa caacatcagg cttctgataa atagcgtaac aacgtattat    1980
caaatgcatc ctgtctgtat                                                 2000
```

<210> SEQ ID NO 81
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
ttaatgaccc ctgccttact gcataaatct cctaattgtg taatcactcc tcactcagat      60
aacgctttac gtatggatta ccaagtaagt gaaatcacta tacaagagat tgcctaattt     120
tgctaagtta gcgttgttcg tgttttataa ttttattgtg agtctttcac cgaagtagaa     180
ggaagtaaac tcgcagtttc ttataaccac ttctaggcga tgtagacgac atagaaaatg     240
gggtaaggaa ctcataattt ttaagtcaat gatacagcct taaaagataa aaattagatt     300
accgtttaat gagggtacgt gaccattaac agtaagaaag cctgcaagca tgggacaggt     360
gctattgcag agctcataaa cgaaatgtcg cttgggcgtc ctgcaccaga tacttagtgg     420
cggatgtcaa tagcgaggac gaatcattgg atgaatatta gctagtggat acggaaaaac     480
gtgactacga ttgcggcatc gagttcttaa ccctctcatg gaggcatctc tcgaccttac     540
acagtgagag tgcattttgt tcgccagtct actatgacac attaaggctc aaacacgctc     600
tgcttattca tttggccttg gggttctaga tcacactaca attgcccttt gcaagaaaaa     660
caaatgtcat tgaaaaatta actgctgtct tataaaccta aactaccaga tactgtaatt     720
ggttttaggt ttgagcatcc accaacacca atagccaaga ttgttaaact ctaataactg     780
tctaatacac gtgcatattc atagtgaatc agtgcggttc attttctgaa gagctccaat     840
ctgaacgata caaggcgtcc tgcgcgtgga ttaaaaacaa cttaagcgtt acgcagagca     900
gtattccatt ttataatata ccgtttgccg caggaggtta tattgtagaa gattagttca     960
ttttgtgggg gatttacagg ccaatattta ccaaatttta cgaggtagtt gaacctagtg    1020
ttacttcgtg aggctcgaac ggtcttcccg ctccaactgt acctttagat gggggcttct    1080
ttggatgtaa cgaagtaccg gcttaatatg agacgtttgt acgcgaggca ttcttattta    1140
acccatactt aatcaattca aaatttatct tggtgagtag cactggagaa tttggtatcc    1200
atagcggacc gatagaaaga ttgttatacc aaaattcatg aatgacgctt agtattttct    1260
agtttgataa catggttaag actacattct atccgaattc ttattaaaat tgaaatgacg    1320
cattgcatgc tgtgattcca aaaccatgcc gacaggaggt cttcttaaaa attcagcgtg    1380
aggttactac accttcaaaa gtgcataatt ggtggacaac taaaggataa ttgggtaaga    1440
tctttctaca ttccattaaa aaattctaac aaacccctatc tcatgttaag tacttatgtt    1500
gcctcttact acattgaccc tacactcaga tatgataaat tgatgtttaa cctaactatt    1560
taaaagctca ataccttcct ttttacgcgc aataaaaggt taggcacttt taatgtgaaa    1620
tttcagcgaa atattcgatc ttgatataac taagtttaca gttcctatta ctactcatta    1680
taatagaatg tatgggctat gaataataaa tggacccctta gaaggataaa tgcattgatt    1740
cgatgctaga gtaaactgat ggctcagaca gaatcatgcc catggggaaa cataacacct    1800
aatcagcatc aactaaaagt cacatgtacg agagcagaat caaatacaaa tcaattatat    1860
aacgtgaacg tagaatccgg accagggacg tttctactct gactatatta ccgccagctg    1920
ctatagtaat cgcgtatgga gcatgtattt gctgactaat gctaaagtac aacattactg    1980
tgtaatttaa aatgctacct                                                2000
```

<210> SEQ ID NO 82
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82

```
tgtacttgtc ttcttgtttg tcacatacgg accctaaatg accttgtcta gttatccgat      60
acaccttgct taagtagcct ccccctagggg gaacttatta cggaataaca gttttacagt     120
attaatcaaa ctcttatcca cgttttcctg tgatcacaac gtattgtttc ccttgatttg     180
ttgagaatct ctattgagcc tttatctat tagagtctcc gtcgcacata atcccggtgc      240
gttgaacaga tactggctag actccttact tttctatcag ttgaacggag gatacgagct     300
tcaaaataat gatttgtttg tagatgtcag agcatcgtcg tgagaggaac ccggataggg     360
ggaataacag gtagcgttgc ggttgcctga ctaaaaccca ggactcaagt ttcattatta     420
acattatttg catgaatgac agtgtcgcag atctggtata atgaccaacg atcgtttagt     480
agataaattc caatctaaca aacactaacc agtatctcag cccacattgc atcttgtttt     540
agcaatcctg cagatatcag aaccctcctg cagtgaattg actagtgcac gacggtaaca     600
tatctcttta atagcgcacc gtcctcaacg tagatgttac gtctggggtt atattgggcc     660
ggaatgtcct gggcttggac taatgaaggc aaaggctata atgtgctta ttatttactt      720 ctgcgtactt atttggagaa tgtcatatta aagatgtcgc ggtggtcgga ttaattgaat     780
aatgtgcgac ttggatgcac ctcaatcttc attgttttga aaagtctgga gacgtgcaat     840
tacactctat atgtctttgt attaatcgtt ataagctcta aaggagatag caagctcggg     900
caaatggtag attaatgctt caagaaaata caagcctggg gattcacatt ccgaatatac     960
aactaatgac gctctcattc tcttgcaagt atagtaatcg gcccgctact ctatggggag    1020
tatggcatca ggagagagta tcattgacat tcgaagtttg catactgagc aataagcggg    1080
taatgcttca aaacaaagtg cactcactta atgtcggaca ttgtttataa gtgttagcgc    1140
tcaattttcc gcaatcacgc tcgagcacta atagttggag ttcgctttag tttgataata    1200
acaaatatga ctttgtcgcg agattgccta tttgcatcca ggactatcga acgcaacaaa    1260
ctcgtgaaga ggccgcattt taactgcagg atagtaagat ctaattatga aatacatagt    1320
ccagaaaatc attcgagact acttaacaaa tagtttcaga ggttctagac tttctcaaat    1380
gtatgtagtt cgtgaatatg tagttatact caattacgac tttgatttt atttaccgcc     1440 taagaaactt gattgaaata atctagaagc ctcaatcctg ctccatcaca aacataatat    1500
actgaaagct agagggcgtt accacagtgg tacgtctaga ttccaaagcg tgctaggaga    1560
ttagtggtcg aaacgcaggt tccgcgagca gtatcaccct acaaagtagc tggttacagt    1620
caacacctag cagcaatttc ttcacttttg ttacgatacg tccgtggcat gatcgtcgtt    1680
gcctaattct acgacttaaa gataccgaaa aaagcaaaat ctagaaccat gatagagcta    1740
caaaatccct ctacccgttc gtacgtgctt cctaatcaga tcaactatgt gagcgacata    1800
gttttagcta gtacttgagc gggagttttg ttctcgtctc tgaatatata aagtgtttaa    1860
tgaagtgcta tgagggccac tcatctttag catactaaat catcagacat aaaggtcacc    1920
cgaaataatc aagcagaaga ctaacagaac atgctaagag aggtctttca actacgcact    1980
tgatagataa ccgttagctc                                                2000
```

<210> SEQ ID NO 83
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 83

```
tcacgacgag tgaggtctga gaccgtcatc aaagatcgta acactttta ccgggctgcc      60
ataacgtaag atgcatgact gcaagaaagt tcacggtggt aatttcaatg agtcattgtc    120
attccctgaa ggacgtataa tactatgtta cgtagattat tagggatcct tatgcgttga    180
ggagatatct tgccttgagt gaaagaaact catctgttta gaaacatacc aaatatgtca    240
gacacggtcg gctttgataa gagtccctaa ctaattggct gcacattacg attcgccgaa    300
aatatatgtt gggagtagtg tacacgattt tagacaaatt cccgagatga tgaccgtgac    360
atgtacaatc gcactaaaaa tccccggtat tagactttga agtggttttg gtatgtgatc    420
ttaagcatat tcactatact agcataacaa tggtggttgc ttttggacgc aagttctgag    480
tatatgacta tgaagcggaa tcgattaatt atgtcttcca ataaagctta gaagtatggt    540
tcgtgaacag cttccagtat aatttagaga ggccgacaat atatataggg ttttatttac    600
tattggccaa gaacatcctc agtcgatcta aacttcttcc aaagcactaa ttctatcgca    660
aaatggtatt ataacaacac taatcttgga gtcaactcat atacgcgcgt gtagagtcat    720
gtaatactca gcggctaact acatgtatta tgtcaagtct tccttgctat gaatactggt    780
attcctttgt ggattaaaac ggtaccgtca tgtaattttg agataaagat ctaggacggg    840
gaagaaaata gtaatacggt atgtatgcgt tgagttgggt ctggatattc agtcaactat    900
gggtaactga ggactttgac gctgcatccc tgctggtgc gtagtcctaa aaaaaattct    960
ctgggacaat atgtcttcac aagatccttg tgagaatccc gcttccggtc cggctgggcc   1020
atatagactc ctattacttt caaacttcgc acagaatctt aaatatgaga ttgtaaggaa   1080
actatcagat ctgctctaga caccgacgga ggagctcccg gaacgttcca aagcttttt    1140
ttctaagtgt tgcacttggc cggtcgtaca cgcagagcgg tagataaccc aaatacagtt   1200
cttctctatg tctacgccca ttatgggacg cgtggagtct ctgtgacgtt gacggtttat   1260
aggttaagta tgcttacgga tgaatattaa tgaatcgtcg tagttattga agacggccga   1320
tgtagtatgc accgtcagcc gattccaaac tagtatcttg ctcctgagtt actctgttag   1380
attcctgtca gtttatccat tttagtgtag aaatatcctt gaatggttgt accatggctc   1440
ctagaactag acaagataaa atgttatacc gtctggtgaa catttaacct cgtacttatc   1500
cggactaatg gtaattgtcg accgcctcct gaaaactcgc attggtgtcg aaaaaagcaa   1560
tgagcgcgta tttttatgga gataggtgca tgtattagtc tgtattctta gatgctctgt   1620
cgataacatg atgtaatgcg aattgattag aacaatctga gaggctgaaa ttgattgcct   1680
gcccaaacac gatacggttc gatagctagc tgccgatgcg cttcgatatt aaacgtaggc   1740
aaagacttcc attctgttgg tggtaatcct atcgattcct taatgaaccc acgacattgg   1800
atattgatat cgtgcttaga tatttgccac catatgatgt atataattaa aatacatatg   1860
cttaaggcga tagtatttac tccctgtacg cgcagttacc gttggcatgt aacaatttaa   1920
tggcccaatg aagcgactac gaaccatata atttgctaca atagtactat taacatgcta   1980
tgaatttatg caaaaaaaaa                                                2000
```

<210> SEQ ID NO 84
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 84

```
gagttgattt tccgcatttc atggaaatat aatagggtaa cgtttagtta cggaacgtat      60
tcttttgaaa actctactta gtgtcgcaac taaacttctc tgttttagta cagtcaggat     120
tagagactac taagaaattc ctgatctgct cgctactgcc acactttacg caggaggctt     180
gttttcgcag taaccggtga gttaaggtcc aacagggtca gatgtcccctt tgtcaccac     240
gaatcactgg ctcattagaa attgatagat ttgttaaaac gaacctctat gtcaacaaat     300
gcttggaacg tcattatgac agtgttttga tgtcagttta ccagaaggg cgagagggtc      360
atggcgcggt caattagagg ttcgcatatt agtacttagg tattgtcaga tcaccggagt     420
ttggaaaccc tgcttgtgtg atacctacaa cttaacttgg cccaacatga gaacgttcca     480
tgcttctggt atccgtgttt aagctctcag tggagaaatt cttaaaatga tattcgtaac     540
taaaggcatg aaacaaaatg tgaggatcgg ttataatgga cacagtcctg accccttcga     600
ttgacctaaa atattgaaac tacattcaag tagcgagaat tttttaattg ttcctaaagt     660
tttattatta gataagtggt cgatgtgtag gaaataagag atgataagaa aaccagacgt     720
tatttaaagg gaaatgtcca ccagtgcccc agcgttataa catgatagcc aagaatttgg     780
ttatacgcaa agttcgattg cgtgctcggt tactggagat caaattaatg gagcttcaat     840
aatagtacta aatcatgttt tcaatttctt agcacatccc cactaatagt ttgtctcaga    900
tattatatga tatagttgat cgaccctgtt atacgcctaa aaccaattct ctttcgctac     960
ccgagagtga aaacatattc aaagttgtca gcctcgacgt ttaatcttcg taataatttg    1020
tcggtaacag attaaatacg gaagacaaat attattatct tcaactgtcc aaattctccg    1080
tctccatttg agacttactc atacttcagt gaccttggca ctatagctga tgtttggaga    1140
gaattaaacc gagatactta taataatgag agctaatgaa atggtagttc gtatatgcgg    1200
ttatagactg taagaactat ccaacagact ctgccgcact ctcagatttc atcttaggct    1260
aggttataat gtatgggacg gctcggatat tctattgaat ttaacaattt cgtccaacaa    1320
cccttggtaa ctgagtttcc cgattacatg acgatccagc ttaccgtaac catagaactt    1380
ggcaatcctc tccttaaggc gcatgactag atcatcaatc gcacttcttc aatcaagttc    1440
tctatctggc gcggacatac tgttttacgt ctcgtttcat tgtaaaaacc cttctgtgta    1500
ataagaacac gcgactttga tggttgcgat ccctacgtaa cgtgcactta actacatata    1560
cttggtgaga ttgtgctcca tattgaaagt cgatgttaat caagacggag ttgtgattaa    1620
taaaatggca taatacacct gtgtttttcc tatataatcc agagaggaaa ataactgttt    1680
tccgaccaag tttgtactag atttatgatt ttccgaatat gcatctgcgt gagtgtgtac    1740
gtctgtgtgc atacgtcatt cagaaagatc ttccgtatgt gagaccttt ggatcagttg     1800
ttcatttttg tacctgccta ctttagacca ggttctaaaa ggctcattta acacatgatt    1860
attatagatc ataaccat tactcctaat caaatttgtg ccatcgttgc aaccgaaatc      1920
gtctagcaag atgatcatcg agcaataccg accctttata taggctcaac cctatattca    1980
gaggaaaatc acggtttgtc                                                2000
```

<210> SEQ ID NO 85
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 85

```
gtccatcatt gactctgttt tctcgaggaa ctctgcaaac cagataagag attattagca      60
tatatgtacc tagaaggaca tattatcgtg gacatcccgg gtgtttgcta tttgagattt     120
attgattgtt ttttggtaaa agatctgatt tacatggcat tatagccgag gctcatgttt     180
acattagcat agtaggctgg actagttgcg agagattttg ttacccggga tcaattgcca     240
ttacatcaaa tcacgtgaaa cgcttttcca atacatgcat atcccagccg atacttagta     300
cgagatgata gttgtacgac ggatatataa ttacgtctat acgttataaa ttgtcacctg     360
tcaccacttt ctgaattaaa agctgaggga cgagccgtat taatactaag agcgtaagag     420
cctcctaggg ttatataact tccgcactca gctattatta ttgaacctgc gtacaagtat     480
ctacttattc aagttactac gtatgaatta gtaagcatct tgttttactt atgaccgcaa     540
tttcatacgt tgcatgataa gacaagttca agcacaataa ctacggcagt aggaattgtg     600
gctcgacaag agagagctgt tttcgccgtt ctggggatga gcatatttaa agttgtttaa     660
cacatccttt aacgataaca aaagacatac acaggatgag gtatttctgt caagagaatt     720
ggtagtttgt gttaagaaga tccctgaccg tccttagatg gaagaattaa cgtccatagc     780
tggaggtgtt gtctttattc acggaagcat aagagactcg tagtacagaa taagacggtc     840
tcagggtatc caccaggatc aacgccagaa agtgggcaac agatcggaag tggaattcgg     900
aacaaacttc atatgtgaaa gaaaagcttt gatacgactt ccatgccttg gtgataggtc     960
aaatttagct attagaaact gcaatgggag atgttcgtgc atgggaagta aatgtatcga    1020
ccataatcgc tctgcgggct agagcttgcg gacagttagc ggttctttag acgggctgaa    1080
ccctatcgag aaccgataca gcaatgtagt ccattacgac atatgtgctt cctcgacttt    1140
actggagaac cttaagacgc gatggattat ttaactaaat ttccagttat ctgaactggc    1200
ataatttaca acaaacctaa acatttttcca tagaaactcg ttatgagcat ttcatgcagt    1260
gcgtccactg tgatatctgt aatggtaatc ggtcctcatg cgatacggct cggtagtttg    1320
tcttgcgact taaggcaatg atgtgtggca tgctgtccag aagcagatag atcagggtca    1380
agtattgccc gcccatttaa ttactaaaga gaataatgca cataataatc tctattgtta    1440
atgatataat tattcctagtg atttatatct ttataaggta agcgatttca acaaattaaa    1500
ttaaacgcca taaatttcta gcaatttaga tactgtatgg gactattagg gactccataa    1560
ttaacgtatg acatactaca ctaataacta aactctattt gacagttgca ttgcttaaac    1620
acccttgtgt gttaaaccat acaaccttat gtctggctat atttgtactt caggaccggg    1680
attcatgata agtgcttagg aacctagacg atgaatcaag atcaacgtct tatttataaa    1740
acgttgacac aatattaatc ctacaagatc taactttacc attaaacaga acttgctaat    1800
ccctaatgac caacagactt ctggcaacga gaaaaaaata atcataattt gtgcggtaca    1860
ctttagcatt aatttctagg attcagctag ctgggcctag ggaacacgag ctttacgtgg    1920
cgtcgtccga atcgttagag aaacattgtg agatactcga tattttttatc ggtagaatcc    1980
tccctcattc ttacaatgta                                                2000
```

<210> SEQ ID NO 86
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86

```
ctcaacagca ttctatagcc actaatctta tctcacaggc gcattgctgc cataccgtta        60
gagggtttat gagtgtggtg ccaaatttaa tttccagcta ttgctgagaa gtcatataag       120
tttaagtgcc tctattcatg aatctacgaa gactacgccg tctgcgcact ggctttgccg       180
tcccacttaa tttaacgtta atatgcaggt ccgggttaat tcatgaaatt tatacgaggg       240
ggtagattgt cgcattatac gctcacctac aaatctgcct atcagcacag ccattatgac       300
tagatttacc ggggaatttt catatacaca aaccacactc attttcccac ttataggatt       360
gagtctcaga tcacacttgt gctgcttgct gcaaatcctt ttatcattgt tcatggttac       420
ttgtttaact aatatcattc atttaagata gggtatcttt ataccttgag gccaagtttt       480
ttcacagaat actgaacatc gaaaccttta cttcaaatag atcaggtaag attgttttc        540
atttaaagcg attcgctcat acagctttct gttaatagtg atatggattg gaaactaaat       600
taccgagata tatcgtcatc gtcggcaagc agctgcttta tactaggata cagaagacgg       660
ccgtttccag taaaaaaacc gccgattcga tcttcgatta ttacctttttt acttgcggca      720
ccaaatgtag ctgaattatg ttatgagcta tgcgtagtat acccccttttg tcctagtgct     780
aggctctatc attttatgaa atttaactct tgctccagga tacgtcggat gtacttttaa       840
caaaatctac tgagaggaca ggattgacca cgtaatagta gaactgatag gcgggatgat       900
aggatcatgg gcagtattgc tgattttaga ccttggagat agctgcttaa tgagctcctc       960
gacctcacac ttactgcaag gtcaagataa gaaaatctcc taaagatcaa accattccaa      1020
attcgtgttt acataaattt tactattata catcgtaatg ttaagtgatt tagctactgt      1080
gtgtctagga tccaggatag tcgtctaaga agccgaccaa cgtgctaaat aggatttgaa      1140
cagcgttata gtttagttta taaggttgtc tattttatca gttactgcac gacacatata      1200
ctctcagaga atagggtatc acggtataca tcgctatcat attgactaac gattgttcac      1260
ggcttatatt ttcacgagca ttccaatgtg gtaaccattc gcaatcatct gggctctcag      1320
ttgttaatgt agaatttaac caggttccgt attagtcgaa atcgatgctc tatgacctca      1380
accttcctct tgtcatgata gggtgactaa agaagtttcc gatacgcgac gtgaagtccg      1440
attattatcc agatggtaaa gtgaagctta aaacataaga gatcattctc tctgatgaga      1500
cataatgata tcatttcaaa gttctgttaa taatacaact gctagtcaac ggaatccttt      1560
ccatctaaag gcgaacacta actaatttga atgagaaaga taaacactaaa accgccaacc     1620
tagtagttac ttgagctaac acatatatta cttaagtagc tttatctctg gtctaagtcg      1680
gaggtcacaa tgacttggac ttcttttagt ttttcgagta caactagaca atgacctccc      1740
gacgtagcat atagaaagtt agaacatagg attaccgagt ggtaatagcc caatcaaatt      1800
atggtgcgaa aagatagtac tgtactcatt acttccggta tgggacaaag ccgatctatt      1860
tgtcggagca cgttaatttt atgaccggct accctacgtt tactgagtct aaaaatttgt      1920
aaatacaaaa attttcccg cgctaagtta accataactc tcaagttata cggggtaatg       1980
gatcttaagt tcccggaaaa                                                  2000
```

<210> SEQ ID NO 87
<211> LENGTH: 2000
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 87

| | | | | | |
|---|---|---|---|---|---|
| gtaagactga | ttaagaaatt | acatagggac | ctggaaccgg | tatcagattt | caaattttgg | 60 |
| ataataaacc | gccaggtgtt | aacccatcaa | catctagtat | tggcgtagtg | agatctcttg | 120 |
| catttcagac | atcctgggac | ggcaggagtt | tctatccatt | ttccgcaagt | gttatgctcc | 180 |
| aattgacaga | tatgtcgccg | aggaacacca | atctggagaa | tatttagtcg | agaggcacaa | 240 |
| ctggtgttat | aatcttagtg | ttatcaagat | gaccttttgg | agtcctttgg | atacatgaac | 300 |
| ccatacaaat | tatcagcgct | ctactcttct | gtaacacctc | ggaaatacac | tgaaacagat | 360 |
| gtcagagata | accatgagtg | gtgattgcaa | tcggtgacca | tgttcgtaga | tcagtcctac | 420 |
| gagcgtccat | atggcgacga | gggaactcca | cctttcgagc | aatcatattg | gattgagcaa | 480 |
| atggtcattc | aaaaatatac | tgttcactct | gccaatataa | aaatagcact | cgttttttct | 540 |
| attaggacga | tactaagtgg | gcactttatc | cctaaataac | tttcacaaac | ccgattatag | 600 |
| atcccccgta | tccaactggt | agaaggcggc | tcggatctat | caagcatttg | ccgaattttg | 660 |
| cgtgaaattt | ttccactgac | tgctaagcat | aaaccgatga | agccaatctt | gaatgggtta | 720 |
| tcttgaaaat | attttgctag | atttcataga | aactttgatt | aactatatac | gatatactta | 780 |
| tgaataacgc | gaattacata | tatagacatg | ttctacgttc | cctgaccttg | cgtcaacaaa | 840 |
| aatcggttat | gtcttaatca | gaattgtatt | ataatacata | cgtagccgtt | ttttaactac | 900 |
| tgcttataag | agaatatttc | tatacttact | acacagatgt | ttggactata | aatagaatga | 960 |
| catgggggca | ggggaatatg | tataaatgcc | tgtgtgatct | ccaactgcgc | attttgccga | 1020 |
| tgatatgtag | ataatacttt | gagtcttgga | cggccaacgc | gcacagacta | cacactacta | 1080 |
| tagacaatgg | atgatttcag | acgcaataaa | atgctaaaat | cctaccgatt | gtcatatttt | 1140 |
| taagtctata | cctcaccgta | tattgaattc | atgtcgtatc | cgagcgattt | tcgatttgcc | 1200 |
| ctgagaccat | agataaaact | cactgagctc | taacgtaaga | ttcaattcaa | tcaattataa | 1260 |
| gagcaaaagt | gtaacccgtc | gaagttatta | agctgaaata | gtcgcaaaaa | ctgtcaggta | 1320 |
| tgctgtcca | agttagcggg | gcgccatgag | aatgtgaatg | acacggctcc | ttgatatcac | 1380 |
| agcgtcaatg | tttaggtgga | ttagagcaga | gatataacga | atgctcatcc | gatatgacgt | 1440 |
| ataaacaaat | gagtaatgtt | aacactttta | tactccggta | cctcagtatt | ccagatctga | 1500 |
| cgtccgtgga | cacagtcctc | aattacgctg | ttattgtatg | gactacccat | cgctgcttga | 1560 |
| cacgatcttg | aatttatata | gctacgaatg | cagaggtttt | gcaccgcttg | gcactaccga | 1620 |
| gtataaggat | tatgtcagtc | gaggcctgaa | gcggggactg | tgaaaagcac | tccacacaca | 1680 |
| acagccaatg | tagagccttc | gtgtttgaaa | ttctaggttt | tcaacatagt | tttttggctg | 1740 |
| ctattctatt | aactactagc | tttacttgta | atcttcggct | aaagtaggaa | tgtattaatt | 1800 |
| cgctcaccga | atatcgccca | tccttgacca | cgatgtcccg | tcaatttgta | aaaggcatct | 1860 |
| agtattcatc | acggtatggt | atcccttaag | ttgtgtatgg | ctacaaaaaa | gtaatggaat | 1920 |
| ctaactaatt | ccatcatgcg | cgattcatga | gctcgtgtct | gtatgaaaga | atataccatt | 1980 |
| caatagacac | aacaatgatt | | | | | 2000 |

<210> SEQ ID NO 88
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88

| | | | | | |
|---|---|---|---|---|---|
| caagctagtc | taaactaaca | acagcaggag | ggcgagaacg | ttggccacaa | gacattaggc | 60 |
| gttctgttta | tcaagcatcg | acgtctaata | attttaatac | taaaattcgt | cactatctag | 120 |
| ttgttcacca | tggattttta | tgtaggcgat | atcaattcag | taaggtaacc | ctagttctct | 180 |
| gggctcatgt | atgaaatcgg | gaagaaagat | atgaatgaaa | agaacctaac | tactgaaggg | 240 |
| tagtcgacga | gaggcagcta | ataggcaacc | tttgtccctt | cggacggact | ggttgctgaa | 300 |
| attaatttac | ataaattaat | gaaacatccc | caacgccacc | ttacccatag | ggcgtctcac | 360 |
| gctatacggt | ctattttaat | gcctaagaat | ttacgatgag | cctataaata | ccttagttgt | 420 |
| gaacgaaacg | cagcacacga | caatcgtaca | acctcacttt | taatgttata | tacgggcgcg | 480 |
| gcttggtaaa | tgccgtagct | ctagtaacat | aatgcatcct | caccatacca | gcaaagctaa | 540 |
| aaatcttcaa | atattcgtat | aaaactaacc | agtttaacgt | gtatgaggcg | gtctttttac | 600 |
| cagtttggga | gcatattgca | cgtactatct | tcttttagc | agacctggga | tctgagaact | 660 |
| tccctgggt | agtcttacga | ttatagttag | cctaatagat | tatttgttcg | ttaggaagaa | 720 |
| ttcatatata | ctaggttatc | cttcaggttg | aaaattaagg | acgttacaga | tttttcacaa | 780 |
| ttataccgac | taccataagt | gggagcgcga | atagcatttg | agtatttgga | tcaagcatct | 840 |
| gctgggttac | acgtattaat | tagacccttg | ccgagatcta | gggaaacaaa | atccagaccc | 900 |
| gcagtacgtg | ggtggtatga | cgcttcttag | gataggagcg | caagtccata | gacctttata | 960 |
| ttactacgtt | tacctgatct | aaataatctg | atagaaaatt | aaccaggagt | cccattaagg | 1020 |
| tattcaacca | cggaacagag | tataatctgg | ttgataaagt | cgttttgatc | tgttaaagat | 1080 |
| ttgttaaact | aaacgagact | tctttgggta | acatcataca | agtctgataa | aggatgatgc | 1140 |
| agggactagt | ctaaaatgag | ggagtctttg | ggtatccacc | aaataatttc | aggagttaag | 1200 |
| agcacttcca | acgatgcagt | cctttggcct | tctcgtgcga | caaggcaaga | aaagttttata | 1260 |
| actctacagc | ttgtgtaact | cgaaagctga | cctactatat | aatgttattg | gaaatcaaac | 1320 |
| tcagggttat | cttcaaacag | tttgttattg | gctagacagc | tattacctt | aattggtcct | 1380 |
| taatcttgcc | tatggacatg | ctccacacat | taaacatact | taatgcatg | caattataga | 1440 |
| ttgtcccgtt | cattcactat | agcttcataa | tggttggggt | agtacacgca | aagtctactt | 1500 |
| atatgggcaa | cgcgccggcc | cgtctttcct | gttaagttac | gggaggtcgc | taattactat | 1560 |
| tttactggga | atgcgcaatc | aaatcttgat | tgagaccaac | gccaggcccg | aactattctt | 1620 |
| attgttccag | agtctttact | tgaatgcata | gtatcgggat | ggggtgatgc | cggccaccgg | 1680 |
| atcaccatgg | atatacgtca | gttggcccac | gtgttaatta | atgtcatatt | gttatgggct | 1740 |
| aatacattac | tgtattgttt | aaatacaatt | cgtcatgcat | tatcagtact | gtgtaattta | 1800 |
| tataagcgtt | catcattgaa | cgtgtatttt | gttggtgcgt | actgagttag | atattggaga | 1860 |
| aattccctaa | ccaaggaaca | atgactggac | ttgttagcga | tgtaagagta | atgcaaaagt | 1920 |
| taatgagact | gatattggaa | acagtattgt | ttaggctagt | ctagaaataa | actgctcata | 1980 |
| aagaatcttg | cagttaatat | | | | | 2000 |

<210> SEQ ID NO 89
<211> LENGTH: 2000
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 89

```
ttcactatta agtacaccta gtcagacgtg aaagttagtt cttttcacgt ctcatatagt      60
gctattttcg accacgtctt gcaatcgtga tagacagagc tgtcattaac aagatcaagt     120
tataaaattg tacgggttgt acctgcttat agttatatgt tgaaattgca aggccgcgtt     180
gtgaccggtt tgacggaatc tgaagggatt agaggagttt atatttaatt tctttcatgt     240
agagatagaa cccaataacc tctcgctaca tagaactaac gttttcgcag tgatttacct     300
tgtgaagtgc acagtacact tcactgcctt ttactcgcat attgatacag tagccaaaag     360
tatcattatt agtgcataac cttcacctat tccaacggtt ttacgcattc tgcgtacgtt     420
cgattgaaat agaacaaata taactataat tggtacccat gatgtaacat tttacctcag     480
taatatgtcg aagataggct aagtcoccag ctagcgtaac tagctaagcc ttgatgcgta     540
ttccttaatc ttgtttaacg tctctgctta cgctagtttt tagtagagca taagatagca     600
atttcaggat ggaacgagtt atagaacaga ccactcctac agtgagtagg gtcacatgta     660
ttgtccgaca ctgtttattc aattccaatc ttttaagtgc gaatataata agaagcaccc     720
tttcaaacaa ttgttataat acgttttcat gacaccaacg atgtcgacta tgatgtgctt     780
ctcttttggt tagacatctt tgcatttcga cgactccttt tcattgagca ggttttagtt     840
agctaagtgt ttcctacatt gtagcgcatt agtctaatag agagtgagca ttagtcacaa     900
tatagtccaa tggatctgag aagccttatg aggcgtgctt agggaacaat gcagtttag      960
gcagaaaagag ttacccttta agggtggtat tcttatctca tatctatctt attggtgcaa    1020
agtttgtctt tgaacgacag agtaactcca ttcgcagcct tgctaaaagt ggagagacgc    1080
aaaagtggag gcacaggtcg tttcttttag tcgtatatcc agtttatgag cttcacattt    1140
aagatcaaat cccttctcga aataaaaagg attcccactt taaataggcg attgattgtg    1200
cgcactattt attcgtaatc tatacgtaaa gaaactgaac gccacagcct aatacatgct    1260
agtatttcat acatgtgagc cgaagacacg cacttccttt ttgatgcgag aatttagggc    1320
gaccaagtct ggtaacattc tgtcctagtt gccgagtaac atagatataa gccttagcag    1380
ggcgcggcta taccttggta gtaagacggg tgtttgagta atattagtag cttaattaac    1440
agcggtcaat cgccaaacgg aattgtaact ggaatgtcgt ataatcccat ttatatctca    1500
gcacataaat caaaatggct gtgagattta aagaggttag taattgttca gaaatccgaa    1560
atcctcataa ccaaataaaa ttcgcatatg catacttgat cggcggagcg atgaaagaat    1620
tacactttta gtatccaatt ataaacatca tttgcggcct acttttccca gtaaatcaat    1680
acgtggagaa ctggctcgta ctctgctcta cacttattga atgagttagc caatgtagag    1740
ctggatacta agctctagaa gttactccag aacaattacc acgttaataa cttctattat    1800
tcagagtcgt aacagccctc aagtcctctc ttgttcgcct gtcagcaatc tcctacggac    1860
ctaccctgcc aggtagttgc tgtctaagcc actattagag ttgctagatt tgttaattat    1920
aatgcttcgc catagtcatc cacggtcagg gcggtacctc gcagcttgtg taagggatcc    1980
ctcgagtaac tcttgatgat                                                2000
```

<210> SEQ ID NO 90
<211> LENGTH: 2000

<210> 212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 90

```
cgtagtattt tgtgagctag atggagtact ccgattcaag gtattatgaa cgatagatac      60
cgtggctata tcataggatt gctacactgt aggttccaga ccttagcgaa gcggatacct     120
tccgttcggt tatctgttaa aaactttaca tcttcatgat aaagtgtgcc tacctttgta     180
tcactgatgt acttccctac aatagatact ctttaagacc tgagtacgcc gaaagaatct     240
gttcgatcta gcaacgacaa aacagttatc agcatatccg tatattgtgg tgtagcgtct     300
tcgtgtacta atttagattt ctgcatctgt ctagttacgt gtagggccta tgacggtccc     360
ttgcttttcc cgggaaatat caattgcagt tgtgaaaatt gtttatagga aaacacaaat     420
ctaaataaat tactccaagg atcttctccc agatgactat tcttagataa tgagaaaggg     480
agactcgatt aagtaatatt gtcgagcacc acaatctgcc tatattctaa cttagtaata     540
attaattaat tatgagtcaa ccaaagggtc gtttagctga ttcatataca tactatattt     600
gatcaccacc tacgagcagt tggcataatt tccttgttga ctagttttga cccacgtgat     660
tcccctaaat tttttgtgct ctatgaccga caaccacagt gtaatgtctc aggtaaaaat     720
gagtacatac tactttttcca gattgcataa gttatagact tcggtatttt ccaaatatta     780
ttgcattgta ctacaaaact aacgggtatg agtagacaca aacgatcacg ggtttcacttt     840
atgaataacg ttgtaacgat aagtgcgcct cgcctgcacc gcatcactaa cgcctttttc     900
gaggtaatac cacgttccga agaatctatt tagttcctcg aataaaacat tattgataag     960
tagtgaatca ccagcctccc aaaaatacca gaagagagaa acaggtcttt caattgctgg    1020
tactatttga tatcctttac acgttttcta ttctccagtg taagtctcgt tatgcaagtt    1080
tgtcaatatc agaacaatat gatatacaac acctcgcaag ctgctagcag ttagatgcga    1140
tccgatgatg atcgataaaa acttatgtac tggacctgct ggtttagcct ttaagaataa    1200
gttgattctt gacatacagc tcgggcgata ggattgaaga gtaaaagcga tgtaaaccag    1260
gtctgtgttc gatgcagagc aagttcctgc atcggatttt tcggatatgc agcttagatg    1320
gttactcaaa tccaattccg ggctgttgtc tgtacaattt gggaggttga cattgccacc    1380
tgggcaaatg ttgtccgaga attcgcccga tgagagaagg gacttggtgg agtcacaaga    1440
ataggcgatt tcgccccaaa tttaatatcc aaaagaaggc gttctactaa ccgtaacgtt    1500
agacatattc gtacagtgaa gttcgcacta tgtgtgcatt actcaagtat ctgttgtata    1560
ggataccttaa gtggttcagt attaaacacg attctttat cttgtatgtt gtaatagcga    1620
tcgttactta tcaacagagt taaaccatgg tacaagtgca caagtcatta agcatctaga    1680
ctgcactaca tcgcttctat attcaccata tgacgttaca atctcccaaa gtaagtatgt    1740
gacaacttct ccggccagct acatccggta gaattgtgtt aactaacagt gtaattatac    1800
tccatcatac gatttaaccg gttgaatgac taaaacttaa gtagttctcg catgggtctc    1860
cgcctcactg gtaatatgtg accgctctat tgaattcgag accaggatca attacatcct    1920
caccgggtaa agagtagatc aggatttta agtgagtaac ctggcgatga atacaaggtt    1980
gtactgcagt tttaccctga                                                2000
```

<210> SEQ ID NO 91

<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 91

| | | | | | |
|---|---|---|---|---|---:|
| gatttaaatg | gtaattaaaa | tcgaaggttt | taaaaggtga | gaatttttttt | 60 |
| atctgttacg | cccctaatat | tcggtttcat | gatttgctta | atattgtatc | 120 |
| tattgttaaa | cagtctctgt | actttcttga | tgaccaataa | tgaacagatg | 180 |
| atattgaact | tcaattgaat | gcgtgcatgc | cattattcgt | catcgagaat | 240 |
| acaattgcag | ccttctagcg | ccaattgcga | ttagtaagct | tcgccctcac | 300 |
| atattagact | gatcggagac | attaacaagc | tgcttattcc | gtcttgaaga | 360 |
| tactgttacg | gtgtccttag | gcgtcatata | tcaactaata | taaaccggta | 420 |
| aatagccgat | attcagtgat | tgtttgccat | aggctacttt | cttcccaaa | 480 |
| cgctatccta | tgatttctgc | gtcagggggtt | aattacggcg | acaccagcct | 540 |
| cagactagga | taatatttca | ctggcaatac | tcatcgatta | attcaactag | 600 |
| ttcacactcc | gcaaaaaagg | gcaaaacaaa | gtcgtcaagc | cgggaataag | 660 |
| gcagtcttcg | taataaaatt | tgaactcagt | tattgcgaat | ttactcgtat | 720 |
| ttatcattct | ctgattactc | aaaaacgctc | catgagggta | gtagcacata | 780 |
| ctcatagtgg | cttctttctc | tcaatccctt | tgatactcat | ttttatatta | 840 |
| acgattgttg | aaggccagca | aaccatataa | gtggacagaa | cagggaacaa | 900 |
| tacagaaagt | agtaactagt | caagaaagtc | tagatgaatc | tataagttgt | 960 |
| ctatgatcgt | agcatttttca | gtctacttga | gggagaggct | gtaaggaatt | 1020 |
| gatatatatc | gctggaacca | agttatcgca | tggaaacttg | atcacgtaca | 1080 |
| tacgcgcaaa | ttagatctga | aatccctctg | tcctcatttt | ttaattaata | 1140 |
| caaaggcctt | cttttctgaa | tgttattaga | cggaacacgg | aactgcgatt | 1200 |
| actacacaac | acgaactgac | cagatttgcg | tgtaatcgtc | acgtgccgtt | 1260 |
| gtaaaccccg | gcgcaagggc | gaattgtgaa | aaaatgagtc | aattcgctac | 1320 |
| aacgagctcc | tggacgacac | aacctcgtat | agcaaggcgt | agctcaatgc | 1380 |
| caggtattgt | agcccatgac | aacaagaaat | aaagctatag | taggcatcat | 1440 |
| tccggcagct | tttttctgac | ttccacctca | ttgcgtctta | tgtcattact | 1500 |
| acctatatga | gtcttcatcc | ctgggacact | gaagggagta | cgccagtatt | 1560 |
| ataaacctcg | attactcctt | tatgagaaca | atacttacac | tcgacggggt | 1620 |
| tgatcttaag | attatctacc | atttgttcac | ccttgaaaaa | agagacttac | 1680 |
| ttttctatac | tgggccccga | ccgctgacat | gcagaatatt | gaggagatgc | 1740 |
| ttacaaaaat | taaagcagat | actcaacgca | tattctatga | aaatcaggga | 1800 |
| ggtgctttag | gatgatttac | atgaaacttt | aaaaggaccg | ggataaactg | 1860 |
| tttcactgcc | acagggatct | tattcattcg | gatatattat | tgccactcaa | 1920 |
| gttagtaagt | gttaaagtgt | atcattattg | cccattcttc | agactcgaga | 1980 |
| caaatgctgg | acgtgtgtac | | | | 2000 |

```
<210> SEQ ID NO 92
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92
agatccacgg ccctgaaatc gccatcgctg ttcttctttg atgaataatg caagggctga     60
gttcatcagt gtattcgaat gctactatat ttcagtattg tgagtatcac agctgtaatc    120
ttcggaaata caaggatgtt tgtcgacctc gctaacacta gattattttg ccccgttact    180
atttatattt ttatgacttc aaaatgcgct tcaagattgt aactctggtt gatataggat    240
gcagggaccg gctcagggcc gctctgcact acattaatac ctcagggatc tctatttcgt    300
tagagcacac gacttagtga ctagaatagc tttaaatgta aaacttcatc atatattcct    360
cctggctaag ccttaatttc attcttgggg ctgttgccaa gactgctcaa gagttagttt    420
ttctttctcc ttgtagtacc cgttctccta agtgcaaata atctatacac acttcatatt    480
gggtatacca ttcttggttt attgtcacct gttatgtatt ttgcatcaaa ataatcatcg    540
atgtatacgt taacccagga gacaatcgac cggctaattc cgggaacgta gatgtatgta    600
aagtaacatg tatttcaatt tcttctgaag tatgagattt cagttgcaca aaaggtactc    660
agcatgtctt atcatccata gggccgcaat tatagaggat cttgagtgga gggtccatac    720
gaggccttag gaagccggct tatctcagcg aaggttatcg agatgctaaa tttacggata    780
aagatccgtt actcttcttt agaactaccg ttccaactcg aacatagaat cggctccgaa    840
ttcttgggta ccttgcagaa ctgaaaaata gatatctcgg tatctaaagg cagaaatagt    900
tttcgctctg gattggtttc taaagtgaat ctcaagttct aggtaagcat tcaagtccat    960
tggggaccat taggggttaa tacgcactga cgtcggtctt tcgattgata aatacttaac   1020
ctcgttagca gtgagggtca acaatcatta atctccagct atagagcggg ttagccagat   1080
tttatatcgg cgtcattcct tttatctttg aaatttaggc caaaagaag ggaactggtt   1140 ctattcgcga attgaaccgc atttatggta atagatctga ccacgtgcta ctgctcactt   1200
acaatagcta gttttcggct caaactttgt ataaggctca ctaggcatat aacgagttaa   1260
aactttccac atgatacgtg actagcttcg cccgacatac tatatataag gtctaccgtt   1320
gcgggaaaag atgaagatga tattatcaag tctttgacta ataaattaac ttatgcttac   1380
aaatttccaa aatagatatt ccagtcgtct atccttctat tacagagaaa ggcagactta   1440
atccgttcat tatataattt atttagatgt tagtctttct ggtgggtcga ttgttagtct   1500
ttacatagaa ctcctttaat gttcataagt ttccatcagt agaaagtgag cttatgggtt   1560
attcaccttt gatattaaaa gatttactac tgctataatc tacctagctc agctgagagg   1620
caagaggatc acatgttatt gttataatgc tttgattggt aaactatagt gtcaaggcaa   1680
ttcgagtgtc gccaagttac gtcgattaga tcgatcatta aaatctaata atgtttagag   1740
tttgttagag taatggtgtt gatcggcaca taagagtcag aacgcgggag tattgatatt   1800
ttgccgaatt gcaaatttat caacatcggt tctacgtatc gttgatgtcc taaggcctta   1860
gttacgtagc ttacatttaa tgcgcatagg gttgaagcgt gtgttaatcg ctctttcaaa   1920
taagtgttag gaaatatacg aagtaacgaa tatcagccta attccagcga ctaaaatgaa   1980
acaagagcat ccggtggtag                                               2000
```

<210> SEQ ID NO 93
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
ttgatagtgt gattaattag ctggtcatta tcggtatcgt tgacaacagt aggatgatgg      60
cgattgtctg cagatttcgt ccattaatat aagtaatact tgttatgatg tccaacttag     120
atatattgga gttttattgc tctatttcct gtacccttgt gacgagtaac tgctccgtga     180
tataggcaag ttaagtgtgt cgcaatatgg cagtaggctg aataccacac atactgtctt     240
tctaaataac actaggcgac tacctttaac ttcatctaag gacgttattt cacactaagc     300
actccgtccc gagaacaggg tctattgagg ctactgattg cgtaaagtag ttggacacgc     360
atgggttcta gatcctcatc tctggtttct caacatattg agttatactt tctgttagtt     420
gttaagccgg gcgatcaaag catttctact tcagaaatgg aggactgtag ttatatacta     480
cattctgaag cggtaccatt aatgctttcc gcattgatga atatctatat ttacagtttg     540
gtgaacacaa ttaggagagt cggactgcgc aaacagaata tttagttact tatagttaat     600
atacacctat acacggtaga aggtcagttc atatagactt ctgggtgtgt acttcatcag     660
aagtctcctg tctgtttagc caatcgccac cttctcagtc ccgtgggagt accactcgaa     720
tagatcgttg ttttcgttgt tgataaacgg accccgtctt attttcgtta ccatttaata     780
cgatatcata taattgaaat attaggaaac ggcatttcaa atacgaacga tttgaacttc     840
acctaccttt tgacatttat attacaattt tatagggcaa aacgtaatgc acctaaattt     900
actgcacttc agatctacca attgatttgt cacaccagct atttaacgaa caatatgact     960
aaatattagc tggtatgcaa tctgaaaagt caacatggta tttctgctta caccggtagg    1020
gttaatggaa gttctgcgcc cattcgaatt ttagaactga acaataattc atgaaaattt    1080
acgttagcag tacctttttg tcttactagt tgttgcagaa atttaaacat tacttggtag    1140
cctgctgtgt atataaaaga gcgatctccg ataagttgtt aatctgttgc tacctaagcg    1200
cttactgtgt gccttggctc gcgtatatgc ccaggtcaac atttatttgt cgctcgactc    1260
gaaataatct atatcataag atgggaacga gtatgctcca tgagggagcc ggactaggca    1320
ttcaattttg tttgagtctt tagtaaccat acctattcat gcgtagttaa cttcgtagta    1380
aagcagcgtt tatacataaa caccaaaaaa tgtcctaggg gcataccaag aatctaagaa    1440
acagcgcagt agttcgttcg gtttggcaac catacgaaag tatcattgca cacgacgcat    1500
acagcatcct aggagtttac tatgtcttcg tttttttgta ggccccacac acattaaatt    1560
cgatttatta cactcagagt acctgtccgc caattcacgt gagtaccttc gcgcagcaga    1620
taatacattg ctatgcgttc agaccattgt aagaaaacag atcatgactc tagaaaaagt    1680
ggccttagat caataaatgt taaatccggt tctctctaac ctcgccgtac acagttaaaa    1740
tcaacgcgca tacataaaca ttgatcttat gggggctcac atagtgagac aatagtagta    1800
cccagtgtta tacctaatct aatatatagg ctaaaggta gattaattgt ctgatcatag    1860
atctcaaccg atcatggata gctgggaata cgttataaag gtaggtctac gacccgcgaa    1920
atctcgagga accacaacag aaaccattgt ctgtacgagc gacagcgtat gtactccgtg    1980
gctggtctac ctcggtaatg                                                 2000
```

<210> SEQ ID NO 94
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94

```
gggtagtttt ttctccaagg atccccttaa ctagggtgaa gattgggatt aaacctaaga      60
taaagatata acggtcactg gcgacaagct tacaaatttg cgctttacaa cagaccaagg     120
cgaaagtaat cttggcccta ctaaaccaag ggaaatcagt agtagtgttc tccaaatagg     180
caaggctaat atctatactg tccctgcatg atgtgttaag ccataggcgt gtaatgttat     240
tccttttcct aaccagcttt taatgtatcc ttgtgtagga agaactgcga agttatgtta     300
ctccgaagcc aaccaacatg tgtcctcttg gcaccatgat tcgaaggtga tattataagt     360
tattcgaccg tgaagattac atattactgg atggtgtata aatagaccat acgttcattg     420
aagcgtgact gaagccgaca acggcttacg taatgattca aaatcggtaa taaggataac     480
ggttatatat agtagaattc gagatggaaa aaccaacttg ctaatgacaa tattaagggt     540
atatcacact gtggtttgta aagtagtcac ctattcgtga tgccgtgtac ttcaacttat     600
agtaaaaagt attgttttct aaccagcggt aacctgttgc aaaaaaccac gtttaaccga     660
ttgatagctt gtggtaaagt ggcatagagt atacttcctc catctgtagt acttaatagg     720
tgttccagtt gcagtataaa cctttcttcg agtatcatca ctaagaccat tagacatagg     780
atatatacaa taagagctgg aacttgaatc ttctaatgac agactttact aattatagtt     840
caagcgcagt ttaactataa atacaattgt caattcatca tatggtaggc aagattcctt     900
tagcctggcg tacagtggcc cggaggcctt gaccaaaaca tggttctgtt atatcacgag     960
atggattgac tatgctcgtg aatctggaga ggcactaact tggtaacgcc cgtactctac    1020
cgcagcggga caggtgatag actgtctatg taaatcgtca tcaatctata tttcaataca    1080
actataaatc cagacaagta tccttgagat aatagttaat ctatcctaac taataagaag    1140
aaaagagacg atacggtagt agattaagct ttcgcggaaa caagaggaat ctacagaaaa    1200
caccctaaat aagctattcc atgccgcctt tgctatgaac gaagtacgga agcatgatgc    1260
ttatcaacgt caggaaccta gctcaaatca aggtcttacc agtgacgata acatgggtgc    1320
ggatggttat ttgtggagag gcgtaataca atgtacttgt tttcaggata tcaatttaat    1380
ttcacttaga atacgagacg gccgacaact ttaacgaata catttgcatc ccacattaat    1440
acctgagtgc cgctcatatc gtcctagcac aattttttaac agaagttttg gtggtgagta    1500
gaacaacaac atgtagtcat cttaagcgta tgaaatctgg ctctcaaatt catgtttaat    1560
agtgtttaat ctttatatgta taaatcgttt ttatggttta gacgaagcac tcaaaaatat    1620
agactgatgc ctatgacctg tgctatcttt atttccagg gcaaagatga tctttccgag    1680
tccatatctt gaatgacttc ccgcctgaac caatacctgg tcggaaggag gactcattaa    1740
taaacatgca taaatggcag atctgaactg gacggctgac ttatctcaca atgtgttcta    1800
aagtccacac cgtttctgta ccaatgaaag gacgaattat acatgcattg gtttggttaa    1860
aaccaatact tggtaacgat ctggaccggg cggttagaat gatgaattaa tgcgccgtat    1920
gtggaatgaa gtcctgttaa aatgcaaaag gtggctcttc gagagttgtt gggttgaatg    1980
```
agagaaacgc caccttcaca                                              2000

<210> SEQ ID NO 95
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95

| | | | | | |
|---|---|---|---|---|---|
| tagtatctag | tttcaggtgt | gcacagaata | gttatcctcc | tttgtctgtg | gctatttgga | 60 |
| gaacgtatta | gaggaagcat | atggcaaaat | ggcctgtaca | cgatagatgg | tatcatgttt | 120 |
| ggaggacgct | aggcatttcg | ccctaaacac | cgcaacgata | cctaaagagc | tcgtcaatgg | 180 |
| gcttgccgat | taaatacgca | agttttagtc | agtccagacc | acatttaccg | gtaattatgc | 240 |
| acagacaaga | tattatgctg | gtttatagcc | catatttgtc | tcccccctaaa | gtgagctctg | 300 |
| atatttggtt | aggtcgagta | gtacagtttg | ctatctatgg | atacgatgta | attgtgcttg | 360 |
| agatacgtgc | atcacgaaca | ttgctaagcg | gattcgcaat | gttcgtgatg | catggagtag | 420 |
| tctaagcaat | ccaacaagcg | cctgaatata | atttgtcac | aagtaaacct | tcatattgtc | 480 |
| taacatacag | agctgtttta | ccccctcatg | atctaaatct | ttcgcttctt | cccaaactgc | 540 |
| acgcccatt | cgcctgttag | cgcattcaac | cctaatacag | ctgttgtggg | gatactctga | 600 |
| ttgaaacaaa | gttctctatg | gaagcttcat | cattaggcca | tacgaaatag | aatcccctgt | 660 |
| tgtccaggtg | cttctcgact | gcgttgcggt | tcttattttg | gctttgctaa | taggaacttc | 720 |
| tctcttcgag | ctcggtcgaa | cgccagttcg | tcaactatac | cgccttcttt | tgcgcaagg | 780 |
| tcatcgaaac | tgaggtccat | cctgggacaa | gagatcagtt | aagcctacac | ttgtgtgaga | 840 |
| ctccgcagaa | aatcgggacc | aaagcgttag | ggcttcccaa | ttatgaggat | ctatggtgtc | 900 |
| attgaaattg | ataatcctta | tagggccatt | tttatccctg | acctgaattc | tatttggtga | 960 |
| ataaagtatt | ggtcgccttt | cgagggatac | tactatgtta | tggacctaat | ggatgaccat | 1020 |
| ctggaacatt | agcaacagca | actctaatct | tattttatca | tcttcagtgt | aatatatcgt | 1080 |
| acatttagg | ctttccttta | tgttaaattg | ttattatgaa | agaggtgtat | tataagctag | 1140 |
| ttaagcgcgt | taaacacaa | gtggtctgct | gtcattcata | taccaaagaa | ggtcttgatg | 1200 |
| gacaatgtct | tcacaagacc | atgcatagat | tctaaatcga | tatgacacct | aacaaatgcg | 1260 |
| ggctaatatt | cgatttctga | ctcccacact | gtgagcacgt | ttattgcgga | gacttttaag | 1320 |
| cgagatactc | ttactcccca | ttgccatata | tgtaaaatgg | acttccaatt | ctgcatattt | 1380 |
| cagtacatcc | ggactgcgtt | ataagcattg | tcgtggatgc | atcaccatcc | catagttcca | 1440 |
| cttcttttt | ttagttcaga | tccaaactac | actataggg | gacttattgt | cgatcaaaat | 1500 |
| tattatatgt | aagtaataga | tcatacatca | acaccgaggt | ctttgtccaa | tagaaatagt | 1560 |
| atgtcctgga | gttttatcaa | atacctgcca | tgtgcaagtt | cacagaatag | gacgcttcta | 1620 |
| cagaattcat | aaaatcccac | atccttagcg | taagttgtca | gatgaattaa | ttatattttt | 1680 |
| gatacggccc | cagttattct | cgaagtccac | tcttaaaaaa | agttattgta | cgaacttgca | 1740 |
| taaatcgata | acctgttacc | aacatgcccc | ggcataaatc | aacaacgtgg | ttcggatacg | 1800 |
| acaatatcaa | tcaatccgaa | attcaaaata | gaatattcaa | cttgacttaa | tcgcagttca | 1860 |
| ttcgtgaata | gacacatatt | agctctcgcg | cgctttctta | tcttcacagc | ttcttctcga | 1920 |
| tacctgaata | agtacgggac | catttatgtt | cataagcatt | cagtgaaact | gcagtctaaa | 1980 | tactattggc atatacttat 2000

<210> SEQ ID NO 96
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 96

| | |
|---|---|
| gatatgccat ctatcgaggc ctgttagctt aggacattac atgacagtga gacctagata | 60 |
| tatagttgca tgagtagatg taaccgaagg tactcaggga cagaactgac ggattgacgt | 120 |
| ttttcagtat cgtaaaagtt tgagatccaa caatgaaagc ttgatgcgcc agatgatgga | 180 |
| aatgcgcaaa ctgtcgtgtg ataacacggg aattggtgct aagctggaat ggtctaattc | 240 |
| aagttccaat ccatatccat ctatgtgcga ggaatttgta acggtaatta tattgcctta | 300 |
| caattattat caaccaacac acttgaacga tgtaattggg ggtatatacc aataatagta | 360 |
| ctgccaacta ctgttttttg caagaattaa tcgtagtccg aattaaaaga aaagacggtg | 420 |
| tacgcaaccc aagtaattaa acgaataatc atacggtcga tatgctcatt cgataaaacg | 480 |
| cgagatcttt aagttctctc accggggtaa tgcataattg ccttaattgg aaattgcttt | 540 |
| aggtgagagt cagtaaacca ttggtgagat gtggttatac tgcacctcac gcaaattaat | 600 |
| attctaactt taacctgaat tatgggttcc cctcatcggg aagtatatct agtgccaacc | 660 |
| tatcacagtt gcgcacatat gtttagaaat ggttagtcgg tcaggggaac tcacgtaagc | 720 |
| ggtagtagta gaatttaatt tatggtctcc taaagcatcg acatagtaca ctgcgaccat | 780 |
| tctaacacat actaaacttt gaacttactg atatctttta tgtttgactt ccttgctacg | 840 |
| caagtccagg cccagacagc tgagttgtcc ttacacgagc tatttgctga tcatatggtt | 900 |
| taatcggcac gcgaattgca agtttgattt aaggtgagcg catacttgaa tacagccagg | 960 |
| gagctcccta ctcagcgatc gtcttcagag atttcacgaa aatataagca ttcccatcag | 1020 |
| aaattctaat taaaccttac cggaggtggg gattactcgc agagttaaat aatgagccca | 1080 |
| cattatgcgt ttgcttctgg agattatggg tggttttttcc cgtaccgcct aatatagtat | 1140 |
| gcttcgactc agcaacttca ctctaaaccc tagagagcct ctgtatgtac gcgcgtggat | 1200 |
| gaaatcaaga atggttggag tcaatgactg gggcacaagt gtaatctggt tcgattaata | 1260 |
| catggcacta ggtgctacga ggacgagtga atgcaatata tgagtccttg ctaataagca | 1320 |
| tcgaagatac tctccggtac tccttcatat tcgactaatc ggtgcactca actttagggg | 1380 |
| ggctccttat tataaaatac atataggggtt tgtttaaatg atttgttcta ttaatacggg | 1440 |
| caaaattaat gcaatgttca cctaggcacg ttggtactcg ccgccaaaca ttggcattaa | 1500 |
| tggggatact tagaaacaac ataacatgaa aaatatctag gaacgccaac atatacgccg | 1560 |
| tgaccgtctg tcttaataga ctcttttttgt ttaaagggta ctgagtgatt aactaatgct | 1620 |
| ttccaatcct ttccgttaga aggctattac tacaagtgtt tcccacgtgc cgttaaaaat | 1680 |
| agaattatct ttgtgggttt acgagcgcgt actgaaaaca ggtttcttgg atgggataat | 1740 |
| attatagata gcaataaagt aaactggaaa acagtattgg atagcatgtg atggaccttg | 1800 |
| accccttgt ggcataagat aatctcagcg tttcgttaca cttacattca ctgttaatgt | 1860 |
| ctataggcaa gttactattt ggagtatttc aaagtgaacg gaagaaatag aagtgctaac | 1920 |

```
aaactccgtc atagtaggat catatctcca gagcgacctc atacatgcta aaaacctagt    1980
agacttcgta ctatggattt                                               2000
```

<210> SEQ ID NO 97
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97

```
aagacacttt accacataag taaaccgttg acattatcgt ggcggagaga tactgcttgt      60
actgggacac tcagtatttt gtggaatatt gtacctagcg cctcgttccg tgaaagtgtg     120
gcatggattt tcataatttt atgctgtcct cattgcctac aattaatcca gtaagcacta     180
gagaaatatc tgctcctatg ctgagattag ccttatgagg tctttatatc tttctgtaaa     240
ggccattgtt cttttgatcc tggagtctct gaattttgat ttgtccctca aagccttatg     300
tgtacccggt cccggagcat gaagacgtat atcttgaagt aatccgaaag tatttaggtg     360
tcgttgtcca gtagtaatcc cggttatggg ttataattaa gtgttaacat ccgagcttgg     420
tctgtataat agtgtgtttg aatagtaaat atcaggactc tacagggacc tattctactt     480
cgggttgtgt atcttccttg gaataacttt tgctacgcaa aaaagctata acaaggtctg     540
gagacggatg tgatttagta gggcaaatag atttaggtct tcgatagtac agaatactat     600
gctacaacca atctcttcat ggctttatca atacaatgtt cttccttaac tcagacggga     660
gcaattatag ttagctgaag gttgcctcac aatatgtgtc agagctagcg aaaagctcct     720
accaatatac atcagataag gagttcatac atctgtggcc gatcaagcaa gcaaggccgt     780
ccggttcacg acctgggtag tctgagtttg gaggagaagc catcgcctct cgcattctac     840
tagagaaaga tttcacactt actgacagag ctacactggt acgacgaatc tacaaaacta     900
agcaaagtcc tagggtgagc aatgcatggt aactagtacg attgatcagt gcgtggtata     960
ctatccggat agtccagacg tcaagaccta atcatcgtac gtaattaaat aataatgcat    1020
tcaactcttc ggatacgata tatacttata tgcattaact atactttctc atgcattgta    1080
tctaacaaaa tctgtacggc agaattaatt actaaagtct taatgattcg aatattaata    1140
tcaattttat tacgaaacaa ccaaactgac aacgtagaga ggcaactacc cagagtcgcc    1200
aagaatactg tttacgaatt gtagaaaaga tgtaagaatg ttcggatgtc ggattactta    1260
attgcgaacg tttgtcaagt cgttgcagga taccctcatc tcctcttcct agtgaattat    1320
ctgaaagtac tattatacaa tctaaatcgg atacattcgt ttgtaacacc acatggttgg    1380
ctcagctgac catttacgcg cgatattctg tgctatccga aggcgtaaaa ggaattcaag    1440
tcagtctcct cttcgttatg tagaaaggga ggactcctcc gccgtatatt cagctggctt    1500
taactaggaa catagttgca gttcaaacag tagaaaatcc tggaagacat ttcttgatag    1560
tctatctcag aaaaaggggg gtgacgttca tgtttactaa gacttgaaat gtggctccgt    1620
atctgcacaa ccaggtttgg gcggatgccg gccgccatgt aacactgaac ctcgcaagaa    1680
atgcacaatt gaacaaatga atactcacat cttatcgctt aatgttaaat tcaaggcgag    1740
actggctcga attattggag cctatgaaga tgtatattaa tgccaaggca ccgcacatag    1800
taaagactat actaaccaag tgtgatattc aatcgatcgt tgtggggaat caggtacagt    1860
tagtggcgaa cagctttgac atccgtttaa ctttggcagc accacaaacc ctttgcgtac    1920
```

```
gtttttgtgt tataaccaag ttatgttgca acctactttg acctcttatt tctttgccgc   1980
aagactgaat gtcgtattat                                                2000
```

<210> SEQ ID NO 98
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 98

```
gagcaaccta cggatatact atcgattctg gacatggtaa gtgtgttgcg tggttaataa     60
aaagatttcg tggtcggggg tagatatacc tgtaaggttt ccaacagacc gctttgtaga    120
aagagactta gtccctttgc aaaatgaggg gaccgactaa gaaagcgttg aattcaggta    180
atacttttg acgttaccat agttgttgca gtcccggagt taaacagaga cacatcgtgg     240
cggagtccgt agtatcgcat gcgtggattt attgttgtaa tcagatgttc aatatggcgt    300
caatatacaa ataaacaggt cagatggagt tagccttact taaaaaacga aaacaatgta    360
tgccctaagc aaaaaaacta gataaggacg atcaccacag ttttaagaga tctatatgcc    420
cctttgacat ccttattctg acaatgggca gatccaacta caagatgtcg taccgctaac    480
acttgactaa ctaacgtcaa gtaaaaagtt cgttagtcat attatcaagt atggacttat    540
tcatcgacag gttgtaatta gccctcccct agattagctg ggctgaaccc ctattcctac    600
gctcccttgt cacatgtatt ctctacctca ataggccgga aactcgcaag cccaagtata    660
gcgtacggat taaattcgcg caatcgctct tgaccatgtt aaatgcttgc gcgtaacatc    720
gaaaaggagg caagacattt cagaagtaac atatcagttg acggcttacg gtgctgaggt    780
ttaaaatccg actgattgct atcctatcgc tgaggaatga ctaaccttgc aaatccaagt    840
ctagaactgt cctagttctg taccatgccc agcgttcgga tgtcagtacg tgtatgcagc    900
atttaggagg tgatgtctcc cagtcggtca ataagctttg cttacctcac ggataactaa    960
gttcatctcc agtgtacgaa gattctctag cactaactat tcattgtaac taattggtat   1020
ccgactttaa gccatagtgt ggcatgacgt aagttatgtc agttctttgg aacttttttgc  1080
gcagctgtgt tgacgaaaca caggttgcag gttggtctag gtaagggatg cactcactgc   1140
gatgtgatcc tttaatggcc atttaaatct atctcgagta tagcgtgtat acttactatg   1200
aagcaaatta gtatacatat aacaatgaat atacacatag tgggaggttg ccattcatcc   1260
atgtaggcat gtaatatggc acctcctctt tggatacaga ggcccatgcc tccgaatcac   1320
atatttactt aaacagttaa cggaattcag gtatcccgtt tcattattcg aaacgtctct   1380
ggggttacct tacttacgtt atctgcatga gaatagagtc catcggcgtt tctaacaatc   1440
aatcatgctt gcaattcagc gagtgtagag gaattgtaag aacgccggat gctcccttta   1500
ccttatccgc acaggcccct acgattgaac tattgaaagt tttattacaa atctcatata   1560
tgggggagca gttaaagttc tgcataagaa ggacctagga taatgccata aaaggttgat   1620
atggaaatac tattggaata agaaagtata tggtgtctat aatggatata tcagtaaacg   1680
aaggcatttc ttcactttg atttcattaa ctgtaatctc tatttgtgtt ggcgaatccg    1740
gtaaacagag gttataact ggtttaccttt agtcgagtgt cttagatata catgtcgatt    1800
cagatcaatc ctactcatcc caaacgcaca tgtcacgata cgtactttat acagtaagag   1860
```

```
gcacaatgtg ggtgccctct ctcgtccgac ttattgcgga cggagaaata gttagtacgg    1920
actgtcacaa gtctgtaacc actaaagatc gggcagctca gacattattg aaggtaggcc    1980
aaagtatcat taatgctttg                                                2000

<210> SEQ ID NO 99
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
attaataaat gtctaacggt ctagaaatgc acctaatttg ctactgctga actcctgatt      60
actcctcctc gtttatactt gttcattaag aattttttcc gtctagatta agtacacgg     120 aatacacacg attaaataca ccgccacaga tcttcgctat caatattaca ttttgttcac    180
tcattacgat aagcgtggct tggctgagtt ctagacttat cgtgttaacg tcaatgaaaa    240
cttatggatt tgaagctacg atgctaatct aactttacct taagcaagaa agaccttcgt    300
taataggacc cttaaagcct gtgatgtcgg ttaaacggtt ctagtttgat agtgacgtta    360
gggactcggt atacatctta gccgaactgt ctaaattact ttagagaaac ttttccctgg    420
gggaggcacg ttccgtttat ggacctcatt tgagactcaa tatgtacaac taatagtgtg    480
attagatcct gattcccata cgtatcggct cgcccttaat caatacagat ccgtgctatg    540
tccatactgc gattccaaag gttgtctaac aagacaaact tgagagaggc ttcacaaagc    600
aacccagcac ccttgtcctc ttttttaggg gtacgctgac atctggatgc attaagaaat    660
acgtatctag aaggatcgcg ataagtcgca caagtttacc accttatatt ctgcaggctg    720
ctattggagg taatacgtgc tcgcacacgc ccaagtgagg cattcttaca agacttacct    780
tacagcctat taataacgtc gaattttgcg cagcaaccaa ttccagggca aactataagc    840
cttattgagg ttaatagggc gcaatatatt tacgatagaa ggtaaatcta taatactgtc    900
acttgtcaat gatgatggtc taactaattg attcccatgc aagtggcgaa ccaggcttac    960
tttagtttaa tagcgatcaa gtatactaag cacacactga atgtatcaca taagatacgt   1020
aaaataaatc aactcattaa atcaaagaca gattcacaaa tgtttcgtgt tttaacagat   1080
ctgaatataa actctgctga tgtgatcgta ggacgtaaga aggtatagtt gaagaatagc   1140
gtgaatatct gatctctgtt agcaaataca tcacgattat caccaggttt accacaacaa   1200
taagattgtg actgacacta ctttctatat gaatgtattc tcatgaggat gcgtaagacg   1260
tataggatca tactgaatta taactccata ttagggtcta tatcacatac atctccaagt   1320
taaaaagtct attggcgatt ccacacaact cgcgctagta gtacatttta ccggtaccgg   1380
tacagtctaa gttattgatc taggttcaac ttctaaaata ctgaagtctc aggtatatag   1440
aatttatact actcgcggga cgtaaagccc ctctgtggtt agcgtcgcag cgtcgagtaa   1500
attccttata gagcctaaac cttgataatt tcgacgtacc gttataacgc aattaataga   1560
cttctcattt tcctgccgag tcgggtctgg tatagtctag gacggggggta gatatgatcg   1620 tcgtcttctc taatctaatt taatctataa ccacagcgta caagtaaggt atgtaagata   1680
cagagataaa ttagagattt gtgttactcc gcatgttgaa ctaaacccaa aggttcacgc   1740
cgtatgcctt tcaagttcct ccgctcaaaa ggctccgggt gtcccctacc cgatatggcg   1800
gaaatcgtta attctcataa cgaccaacct taccttggac acacctaagc actaagtcgg   1860
```

```
taaatggagt acacaatgtg ggagttgtgt ttaacataat gaggctcgtt cagactatgt    1920
tcgaggcgta taacgatttg tgacagattc ctcatcaact cgggtcagat ttatagcaat    1980
ggtaaattcc ctatatccta                                                2000
```

<210> SEQ ID NO 100
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 100

```
tatggtgtgg cacatatgaa taaaacaagg agaagcagcc gacaatactt agaacgtgtc      60
agaacaatca agatgtctga acgttcaac aatcgagtta ttccgggcta atttattccc      120
atccttatat acagagccgc acaataccaa gtaacgtgct ttgggccacg aactcactct     180
agtcttccgg accctccggt actactcggt atggtggata ttcatgagaa tggttttagt     240
cttaaaaaaa tgtgaacaag aaaacattta cgtccaagaa agcggtattt tgtttgggtc     300
taggaaacaa tcagtcgtgg acctgggcga gatcggctgt tttcgaccga ttttatgcta     360
agcagaagga agtgaccgag gttgtgttta gatccagtaa aagtcgtcat acccgaggag     420
atttctgtgg tgcctagtga ctagcgatcc cgtgcagcag ttcaaatgcg ctggatagtt     480
cgctcctgca ccactagttc acaccagaag tatgtctttt aagagactgt ctaagaaata     540
tagtctctaa acgtgactat cgttcactcc ctgtacaaat ctaggactaa cgggtataga     600
ttaaacgtat tagaatttcg gagcattaga attttgttgt tctaagttag gatgatttca     660
agtgtccatg taaattgagg tcaatatagg acgatctaca tccgagatag gccaagtacg     720
attctgtgtt acattttgcg ttcgcacaag ctaggacgag ggtatgagca ttttgtgcta     780
accgaatgag atgcagctta ttgtatcctt acccgcaaca tagggcatga aggcgtggtt     840
cgagaatcgc gcgagataaa tacatgtttc gatttatgtc aaccactgca atggtttata     900
aatgttattc aagcatcgat tcaataacct ctggatgtag taatatctgc gggtgtgtaa     960
gtgcgatatc ctaagtcggg agatttaaca ataccttggg atgctccgga caattttcga    1020
cgtacgcaat tatgaacatg cattgattga ctaaacttaa gaaacataat cagtgtatag    1080
tattgtaaca atggattctg agtgtctaat gttttctcgc tccatgttat aacacataat    1140
tatacttata ataccatccc atctttaagt acaaaacctt gttgcgctgc tttatggaga    1200
ctattgagcc caacgggttg agtggttatt actatttgaa gtaaaagcag tatctactca    1260
gattcctaga ggtaaaatatg aacttgtttt ctatctggtt atctattttt agttttatgg    1320
atatggacga agttaaaagt tatagacctg acattcttct cccataggta tagaagtgga    1380
gttaaacaag ttcttagtgg gggaaatgac gtacagacta ctatcttgat gatagctttt    1440
cgatcaaaca agagtttcaa ccgctgtaaa ggtttatatg cgatgtagtg tggtacgata    1500
acgtactttg ccgatcattc actgattcca ttaggtacga cactctcagt tacaaagcgg    1560
tactaaccta gcaaaagtg aatatcgccc tacaaactat tactggagtg cggtggcagc    1620
tttggcgaaa attggccgaa ctctttgctg tttatatggt aactattctc actatgctac    1680
tgattggaaa aagatatttg ccaactaata gtcgtaatgt tagtattgat agggataata    1740
ggcatttaaa gttccctgaa acatacggta aataagatct cttttaacaa caccagggt    1800
```

| | |
|---|---|
| ggctcactgg ggtagcaaat acttaacgat cccttttttca tcaagtgagt tatctgcttt | 1860 |
| ggattcttac aactagatgt tataaagaaa gaagctgcgc agtttgcatg actaaaattt | 1920 |
| atatgaagta gtagttatta gtactatctc ttagtaggct agaatgtaaa cctgcagaca | 1980 |
| tcatggaatg cacatacccg | 2000 |

<210> SEQ ID NO 101
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 101

| | |
|---|---|
| tcaatagccc agtcggtttt gttagataca ttttatcgaa tctgtaaaga tattttataa | 60 |
| taagataata tcagcgccta gctgcggaat tccactcaga gaatacctct cctgaatatc | 120 |
| agccttagtg gcgttatacg atatttcaca ctctcaaaat cccgagtcag actatacccg | 180 |
| cgcatgttta gtaaaggttg attctgagat ctcgagtcca aaaagatac ccactacttt | 240 |
| aaagatttgc attcagttgt tccatcggcc tgggtagtaa aggggggtatg ctcgctccga | 300 |
| gtcgatggaa ctgtaaatgt tagccctgat acgcggaaca tatcagtaac aatctttacc | 360 |
| taatatggag tgggattaag cttcatagag gatatgaaac gctcgtagta tggcttccta | 420 |
| cataagtaga attattagca actaagatat taccactgcc caataaaaga gattccactt | 480 |
| agattccatag gtagtcccaa caatcatgtc tgaatactaa attgatcaat tggactatgt | 540 |
| caaaattatt ttgaagaagt aatcatcaac ttaggcgctt tttagtgtta agagcgcgtt | 600 |
| attgccaacc gggctaaacc tgtgtaactc ttcaatattg tatataatta taggcagaat | 660 |
| aagctatgag tgcattatga gataaacata gattttgtc cactcgaaat atttgaattt | 720 |
| cttgatcctg ggctagttca gccataagtt ttcactaata gttaggacta ccaattacac | 780 |
| tacattcagt tgctgaaatt cacatcactg ccgcaatatt tatgaagcta ttattgcatt | 840 |
| aagacttagg agataaatac gaagttgata tattttcag aatcagcgaa aagacccccct | 900 |
| attgacatta cgaattcgag tttaacgagc acataaatca aacactacga ggttaccaag | 960 |
| attgtatctt acattaatgc tatccagcca gccgtcatgt ttaactggat agtcataatt | 1020 |
| aatatccaat gatcgtttca cgtagctgca tatcgaggaa gttgtataat tgaaaaccca | 1080 |
| cacattagaa tgcatggtgc atcgctaggg tttatcttat cttgctcgtg ccaagagtgt | 1140 |
| agaaagccac atattgatac ggaagctgcc taggaggttg gtatatgttg attgtgctca | 1200 |
| ccatctccct tcctaatctc ctagtgttaa gtccaatcag tgggctggct ctggttaaaa | 1260 |
| gtaatataca cgctagatct ctctactata atacaggcta agcctacgcg ctttcaatgc | 1320 |
| actgattacc aacttagcta cggccagccc catttaatga attatctcag atgaattcag | 1380 |
| acattattct ctacaaggac actttagagt gtcctgcgga ggcataatta ttatctaaga | 1440 |
| tggggtaagt ccgatggaag acacagatac atcggactat tcctattagc cgagagtcaa | 1500 |
| ccgttagaac tcgaaaaag acatcgaagc cggtaaccta cgcactataa atttccgcag | 1560 |
| agacatatgt aaagttttat tagaactggt atcttgatta cgattcttaa ctctcatacg | 1620 |
| ccggtccgga atttgtgact cgagaaaatg taatgacatg ctccaattga tttcaaaatt | 1680 |
| agatttaagg tcagcgaact atgttttattc aaccgtttac aacgctatta tgcgcgatgg | 1740 |
| atggggcctt gtatctagaa accgaataat aacatacctg ttaaatggca aacttagatt | 1800 |

| | | | |
|---|---|---|---|
| attgcgatta | attctcactt | cagagggtta tcgtgccgaa ttcctgactt tggaataata | 1860 |
| aagttgatat | tgaggtgcaa | tatcaactac actggtttaa cctttaaaca catggagtca | 1920 |
| agttttcgct | atgccagccg | gttatgcagc taggattaat attagagctc ttttctaatt | 1980 |
| cgtcctaata | atctcttcac | | 2000 |

<210> SEQ ID NO 102
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 102

| | | | |
|---|---|---|---|
| tactcttaat | tcattacata | ttgtgcggtc gaattcaggg agccgataat gcggttacaa | 60 |
| taattcctat | acttaaatat | acaaagattt aaaatttcaa aaaatggtta ccagcatcgt | 120 |
| tagtgcgtat | acatcaagag | gcacgtgccc cggagacagc aagtaagctc tttaaacatg | 180 |
| cttttgacata | cgatttttaa | taaaacatga gcatttgaat aaaaacgact tcctcatact | 240 |
| gtaaacatca | cgcatgcaca | ttagacaata atccagtaac gaaacggctt cagtcgtaat | 300 |
| cgcccatata | gttggctaca | gaatgttgga tagagaactt aagtacgcta aggcggcgta | 360 |
| ttttcttaat | atttaggggt | attgccgcag tcattacaga taaccgccta tgcggccatg | 420 |
| ccaggattat | agataacttt | ttaacattag ccgcagaggt gggactagca cgtaatatca | 480 |
| gcacataacg | tgtcagtcag | catattacgg aataatccta tcgttatcag atctcccctg | 540 |
| tcatatcaca | acatgtttcg | atgttccaaa accgggaaca ttttggatcg gttaaatgat | 600 |
| tgtacatcat | ttgttgcaga | ccttaggaac atccatcatc cgccgccctt catctctcaa | 660 |
| agttatcgct | tgtaaatgta | tcacaactag tatggtgtaa aatatagtac ccgatagact | 720 |
| cgatttaggc | tgtgaggtta | gtaactctaa cttgtgcttt cgacacagat cctcgtttca | 780 |
| tgcaaattta | attttgctgg | ctagatatat caatcgttcg attattcaga gttttggtga | 840 |
| ggagccccct | cagatgggag | cattttcact actttaaaga ataacgtatt tttcgccctg | 900 |
| tcccttagtg | acttaaaaag | aatgggggct agtgcttaga gctggtaggg cttttttggtt | 960 |
| ctatctgtta | agcgaataag | ctgtcaccta agcaaattaa tgctttcatt gtaccccgga | 1020 |
| actttaaatc | tatgaacaat | cgcaacaaat tgtccaaagg caacaatacg acacagttag | 1080 |
| aggccatcgg | cgcaggtaca | ctctatccac gcctatcaga atgtcacctg gttaatggtc | 1140 |
| aatttaggtg | gctggaggca | catgtgaagc aatatggtct agggaaagat atcggtttac | 1200 |
| ttagatttta | tagttccgga | tccaacttaa ataatatagg tattaaagag cagtatcaag | 1260 |
| agggtttctt | cccaaggaat | cttgcgattt tcatacacag ctttaacaaa tttcactaga | 1320 |
| cgcaccttca | ttttgtcgtc | tcgttgtata tgagtccggg gtaagaattt tttaccgtat | 1380 |
| ttaacatgat | caacgggtac | taaagcaatg tcatttctaa acacagtagg taaaggacac | 1440 |
| gtcatcttat | tttaaagaat | gtcagaaatc agggagacta gatcgatatt acgtgttttt | 1500 |
| tgagtcaaag | acggccgtaa | aataatcaag cagtctttct acctgtactt gtcgctacct | 1560 |
| agaatcttta | atttatccat | gtcaaggagg atgcccatct gaaacaatac ctgttgctag | 1620 |
| atcgtctaac | aacggcatct | tgtcgtccat gcggggttgt tcttgtacgt atcagcgtcg | 1680 |
| gttatatgta | aaaataatgt | tttactacta tgccatctgt cccgtattct taagcatgac | 1740 |

```
taatattaaa agccgcctat atatcgagaa cgactaccat tggaatttaa aattgcttcc    1800
aagctatgat gatgtgacct ctcacattgt ggtagtataa actatggtta gccacgactc    1860
gttcggacaa gtagtaatat ctgttggtaa tagtcgggtt accgcgaaat atttgaaatt    1920
gatattaaga agcaatgatt tgtacataag tatacctgta atgaattcct gcgttagcag    1980
cttagtatcc attattagag                                                2000

<210> SEQ ID NO 103
<211> LENGTH: 2534
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 103
ttatcccctt cctatgacat gaacttaacc atagaaaaga aggggaaaga aaacatcaag      60
cgtcccatag actcaccctg aagttctcag gatccacgtg cagcttgtca cagtgcagct     120
cactcagtgt ggcaaaggtg cccttgaggt tgtccaggtg agccaggcca tcactaaagg     180
caccgagcac tttcttgcca tgagccttca ccttagggtt gcccataaca gcatcaggag     240
tggacagatc cccaaaggac tcaaagaacc tctgggtcca agggtagacc accagcagcc     300
taagggtggg aaaatagacc aataggcaga gagagtcagt gcctatcaga acccaagag     360 tcttctctgt ctccacatgc ccagtttcta ttggtctcct taaacctgtc ttgtaacctt     420
gataccaacc tgcccagggc ctcaccacca acttcatcca cgttcacctt gccccacagg     480
gcagtaacgg cagacttctc aagcttccat agagcccacc gcatcccag catgcctgct     540 attgtcttcc caatcctccc ccttgctgtc ctgccccacc ccacccccca gaatagaatg     600
acacctactc agacaatgcg atgcaatttc ctcattttat taggaaagga cagtgggagt     660
ggcaccttcc agggtcaagg aaggcacggg ggaggggcaa acaacagatg gctggcaact     720
agaaggcaca gtcgaggctg atcagcgggt ttaaacgggc cctctagact cgacgcggcc     780
gctttacttg tacagctcgt ccatgccgag agtgatcccg gcggcggtca cgaactccag     840
caggaccatg tgatcgcgct tctcgttggg gtctttgctc agggcggact gggtgctcag     900
gtagtggttg tcgggcagca gcacggggcc gtcgccgatg ggggtgttct gctggtagtg     960
gtcggcgagc tgcacgctgc cgtcctcgat gttgtggcgg atcttgaagt tcaccttgat    1020
gccgttcttc tgcttgtcgg ccatgatata gacgttgtgg ctgttgtagt tgtactccag    1080
cttgtgcccc aggatgttgc cgtcctcctt gaagtcgatg cccttcagct cgatgcggtt    1140
caccagggtg tcgccctcga acttcacctc ggcgcgggtc ttgtagttgc cgtcgtcctt    1200
gaagaagatg gtgcgctcct ggacgtagcc ttcgggcatg gcggacttga agaagtcgtg    1260
ctgcttcatg tggtcggggt agcggctgaa gcactcacg ccgtaggtca gggtggtcac    1320
gagggtgggc cagggcacgg gcagcttgcc ggtggtgcag atgaacttca gggtcagctt    1380
gccgtaggtg gcatcgccct cgccctcgcc ggacacgctg aacttgtggc cgtttacgtc    1440
gccgtccagc tcgaccagga tgggcaccac cccggtgaac agctcctcgc ccttgctcac    1500
catggtggcg accggtgggg agagaggtcg gtgattcggt caacgaggga gccgactgcc    1560
gacgtgcgct ccggaggctt gcagaatgcg gaacaccgcg cgggcaggaa cagggcccac    1620
actaccgccc cacaccccgc ctcccgcacc gccccttccc ggccgctgct ctcggcgcgc    1680
cctgctgagc agccgctatt ggccacagcc catcgcggtc ggcgcgctgc cattgctccc    1740
```

```
tggcgctgtc cgtctgcgag ggtactagtg agacgtgcgg cttccgtttg tcacgtccgg    1800
cacgccgcga accgcaagga accttcccga cttaggggcg gagcaggaag cgtcgccggg    1860
gggcccacaa gggtagcggc gaagatccgg gtgacgctgc gaacggacgt gaagaatgtg    1920
cgagacccag ggtcggcgcc gctgcgtttc ccggaaccac gcccagagca gccgcgtccc    1980
tgcgcaaacc cagggctgcc ttggaaaagg cgcaacccca accccgtgga agctctcagg    2040
agtcagatgc accatggtgt ctgtttgagg ttgctagtga acacagttgt gtcagaagca    2100
aatgtaagca atagatggct ctgccctgac ttttatgccc agccctggct cctgccctcc    2160
ctgctcctgg gagtagattg gccaacccta gggtgtggct ccacagggtg aggtctaagt    2220
gatgacagcc gtacctgtcc ttggctcttc tggcactggc ttaggagttg gacttcaaac    2280
cctcagccct ccctctaaga tatatctctt ggcccatac catcagtaca aattgctact     2340
aaaaacatcc tcctttgcaa gtgtatttac gtaatatttg gaatcacagc ttggtaagca    2400
tattgaagat cgttttccca attttcttat tacacaaata agaagttgat gcactaaaag    2460
tggaagagtt ttgtctacca taattcagct ttgggatatg tagatggatc tcttcctgcg    2520
tctccagaat atgc                                                      2534
```

<210> SEQ ID NO 104
<211> LENGTH: 2383
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104

```
gtccaagggt agaccaccag cagcctaagg gtgggaaaat agaccaatag gcagagagag     60
tcagtgccta tcagaaaccc aagagtcttc tctgtctcca catgcccagt ttctattggt    120
ctccttaaac ctgtcttgta accttgatac caacctgccc agggcctcac caccaacttc    180
atccacgttc accttgcccc acagggcagt aacggcagac ttctctactc ttaattcatt    240
acatattgtg cggtcgaatt cagggagccg ataatgcggt tacaataatt cctatactta    300
aatatacaaa gatttaaaat ttcaaaaaat ggttaccagc atcgttagtg cgtatacatc    360
aagaggcacg tgccccggag acagcaagta agctctttaa acggtctaag tgatgacagc    420
cgtaagcttc catagagccc accgcatccc cagcatgcct gctattgtct cccaatcct    480 cccccttgct gtcctgcccc accccacccc ccagaataga atgacaccta ctcagacaat    540
gcgatgcaat ttcctcattt tattaggaaa ggacagtggg agtggcacct tccagggtca    600
aggaaggcac gggggagggg caaacaacag atggctggca actagaaggc acagtcgagg    660
ctgatcagcg ggtttaaacg ggccctctag actcgacgcg gccgctttac ttgtacagct    720
cgtccatgcc gagagtgatc ccggcggcgg tcacgaactc cagcaggacc atgtgatcgc    780
gcttctcgtt ggggtctttg ctcagggcgg actgggtgct caggtagtgg ttgtcgggca    840
gcagcacggg gccgtcgccg atgggggtgt tctgctggta gtggtcggcg agctgcacgc    900
tgccgtcctc gatgttgtgg cggatcttga agttcacctt gatgccgttc ttctgcttgt    960
cggccatgat atagacgttg tggctgttgt agttgtactc cagcttgtgc cccaggatgt    1020
tgccgtcctc cttgaagtcg atgcccttca gctcgatgcg gttcaccagg gtgtcgccct    1080
cgaacttcac ctcggcgcgg gtcttgtagt tgccgtcgtc cttgaagaag atggtgcgct    1140
```

| | |
|---|---|
| cctggacgta gccttcgggc atggcggact tgaagaagtc gtgctgcttc atgtggtcgg | 1200 |
| ggtagcggct gaagcactgc acgccgtagg tcagggtggt cacgagggtg ggccagggca | 1260 |
| cgggcagctt gccggtggtg cagatgaact tcagggtcag cttgccgtag gtggcatcgc | 1320 |
| cctcgccctc gccggacacg ctgaacttgt ggccgtttac gtcgccgtcc agctcgacca | 1380 |
| ggatgggcac caccccggtg aacagctcct cgcccttgct caccatggtg gcgaccggtg | 1440 |
| gggagagagg tcggtgattc ggtcaacgag ggagccgact gccgacgtgc gctccggagg | 1500 |
| cttgcagaat gcggaacacc gcgcgggcag gaacagggcc cacactaccg ccccacaccc | 1560 |
| cgcctcccgc accgcccctt cccggccgct gctctcggcg cgccctgctg agcagccgct | 1620 |
| attggccaca gcccatcgcg gtcggcgcgc tgccattgct ccctggcgct gtccgtctgc | 1680 |
| gagggtacta gtgagacgtg cggcttccgt ttgtcacgtc cggcacgccg cgaaccgcaa | 1740 |
| ggaaccttcc cgacttaggg gcggagcagg aagcgtcgcc ggggggccca aagggtagc | 1800 |
| ggcgaagatc cgggtgacgc tgcgaacgga cgtgaagaat gtgcgagacc cagggtcggc | 1860 |
| gccgctgcgt ttcccggaac cacgcccaga gcagccgcgt ccctgcgcaa cccagggct | 1920 |
| gccttggaaa aggcgcaacc ccaaccccgt ggaagctcca aaggactcaa agaacctctg | 1980 |
| gatgctttga catacgattt ttaataaaac atgagcattt gaataaaaac gacttcctca | 2040 |
| tactgtaaac atcacgcatg cacattagac aataatccag taacgaaacg gcttcagtcg | 2100 |
| taatcgccca tatagttggc tacagaatgt tggatagaga acttaagtac gctaaggcgg | 2160 |
| cgtattttct taatatttag gggtattgcc gcagtcatta cagatactca ggagtcagat | 2220 |
| gcaccatggt gtctgtttga ggttgctagt gaacacagtt gtgtcagaag caaatgtaag | 2280 |
| caatagatgg ctctgccctg acttttatgc ccagccctgg ctcctgccct ccctgctcct | 2340 |
| gggagtagat tggccaaccc tagggtgtgg ctccacaggg tga | 2383 |

<210> SEQ ID NO 105
<211> LENGTH: 2673
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 105

| | |
|---|---|
| tactcttaat tcattacata ttgtgcggtc gaattcaggg agccgataat gcggttacaa | 60 |
| taattcctat acttaaatat acaaagattt aaaatttcaa aaaatggtta ccagcatcgt | 120 |
| tagtgcgtat acatcaagag gcacgtgccc cggagacagc aagtaagctc tttaaacatg | 180 |
| ctttgacata cgattttaa taaaacatga gcatttgaat aaaaacgact tcctcatact | 240 |
| gtaaacatca cgcatgcaca ttagacaata atccagtaac gaaacggctt cagtcgtaat | 300 |
| cgcccatata gttggctaca gaatgttgga tagagaactt aagtacgcta aggcggcgta | 360 |
| ttttcttaat atttaggggt attgccgcag tcattacaga taaccgccta tgcggccatg | 420 |
| ccaggattat agataacttt ttaacattag ccgcagaggt gggactagca cgtaatatca | 480 |
| gcacataacg tgtcagtcag gtcatcgacc tcgtcggact ccgggtgcga ggtcgtgaag | 540 |
| ctggaatacg agtgaggccg ccgaggacgt caggggggtg taaagcttcc atagagccca | 600 |
| ccgcatcccc agcatgcctg ctattgtctt cccaatcctc ccccttgctg tcctgcccca | 660 |
| ccccaccccc cagaatagaa tgacacctac tcagacaatg cgatgcaatt tcctcatttt | 720 |
| attaggaaag gacagtggga gtggcacctt ccagggtcaa ggaaggcacg ggggagggc | 780 |

```
aaacaacaga tggctggcaa ctagaaggca cagtcgaggc tgatcagcgg gtttaaacgg      840
gccctctaga ctcgacgcgg ccgctttact tgtacagctc gtccatgccg agagtgatcc      900
cggcggcggt cacgaactcc agcaggacca tgtgatcgcg cttctcgttg gggtctttgc      960
tcagggcgga ctgggtgctc aggtagtggt tgtcggcag cagcacgggg ccgtcgccga      1020
tgggggtgtt ctgctggtag tggtcggcga gctgcacgct gccgtcctcg atgttgtggc      1080
ggatcttgaa gttcaccttg atgccgttct tctgcttgtc ggccatgata tagacgttgt      1140
ggctgttgta gttgtactcc agcttgtgcc ccaggatgtt gccgtcctcc ttgaagtcga      1200
tgcccttcag ctcgatgcgg ttcaccaggg tgtcgccctc gaacttcacc tcggcgcggg      1260
tcttgtagtt gccgtcgtcc ttgaagaaga tggtgcgctc ctggacgtag ccttcgggca      1320
tggcggactt gaagaagtcg tgctgcttca tgtggtcggg gtagcggctg aagcactgca      1380
cgccgtaggt cagggtggtc acgagggtgg gccagggcac gggcagcttg ccggtggtgc      1440
agatgaactt cagggtcagc ttgccgtagg tggcatcgcc ctcgccctcg ccggacacgc      1500
tgaacttgtg gccgtttacg tcgccgtcca gctcgaccag gatgggcacc accccggtga      1560
acagctcctc gcccttgctc accatggtgg cgaccggtgg ggagagaggt cggtgattcg      1620
gtcaacgagg gagccgactg ccgacgtgcg ctccggaggc ttgcagaatg cggaacaccg      1680
cgcgggcagg aacagggccc acactaccgc cccacacccc gcctcccgca ccgccccttc      1740
ccggccgctg ctctcggcgc gccctgctga gcagccgcta ttggccacag cccatcgcgg      1800
tcggcgcgct gccattgctc cctggcgctg tccgtctgcg agggtactag tgagacgtgc      1860
ggcttccgtt tgtcacgtcc ggcacgccgc gaaccgcaag gaaccttccc gacttagggg      1920
cggagcagga agcgtcgccg gggggcccac aagggtagcg gcgaagatcc gggtgacgct      1980
gcgaacggac gtgaagaatg tgcgagaccc agggtcggcg ccgctgcgtt tcccggaacc      2040
acgcccagag cagccgcgtc cctgcgcaaa cccaggctg ccttggaaaa ggcgcaaccc      2100
caaccccgtg gaagcttgcg acctggaatc ggacagcagc ggggagtgta cggccccgag      2160
ttcgtgaccg ggtatgcttt cattgtaccc cggaacttta aatctatgaa caatcgcaac      2220
aaattgtcca aaggcaacaa tacgacacag ttagaggcca tcggcgcagg tacactctat      2280
ccacgcctat cagaatgtca cctggttaat ggtcaattta ggtggctgga ggcacatgtg      2340
aagcaatatg gtctagggaa agatatcggt ttacttagat tttatagttc cggatccaac      2400
ttaaataata taggtattaa agagcagtat caagagggtt tcttcccaag gaatcttgcg      2460
attttcatac acagctttaa caaatttcac tagacgcacc ttcattttgt cgtctcgttg      2520
tatatgagtc cggggtaaga atttttttacc gtatttaaca tgatcaacgg gtactaaagc      2580
aatgtcattt ctaaacacag taggtaaagg acacgtcatc ttattttaaa gaatgtcaga      2640
aatcagggag actagatcga tattacgtgt ttt                                  2673
```

<210> SEQ ID NO 106
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 106

```
gcatttcagg tttccttgag tgg                                              23
```

<210> SEQ ID NO 107
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
gcactgttgc tcttgaagtc c                                          21

<210> SEQ ID NO 108
<211> LENGTH: 281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108
caggccaggc ctggcgtgaa cgttcactga aatcatggcc tcttggccaa gattgatagc    60
ttgtgcctgt ccctgagtcc cagtccatca cgagcagctg gtttctaaga tgctatttcc   120
cgtataaagc atgagaccgt gacttgccag ccccacagag ccccgccctt gtccatcact   180
ggcatctgga ctccagcctg ggttggggca aagagggaaa tgagatcatg tcctaaccct   240
gatcctcttg tcccacagat atccagaacc ctgaccctgc c                      281

<210> SEQ ID NO 109
<211> LENGTH: 140
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109
gtgtaccagc tgagagactc taaatccagt gacaagtctg tctgcctatt caccgatttt    60
gattctcaaa caaatgtgtc acaaagtaag gattctgatg tgtatatcac agacaaaact   120
gtgctagaca tgaggtctat                                              140

<210> SEQ ID NO 110
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
cttgtccatc actggcatct gg                                          22

<210> SEQ ID NO 111
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111

```
tttggtggca atggataagg c                                            21

<210> SEQ ID NO 112
<211> LENGTH: 142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112
actccagcct gggttggggc aaagagggaa atgagatcat gtcctaaccc tgatcctctt   60
gtcccacaga tatccagaac cctgaccctg ccgtgtacca gctgagagac tctaaatcca  120
gtgacaagtc tgtctgccta tt                                          142

<210> SEQ ID NO 113
<211> LENGTH: 311
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 113
caccgatttt gattctcaaa caaatgtgtc acaaagtaag gattctgatg tgtatatcac   60
agacaaaact gtgctagaca tgaggtctat ggacttcaag agcaacagtg ctgtggcctg  120
gagcaacaaa tctgactttg catgtgcaaa cgccttcaac aacagcatta ttccagaaga  180
caccttcttc cccagcccag gtaagggcag ctttggtgcc ttcgcaggct gtttccttgc  240
ttcaggaatg gccaggttct gcccagagct ctggtcaatg atgtctaaaa ctcctctgat  300
tggtggtctc g                                                      311

<210> SEQ ID NO 114
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114
tcctaaccct gatcctcttg tcc                                          23

<210> SEQ ID NO 115
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
ccgtgtcatt ctctggactg c                                            21

<210> SEQ ID NO 116
<211> LENGTH: 188
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic polynucleotide"

<400> SEQUENCE: 116
cacagatatc cagaaccctg accctgccgt gtaccagctg agagactcta aatccagtga      60
caagtctgtc tgcctattca ccgattttga ttctcaaaca aatgtgtcac aaagtaagga     120
ttctgatgtg tatatcacag acaaaactgt gctagacatg aggtctatgg acttcaagag    180
caacagtg                                                             188

<210> SEQ ID NO 117
<211> LENGTH: 259
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117
ctgtggcctg gagcaacaaa tctgactttg catgtgcaaa cgccttcaac aacagcatta     60
ttccagaaga caccttcttc cccagcccag gtaagggcag ctttggtgcc ttcgcaggct    120
gtttccttgc ttcaggaatg gccaggttct gcccagagct ctggtcaatg atgtctaaaa    180
ctcctctgat tggtggtctc ggccttatcc attgccacca aaaccctctt tttactaaga    240
aacagtgagc cttgttctg                                                 259

<210> SEQ ID NO 118
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
cagacuucuc cacaggaguc                                                 20
```

SYSTEMS AND METHODS FOR TARGETED INTEGRATION AND GENOME EDITING AND DETECTION THEREOF USING INTEGRATED PRIMING SITES

RELATED APPLICATIONS

This application is a 35 U.S.C. § 371 national stage filing of International Application No. PCT/US2018/042040, filed on Jul. 13, 2018, which in turn claims priority to U.S. Provisional Patent Application No. 62/532,509, filed on Jul. 14, 2017, and U.S. Provisional Patent Application No. 62/582,563, filed on Nov. 7, 2017. The entire contents of each of the aforementioned applications are expressly incorporated herein by reference.

SEQUENCE LISTING

The instant application contains a Sequence Listing which has been submitted electronically in ASCII format and is hereby incorporated by reference in its entirety. Said ASCII copy, created on Sep. 27, 2018, is named 126454-01920 SL.txt and is 304,661 bytes in size.

FIELD

This disclosure relates to genome editing systems and methods and compositions for editing a target nucleic acid sequence, or modulating expression of a target nucleic acid sequence, and applications thereof.

BACKGROUND

CRISPRs (Clustered Regularly Interspaced Short Palindromic Repeats) evolved in bacteria and archea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of a Cas9 protein to a target sequence in the viral genome. The Cas9 protein, in turn, cleaves and thereby silences the viral target.

Recently, the CRISPR/Cas system has been adapted for genome editing in eukaryotic cells. The introduction of site-specific double strand breaks (DSBs) allows for target sequence alteration through endogenous DNA repair mechanisms, for example non-homologous end-joining (NHEJ) or homology-directed repair (HDR).

In addition, targeted integration of a nucleic acid (e.g., a transgene) may be achieved using the CRISPR/Cas system. Applications of targeted integration include the delivery of therapeutic transgene expression cargos to cleavage sites in the genome that are amenable to robust expression and tolerant to insertions. Moreover, when endogenous control of gene expression is required, targeted integration of a corrected gene/exon at the site corresponding to the endogenous gene/exon is an attractive strategy.

Targeted integration of the exogenous DNA cassette (e.g., transgene) with high-efficiency and accuracy is the ultimate goal. However, quantitative assessment of targeted integration is not straightforward. Currently, targeted integration is primarily detected and measured using two separate methods: flow cytometric analysis of transgene expression and digital droplet PCR (ddPCR). The limitation of flow cytometry is that the method relies on the detection of a phenotypic output which may not correlate with actual genomic integration. For example, the integrated nucleic acid may be epigenetically silenced which may lead to a lower perceived integration rate. The integrated nucleic acid may also integrate at an off-target location or an un-integrated donor template may be expressed by the cell, which may lead to an increased perceived integration rate. Thus, under these alternative scenarios, the resulting detection of integration frequency may be inaccurate.

ddPCR is an on-target quantitative assay that may be used to measure targeted integration. A donor template is often provided along with a DNA nuclease to induce a double- or single-stranded DNA break from which repair is initiated. Although ddPCR provides an accurate rate of targeted integration, it does not provide information about other types of on-target editing, such as insertions or deletions (indels). Indel measurements can be made via other methods, which often have biases. Multiple methods are sometimes combined to fully characterize on-target editing, but the results are usually not ideal and often inaccurate. Therefore, there remains a need in the art for methods to detect and quantitatively measure all possible on-target gene editing outcomes, including targeted integration.

SUMMARY

The present disclosure provides genome editing systems and related methods which allow for the detection and quantitative measurement of on-target gene editing outcomes, including targeted integration. The compositions and methods described herein rely on the use of donor templates comprising a 5' homology arm, a cargo, a one or more priming sites, a 3' homology arm, and optionally stuffer sequence.

The compositions and methods described herein allow for the quantitative analysis of on-target gene editing outcomes, including targeted integration events, by embedding one or more primer binding sites (i.e., priming sites) into a donor template that are substantially identical to a priming site present at the targeted genomic DNA locus (i.e., the target nucleic acid). The priming sites are embedded into the donor template such that, when homologous recombination of the donor template with a target nucleic acid occurs, successful targeted integration of the donor template integrates the priming sites from the donor template into the target nucleic acid such that at least one amplicon can be generated in order to quantitatively determine the on-target editing outcomes.

In some embodiments, the target nucleic acid comprises a first priming site (P1) and a second priming site (P2), and the donor template comprises a cargo sequence, a first priming site (P1'), and a second priming site (P2'), wherein P2' is located 5' from the cargo sequence, wherein P1' is located 3' from the cargo sequence (i.e., A1-P2'-N-P1'-A2), wherein P1' is substantially identical to P1, and wherein P2' is substantially identical to P2. After accurate homology-driven targeted integration, three amplicons are produced using a single PCR reaction with two oligonucleotide primers (FIG. 1A). The first amplicon, Amplicon X, is generated from the primer binding sites originally present in the genomic DNA (P1 and P2), and may be sequenced to analyze on-target editing events that do not result in targeted integration (e.g., insertions, deletions, gene conversion). The remaining two amplicons are mapped to the 5' and 3' junctions after homology-driven targeted integration. The second amplicon, Amplicon Y, results from the amplification of the nucleic acid sequence between P1 and P2' following a targeted integration event at the target nucleic acid, thereby amplifying the 5' junction. The third amplicon, Amplicon Z, results from the amplification of the nucleic acid sequence between P1' and P2 following a targeted integration event at the target nucleic acid, thereby amplifying the 3' junction. Sequencing of these amplicons provides a quantitative assessment of targeted integration at the target nucleic acid, in addition to information about the fidelity of the targeted integration. To avoid any biases inherent to amplicon size, stuffer sequence may optionally be included in the donor template to keep all three expected amplicons the same length.

In one aspect, disclosed herein is an isolated nucleic acid for homologous recombination with a target nucleic acid having a cleavage site, wherein:
(a) a first strand of the target nucleic acid comprises, from 5' to 3', P1-H1-X-H2-P2, wherein
P1 is a first priming site;
H1 is a first homology arm;
X is the cleavage site;
H2 is a second homology arm; and
P2 is a second priming site; and
(b) a first strand of the isolated nucleic acid comprises, from 5' to 3', A1-P2'-N-A2, or A1-N-P1'-A2, wherein
A1 is a homology arm that is substantially identical to H1;
P2' is a priming site that is substantially identical to P2;
N is a cargo;
P1' is a priming site that is substantially identical to P1; and
A2 is a homology arm that is substantially identical to H2.

In one embodiment, the first strand of the isolated nucleic acid comprises, from 5' to 3', A1-P2'-N-P1'-A2. In one embodiment, the first strand of the isolated nucleic acid further comprises S1 or S2, wherein the first strand of the isolated nucleic acid comprises, from 5' to 3',
A1-S1-P2'-N-A2, or A1-N-P1'-S2-A2;
wherein S1 is a first stuffer, wherein S2 is a second stuffer, and wherein each of 51 and S2 comprise a random or heterologous sequence having a GC content of approximately 40%.

In one embodiment, the first stuffer has a sequence having less than 50% sequence identity to any nucleic acid sequence within 500 base pairs of the cleavage site, and wherein the second stuffer has a sequence having less than 50% sequence identity to any nucleic acid sequence within 500 base pairs of the cleavage site. In one embodiment, the first stuffer has a sequence comprising at least 10 nucleotides of a sequence set forth in Table 2, and wherein the second stuffer has a sequence comprising at least 10 nucleotides of a sequence set forth in Table 2. In one embodiment, the first stuffer has a sequence that is not the same as the sequence of the second stuffer.

In one embodiment, the first strand of the isolated nucleic acid comprises, from 5' to 3', A1-S1-P2'-N-P1'-S2-A2. In one embodiment, A1+S1 and A2+S2 have sequences that are of approximately equal length. In one embodiment, A1+S1 and A2+S2 have sequences that are of equal length. In one embodiment, A1+S1 and H1+X+H2 have sequences that are of approximately equal length. In one embodiment, A1+S1 and H1+X+H2 have sequences that are of equal length. In one embodiment, A2+S2 and H1+X+H2 have sequences that are of approximately equal length. In one embodiment, A2+S2 and H1+X+H2 have sequences that are of equal length.

In one embodiment, A1 has a sequence that is at least 40 nucleotides in length, and A2 has a sequence that is at least 40 nucleotides in length.

In one embodiment, A1 has a sequence that is identical to, or differs by no more than 1, 2, 3, 4, 5, 6, 7, 8, 9, 10, 15, 20, 25, or 30 nucleotides from a sequence of H1. In one embodiment, A2 has a sequence that is identical to, or differs by no more than 1, 2, 3, 4, 5, 6, 7, 8, 9, 10, 15, 20, 25, or 30 nucleotides from a sequence of H2.

In one embodiment, A1+S1 have a sequence that is at least 40 nucleotides in length, and A2+S2 have a sequence that is at least 40 nucleotides in length.

In one embodiment, N comprises an exon of a gene sequence, an intron of a gene sequence, a cDNA sequence, or a transcriptional regulatory element; a reverse complement of any of the foregoing or a portion of any of the foregoing. In one embodiment, N comprises a promoter sequence.

In one aspect, disclosed herein is a composition comprising an isolated nucleic acid disclosed herein and, optionally, a pharmaceutically acceptable carrier.

In one aspect, disclosed herein is a vector comprising an isolated nucleic acid disclosed herein. In one embodiment, the vector is a plasmid vector. In one embodiment, the vector is a viral vector. In one embodiment, the vector is an AAV vector, an adenoviral vector, a lentiviral vector, an integration-deficient lentiviral vector (IDLV), a retroviral vector, a HSV vector, a naked DNA vector, or a lipid nanoparticle.

In one aspect, disclosed herein is a genome editing system comprising an isolated nucleic acid disclosed herein. In one embodiment, the genome editing system further comprises a RNA-guided nuclease and at least one gRNA molecule.

In one aspect, disclosed herein is a method of altering a cell comprising contacting the cell with a genome editing system.

In one aspect, disclosed herein is a kit comprising a genome editing system.

In one aspect, disclosed herein is a nucleic acid, composition, vector, gene editing system, method or kit, for use in medicine.

In one aspect, disclosed herein is a method of altering a cell, comprising the steps of: forming, in a target nucleic acid of the cell, at least one single- or double-strand break at a cleavage site, wherein the target nucleic acid comprises a first strand comprising: a first homology arm 5' to the cleavage site, a first priming site either within the first homology arm or 5' to the first homology arm, a second homology arm 3' to the cleavage site, and a second priming site either within the second homology arm or 3' to the second homology arm, and recombining an exogenous oligonucleotide donor template with the target nucleic acid by homologous recombination to produce an altered nucleic acid, wherein a first strand of the exogenous oligonucleotide donor template comprises either: i) a cargo, a priming site that is substantially identical to the second priming site either within or 5' to the cargo, a first donor homology arm 5' to the cargo, and a second donor homology arm 3' to the cargo; or ii) a cargo, a first donor homology arm 5' to the cargo, a priming site that is substantially identical to the first priming site either within or 3' to the cargo, and a second donor homology arm 3' to the cargo, thereby altering the cell.

In one embodiment, the first strand of the exogenous oligonucleotide donor template comprises, from 5' to 3', the first donor homology arm, the priming site that is substantially identical to the second priming site, the cargo, the priming site that is substantially identical to the first priming site, and the second donor homology arm. In one embodiment, the first strand of the exogenous oligonucleotide donor template further comprises a first stuffer or a second stuffer, wherein the first stuffer and the second stuffer each comprise a random or heterologous sequence having a GC content of approximately 40%; and wherein the first strand of the exogenous oligonucleotide donor template comprises, from 5' to 3', i) the first donor homology arm, the first stuffer, the priming site that is substantially identical to the second priming site, and the second donor homology arm; or ii) the first donor homology arm, the cargo, the priming site that is substantially identical to the first priming site, the second stuffer, and the second donor homology arm.

In one embodiment, the first stuffer has a sequence having less than 50% sequence identity to any nucleic acid sequence within 500 base pairs of the cleavage site, and wherein the second stuffer has a sequence having less than 50% sequence identity to any nucleic acid sequence within 500 base pairs of the cleavage site. In one embodiment, the first stuffer has a sequence comprising at least 10 nucleotides of a sequence set forth in Table 2, and wherein the second stuffer has a sequence comprising at least 10 nucleotides of a sequence set forth in Table 2. In one embodiment, the first stuffer has a sequence that is not the same as the sequence of the second stuffer.

In one embodiment, the first strand of the exogenous oligonucleotide donor template comprises, from 5' to 3', the first donor homology arm, the first suffer, the priming site that is substantially identical to the second priming site, the cargo, the priming site that is substantially identical to the first priming site, the second stuffer, and the second donor homology arm.

In one embodiment, the altered nucleic acid comprises, from 5' to 3', the first priming site, the first donor homology arm, the priming site that is substantially identical to the second priming site, the cargo, the second donor homology arm, and the second priming site. In one embodiment, the altered nucleic acid comprises, from 5' to 3', the first priming site, the first donor homology arm, the cargo, the priming site that is substantially identical to the first priming site, the second donor homology arm, and the second priming site.

In one embodiment, the altered nucleic acid comprises, from 5' to 3', the first priming site, the first donor homology arm, the priming site that is substantially identical to the second priming site, the cargo, the priming site that is substantially identical to the first priming site, the second donor homology arm, and the second priming site.

In one embodiment, the altered nucleic acid comprises, from 5' to 3', the first priming site, the first donor homology arm, the first stuffer, the priming site that is substantially identical to the second priming site, the cargo, the priming site that is substantially identical to the first priming site, the second stuffer, the second donor homology arm, and the second priming site.

In one embodiment, the step of forming the at least one single- or double-strand break comprises contacting the cell with an RNA-guided nuclease. In one embodiment, the RNA-guided nuclease is a Class 2 Clustered Regularly Interspersed Repeat (CRISPR)-associated nuclease. In one embodiment, the RNA-guided nuclease is selected from the group consisting of wild-type Cas9, a Cas9 nickase, a wild-type Cpf1, and a Cpf1 nickase. In another embodiment, the step of forming the at least one single- or double-strand break comprises contacting the cell with a Zinc finger Nuclease (ZFN). In another embodiment, the step of forming the at least one single- or double-strand break comprises contacting the cell with a Transcription activator-like effector nuclease (TALEN).

In one embodiment, the step of contacting the RNA-guided nuclease with the cell comprises introducing into the cell a ribonucleoprotein (RNP) complex comprising the RNA-guided nuclease and a guide RNA (gRNA). In one embodiment, the step of recombining the exogenous oligonucleotide donor template into the nucleic acid by homologous recombination comprises introducing the exogenous oligonucleotide donor template into the cell.

In one embodiment, the step of introducing comprises electroporation of the cell in the presence of the RNP complex and/or the exogenous oligonucleotide donor template.

In another aspect, disclosed herein is a method of integrating an exogenous nucleic acid into a target nucleic acid in a cell, comprising (a) introducing the exogenous nucleic acid into the cell, wherein a first strand of the target nucleic acid comprises, from 5' to 3', P1-H1-X-H2-P2, wherein P1 is a first priming site; H1 is a first homology arm; X is a cleavage site; H2 is a second homology arm; and P2 is a second priming site; and wherein a first strand of the isolated nucleic acid comprises, from 5' to 3', A1-P2'-N-A2, or A1-N-P1'-A2, wherein A1 is a homology arm that is substantially identical to H1; P2' is a priming site that is substantially identical to P2; N is a cargo; P1' is a priming site that is substantially identical to P1; and A2 is a homology arm that is substantially identical to H2; and (b) introducing one or more nucleases into the cell, wherein the nucleases cleave the target nucleic acid at the cleavage site, such that the exogenous nucleic acid is integrated into the target nucleic acid.

In one embodiment, the first strand of the exogenous nucleic acid comprises, from 5' to 3', A1-P2'-N-P1'-A2.

In one embodiment, the first strand of the exogenous nucleic acid further comprises S1 or S2, wherein the first strand of the isolated nucleic acid comprises, from 5' to 3', A1-S1-P2'-N-A2, or A1-N-P1'-S2-A2; wherein S1 is a first stuffer, wherein S2 is a second stuffer. In one embodiment, the first strand of the isolated nucleic acid comprises, from 5' to 3', A1-S1-P2'-N-P1'-S2-A2.

In one embodiment, each of S1 and S2 comprise a random or heterologous sequence having a GC content of approximately 40%. Additional features of the stuffer sequences are described herein. For example, in one embodiment, the first stuffer has a sequence having less than 50% sequence identity to any nucleic acid sequence within 500 base pairs of the cleavage site, and wherein the second stuffer has a sequence having less than 50% sequence identity to any nucleic acid sequence within 500 base pairs of the cleavage site. In one embodiment, the first stuffer has a sequence comprising at least 10 nucleotides of a sequence set forth in Table 2, and wherein the second stuffer has a sequence comprising at least 10 nucleotides of a sequence set forth in Table 2.

In one embodiment, the first stuffer has a sequence that is not the same as the sequence of the second stuffer. In one embodiment, A1+S1 and A2+S2 have sequences that are of approximately equal length. In one embodiment, A1+S1 and A2+S2 have sequences that are of equal length. In one embodiment, A1+S1 and H1+X+H2 have sequences that are of approximately equal length. In one embodiment, A1+S1 and H1+X+H2 have sequences that are of equal length. In one embodiment, A2+S2 and H1+X+H2 have sequences that are of approximately equal length. In one embodiment, A2+S2 and H1+X+H2 have sequences that are of equal length.

The cargo sequence (N) can comprise any nucleic acid sequence to be integrated into the target nucleic acid. For example, in some embodiments, the cargo sequence can comprise an exon of a gene sequence, an intron of a gene sequence, a cDNA sequence, or a transcriptional regulatory element; a reverse complement of any of the foregoing or a portion of any of the foregoing. In one embodiment, N comprises a promoter sequence.

In one embodiment, following integration of the exogenous nucleic acid, the target nucleic acid comprises, from 5' to 3', the first priming site, the first donor homology arm, the priming site that is substantially identical to the second priming site, the cargo, the second donor homology arm, and the second priming site. In one embodiment, the altered nucleic acid comprises, from 5' to 3', the first priming site, the first donor homology arm, the cargo, the priming site that is substantially identical to the first priming site, the second donor homology arm, and the second priming site.

In another embodiment, following integration of the exogenous nucleic acid, the target nucleic acid comprises, from 5' to 3', the first priming site, the first donor homology arm, the priming site that is substantially identical to the second priming site, the cargo, the priming site that is substantially identical to the first priming site, the second donor homology arm, and the second priming site.

In another embodiment, following integration of the exogenous nucleic acid, the target nucleic acid comprises, from 5' to 3', the first priming site, the first donor homology arm, the first stuffer, the priming site that is substantially identical to the second priming site, the cargo, the priming site that is substantially identical to the first priming site, the second stuffer, the second donor homology arm, and the second priming site.

In one embodiment, the nuclease is an RNA-guided nuclease. In one embodiment, the RNA-guided nuclease is a Class 2 Clustered Regularly Interspersed Repeat (CRISPR)-associated nuclease. In one embodiment, the RNA-guided nuclease is selected from the group consisting of wild-type Cas9, a Cas9 nickase, a wild-type Cpf1, and a Cpf1 nickase. In one embodiment, the RNA-guided nuclease is provided as a ribonucleoprotein (RNP) complex comprising the RNA-guided nuclease and a guide RNA (gRNA). In another embodiment, the method further comprises introducing one or more gRNAs into the cell. In one embodiment, the nuclease is a Zinc finger Nuclease (ZFN). In another embodiment, the nuclease is a Transcription activator-like effector nuclease (TALEN).

In one embodiment, the exogenous nucleic acid is provided as naked nucleic acid, e.g., naked DNA, or naked RNA. In another embodiment, the exogenous nucleic acid is provided in a vector. The vector can be, for example, a plasmid vector. In other embodiments, the vector can be a viral vector, for example, an AAV vector, an adenoviral vector, a lentiviral vector, an IDLV vector, a retroviral vector, or a herpes simplex virus (HSV) vector. In other embodiments, the vector is a naked DNA vector. In other embodiments, the exogenous nucleic acid is provided in a lipid nanoparticle.

In one aspect, disclosed herein is a method of altering a target nucleic acid in a cell, wherein the target nucleic acid comprises a first strand comprising: a first homology arm 5' to a cleavage site, a first priming site either within the first homology arm or 5' to the first homology arm, a second homology arm 3' to the cleavage site, and a second priming site either within the second homology arm or 3' to the second homology arm, the method comprising: contacting the cell with (a) at least one gRNA molecule, (b) a RNA-guided nuclease molecule, and (c) an exogenous oligonucleotide donor template, wherein a first strand of the exogenous oligonucleotide donor template comprises either: i) a cargo, a priming site that is substantially identical to the second priming site either within or 5' to the cargo, a first donor homology arm 5' to the cargo, and a second donor homology arm 3' to the cargo; or ii) a cargo, a first donor homology arm 5' to the cargo, a priming site that is substantially identical to the first priming site, and a second donor homology arm 3' to the cargo; wherein the gRNA molecule and the RNA-guided nuclease molecule interact with the target nucleic acid, resulting in a cleavage event at or near the cleavage site, and wherein the cleavage event is repaired by at least one DNA repair pathway to produce an altered nucleic acid, thereby altering the target nucleic acid in the cell.

In one embodiment, the method further comprises contacting the cell with (d) a second gRNA molecule, wherein the second gRNA molecule and the RNA-guided nuclease molecule interact with the target nucleic acid, resulting in a second cleavage event at or near the cleavage site, and wherein the second cleavage event is repaired by the at least one DNA repair pathway.

In one embodiment, the first strand of the exogenous oligonucleotide donor template comprises, from 5' to 3', the first donor homology arm, the priming site that is substantially identical to the second priming site, the cargo, the priming site that is substantially identical to the first priming site, and the second donor homology arm.

In one embodiment, the first strand of the exogenous oligonucleotide donor template further comprises a first stuffer or a second stuffer, wherein the first stuffer and the second stuffer each comprise a random or heterologous sequence having a GC content of approximately 40%; and wherein the first strand of the exogenous oligonucleotide donor template comprises, from 5' to 3', i) the first donor homology arm, the first stuffer, the priming site that is substantially identical to the second priming site, and the second donor homology arm; or ii) the first donor homology arm, the cargo, the priming site that is substantially identical to the first priming site, the second stuffer, and the second donor homology arm.

In one embodiment, the first stuffer has a sequence having less than 50% sequence identity to any nucleic acid sequence within 500 base pairs of the cleavage site, and wherein the second stuffer has a sequence having less than 50% sequence identity to any nucleic acid sequence within 500 base pairs of the cleavage site. In one embodiment, the first stuffer has a sequence comprising at least 10 nucleotides of a sequence set forth in Table 2, and wherein the second stuffer has a sequence comprising at least 10 nucleotides of a sequence set forth in Table 2. In one embodiment, the first stuffer has a sequence that is not the same as the sequence of the second stuffer.

In one embodiment, the first strand of the exogenous oligonucleotide donor template comprises, from 5' to 3', the first donor homology arm, the first suffer, the priming site that is substantially identical to the second priming site, the cargo, the priming site that is substantially identical to the first priming site, the second stuffer, and the second donor homology arm.

In one embodiment, the altered nucleic acid comprises, from 5' to 3', the first priming site, the first donor homology arm, the priming site that is substantially identical to the second priming site, the cargo, the second donor homology arm, and the second priming site. In one embodiment, the altered nucleic acid comprises, from 5' to 3', the first priming site, the first donor homology arm, the cargo, the priming site that is substantially identical to the first priming site, the second donor homology arm, and the second priming site.

In one embodiment, the altered nucleic acid comprises, from 5' to 3', the first priming site, the first donor homology arm, the priming site that is substantially identical to the second priming site, the cargo, the priming site that is substantially identical to the first priming site, the second donor homology arm, and the second priming site.

In one embodiment, the altered nucleic acid comprises, from 5' to 3', the first priming site, the first donor homology arm, the first stuffer, the priming site that is substantially identical to the second priming site, the cargo, the priming site that is substantially identical to the first priming site, the second stuffer, the second donor homology arm, and the second priming site.

In one embodiment, the cell is contacted first with the at least one gRNA molecule and the RNA-guided nuclease molecule, followed by contacting the cell with the exogenous oligonucleotide donor template. In one embodiment, the cell is contacted with the at least one gRNA molecule, the RNA-guided nuclease molecule, and the exogenous oligonucleotide donor template at the same time.

In one embodiment, the exogenous oligonucleotide donor template is present in a vector. In one embodiment, the vector is a viral vector. In another embodiment, the vector is a plasmid vector. In another embodiment, the vector is naked DNA. In one embodiment, the viral vector is an AAV vector, an adenoviral vector, a lentiviral vector, or an integration-deficient lentiviral vector (IDLV).

In one embodiment, the DNA repair pathway repairs the target nucleic acid to result in targeted integration of the exogenous oligonucleotide donor template. In one embodiment, the altered nucleic acid comprises a sequence comprising an indel as compared to a sequence of the target nucleic acid. In one embodiment, the cleavage event, or both the cleavage event and the second cleavage event, is/are repaired by gene correction.

In one embodiment, the first donor homology arm and the first stuffer consist of a sequence that is of approximately equal length to a sequence consisting of the second donor homology arm and the second stuffer. In one embodiment, the first donor homology arm and the first stuffer consist of a sequence that is of equal length to the sequence consisting of the second donor homology arm and the second stuffer.

In one embodiment, the first donor homology arm and the first stuffer consist of a sequence that is of approximately equal length to a sequence consisting of the first homology arm, the cleavage site, and the second homology arm. In one embodiment, the first donor homology arm and the first stuffer consist of a sequence that is of equal length to a sequence consisting of the first homology arm, the cleavage site, and the second homology arm.

In one embodiment, the second donor homology arm and the second stuffer consist of a sequence that is of approximately equal length to a sequence consisting of the first homology arm, the cleavage site, and the second homology arm. In one embodiment, the second donor homology arm and the second stuffer consist of a sequence that is of equal length to a sequence consisting of the first homology arm, the cleavage site, and the second homology arm.

In one embodiment, the first donor homology arm has a sequence that is at least 40 nucleotides in length, and wherein the second donor homology arm has a sequence that is at least 40 nucleotides in length. In one embodiment, the first donor homology arm has a sequence that is identical to, or differs by no more than 1, 2, 3, 4, 5, 6, 7, 8, 9, 10, 15, 20, 25, or 30 nucleotides from, a sequence of the first homology arm. In one embodiment, the second donor homology arm has a sequence that is identical to, or differs by no more than 1, 2, 3, 4, 5, 6, 7, 8, 9, 10, 15, 20, 25, or 30 nucleotides from, a sequence of the second homology arm.

In one embodiment, the first donor homology arm and the first stuffer consist of a sequence that is at least 40 nucleotides in length, and the second donor homology arm and the second stuffer consist of a sequence that is at least 40 nucleotides in length.

In one embodiment, the first suffer has a sequence that is different from a sequence of the second stuffer.

In one embodiment, the first priming site, the priming site that is substantially identical to the first priming site, the second priming site, and the priming site that is substantially identical to the second priming site are each less than 60 base pairs in length.

In one embodiment, the method further comprises amplifying the target nucleic acid, or a portion of the target nucleic acid, prior to the forming step or the contacting step.

In one embodiment, the method further comprises amplifying the altered nucleic acid using a first primer which binds to the first priming site and/or the priming site that is substantially identical to the first priming site, and a second primer which binds to the second priming site and/or the priming site that is substantially identical to the second priming site.

In one embodiment, the altered nucleic acid comprises a sequence that is different than a sequence of the target nucleic acid.

In one embodiment, the gRNA molecule is a gRNA nucleic acid, and wherein the RNA-guided nuclease molecule is a RNA-guided nuclease protein. In one embodiment, the gRNA molecule is a gRNA nucleic acid, and wherein the RNA-guided nuclease molecule is a RNA-guided nuclease nucleic acid. In one embodiment, the cell is contacted with the gRNA molecule and the RNA-guided nuclease molecule as a pre-formed complex. In one embodiment, the RNA-guided nuclease is selected from the group consisting of wild-type Cas9, a Cas9 nickase, a wild-type Cpf1, and a Cpf1 nickase.

In one embodiment, the target nucleic acid comprises an exon of a gene, an intron of a gene, a cDNA sequence, a transcriptional regulatory element; a reverse complement of any of the foregoing; or a portion of any of the foregoing.

In one embodiment, the cell is a eukaryotic cell. In one embodiment, the eukaryotic cell is a human cell. In one embodiment, the cell is a peripheral blood cell. In one embodiment, the cell is a CD34+ cell. In one embodiment, the eukaryotic cell is an immune cell, an epithelial cell, an endothelial cell, a neuron, or a stem cell. In one embodiment, the eukaryotic cell is an immune cell. In an exemplary embodiment, the immune cell is a T cell, a B cell, a natural killer cell, a monocyte, a macrophage cell, or a dendritic cell. In one embodiment, the eukaryotic is a T cell, e.g., a helper T cell, a regulatory T cell (Treg), or a Natural Killer T cell (NK T cell). In another embodiment, the eukaryotic cell is a stem cell. In exemplary embodiments, the stem cell is an embryonic stem cell, an induced pluripotent stem cell (iPSC), or a hematopoietic stem/progenitor cell (HSPC).

In one embodiment, the cell is from a subject suffering from a disease or disorder. In one embodiment, the disease or disorder is a blood disease, an immune disease, a neurological disease, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or a pain disorder.

In one embodiment, the cell is from a subject having at least one mutation at the cleavage site.

In one embodiment, the method further comprises isolating the cell from the subject prior to contacting the forming step or the contacting step.

In one embodiment, the method further comprises introducing the cell into a subject after the recombining step or after the cleavage event is repaired by the at least one DNA repair pathway.

In one embodiment, the forming step and the recombining step, or the contacting step, is performed in vitro. In one embodiment, the forming step and the recombining step, or the contacting step, is performed ex vivo. In one embodiment, the forming step and the recombining step, or the contacting step, is performed in vivo.

In another embodiment, the cell is a plant cell. In one embodiment, the plant is monocotyledonous, for example, maize, wheat, rice, corn, or *Setaria*. In another embodiment, the plant is dicotyledonous, for example, potato, soybean, tomato, tobacco, or *Arabidopsis*. In one aspect, disclosed herein is a method for determining the outcome of a gene editing event at a cleavage site in a target nucleic acid in a cell using an exogenous donor template, wherein the target nucleic acid comprises a first strand comprising: a first homology arm 5' to a cleavage site, a first priming site either within the first homology arm or 5' to the first homology arm, a second homology arm 3' to the cleavage site, and a second priming site either within the second homology arm or 3' to the second homology arm, and wherein a first strand of the exogenous donor template comprises i) a cargo, a priming site that is substantially identical to the second priming site either within or 5' to the cargo, a first donor homology arm 5' to the cargo, and a second donor homology arm 3' to the cargo; or ii) a cargo, a first donor homology arm 5' to the cargo, a priming site that is substantially identical to the first priming site 3' to the cargo, and a second donor homology arm 3' to the cargo, the method comprising: i) forming at least one single- or double-strand break at or near the cleavage site in the target nucleic acid; ii) recombining the exogenous oligonucleotide donor template with the target nucleic acid via homologous recombination to produce an altered nucleic acid; and iii) amplifying the altered nucleic acid using a first primer which binds to the first priming site and/or the priming site that is substantially identical to the first priming site; and/or a second primer which binds to the second priming site and/or the priming site that is substantially identical to the second priming site; thereby determining the outcome of the gene editing event in the cell.

In one embodiment, the step of forming the at least one single- or double-strand break comprises contacting the cell with an RNA-guided nuclease. In one embodiment, the RNA-guided nuclease is a Class 2 Clustered Regularly Interspersed Repeat (CRISPR)-associated nuclease. In one embodiment, the RNA-guided nuclease is selected from the group consisting of wild-type Cas9, a Cas9 nickase, a wild-type Cpf1, and a Cpf1 nickase. In another embodiment, the step of forming the at least one single- or double-strand break comprises contacting the cell with a Zinc finger Nuclease (ZFN). In another embodiment, the step of forming the at least one single- or double-strand break comprises contacting the cell with a Transcription activator-like effector nuclease (TALEN).

In one embodiment, the step of contacting the RNA-guided nuclease with the cell comprises introducing into the cell a ribonucleoprotein (RNP) complex comprising the RNA-guided nuclease and at least one guide RNA (gRNA). In embodiment, the step of recombining the exogenous oligonucleotide donor template into the nucleic acid via homologous recombination comprises introducing the exogenous oligonucleotide donor template into the cell. In one embodiment, the step of introducing comprises electroporation of the cell in the presence of the RNP complex and/or the exogenous oligonucleotide donor template.

In one embodiment, the first strand of the exogenous oligonucleotide donor template comprises, from 5' to 3', the first donor homology arm, the priming site that is substantially identical to the second priming site, the cargo, the priming site that is substantially identical to the first priming site, and the second donor homology arm.

In one embodiment, the first strand of the exogenous oligonucleotide donor template further comprises a first stuffer and/or a second stuffer, wherein the first stuffer and the second stuffer each comprise a random or heterologous sequence having a GC content of approximately 40%; and wherein the exogenous oligonucleotide donor template comprises, from 5' to 3', i) the first donor homology arm, the first stuffer, the priming site that is substantially identical to the second priming site, and the second donor homology arm; or ii) the first donor homology arm, the cargo, the priming site that is substantially identical to the first priming site, the second stuffer, and the second donor homology arm.

In one embodiment, the first stuffer has a sequence having less than 50% sequence identity to any nucleic acid sequence within 500 base pairs of the cleavage site, and wherein the second stuffer has a sequence having less than 50% sequence identity to any nucleic acid sequence within 500 base pairs of the cleavage site. In one embodiment, the first stuffer has a sequence comprising at least 10 nucleotides of a sequence set forth in Table 2, and wherein the second stuffer has a sequence comprising at least 10 nucleotides of a sequence set forth in Table 2. In one embodiment, the first stuffer has a sequence that is not the same as the sequence of the second stuffer.

In one embodiment, the first strand of the exogenous oligonucleotide donor template comprises, from 5' to 3', the first donor homology arm, the first suffer, the priming site that is substantially identical to the second priming site, the cargo, the priming site that is substantially identical to the first priming site, the second stuffer, and the second donor homology arm.

In one embodiment, the altered nucleic acid comprises, from 5' to 3', the first priming site, the first donor homology arm, the priming site that is substantially identical to the second priming site, the cargo, the second donor homology arm, and the second priming site. In one embodiment, the altered nucleic acid comprises, from 5' to 3', the first priming site, the first donor homology arm, the cargo, the priming site that is substantially identical to the first priming site, the second donor homology arm, and the second priming site.

In one embodiment, the altered nucleic acid comprises, from 5' to 3', the first priming site, the first donor homology arm, the priming site that is substantially identical to the second priming site, the cargo, the priming site that is substantially identical to the first priming site, the second donor homology arm, and the second priming site.

In one embodiment, the altered nucleic acid comprises, from 5' to 3', the first priming site, the first donor homology arm, the first stuffer, the priming site that is substantially identical to the second priming site, the cargo, the priming site that is substantially identical to the first priming site, the second stuffer, the second donor homology arm, and the second priming site.

In one embodiment, when the altered nucleic acid comprises a non-targeted integration genome editing event at the cleavage site, amplifying the altered nucleic acid using the first primer and the second primer produces a first amplicon, wherein the first amplicon has a sequence that comprises an indel as compared to a sequence of the target nucleic acid.

In one embodiment, when the altered nucleic acid comprises a targeted integration genome editing event at the cleavage site, amplifying the altered nucleic acid using the first primer and the second primer produces a first amplicon, wherein the first amplicon has a sequence that is substantially identical to a sequence consisting of either i) the first donor homology arm and the first stuffer, or ii) the second stuffer and the second donor homology arm.

In one embodiment, when the altered nucleic acid comprises a targeted integration genome editing event at the cleavage site, amplifying the altered nucleic acid using the first primer and the second primer produces a first amplicon and a second amplicon, wherein the first amplicon has a sequence that is substantially identical to a sequence consisting of the first donor homology arm and the first stuffer, and wherein the second amplicon has a sequence that is substantially identical to a sequence consisting of the second stuffer and the second homology arm.

In one embodiment, the cell is a population of cells, and when the altered nucleic acid in all cells within the population of cells comprises a non-targeted integration genome editing event at the cleavage site, amplifying the altered nucleic acid using the first primer and the second primer produces a first amplicon, wherein the first amplicon has a sequence that comprises an indel as compared to a sequence of the target nucleic acid.

In one embodiment, the cell is a population of cells, and when the altered nucleic acid in all the cells within the population of cells comprises a targeted integration genome editing event at the cleavage site, amplifying the altered nucleic acid using the first primer and the second primer produces a first amplicon, wherein the first amplicon has a sequence that is substantially identical to a sequence consisting of either i) the first donor homology arm and the first stuffer, or ii) the second stuffer and the second donor homology arm.

In one embodiment, the cell is a population of cells, and when the altered nucleic acid in a first cell within the population of cells comprises a non-targeted integration genome editing event at the cleavage site, amplifying the altered nucleic acid using the first primer and the second primer produces a first amplicon, wherein the first amplicon has a sequence that comprises an indel as compared to a sequence of the target nucleic acid; and when the altered nucleic acid in a second cell within the population of cells comprises a targeted integration genome editing event at the cleavage site, amplifying the altered nucleic acid in the second cell using the first primer and the second primer produces a second amplicon, wherein the second amplicon has a sequence that is substantially identical to a sequence consisting of either i) the first donor homology arm and the first stuffer, or ii) the second stuffer and the second donor homology arm.

In one embodiment, the cell is a population of cells, when the altered nucleic acid in a first cell within the population of cells comprises a non-targeted integration genome editing event at the cleavage site, amplifying the altered nucleic acid using the first primer and the second primer produces a first amplicon, wherein the first amplicon has a sequence that comprises an indel as compared to a sequence of the target nucleic acid; and when the altered nucleic acid in a second cell within the population of cells comprises a targeted integration genome editing event at the cleavage site, amplifying the altered nucleic acid in the second cell using the first primer and the second primer produces a second amplicon and a third amplicon, wherein the second amplicon has a sequence that is substantially identical to a sequence consisting of the first donor homology arm and the first stuffer, and wherein the third amplicon has a sequence that is substantially identical to a sequence consisting of the second stuffer and the second donor homology arm.

In one embodiment, frequency of targeted integration versus non-targeted integration in the population of cells can be measured by: i) the ratio of ((an average of the second amplicon plus the third amplicon)/(first amplicon plus (the average of the second amplicon plus the third amplicon)); ii) the ratio of (the second amplicon/(the first amplicon plus the second amplicon)); or iii) the ratio of (the third amplicon/(the first amplicon plus the third amplicon)).

In one aspect, disclosed herein is a cell, or a population of cells, altered by a method disclosed herein.

In another aspect, disclosed herein is a cell, or a population of cells, comprising a donor template disclosed herein.

In one aspect, the invention provides a cell comprising an altered nucleic acid, wherein a first strand of the altered nucleic acid comprises, from 5' to 3', a first priming site, a first donor homology arm, a cargo, a priming site that is substantially identical to the first priming site, a second donor homology arm, and a second priming site. In another aspect, the invention provides a cell comprising an altered nucleic acid, wherein a first strand of the altered nucleic acid comprises, from 5' to 3', a first priming site, a first donor homology arm, a priming site that is substantially identical to a second priming site, a cargo, a second donor homology arm, and the second priming site. In another aspect, the invention provides a cell comprising an altered nucleic acid, wherein a first strand of the altered nucleic acid comprises, from 5' to 3', a first priming site, a first donor homology arm, a priming site that is substantially identical to a second priming site, a cargo, a priming site that is substantially identical to the first priming site, a second donor homology arm, and the second priming site.

In one embodiment, the altered nucleic acid further comprises a first stuffer and/or a second stuffer. For example, the altered nucleic acid can comprise, from 5' to 3', (i) a first priming site, a first donor homology arm, a cargo, a priming site that is substantially identical to the first priming site, a first stuffer, a second donor homology arm, and a second priming site; (ii) a first priming site, a first donor homology arm, a first stuffer, a priming site that is substantially identical to a second priming site, a cargo, a second donor homology arm, and the second priming site; or (iii) a first priming site, a first donor homology arm, a first stuffer, a priming site that is substantially identical to a second priming site, a cargo, a priming site that is substantially identical to the first priming site, a second stuffer, a second donor homology arm, and the second priming site.

In an exemplary embodiment, the cell is derived from a cell comprising an unaltered nucleic acid, wherein a first strand of the unaltered nucleic acid comprises, from 5' to 3', the first priming site, a first homology arm substantially identical to the first donor homology arm, a cleavage site, a second homology arm substantially identical to the second donor homology arm, and the second priming site.

In one embodiment, the cell is a eukaryotic cell. In one embodiment, the eukaryotic cell is a human cell. In one embodiment, the cell is a peripheral blood cell. In one embodiment, the cell is a CD34+ cell. In one embodiment, the eukaryotic cell is an immune cell, an epithelial cell, an endothelial cell, a neuron, or a stem cell. In one embodiment, the eukaryotic cell is an immune cell. In an exemplary embodiment, the immune cell is a T cell, a B cell, a natural killer cell, a monocyte, a macrophage cell, or a dendritic cell. In another embodiment, the eukaryotic cell is a stem cell. In exemplary embodiments, the stem cell is an embryonic stem cell, an induced pluripotent stem cell (iPSC), or a hematopoietic stem/progenitor cell (HSPC).

In one embodiment, the cell is from a subject suffering from a disease or disorder. In one embodiment, the disease or disorder is a blood disease, an immune disease, a neurological disease, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or a pain disorder.

In another embodiment, the cell is a plant cell. In one embodiment, the plant is monocotyledonous, for example, maize, wheat, rice, corn, or *Setaria*. In another embodiment, the plant is dicotyledonous, for example, potato, soybean, tomato, tobacco, or *Arabidopsis*.

BRIEF DESCRIPTION OF THE DRAWINGS

The accompanying drawings are intended to provide illustrative, and schematic rather than comprehensive, examples of certain aspects and embodiments of the present disclosure. The drawings are not intended to be limiting or binding to any particular theory or model, and are not necessarily to scale. Without limiting the foregoing, nucleic acids and polypeptides may be depicted as linear sequences, or as schematic two- or three-dimensional structures; these depictions are intended to be illustrative rather than limiting or binding to any particular model or theory regarding their structure.

FIG. 2A depicts exemplary DNA donor templates comprising either long homology arms ("500 bp HA"), short homology arms ("177 bp HA"), or no homology arms ("No HA") used for targeted integration experiments in primary CD4+ T-cells using wild-type *S. pyogenes* ribonucleoprotein targeted to the HBB locus. FIGS. 2B, 2C and 2D depict that DNA donor templates with either long homology arms and short homology arms have similar targeted integration efficiency in CD4+ T-cells as measured using GFP expression and ddPCR (5' and 3' junctions). FIG. 2B shows the GFP fluorescence of CD4+ T-cells contacted with wild-type *S. pyogenes* ribonucleoprotein and one of the DNA donor templates depicted in FIG. 2A at different multiplicities of infection (MOI). FIGS. 2C and 2D shows the integration frequency in CD4+ T cells contacted with wild-type *S. pyogenes* ribonucleoprotein (RNP) and one of the DNA donor templates depicted in FIG. 2A at different multiplicities of infection (MOI), as determined using ddPCR amplifying the 5' integration junction (FIG. 2C) or the 3' integration junction (FIG. 2D).

FIG. 5C depicts the percentage of GFP+ cells detected on day 7 in the live CD34+ cell fraction which shows that the integrated transgene is expressed from a genomic context.

FIG. 9A depicts the design of an exemplary donor template for testing targeted integration efficiency at the TRAC locus. The donor contains a 5' homology arm, a stuffer sequence, a first priming site, a P2A self-cleaving peptide, a GFP sequence, a polyA sequence, a second priming site, a stuffer sequence, and a 3' homology arm. FIG. 9B depicts the targeted integration efficiency of donor templates configured as shown in FIG. 9A at three cut sites in the TRAC locus (TRAC1, TRAC4, and TRAC13).

Targeted integration was assessed by flow cytometry measuring GFP expression, ddPCR, and sequencing of amplification products generated from the integrated priming sites. FIG. 9C provides a complete picture of all on-target editing events at the TRAC1, TRAC4, and TRAC13 cut sites. Sequencing of amplification products generated as depicted in FIG. 1A allows for the accurate quantification of insertions, deletions, and targeted integration events.

FIG. 10A depicts the design of exemplary donor templates for testing targeted integration efficiency at the TRAC locus, with and without the use of stuffer sequences. The top donor template depicted in FIG. 10A contains a 5' homology arm, a stuffer sequence, a first priming site, a P2A self-cleaving peptide, a GFP sequence, a polyA sequence, a second priming site, a stuffer sequence, and a 3' homology arm. The bottom donor template depicted in FIG. 10A contains a 5' homology arm, a first priming site, a P2A self-cleaving peptide, a GFP sequence, a polyA sequence, a second priming site, and a 3' homology arm. FIG. 10B depicts the targeted integration efficiency of donor templates configured as in FIG. 10A at three cut sites in the TRAC locus (TRAC1, TRAC4, and TRAC13). Targeted integration was assessed by flow cytometry measuring GFP expression, UDITAS™, and sequencing of amplification products generated from the integrated priming sites.

DETAILED DESCRIPTION

Definitions and Abbreviations

Figure 1A:
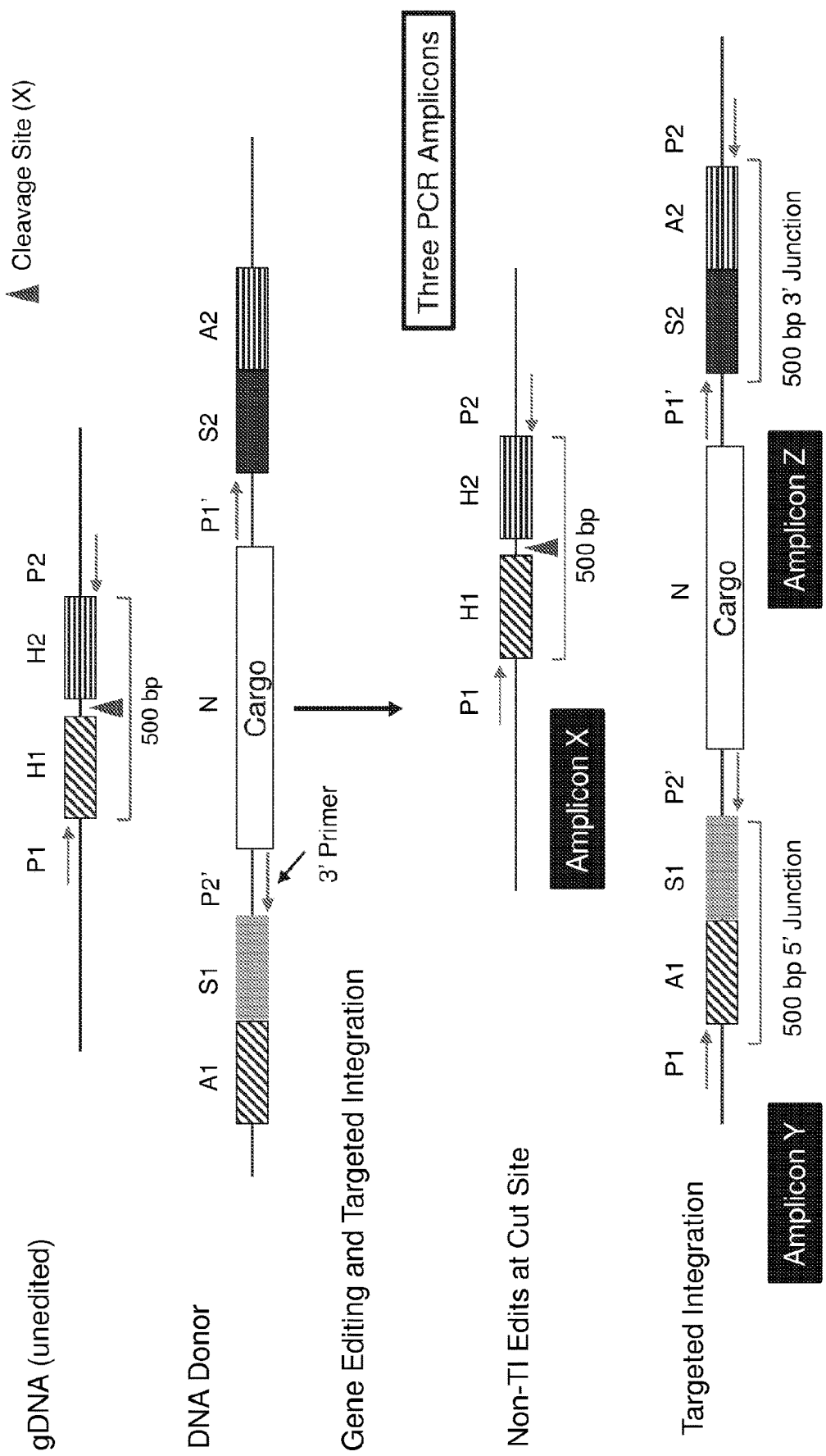
FIG. 1A is a schematic representation of an unedited genomic DNA targeting site, an exemplary DNA donor template for targeted integration, potential insertion outcomes (i.e., non-targeted integration at the cleavage site or targeted integration at the cleavage site) and three potential PCR amplicons resulting from use of a primer pair targeting the P1 priming site and the P2 primer site (Amplicon X), a primer pair targeting the P1 primer site and the P2' priming site (Amplicon Y), or a primer pair targeting the P1' primer site and the P2 primer site (Amplicon Z). The depicted exemplary DNA donor template contains integrated primer sites (P1' and P2') and stuffer sequences (S1 and S2). A1/A2: donor homology arms, S1/S2: donor stuffer sequences, P1/P2: genomic primer sites, P1'/P2': integrated primer sites, H1/H2: genomic homology arms, N: cargo, X: cleavage site.

Unless otherwise specified, each of the following terms has the meaning associated with it in this section.

The indefinite articles "a" and "an" refer to at least one of the associated noun, and are used interchangeably with the terms "at least one" and "one or more." For example, "a module" means at least one module, or one or more modules.

The conjunctions "or" and "and/or" are used interchangeably as non-exclusive disjunctions.

"Alt-HDR," "alternative homology-directed repair," or "alternative HDR" are used interchangeably to refer to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Alt-HDR is also distinguished by the involvement of a single-stranded or nicked homologous nucleic acid template, whereas canonical HDR generally involves a double-stranded homologous template.

Unless indicated otherwise, the term "HDR" as used herein encompasses both canonical HDR and alt-HDR.

As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

The term "approximately equal" is used herein to describe parameters that are identical, nearly identical, and/or functionally identical. The term may be used, for example, in reference to the comparative lengths of portions of a donor template, e.g., the length of A1+S1 of a donor template are "approximately equal" to A2+S2 of the same donor template, such that upon integration of a portion of the donor template into a target nucleic acid, and subsequent amplification using PCR primers, amplicons of similar size having similar amplification efficiencies may be produced, thereby facilitating the quantitation of editing outcomes based on the relative quantities of these amplicons using a single PCR reaction.

The term "approximately equal," as used herein in reference to the length of two nucleic acid sequences, may also refer to nucleic acid sequences that differ in length, e.g., by less that 25 nucleotides or base pairs. For example, a first sequence is approximately equal in length to a second sequence when the first and second sequences differ in length by less than 25, less than 24, less than 23, less than 22, less than 21, less than 20, less than 19, less than 18, less than 17, less than 16, less than 15, less than 14, less than 13, less than 12, less than 11, less than 10, less than 9, less than 8, less than 7, less than 6, less than 5, less than 4, less than 3, less than 2, or less than 1 nucleotides or base pairs in length. The term "equal" as used herein in reference to the length of two nucleic acid sequences refers to nucleic acid sequences that are the same number of nucleotides or base pairs in length. For example, a first sequence is equal in length to a second sequence when they both consist of, e.g., 25 nucleotides or 25 base pairs.

"Canonical HDR," "canonical homology-directed repair" or "cHDR" refer to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single-stranded portion of DNA. In a normal cell, cHDR typically involves a series of steps such as recognition of the break, stabilization of the break, resection, stabilization of single-stranded DNA, formation of a DNA crossover intermediate, resolution of the crossover intermediate, and ligation. The process requires RAD51 and BRCA2, and the homologous nucleic acid is typically double-stranded.

As used herein, the term "cleavage event" refers to a break in a nucleic acid molecule. A cleavage event may be a single-strand cleavage event, or a double-strand cleavage event. A single-strand cleavage event may result in a 5' overhang or a 3' overhang. A double-stranded cleavage event may result in blunt ends, two 5' overhangs, or two 3' overhangs.

The term "cleavage site," as used herein in reference to a site on a target nucleic acid sequence, refers to a target position between two nucleotide residues of the target nucleic acid where a double-stranded break occurs, or alternatively, to a target position within a span of several nucleotide residues of the target nucleic acid wherein two single stranded breaks occur, as mediated by a RNA-guided nuclease-dependent process. A cleavage site may be the target position for, e.g., a blunt double stranded break. Alternatively, a cleavage site may be a target site within a span of several nucleotide residues of the target nucleic acid for, e.g., two single strand breaks or nicks which form a double strand break and which are separated by, e.g., about 10 base pairs. The double strand break(s) or the closer of the two single strand nicks in a pair will ideally be within 0-500 bp of a target position (e.g., no more than 450, 400, 350, 300, 250, 200, 150, 100, 50, or 25 bp from the target position). When dual nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20, or 10 bp).

"Domain" is used to describe a segment of a protein or nucleic acid. Unless otherwise indicated, a domain is not required to have any specific functional property.

As used herein, the term "endogenous" gene, "endogenous" nucleic acid, or "endogenous" homologous region refers to a native gene, nucleic acid, or region of a gene, which is in its natural location in the genome, e.g., chromosome or plasmid, of a cell. In contrast, the term "exogenous" gene or "exogenous" nucleic acid refers to a gene, nucleic acid, or region of a gene which is not native within a cell, but which is introduced into the cell during the methods of the invention. An exogenous gene or exogenous nucleic acid may be homologous to, or identical to, an endogenous gene or an endogenous nucleic acid.

"Gene conversion" refers to the alteration of a DNA sequence by incorporation of an endogenous homologous sequence (e.g., a homologous sequence within a gene array). "Gene correction" refers to the alteration of a DNA sequence by incorporation of an exogenous homologous sequence, such as an exogenous single- or double-stranded donor template DNA. Gene conversion and gene correction are products of the repair of DNA double-strand breaks by HDR pathways such as those described below.

The terms "homology" or "identity," as used interchangeably herein, refer to sequence identity between two amino acid sequences or two nucleic acid sequences, with identity being a more strict comparison. The phrases "percent identity or homology" and "% identity or homology" refer to the percentage of sequence identity found in a comparison of two or more amino acid sequences or nucleic acid sequences. Two or more sequences can be anywhere from 0-100% identical, or any value there between. Identity can be determined by comparing a position in each sequence that can be aligned for purposes of comparison to a reference sequence. When a position in the compared sequence is occupied by the same nucleotide base or amino acid, then the molecules are identical at that position. A degree of identity of amino acid sequences is a function of the number of identical amino acids at positions shared by the amino acid sequences. A degree of identity between nucleic acid sequences is a function of the number of identical or matching nucleotides at positions shared by the nucleic acid sequences. A degree of homology of amino acid sequences is a function of the number of amino acids at positions shared by the polypeptide sequences.

Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

An "indel" is an insertion and/or deletion in a nucleic acid sequence. An indel may be the product of the repair of a DNA double strand break, such as a double strand break formed by a genome editing system of the present disclosure. An indel is most commonly formed when a break is repaired by an "error prone" repair pathway such as the NHEJ pathway described below.

Indels, gene conversion, gene correction, and other genome editing outcomes are typically assessed by sequencing (most commonly by "next-gen" or "sequencing-by-synthesis" methods, though Sanger sequencing may still be used) and are quantified by the relative frequency of numerical changes (e.g., ±1, ±2 or more bases) at a site of interest among all sequencing reads. DNA samples for sequencing may be prepared by a variety of methods known in the art, and may involve the amplification of sites of interest by polymerase chain reaction (PCR), the capture of DNA ends generated by double strand breaks, as in the GUIDEseq process described in Tsai et al. (Nat. Biotechnol. 34(5): 483 (2016), incorporated by reference herein) or by other means well known in the art. Genome editing outcomes may also be assessed by in situ hybridization methods such as the FiberComb™ system commercialized by Genomic Vision (Bagneux, France), and by any other suitable methods known in the art.

The term "isolated gene" or "isolated nucleic acid" is a gene or nucleic acid that by virtue of its origin or source of derivation is not associated with naturally associated components that accompany it in its native state; is substantially free of other proteins from the same species; is expressed by a cell from a different species; or does not occur in nature. Thus, a nucleic acid that is chemically synthesized or synthesized in a cellular system different from the cell from which it naturally originates will be "isolated" from its naturally associated components. A nucleic acid may also be rendered substantially free of naturally associated components by isolation, using protein purification techniques well known in the art.

Conventional IUPAC notation is used in nucleotide sequences presented herein, as shown in Table 1, below (see also Cornish-Bowden A, Nucleic Acids Res. 1985 May 10; 13 (9):3021-30, incorporated by reference herein). It should be noted, however, that "T" denotes "Thymine or Uracil" in those instances where a sequence may be encoded by either DNA or RNA, for example in gRNA targeting domains.

TABLE 1

IUPAC nucleic acid notation

| Character | Base |
|---|---|
| A | Adenine |
| T | Thymine or Uracil |
| G | Guanine |
| C | Cytosine |
| U | Uracil |
| K | G or T/U |
| M | A or C |
| R | A or G |
| Y | C or T/U |
| S | C or G |
| W | A or T/U |
| B | C, G or T/U |
| V | A, C or G |
| H | A, C or T/U |
| D | A, G or T/U |
| N | A, C, G or T/U |

A "kit" refers to any collection of two or more components that together constitute a functional unit that can be employed for a specific purpose. By way of illustration (and not limitation), one kit according to this disclosure can include a guide RNA complexed or able to complex with an RNA-guided nuclease, and accompanied by (e.g., suspended in, or suspendable in) a pharmaceutically acceptable carrier. The kit can be used to introduce the complex into, for example, a cell or a subject, for the purpose of causing a desired genomic alteration in such cell or subject. The components of a kit can be packaged together, or they may be separately packaged. Kits according to this disclosure also optionally include directions for use (DFU) that describe the use of the kit e.g., according to a method of this disclosure. The DFU can be physically packaged with the kit, or it can be made available to a user of the kit, for instance by electronic means.

"Non-homologous end joining" or "NHEJ" refers to ligation mediated repair and/or non-template mediated repair including canonical NHEJ (cNHEJ) and alternative NHEJ (altNHEJ), which in turn includes microhomology-mediated end joining (MMEJ), single-strand annealing (SSA), and synthesis-dependent microhomology-mediated end joining (SD-MMEJ).

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. These terms refer to compositions that can be chimeric mixtures or derivatives or modified versions thereof, single-stranded or double-stranded. These terms also refer to compositions that can be modified at the base moiety, sugar moiety, or phosphate backbone, for example, to improve stability of the molecule, its hybridization parameters, etc. A nucleotide sequence typically carries genetic information, including, but not limited to, the information used by cellular machinery to make proteins and enzymes. These terms include double- or single-stranded genomic DNA, RNA, any synthetic and genetically manipulated polynucleotide, and both sense and antisense polynucleotides. These terms also include nucleic acids containing modified bases.

"Prevent," "preventing," and "prevention" refer to the prevention of a disease in a mammal, e.g., in a human, including (a) avoiding or precluding the disease; (b) affecting the predisposition toward the disease; or (c) preventing or delaying the onset of at least one symptom of the disease.

The terms "protein," "peptide" and "polypeptide" are used interchangeably to refer to a sequential chain of amino acids linked together via peptide bonds. The terms include individual proteins, groups or complexes of proteins that associate together, as well as fragments or portions, variants, derivatives and analogs of such proteins. Peptide sequences are presented herein using conventional notation, beginning with the amino or N-terminus on the left, and proceeding to the carboxyl or C-terminus on the right. Standard one-letter or three-letter abbreviations can be used.

"Replacement" or "replaced," when used with reference to a modification of a molecule (e.g., a nucleic acid or protein), does not require a process limitation but merely indicates that the replacement entity is present.

"Subject" means a human or non-human animal. A human subject can be any age (e.g., an infant, child, young adult, or adult), and may suffer from a disease, or may be in need of alteration of a gene. Alternatively, the subject may be an animal, which term includes, but is not limited to, mammals, birds, fish, reptiles, amphibians, and more particularly non-human primates, rodents (such as mice, rats, hamsters, etc.), rabbits, guinea pigs, dogs, cats, and so on. In certain embodiments of this disclosure, the subject is livestock, e.g., a cow, a horse, a sheep, or a goat. In certain embodiments, the subject is poultry.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The term "substantially identical" as used herein in reference to two nucleic acid sequences refers, in some embodiments, to a sequence identity of at least 95% between across an at least 20 nucleotide contiguous stretch of each of the two nucleic acid sequences. For example, a first nucleic acid sequence is substantially identical to a second nucleic acid sequence when the first nucleic acid sequence has at least 95%, at least 96%, at least 97%, at least 98%, at least 99%, or 100% identity across an at least 20 nucleotide contiguous stretch of the second nucleic acid sequence. In some embodiments, a first nucleic acid sequence is substantially identical to a second nucleic acid sequence when the first nucleic acid sequence has at least 95% identity across the entire length of the second nucleic acid sequence. In some embodiments, the term "substantially identical" is used in the context of priming sites, and refers to the ability of the priming sites to support priming with the same PCR primer during an amplification reaction. In some embodiments, the term "substantially identical" is used to describe the relationship between the homology arm of a donor template and the homology arm of a target nucleic acid, and refers to a nucleic acid identity between the homology arms that allows for the efficient recombination of the donor template at the target nucleic acid with tolerance for some degree of polymorphism, e.g., to eliminate PAM or protospacer sequences in the recombined locus.

"Target position" as used herein, refers to a site on a target nucleic acid (e.g., the chromosome) that is modified by a RNA-guided nuclease-dependent process. In an embodiment, a target position can be a site between two nucleotides, e.g., adjacent nucleotides, on the target nucleic acid. The target position may comprise one or more nucleotides that are altered, e.g., corrected, by a template nucleic acid. In an embodiment, the target position is within a "target sequence" (e.g., the sequence to which the gRNA binds). In an embodiment, a target position is upstream or downstream of a target sequence (e.g., the sequence to which the gRNA binds).

"Treat," "treating," and "treatment" mean the treatment of a disease in a subject (e.g., a human subject), including one or more of inhibiting the disease, i.e., arresting or preventing its development or progression; relieving the disease, i.e., causing regression of the disease state; relieving one or more symptoms of the disease; and curing the disease.

Overview

The present disclosure concerns genome editing systems comprising a donor template specifically designed to allow for the quantitative assessment of gene editing events that occur upon resolution of a cleavage event at a cleavage site of a target nucleic acid in a cell. The donor template of the genome editing systems described herein is a DNA oligodeoxynucleotides (ODNs), which can be single-stranded (ssODNs) or double-stranded (dsODNs), and can be used to facilitate HDR-based repair of a double-stranded break. The donor template is particularly useful for introducing alterations into a target DNA sequence, inserting a new sequence into the target sequence, or replacing the target sequence altogether. The disclosure provides donor templates comprising a cargo, one or two homology arms and one or more priming sites. The priming site(s) of the donor templates are spatially arranged in such a manner such that the frequency of integration of a portion of the donor template into the target nucleic acid may be readily assessed and quantified.

Figure 1B:
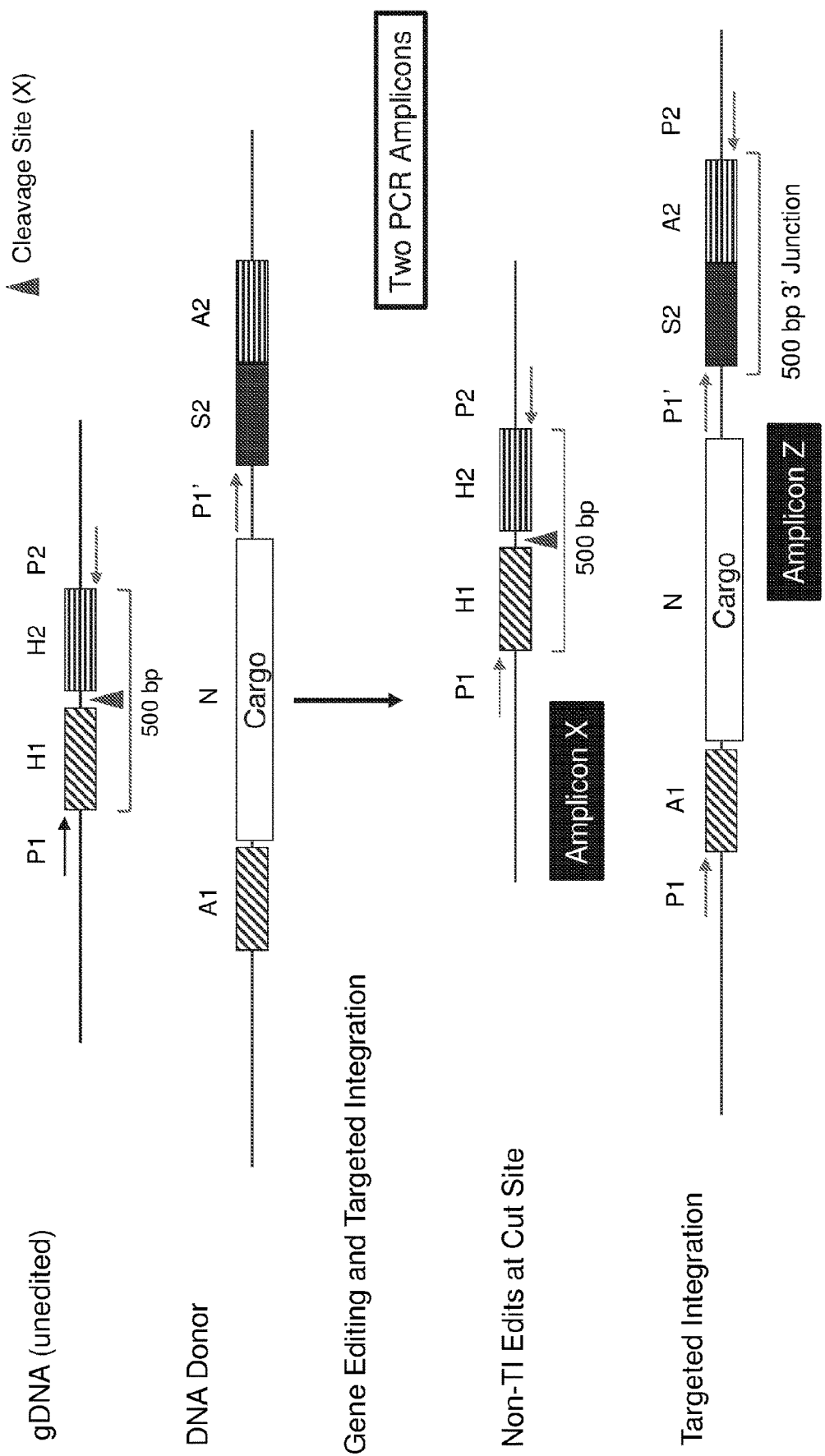
FIG. 1B is a schematic representation of an unedited genomic DNA targeting site, an exemplary DNA donor template for targeted integration, potential insertion outcomes (i.e., non-targeted integration at the cleavage site or targeted integration at the cleavage site), and two potential PCR amplicons resulting from the use of a primer pair targeting the P1 primer site and the P2 primer site (Amplicon X), or a primer pair targeting the P1' primer site and the P2 primer site (Amplicon Y). The exemplary DNA donor template contains an integrated primer site (P1') and a stuffer sequence (S2). A1/A2: donor homology arms, S1/S2: donor stuffer sequences, P1/P2: genomic primer sites, P1': integrated primer sites, H1/H2: genomic homology arms, N: cargo, X: cleavage site.
Figure 1C:
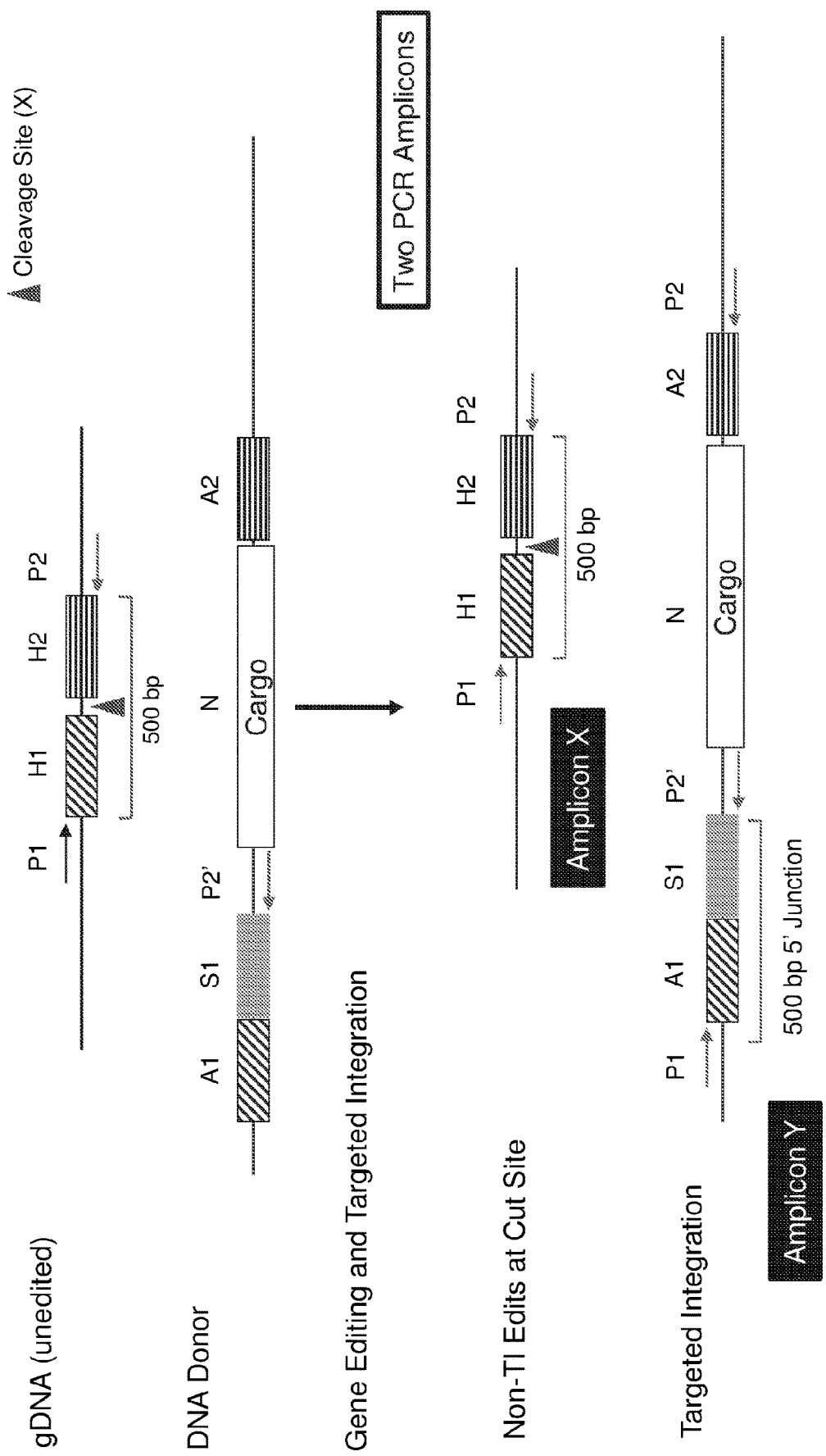
FIG. 1C is a schematic representation of an unedited genomic DNA targeting site, an exemplary DNA donor template for targeted integration, potential insertion outcomes (i.e., non-targeted integration at the cleavage site or targeted integration at the cleavage site), and two potential PCR amplicons resulting from the use of a primer pair targeting the P1 primer site and the P2 primer site (Amplicon X), or a primer pair targeting the P1 primer site and the P2' primer site (Amplicon Y). The exemplary DNA donor template contains an integrated primer site (P2') and a stuffer sequence (S1). A1/A2: donor homology arms, S1/S2: donor stuffer sequences, P1/P2: genomic primer sites, P2': integrated primer sites, H1/H2: genomic homology arms, N: cargo, X: cleavage site.

FIGS. 1A, 1B and 1C are diagrams illustrating representative donor templates and the potential targeted integration outcomes resulting from the use of these donor templates. The use of the exemplary donor templates described herein results in the targeted integration of at least one priming site in the targeted nucleic acid which may be used to generate an amplicon that can be sequenced to determine the frequency of targeted integration of a cargo (e.g., a transgene) to the targeted nucleic acid in the target cell.

For example, FIG. 1A illustrates an exemplary donor template comprising from 5' to 3', a first homology arm (A1), a first stuffer sequence (S1), a second priming site (P2'), a cargo, a first priming site, a second stuffer sequence, and a second homology arm. The first homology arm (A1) of the donor template is substantially identical to the first homology arm of the target nucleic acid, while the second homology arm (A2) of the donor template is substantially identical to the second homology arm of the target nucleic acid. The donor template is designed such that the second priming site (P2') is substantially identical to the first priming site of the target nucleic acid (P1), and such that the first priming site (P1') is substantially identical to the second priming site of the target nucleic acid (P2). Upon resolution of a target nucleic acid cleavage event using a nuclease described herein, a single primer pair set can be used to amplify the nucleic acid sequence surrounding the cleavage site of the target nucleic acid (i.e., the nucleic acid present between P1 and P2, between P1 and P2', and between P1' and P2). Advantageously, the size of the amplicons (illustrated as Amplicon X, Y and Z) resulting from resolution of a cleavage event without targeted integration or with targeted integration is approximately the same. The amplicons may then be assessed—for instance by sequencing, or hybridization to a probe sequence—to determine the frequency of targeted integration.

Alternatively, FIGS. 1B and 1C illustrate exemplary donor templates comprising a single priming site that is located either 3' (FIG. 1B) or 5' (FIG. 1C) from the cargo nucleic acid sequence. Again, upon resolution of a target nucleic acid cleavage event using a nuclease described herein, these exemplary donor templates are designed such that a single primer pair set can be used to amplify the nucleic acid sequence surrounding the cleavage site of the target nucleic acid, such that two amplicons of approximately the same size are obtained. When the priming site of the donor template is located 3' from the cargo nucleic acid, amplicons corresponding to a non-targeted integration event, or an amplicon corresponding to the 5' junction of the targeted integration site may be amplified. When the priming site of the donor template is located 5' from the cargo nucleic acid, amplicons corresponding to a non-targeted integration event, or an amplicon corresponding to the 3' junction of the targeted integration site may be amplified. These amplicons may be sequenced to determine the frequency of targeted integration.

Donor Template

Donor templates according to this disclosure may be implemented in any suitable way, including without limitation single stranded or double stranded DNA, linear or circular, naked or comprised within a vector, and/or associated, covalently or non-covalently (e.g., by direct hybridization or splint hybridization) with a guide RNA. In some embodiments, the donor template is a ssODN. Where a linear ssODN is used, it can be configured to (i) anneal to a nicked strand of the target nucleic acid, (ii) anneal to the intact strand of the target nucleic acid, (iii) anneal to the plus strand of the target nucleic acid, and/or (iv) anneal to the minus strand of the target nucleic acid. An ssODN may have any suitable length, e.g., about, or no more than 150-200 nucleotides (e.g., 150, 160, 170, 180, 190, or 200 nucleotides). In other embodiments, the donor template is a dsODN. In one embodiment, the donor template comprises a first strand. In another embodiment, a donor template comprises a first strand and a second strand. In some embodiments, a donor template is an exogenous oligonucleotide, e.g., an oligonucleotide that is not naturally present in a cell.

It should be noted that a donor template can also be comprised within a nucleic acid vector, such as a viral genome or circular double-stranded DNA, e.g., a plasmid. In some embodiments, the donor template can be a doggy-bone shaped DNA (see, e.g., U.S. Pat. No. 9,499,847). Nucleic acid vectors comprising donor templates can include other coding or non-coding elements. For example, a donor template nucleic acid can be delivered as part of a viral genome (e.g., in an AAV or lentiviral genome) that includes certain genomic backbone elements (e.g., inverted terminal repeats, in the case of an AAV genome) and optionally includes additional sequences coding for a gRNA and/or an RNA-guided nuclease. In certain embodiments, the donor template can be adjacent to, or flanked by, target sites recognized by one or more gRNAs, to facilitate the formation of free DSBs on one or both ends of the donor template that can participate in repair of corresponding SSBs or DSBs formed in cellular DNA using the same gRNAs. Exemplary nucleic acid vectors suitable for use as donor templates are described in Cotta-Ramusino.

A. Homology Arms

Whether single-stranded or double-stranded, donor templates generally include one or more regions that are homologous to regions of DNA, e.g., a target nucleic acid, within or near (e.g., flanking or adjoining) a target sequence to be cleaved, e.g., the cleavage site. These homologous regions are referred to here as "homology arms," and are illustrated schematically below:

[5' homology arm]-[replacement sequence]-[3' homology arm].

The homology arms of the donor templates described herein may be of any suitable length, provided such length is sufficient to allow efficient resolution of a cleavage site on a targeted nucleic acid by a DNA repair process requiring a donor template. In some embodiments, where amplification by, e.g., PCR, of the homology arm is desired, the homology arm is of a length such that the amplification may be performed. In some embodiments, where sequencing of the homology arm is desired, the homology arm is of a length such that the sequencing may be performed. In some embodiments, where quantitative assessment of amplicons is desired, the homology arms are of such a length such that a similar number of amplifications of each amplicon is achieved, e.g., by having similar G/C content, amplification temperatures, etc. In some embodiments, the homology arm is double-stranded. In some embodiments, the double stranded homology arm is single stranded.

In some embodiments, the 5' homology arm is between 50 to 250 nucleotides in length. In some embodiments, the 5' homology arm is between 50-2000 nucleotides in length. In some embodiments, the 5' homology arm is between 50-1500 nucleotides in length. In some embodiments, the 5' homology arm is between 50-1000 nucleotides in length. In some embodiments, the 5' homology arm is between 50-500 nucleotides in length. In some embodiments, the 5' homology arm is between 150 to 250 nucleotides in length. In some embodiments, the 5' homology arm is 2000 nucleotides or less in length. In some embodiments, the 5' homology arm is 1500 nucleotides or less in length. In some embodiments, the 5' homology arm is 1000 nucleotides or less in length. In some embodiments, the 5' homology arm is 700 nucleotides or less in length. In some embodiments, the 5' homology arm is 650 nucleotides or less in length. In some embodiments, the 5' homology arm is 600 nucleotides or less in length. In some embodiments, the 5' homology arm is 550 nucleotides or less in length. In some embodiments, the 5' homology arm is 500 nucleotides or less in length. In some embodiments, the 5' homology arm is 400 nucleotides or less in length. In some embodiments, the 5' homology arm is 300 nucleotides or less in length. In some embodiments, the 5' homology arm is 250 nucleotides or less in length. In some embodiments, the 5' homology arm is 200 nucleotides or less in length. In some embodiments, the 5' homology arm is 150 nucleotides or less in length. In some embodiments, the 5' homology arm is less than 100 nucleotides in length. In some embodiments, the 5' homology arm is 50 nucleotides in length or less. In some embodiments, the 5' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In some embodiments, the 5' homology arm is at least 20 nucleotides in length. In some embodiments, the 5' homology arm is at least 40 nucleotides in length. In some embodiments, the 5' homology arm is at least 50 nucleotides in length. In some embodiments, the 5' homology arm is at least 70 nucleotides in length. In some embodiments, the 5' homology arm is at least 100 nucleotides in length. In some embodiments, the 5' homology arm is at least 200 nucleotides in length. In some embodiments, the 5' homology arm is at least 300 nucleotides in length. In some embodiments, the 5' homology arm is at least 400 nucleotides in length. In some embodiments, the 5' homology arm is at least 500 nucleotides in length. In some embodiments, the 5' homology arm is at least 600 nucleotides in length. In some embodiments, the 5' homology arm is at least 700 nucleotides in length. In some embodiments, the 5' homology arm is at least 1000 nucleotides in length. In some embodiments, the 5' homology arm is at least 1500 nucleotides in length. In some embodiments, the 5' homology arm is at least 2000 nucleotides in length. In some embodiments, the 5' homology arm is about 20 nucleotides in length. In some embodiments, the 5' homology arm is about 40 nucleotides in length. In some embodiments, the 5' homology arm is 250 nucleotides in length or less. In some embodiments, the 5' homology arm is about 100 nucleotides in length. In some embodiments, the 5' homology arm is about 200 nucleotides in length.

In some embodiments, the 3' homology arm is between 50 to 250 nucleotides in length. In some embodiments, the 3' homology arm is between 50-2000 nucleotides in length. In some embodiments, the 3' homology arm is between 50-1500 nucleotides in length. In some embodiments, the 3' homology arm is between 50-1000 nucleotides in length. In some embodiments, the 3' homology arm is between 50-500 nucleotides in length. In some embodiments, the 3' homology arm is between 150 to 250 nucleotides in length. In some embodiments, the 3' homology arm is 2000 nucleotides or less in length. In some embodiments, the 3' homology arm is 1500 nucleotides or less in length. In some embodiments, the 3' homology arm is 1000 nucleotides or less in length. In some embodiments, the 3' homology arm is 700 nucleotides or less in length. In some embodiments, the 3' homology arm is 650 nucleotides or less in length. In some embodiments, the 3' homology arm is 600 nucleotides or less in length. In some embodiments, the 3' homology arm is 550 nucleotides or less in length. In some embodiments, the 3' homology arm is 500 nucleotides or less in length. In some embodiments, the 3' homology arm is 400 nucleotides or less in length. In some embodiments, the 3' homology arm is 300 nucleotides or less in length. In some embodiments, the 3' homology arm is 200 nucleotides in length or less. In some embodiments, the 3' homology arm is 150 nucleotides in length or less. In some embodiments, the 3' homology arm is 100 nucleotides in length or less. In some embodiments, the 3' homology arm is 50 nucleotides in length or less. In some embodiments, the 3' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In some embodiments, the 3' homology arm is at least 20 nucleotides in length. In some embodiments, the 3' homology arm is at least 40 nucleotides in length. In some embodiments, the 3' homology arm is at least 50 nucleotides in length. In some embodiments, the 3' homology arm is at least 70 nucleotides in length. In some embodiments, the 3' homology arm is at least 100 nucleotides in length. In some embodiments, the 3' homology arm is at least 200 nucleotides in length. In some embodiments, the 3' homology arm is at least 300 nucleotides in length. In some embodiments, the 3' homology arm is at least 400 nucleotides in length. In some embodiments, the 3' homology arm is at least 500 nucleotides in length. In some embodiments, the 3' homology arm is at least 600 nucleotides in length. In some embodiments, the 3' homology arm is at least 700 nucleotides in length. In some embodiments, the 3' homology arm is at least 1000 nucleotides in length. In some embodiments, the 3' homology arm is at least 1500 nucleotides in length. In some embodiments, the 3' homology arm is at least 2000 nucleotides in length. In some embodiments, the 3' homology arm is about 20 nucleotides in length. In some embodiments, the 3' homology arm is about 40 nucleotides in length. In some embodiments, the 3' homology arm is 250 nucleotides in length or less. In some embodiments, the 3' homology arm is about 100 nucleotides in length. In some embodiments, the 3' homology arm is about 200 nucleotides in length.

In some embodiments, the 5' homology arm is between 50 to 250 basepairs in length. In some embodiments, the 5' homology arm is between 50-2000 basepairs in length. In some embodiments, the 5' homology arm is between 50-1500 basepairs in length. In some embodiments, the 5' homology arm is between 50-1000 basepairs in length. In some embodiments, the 5' homology arm is between 50-500 basepairs in length. In some embodiments, the 5' homology arm is between 150 basepairs to 250 basepairs in length. In some embodiments, the 5' homology arm is 2000 basepairs or less in length. In some embodiments, the 5' homology arm is 1500 basepairs or less in length. In some embodiments, the 5' homology arm is 1000 basepairs or less in length. In some embodiments, the 5' homology arm is 700 basepairs or less in length. In some embodiments, the 5' homology arm is 650 basepairs or less in length. In some embodiments, the 5' homology arm is 600 basepairs or less in length. In some embodiments, the 5' homology arm is 550 basepairs or less in length. In some embodiments, the 5' homology arm is 500 basepairs or less in length. In some embodiments, the 5' homology arm is 400 basepairs or less in length. In some embodiments, the 5' homology arm is 300 basepairs or less in length. In some embodiments, the 5' homology arm is 250 basepairs or less in length. In some embodiments, the 5' homology arm is 200 basepairs or less in length. In some embodiments, the 5' homology arm is 150 basepairs or less in length. In some embodiments, the 5' homology arm is less than 100 basepairs in length. In some embodiments, the 5' homology arm is 50 basepairs in length or less. In some embodiments, the 5' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 basepairs in length. In some embodiments, the 5' homology arm is at least 20 basepairs in length. In some embodiments, the 5' homology arm is at least 40 basepairs in length. In some embodiments, the 5' homology arm is at least 50 basepairs in length. In some embodiments, the 5' homology arm is at least 70 basepairs in length. In some embodiments, the 5' homology arm is at least 100 basepairs in length. In some embodiments, the 5' homology arm is at least 200 basepairs in length. In some embodiments, the 5' homology arm is at least 300 basepairs in length. In some embodiments, the 5' homology arm is at least 400 basepairs in length. In some embodiments, the 5' homology arm is at least 500 basepairs in length. In some embodiments, the 5' homology arm is at least 600 basepairs in length. In some embodiments, the 5' homology arm is at least 700 basepairs in length. In some embodiments, the 5' homology arm is at least 1000 basepairs in length. In some embodiments, the 5' homology arm is at least 1500 basepairs in length. In some embodiments, the 5' homology arm is at least 2000 basepairs in length. In some embodiments, the 5' homology arm is about 20 basepairs in length. In some embodiments, the 5' homology arm is about 40 basepairs in length. In some embodiments, the 5' homology arm is 250 basepairs in length or less. In some embodiments, the 5' homology arm is about 100 basepairs in length. In some embodiments, the 5' homology arm is about 200 basepairs in length.

In some embodiments, the 3' homology arm is between 50 to 250 basepairs in length. In some embodiments, the 3' homology arm is between 50-2000 basepairs in length. In some embodiments, the 3' homology arm is between 50-1500 basepairs in length. In some embodiments, the 3' homology arm is between 50-1000 basepairs in length. In some embodiments, the 3' homology arm is between 50-500 basepairs in length. In some embodiments, the 3' homology arm is between 150 basepairs to 250 basepairs in length. In some embodiments, the 3' homology arm is 2000 basepairs or less in length. In some embodiments, the 3' homology arm is 1500 basepairs or less in length. In some embodiments, the 3' homology arm is 1000 basepairs or less in length. In some embodiments, the 3' homology arm is 700 basepairs or less in length. In some embodiments, the 3' homology arm is 650 basepairs or less in length. In some embodiments, the 3' homology arm is 600 basepairs or less in length. In some embodiments, the 3' homology arm is 550 basepairs or less in length. In some embodiments, the 3' homology arm is 500 basepairs or less in length. In some embodiments, the 3' homology arm is 400 basepairs or less in length. In some embodiments, the 3' homology arm is 300 basepairs or less in length. In some embodiments, the 3' homology arm is 250 basepairs or less in length. In some embodiments, the 3' homology arm is 200 basepairs or less in length. In some embodiments, the 3' homology arm is 150 basepairs or less in length. In some embodiments, the 3' homology arm is less than 100 basepairs in length. In some embodiments, the 3' homology arm is 50 basepairs in length or less. In some embodiments, the 3' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 basepairs in length. In some embodiments, the 3' homology arm is at least 20 basepairs in length. In some embodiments, the 3' homology arm is at least 40 basepairs in length. In some embodiments, the 3' homology arm is at least 50 basepairs in length. In some embodiments, the 3' homology arm is at least 70 basepairs in length. In some embodiments, the 3' homology arm is at least 100 basepairs in length. In some embodiments, the 3' homology arm is at least 200 basepairs in length. In some embodiments, the 3' homology arm is at least 300 basepairs in length. In some embodiments, the 3' homology arm is at least 400 basepairs in length. In some embodiments, the 3' homology arm is at least 500 basepairs in length. In some embodiments, the 3' homology arm is at least 600 basepairs in length. In some embodiments, the 3' homology arm is at least 700 basepairs in length. In some embodiments, the 3' homology arm is at least 1000 basepairs in length. In some embodiments, the 3' homology arm is at least 1500 basepairs in length. In some embodiments, the 3' homology arm is at least 2000 basepairs in length. In some embodiments, the 3' homology arm is about 20 basepairs in length. In some embodiments, the 3' homology arm is about 40 basepairs in length. In some embodiments, the 3' homology arm is 250 basepairs in length or less. In some embodiments, the 3' homology arm is about 100 basepairs in length. In some embodiments, the 3' homology arm is about 200 basepairs in length. In some embodiments, the 3' homology arm is 250 basepairs in length or less. In some embodiments, the 3' homology arm is 200 basepairs in length or less. In some embodiments, the 3' homology arm is 150 basepairs in length or less. In some embodiments, the 3' homology arm is 100 basepairs in length or less. In some embodiments, the 3' homology arm is 50 basepairs in length or less. In some embodiments, the 3' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 basepairs in length. In some embodiments, the 3' homology arm is 40 basepairs in length.

The 5' and 3' homology arms can be of the same length or can differ in length. In some embodiments, the 5' and 3' homology arms are amplified to allow for the quantitative assessment of gene editing events, such as targeted integration, at a target nucleic acid. In some embodiments, the quantitative assessment of the gene editing events may rely on the amplification of both the 5' junction and 3' junction at the site of targeted integration by amplifying the whole or a part of the homology arm using a single pair of PCR primers in a single amplification reaction. Accordingly, although the length of the 5' and 3' homology arms may differ, the length of each homology arm should be capable of amplification (e.g., using PCR), as desired. Moreover, when amplification of both the 5' and the difference in lengths of the 5' and 3' homology arms in a single PCR reaction is desired, the length difference between the 5' and 3' homology arms should allow for PCR amplification using a single pair of PCR primers.

In some embodiments, the length of the 5' and 3' homology arms does not differ by more than 75 nucleotides. Thus, in some embodiments, when the 5' and 3' homology arms differ in length, the length difference between the homology arms is less than 70, 60, 50, 40, 30, 20, 10, 9, 8, 7, 6, 5, 4, 3, 2, 1 nucleotides or base pairs. In some embodiments, the 5' and 3' homology arms differ in length by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 nucleotides. In some embodiments, the length difference between the 5' and 3' homology arms is less than 70, 60, 50, 40, 30, 20, 10, 9, 8, 7, 6, 5, 4, 3, 2, 1 base pairs. In some embodiments, the 5' and 3' homology arms differ in length by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 base pairs.

Donor templates of the disclosure are designed to facilitate homologous recombination with a target nucleic acid having a cleavage site, wherein the target nucleic acid comprises, from 5' to 3',

P1-H1-X-H2-P2, wherein P1 is a first priming site; H1 is a first homology arm; X is the cleavage site; H2 is a second homology arm; and P2 is a second priming site; and wherein the donor template comprises, from 5' to 3', A1-P2'-N-A2, or A1-N-P1'-A2, wherein A1 is a homology arm that is substantially identical to H1; P2' is a priming site that is substantially identical to P2; N is a cargo; P1' is a priming site that is substantially identical to P1; and A2 is a homology arm that is substantially identical to H2. In one embodiment, the target nucleic acid is double stranded. In one embodiment, the target nucleic acid comprises a first strand and a second strand. In another embodiment, the target nucleic acid is single stranded. In one embodiment, the target nucleic acid comprises a first strand.

In some embodiments, the donor template comprises, from 5' to 3',

A1-P2'-N-A2.

In some embodiments, the donor template comprises, from 5' to 3',

A1-P2'-N-P1'-A2.

In some embodiments, the target nucleic acid comprises, from 5' to 3',

P1-H1-X-H2-P2, wherein P1 is a first priming site; H1 is a first homology arm; X is the cleavage site; H2 is a second homology arm; and P2 is a second priming site; and the first strand of the donor template comprises, from 5' to 3', A1-P2'-N-A2, or A1-N-P1'-A2, wherein A1 is a homology arm that is substantially identical to H1; P2' is a priming site that is substantially identical to P2; N is a cargo; P1' is a priming site that is substantially identical to P1; and A2 is a homology arm that is substantially identical to H2.

In some embodiments, a first strand of the donor template comprises, from 5' to 3',

A1-P2'-N-P1'-A2.

In some embodiments, a first strand of the donor template comprises, from 5' to 3',

A1-N-P1'-A2.

In some embodiments, A1 is 700 basepairs or less in length. In some embodiments, A1 is 650 basepairs or less in length. In some embodiments, A1 is 600 basepairs or less in length. In some embodiments, A1 is 550 basepairs or less in length. In some embodiments, A1 is 500 basepairs or less in length. In some embodiments, A1 is 400 basepairs or less in length. In some embodiments, A1 is 300 basepairs or less in length. In some embodiments, A1 is less than 250 base pairs in length. In some embodiments, A1 is less than 200 base pairs in length. In some embodiments, A1 is less than 150 base pairs in length. In some embodiments, A1 is less than 100 base pairs in length. In some embodiments, A1 is less than 50 base pairs in length. In some embodiments, the A1 is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 base pairs in length. In some embodiments, A1 is 40 base pairs in length. In some embodiments, A1 is 30 base pairs in length. In some embodiments, A1 is 20 base pairs in length.

In some embodiments, A2 is 700 basepairs or less in length. In some embodiments, A2 is 650 basepairs or less in length. In some embodiments, A2 is 600 basepairs or less in length. In some embodiments, A2 is 550 basepairs or less in length. In some embodiments, A2 is 500 basepairs or less in length. In some embodiments, A2 is 400 basepairs or less in length. In some embodiments, A2 is 300 basepairs or less in length. In some embodiments, A2 is less than 250 base pairs in length. In some embodiments, A2 is less than 200 base pairs in length. In some embodiments, A2 is less than 150 base pairs in length. In some embodiments, A2 is less than 100 base pairs in length. In some embodiments, A2 is less than 50 base pairs in length. In some embodiments, A2 is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 base pairs in length. In some embodiments, A2 is 40 base pairs in length. In some embodiments, A2 is 30 base pairs in length. In some embodiments, A2 is 20 base pairs in length.

In some embodiments, A1 is 700 nucleotides or less in length. In some embodiments, A1 is 650 nucleotides or less in length. In some embodiments, A1 is 600 nucleotides or less in length. In some embodiments, A1 is 550 nucleotides or less in length. In some embodiments, A1 is 500 nucleotides or less in length. In some embodiments, A1 is 400 nucleotides or less in length. In some embodiments, A1 is 300 nucleotides or less in length. In some embodiments, A1 is less than 250 nucleotides in length. In some embodiments, A1 is less than 200 nucleotides in length. In some embodiments, A1 is less than 150 nucleotides in length. In some embodiments, A1 is less than 100 nucleotides in length. In some embodiments, A1 is less than 50 nucleotides in length. In some embodiments, the A1 is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In some embodiments, A1 is at least 40 nucleotides in length. In some embodiments, A1 is at least 30 nucleotides in length. In some embodiments, A1 is at least 20 nucleotides in length.

In some embodiments, A2 is 700 nucleotides or less in length. In some embodiments, A2 is 650 basepairs or less in length. In some embodiments, A2 is 600 nucleotides or less in length. In some embodiments, A2 is 550 nucleotides or less in length. In some embodiments, A2 is 500 nucleotides or less in length. In some embodiments, A2 is 400 nucleotides or less in length. In some embodiments, A2 is 300 nucleotides or less in length. In some embodiments, A2 is less than 250 nucleotides in length. In some embodiments, A2 is less than 200 nucleotides in length. In some embodiments, A2 is less than 150 nucleotides in length. In some embodiments, A2 is less than 100 nucleotides in length. In some embodiments, A2 is less than 50 nucleotides in length. In some embodiments, A2 is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In some embodiments, A2 is at least 40 nucleotides in length. In some embodiments, A2 is at least 30 nucleotides in length. In some embodiments, A2 is at least 20 nucleotides in length.

In some embodiments, the nucleic acid sequence of A1 is substantially identical to the nucleic acid sequence of H1. In some embodiments A1 has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides from H1. In some embodiments A1 has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs from H1.

In some embodiments, the nucleic acid sequence of A2 is substantially identical to the nucleic acid sequence of H2. In some embodiments A2 has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides from H2. In some embodiments A2 has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs from H2.

Whatever format is used, a donor template can be designed to avoid undesirable sequences. In certain embodiments, one or both homology arms can be shortened to avoid overlap with certain sequence repeat elements, e.g., Alu repeats, LINE elements, etc.

B. Priming Sites

The donor templates described herein comprise at least one priming site having a sequence that is substantially similar to, or identical to, the sequence of a priming site within the target nucleic acid, but is in a different spatial order or orientation relative to a homology sequence/homology arm in the donor template. When the donor template is homologously recombined with the target nucleic acid, the priming site(s) are advantageously incorporated into the target nucleic acid, thereby allowing for the amplification of a portion of the altered nucleic acid sequence that results from the recombination event. In some embodiments, the donor template comprises at least one priming site. In some embodiments, the donor template comprises a first and a second priming site. In some embodiments, the donor template comprises three or more priming sites.

In some embodiments, the donor template comprises a priming site P1', that is substantially similar or identical to a priming site, P1, within the target nucleic acid, wherein upon integration of the donor template at the target nucleic acid, P1', is incorporated downstream from P1. In some embodiments, the donor template comprises a first priming site, P1', and a second priming site, P2'; wherein, P1', is substantially similar or identical to a first priming site, P1, within the target nucleic acid; wherein P2' is substantially similar or identical to second priming site, P2, within the target nucleic acid; and wherein P1 and P2 are not substantially similar or identical. In some embodiments, the donor template comprises a first priming site, P1', and a second priming site, P2'; wherein, P1', is substantially similar or identical to a first priming site, P1, within the target nucleic acid; wherein P2' is substantially similar or identical to second priming site, P2, within the target nucleic acid; wherein P2 is located downstream from P1 on the target nucleic acid; wherein P1 and P2 are not substantially similar or identical; and wherein upon integration of the donor template at the target nucleic acid, P1', is incorporated downstream from P1. P2' is incorporated upstream from P2, and P2' is incorporated upstream from P1.

In some embodiments, the target nucleic acid comprises a first priming site (P1) and a second priming site (P2). The first priming site in the target nucleic acid may be within the first homology arm. Alternatively, the first priming site in the target nucleic acid may be 5' and adjacent to the first homology arm. The second priming site in the target nucleic acid may be within the second homology arm. Alternatively, the second priming site in the target nucleic acid may be 3' and adjacent to the second homology arm.

The donor template may comprise a cargo sequence, a first priming site (P1'), and a second priming site (P2'), wherein P2' is located 5' from the cargo sequence, wherein P1' is located 3' from the cargo sequence (i.e., A1-P2'-N-P1'-A2), wherein P1' is substantially identical to P1, and wherein P2' is substantially identical to P2. In this scenario, a primer pair comprising an oligonucleotide targeting P1' and P1 and an oligonucleotide comprising P2' and P2 may be used to amplify the targeted locus, thereby generation three amplicons of similar size which may be sequenced to determine whether targeted integration has occurred. The first amplicon, Amplicon X, results from the amplification of the nucleic acid sequence between P1 and P2 as a result of non-targeted integration at the target nucleic acid. The second amplicon, Amplicon Y, results from the amplification of the nucleic acid sequence between P1 and P2' following a targeted integration event at the target nucleic acid, thereby amplifying the 5' junction. The third amplicon, Amplicon Z, results from the amplification of the nucleic acid sequence between P1' and P2 following a targeted integration event at the target nucleic acid, thereby amplifying the 3' junction. In other embodiments, P1' may be identical to P1. Moreover, P2' may be identical to P2.

In some embodiments, the donor template comprises a cargo and a priming site (P1'), wherein P1' is located 3' from the cargo nucleic acid sequence (i.e., A1-N-P1'-A2) and P1' is substantially identical to P1. In this scenario, a primer pair comprising an oligonucleotide targeting P1' and P1 and an oligonucleotide targeting P2 may be used to amplify the targeted locus, thereby generation two amplicons of similar size which may be sequenced to determine whether targeted integration has occurred. The first amplicon, Amplicon X, results from the amplification of the nucleic acid sequence between P1 and P2 as a result of non-targeted integration at the target nucleic acid. The second amplicon, Amplicon Z, results from the amplification of the nucleic acid sequence between P1' and P2 following a targeted integration event at the target nucleic acid, thereby amplifying the 3' junction. In other embodiments, P1' may be identical to P1. Moreover, P2' may be identical to P2.

In some embodiments, the target nucleic acid comprises a first priming site (P1) and a second priming site (P2), and the donor template comprises a priming site P2', wherein P2' is located 5' from the cargo nucleic acid sequence (i.e., A1-P2'-N-A2), and P2' is substantially identical to P2. In this scenario, a primer pair comprising an oligonucleotide targeting P2' and P2 and an oligonucleotide targeting P1 may be used to amplify the targeted locus, thereby generation two amplicons of similar size which may be sequenced to determine whether targeted integration has occurred. The first amplicon, Amplicon X, results from the amplification of the nucleic acid sequence between P1 and P2 as a result of non-targeted integration at the target nucleic acid. The second amplicon, Amplicon Y, results from the amplification of the nucleic acid sequence between P1 and P2' following a targeted integration event at the target nucleic acid, thereby amplifying the 5' junction. In other embodiments, P1' may be identical to P1. Moreover, P2' may be identical to P2.

A priming site of the donor template may be of any length that allows for the quantitative assessment of gene editing events at a target nucleic acid by amplification and/or sequencing of a portion of the target nucleic acid. For example, in some embodiments, the target nucleic acid comprises a first priming site (P1) and the donor template comprises a priming site (P1'). In these embodiments, the length of the P1' priming site and the P1 primer site is such that a single primer can specifically anneal to both priming sites (for example, in some embodiments, the length of the P1' priming site and the P1 priming site is such that both have the same or very similar GC content).

In some embodiments, the priming site of the donor template is 60 nucleotides in length. In some embodiments, the priming site of the donor template is less than 60 nucleotides in length. In some embodiments, the priming site of the donor template is less than 50 nucleotides in length. In some embodiments, the priming site of the donor template is less than 40 nucleotides in length. In some embodiments, the priming site of the donor template is less than 30 nucleotides in length. In some embodiments the priming site of the donor template is 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 nucleotides in length. In some embodiments, the priming site of the donor template is 60 base pairs in length. In some embodiments, the priming site of the donor template is less than 60 base pairs in length. In some embodiments, the priming site of the donor template is less than 50 base pairs in length. In some embodiments, the priming site of the donor template is less than 40 base pairs in length. In some embodiments, the priming site of the donor template is less than 30 base pairs in length. In some embodiments the priming site of the donor template is 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 base pairs in length.

In some embodiments, upon resolution of the cleavage event at the cleavage site in the target nucleic acid and homologous recombination of the donor template with the target nucleic acid, the distance between the first priming site of the target nucleic acid (P1) and now integrated P2' priming site is 600 base pairs or less. In some embodiments, upon resolution of the cleavage event and homologous recombination of the donor template with the target nucleic acid, the distance between the first priming site of the target nucleic acid (P1) and now integrated P2' priming site is 550, 500, 450, 400, 350, 300, 250, 200, 150 base pairs or less. In some embodiments, upon resolution of the cleavage event at the target nucleic acid and homologous recombination of the donor template with the target nucleic acid, the distance between the first priming site of the target nucleic acid (P1) and now integrated P2' priming site is 600 nucleotides or less. In some embodiments, upon resolution of the cleavage event at the target nucleic acid and homologous recombination of the donor template with the target nucleic acid, the distance between the first priming site of the target nucleic acid (P1) and now integrated P2' priming site is 550, 500, 450, 400, 350, 300, 250, 200, 150 nucleotides or less.

In some embodiments, the target nucleic acid comprises a second priming site (P2) and the donor template comprises a priming site (P2') that is substantially identical to P2. In some embodiments, upon resolution of the cleavage event at the target nucleic acid and homologous recombination of the donor template with the target nucleic acid, the distance between the second priming site of the target nucleic acid (P2) and now integrated P1' priming site is 600 base pairs or less. In some embodiments, upon resolution of the cleavage event at the target nucleic acid and homologous recombination of the donor template with the target nucleic acid, the distance between the second priming site of the target nucleic acid (P2) and now integrated P1' priming site is 550, 500, 450, 400, 350, 300, 250, 200, 150 base pairs or less. In some embodiments, upon resolution of the cleavage event at the target nucleic acid and homologous recombination of the donor template with the target nucleic acid, the distance between the second priming site of the target nucleic acid (P2) and now integrated P1' priming site is 600 nucleotides or less. In some embodiments, upon resolution of the cleavage event at the target nucleic acid and homologous recombination of the donor template with the target nucleic acid, the distance between the second priming site of the target nucleic acid (P2) and now integrated P1' priming site is 550, 500, 450, 400, 350, 300, 250, 200, 150 nucleotides or less.

In some embodiments, the nucleic acid sequence of P2' is comprised within the nucleic acid sequence of A1. In some embodiments, the nucleic acid sequence of P2' is immediately adjacent to the nucleic acid sequence of A1. In some embodiments, the nucleic acid sequence of P2' is immediately adjacent to the nucleic acid sequence of N. In some embodiments, the nucleic acid sequence of P2' is comprised within the nucleic acid sequence of N.

In some embodiments, the nucleic acid sequence of P1' is comprised within the nucleic acid sequence of A2. In some embodiments, the nucleic acid sequence of P1' is immediately adjacent to the nucleic acid sequence of A2. In some embodiments, the nucleic acid sequence of P1' is immediately adjacent to the nucleic acid sequence of N. In some embodiments, the nucleic acid sequence of P1' is comprised within the nucleic acid sequence of N.

In some embodiments, the nucleic acid sequence of P2' is comprised within the nucleic acid sequence of S1. In some embodiments, the nucleic acid sequence of P2' is immediately adjacent to the nucleic acid sequence of S1. In some embodiments, the nucleic acid sequence of P1' is comprised within the nucleic acid sequence of S2. In some embodiments, the nucleic acid sequence of P1' is immediately adjacent to the nucleic acid sequence of S2.

C. Cargo

The donor template of the gene editing systems described herein comprises a cargo (N). The cargo may be of any length necessary in order to achieve the desired outcome. For example, a cargo sequence may be less than 2500 base pairs or less than 2500 nucleotides in length. In other embodiments, the cargo sequence may be 12 kb or less. In other embodiments, the cargo sequence may be 10 kb or less. In other embodiments, the cargo sequence may be 7 kb or less. In other embodiments, the cargo sequence may be 5 kb or less. In other embodiments, the cargo sequence may be 4 kb or less. In other embodiments, the cargo sequence may be 3 kb or less. In other embodiments, the cargo sequence may be 2 kb or less. In other embodiments, the cargo sequence may be 1 kb or less. In one embodiment, the cargo can be between about 5-10 kb in length. In another embodiment, the cargo can be between about 1-5 kb in length. In another embodiment, the cargo can be between about 0-1 kb in length. For example, in exemplary embodiments, the cargo can be about 1000, 900, 800, 700, 600, 500, 400, 300, 200, or 100 base pairs or nucleotides in length. In other exemplary embodiments, the cargo can be about 100, 90, 80, 70, 60, 50, 40, 30, 20, 10, 9, 8, 7, 6, 5, 4, 3, 2, 1 or 0 base pairs or nucleotides in length. Those of skill in the art will readily ascertain that when the donor template is delivered using a delivery vehicle (e.g., a viral delivery vehicle such as an adeno-associated virus (AAV), adenovirus, lentivirus, integration-deficient lentivirus (IDLV), or herpes simplex virus (HSV) delivery vehicle) with size limitations, the size of the donor template, including cargo, should not exceed the size limitation of the delivery system.

In some embodiments, the cargo comprises a replacement sequence. In some embodiments, the cargo comprises an exon of a gene sequence. In some embodiments, the cargo comprises an intron of a gene sequence. In some embodiments, the cargo comprises a cDNA sequence. In some embodiments, the cargo comprises a transcriptional regulatory element. In some embodiments, the cargo comprises a reverse complement of a replacement sequence, an exon of a gene sequence, an intron of a gene sequence, a cDNA sequence or a transcriptional regulatory element. In some embodiments, the cargo comprises a portion of a replacement sequence, an exon of a gene sequence, an intron of a gene sequence, a cDNA sequence or a transcriptional regulatory element. In some embodiments, the cargo is a transgene sequence. In some embodiments, the cargo introduces a deletion into a target nucleic acid. In some embodiments, the cargo comprises an exogenous sequence. In other embodiments, the cargo comprises an endogenous sequence.

Replacement sequences in donor templates have been described elsewhere, including in Cotta-Ramusino et al. A replacement sequence can be any suitable length (including zero nucleotides, where the desired repair outcome is a deletion), and typically includes one, two, three or more sequence modifications relative to the naturally-occurring sequence within a cell in which editing is desired. One common sequence modification involves the alteration of the naturally-occurring sequence to repair a mutation that is related to a disease or condition of which treatment is desired. Another common sequence modification involves the alteration of one or more sequences that are complementary to, or code for, the PAM sequence of the RNA-guided nuclease or the targeting domain of the gRNA(s) being used to generate an SSB or DSB, to reduce or eliminate repeated cleavage of the target site after the replacement sequence has been incorporated into the target site.

Specific cargo can be selected for a given application based on the cell type to be edited, the target nucleic acid, and the effect to be achieved.

For example, it may be desirable, in some embodiments, to "knock in" a desired gene sequence at a selected chromosomal locus in a target cell. In such cases, the cargo can comprise the desired gene sequence. In some embodiments, the gene sequence encodes a desired protein, e.g., an exogenous protein, an orthologous protein, or an endogenous protein, or a combination thereof.

In embodiments, the cargo can contain a wild-type sequence, or a sequence comprising one or more modifications with respect to a wild-type sequence. For example, in embodiments in which it is desirable to correct a mutation in a target gene in a cell, the cargo can be designed to restore the wild-type sequence to the target protein.

It may also be desirable, in other embodiments, to "knock out" a gene sequence at a selected chromosomal locus in the target cell. In such cases, the cargo can be designed to integrate at site that disrupts expression of the target gene sequence, for example, at a coding region of the target gene sequence, or at an expression control region for the target gene sequence, e.g., a promoter or enhancer of the target gene sequence. In other embodiments, the cargo can be designed to disrupt the target gene sequence. For example, in some embodiments, the cargo can introduce a deletion, insertion, stop codon, or frameshift mutation into the target nucleic acid.

In some embodiments, the donor is designed to delete all or a portion of the target nucleic acid sequence. In such embodiments, the homology arms of the donor can be designed to flank the desired deletion site. In some embodiments, the donor does not contain a cargo sequence between the homology arms, resulting in a deletion of the portion of the target nucleic acid positioned between the homology arms following targeted integration of the donor. In other embodiments, the donor contains a cargo sequence homologous to the target nucleic acid in which one or more nucleotides of the target nucleic acid sequence are absent from the cargo. Following targeted integration of the donor, the target nucleic acid will comprise a deletion at the residues absent from the cargo sequence. The size of the deletion can be selected based on the size of the target nucleic acid and the desired effect. In one embodiment, the donor is designed to introduce a deletion of 1-2000 nucleotides in the target nucleic acid following targeted integration. In other embodiments, the donor is designed to introduce a deletion of 1-1000 nucleotides in the target nucleic acid following targeted integration. In other embodiments, the donor is designed to introduce a deletion of 1-500 nucleotides in the target nucleic acid following targeted integration. In other embodiments, the donor is designed to introduce a deletion of 1-100 nucleotides in the target nucleic acid following targeted integration. In exemplary embodiments, the donor is designed to introduce a deletion of about 2000, 1500, 1000, 900, 800, 700, 600, 500, 400, 300, 200, 100, 90, 80, 70, 60, 50, 40, 30, 20, 15, 10, 9, 8, 7, 6, 5, 4, 3, 2, or 1 nucleotides in the target nucleic acid following targeted integration. In other embodiments, the donor is designed to introduce a deletion of more than 2000 nucleotides from the target nucleic acid following targeted integration, for example, a deletion of about 2000, 3000, 4000, 5000, 6000, 7000, 8000, 9000, 10,000 nucleotides or more.

In some embodiments, the cargo can comprise a promoter sequence. In other embodiments, the cargo is designed to integrate at a site that is under the control of a promoter endogenous to the target cell.

In one embodiment, a cargo encoding an exogenous or orthologous protein or polypeptide can be integrated into a chromosomal sequence encoding a protein, such that the chromosomal sequence is inactivated, but the exogenous sequence is expressed. In other embodiments, the cargo sequence may be integrated into a chromosomal sequence without altering expression of a chromosomal sequence. This can be achieved by integrating the cargo at a "safe harbor" locus, such as the Rosa26 locus, HPRT locus, or AAV locus.

In some embodiments, the cargo encodes a protein related to a disease or disorder. In one embodiment, the cargo can encode a wild-type form of a protein, or is designed to restore expression of a wild-type form of a protein, where the protein is deficient in a subject afflicted with a disease or disorder. In other embodiments, the cargo encodes a protein related to a disease or disorder, where the protein encoded by the cargo comprises at least one modification, such that the altered version of the protein protects against the development of the disease or disorder. In other embodiments, the cargo encodes a protein comprising at least one modification, such that the altered version of the protein causes or potentiates a disease or disorder.

In some embodiments, the cargo can be used to insert a gene from one species into the genome of a different species. For example, "humanized" animal models and/or "humanized" animal cells can be generated through targeted integration of human genes into the genome of a non-human animal species, e.g., mouse, rat, or non-human primate species. In one embodiment, such humanized animal models and animal cells contain an integrated sequence encoding one or more human proteins.

In another embodiment, the cargo encodes a protein that confers a benefit on plant species, including crops such as grains, fruits, or vegetables. For example, the cargo can encode a protein that allows plants to be cultivated at higher temperatures, have a prolonged shelf life following harvest, or conver disease resistance. In some embodiments, the cargo can encode a protein that confers resistance to diseases or pests (see, e.g., Jones et al. (1994) Science 266:789 (cloning of the tomato Cf-9 gene for resistance to Cladosporium fulvum); Martin et al. (1993) Science 262:1432; Mindrinos et al. (1994) Cell 78:1089 (RSP2 gene for resistance to Pseudomonas syringae); PCT International Patent Publication No. WO 96/30517 (resistance to soybean cyst nematode)). In other embodiments, the cargo can encode a protein that encodes resistance to an herbicide, as described in US2013/0326645A1, the entire contents of which are incorporated herein by reference. In another embodiment, the cargo encodes a protein that confers a value-added trait to a plant cell, for example and without limitation: modified fatty acid metabolism, decreased phytate content, and modified carbohydrate composition effected, e.g., by transforming plants with a gene encoding an enzyme that alters the branching pattern of starch (See, e.g., Shiroza et al. (1988) J. Bacteol. 170:810 (nucleotide sequence of Streptococcus mutant fructosyltransferase gene); Steinmetz et al. (1985) Mol. Gen. Genet. 20:220 (levansucrase gene); Pen et al. (1992) Bio/Technology 10:292 (α-amylase); Elliot et al. (1993) Plant Molec. Biol. 21:515 (nucleotide sequences of tomato invertase genes); Sogaard et al. (1993) J. Biol. Chem. 268:22480 (barley α-amylase gene); and Fisher et al. (1993) Plant Physiol. 102:1045 (maize endosperm starch branching enzyme II)). Other exemplary cargo useful for targeted integration in plant cells are described in US2013/0326645A1, the entire contents of which are incorporated herein by reference.

Additional cargo can be selected by the skilled artisan for a given application based on the cell type to be edited, the target nucleic acid, and the effect to be achieved.

D. Stuffers

In some embodiments, the donor template may optionally comprise one or more stuffer sequences. Generally, a stuffer sequence is a heterologous or random nucleic acid sequence that has been selected to (a) facilitate (or to not inhibit) the targeted integration of a donor template of the present disclosure into a target site and the subsequent amplification of an amplicon comprising the stuffer sequence according to certain methods of this disclosure, but (b) to avoid driving integration of the donor template into another site. The stuffer sequence may be positioned, for instance, between a homology arm A1 and a primer site P2' to adjust the size of the amplicon that will be generated when the donor template sequence is integrated into the target site. Such size adjustments may be employed, as one example, to balance the size of the amplicons produced by integrated and non-integrated target sites and, consequently to balance the efficiencies with which each amplicon is produced in a single PCR reaction; this in turn may facilitate the quantitative assessment of the rate of targeted integration based on the relative abundance of the two amplicons in a reaction mixture.

To facilitate targeted integration and amplification, the stuffer sequence may be selected to minimize the formation of secondary structures which may interfere with the resolution of the cleavage site by the DNA repair machinery (e.g., via homologous recombination) or which may interfere with amplification. In some embodiments, the donor template comprises, from 5' to 3', A1-S1-P2'-N-A2, or
A1-N-P1'-S2-A2;

wherein S1 is a first stuffer sequence and S2 is a second stuffer sequence.

In some embodiments, the donor template comprises from 5' to 3',

A1-S1-P2'-N-P1'-S2-A2, wherein S1 is a first stuffer sequence and S2 is a second stuffer sequence.

In some embodiments, the stuffer sequence comprises about the same guanine-cytosine content ("GC content") as the genome of the cell as a whole. In some embodiments, the stuffer sequences comprises about the same GC content as the targeted locus. For example, when the target cell is a human cell, the stuffer sequence comprises about 40% GC content. In some embodiments, a stuffer sequence may be designed by generating random nucleic acid sequence sequences comprising the desired GC content. For example, to generate a stuffer sequence comprising 40% GC content, nucleic acid sequences having the following distribution of nucleotides may be designed: A=30%, T=30%, G=20%, C=20%. Methods for determining the GC content of the genome or the GC content of the target locus are known to those of skill in the art. Thus, in some embodiments, the stuffer sequence comprises 20%, 25%, 30%, 35%, 40%, 45%, 50%, 55% 60%, 65%, 70%, or 75% GC content. Exemplary 2.0 kilobase stuffer sequences having 40±5% GC content are provided in Table 2.

TABLE 2

Exemplary 2.0 Kilobase Stuffer Sequences Having 40 ± 5% GC Content

| SEQ ID NO. | GC Content | Stuffer Sequence |
|---|---|---|
| 1 | 38.40% | TCAATAGCCCAGTCGGTTTTGTTAGATACATTTTATCGAATCTGTAAAGATATTTT ATAATAAGATAATATCAGCGCCTAGCTGCGGAATTCCACTCAGAGAATACCTCTCC TGAATATCAGCCTTAGTGGCGTTATACGATATTTCACACTCTCAAAATCCCGAGTC AGACTATACCCGCGCATGTTTAGTAAAGGTTGATTCTGAGATCTCGAGTCCAAAAA AGATACCCACTACTTTAAAGATTTGCATTCAGTTGTTCCATCGGCCTGGGTAGTAA AGGGGGTATGCTCGCTCCGAGTCGATGGAACTGTAAATGTTAGCCCTGATACGCGG AACATATCAGTAACAATCTTTACCTAATATGGAGTGGGATTAAGCTTCATAGAGGA TATGAAACGCTCGTAGTATGGCTTCCTACATAAGTAGAATTATTAGCAACTAAGAT ATTACCACTGCCCAATAAAAGAGATTCCACTTAGATTCATAGGTAGTCCCAACAAT CATGTCTGAATACTAAATTGATCAATTGGACTATGTCAAAATTATTTTGAAGAAGT AATCATCAACTTAGGCGCTTTTTAGTGTTAAGAGCGCGTTATTGCCAACCGGGCTA AACCTGTGTAACTCTTCAATATTGTATATAATTATAGGCAGAATAAGCTATGAGTG CATTATGAGATAAACATAGATTTTTGTCCACTCGAAATATTTGAATTTCTTGATCC TGGGCTAGTTCAGCCATAAGTTTTCACTAATAGTTAGGACTACCAATTACACTACA TTCAGTTGCTGAAATTCACATCACTGCCGCAATATTTATGAAGCTATTATTGCATT AAGACTTAGGAGATAAATACGAAGTTGATATATTTTTCAGAATCAGCGAAAAGACC CCCTATTGACATTACGAATTCGAGTTTAACGAGCACATAAATCAAACACTACGAGG TTACCAAGATTGTATCTTACATTAATGCTATCCAGCCAGCCGTCATGTTTAACTGG ATAGTCATAATTAATATCCAATGATCGTTTCACGTAGCTGCATATCGAGGAAGTTG TATAATTGAAAACCCACACATTAGAATGCATGGTGCATCGCTAGGGTTTATCTTAT CTTGCTCGTGCCAAGAGTGTAGAAAGCCACATATTGATACGGAAGCTGCCTAGGAG GTTGGTATATGTTGATTGTGCTCACCATCTCCCTTCCTAATCTCCTAGTGTTAAGT CCAATCAGTGGGCTGGCTCTGGTTAAAAGTAATATACACGCTAGATCTCTCTACTA TAATACAGGCTAAGCCTACGCGCTTTCAATGCACTGATTACCAACTTAGCTACGGC CAGCCCCATTTAATGAATTATCTCAGATGAATTCAGACATTATTCTCTACAAGGAC ACTTTAGAGTGTCCTGCGGAGGCATAATTATTATCTAAGATGGGGTAAGTCCGATG GAAGACACAGATACATCGGACTATTCCTATTAGCCGAGAGTCAACCGTTAGAACTC GGAAAAAGACATCGAAGCCGGTAACCTACGCACTATAAATTTCCGCAGAGACATAT GTAAAGTTTTATTAGAACTGGTATCTTGATTACGATTCTTAACTCTCATACGCCGG TCCGGAATTTGTGACTCGAGAAAATGTAATGACATGCTCCAATTGATTTCAAAATT AGATTTAAGGTCAGCGAACTATGTTTATTCAACCGTTTACAACGCTATTATGCGCG ATGGATGGGGCCTTGTATCTAGAAACCGAATAATAACATACCTGTTAAATGGCAAA CTTAGATTATTGCGATTAATTCTCACTTCAGAGGGTTATCGTGCCGAATTCCTGAC TTTGGAATAATAAAGTTGATATTGAGGTGCAATATCAACTACACTGGTTTAACCTT TAAACACATGGAGTCAAGTTTTCGCTATGCCAGCCGGTTATGCAGCTAGGATTAAT ATTAGAGCTCTTTTCTAATTCGTCCTAATAATCTCTTCAC |
| 2 | 38.90% | AAAACGTACTACGTCCACTAATATAGTGCTCAGGGCCTTTAAAGTTATGAACAGGA ATACGGCGATGACGATAGAGATGTACAACTCAGTGCGAACCCCAGTGTATGTACAA AAAGTTACTAATTCACTTTACTGTTTTGAGGATGTACCTGCCAAAAAGATTCAGAT TATCAAAGTCAGATCTTTATATGACGGAACGCGCAAAGGATCCTATTAGGATGCGC CTCAAAAAGCCATCTAAAAAGTTCATGTATTGAGCTTATTAGTAAAGGTATCAACA AAAATGATTCCACCTTATATAAATAAGCTTGATCCCATTAATTGAATAATAAAGAC CGAGTAATCACTTTTATGCATGTAACAAAAATCCCGTTTGCGGCTATGCTACAACG GTCATCCCATAGAATATTATCATCGTACAAGCCCAAGACCCGATGCTCAACATTAG AGCCAAATAACGTGCACACTCCTAATATGAGATGACTGCCGCTTTTAACACCAGAT CTGTTAGTTAGGCCACGCACTTCCAAGTTTATCTAGAGTGCATGTCTTTATATATG TTGGTCCCCTGTAATGACTTATAATATTTCCTTCGACTGTGTTGAACATCGTAAC AATAAAGACTAAAGCTCTGGGTATATAAGGTTGCAGTGGTACCTTATTAGGTCCAT TATCGCAGAATACTGCGGATGGACAATCTTGCCAATTTAATTGACTATCTATTAGT TTGCACAATATAACGATTCGTCTTGGACAAATTTGGCGAGTGAGCCCCTTACTCGC TCAAAATGTTACAATTGCCGAGCTCGGAGTTGAATGATTAGTTACATATTATAGAA CACAATGCAGATGTAGTTAGACAAGATGTGTTGATGAATGTCAAGTCTGACTGGAG TAAAGGAACAAGAGCACCCACCTACGTATATTGCGCATTTTAAATGTAGCCTCGAC TCTAACACGTGCGACGTGAGTCATAATTGTGCATGTTATTAGATCTATGGAATGTT GTTTTTTTAATTATCAAACGTACGTCAAACCGCCAAACTCCGTGTGCCATAGAGTA TACTCCTGAAGTTCGAAATTAGGCCATAAAGTCTTTCTTGCTGGTTGTGAAATGAA GGGGTGTTTCATAATTTAACTTTGACTGCTTCTGTTGGGACGACGTACCCGTTCGT TTGTTTGTCCTACTATTTAGTATCTTAAAACAGTCCATTTACCGTTAATGTTCTTA ACCCTTAAAGATACAAACTTAGCTCTGTAATCAACTTCAAGACGTCTTTGACAGAA CGTCTAAGACCCAGATCTGTGTTAGCCAACTCGTATTCAATTTCGTACCGGTGGAC TTCGGCCCCTCACACTGCCATTAGTTGATGCTGAACTTTGTATTTGCTGGGTAGGA TATATAACGATTTTGCAGATGTGTGCTAAGTATATTGTCTTAGTGACGGTCCAG CATATAAAACACCTACACAAGAAGGTTATTCTTAATGGTTGATTGAATATTATTAA ATTGTTGCTTTTACTTTTTCCTCCTACAAATTGTCATGAGCTCAAATTTGTTGACC TAAGGTATTAATATTGTATCCTACACGGATTGTGAACGGTAGGGTCGTAACAATCG TACTTTACGGCTTAAAAATTGTAAGCACCTTGCCAGGTAGATGAAAACTTAAAGGA TAGAAGTATAGTAACTCACATGCTTGCGGCAGCATCGTAGGGCAGAGGTGTGATCT TGGTGATTGAAATTAAGGGGTAGGATGATCGGCCGCATATATCGGCTACTAGGATT AGATAGATGCAACGCTTTACTTTAATCAAGTGACGTCCGTATAAGTAAGACATCTA ATGGCTGTATTTTTGTATACAAGTATAAGGAACCGGGGAGTCTTTATAGCGACGCG TAATTATATATTCCAAATCAGTTAAGTGGCGTCGGTTACGAAACTAAAGAGAGTGT TCAAGACGCAATGAAGAATCGTGAGCGTAATTGTTCGCGC |

TABLE 2-continued

Exemplary 2.0 Kilobase Stuffer Sequences Having 40 ± 5% GC Content

| SEQ ID NO. | GC Content | Stuffer Sequence |
|---|---|---|
| 3 | 39.30% | AACCCTCGTGTCCGGTAAAACACGCTTCGAATACAAAAGATTATATAGGTACGGAA GGCTGGGAATCTTTCTTCGATGGAACTGAGATTATATTCCACTGTAACCTTATTAT GACTATAGATTTCCAACATACGGATAGATTAATACCGACTGTAGATTCCATACTTG AACTATGAAGCCGTACGAGTACCCATACTATAACTAAGACTATGACACGTGTGAAT TCGTGTTTATCATAGTGCAAACTCTTGCTATTCCACATGGGAGTTTAGAACTCAGC TGTTCCTATACAATTAGCACTACAAACCCACTAATATGGATAGCATGATACCATCT GAGGAGGATTTGGTGTTACCATGTTGTAATCTAAGAAGTTTCACAAAATCAACGTT AGATAAACGGCAATATACGCGCACTAATAATGAACCCCAAGATATCAGTTGAAAAA TTTTCGATCTCCTCTTTAAATTAACAAATATTGCAGAGTAAGTACCGAATTGTGA CACAAGTGCCGTTTGCCCGTCTTTTTCACAGCCTATAAAGTTCAGATCTATATGGG CTCCCACTTAACCTTCAGATAGATAACAAGTTACTGGAAGTGATTCTATCATAATA CAATCAACTATAACACATCCAATGATATATCTCGAGAAAGTCGTAGTCTAGAGCTC CTTCTATTATCCGGTCTTACCTAAATAGTTATATTTAGTTGCCCATTTAAAATTGG ATAGGAGGAGGGGTGCTCATGATTTAAAAACCAACTGTGCATGCGGTTCTTTGATG TGGATCCACCTTGCAAAGCGCTAAAGATAAAAGTAGTCACTACAGGAATTCAACTT CCGTCGTTGTCAGCTGGCGCGGGAACCCATCTTGTGTAAAAAACTGTATAACCAGA CACGTGGACTCGACCGAGAAACAGTCAGAACCTGTCACAAGAAATAATCTTGATTA AAGGCTTTCACGGCAAACGGACCTCTTCCCTGCTGAAGTGTACGATTGAATATCCA CATCGAAGGTCAATTACCCTCATCTTTTACATGGTCATAAGACAATAATCTCCTAT TTGGATTAAAATCCGCGCACGAAAGATAAGAGTGGAATCGATTGCATTATCGAGTT TTTAAGCCCCATACCCGACAGATGTGTAAAAAGTGTAGTGGTAATGGCGTCACCAA GACCTATGCTTCTCATAATAATAGGACGTATGCCCTAGCTACTGCTAACGGTCGCT CTTACAATACTAGCTAAAAGAAACAAATTTGAAAAGTTATGTAGGAAGTCATTGGC GGTGAAAAAGTGAGAAAAAAGGTCCCCGGAGACTGTGCTTTCATGTTATCAAAGTA CATGCCGAGTGAAGAGTTTGTTTTGATCAACTTTTATTATCTGGAGTCATTATACG ATATTGCCATGGTTCCTTGGCTGTCCAACCAGGGGTCTTTTACACCAGATAATCTT CTACTACACTACACCTCAGGTACGATTCTTTCGTTATCAATCGACTACAAGATTAT AGTGTCTCTAAGGCGTGATGTAGGTTTTCCCTCAATGACAAAGACTTTACAGCAAT CCGGTTCAATACGAGAATTAAGTGTGCGAGTAACAGCAAAGTAAAATCTAACAGAA AGGAGACTCAGAAAACAACCTATTGAGGACTGTAATATCAACTCAGCATTATTGTT TACTTTAAAATCTAATAATCGTTTCGAGGATATGAGCACGGTATCCTAACATCAAG ACAAATACCACATCATCTAAATACAACTGGTTGCAATGAGTCGAATCGCGAACAAA TAAAGCAACTATAAGCACGATAAACCACTGTTATGGGAATGATAAACAGTCTTATG ACGTGGTCTATCTGTCGTAGGTGGTAAAGCCTTCTGAAGATCACTATCCAGTTCTG GCCTCAAGAACCATTTAGACAGCCTTTTCTAAACATGATCGTTGCTATAAGGACCG GGGACACCTAGACAAACTCACGGAAGGGATAACTTACATC |
| 4 | 38.90% | ACTGCTTATATAGGAGGTACAAACAGATACAATCCTTAGTTAACTAGAGAGAATGC TTTTTTTCGACCGACACGCTTATAACTTCACTGGGCATGGTCACCATATTTAGGTA AAACAAACTGCTGCGCTATATGTCGTACACATCCTGAGTGTACCAATATGTAGGTG GAAGGCAAGTTCAATGAGACGTCAGTTACCAAGCAAATTTACATTCTAGCAGTTAT AAATGTATTATGACGCAGTTCTTGTGGTGAGCGATCATTTACATTAAAACTTTATT CAAGAGCGTATATTAGCATATATTTTCCGGAGAGTGCACTACGGGCCGAAATTTAG GCTGGAACTCCGCAAATTGGTTACGACCCTGTATACATAGTTCTTATTATTAAGTA AAATGTGTGAATAAAACCTACACGACGCGTCATATACGTAAAAGTTTATCTCTTGT AGTAATCAACTAAATTAACTTACTACTATCTGGTCGTCCGTATGACCCTGTGAGCA GATTATTTTCGACTCGACATCTATGAATTCTACGGCACGAAAAGTTGGTAACTTGT ACTGGGTTAAACAATGTGTATTCGGGAGTCTGCGGAAGAACGTTTTTAATGTAACT TCCTTTGCAAACCAAAATTTGGTCTATTCAAACTGACACTAGCGTAATCTATACCG CATGAGATCCTGACATGATCCTATATCTATGCGCATAGGTACTCGCACCAATAAGT GGGTCGTAGAATTTCACGTAACTCAATGTTGTCTCCTTTCATTTTTGTTAATTCG AGAAAAACTACAAAAATAGTTAGTAAAATGCTCAAGGAGTCAGGTGCTACCTGTGGA ATACATCTATGTCCAATGGAACTTGCTCCCTCGGATGTGCGATTTCGTTGTTCAGT TGGGCCTTTAAGGAATACAGCAACTCCAACTCTTTGATTTTAGGTAAGTATTTGAT TCGCGGAAAGTACAGTGTATAATCTGTTATTTGCCAAGACGTCATCGAAATCGAGT GTATCGAGATCAGACCATCGCGCTATCGCAAGATATGAAGAGCATAGACAGATCAC GATGCCAATCAGTGTCGATGGTGCGAAGACGCAGCCCCTGTGATCAAATCGTCCGT TTCTCGATTTACTAGCGGAAAACAAAAACGAAGCGGTGAATACCCTGCGAGCTAAT GTCTTTACCCGGTTATACGAGCTGATAACTCGGAAAATGCTAATATCGAGGCTGCG CACTTAAAAAAATACTTTAATAATATTAATAAGCATAGCTGTATCATAACTTAAAA TTCTACTGTATGATTTAGAATCTAACAGTGTTAACGATCTACAGACCGCACTAAGA TGAAGACGGACTAATCTCCTCCCTAATTTTCCTTGTTGATTAGCAAAGGGAGATCC TTTTGTTATTTGAGGTTTACGAGAAAGATGTAAGAGTCGAAATAATTACGTAAACC TCATAGTCGTCACCTAGAGCAACTATAACATGAACCACTCGCCTTGGTTAAATATA AAATAACTTCTTCTCTGTAACATTGTTGCACACAAGCGAGCGACAAAATTTCACAA CATTTGTTGCGTAGATAATATTACTGCATCATTTTTGCGTCAGAGTGAATGTCACT TATATAACTAGGAAAATTAGTAGGATAGCTCTTGCGGTTGAGAGTAATGTCGACT GAATCGACCGCCATAGATGGTAGAGGGAGTGATTCAAATAGATTAATGTATGCGCT CCATCTATAAGGACGGACAAGGATCAATGTTCCCTTATACTTAGCTAACAGGACCC TCTCCGAAGGTCTGATAATGCACTCATATAAGCATCGATGCGTCCTGAGTAGAAAA ATCTTTACAAACTTTTAATAGATAAGTTATCTTGGAGGTGCTATCTATTCAAATCT CTGAACAGATCTGCGGCATGATAATGTCTTTGTACCGGTGTGAATAATGTGAGTCA GACGTCTGTGCGAAGTGGGAACCGAAATCTTTTAATCATT |

TABLE 2-continued

Exemplary 2.0 Kilobase Stuffer Sequences Having 40 ± 5% GC Content

| SEQ ID NO. | GC Content | Stuffer Sequence |
|---|---|---|
| 5 | 40.90% | GATTCGGTCGCGTTCCATAATCGAACCCTTAAGCCCATCTTCCAGCTGTTAACGTT ATGTACCATCTTACCTCAATGTCAGCGATCTATGAGGTTCATGTTTTTGGTGGATT AAAAAACTTCTTTATAGTGGTTTAGACAGAACGTTTAGCGCTGCGCTCGAAGTGTC TTATCTAACGGAGGACTAAAATTACCTGGTCACTCCTTAGACTTTTCGTAGTACTT AATTGCCGGACATCCGTTGGGCTACACCAGCAAGAACACAAAGTGGTATGTGTGAA GCTAGACTGACCTCATGATTCGTACTACATTATAAGAATCAAGCTTCCCGGATTTG TGTTCTGAGATATTACCACGTACATTTTTAAGGGGGTTCTTGACATCGTAACGCTA AGGCTGATTAAAGAGGAGGGTGCTATGCAGAGTTTATTGGTGTTTCATCAATGTAT CACACAAAATTAGCTACTATAGGAAGTAGCTTTGGTGCGAGCAGGGGGCGGTATGG TTAAGAAAGCTATGGTAAGAAAGGCCCAGGTGATACTACGTGTAAGGTTGTGAAGA GCCACAAGAGCCAAGTTTTGATATTCGACTTCCTCCGAATCTACAGCTTATCGAGG GTTAAACGTTACGCATATTACGAGATTACATGATAGCTTCTCAGTTCTAGCACATT TATGAGACCCTTTGAATGGTGTCAATAAATAGGAGGTCCCCATATGACAAGTAGAA TACTAACTATAAGAGATTTGTAACGCTGGATACCATTTGCAGAGGATTGGCCCAAA GAATGATTGCCCAACGCTTATATTGTCAGACCTTGCATTAGAAGAATAACGCAGAA TACGACTGCAGTTTGATATAATTTTGGCTCTGGGTTGCCTTAGTATCATTACTAAT AGACTTGTGGTCTATATCCATTTGTTTAATGGAATAGACTGGGTAAAACACACCTC TTCCAGGCTGTAGTTCTTCATGTTGTAAGGATCCGTCATGGCGTGCAAACTAGGGG AGGTATTTTTTGCTAATTGCGGTAACGGCTCCAGTTGGGATATCGTCAATATGTGC CACTCGGCCCTTTCTCTGAGACGCTAAGATTTCCGTAAGGTATAGCGATAAGAGTC TCTAATGCCAGAGGAATTGTTACCGCGAGCAAGATTCATGTCTATATATAAAATAT CATCCACTTTGAATTACTGGTTGGAATCATCGTTCGCGTTATAACAAAAAACCTTT TAATTATGTTACCACAGATCTCGAAGTCCCTTTTGAGGCAGAAGTTTAAATATAAG CTCTAATTGTCGCATCTAACGGGTATATCGTCTCAACGGTAGGTCAAAAACATTTG TTAACTTCAGACTGTACATTCGCATTTAACTCGCCATGTAAACCGCAATACATCTC GTGCCTATCTCTCCTAGTAACGTATTATCGCTGGGTGAAAGCGCAACTAAGTAATA AGTGAATGTCATTCACAATACCTAACTCTATCCGACGCGTAAGAGCGACCCAGCAG TTTAATGACATGATAAATCAAATTCTATGCAAGGCAGTACTTGCTTTGTGGACGAT AGCGATTTTCCACCGTATTGCGAAGTCAGTTATGCTGAAATTTTATTCCATTCGCA TAACACCAAGGCTTACTCTTAGGAAAAAATGTAATACCGATTTTGGTATGAAGTAT GTTACAGTACAGAATGAAATGCCCGGCGGCGTGGTCAAACTGTTTCCTGAGGTTCA TATAGGGAAAGGTCATCCCTCAGAATTGGCCCCGTAATCGCAAAGCCTACGGGAGC TTTCTTAAGTCCAACCGGTAAAGCCAAATCTCAATTCATATGAGGAAATGTTTGAC CGATAAAGAATAGATTGTCGAACTAACAGTCACAGAGAAAATACGAGTAGCATCAC CTAAACAAAGCAGGTAATAAAATAGACTAATGGAGATCATCGTATCGGCTTATGAC CTGCGTCCATTTAAAGGCAATGAATACATTACCGACTAGA |
| 6 | 40.80% | AGTTATGAGGTTCACTTCTCATATAACACTATCAACAATGATCATCTCTTGCGAAA CAAGCGCCCTACACAGCTTCAATGGAACCAAGAGCCATAATGAGGTAAGGGACGGC TAGTTACTAATAAAGGAATCGATTTTACAAACACTAAATGAAAAACTTGCGCTGGT TGCAATGCTATAAAAAAATGAAATGCAAACCAGTGAAGATCCCGATCAACCGTTCG CTGATTTTTATTGATGCTGTACGTTGTGTTAGTTTAATGATATATAGGCCATCTCC AGGTTACTTAGGACGCCAAAATTACTATTTTGAAGCTCAACCGTGGTATAATAGCT ACAATAATTAATTGATGCCTGCAGGTCGTATCTCGAACGATTGTACGCATTACCTA TGATATGAACAGAATCTGTATCCCATACTTAAAATCTTGACCTTGTAAAGATTTCG CATACGCATTAAGAAATTTCGTTCTACCCGCACGGATTGTCCAAGTATATCTGGCC ATTCACAGAAGTTACTAATCTTCATCTCTAAGTTTAAGGCCGACAAAGGGTCCAAA ACCTGCGTAGGTTACAACGCAGCTTACACTCAGTGACTAACCAACGCTCAGTAGGG TAACTGGACTTGTTCTCGCTATTCAGCTGGTACTGTAATGATCAACTTAGAACGGC CCTATGGCTAAGCAAGGAGTACGCAATGTTTTAGAATACGTGTTTGCTCACACAGG TAGTAGTTTAATATACCCCTGACAAGATATGTTAACATAGATGAAGTTTGGTATT ACTTATAGCCAGACTATTCTTCAACATATACACTGGGTTTTAGGAGTGTGCAATTT ATAAGGACAGTTATATTCCTACAATCGTTGTATGATCCTTTTGGGTTTGGTAGAAC TACGTTTGGGCCGCGCCTTTGGTCAACCACGGACTTTCTGTCTAGATGCCAATTCC TACAAGCTTAGTCCTATCAATTTAGTAGAGAACAAATTTTGTCATCACTGAATTGT CGTCTTACTATCGGATCATTCTCCGCTAATTATAGGATTATTAGTAACGCGTATAT AGGAGCGATTAATGACTCATCAATGAATAGCATCACTAGGTGTATTATATGAACCT CTCTCTATTCTATTAACTGCCCACTGTGGGTAATTTGAGTTATACCTGACCGGTCC CTCGGATCCTTAATCCTTTGATGTCGATAGGTAACTGAAGTGTAAGATCCTGATAT ATGAAGCCGGTAAGGAGACGGAGATTTTATATTAGTGTTCTTGGATACTGTGCTAG AAGGTTCTACTCTAACTCAAACAGGTTATAAAGTAGGAAGGAAAAAGTTGATAGTG GTAAACTAATTATGAGTTGGCTTGCTTATTCCAAGTTAGCGAGGTTTTCATGACGT AAGTCTGATAAGGTTTGCTGGAAGCTGAAAAGTTTTACAAAAACGTTGTTTTAGAA TGGTTTGTCCCCGAAAATCGAACCTGGCATAGCCCTCAGGAGACGAACAAGCCCAG GCAAACCGGGGTTTCTCGCTTATTGCTATAATCACCTCTAGTGTTGTAGAAGCAA TTACGGTGGGGAGGCGTCAATGTGGCCTGAGTTCCGTTGAGGACTTTTCACGTGTA GGACCCATTAATAGAGGAGATATATGTCTTTCAGCTGCGGAATTCATAATAGTGGA AAGAAGAAAAGGGATTACTAGATTAATATTACTCATCCCAGACTTAAGTTGAAAGC TACATCTTCACACCCAGGAAACCGGACCGCCTTTGTTCAGGTCTAAGTAGTCTGGA ACAGAACCGTATCAACTGCCCCAATTCATAGGTGTTAGCGTGACAGCGATCGCGGA TTTTTAGTCCAGACTGGCTGGGCATCCGCTTCAATAAGTTAGAGGACTACATACA ACGATGGACCCAATTGGCAATAGTCGTGGTAAACTTCGAAGGGGCGGTGTAAGATT CAAGCTGTAGTCGTGATGAAGGAGATCATCGTATAAACAG |

TABLE 2-continued

Exemplary 2.0 Kilobase Stuffer Sequences Having 40 ± 5% GC Content

| SEQ ID NO. | GC Content | Stuffer Sequence |
|---|---|---|
| 7 | 39.70% | ATACATCTAGACTACTAAGAGGGATTATCCCAGCGCAGTCCCACCCAAACATCAATCTGTCCCTTTGTTCTAATATATCTCTGGTCGCGAATGAGTAAACGGGGCTAAAGGTCCATTATTTTTATGTAGGAGCATGTTGCTTATTATGGCATAGCAGTCGCCATCCCCCTGTCACTCGATCTAGATACATCTCACATTGATTGGAAACTTCTACAAAACGTTAGTACTTAAGATGAGTGATTTAGTGCATTTCTCGTTTTCACAAACTTTGCTAAACAAACGTATTGAGTGGCGCGTTTTTTGATTTGTCGCATAACCGTTTACTCCCTGTTCGAAGGAAATCGATCTCCTTATAAATAATGAGTACATTATACAGCTAGCATAATCTGCGTGTGGCAAAAGTGAACGTTTAATCTACAATTGATGGAAAAATAGCCCGTTAGTCCTTTTAAAGACGTCTTGGAAAAATATTGAGACAACCTTCGTCCAAAATATGTCAAAGCTTCGTCACATCTTTTCACCTATTACTAACTCCGTAGTTCAACTGACTTTAGAGGGCAAGTTTTGAGACAATATCTTAGGGCTGACTAATAAGACGGTTATATTTCAAGAAGGAAAGATCTTAAGAGTCAAAAAAACGTCAGGGCTATCGTTACGATATTGGTATGAACAGTAATGATATATTTTGCAGATCTTAATATAACGACATTCGAACACAATAGCGTCAGACAAAGGTTACCACTCCTCTATAATTACTGCAGCTTCAATTGATGAGCGTCATTTAATTTTGGCCGGACATTTACATCGTGAGCTGGCAGCACGCTCAGCTTTATTGTTCTTGCCAGAACATTACGAATAGCCGTTCAATGCCAATTAGTATGATAAAAGTAGTGAGTGTAAAACATGGCCTGGGTTTAAAGAATGAGTAACTATTATTTTGTAGGAATAACTGATTCCCTTGAGTTCTATCTTAAGTTGTACAGAATCACACTCCTACAGCGAATAAGCAACGACATAGAATCCGTTATTTCGTATGTCTCGGCGGGACATGTATAAGTAGCATACGTTATATCGGTTGTCGCACGAACCGCCTTCATTCCAAAGGCGCTTACAAATCTGCAGTAAAAAGCTTAGCATTTACTATAGAGTATCGGCGTTGACCGTTAAGCCCGTCCCGTCCATTCAATCACTCAATTGATCATCTTTTGGCAATAGTCGTCATATGAGAAAATAGCTCTGTCGTTGTTATTATTGGCTAGAGTATAAGCTGTTAAACTACAGAATGACGTTTTGTGGAAAGTGGACGTAAGATCCTTGTTCGCGAAGACTCGCACGGTGGGGAACAATTCCTGGGAATATTTGATCTACGTACGGTTATTCTGCATGTGATTACAATATTTCCAACGCAGTCCTTTTGACATTATATGAAACCAGACCCGATGCATATGTTTTCTGACTGGTGGTTTGAGTCAGAGTCAACAAAAGTATCAGTCTTTCGTTACTAAATCTTCCTAAGTAAATGGTGGGCGACCATTCCTTGTAACCTGTTCTGTTATAGGTACTATTCCAGCCTGGAAATCGTGGAACACATCGATCTAGTTGTCTATCTATAAGAGAACACTCGGTTCCAAATATGTAATCCGCACGTAAGAGGAGTCTCGTACATGATATATAACGTTGGGTACATTTCTTAGACATTCCGGTGATACATAATGTACAAGTCACATGATTACACCAGCTGGTAGATAGAATACCTGAGACTGGGTCCTAGATGATTATAACAAGTGTTACATGGACGCTCTCGTTTTGTTGTTGGCTTAACACCAGGGCTTGCTCCATGTTCTCATGTCGTTATTACTGAATTATCTTCCATTATGATCCTGGACGGATGAACGAAGCAGAAGATAACAAAGATGACTGAATGCCGGAAAAGGAATTAGGCCCTGATATATCGCGCTTCTTTATGCATGTTTACGCTGTACCAATAAACGCAAGAGG |
| 8 | 40.80% | GTACCCGTATATCGTCACTTCATTTGAAGCTATTATTAATGTAAAATCCTTCCGTCACACACTCTTTTCAAAAAGGGAAGTCTAAATTAACATTCAGATGAAAAGCGCTGACCCACATGGGAATATCCTTTCTACGCTATCAGCCGAAAAGCTCCAGCGATTAGCTAAATATCTAAGCCTCCAGAACAGAGTTATTATATATTGGTTCGAATATGCTAATATTACAGTAGAAAGTAAGGTACCGGCACTTTTAACGCCGAAGTCGACCGGTGTAGCTGTGAAAAATATATTTAGTACACGTAATATTAATTGGAAATTGATGAGATCGAATCTTCAGGAGAATCTGACGAGCATTACTAATCGCGCGTGACGGGAACGTTAATATACAAGCGTCTATTCTAGGTTATAATAAACTCCTATCTGGCAAGTTGAATGGTTTTTTCAAAACTTTAACGTTCTGGCTATACAAAGCTAGTTGCTTTAACTTATCGCATACTATGATCCTTCCCATCAATCAATCTCAGTGACTATAAACGCAAGTGACACAATTGTCTGCGTTCCACATTTCTAAATCTCTTATCGCTCATTCCCTCTACACAAAGTTCGATTACCAAACGCGGGTCTACACACAAGCTTACAAGGATTACAATATCCAATTTTTTGTTATCAAAGGCGAACTCAACGAATTTAATCGTTGGTCATTGGTATGGAATGGCGATTATAAGAAAACTCTTTTAGTCATAGTAGCTCGAGATGAAGTGAACCGGGCCAGTCGGTAGTTTCACTATCGCGCAGTAGTCACGATCAGTTCTTAGAATCTATCTCCTAATCAAGTCCAACAAGCAATCCGAAATGTTGCTTTCTATAAAGGGTATGTGTACCTGCCAATATTAAACTTGATTCACTCAATAGTGATTTTAAATATGTCCATATTTATGCAAGAATCATTGACATTAGTAAATTCAGCCGTGCATTTGACACAATAAAGGTAGATTTAGACTGCATATTTCCCGCATATTTATTATTGTCAACGCACAAAGTTGATGGACCGACCACGATCGCATCGAAGACCGTCTAAACGACGATATTCTTCGGAGATCCATATTTGTTTTCAATTACCGACCATTGTTCATCAAGTGTAGTTCAGTCGGAAATTTTTCGTGTGCTTTTTAAAATACCAAATCTGAGGAAAAAGCTCGCTAGATGTTGAGTCAATCCGTAAGAATATGCCCCAGGAGACATATGTAAGTCACAGCCGTAGACTCTCGGTTACCCCACGATATGTTCCATATGCAACGTTTGTTGAGTAATATGCAGTTCAGTCGGGCGTATTATCAACAGACAGACTGGCACAGTAAATTTTATCATCGGGTTTAAAATATCTAGATACCTCAGTTTCAAGGGGGAGTTGAACTTTAACACGAGATCAAACTACATACACAAGATTATCAGTGGGTACGCTGAGACTTATCCTTAGCCTGGAGAGAGTCCAGCTACAGGAACTGCTAGTACTTAGCGTGCGACCTCAAATCGAGAGAACTAATTACCCTGATCGACAGATCGGGCAAGTTAAGCAAACGCGGCTCGCGTGTAGAACCATAACAATTGGAGATGCTCCTGCTTAAGAGATTATAGAACCGCAACCCATCAATCGTCAGTTACCCGAGGGCTCACGCACGCGGTGATGGAAGTTAGTTCCTTTGTACGCACGAGCTGCAATACGTGGTGATTATAATCGGCGCACACTAAAGGGGTGGATACAATAGTAGAAGCATATACGTCATAGGCGTACGCGGGCGAAAATTTTAATCGTTAACGTGGCACTAACAGCGTTTTGTCTCCCCACTCGTGGGTTGCGGTGCATCGCACATATTCCCACAACACCTCTTAATGCTTTATTATTGTATTAATGGCGCGAATCTGCCTGATATTAGTATTCGCACTAGTGGGTAACGAAATCTTAGTCGCTGGCTACTGCAGAACTAATTGCGTTGCGAT |

TABLE 2-continued

Exemplary 2.0 Kilobase Stuffer Sequences Having 40 ± 5% GC Content

| SEQ ID NO. | GC Content | Stuffer Sequence |
|---|---|---|
| 9 | 40.80% | ACTAGCTACAGATCTGTAATAGAAAAATGCAGATGCTTGTTCTGCGTCGACTCGCT CATCAACATCCTGTCTCACAAGTTATGCATCCTGTGCATTTTATTGAAGCTTTGAT GGGGATTAGATCGTGTATGGAAATGTTTATTCGCCTGGATAAGATCTGTCGGCTTA TTCGTGGCCAATAATAGGTCAATTTGCGGAAACATAAAGACTCGCATACCAATACT CGCTTATCCTGAGGTTAAATTTAGTGTATGTAGACGAACAACAGTATTTAGTAGTA TGACGTTCCCCCGTATTGCCAGAACTCCTGAATATTTGGATATGAGGTATGACTAC GAAAAAAATACTACGTTGCTCATAACCATTGGTGCAGGGATACCGAACTCATTGTT AAGGGACGCCACAGTCCAGTCTCTTTTCGTTCAGAGCGTGTTTTTCAAAGTGCTTG TATTAGTGTGGACAGAGTTTACTGATCTCTCCGCACTTGGACTGATTGTGATCCCG ATCATCTCTTTTCATAATTGTAACACGCTTTCATAGTACACTTCTGTACATTGAAG AGTGCTTGCAGCCGGACAGTCCTATAGAATTTGGCGTTTGTTCGGCCAATGTGTGC ATTTTAACTTTAGGCGCCATCTCTTGAGATTACTCCTTTGAAAAATTTTGGCGGAG GTTAACTCTGGTCTTTAACATAGGCGTGCTTAACACGAGCTTTACGGTCAGGTACA GGTAACAAAACAGGTCTAAATTTATTTAAGCAGCTTCTGATACTTTCCAAGGGTCA CAGTTGGGGAGCCTTCCGAGGTATGACAATCAGTTTTCAAAAGGTGTAGAATATCA TATATTCTATCTAGGCCAGAGCATTCTAAGCTGTTAAAAGAGTGCTATGCTCAGAA GTTGACTGTTCTAATCGAAAATCGGACATAGATAACCCGCATACCACAAGTCCCGT TGTAACGTACCCATCGTTTTTGATTCTATGTCTTTGCTAATGATTGGCGATTGAGA CATCCTACTTCTGTAGCTTGGCTGTTATGCGATCCAAAATGGTATCCAGTGGTGGA TGTCCGCCGCAAACTGAAACTCCCTATCAGTTCTTTGAAATTAATTTGCGGGCTAT CCGACTCATTCTTTAGGAATTAACAGAAGAACACGCGTCTGTACCAAGGTTCTTCT TTGTTATATCACATAACAATGAATCACGTTCTATGATGAATCCAGGTATAGAAGTT GTAGGTAAGCACTTGTATAAGGGGGCGCTCCTCTCAGATTGATTCATTATTTACTA AAAAAGGAGCGTGTTATTACTTCTAACAACTCCTCGCCATTATATATTATTTAACT ACCATTCCCACTAGAAATGGATATCGTGTTCTAAGACCCTAATTGTGCTCATTAAA CTAACTACCGCACCAACCGCCTTGAATCACCGGACCACACTAGTTAAGCTGCCGAT ACCCAATATGGTATTTTAGTGTATACCGGATATGACCTTATTTACGAATGGATTGA GCTCACCCCATAGATCAGTACCAGCGTTATTATGAAAATCTTGTTATTTTAACAGA GAGACATGCTTGGTCATTACTACGAATTTGAGTTTACGTTATACAAGGCGATCCAA ACGGACAATAGCGCGATACGAGATTATAGTACCAATAGCACGAATCAGTTTTAGCG ATCCGTCCGATCTGTCAAGCCGAATGACTCTGAAACGTTAGTATCTGAAACGTTT CATTCAGCCTAAGATATGTATAGTATCATTATACCGTGTGGGTAGAACAATCAAAT GCAGATAAAGCTATTTAATGCACTTCACATAACCTCTCCGTTGGAAATCCATGTAT TCTCTAATCAATTGAATTGTACCTTAGAAAGCACAGGGGGACACCTGAAGACCTCC CATCTCTTAAGGTTACCGGCACGTGAAACTTCAAAAGTCAGACAATCAAACGGCAA CGTGAATGTCTTCGGAAGTGGTGGTATGCACATCGCGTCA |
| 10 | 41.70% | TTAATAGAAGTAATAAGTGCTATTGGACTAAAATCGCGTCAATTAGCTATAGAACA GCTCTGTGACGAACTATCAATGGGGCATTCGTTCACTAGTGGATACCGTACAAGCT CGCCGTGATCGTGCGTCAAGGATAGTGCCAGAGCGCCGCGCTATATGTGTAACGAC GCATAAGTAGATGTTTATGTTATTGGGCAAAGTCATTCTTATCCATAATAAGCGCT GCCGATAAAGATTCATCAGAGATATTGAGATTCTCCATACTTGACTAATCTCTGAG TAATTAAAATATATTTCTAATCGGATAAGTTAGGGATCACCGAACCCAATGAACTT AGTTTAATGTGTTCTCGCGAATATCCCCATGATATAAAGATCCGAATACCTCAGCT CCGTGCGTGCTCGTGCAGTCGTGCGTTTTCTATGAATCAACCATCAGTAACGAGTA GCGGTAACTACTTCTCGAGTTTAACCAAAGCCTATGTATACTAGCGTGCAATCACG TGCGGAAGGTCCGACCTACAGCAGCATTTTCGTTCGAAAAACGAAAACTAATGTGC ACTATGTTGAATGGGCATTCAGGCCTTAACTTCTAACGTTAAACTAGATTTGCGAT TATTAGGTATGAGATCGACCAGGTCGCCACAGATAATTAAAGATAGCCCTAGCAAA GTGATAAGGTCCGGATGTTAGAACTTGCAAGAGTGTGTAAGATTATTTACTCTCGG TGCGTCGACAGGCGAAACCCATAACTTTTATCGGTCAAGATTACGACCTTCAGCTA GTATCTTGAGATTTGAAAGGGCCTAAAAGCAATTTAGTGTACTTGTGTAACATAAC CTTAATTATTGATGGTTCTATCGACTCCCAGCGGTAATAATCTTGTAATATTGTCG GATTTAGTTGAAGGGCAGGTTGACATACCGAACAATAGCTAGTATCAATGTATAAC TAGCAGGCATCTAATTTCGTAAACACTCCTGACACTTGTCGTGTCTAAGCATGTTA GGACAAAAGACCAGTTTTTTTAAACCTGACTGTACCGGCAACGCCACAGATTTTAT GTCTCGCATACGTACGAACTGAATTTGAGGGGGCTCAGGTTTGGACTTACACCGCA CGTGACTATACTGAGATCGAGGCTCCATTAACGGCAACATAAGACTAGCACTGTAT GATCTGAAGCCAGGCTCTGGTGAAATTGCGGGTAGTTAACGACATTTATCGACGAA CCCTTGATAAAAGTGATTATGTTGTATCTGCGTGATATATTCTTTTCGTGTTCAG TCTCTAGAACTTCGTGCGTAATAAAGATTATAGAGGAACGGTTAACCTCATTACAA GACGGAGACCGTTCATAGACGCCGATGGATTACAGGGTCTACTATAGCTACCTAGA ACACTGGTGAACATAGGGATAACATACAATTAACAATATTCCGAGCCAAATTATGT CTTGAGTCTTGGTTGTTATCTATATCGTTATTATGTTAGAAACTAATAAATGCGAT AAGAACTAGATTTTACAGTAGATCCAAATACCGGAATCTATCGGGACGATTGATTA AGACTTACTCAAACCTAACTTTAGCCCGATTTTGCAATTAGAGATACGTCGATTTC GAGACAAGAGTAGCGTCCCCATGGCAAATATCCACGGACAGATAATGACACGTGAG GGATGGCAAGAGTAGTTGCTCAGGATGTAGGCGTTGATGGTCTGGCGCTAATGTCG TGGCTACCTGTTGAGTCTCGCGTAATGACTAGTAGTGTTGCAATGTATGACCAAGT TCCTTCCTAGTGTTACCACTTTGACACATACCCAGGGGTTTGCCGCATGTCGCTAC TATAGTATAGGTGCTGCTATGAAGCTTCTGAATCAGCGGCTAACAAGTACCTAAGA AAATTGGACATCTTTTGGATGACAGTGCACAGGAGCCTATACTGAATTATCGGTGA TCGATGCTTCATGTAATCAAAACCAGCGCGTACACACTTT |

TABLE 2-continued

Exemplary 2.0 Kilobase Stuffer Sequences Having 40 ± 5% GC Content

| SEQ ID NO. | GC Content | Stuffer Sequence |
|---|---|---|
| 11 | 39.10% | TACTCTTAATTCATTACATATTGTGCGGTCGAATTCAGGGAGCCGATAATGCGGTT ACAATAATTCCTATACTTAAATATACAAAGATTTAAAATTTCAAAAAATGGTTACC AGCATCGTTAGTGCGTATACATCAAGAGGCACGTGCCCCGGAGACAGCAAGTAAGC TCTTTAAACATGCTTTGACATACGATTTTTAATAAAACATGAGCATTTGAATAAAA ACGACTTCCTCATACTGTAAACATCACGCATGCACATTAGACAATAATCCAGTAAC GAAACGGCTTCAGTCGTAATCGCCCATATAGTTGGCTACAGAATGTTGGATAGAGA ACTTAAGTACGCTAAGGCGGCGTATTTTCTTAATATTTAGGGGTATTGCCGCAGTC ATTACAGATAACCGCCTATGCGGCCATGCCAGGATTATAGATAACTTTTTAACATT AGCCGCAGAGGTGGGACTAGCACGTAATATCAGCACATAACGTGTCAGTCAGCATA TTACGGAATAATCCTATCGTTATCAGATCTCCCCTGTCATATCACAACATGTTTCG ATGTTCCAAAACCGGGAACATTTTGGATCGGTTAAATGATTGTACATCATTTGTTG CAGACCTTAGGAACATCCATCATCCGCCGCCCTTCATCTCTCAAAGTTATCGCTTG TAAATGTATCACAACTAGTATGGTGTAAAATATAGTACCCGATAGACTCGATTTAG GCTGTGAGGTTAGTAACTCTAACTTGTGCTTTCGACACAGATCCTCGTTTCATGCA AATTTAATTTTGCTGGCTAGATATATCAATCGTTCGATTATTCAGAGTTTTGGTGA GGAGCCCCCTCAGATGGGAGCATTTTCACTACTTTAAAGAATAACGTATTTTTCGC CCTGTCCCTTAGTGACTTAAAAAGAATGGGGGCTAGTGCTTAGAGCTGGTAGGGCT TTTTGGTTCTATCTGTTAAGCGAATAAGCTGTCACCTAAGCAAATTAATGCTTTCA TTGTACCCCGGAACTTTTAAATCTATGAACAATCGCAACAAATTGTCCAAAGGCAAC AATACGACACAGTTAGAGGCCATCGGCGCAGGTACACTCTATCCACGCCTATCAGA ATGTCACCTGGTTAATGGTCAATTTAGGTGGCTGGAGGCACATGTGAAGCAATATG GTCTAGGGAAAGATATCGGTTTACTTAGATTTTATAGTTCCGGATCCAACTTAAAT AATATAGGTATTAAAGAGCAGTATCAAGAGGGTTTCTTCCCAAGGAATCTTGCGAT TTTCATACACAGCTTTAACAAATTTCACTAGACGCACCTTCATTTTGTCGTCTCGT TGTATATGAGTCCGGGGTAAGAATTTTTTACCGTATTTAACATGATCAACGGGTAC TAAAGCAATGTCATTTCTAAACACAGTAGGTAAAGGACACGTCATCTTATTTTAAA GAATGTCAGAAATCAGGGAGACTAGATCGATATTACGTGTTTTTTGAGTCAAAGAC GGCCGTAAAATAATCAAGCAGTCTTTCTACCTGTACTTGTCGCTACCTAGAATCTT TAATTTATCCATGTCAAGGAGGATGCCCATCTGAAACAATACCTGTTGCTAGATCG TCTAACAACGGCATCTTGTCGTCCATGCGGGGTTGTTCTTGTACGTATCAGCGTCG GTTATATGTAAAAATAATGTTTTACTACTATGCCATCTGTCCCGTATTCTTAAGCA TGACTAATATTAAAAGCCGCCTATATATCGAGAACGACTACCATTGGAATTTAAAA TTGCTTCCAAGCTATGATGATGTGACCTCTCACATTGTGGTAGTATAAACTATGGT TAGCCACGACTCGTTCGGACAAGTAGTAATATCTGTTGGTAATAGTCGGGTTACCG CGAAATATTTGAAATTGATATTAAGAAGCAATGATTTGTACATAAGTATACCTGTA ATGAATTCCTGCGTTAGCAGCTTAGTATCCATTATTAGAG |
| 12 | 40.90% | GGCCCTATAGATTTTAACCTAAGCTCTAGCTTGTGTGTGCTCAGAGTACTGCTCAT AAATATGCTCGATAAAGGAGGTAAGGCATATCGTAATTTGGAAGATAATACCACAC TTATTGGTAACACGTTGGAATCACATATTAATTATGAGCCAGCCTTGGCATTCGAG CAGGGATATGTGGGAGTATCAGTTGAGTTTGGCTCCTTGCTACTGCCCTCTGATGC TCTGCTTGCTCTAGCTTAGGTCATTAATGATAAAAAAGAGCCAGAGTGTGGGCTAA ACAGGCAACGGTACCGTTGTAGAGCGAGGTATTGCTATCGGGAGACGTCGGGTCAA AGTGGGATTCATGCAGTAAGTTTGCCAAAGGGTCTGCTTAAAGAGACCGATTCCGG AAGGCTATATGCCATAGCAAGGTATGCACTGCATTGAGCTGAAAACTCTTGAGCAT AGTATTTACTAAATAAAGAATCTGATATCTTCTAGCGTGTTCACTGGACTATTATT TAGATGGTCGCCAACAACAAGCGTGCGAATCATATAGACCCAACCCAGGGTGGTAT TGAATTCTATATTAAAATGTCTCGCCCTTATAACTCTCTAGGTTTCCATAGTACAA ACCTAGGTGTCGTCAACTGCATGCACTGCTTTTTGTATCGGTAATGTTGATCGACC CGATGGGCTTTTTTTAATAAAGGTCTTGTTTAGTTGATCATACTACCAATTTTGGT GGTCGATGGCTCAATGACCAATGGAATCTTTATAGTAAAAGAGCCCTTGGCACCAA CGAATCATGGAATTTAGGACGATGTCTCATTTACCCATATTTTGCATTCAGACTATG ACTTTCAATAATAGAATATCATCGTCAAACACCGTGGATATGGCATCGACAAGTGT TGGGATGCCCACTGAATAACGTCTCTTCGTCATCTTTAGGGCGGCTATCCATTAAG GAGGATTTATTTTTATAGCAGTCTTAGTCCGAGGCATTGGCGCCAAACATCGGCT CAACACTAGACACGTCTTTAATGGAAAGTATCTAGTGTTACTGCGGTACGGAAAGC AAGTTCAGTACTTTTATCCAATCTAAGTATCACCCAGCTTATATTTAAAAGCTAGG TAATAGGGAAGTTACTAATAACTCATGCGCGTGTAGTGTAGTCTTGCTGTCGCTTA AAGCAACTGAATGAATGTACGGCTGACAAAGGCTTACCCAAGAAAACTCTCTTGTA CGCTACAAGAAACCTGTAACAAGAGAAAAATATTTTAGCCCACGTATAGTGAGGCC AAACTTGATGCCCGTAAAAGCAAACAAGTAATATTCAGCAGAATTTGCGGTCATTC AAGTGTTTAGGTACGTAACTTTTACAGAATTAGCTGTTGATTAGGTAATACTAAAT CAAAATGTCGTAATACCGAAGCAGAAGTATATGATCTAATTTGTCGCCTCGCTTCA TGCTACGAATGTTACTTCGTTTATTACAGCTGCAAACTTGCAGTGACTTGCATTTG ATAGGATTCTTCCTAGGGAACCATACTGGGCCGCGGACAGGGAGTCAGGAACTCAT AACGGATGAAGATGTAATCTCTATAGGGGTGAATAACAGGATTGAAGATAGTAATC TAAGTACTCTCATCTCGTGGACGACTTTAAGCGCACTGACAGCGACTCGCGATTCG ACGAACACCCGTGATCGATTTACACGTTCATTCTGAAAGATATACAGGTAATAATT CTAAAAGATAATTGAGTACCAATATATAGGTTTTATGATCTTAGGCGCATGTCACT GACGAGAGAAAAGATAGTCTTGCCGCCTCTAAGTGTTCTATTTCTGGACGTGCCTG GGCATTAAGGGCGACGTTGACTTTTATACACATTTCATGTCCACTAACAATTTTAT ATCACGTAGCAGGACATAAAGGGAGGACTCTATAAAAAGTTTCGCTATATACGTAC AGTACGTTCAAAATCTCCAGAGGAAAGCTTGTAAAAAAG |

TABLE 2-continued

Exemplary 2.0 Kilobase Stuffer Sequences Having 40 ± 5% GC Content

| SEQ ID NO. | GC Content | Stuffer Sequence |
|---|---|---|
| 13 | 40.40% | CGCTCGACACGAGTATAACAAATATCGATAGATGCTATAGTGATAAGGTATAAGTA AAATAGTACTGCGAATACAAATAGCTTGGAGAAATACGTTCATCCTTTAACTTCAA AAATTTTTGGACCTCAGGCACGTTGTCATTATTACTGGCAGGTGATACCACCCAAA AATCGTACCCGCAATATATCTTCGGTAATTCTTGCCAAGTTGGGATTTTACATACT TAGTATTAATAGTGGGATCAGCTTCGATCGAAGACCATAACTCAGTATGTGTATTC CTCATACAAGATTTCTGAAGGACGAAGGCTCATCAATGCTGAGGTGTTATCAGGTC AATAACAAGCCGCATTAACGCCGTAACCCTAATGCCATAATTCTTTGACGAAATGC CAAATAGTTTCATCAGGAATCACATTATTGGATAAGGAAGCACAACAAACGCTTT AATCTATACCCCTAGAATTAAGAGGACAGCATGATAGGCTTTGCAATGAACCAGTC TCCTAAGCGTACCACCACTCCGGAGCCTTATGGCGCGCCGGTATTATGGCGATGCA CTGCCTGGGCGAAACTCGAGTGAATCATTTTTCCCGATATACACAGCAGTACGCCG ACGGTCTGGTAAAAAAAACGTTATAGGCTTTGACCGCATGGTGATCGTGGTTAAGT GCCTTTACCTAGAGTGCTGCTAGATGTAACACAATTGATCTGACAGTTTACGACCT TGTAATCCAAGAACCATATAGATGACCCGCTGAGTTAGTAAGATAATGCACGCTCC GGGGCTAAATCTAGTGCGGTTCATGAATACCGAATCAACTACGGTTATTGGCTGCG GTAGAATATTTAGTTGTGTTAAATATACTCTAAGATGAACATGTATCACTATAATC ACTCACCCCTCTGCGTTCATAAGTAAGTGGCTAGTGTGATAGTAACTTGTATCAG CGACCACTACTATATGTGGAAGCTTTTGAATGAGAATCTCCGCACATGATGATGTA TTGATACAATTCTTTTGTTCGAAAAAGCTTCGGTGTTTTTTAGGACAGGAGATTAA CGCTTTAGAGTCATACATATATGTCAAGAAACCGGGGAAAAAATGCCAGCCCAGAG TGTTCTAAACGATAGGTTGTTCAGTTTTTAATAACCCGCGACGCGTCAAGTAACGT CACGGGTCAGCTACGATTACCAATTTGCTATAAACTTTCCCCCGACGAGCCAAATC CCTCAAAGCTGCCAGATAAAAGGATAGCAACCTGTACTCCCCGTCAAATCTAATGC ATTCTTGTTTTTTAAGTCTCGTGTAACATGCGTTGGCTAATCTTCTCTACCGGGTC CAGTGCCCTTTCAGCTTATGCCTCACCTTTGATTAGTAATGGACATCAGCTTTTAG TCACATCGGAGTGCCAATTATACCGTTATATCTTTCTGATGCAGACCGACCTGT CGTGTACCGATTCATCCTAGGGTAACTAGCCGTGGCAAAATATCTTTATCGTGTTG TCAGGACTTGGTTGTTATATACTCTAGCCCGTAGATTTAAAATAAATTAAGTGTAG ATCGTCCAAATATCTAAAGCAATCGCAGTTTTTATCACATCATGTGTTAAAATGCG ATCAAAAGAAAAATACTGTTATTTCGAGAGTCAAGGCTGTGAGGAAATATGATGAA GACTGCCATCCTGGTGGACTGGCGGCCCCAACGTTGAAGTTTCTATTTGATCGGTT ATTAAAGGATACTCGAGAACAACATCGAAGGAATAAACTTTTATAGAAAAGTCTCCG AAATGAATAACTTAAGATATAAATTTATCGCGCGATAGTTCTGGTGGATGATAGCT TTATTCCTCTTAATGCAGTATAGCTATTGCACCTATTAATTTGTATAATAACGTAT CATGTTAGACGGTCAGCATGATATTCCGGATAGTGGAAGCAAATTACGACATCTAA ATATGTCGCTAGTATTTGAGTCATTATAGCTTCGAGGCTT |
| 14 | 42.10% | CTCTAACGTGCATTTCTTCGTCGCCTTTGTAAGACCCCACAAAAACATGACGCTTT AGGGATATGGTCCAAGACTCCGAATTGAAAGTATGCTGGTATGATATGGGACGTTT TTGAAACCCCCCTCTCACGCGGGTAATTGGGTTTTTAGTTAGTGTATCATAGTAGG TATATCTACGAACTACGTCTGACTGAGAGAGACTTTGTGCCTCTCAACCGCTATGG TGTCAGCGACTGATATTGGAGTTATTTACCCGTCGTTATACGTGGGTAATCTTTAC TACGGTTCAAGGTAACTAATCTAGTGTAGGTAGAATGCTGAAGAATTACCCGTTGG ACCCGGTAGTCCGTCCGCTCCACGCATGGAATGCATGAGTAACGTCTAGGTGAATA TCCGGAGTGCATAACTTTTTGGTATCTAGTCCGCTACTGGATGCAGAATGACATAT TTTTTTCGAGTGCTTACTATTACTCTTCTCAAACAGAACGATCATTATGTTGCTTA AATTCACGCTATGTTCTCGATGTAAAACAATTTTCGTAGAGAAAGATGCGTAAAAC GCAGAGTTAGCATATAAAAAGTACAATCAAGCCCGAAGCACTCACAAGAAACATAG GGGCTAAATGTTACCGTCCAAGTGAGTAGGATTTAATATCAAGCCGGGCTTATTGG GTACAGTACGTGGACGGACTACGACGCATGTGTGTTATAGAATGAAGTGCCTACAA CTGAAGCACAATTACTAAAGGAATGTACCTGGGTTTACACTAAGCATCCCATCCTC TTCGCGGTTCAGCCTGATGTAAACGTAAATCTCGTCTTCCCATTATTAAGACGCCT CGATCTACGATAGGTGATACGTGTACATCGGTGGACCATGTGTTTTGATATTCAAC GATGTAAGTATGGTTCCCTGCAGTGAACCCCTCTTCAAGTCGTCGATGTACCTGCA AGTGTACAATCGGAAGACCATGGGTCCATATGTAAAAATAAGTTAGGGGTCTTTTG GTCTGTGTTGGTTATAATCGATATTGCCAAAATATTATGGACAGTTAGTTCGAATT TTGTGTATGGTAGCCGTCGAAAAGGGTGGACGTTAAGTATATCCATCCCAGCGGCT GGGAGATATGTAGACCGACGAGTGTTAAGTTATTCCACTTACTTTAGGACGAAATC AATACGATTATTTTACATCGGAGGACATGACAACAAAAAACTACTCGGTTTCGACA GGTGGAAGATGTCGCTGCGCACCAGTAGAGCTTAGGAGAGCGACGGTACTCATTTG CAGCATGGGTACGTAATCACGTTAGTAAATAAGTAAGTATGCCTTCTCTTATGTCA TTTTTATAAGCTATAATGGTGTTGTGCCAACTTAAAGATTGACACATGATATGCTAC CAGATAAGCCTCGAGTCGCCTATATTTTGCTACTAAACCTGATTAACTAGAGAATA GGTATAATCCCTGGTAACCAGTAATTTTAATACTATGTTGCCACTTGATGTAGACC TGGCTGTGGTTACTAAGGTGCTTTGAAACCATTGACCACCCGTTTCTGCTCGGGTT GTGCATCTAACGTAAATATTCAGAGATAACGTGGCTCTGCTATTATTTTTATATTG CCTGCTGACATATCATCATCCTTGAATGGCCAGCAACAGTTCTTGATCGGCAGAGG CCCCATGAACTAGGGTAATATAGCAGATTAACTATCGGTTAACTGTATTAAACTTG TGTAATACTTTATATTGACTAATTGGGATTGCCTTTGTCGTTATCTCGTTTATCTTG AAAACGGTGATGTTTTTAGAGGCGATAGTATTGAATAGCTCGAATGATCACCAGCC ATCAAGAATGTAGCTAACTCCGAAACTCCTTGACGAGAGCTCAAGCGAATACTAGG TCGGCGCTGCTATCCGCAGAGTTCAGGGTTCTACCCGGGGTATAAAATCCCATTGA TCATTCAGATATTATGGACTTGGCGTTTATGCGACGAGTC |

TABLE 2-continued

Exemplary 2.0 Kilobase Stuffer Sequences Having 40 ± 5% GC Content

| SEQ ID NO. | GC Content | Stuffer Sequence |
|---|---|---|
| 15 | 39.60% | AAGAAGCAGCTAGTGCTACTTCGGAATAGTTGTCGTTTAAGTCCGTTCAAACATGA CGCTCTAGTCATTTTGAAACCTAAACCAGTAATAATAGACTGACTCAGAATGATTA TACTGCTATCTCTAGTTTAAGGAGATCCAGCGAAATAACTTGGTGAACTATGCCGA GATACTATAAAAGATCAAGGACGGGTCGCTCACGGTTTTGGTTTATTTTACTACT TCTTCGTGGCTGTATTAGTCGATGCAAGTTCTAATAAATAGCAAACGTTTTAAGTG GGATTAGTACATATTGATGGACGTCCACCACGTCAAATCTCGCAGCGTCATAGAAG GAGCTATAACCATTCACTGCGACTACGACATGTGTTTGGGTAGTGCCAACTACCCG CTTCCGCGTCCCTGCCGTTCTGTACACTTATAAAATTGATATTTTAATCAGTGGAT GTGCTGATACGGGCACTGAGATGATGAATAGTATTAGGCTGTAGTACCTTATGTA CGCAAGAAATTTTAGAGTAAAGATTAGTCTGTGGGTAAGGAAAAAGCTAAGTTATG ATTATCCATGGCCATGGCATCTACAAGCTGATGAACGTACCAACATTATCTAATTT AAGAACTTAACTTGTCTTATCCTCTCTTAAAGTCTTAATTTGCACTATTAAGCTTA GGGAAGTCGCAACCAAACTCGTGTAGTATTGAGATAAATTATTAAACTTTCTTAGT ATCTACTGATATCCGTATCAAGTATGCTTATAAATTCTTGTTCTGCCTGACAGGCT AGTGAATCCTGCACCCGGGACGATTGCAGGTGTATACAGGCCGTCACGCTAGCAAT CAATACCAATACGAAATAAGGGCTAACATTTTTCGTAACAGATTAGAAGCAGTCCC GTTCAGAACTTACCACTGCACCAACGGAGGTACTGAATTCGGACTCATAGAATCCT CGAGTAGTAAGACCGTAGAAGAGACAGTGCATATTAATGTCATAGATCAATTTATA TTTTATATGGTTGCCCATTTCATGATACCCCTTTAAATTTATAACTTAGAAAAGGA GCCGCACTAATAATGAGCGGCATGCTGTAAAAAAGTAGGCCAAAACGCAAGATAAG GTACCTTTGTTGTCCAATCAAATTAATTGATTTATTCTTCGATCGATCGACCGTCA TAGTTGAAGTAACTATTTAGTTACGGCAGATACAGCGTATCAATTCATTCGGTGAC TTTGCTTAGATAACTGCTCGATAATCCGGAATTATCATCGTTCAAAGTCCTTCCCT TACTAAGGCTCTTGGATTCAGATGATCGGTCATCCCTAACAAACAGCCCACTGCCA TGCTGCTATGGTGACATTCGTTACTACATTGATTTCTGCAGACCTTCATCCATAAT ACGATGGTAACGTCTCGCTTACTATGCACGGTGTGCCCCTGCCTATATCTTCACGA TATACCAAGTGGAGAACCGTAGGCATGTAGTCATTCAGGTGGCCACTCTCCTTCAC ATTATGTTTAGAGGTCATGAATAACCCTAATCGTGTGACCTCAAACAGCATCGTAT TCCGAATAAGTAACAAGTAGGGGTGTTTCAAGTTGCATGACACAATAGGATATGAT TCTCAACCAAACTTGGCAATAAACGCATAGGTTTAGCAGTACTAACAAGCCATTAT GTTTAATATAGAGCATGGCTTACTCTGTCATGTTCAAGGTGGCTAAACCCAACGCG TTAATACACTCATCGGTTACAGTGTTTTTAGAAGAGCAATTGATATCTCTTCAGGT GATACCTGGTTCATTATCCTAATTCAGTTGGTTCAGGAAGCCTTATAACTACCAAT TCGATATTTTTAAGCATATAGATTAGGTGATACCACACCGTAGGAAATTGTGCAGA ATTTGGTGTCTAGAAATTTAACATTAAGTGATCAGAAAATTCTCTGTGTTAAACGA CTGTTGCGAATCTGTGTCTTTCAACCTCAAGTACGATCTC |
| 16 | 40.10% | TAACAACCTGTAACTGTCAACTAATGACCTCCTTACCAAAATTGAGGGTAGTTGGT TCAAAGAGAATGCAGCATGACGCAGAGCTTGTAGTCACATCGTTCTTCTAGTACGC AGAGTGTAGAGTTAAGATTATTAAACTCAGAGCACGTTGTGGACAAACCAATACCA GTCCATTCAATTACATGGTATCTAACAGTATCGTACAACTTTAATATGGTCTAGGG CTAGTGAAGTGTACCAACTACTTGATACGCAGTAAATAATTTCATCCTATCTTTAC GTCGCCATCGAAAAGCAAAGTTATGGCGCGTGGAAATTCAGATGAACCATAACCAA ACAGATAAATTGGCAGCAGTTTTTTGTAGACATTTATATAAGAGAGCTCGAGGCG TAGGTTAATTCTATACAACGCTATGATAGTCAAGTTCTACTTGACCAACTACGCTG GGAATGTTTATTAAATTCAACTGGGGGCAAACTAGCATATACTGTCTGAGTGTCCT TCGATGGTTCTATACAAACGGGGTGTCGAGGTACTAGTGGAATGGAGAAACTACCG ACAAACGCATATCTTATCTTCTACTCGGGATTTATGAAATTTTTTGCGTATACTAT TCCTGTGAGCAATGTTCAACAGCGTAGTGAGCCTCATAACGTCACATCAATTGTTT CACGTCTGTGGCTATCGAGTATTCCTTAACTTAACTAGAGTATAGACATTAGAGTC TAATTCTATGCAAGTTAGATAACTACTACTACTGTCGTACTTCATTCAGTTCCTGC TCGTACTCGGCGACGCTATAACCGGCCTAGTTTGTGCGTCGCCAGATAACTGTTCC TTTTAAACGTATAAAAAGTACGAAAGATTAAACCCAGCGGAAGTTGGGCCCCATAAA TGTCATATAGGGACTCAGACTACTGTTAAAAACTCCTAGTATACATTGTAGATAAT CAACTAAAGTTGGACTATCAAGAATCAAACTGTAATCAGGTCACAGAACAAATGGA CTAATAGAGCTATCTAATCATCATACAGATTTATACCCAGTGGAAACAAAACTTTA CCCCTTGAGGATTTACTGGAGTTGTGTCAAGTTAGAAATCGGTCAACATAAATTAG AAAATGCCTTGGAACGCTGTATAACTGATCACATATAGCTGTGCCTAATGCTTCAA TCGTCAATGCTGACCACAATCTACCTGACTTGGAAATCCGCTACACCCATATCCAT ATACTTAAAGAATCCGTACTTTATATCCTATTCACCGATGTCCGATGTGGCGCTAT GTGTGTCTAGTAGTATATCAGTTCAAGGCGAGAATGAAGAAGAATACAGGGTCTCT TTAGAGCACTGTGTCACTGTTTCTTAGGCCAGTTAATTCTAGAAATCAAATAAATG AATAACTCGCGACGGCTCAAAAGAAATCTATGGTTTACGCATAAGCTGTAGGTACT TCTAAGCTTGATTTGCTTCCGGGGGATCCTAATCTAAATGTGAAGGGGCAGATTTA GATCTCTGCTCATTGAGTGGGAGGTTGGACATTGAACATAGAACTACCTTCCCTGC GTGCTGTAAGATTATGAGAATCTATGCTCGGTCGTTGTCTAAAAATCAGACTACAA GGGTAAGAATAATAACAGACCGAAATAGATGTCTCCTTCAAGATAGTCAGTTTGCG CAAGTCGGCAGGAACGTTAAGTAATCCTGAGTTATAATAGCGCCCTTTTAAGCTT TCCTGGCGAAAACCGAACCAAGCCCCCGTAACACAATGTCTACTATCCGTACGAAAG TTAGTGTAATAACGACTGTACCTATTATAAGCACATTTGGTTGGCTATCTTCTCCC TAGATTCCTGGCGGAAAAGAAGCATGTCTACGTTCGATAGGACTCATTTTTGAGGA AAACTATTATAACGGCTATAACGCGCGATTAATCCCTGTCGGTCCATCATTCACGT GAGTGTAAAATTGTGATTAGTACTTAAACGGGTTCGTGGA |

TABLE 2-continued

Exemplary 2.0 Kilobase Stuffer Sequences Having 40 ± 5% GC Content

| SEQ ID NO. | GC Content | Stuffer Sequence |
|---|---|---|
| 17 | 40.70% | TTGACGATTTATATAGCTACTACTTAGCCTTACTACATATTCCGGCGTGCCGGTAG ATATGACTAAGTTAATACTTACAGACATTCAATATTAGGATTTCGGTGACCTCGAT CTCTCTTGATTGAATAAAAAATGGATATTAATGCGTCGATAGTTGTGATAAGTTAT GTATGATGTCCTGAGGGACATATGATAATCTTCTAATAGTTACCTTAAACCGAATT GTGTTTATGATGAAAAATATAGGTGAAGTTAGCACCTATCACCAGACTTTGGGATA GTTAGTCCGTACCAAGCAGCAGTTCAACTGACAGGAACGTCAATTCTGTCTCTCAT TACTTTGGCCATGGATTGAAAATCGACTTCAGTCTGACTCACAACAGTTATAGAAG GATTTTGGCTCACCACTCTTCGAAATAGGTCATTTAATGCGTACTGCTTTTTTTGA CGGCCCTTTATTCATTCTATTGAGGGAATCCCTAACTTTAGCCACACGCAAACTGG TTTATATGGATACTCTCAAGATTGTTTACATATCCAGAAGCTTATACTTCCTCAAT GTGATGCACACAAGGTGGGATCATCTTGTTTCTACAATGCGAATGAATTAAAAAT CGCCCTTCCTGGCACATCTTGCTGTACGGCTACAGAGTAAAATTAGCTCGTTATTT ATGAGTGTTTACACAACCCAAATCTAAGTCGAATGTACTTTAAACTTGGCGTGGAT TCATAGACATGCAATCAGTGTTAAATTGTCACTCAAACACGTGCCTGACTTCAGAC AAATTCATGGATTCAAGCTGCTAATATTCACAATAGACGAGATAGGGGCGTAGCTT TTTCTGTACGATGGGGGAATATACGAGCATTTCTATGAACCAAAACAGGCAAAATG AGCAAATACCTTGTGCATCATATAGTTTCCATCAACTGGAGAAAGCCTCTTGATCG GCTACAACTTTTCAAGTCCTTGCGGCGTTGGCCCTGAAGTACTATAGCCTTTTGTT CTCACTAATCTAGCCAATCACTTGTTGACTATTCTTGCCTCACCCATAGAGTGGTA ATGGAATTCCAAAAACCTATTCCCGAGTTTAACCCGTATTGTTTGAGAGGAGTTCC TAGTGTCTTCATTAAATTGCACATGGACTCTACGGAAATTACTTTTTATTAAATCA TAGAATCTCTGTCATCAGTCCATGCGTCCTCAGTCAATAACGGTCGCCGTGTCTAC GGAAAGGTTCATTCTATGCCTGTAAAGTACATCTAACACAATTTAGTGTGGGTCTT CTACTACAGTTCACCCGGGAAACGTTTTATGTACGAGTGTTGGTAAAGCGTCCTCA TCAAGTCGATCCATTGTAAGGAATCGACTATATACTCCAGCTTAACTAGGACCCCG TTACATCTTAATGGTAGGTCTAAGAGGTGATAAGACTGGAACCTACATCATGAGTT GAGTGAGCAATGAGAGCCAGCAAATGGTGGGAAGACTAGACCAACACAGGATCTCA TGCTTCCTGTAGCAGTGCAACTCAGTTCGCTGCGAAAATAATTAACATATCCCCTA TTGGCAAAACCCTGCATACGTATTTAGCAAATATCTGTAGGGGTCGTCCAATAGCA GTGCCGTTTTATAAATTGGGTTGATACATAACACTGAATCAAGTGAAATCGAACGG TGGTAAAATGGCTTGAAAGGGGAAGTTGTTTAACATTCGCTAGCGACACATGTTGC ATGGTTAGGGTTGCTATTTCGCCTCATTCTCGTTACGACATTCTCAACCAGTAGCC CACCAACCCAATTAAGGTCACGCACGAACCTATCATCCACTTACCTCTTACAACAT AAAAATAGTCAATACACCTTCCTCAATTAGCCTTAATCAAATAAAGCTAGTTATTTT TGTCTCCTGGGGATCAGGGCGCTTACTTCGTACTCGCTTCCCCCGCTAGGAAGGCC ACTGGTTCCCGAAGAAACGTGAATAATTGCACATGCTTTA |
| 18 | 39.50% | AGTATGGAAGGTGCCTCGGTAATTACGGAAAGAGCTTATCTGCCGGAAACTTTTAT TTTGTTTCATCAAAAGGTTATACGATAATACCGCATCTACCTTTTCGTATCAAAAT TGGTCCACAAATCCAACTTATTGTCATCTTGAATCACACATTCATCTTTCCGTCTA ATGAAGGAGCGTCATTACTTGTTGTATGAAACGCAAATTCTCTACACTAGTAAGTG AGACATTAACTACAGCCTATTAAATAATTCAGGTAGACTGATGAGTAATATTTCTT CTATATATATGTGATACTCACTCTCTACTGAGTTGACTAGTGGACTCTTTGTTCTT GTACACACACAACAGAGAAATGCCTAGAACAAAGTCAAAGAAAGCGCCTAGATGAC TTTGTAAATTGCACCAGATCTGAAGTCGAGTCGTGAATAGAACTTTGCATAAGACT CTAGGACTTCCGATGGCGTATTATACTTAGGAAACCAAGCCGGTAGTAAGAATCGA GGATAATACTCTGGGAAGTCTTCCGTATTTGCGTCAACAACCAGCTTCTGGATCAA GCATTTCTTAACTAGATTAAGCTTCCTCTTTCGTTTTAAAGCGTTTTACTTCAGCA ATTGTAATCCCTACATTTGTATTAGCCGAATAGAACGATGCTCCTACAACACCAGG CCGACCTCATGTTACGATGGCCGAGACCATAACTCTTCGATGAATCATTAGTGGAA GAGTTATCTACTGACGGCATGATCCTGGGACATGAAATTGGAAAGCATTTGCACAC GTTAATTCGCCTTTTACTTCAACGCTCGGACCCGGTATAAGATAAAATTAGACCGT TATCTTCGTAGATCGTAATACGTATCATCTCGTATATGCCGCTTGTATTCAACGGT TTCCTTTTTAGACTGGAGCGATCTACGCTGGCTTGGTTTAAGGACTATGCTAGGGT TTGTACGTAATCCCTTTAATAATTAACGACCGAGCTGACAAACTGAATAAGTACAG CATCAACAGGACGGTTCGATTGACAGCTGGAAACCTATTAGGCATCTTGGCCCTTA GCATAAGTCCCAGTATTATTTGTTCCTCCAGTAAAAATCTCCCCGGAATTAGAGCA GCGGTGAAATTTATGGACTTGACCTTTTTGGTTTAGTCGTAGAGGGACAAATATCA TCTCATCTGAACGCTCATCACCAGTTAGTTCATCCAAATTCAATTAGGAGGCGTCA TATTGTCGGGCGTCTGTAACGGAGCCAGATCTAGAAGTTCATTGCTATAAAGAATT AGTGTGCTTGGCACATCACCTAATCAAATTTTGGGAAGCAGCATAGCTATTCAGGT GTTGGTCAACCAGATAAAGTCTATGAAGAAAAAAACCTGTGTTAGTTCTGCGTATT AGTATTGTAGTATAATGTACGACATCCCGAAAGTTAAATTCAGGTCGCAGAGTCCC TAGTCCACCGTTCTAACTCACAAATCGATGTTCGGACATAGCTATTTAACAGTCCA TATTTACCTTAAGTGTTTCGACTTATGTATGCTAGTTAGGTGTGGCTCGCCTTC CCACTGTTAGACCACATCTAGACGGACATCGTTAATAATATCTGATATACACAAAA ACGTTTACCATAGAAAACACTATATTCATGGACACTTTATCATATTCCTCGCCCAT CCTCACGACCCAGATAATAGGGAGTTGTAGTTTTTCTAAACGGTTTTAATATGCAG GTCCATAAAGCATGCAGTACATTACTGTTTAAAACTTTAATTCAGATATATCCTGG AGAAGAAAATCTCGATTGGTTAATCACTTCATTGTTAAATTCGATTTCGCTATACG TTTCTGTACTAGGAAATTTTTCATATTAGGCACGCGGTGTTGGTTCCGTAACACTA TTAAATTTCCTCCCGGTTCGATCATGGCTTGCGGTAAGTCCTCAATTTAACATAATT GAGATACCGAAATCAACCCAGCGTCGCAGTATTTTGAGTT |

TABLE 2-continued

Exemplary 2.0 Kilobase Stuffer Sequences Having 40 ± 5% GC Content

| SEQ ID NO. | GC Content | Stuffer Sequence |
|---|---|---|
| 19 | 39.60% | GGTTAAATGCATGCTCACGCCTCGCCAGGTTGTTAAACCATGTACTTACTCAATTT GACAACTGATGTCCACTCTCCACCTCGCGCGATGCTACTTTCTTAATACTAACGCC ACCTTGTCAAACACCTAGATCGTTCTAAGTGTAGCACCAGACAGAGTAGACACCGT AAAAGGTGAAAAGGGGATTAATTTCTCCTCCTTTTGCACAAAAAAGTTAAGGGGTA GGCCGGAGGAAGGTTAACGCGAAGCACCTGCGTAATCGGTTTCGTGCTATATCGGA GATATACCGTAATGACTCGTCGACGAAAGTCGAAGGCTTTAAGCTCCATGCCCCAT GTTGGTGCGTTAGGACTTTGGTAAAGTGGTAAAATTTAGATCTCTTTGTGTCCTTT ATATCAAGTTAGTGTGAATGCTGAGTTTTCTCATTTTTTAATGTAAGTGATTAATA TGAAGATGTGTAGTCTAATTTGGAGAACCAACTTAAAACGGAATAGGATCGGTGTA TCAATGCATATGAAACCGGTAAATTTAGTCCTGTTGACCTGAAACTGATGGGAACA AACCCTCAAACGCTATCGCAACACCGTCCTAGGTTCCATGCACTATTAACCTGTTA TTGCCCGTGCGGAGATCTGGTTTTTATTGTTTTATACTCTAGATATATTAGCGGTT ATGTTTTTCTGTTAATTTAAGATGCATAGTCTACTTTGACCTCCGGCAACGTGATT TGTAGAAAATATTTCCCACACACTATATGTGCTACTCAGGTTACCCATAGTTTA TGTAATAAGTATCACTTTAAACCCTCCACCCGCCCATACAATAGAAGCCCTTCAAT TATACGAGGAGGTATTGACCTGACTAGTTTACCAAAGCCAAAGATACCTGGACAAG TTGGACAAATACTAAAGGACTACTGTAGCATAGTGTTTGCGGGCCAGTATACGCTT ATTTAAACGATACTACTGATAAGAAACACTGGGGTCAACGTGCTTTCATCACCTGT CCATTACTCCAACAGTCCCAATTTTTTAAAGAAGGAATTTTCGGGACAGTGAACGC GGAATCGCTAATAATATTCAGATAGATAGCTCGACACAATATAACTAATCAGACAA AAACTATTCAAAACTTTCTCCTAGGTAGTGCGCGGCTCTTTTACGTGGGGTTTATT CACCTGCGAATTATCCTGATGCCCAGGAGCAAACTCATTATAATACCACCAGGTGA CAGCCTACAAGTTTCATGGCATGGCTGCAACCTGCACACGAACGCTTATGCAGCAT GTGCTCTTGAGTTATACCAGCTACTTGATTCGATATATGGTTTTTGTGAAGAATTT GATACCATTGACACGGGATGTTGCAAATATTTAATAAGTCCATGCATACTAATACC AACGCCAGAGATAGATTGTCAGTAGAACTCTTGAAGTCAATATGGACCGAGTGACT TGGGTGGTTTATCCCACTGTTAGAAAGTTATCGTAAAATAAATTCTTGGTCAAATC TAATCCTTATAAACACTCTGTTATTACTCTGCTTCGAATATGTTGTTATTGACCAT GCTGATAACTACACCCTTTATGTTAATTCAAGGCATTCTCTGAAAGTCAACAATTA ACTTCATATCAGACATTTGACCTATTCCTCACTTTTCTATAACATGACAATCACGG TGATTAAAAACATGACGCGTATCGGCAGCAAACCACTGTACTGATATGTAAGAGCG CCCGTCGCATAGATATTTTAGACTCTGTCCAAATCACTCTACGCCAACTTGAGGTC AGAATGCATACCGTGGTAAGCTGAATAGTTCTTATACACTTTCTAATTTACCCAGA TGACGATTTTTTGTTATATGAATGACGATCTTGGCATTATACTGCCAAGACTGCAA TCAAATCCTAAATTCATAATTTAGTAAGTCAATAGCAGATCTGAATCCCATAAATG AATTCTATCGAAGTACCTACACTATGTCACGTAGAACAAG |
| 20 | 39.60% | CTAGGTAAATTCTTAGGTAGCCGAGTTGAACTATTAATAAGTCTCGTCTGTGAGTA TGTCTTCCGTTAGGTATTTTCATATAGCTTCATGTGCCTGTAAAGACAGAAGTATA ATTGGATACATCAGACTTTTTATCCCTTTTACAGTCTAGAAAGACCTACTTGAAAC ATGTTTCTTAATGGGTAACGTAGTGAATTATGCTCGTTTTTCCTTTGGTAGAATGA TATTTATCTCCATATGCTCTGAGTTGGATAATTTGTAAAGAATTATACACGTTAAT TCAACCTCTTTATCAATGAACTACGCGGGCTTGATCAGAGTAAACTCACAATAGTA TCTTGATCTTCACAATCTGATGGATATTGATGCGAGTTATACGACCTGTGGCATAT CAACAATGAAGTGAAGTGTCTGTCCTTATGATTCGAAACAAAATAAGTGTCCTTGC TAGCTACACCCACACCGCGGTGTGCATCCCATAAAGGCTCAGGTATAGTCTTGTCA TAAGCGCTACACTGCCATTCGTTTAGAATCATTGTTTAGCAATCTCAAAAGTAATA ACATCCGACTTTCGAATAGGTTCAGTTTCCTGATCTACTGGAGCCTATATATATGC ACAGACGAATCTCGTACATGGCATAAGCAAGTCATGAGAAGAGGCTGTACCACGTA AATATAAGCCTCTGATTACGCTGAAGCTTAATAATCATCACCCATCTACGAATCCG ATTGAGGGCATAGGCTTTCATGTCTTTTTCGCTGTAGGTCTATGCGATTGTGAGAC TATTGAGTTTTCCACAATATGGTGGTAGGTACTGAGTAGGGTACATTTCACTGTCC TATTGCGCTGTCGTATGTCTATCCGCCGTTGCCGTCGTCGATGTTATACCATTTGA CTAACAGTGTTATGAGTCACTCCCTTGGATGCGATGTACCTTCTGTTGTGAGGGAT GTAAGTTGCAGTTAAGCACTATTAGCGAATAACGCTAGGATTCTGGAAGAAGAAAA CACAGGGTCGCTTCAGGTCTCGAGAATCTTACGGTTAGAAAATTTGGATCTGAATA AAGAGATGTCTAGCCAGTGTGGGGGTTGAATAAGCTAAATGTCTGCAATGTGTATG CTTCTGCACAGATATTAACAAATCCGCCATATTTAGGCACATTTGGTAATGGCTGA CAATCGGATCTCAAGAATTCTATACTGAGTTATCGGACTACAACTAAAAAGATGCT ATATAAAATTGTCATAATTCATGAAAAGCCAGTAGGCCGACCATCATCGCTCTAAG TTGAGTTGTTTGACGCGAGGCAACATTACGTGCATGGACGATATACACGTTACTAG TTGTATGGTATTTCGGCTAAGTTTCCTAGCTAATTTCATTAAAAGCTGCGCATTGG TGTTTTTCAGCCTATATACTGACGTAGTAAACTTACATACTTAATTATACTAGGTA ATGATATAGAAAATGGCTGTACATCCTTTCTGAAATGCTTCCATGCAATGGTGCTA CAAGTCTTAGATTTACATTATAATCGGAAAAACATCAACAGTATGATTACCTAGGA GGAGCTAGCATATCCAGAAAGTAGAATAGCAGAAGCCACCAACAGACTGGGTGAGA GTGACGTTATGACGGATGGATCATACCCCATCTTAGGAGGGTCAGGTCATTTCTCA ATCATATGTTTCCAGATGCGATGCAAAGACAAGGCCCAGAAATTTCAATTGTAGGC CAATCGTCCGGTCGTATTAATCTCAACCAAGTAAATAAAAAGCATGTGGGCTGGGC GCAGTCAAAGTCGCTTTTCTTGGTCCTTACTAATCTGAAGAATATACAGTAAACAG AGGATAGTGGGCTAGTTCAGAGTAATAGGCAACAAACCCTTTCATGCATTACTGT AGAATTTGATACTATTGCGTGTATCGCTTTTAACTTTATAAAGAGTCGATACAGCG CAGGCTCATAATGTTTGGAGTCTGTCTAATAAACATCTAA |

TABLE 2-continued

Exemplary 2.0 Kilobase Stuffer Sequences Having 40 ± 5% GC Content

| SEQ ID NO. | GC Content | Stuffer Sequence |
|---|---|---|
| 21 | 40.50% | TTTATCTATTTCATATATTGCTAGATAAAGTTGACTGACTTATTACGATTATTGTCCCAGACAGCCGAGCTGGGCCGTGCGTCAATGCACGGGCTCAGCCTCCTAATGTTAGCATTTGTTACTCTTGGAACATTTGGATATAGTTGATTTTTTGATAGTGCAAAGGTTCTCGGTCATCCGGTATAACGATACTCCCTACCCTAGACATTCAATCGGTGCGATGGTAAGTCCGTTTCGCACTGAAAGCCTGTAGAGTCTATTTGATGTTTACTTAATGCGATTTGACTCAAATGTAGGTTAGGAGTCCGTTCGCATCCTATGCAGTGATAAACTATCTAGTGTGTTTAAAAAGACGCAACCACTACCAATCAGACCAGCAAATTTACATCAATTTATGTCAAAACGCCCTTACTTCGTCTAAATATAGATATATCACCACATCAAGCCTGCACTTCTCACACTATGTTCTATGTCATGTCGTTGTACCGAACAATTGATATTTAACCGGAGTTGAAGATCAGCTAAAGAGAGAAGTTATATAACCAACAAATACAGCCCACCCATCAATGATCGTGAAAACAAACTGTACTTAACAGTTCAAGAACAGTCACCATTTCTCGACGTACAAAAGATTCTTCCATTATGGTTCGATACAAATTGTTCAAACGCCTGTCTATAGCAGGGCTCCGCCATATTTCGAGCATACTAAATCATTGGGTGGTCAAACAGTCTCACAAACAGGTCTGTTGCGATTCATACGAGACGACCATACTTAGGCGTTGAAATGTCGTTGCATTTAAGTAACAAATACTATAGACCGCTGGTAGTCGCCATATAACTCTGGCTCCAGATTATACATGACCTGTTTAGAAAGGCAATGGGAAGAGGGCAAAACCCCAAGATTGTTCCTAATAGTTGTAGATAAATGGATGATATCTGCATCATCACTGTTTAGAGAATCCCGCTTTCCTTTATTCGGTTATACTCACCGTTTCTCGGCGGGTTGAGACATGCATAACTTCTATCTATCGTTGAGAATTATCAACTTCAATTCCCGAGACTGTCATTATCTATAGTTGAGGAACCTTCGTCGCTGCTATTGAATAGTAAGAACCCCTCTAGTCCAGCTGATGCTTGTGGTAACTGCACTAGTAATTCATCTGCCATCCGTGCTTAATTGGGCATGCTTTGTTGCATCCCACTCCCGAACTTGAAGGTTGGAACTCTCGTTTTGCCAGCACAGTTAACAGGGAGTAAGACCTATTGGTGTGACATAACAGTTAGGTAAATCCATCTAAACACGTGTGTTTACTAATATTCAGTCGGTGGACTAACAGACAGGAGCTTACCCATCCGTGGATGTTTTCTTAAGGGTGTCGTTAGAATGAATAGTACATGTATAGTACTGTCCGAGGTGTAGATAGAATAAATGTGACCGTGATCTCAGATTTATGGTTCAAACGTTCTAATTTTCCGAGGAGTAGTACATGTTGGTACCTTTTCACATTATGGTGCTAATTAGGCATGTATAATATCATATCATAGCTTTGCCCATACTGACTATACTAAAATTGCTATTTTGGAAAGTTTATAAGGCCGTTTCTCATTGTATCTAAGACCTAAGCTTCGCGTCAAGAAATACCCTTACAATCGGCCTATTTAAAATTATTCATTTGTCTAGGGCGCGATGATCCTTTCCGAATATTTTATCGATTACTACTTATGGATACCCGTTAGACGCTTATCCTCCTACTACACCGTACTAATTACGTACTTTTTTCGAAGTACGATCTGATTAGTGTCGACCACCTTGCCCTTAAATCTGATCGCTCCCACCAGTACGCAGGACACACGTAACGGTTTCGATACCCAGCGAGATCAGCCTTACCAGTGCTTGTGTGGTATAACCACACTATTTCAATGCACAATGACAAGAGTACTATGTTAATTCACATGCCTATCTAGTTCAATTACGTTCAGACTCATAAAATGCCATTGCT |
| 22 | 42.00% | TCGAAATTGGATCGACGGAGCTAATACGCAAATTATTTGTTTGTGATTTCTATCGCGCTTCAAAACCTACAAAAAATAACAGCCTTTGGTGTAATTCGTCGTGGCCATAAATATGGCTTATTCTATATATCCGAGGCCCAGGCCATAACAAATTCTCCAAGATTTACTAAATTAGTACGGCCTTCATTCCGACGGGAAGTTTAAACTCAAGCCATGGAGTCCGGTAGTCTTTCAACTTTGTCGTATGACGGTATGCTACATGCCCCAATCCGCTATTGAACAATGGCAAACACTACAGCAGTTAGCCAGAGAATTACGCTCTTTCACTTTCCTAGAAGTACACAAGTCCTGAACCTACCAACTGACTGTACACACCCTCTATGGTACTTTTGCTGTTTAGTTGCCGAATGATGCATCATGTCTGATTTTTCGGGCTAGCCTTAGCTGAGTGTCAGCTTCACCCTGATAAGACAGGAGTCAGAAACGGAATTTCATTAATACCGCCTAAGGCGAAAGAGAGGCTGTCATGTAAGCGGCAGGTTTCCCCCTTACGGGCCCACACTCTCCCCTCGCTATGAAATGACACTTCACAAACAGTCGCTACTCAGGATTTATTCCAAGTTCCAACGATGTTGAGTACATTGAGAATGTATTATATTAAGCTAATAGGCAGTTTTCTCCAACTATCGATTATTCGGCTGATATAGCCCCATCCTGAGACGTTATTACGTCACTGAGGATGATCTATTCACACAACACTTGGGTTACCATAGTTCGGAATGCGATCTAACGTCTCACAATGGTTTTTGGTGGAAGTATAGTCTTATTCCCCGGGCTATCGCAAGCACCCAGGAGTAGTTTCGTTGGTGTCATGCTTATCCCTACGACCCACCAGAGTGTCCAATCAATTTACACCTAAACTGGAACCTAATATATTAATCAAACTTTAAATCTCTATATATTCAGACTACTTTACTCACTTTGATGTTAGATGCGTAACAAGCATATAAACCCGTTTGTGATCGTACTCAATCGCACCCTTCTCGTTATTGATTGATCCTTGCGCGAGGTAACCTGGGTAATCTCTAAGTTATCGATGCACCGTATCAACATTCATGATCGAAAAAAGTTTAGTGAGAAGGAGTTAATGGATCGTTCCGACTAAACTAATGGAATTATGTATGGGATGTATTTCGTTTGAGCCAATTAACTAGGAACTAACTCATACATCTTGCAATAGTGGTAGCGTAAAATGGTTGAACGTAGTTGAAATAGTAGGGATACGACATGTCCCCTAAGCCTCACCCTTGGTAGTTCTCGTAAGCGGACAACGCGTTATCATCACGCTTTGGAGTGTACTAGTTTATGTCTACTGCGTTCGCTGACAATAAGAACAGCAATATCCCAATTCTCAGTACTGACGTAGGACCATTAGCGCTATAAAAAAGTAGCGTGAACTGTCATTTATTAAGCATTCCATTTTATCCAGTGTCCGCTAGGCGGCTAAATTATACAAACAGAACGGTGTTCTTATACTGTTACTACCTCCACAAGTGGGATTTACGAACGCAGAAAGAGATAAGCTCACTCTCGCTATGTGCACCGATGAGTCATACAGAGGTCATCAGTAAAGGAACTCAATCTAGAGTTACAGTCCAGCAATCCAATCCGGATGCCAACAGGCGTAACGATTATATTCAACCACTAAGCCGCATAAAGTATCGATGATTAGCGGGGGAATACCTCCTAAACAGTTTGACCGGAACGTCTACAATACTTTGCCGGTTATCAATGAAATATGCGGGGACGAACCATGCATCGTTACTCAGCCTTTGGTGTACGCCAGTAGGAGTACTACTTGTTCTTCTTACACGACACGTAGCTACTTCTATGTATAGTAATGTAGTTGACTATAGAATGACGAATAGAGAAGGGAACCAGAGCTCACTTATTCCGTCAACTCGATTTATCATGTTGTTAAAAAAGATAAAATGT |

TABLE 2-continued

Exemplary 2.0 Kilobase Stuffer Sequences Having 40 ± 5% GC Content

| SEQ ID NO. | GC Content | Stuffer Sequence |
|---|---|---|
| 23 | 40.00% | GCTACTATTTTAGATATGCATCAAAGAAAAACAAGGACATCTCCTGTATACGTATAGGTAATAAGAAGAGGATCCAACGGAAAAAGCCACCGGTGGAGATAATAACTATTGTTAGCAAGTCCAGTTTTCTGTCAGGGGCAACGTTAAGATAGAGGCCAGGGTAATTATTTAACTACTAGCTGCACTTCGACTTCATTTTCTGAGCTCTGTAAATACCAATGGAGCGAGTAGCTACGGTTAAACAGATATCGGCTGGATGTCGGTGGTAGGAAAATGTGCCTGTTGCGGCTGATAAGCATTAACTTACCTAAACATAGATTGTTGGTTTTCCTAAGGTTTTATAAGAACGTATATAAAGATTTCTTAAATGACAAGCTTAGCCTGCATAGGCTACATGTGAGTGTGGATGGCTTCGACAGTGATCCCGCAGTGGACCAGATTCCATTACCTGAATGAAAACGTTCAATTAAACCACTTACCGTATCACTCTGTCCTTGTAGCCCTGTAAAATGAGACTTGCGGATACCAAATTAGCCAAATTATTCATCTAACTATAATACTTCTTCCATGAAACATTAATACGGCCACCGGGAAGCCACCGATTCTGTCGCCTTATATTTTTTGCTCTATGTCTTTCTTTTAGTCCGACAACTAATGTGAACAAATTTCGACCTAACAAAATAGAGACAAATAACCCTATATTAATACAACGCTACGAAGATCTTCAATAGGATTGGTCCGATTATAGACCAATTATACTTTTACATAATATGTACAAAACATCTCGGCATTCGATGGCATTGGCGTGGATATTCGATTGTAAAAGCAATGGATTTTCTTGCGCTGAAAATGATGATCGCCCTCGATCATCTGTATAGCACGGGTCGAAGTTTCAGAAATGATAGTTGCTCAATTTGGTTCACTTCGAATTTACGCTGATGTCCCAAGCGACATGTCCCCGATCAACATGGTTGTTGGATATCAAAAGCTGATAAAAAATGTGAAAGGACACGCCTCCAACGCGTAACTGTTTCACCTACTTCCATTTCGAGGAACTGGGTCGATTTAACGACATCAAAGTTGTTTGCTCAGACAGTCTTCCTATGAAAATGAAAAGTGATCTAGGAGTAGAACCCGATGGCTATTAATAAACACACTCTTACTAAATAATTTGGCGAGCATCAGAGCGTAGGTACTCGGAACCTGATTGCCGTTCCGCTTTCTATACACTGTGAATAACAAAGTCATTGAGGTGACAACCTTGCCGCGTGCACGGTCTAAAGCATGAAATTTTAAAGCAACAATCAAATCTCTAACGGCCTATCTCAAGTTACGCAGCTGGCGGTAGGTGGGTTTTCGCACTGACTCTTTAACCAAGCTGCTGCTAAAATACTCTTACCTCACTGTTGATATAATGGTCGCGATTACAGATAATCCCGCACATCTGTCAAATAGAAGATCCAGTAAAGAGTCCAAATCAGAGAGACCCAATAAAGTAACCAAGGCATTACCGTTTCACGAGGTGGACTTTCATGAAAGCATAAGTATGGCGTATAATATAATGTTATTTGGAAAAAAGATCTCCACAACCTGTTTTACCGCTGAAAAACCTAAATACCGTACCAGACGAACCACTTGATAGTCGAATGCGCCATTGAAGGAAACATTCTCCGTTAATCTGATTTTAAGCTCATCAGGCTTTTATCTTTGCGTTATCTACATTTGACGATTACCAAGGATCAATTACGTGATTGGACTATACTTAATATCAATGTACGAAATCGTCTACGATACTACAAGGTAACCACTGATAATTCCTCATTGCTCTATGTTCACACTGACCTTGCTAATCGACGTGGACTTGCGTCCTTGTCTAGCTTATAATAGTGAGATTAATGACAATGCTGGTATAATACCGTGCAACTACACGCATAGAAATTACTCAGCGCTCGAGAAAAGTAGATTACTTCGCTCCTTCGGAGTTTTGCGTATTTTCA |
| 24 | 41.00% | CCTCATTTGCCCTTTTATATTTACCCGAGTTAGTTCACGAATGTGCCATAATTCTGGTCGCAGCAAACTGCGGTGTTTAGAAATAATCTTCCGTTATTCGTTTATCAAGACCTCGTTGTTTAGTAGTTCTAGCTGAATGCGGTCTATTAAGTTGGAGAAGATCTGGGTTCATTACATTAGAACCCAAACTAATTATTAAGTTCTGCTCATTAGCATTAGGTAGAATCTATTCTTGTCCGGCGCTGTTGCTACTGGGTTTAGTCTAAGTAGTACTTTAACTGTTCCTAAGGGATGCTGCAAAATGAGATATACTCCTCCGATAATGATCAATTTGGATTTTGGGCAGCGGTAAATGTTTTATAGTGTGAATTGTGTTACTAAATTTCATGACGTAAGCTGACCTTCTAACCGTCGTGCTTGGAGGATTTACGCGGCGCCAAAAAGAAATATACTAGTCCCAATCGCACTAGGATTTGTTTAAAAAAAGACGGAAAACCTGCAACCAAAGGTGTCTTGTACTGACTCTATCTGCAAAATTTGGATGTTCTAGCTCCGTTTATGGTCGCTACATGGAAACGCTATTGGTTAAAGATTCACTATAGGCCAGTTCAAGTTTCCCGAAAAATCGTGACGGACGTTATACTCTAACATTGATAAGAACCATGTATCAAGCGATCCGCAATATAGGGAAACACGGCGAAGATCAAATTTATAGATGGGAGGAAGCACACACAATATGAGTATTAGTGTGCTGAAATCAGCAGCGTAAAGTGCTTCTGTTCCACCTATACTTTTACGAGTCTCGTAATAGCGTATTACCATGTAAGATGCATTAAAGCTATAACTTTATGGCAAAAAAGGTAATTTATTCGCTCATTACTATTATTTGTCGTTTTGCATAAATAAAGTGTTGTTACTTCAGGAAGCTTTAATTCTCTGTCTGCCTTAACCCGAATTCTACGCGATCTCCGTATAGCAGATGAGAACCGGTGACACGAGACCCGCACTCGCAAGTCGTTTCTTGAGGCTAACGACAAAATGAAGCCATCAGCGAAATCTCATCCGTTAGGCTACCCAAAGTTAAGACTTTCCCTGTATCCCGCTAATGCGTCAATTGGTAGACGTATCGGGATTAGATATTCAAGACCAAGTCAGGTAGAGTTGGCGCTAGTTGAACATGGACCTGGCCTTACAAACAAGAAGACCACGAGAGCCCTAGTACAGGAATTTATCGGAAAAAATAAGAAAATTAAAATCCCCGATCTGTGTGGTGCTCAAATAAGGCAAGGGCGCTTAGCCTCACAGTCGTTACTAAGTCAAGGTTCTAAAAGCACGTGTTTTAGCTTGATGGATCATGACTTCGCTACGGTCACTACTCCACCGTGTTTCTGGAGGTATGCAAGGGAAAATCGAGGGATGTGCTCAAATCTGTGGCAACCGGAGCACCATTCTAGGTAACTTCCATTAACTTTTGATTTAGAGTATATGGTTAAGCTATTAAACGTTTCCTAAGGACAAGTGGGATAGTGATATACTTTTTTCGGCGACATCAATCCAGGATTATCGCTAACAGATCGCCTAGCGCTACCGCATATGATGATATCCTTAGGAAGAGATCCACCCCGGCCAAGAAACTCCACACTCAATAGGCGGTGACCTATTTGTGAGTTATGCAGATGTGTTTCAAGACTCAACGCCGACAAAGTTCACCACCAGAGAGTGTAAGGCTTATCAAATTTCTGATTTTATCGACTTATAAATTTGACACGTCTAACAGATTCGGCCTTTGATTGTAAACATCGCCGCTATGATATTTTCGTGATCCTTTGGGATACGAGATGCATCAGTACTGGCCCCGAATATTTCCATTTTAATTACTGTGTAATGCTTAGGTTCACAATCAACAAGTAGTTCGTGAAAATGTTACTATAATATCCACACAAAGATTTACGCACTCTAATGGTGGACGTTGGACCTCTGTTAACCCGCTTTCGTTATT |

TABLE 2-continued

Exemplary 2.0 Kilobase Stuffer Sequences Having 40 ± 5% GC Content

| SEQ ID NO. | GC Content | Stuffer Sequence |
|---|---|---|
| 25 | 40.00% | ACTAAAGTCCTGGAGAGTATGCTTGGCCTCGTGCGGTAACATTTGAACAGCATGCT<br>AGGTGCTAGTAGACCCTTTCTTGACAGCGGAATTTGCTGTTATTCAAACCACCTGT<br>CAGGCCAATTCTGGAGCGCAACCCACAGTGATAGAAGATAGTCGTTACAATCAAAT<br>CCCACAACTTGAGACTAGCCCTCAGACTGCAACAGTACACAGTTATGCTGTGGAGA<br>CAAATAAAATACGTTATGTATTGGTCATTAGATTTGGCTTTCTTATACGTCGTGTA<br>GTAATGCTTGTGATCGGTTGCCGACATGGTTACGAATAGCTGTTTATTAATTTAAA<br>ATTCAATTCTGTCGATTTAGAGGATGGATAATATCCGCTATGTAGACATGAGTGAG<br>TTCCTTATCCTTCAATTCCCTTTTTTCTGTTATTTTGGATCTACGAATGAGGTATT<br>AAGTTCGTAGCACTCGTCCGTTTCGTGGAATGACTTATTCGAGATGGCTTGATAAG<br>GAATTGTACCTCAAAGGTTTCATTGTTAAGAAGATGAATTTTCACGCCCATGGCAT<br>AAGCATATGATTACGTCCACTAGGTCATAGACACATGATAACTCGTCGCTCAAAT<br>AATCGAAAGAACGTCTATCGGCCAAATTATTACTTTGATCCCAAAGGAGAAATCAT<br>ATTGGGGCGCGGGACTTCATGTGTATTACCATCCAGCAAGCATTTGATAAAAGTAA<br>CTCCTATATTATTATGAATAGCGGTAAGTTTCTTTGACCAACCTGACAATAACACC<br>AAGTGACTCACTGAGCCCGTTATCTACTAGGTATTCGCGAATACCGTAAAAGCTTG<br>ATGCAGGTGACAATGAGAATTATCATTAGCGTACTGTATGCTCAACCTAGCCTCCT<br>TGCAAGATTTCGTTCTATCTATTTTGTATTCATTTCTTTCCGCGACATGCATTCTT<br>TTGCTAGATCCTGGGTCCTGCAATCATTTATAAGCACGCAACTTAGCTTAAAAGTG<br>TGGAGACGAGACGTACAATCACTACTTCCCATCACTTCTTCTCTTATAAGCGTACC<br>GAAAGACCTCGTATTTTATTAAACAATAACGTGCAGTTGGCCTAACATAATTCGAT<br>GTCTTTCAGTGTTCTAGGAAAGGTGCGGTGTGTCTAGCAAGCATGTCAGCCCTACA<br>GATTCTTAACATACCTATGTGTCTAAATCGAGTATACTATAATGATGTACCATAAG<br>CCCTTGCCAAAGGATCATATTCGGACTAGTTATTGCCTTCTGGATGGGGTACTTAG<br>ACTAACATTTTAAACCTCTTGCGATACGACCTGGTGCTAATACACTATTCCTTCTT<br>TTCTCACGCGAACTTTCAGTATCGTACAAAAGTATGGGATTTAAACCTTTTGAAGT<br>TTGGTCGTGATTATTTGTTTTTAGGGCCTCCTCGACGCCTCAAATAGGGATTTCTT<br>CAGCACTACATATTTTGAGCCGTATGCGAACCCTTCTTAGGACCGCGGTAGTTTGT<br>TCACGAGCACGTTGGCCACACCCCAATTATCCAGAAAGCCGGACTTAAGACATATT<br>GAGTTTGTTAGTGCATAAATAGGGTCGCATATTGATCTGCGACTCGAGTAAATGTC<br>GTACTGGTGATATATTCTCCCGTTTTCGAAGGCCCCAATCAATTACTAATTACCCT<br>ATTTACGAATGTCGAGAGATGTTCAAACGAAACATGAGGGCGCATCCCAACGCCCA<br>TTTTGAAACTTGATTGTTGTATAATTCTTAATTTTTGTAGATTCAGCGTTCTTGAC<br>ACATTTTAAAGACGTCAGTTCACCGTACCTACCCCTTCGGTTACGCGAAAAAGATT<br>AGGTTAACGATTTCTATCGTTCGTTGGTTGTTATTTCTGCAGTACATTAATTTTAT<br>AACTTGATATATCAAATCTGTTTTTGATTAATGTTTGAAAGCAAATCGTAACACCA<br>AGGAATGCAAATAATCATACGTGGCGGACCAGCTACTATA |
| 26 | 40.10% | TACATCCCCATCAGTCAAGACGATTCGTTAACAAATATCGCTGACTGGGAGAATCC<br>CAGCATGTCTTGGCTGGCTAAATAGAAGCTACTATGTTACGCACTTCCATTTTGAA<br>TTACAGGCGACAACATTACCAGACTTAGTTAATTATTAAACAAGATCACTTTGCGA<br>CAGTCCTCTGAGGATCAGTTAGAGTGCAATCACTTAAGTAATACAAAAATACAGAA<br>GGATTCTCTGGCGAACAGGTTTATTAGCGCATGGCCAAATTTCTAATCAACCCCTT<br>TAGTTAGTACCCATTTCTAGCCAATATCAAATGTACTCCAAGCCGGCGTATAGTTG<br>TCAGTGTGTGATTTAACGAATAGGATCCCCCCCATAACAAATACTAATAAGAGTG<br>GAGCAATTATAGTTTAGATCGTAAAGGTTTAAATAAATAAACGTCAAGCACAATTA<br>TGGACTCGTATGGGGACAAATTGAGCCTACTAGCAGTTCTAGCGAAATAAGTTGAC<br>CTAACCAGTCCATGGACTGCCGGTTCGTTGAAGTCGGTCCAACGGATTGCAGATCA<br>TTGCTAGGCAGTTGGTAGATAAATTTCTAGTACTTTATAGTCACGTAATTGTCAAA<br>GTCCTACGAGCGTGGTCACCGTATTACTACGACCTCCATAGTTTTCTACCGTGCAT<br>TCTGAAAGAAATATGGCTGGAGTGTCCTAGCTCATGATAGAAAACGCCTACACTTA<br>GCCAATCAGACATTAATGCGGTAACGGATCAAGCATTACAGGGCGGATTGGTCGCA<br>TATCATTGCACGGAAAGCGTTGCCTTAAGTTCGGTACATTCCACTTTCAACTTCAT<br>ATTGACTCAAATAGTGGGACAGTGATTTACGCGGAGTTTTAATCTAAAAATTCTTG<br>AGTTTATGATAGAACAGATCTAAATTACGGTTTTTATATGTAGTGGTATTAATAAT<br>GTTCATAACCCTAGATATTTCCGAGATTAGCACTCGTTCGGCGCATTGCCGGTATA<br>GAACAATATGTGAAGAAATTTGCACCTAAGAAGTTGATATTCTCCTCTACATGCGT<br>ATAATATATAGTACCATAAGTGGATCATTATTAAAATAAATCTGAGTGGGTGGACT<br>TATCTTCTGTCACCCTAACTGGATCAGCAGTGGGCTAGTAGCCATTAAGGAACAAC<br>CACTTGGCCCGAAACTATTTGAAAAGTGATAAATACATACGGATTTACTACATAA<br>CCACTCCTCTTGTTGATAGGCATGCCCAAGGATTCGTATGGGCGATTTTCCATAAA<br>CCTACAGGGTGATTCGCGCATATAAATAACACCAAAGCAGTCAGGCTTTTTGTATG<br>AAGTGTAGCTTCCCTAACAGTATGATAGTTGTGTAGAGTCGCTTCTGAACTGGCTG<br>ACCCTAGTTATAATTAGTTCGGCGGAGGATGGGCCGCGAGACAAAGTATACTCGAA<br>CCTTAGGGCCGCATTCCAAAGGTTATTTAGATAAAAGTACGCAAACCCGCACATGA<br>GTTGAAATAATGAAGTACAATGTTATTTATTGTGCGTGGTAATAGTCTCGTGACTG<br>AAAATTTTTACCTTTAGGGTTCTCTATCCGGAGGAGCGTCATGAGCTCAAATACAA<br>AATCGGAGCATTGACTCAATTACTACTTTATGACAAATTCTACGTCTAAGCGATTT<br>TTCTAAATCGCCGTGATCAACAAACTAGATCTACACCAGTGATGCATGCTCACGGC<br>GAATGTCCTGAAGTCAGATCTAATTCTTAAGGGTTGGATTAGCTGGCTATAGCAAG<br>CCATATTAATATGATTAGTCGTGTATGGTTTACGCTACCTCTCCATAGATATTTCT<br>AACTTACATTTGTAAATGTTTCCAAGCATACCGTCAGTATAAATACCCAATGATGT<br>GGCTCTCCTTCAAGTGTTTAGATAATAGCTATTTCCATAAGGTGCCTCCCCTATCC<br>GCTCATCCTCGGGTTTCATATGTTGTAAGTGGCACTTAGA |

TABLE 2-continued

Exemplary 2.0 Kilobase Stuffer Sequences Having 40 ± 5% GC Content

| SEQ ID NO. | GC Content | Stuffer Sequence |
|---|---|---|
| 27 | 39.50% | TTGTTTCTTGGAGGGTTACTTACGATTATTCAATGTCAAGCTGGTACCAAATAATA<br>TGTTAACATCGACAACCTTGCTGATTCTTTAACTGTACGATTTACTCAATCCTTAC<br>AACAGTCTTTCCCCCCGATGCTTCCGATAATCCGGATGGAATGTAAAAGCTTTAAT<br>TTAGCCATAATGGAGCTACTCTGCAACAGTAAGGCAAAATTTTCTTAAATGGAGGC<br>CAGGCAAGATTTGTCCCCGCCAGAATAGCCTACTCCACAATATTCTCTTTAAATAT<br>TCGCCATGCTATCTCACGCATCCATGAACAGGTTATGAAAGCGTAGAGTCAAACGT<br>ACACTTTAGGTTAGGTGCCTTGTGGGGATTTCACGCCACAAAGTAGAGTAGAAGCA<br>GTGTATCAAACTATGTGTAAAAGTAATTTCATATAGTAATAGCCACCAAGAATGCG<br>AACATAGGTGTCGGCCTGAAGATCTAAAATTATACTTATTAACAATCATGTGAGTA<br>GGTTGGATTTTAACACGTTCATAAGTATCGATCGCTTCGCTTAAATAGAATAAAGT<br>ACACATCATGTGACGACGCGCTTCGATTATTGTGCTGCGTTAAGAGTAGTAGGATA<br>ATTTTTGATAGACCTGTCTATAACACGGTATTTAATCCGAAGTTCACTATACAATC<br>ATAATAGGATATCGTGTTCTGTCTCGATGATCTATTCGTCGCTTCGGGTGCAATAT<br>AGGATTCCTATATGAAACTCACTTCCCTGAGCATTGGGATTTCTTGATAGCTAGAT<br>CGCGTTAGAGTCGGGCGGTGTATAGTCTCGGATACAAGAACATAAGAGTAATTATG<br>TGGAACCTTTTCATGTGATTGTGCTAACTGTGTGATATTCGCAATAATTCCTACAT<br>CTTAGTTTTTAGACTGGACTTTTTTTTCCCAAGCTCTAAGCATACATTATTCGCTG<br>CGTATGTCACTGACCTAGAGGAATAAGTGTTCTGCTGTCAAAACTAACTCTCTCTA<br>GCAGCCTTTTTGACCATATTATCAATTACGCGCCATCCCATAATAACTTCAAAATT<br>TGCAACCATCGGAATTAGAAATCCCGACGTAATCAAGACGAATCTTCGCCGATTAT<br>CGAGCTTACATAATCGAAGGTGCATTTCTGAACCTTGGCTACGCTAACCCTCTAGT<br>CGGGGCAAGATGACTTGGTTATCTGGTTAACTAGGAACTCCTAGCCTCATATTGTA<br>TCAATCTGATCTAATACAGCGTCTACCAATTATTTGATTAGGTTTGCTTGCCCTCA<br>TAGCATCGCAGCGAGTATCTCACAATGTGTATGGGTATTCTTCTAGTTACGAGTTT<br>AGACGGAGAATAAGCCGCTTGTGGTTAACCTCTGTAAATACCTCTAGTTGAATAAG<br>TGTGCAACCCAATTCACATTCGTCATGTTAACAAATCGGCAATCTTTCCACTAATG<br>AGAAAAAACAAATCATTAATATATGTGAAAGTAATTATTGTGTCCTCATAACGGTA<br>AAGACTTACGAGTAGGTAACAATCTCAACTTCACCAATTACCACCTAGATTCCAGC<br>ACCGCCAACGTAATCAGTGTTCCGTGCGTCTTACACAAGAGAACTCCTTAAGCGGC<br>TAGCGTATACTTTTAAGAGCAGTGGGTATGTGGCCCGGGGCATCTATTGTTTACCG<br>TAATATAAGCGCACTAGTCTATTTTTACACTAAATATCATTCCATATCCGGTTCTT<br>TCAGTAACAAAAGTAAACACAGTGTTTTGGAAGCAGTGTATCAAGAATTGTGAACT<br>TCTTTCACCGGCGCAGGGATCCACTGTCTAGAGAGAATCTTAATTCTATCAACCGA<br>CCCTCCATGTCTTATAGATTGTGTCAACGGAGCACCTAACCGTATCCTTAAAAATT<br>TAGAGGAAATAGAACTCTCATTCTTCAGCCTGTTAAGCCAATTAAATCGAAACCGT<br>TGCTATTAGGTGTAACGGTAGATGTGATAAAAGGGTCACA |
| 28 | 40.60% | AGGACGAGCTCTAGGGGTGCCCCTGCTGTTGTTGGTTATTTAAAAGCCGCGATGAA<br>GAGAACGCTAGGGGGAAAAAACGATTTGCCTAGAATAGTGGATCGGCGTTTTGATG<br>TAAGTGTAATTGGGTAGAAGGACTTGTTTTACATTTGCGAAATCTTGCTCGGGGAC<br>GTTATAATATGGCCTTGAAATGGATGATGACAATATAGTTTTAATGTTATTATAAT<br>TAGAGTATCGTATTATTAAAAAGGATGTCCACTGTGGATCCAAGTTAAGCATTAGG<br>CGCGTTGAAGAGATTGTACCGCCCGAACCAATGCAATTGACATGCCTAACTAGCAA<br>GACAAACGTGTTAAGACTAAAGTCCCTCCTATCAACGTACACCTCATACGCTTGAC<br>TAGGTAGAATACTAAAATACTCTCGTAATGAATACCTATTATCTAAGTGACTGCTG<br>CGTTCTTTTAGGTGGTGAACTGGCTCCGGAAAGTGTGCTAATAGTCTATATGTCCG<br>CGCCTGCCACGTAACCACGAGGCGGATCAGCTAGAAACATAAAGCCGTTTGAGCAA<br>TAAGTGACTATACTTAACGGTCTGTAAATTCGCGCTTCAATACCTCTTACTCTCTG<br>CGTTCTATCCCGTCTTTTTATAAATTCAACTATACGCTCCATTGGTTATCGCCATA<br>TGAGTCCTTATCTACTTAAACTGGCTACCAATTCCTTGCTCTAAGCTAATGAAAGT<br>CCATTCGCAGGATTACAACATCAATGCTAACTTTCTCTTGCATACAGTATATCGTC<br>TAATAAATGTATAGGCTCCCGGAGGTCGGAACAGCAGTACTCCCGGCCACGTATCC<br>CGAATACAAACCTTATTAGTAAAGGAAACACTAGTGAGAGCGTACGGGGATTACTC<br>GAAATATCGCAGGAAGGTGGTTAATATGCCAAGGAAATACGAATAATTCTCTCCGC<br>ATTCCGAAACTGTTAGCACATAGACAAGACAAAGAGTTTACTGACACATCTTTTGA<br>CAACCCGCACTCTACAACGACCTACTCTTTATACAAGTACGGATTATTGTAACGCT<br>CCAGCCTAGAGAGAGTAACCCGGAGTTATATGGAGTCGCTTGAGGAGAAATATTAA<br>AGCTGAATTCTGTTACGACTAGTAACATTACCAGCCGAGGTCTGAATAACGTGCCT<br>ATGGCGATCAGGACAATACGAGAGAATTCTTCTACCACACTATGTGCAGCAGCTC<br>ACTCAAGAGTCCTATGTAGACTGTTTAACCAGTAAGGATTGTTGTGCGGAAGTGTA<br>ATATGGTCGAGAAATACCGCTAATATGGATAAGTTAATTGAACTTCGGACGTCACA<br>TTCTCCTATAATGAGGATCTATTCAAATCGTTTTGAAGTAACCTCCTCATTTGAGT<br>AAACTAGGCTTGCCTGGAGATGGGGCCCCCAACTGTAATGTGTTATGTTTAGTTTG<br>AACTCAGTTGGCTCAAAGTATCCCGCAGTACTAATATTAAATCTTGTTATTGTACA<br>GCTGGCGAAGAAAGTTAAGAAATGTGACTCCTATACTATTACTGGATTTACAAAGT<br>AAGCGTCTTTGACATTAATTATGGTATTGACAAATCAAATGAGAGACAGTAAGATG<br>ATGACATTCGCTCATATTGTATGGCTCGTTGACTGATGCAAATAGTACCAAACCCT<br>TTTTTTAGAATTCCAGATGAGGAATTAGATTTTTCAGTCAATAGTTACTTGTTATG<br>CCACGTAGGCTTATGTCCCCTAAATCGCATATAATAAGATAGAGTGCGAATGCGTG<br>CACGTGTACACTAATCAGGGCAAACTAAACATTTAACCTTTGGAGAAATTCCGTGG<br>CGCTGAACTTAGTGATGATATATGATTAAGGGATCCGTTTTGTTTTCGATAATCTA<br>AGAACTGACGAAGGCACTAATATCGGAGTTACACAGGAAATAGAATGTCGCAAGAT<br>GTGCCTTAGGAGTCAGAAATCAACGAGTGTTGATCCCACA |

TABLE 2-continued

Exemplary 2.0 Kilobase Stuffer Sequences Having 40 ± 5% GC Content

| SEQ ID NO. | GC Content | Stuffer Sequence |
|---|---|---|
| 29 | 39.00% | ACAACGACTTTCGAAGGTGGCTGAAGAAAACCACATGATAAAATCGCGAGTATGGTAAAATTAGCTACCTGAGTATATTTAATCGAGGTTATATCTTTTGTGAGTCGGACACAAATTCTATATTTGACGGAGCATAGGGCAGACGGACATATAAAATTATAAACAGTCTGTACGGCGGGGCCTCCAATTGGATTCCCGCGATCATATCAGTCAGTTGGGAACCATAAATTGCGAAACTCAGTACTATGCTTCAATGCCCCTTTCTAACACGTTTATCGCTTCAACCTAACGGTATTTGCACTCCGACTATCGTCTTATGCCTCACAATCAGATGTAATAATGCGGGATTTATAAAGATTTTGAACCATTGGACAACTGACGGCTTCTCATCTCACCTTGACGAGAGTATTTCCTATTAACCTGAATTTCGCTAAATACTTATCTTTATCGCCAATAATTCCTTTATGATACACAGGGCTTCTCCAATTCATCCACGCAGAAACTGCCCAAATGAGGAGAATAAAAAACTTTATAATTAAATGAATTTTATAGCCTATGCGTATCCCCCTACTTCAAATCTGTGCAGTGATGATAAACTATTGTAATGAAGATCATTTAATTCGCGAGATTAAACAGATTCATGTTCTAATGCGATTATTCTGGTGTGATATCGTGCATGGATAATAGAAAGCTGATCCATTTAGAAACCAAGCTTATGCCTATCCGCACCTTTAACACACGCATAGATTAGCGCTCTGCGCGAATCCTGCGCGTTGCAACTGTACTGATACAATGCGCACCAAAACAACTTATACTCTAGCAATGTACACACATATTGCGAGCCAATCTGTTCAGTTTCCCTTTGATATTTCAGGATAATCAGATGGACGCCAAATAGATTACTCTTATACTGAGGAAAATATGAAGTTCAGGTTCAGCGTTACACGCAAATCAGCGATTAGGTCTGCCTAATATGATTTACGTAAATAAATCTACCAACTAGAAATCCGGATATTTTACAATAATCATGGCAACGGGTATGACCACTGGGTTCGATCCATATACCTGATGGGCTCGGCAAAAGTCTGTAAGAATTCTCTACATCCCGATCGATGCTTCTTTATTTATTTTACTTCATAAACTCGTATTTAAGCTATGCATTGCCAACAGGGCTTAAATAAGAAAAAGTGTTGCACACAGAAGTTGCTATGCCGCAATGGAAAGAGTACTTTCATGAAAATACGTAGATATTTAGGAGCTTTCATTTAGTAGGTCATCTGGTTGACCATATACTAATCGGATACTTGCGAATTATTGTCCTTTCAGCAGTGAATCCTGAGACTGATAAGCCAGCAGGCGGGAATCGTATTAGTAAAATTTAAGGACATCTGAGTACGGGCGAAATCTACAACACGACGAAATCATCAATCTATTATGACATAAGTATTGGACAGTACGTCTGACTGGGAAACATAGCTTTATGTTGGATATGTACATTAGTGCAAATCTGTGTTACGTGTTAAATCATCGCGTTCTAGAACTCTTAATCACATAGCGAGCTACCTTGGCGAACACTCGTTACTGTTCTCGTTTTGCTATCATGTCCTAAAAGCGGCAAAAGTTATTACTGCAGGACCGAAAAATATGAAAAACTTATTTTTTCATGGGACTACACAAATCGAGTTGAGCCTTTAAGCGGTTCTATGTTACTTGAGTATCTTGAACTTGGAGGGGGGTTATAATGATAATAGCAATACATAGGTTATGATAAACTGTCCTGTTTTAGATACACGGGAGCCTTAGTAGGCTTATTTTAATAGTGTAGTTGTTGATATGAATAATATAGAAAGGCCATGGAGGAGAAGTGCTATGTTAAGAGGGCAGTCGCGGTCACGTGTGCCATTGACGCTCACTTATATGCTGCGTTTTCGCAGTGTCTCAAAGATTAAATTAGCCTATGGTGTCTATTGTTTTCGTAAACGCCTAGCATGCGTTCGTC |
| 30 | 38.90% | CTTGTGCGTCGAAATCGAAACTCAAATAGTATGTACGCTGAAAATAATAAAGCCTAGCTAACAATCCATCCGCGTTTAGATCGTAATTCACATTTTACCGATAAAAAGTTAAGTACAACATTGGAATTGTTATTACTTAGCCAGCCAATAACGCGTCCTAATTACCAAAAAAAACAGACTCTGAATCATGGTAGATTAATTGGGTATCGATAACATTATCCAAATTCAGGGGGCCATTCGCTTAAGAAAAGAGATGTTAACGTACTCCAGCGATCTGCGGTGTTCTGACTGTAAAAATACGCATACATTTCACCCATAGCAGAAGACGTAGGACGTCTTTTCTACCAGGTGTCTGTATTACATACCCCATGCATATCTAAAAGGATTCTGGACGTATTTTGATTTTTACCAGTTGAGATAGTGTCAAATTCTGACTTTCAAATGACAATCGCAAAAATGTATGCGAAGGCTGATGATCTTGTAATCAATACTGGTGCTAGTCACATACTGTTGTAGATACGCCAGATTTACACTATACACAGTGAACAAGGTCATGTCAATAACAACTATTTTTGTTTATAATCACTAACCCTGCATATGAGGGTCTTGATCCAAGTTCGAATGGTTGAGAATTCCGAGTTTATTGGTAAGGGAAGATGTATCAAATATAATCCTTGCTTACTTCCCAACAGTCACAAGAAGCAGAGTTAACGACTGATTACGGCTGGACCAATAAATATTGAAACATCGCAATAAAACTTGAAGAAATTTGACTACAAAGTTTAAGTGTATACAGTAGATCGGTTAGGGTATACTCAATTAGGGCGGAACCCGCATTCCTGTCGATAAGCTAGTAGTAGGTGGTTTTCAGGTTGGTATCAACCATCAATATTCGACATACATTAATCCAGTGAATAGGGCGTCCGGATTTTGTAAAGCATTAACCTTCTGTATAAATACTGCCAATCATATGGCTTGAGTAACCGTTTTTGTCAGTGGAATCGTCCCCTCGCTAGAAGCATCTGTACGATATCTAATGGCTGTAGTTGCCTTAAATCGGAAAGGTAAGTCGGAACCTGGGCTCTCATTCGAATAAGACCAATCCTAAACGGCGAATTCCTTTATCTTGTTAACTGCTGTGTCAAGTCCTCTTATCGAAAATTCTTACATGTTTACTCTTGCGATTAACTATGGTGAACTAATCCCAACAATGACTGTTCGTAATAGATGTGTTTGTAAAATTAGTATTTTGGTGACATCTCTAGTCATTTCATGCCTTCATAGATCATCGGTATTTCGCAATAATCTGCTCATACTATGTACAGAAATACCTACCTTCTGACACCCTTGCTAGCACTCTGGAACTAAATAACTCATAGACGAAAATACAATGCAAAGCTCATCTTCTTTTGAATATTGAGCGAAGTAGATTGTTGACGTTAAGAAATGAGTAGTTTCATTCGAGAACATCCGTAATCAACTACAATTATAATCTCACAAGATCGGTCTATTAAATCGCTCATACTCCTAGGACTAGAACCAACGATCGAATTTGTGCTTTGGGCTTAGGTAAAGACGTATAATCCTACCTAGAAGTTATCCATTTATCCACTTGATAACATATGTCTATTCCCAATCATAATAAGACGTAGAAGAAAACGACTCTCACAACGACAGTATGCCCTAATATGCGATGGCGACTGAAAATCTTACGGCGCCCGCCTCAATCACGTTCACGTGACCCAGCACATTAGATCCAGGACTGACTCAAGATCATTACTCGGCGATCAACGCACTATCCTCAATTGGCTATGTGCGAACTCCTCGTATAGGATAAGGATATTCCGGTCTCCGTATACGCTAGGCTCAGTAACGCGTCTTACTCTGGGTCAAGGGTTTAAAGATCATAGCGGTATCATACAAAAAATCATATGGCCTACTTTGTCGTTTTAAGCGAAGATCAACGACGTAATAGCTAACTTAATGAGCAAGATTT |

TABLE 2-continued

Exemplary 2.0 Kilobase Stuffer Sequences Having 40 ± 5% GC Content

| SEQ ID NO. | GC Content | Stuffer Sequence |
|---|---|---|
| 31 | 40.20% | TCGATAGGACAGATAAGTGACCGCTTGTTGAGTCTTATATGTATTGGACTTAACAT CGAGCAACAGTCTGTAACATATGTCACTACGTGATTGAAGGCCGTCGTCAGTAATT AAGGATAAGGCGGTAAGACATAAGATACCGTACAAGGATATTTATCGTTATCTCAA GGTCAAATCTAACTATAGGTAACAATTACCTTCTACTAGTAGGGGAATTCCGTTGG ATAGCTAGTAAAAGATTGCTTCAACTAATCCAACAAAGTATTACATCAAAACAGAT TGGTTATCAAGATTGGAGCTTCAGAACTAGAGTGGTGAGCAAAGCACTCTCATGCC TTTTGTAAGAACCGGGAATGAACCGCAAGAATCACTTGACAAAGGTATTGGGTGGT TATGTTGCCGGGAAGCTACGATTATATCCAATAGGCTACGGTCGTTGTACAACCGG TTGTCTATCTGGTACTTGGTTGATGACCTAGGTGCGAGCCATTCTGCCAAATTTAT ATGGAGATTAAGAGTGGTCTTTGCCTGATGAAAGGGCCAACTGCCGAAGTACTTTG GAGCAGTGTTGACTGCAGCTCCAAACATCTTGTATTTTAATATTTCGGAATAGACA TCTATCGTTAGTGAGGAAAGAATTTGATCCCGCGCTATTTTCCCGACATTCTCAAC ACTTGGATTACTTAACTCATAGAATTTTCTACCTATTATATTATAACAAAAAGGTC AGTATTGGTCCTGACGTATCTGATTCACGTATTACGGGGCGGGGTGGAAAAACTTG GTTTCCTAGAGCCTTAGACGAGCGTTAATATACAACAAACTAGTTTCACATAATAT TACGTATGGAGTAGACTCAAACAATGGATCGCGGCGACGTGGATGGTATTATCGCA TGATGCAATTCTAACGATGAATTTGTGTCCGCGCTGTTGTCGTTTTAACAACGATT TTGAGGTTATGATAGTTATAATCATTAGAACATGTCCGAAATTCAAGTGGTTCACC TTAGCTTTGTCAATTTTGTCACACTTCAGGGAGGGTCCAGGAGGAACTGCAATCGT CAGTCTGAATCGTTCGAGCAGTAGAAATGACCTAATTTGCTCGTGACGTACTGACG ATACCAAATCAATGATTGAGTTCGAGGATCTGATGTTTGGAGCTTGCGTTGGACGA TCTGATACTCAAAAGTCGACACTCAACATTTTTTGCCACGACAGATATTCTCCAGA CTTAAGAAATCCTTGCTGAATATCAAACATGCAGCTTAGATTAGTTATTATGTAAA TTGTGAGATACTATGCTAACTCGATAGTGAGGTGTTGGTCTGACACCGTGAATTAA TAGGTCGTCCTTAACAAGTACCACTTAGATTCCTCGCTTTTGAGTCTTTGACGCCT TTGGCCGGATGCATGTATAAATCCTTTTCAAAAGGCTGTTCATTCCCATCCAAGTT CTGTAATAGGTCTATCTTTACTTCTGGTAACAAGAGGGAGTTGGGTTACGACGAGT AATTGTTGTAGCAAGGATAAACTGCTATTTTTGATTAACAGCCTCACATATAATAC GGGCAGCCAAGTCAGCCTGCCGGCAAATTTAGCAGTGTTTCTGCTCGCCAATGTCT CGAGACTCCTAGCTCTCTCGTCCATTGCTGACTAGAACTAGCCAATTCGGCGAGCA TTAGAGTGCTAAAAAAATCGGTACAGGAGCCTAAGGGTATCCGGGCAGAAGCAAGT GGTGCCAAAGACAGTTAGTTTATGAGCTTACGTCCAATGATAGAATTTGCAAACGG TATGGTTACCTTCTTTTCTGTATCTTCTCAATGTAATATGTTAATGAACACATTGT TAATGTGGTTTCATATAGTAAAGTAGAAAACTAGCCGACAACCAAAGTAAGAGGAG CAGTTTTAGAATCAAATACACCAACTTAAAAATTTGCATCTATGTTTTTGACAATT GACATACGACATAATAAAAGTAGGATAGTTGTAGATCGTC |
| 32 | 39.90% | ACAACAATCCAGAATTAAAGAGTCAATGATTAAAGTCTCTATAATTCTTGGTGGTT AAGGTGCAACTTTTGTCAAGCCAATGCTTCTCTAGCTTACGAAAGGAACTAGTATT ACAATTTGTTACCGCATATACTAATGATCAAACATTGTACAGGTACGGTTAATAGG CGCACTAGTAACACCGTCAATTATTATCCTCGTCCGACCTGAGAAAGGATGATAGA TCGTGCATAGAGGGACTTGTGGAACGAAGAACATTTCCTACGCAGCTACAAAAGAT ATATTGCACCAGGGACGTCACACTAAAGATGTATACTACAGCATTGTTTCTCATAA CCTCTAGGTAGGTCTGTAGATTCAGCGTATATCGACTACCTACATCTCGTCTGATA TTCATCTATCGCCTTAAAATTGTGTAAAATAATCTGAGGTCATCAATGGTTTTGTT TTTACATTATGTAAGGTCCGTAATGGTAACTTGTGAACCGACATAGTTCCCCGTCG CTTAGGTGTGCAGATAATTAGATCCAATGGATCAATTCTCGGAGATAGTCTTCTAC GGCATTCTATCTGTACACGTATTGGTACGGGGGTCGTAGGCAGGGAGACATCTACA AAAGTTAGCGGTTGCTGAATTATTAATATACAGCTTTACGCTTATACGGTTGACTA CAAAAAAATTACAAGATTCTTCATGAGATTGTACCTGTCAACTTAATTCGTATCAA AAATTCTAAAGTGCGCATCTAACTTCATACAACGGAGAAAAGTACATATAAGTAGG GTGTGAACGCAGATAACGTTCAAAATGATTTAAACTATGATTGAGATGTCCAAGTT AAGGACGGTAGGGTTGCTACCGTGGACTATAAACCCTAATGCCTAAATCTTTATAT TCGGGAATTGTTTCGGGTTAGGGGGAATACGCACGAGGCTAACACAATATGCATAG TGCGTATCATTAGCGTATGGAGGACGAAAAGAGATATACCCAATTATAGCCTGAAT GTCTTAATCAGACCCTTATCGTCATCTCATTTTTGACTACAATCGGTAATAACTAC TCGGGTTTACTAGATCCTAACGGGATGACTCATAATAGAACGAATAGTGTAAAAGC AACCTACGCGTAAGACCTTCCCGGTCATGAGGATGTCATCCTATGCAAGCGTTCCT CCCGCGAACGCCACGTGATCTCTCGATTCCATTCTATAGGATTCATTAAAGCTCTA CTATTACCCCAATTGCTGGGTGTTCTAAGATCTATAATGTTATTGTCCAGATTAAG TTCTCCTGACTACTCGCGATTGTGTCTTTCGCCCGCTTGTCCCCCCGTAATTGGA TCGGGCCTTCGCGTTCTGCTAATATTTGTTACGTCACGTCGGATAACCCCTACTTG TGCAACATCCTGACGAATGTTGTAAAAGTTTTTCTTTGGAAATTTGTACAGTTAA AAGACAAGATAATATGATTGGATGGCAAGTGACTGTAAAGTTCTATCCAGTGTTTC GTATACGATTAATGAAACTAAACGAGAAACTTTGCTGACCTCCACCCAAGATAGCC TTCACTCTTTCACTAACTCCACGGTGAATTTTTTTAGTAATTTTCATAAAGGCAA AGACTAAGTTTACCTAGTAACGCCAATCCCCCCACCCATAGTACACTGTGATTCGAA AAAAGGATATTTTTGAGCTTCTATGCTTTAGGGATATTTAGTTTAACGGAAAGCAC CGTCAGCTTGGAATATTAAACACGCACATGATTTATGGACCCATAGTTGACATCAA GGTCTTTGATACCGACGGTTTTCGTATTTTCCAGTGAAAGCCGAAGCTTTACAAAG GAGAGAGTAATTGAGCAAATTTCTCACTGCATGTCACAGGGACTGATAAATTAGTC CAAAAACTTTATTACGTTTGACCTTAGAGGTACCCTAATGCGGCTTATTATTTGGA GGCCAGACTATTGCGCGTAACAGGCTGTTTGAGCATCGGT |

TABLE 2-continued

Exemplary 2.0 Kilobase Stuffer Sequences Having 40 ± 5% GC Content

| SEQ ID NO. | GC Content | Stuffer Sequence |
|---|---|---|
| 33 | 38.20% | CTCCTCGAGCTTATAGAAAAGTCAACGAATGTGTAGAACCAAGAAAGTGACCAGCT ATCAAATAAATAACAAGTGAGAGGTACAGCGTATCTAATAGGCGAAAGTCTAGCTC CAGGTATCGGTGAAGTCTAACTATGAATTAAACGCATTGCGTAGCTACATGGTTTT ACACGCACCATTAACAGGCGCATAACTACTGCCTGAATCGCTCTGATATTAAAGTC AAAGGAAGCTAAAGACTTGCTATATCGTTGCATGGTGTTAAGTAAATACGACTCGA GTATTTTAAAAAATCCTCTGAATCGACCAACTATTTATTCGTTCATTCTCTGTCAT TGAGTAGCGCTAATCAATGTAGTATTTGGATCAATAACCCTCTGGGTTAGGCGACT ACATGAGTACCCTTGGAAAAACTCTGGTCGAGCAAAACAAGACACATGGGGTTAAA TAAAGTCTATACAGTTTATAATTATGCAAATTTGACGAATTTTGTACAGAATTTTA TCTATAATCTTACGGGGGTATACATATGACAGCTTTCCGGTGTTACAATACTCCTT GTGCTTTGTACACTTGGCGGAAAATTCACCACAATGTATGGGGTTCCGCGCAAGCT CTCTTTTTCGGTAATCTGGGATTCCTTTTTTGTGCCCTTTTACATAACAAGACGAA TTGGTCTCCTTTTTACTCAGAAAGAATTATAATACTTTTCTTACTTGTCCGTTTCC CCTCATCTTTTTTTACCTCCAAATCCGATTCATCGCCTTAAGTCCAGTGTCTTCCA ATGTAGTGGTTTAACGCGAGCTACATAACCATCCCGGATGTATACGATTCTACAGC GTCTTGAAAATATTATGTTTAGGTTTCGGGTGAAACGCACCTAGAAATTATAGCAA TAATAATCTTAAATCTCCTCATCATAATAGATAGGTTATTGATAGGCGACATGAAA CCCAGCGGATTCACCTATCACCAATCAAACCACAGTTCCTTTTGATGCAGTCATTC CTACAGGCATCCTATTAACAAACAAGCGTGTGCCGATGAAGAATTCGTATCTGTTA AGCATCCGACGGCACATGTGCAAGAGTCGATCTCCTGATACCAATTTTAGTACTTC TCCTCTGATTAAAACAACTTCCAAAGTTCCAACAGATGGAGTATAGATAATCAAGT TTCCAGAATTAATCAGTAATTTGACAAGTGGAAGCGCTAGAGGACTATTCCCGGTA ATACTATAACAAGTAATAGTGACCTTGTGTATAAATAGACGTTGATAGATATATAT ACACTTCTTGATAGCTGAGGTAGACGTTGATACAACCCGCAAGTGAGTCCATTACC TTAGGCCCTACGAACATGCTCAAACCCTTTTATGCTTTCCCAGACTCAAAATCAAT ACGTAGATATATTGTAACCGTATAGAAAAGAGCTTCTGTTGGATACAGTGGTATAA CAGCTCATGTTCAAGGTTTATACGGTATGACAAATGTGATTTTCTTTTATGTGAGA TAACCGAACCAATTTCGAAAGATTACTACTAGTTGAAATACCAATTTTAAAGGTAT CCTTTCCATTAGACCCCTTATATTATTCTACTGTATTAGCAAATTTTAGAAAGTTC GTGTGGTACTCAAATCCGATGAAACTATTCACCGTGACCATTAAATAAGTTTGATG ATCACCGAGAATTCACACCTCGTAAATAACACCTATCTTAATAGAATTCGTGCGCA GCTCTAAGAGAGAGCATCTTCCAAAACGAAGAGCTGTTTACAATTGCTGCCACGTC TTTGATATACACTCTTTTATTGTCCAATCCGATGTTTCACAATAGGATCCATGGTT CCGGTTACTTCCTAGCTAAAAGGGTTTGCCCACGCGGTGAGGGAAGTCTGTCGGTA TATTAGACGTAGTGTTCACGAATAAGTAAGATTTTTAATTTGGAATGGTTTGCAAC AATTACATAAGGATAAGTAAACGCGCCGTATAATGCTCTA |
| 34 | 40.00% | ATCTCATAGATAACTCTATGAGGAGTTAACGCCTAGAAATTTTGGTCTGCATGGTA CAGTTACATATCGTATGAATTCGTCTAACATTTGAACGGACCACACCATCTGATCC GCACTCAATGGACAGTAGGCATTCGGTTACACTTTCGTCTGGAAGAACAGTCCGAA TATGAAAATATGCTTAGATGATTCCAAGTTAATTTCGTCTATAAATAAGTAGCTTT TGCTCTATAAAGATAACCTCCTACAGTCGTAACAGAGCTCATATACGATAAGAAGA GTATACTTTTAGTTTTTCGCACATTTAGCCATTCAATCGAGAACATAGACGCCTCG AGCCGAATTGCTTAGCACATTTTCCTAATAAATGTATTCGAATATCCAAAATGAAC TTGCATGACTCCGTAGCACGCACTAGATTTAGTGTGCCTAAAGATTAATATCCCAA GGTTGGGCTAGAACTAAAAACGCTGTTGCCAATAGGTTAGATTGTAAACTGGCCCT TAACAAGCTGATTATCAGGTGCTTTGGATACTTAGCACATACTTAACACATCGGCG TGAATAAGTGGGAAAATGTGCACAAACTCATTAGAAATTCTGTGATTGGGTCTTTA CGTTATGTTAAAGTTGGTATTGCTTATAATAACTTATTCTCGCAGCGTACTCGAGA ACGTTTGAATTCGTGAGAGCCCTTAAATCAACGACCCCCGGCGTTTAGAAACGGCA ATCCATATACCTGTCATAAATTATCTTAGAATTATTATTATACCCTAGCCTTAGCC ATTTTGTTTACCAGAACACGGATGGATCTAGTTACGATTCATATAAAGTGAGAGAG GCTAGTGTTGTAAGGGAGTGAGAGAGCTTGCATCTTACGAGCTCTTAGCTCCTCTT ATCAAAATATCATTTGGGCCCAACAACGCGTAAGTCAGATGATCTATTAGCAGTTT GGATATGTTCAAGAAGTCCTCCAGCGGGTTTGCGAGATTCTCTGTATCGTTGACTT GTGACATATGATTTGTATTCCAAGACGGTCAGTTGCAATCTTGCCTGAACTAGTTG GATTATCAGCCACCCCAGGCTGTTGCATCTAATTAAGTTTTCCTATCTGTAAAACC TTTCACTTAGCAATGGCTTAATGCTCTTACCGATCAGCTGGAAGCCGGTAGTACTG TCACTTGGTTTTCTTAACCTATCAAAACGGAAACAAGCCGTATTTTTGATGGTAGC ACTTCAAATGGTGGGCAACCGACTAAAGAACGTCACTCTTTAAATTCTCATAAGTT AAAATCGGATGTCGAGTCAATATTTTGTCGGGCATGGGAAAGAGAGCAGTATGCT ACCTTCTTAATCTCTACCTTACTTTAGACAAGCATACGTCAACAACTGTGACTCTT CAAGGACGGGTATTCCCTGACTCAATGCTTTGGAAGAACATTTAACTGGGTTCCAT TATAGTGGTCGGACTCTTTATGCTTATGTCGCACCAGGTCCATCTATCGAATTCCT GTATTCTATAAACACCGGCTGCACTCTAAGAAAGATCGAGCTTCTGATTCCAAAAG TCTATAAATGATCAGTTAGCCTAGCGCCGACACATTGCTCCGTTAGAAGCTTGACG TTTGTTATTATGAGGGATCACAGATTACCGTGTGTCGATTGGTGGCTCACTTATCT ATGAGCCAGTTTCGTTATGGTCATACCTTTAATTAAGGGAACATCGTGCTAAAATT TTTAGAATGGGTACTGTCTAGACTGTCTCGAGGATTCATGCCGATGAAGACCTGA AATTTGAATCGGAACTTTTGTGGCACCGCCGTATCGCAAAATGAGAAAAAGATATC GTTAACCCCTTATAAACCGCAACTAACTAAGTCAAAATAAGTCGACGTGACTTAAG ATACTGATTAAGAAATGGTATCACGGCTCTTTTGCAATACCATTACCAAAATTGCC AATGAAACTGTTTTGGCCTATCTTAAGCCACGAATAATAT |

TABLE 2-continued

Exemplary 2.0 Kilobase Stuffer Sequences Having 40 ± 5% GC Content

| SEQ ID NO. | GC Content | Stuffer Sequence |
|---|---|---|
| 35 | 40.40% | ATTCTTAAAGTCGATTCGGTGTCATAATAGGGTTATCTAACATATGTACAAACGCC CTATAAAGTTATTATCGGACTGGTGCATAAGTAACAGTTCGCTATAAAGTTAAATG CTATCAAGAGAAATAAGGCATACTGTGATGAAAACGAGGTCGTACAGAAACACCTG CAGGAATTAATCTGCCGTATCATACAAGGAATATCGTTGGAGTCAAGATGACTGCC CATTTGCAGTTGTCATCTTAACTGATGATGGTTTCTTGCTTGATAGCACCCGCCTC AGTAAAAACAGATGGAACACTCCAATGCTAGCCAACTGAAATTTAACGTTAGTACC AAAGGCATCCAAGCAGTCCCCTGGCTAAGTTGGAGTGTGGCATCGATATAAAATAG TTAAAAAAACGGTCTGATGTTTCATGCAGTCGCAACCACGCATACGGTTCCGGTTC GCAACGATTGATGTGGCGGTCTCAGTATTTTACAAGTTTTAACATGTCGGCAGCCG CTAGGTAGATACCTGCACCCTGTGGTTTCGTATATAGGGAATTTCGGTGCTTTAAG ATAAGGATTACTCATAGGGGATATTACTCGATTGCCTCGAAAAATGCGATGAGTCT CTATATTCAACGGTCTATTACAGGCTTTCTATTTTCTCGGGACGCCTAGGAGTTGA ATGATGCACATCATTAAGCTACTTATGCGGTCTTCCATACCATTCCAATGTCGTCG AAAGAGGATGCAGTGACAACTCAGGATACTAATAATTCCTTGAGAACTGTCTATTT CAAGCCTATTCTAACATAATTAGTTGCTAGCCATATAAGAAAATATCATCAAACAG ATAGGGTTGATAACGAGGGTGCTGCCCGTATAGTGAACATCGTAACCGGGTTTCA CATCCTAGATTGGTGGCCTCCTACTATGTAAGATGTAGTTATACTGAATGTGGTGT TGTGATCAAGACGTAGGAAAATTTATCAGATATGCCAACTAGTATCATCCTGAGTT ATAAAGGGGTAATTTCGGACAAAGGTGTTGTTTCAAAAGGTTCAAGCCGACGTAC CCGCACATCAACTTATCTTGTAATGATTCAAGGTTTATGTAGCTTGATCACCAAGC AACCCAAGCGAGCTGTACCAGATACGATTATGTTAATAAAGGTTTGGCGTACTAGA CTTAACGCTAAGGTTTCGTAATGTAACGCCTGCATTCACGTCAATAATAGCTCAGT ATGTGAGAAGTCCGATGCTGTTAATTCTAATAACGCTCCCACTTGAAGGAGAAAGC GGGAGTAGGTGCGTTTGTTCAGAAACCACTTAAGCGGTTTGTTTGTACGTACAAAA TTTGCTTTTAGATGTATAGTTGTATACATAACCATCGTCCGAAAGTAACCTTCATA TGAAACTCAAAGGCATTAGTTGGGAAGCAGTATGTGGCGTTTGTGACACATCGGGA TTATAAAATTCCAATATATATTCTAAGTAGCAGTTAAATGAACTCCACTATGGTTA AATACTTGTACCTATCGTTATTCGCAATTGTGCCACTTTTACATAGATTGTGAACC GGTATATCGCGTGGTCAAGACCAGGCTTCAAAGCTGTAGAGAACTGTTTATTCTTT GAGTGACATAGTATCGAGACTTGTATAAACATGGATGGTACACAACGTTGGAAAAG CCGAAAGCCAATAAGATATTTAAGCATTATGCTTTTATGTCAACACTGACTTTCTA AACCACACACCTTAAATCAGTAGAACAGCATTTTGAAGGAGTGGCTAAACCATGTT GCGTGCAATTCTCCGGGCTCGTAAAAACGTGTCGTGCTAAAGGCTCTAAATCTCGC AGTAAAGGAGGCCCTCCAAACTAACTTAACTCATTTTGACGAACTCAAGTAGCTTC TATTAAATTCGTCCGAATACCATGAAGAACGGGATTCGCATACTGCGTTCGCCGTA GTGGAGCTCGTTACAAATCAAATGGATCGATAAACAAACG |
| 36 | 42.30% | TTAGTATAGTTAAGATAATGCGTCGCTAAACAACATAAAGATTCTTTACCGATGAG TTCTCGCTGGTATTCGCTTTTTTAGTCTTACTCGCTCAAGTTATCTTGAGAGATGT GGAACTGAACCACTTGAGGTAGCCCCATCAATTATAAGGAAATTGAAATAGGATCG AAATATTCTGAACTATTTCCATCTAGTCTACTGAAATTAACATTGACACCTTTCAC AAACGAATGGCAAAAAGGACGGATCCATCCCCACAGACAACTTCGTTTATTTCAG CACATTTGTCCCTGGACAACAGCCGTATGTGGTTCGACATACTACCTGATAGTGAG CGGTTATCGAAATGTCCTTGACTAGCTACTAAGAGGCTTTATACAATATTCCTACA CACATAGACCCAGTAGATATGAGTTCTAGTTGGAGATTTTTCAACACAATTACGCC ACGAGGTCCGACAACGTATCCTCCACAGTTAGGAACATTTATTACAAGGAGGTTAG CTCCGTGCTACAGCAACACGAATTACTCCACCGTGTTGAGCAGGTAAACGAGGGCA AAATACACCCCAAAGCGTAACTGCATACGACTTTCCGCTCGAAGATTGTTAAAACA AGACTGCAATTTCTGTGGCAAAAGACACTAAAGATGACAGTACAGCACCCATGGAG AGTTTGTACCCGGTTCGACCTAAGTATCTGTTGTCCAGAATCGTGAAATTTGAAGT GGCCTAAAAGCTGAGACGAGTATAGTAGGGTGGAGGTTTCCTATATGTTGGTCGGT CAGTAAATATTTAAACACGGGAGTTAAACTTATCTTAAATGTATCTATACATTAG TATATAGGCTGAGATTCGATATATATAGACGCCACCCCGAGAAATAGAAAGATAGT GATTCAAATTCCTAACAGTTCGGAGTGGTATACGCATTTCTGAGTAATTTGGCGTA CAAAGTTTGAGTAGAGCACAGAGTTGATAACTAGAGCAATGTCTGAGAGTGGATTA ACTTGGTGTGCTCTGCTAGAAATCCCCAGTGATGATCTCTCATAAAAAGTGACTGC AAGACTAGGATACAATTTATTATCGAAGTATCAAGATCGTGGGTTCCTTTTTTCCT GGTCAAAGATGAATCTGTCTTACTTAACGAAACACAGGAACTTTTCTTGCATAGGC ACCGATCTTGCTATGTATTGAAGCTACTTCAAAGGACCTATCAGCGGGTGTACACA ATGTCGGAACATGCATAAATGGCAGAAGGCGATGAGTCATTTCGCACACCAACAGG CCGACGAGCGTAGGAGCGACTCAGAACACTACCAACTATAGCATAACGATAAACGG AGAACGTCCATGCCGTTATGTGACCATTCGGTTCGGAGTCGTGGGTTACCGACCAC GATAGAACATGGCACACTGCTTTCTCACTTCCCAATAAGAAACACCCTGGACGTA TACCTCGATTGGATCTGGAGACAGTACTCGGATCCACACCTAAGTAGTACCTCACT GTGGGCGATGGCCAAGACGCGAGGTTGACTATCTGCGTGGTGGAAAAGGCCGACAG ATCTTTATCAATTGTAGTGAGCTGATGAGTCCTTTATCCGTTATAAGCTACTTTTA TTGGGTAATAGATGGTGCTCTTACTCCTTCGAGTTAATATATAGAAATCACCGCAA AGTTAAACGCAACATGAGTGGTTTGGATTAACAACTTCTGGAATCATTATAACCTT AGGAGCGTTCTAGTGATGCTGAAATTGAGCAGTAAAAAGTGCCCATGATGTAGGA AAGTCACTATAAAGTGAATCTCTTGTCCTTAAACATAAAGCGCGGTAAACACTCAC GTTAAGATGGTTGTGGCCACAACATGACTCTTTGTGGTTCTTGACGTGTTAACGCGG TGGCACTAGCAGGGATGATACAAGTTGATGCTTACCCATATGATTATTGTTCCCCG GAGCCACCACTAAGCCACTAAATGAAGATTTTTGCGGCGA |

TABLE 2-continued

Exemplary 2.0 Kilobase Stuffer Sequences Having 40 ± 5% GC Content

| SEQ ID NO. | GC Content | Stuffer Sequence |
|---|---|---|
| 37 | 38.20% | GATGTTCTGAAGTTCCTTAGCGTACAAACACAAAACGTGCATTGGAAAATGGAGAG GGAACCCTCTATGTCTGATGATTTTTTCGGTTGAGCTAATTCCAGTGCAATCGACA ATAAGGGCATGTCCGAAATTCGCTTTTTAATGGTAGTAGGTCCGGCATCATTATGT TGTCGGCCTAAATACCATAATCATTGCTCAACCTTCAACTCTTTGCTGGAACAATT AGTACTTTTCGTTTGCGCTTAACCATGCGTATAATGTAATAAAAGCACCAGTTTAT AGATATCGGAAAATTTAGAGTTCATGCCATAGTTTGAACCGACGGTAGGTACCTAT AACGTCTTTTGATTTCCGCAACCTATGTATTGTAAGCAGTTGTCCTAAGGAGTATT TTCACTGTCTAAGTGGTAACCAGCGGCGAGAACATAGTCGGCGGAACGGTTCTGAT TTCGACTAGCATCGGCGACATTGCCTTGTCAATCTCCATAATGATATAAACATGGT CTTTTAACTCTCACAACCTAAATTATTAACAGGTCGATACTTCTCTGGCGAGGTTG TTTTAAAACTTCCACTCCGGATAGGAATTTCATTGAAAATATAAAAGGTTGATGTG TCAATCGAAGTCTAAAAAGAATGAAGATTAGTGTCGCCTAGGACATCTATTTGTTT TAAAGTGCAAGGAACGTGTTCACGTAGAATTGTGAAATTGGATACATGTTTAGTGT CATGCATTGTTTATGGGATTGACTATAACTTAGATAGAGAACTAGTTACCCTTATT ACTTTGCAGTATATGAACGACTGATTGTCAAGACTGAGCCTAAATTAAAGTAATCA GCACATTTTGGATATGGATAGGAGCTCAGTTTCTGGTTTCACTCTCATCGACTTCT TTGTCCAAATACGGCAATCACGTAATGCATAAAAATTCAAACATAATGTGATGAAA GAACATATCACCCGTCTAAAAAATTAAATATATACTATAGTGCTGCAATACATCCT TAAATTGTCCTATATTGGTAAGTCAAACGATACAACCTGCATTCTTGGGGGATAAC TGATGTTTACTGGACGGCGGAAATACTTTAATTTATAGGCTACTCCAGTGCATAGT AAGAATCATAATTTGGTAGCGCCTAGTAAAAGAAATCCTCAAAAACTAAACGCTA TTCTGATCGCTATCATCAAGAAATGAATTGTAAGTGAGGGCTGTATTCTAACTCAT CCTAGCAGGATTTATTGCCTGCATCATCGACATTCTGTTCGAAGCGGTGATCCCCA TTTGGACAAATTCAAGGTTTGGATTATCTAGCGCCCTTGGAGTCTCTTTACGTGTT TAGGTGTTCCTGTAGGAAAATCATCTTATTGTCGCGAATAGAAGGTACAAAAAGAC CTCAAAGTTACCATATGCACCATGGAGATGAAACGGTAAAAGTAACTGGGACCAAA GCTGTCCTTCCGGGATTCATTATTACCATAATCATTAGGCATCAATAATATTCTGT GCGATATGTTGCTCGGCTTATTAACCTCAATGAAACAATATGACCGCATATCGCTA CAGTAAATCTACGACGTTTTTACTGATTGATTGAATCGCACTTTTTAATAATTGTA TGCCCCGATACATAAAATGTCATAATCGAGAAGCATATAGTAGTATTGTAGTATCC TCAGGATCGGTTGGTAGCTTTAATACGTGTAAATTTTTCTCGTAATTATCGAGAGT GTGGAGACGTCCGTGTACTGGATTCGTAAGAATTCAATACCCTGATGTCCGTCCGA GTAGATCGATAAAGTAAGTAGGGATATTCAGATATTTAATGTATTTCCTGTACACT GTGACATCTCTGCAACGAGATTGTTATACTGGCGGCGCGTAGGAAAAATTCAACCA GTCTGTTTGCAGGGATAGTTAAAATTCATTAGAGACCAGAGCAAATAATGAGCATC CGAAATGTATCCAAAGCGATATACGCGCTTACAAACTCTG |
| 38 | 39.70% | TTGATGTGCGAATATAACATTGATCATCAGAGGCAAGGTGATAGGTATTAAAACGT TAGCGTCCACGCTCCTGGTTCTATAAAACTTCTTTAGATGCTGCTAAGTCCATTGA TTTACTGTTTTATAGATACGAGAGTAAATAGTTTAAATTTTTTAAGTTTGAAAT ACGTGTAGCTATCGTTGCGCTAAGGAGAGTTGTCTATGTACTAGTGATTTCAGTCG GAAATAGCAGAAACATGAACCTATCACATGACTGTCGAATGGAAAATTTGGAGTCT GGAACATTCAGTATGAGATATACATTAATCCATGACTCAGAGGAATTGACCCACTA ATGTTATTCTTAGTTGCAATTCCAGGTATGTCTAGAATTTGCAATCGGTTAGCCGT TGTGTACTTCGTATCAATTTTCAAACAGAATACAAAACCACGCTAGTTAGCCGAAA TTACTCCTAATTGTCGTCACTATGTAAGAGATTTAGAAAAAATAGTATTTGGTACT ACTAAGATAATCGCTGTCCACTATAAACTTGTAGGTAGTTAGTCGAGTGTTCTGCA AGGGTACATTCATGGAATTCGCGAGCAACGTTCGCTTCTCCCAAATATTGATATA AAGACGATCCATTCTATGTATTTTCGCACTAGTAAAATACCTATCTACTCGACTTA CGCTATAGCTCAGGGATCTATTTGTAGGCATCCACAGCTCAGACGAAATAATAGAT TTACGAACTGATAGCGGCCCTCCATGCCTGCTAATCATGTTCATACATCCAAACAA ATCGTTTTGTTGGTAGACAACAACATAGCGATAATTTCAACTGGTTGAAATGGTTG TATAGCTGAATATAAACGATCCCAAAAAATTCAAGATGGTGGCTGCACCGGAACGA CGTTAATAGCGTGAGGAGGTGTTAAAAGCAACAAAATCACACCCGCCGTCTTCTAG GGTAAGCGGGTGCCAGCCGGGTCTACTGGATAAGTAGATATTTAGCAAAGAACCTC AGTTATCCATTTTCTGGTTACGTGCACAATTAGTTTTGCATCTGCCGGCTTTTGTC TCTGGCACTTGACAAACCTAGCAAAACTCAACTGAGGGGTTAACACGCTCTAAGAT TCCTCTTACTAGATGAGGTATTCATCTGCGTATCTGATTCTACGTTATAGGCTTTT TCTCTCGAATACTAATGTCTGGACTGATCAATAAGAATTGGCTAATTGCGGAAGTC AAAATAGAACCAATTATATTCATACTTCTATTATTAGTTCTAGGATGATTTTCCCG ACCATCGGTAGTAGGAGGAGGTGATGTAACTCAGTAGTATTATGCTGAGTGATTGC ACCTCTGATTCTATTAATATGGGGGATGCTGCTTGCCTCGTGGGTTAGTGTCCGG ATGAAAACCCCCTAACCTATTCACGTATAGTATCCCAGTCAATTGAGTCAGTGAC CTTAATCCTAACAAAAATACAGAATGCTGTGAATGACCTCGTTCTTCTTATTGTG CACGATCTGATTCGAAAATGAACGGTATAGAGTCTGAGCATCACGATATAAGAGAT TCATTCTGTATTATTTACGAAAGGCGTAGCACCATTCGATCAGCGAGCAGAACCAC GGGGCAGTATTGAATTTCCGTTTTTCCGATTTCAAAACGGCTAGAAATGGCTGCTG GATGATAGATGCCCAACTCACACGGTTGAACTTGCTTATCAATTGTGCGGTTCATA TCAGACATAGCAGTCTGCTTGGAAGATATTGAGTAACTTCGACATTCAAACGCGCA AAGCTATTGAGTTGCCCCTGATGCTGTCTATCGTGTATTAAGTGATCGTGGGAATT AGACATACAACTTTACCTCTTCTAGCTTGTTTATAGAGCCTCACCGAGGTATAAAT CATTAATTACCCAGGGAGACCGGTTTTGCTATTACCTTGTAATGTTCAAAAAGAAG TGGAACACAGTGAAAGCCTCATTTCTCAAGCAAGTGAGTA |

TABLE 2-continued

Exemplary 2.0 Kilobase Stuffer Sequences Having 40 ± 5% GC Content

| SEQ ID NO. | GC Content | Stuffer Sequence |
|---|---|---|
| 39 | 40.40% | TGTAGACATTTGTCTTCAATCTAACCTCTTTCTCACGAAATAAGGGCTTGTATTGT TCCTTCGTTTGTTTACCGCACAGAAACAGCTTCACTTAACATACATTGTAAGTGTG TATTTCTCGGGGTACGTAACATAACGAAACTTAAAGCAATCAGACATACAGTGCCA TTCCCTACGGTACTGTCTCAGTATGTTAATACTACTCATTTGCAAAAGGATGTACG CACTTCATACTACAGCTGCTGACGGTGTATATCAAACAATTATATTAACGCTCGTA GGATAGTTCACGTCCGCCATATCTTTGATTTAGGCTTCAAAATTCAGAATAATACG AAATAGTCTGTCTACTAGGCCAAAGTCACTTAAGGGCTAAGAGTGTAATGAGTAAT CAAAATAATAATCGTTGAGTCGTCAATTGGAGCATCAGTTATGGCATTAAAACATC TAGTGGGTCGAAAGGATCAGGAAATTATGTATGGGTGAGAGTCGCTGCTACGGTAT CGCTTTTGGATTGAGGGCTACTACACTCAGTACCCACAGTGTGTGTATTAATAAGA ATCGCAATATGCGTCCTTTTAAGTTTTAAGGTACCCTACCTTTCATATCTAGTGGA AATCATTTACGCCTATGCGACAAATTAGAGACTTTTATTTGTAAAACATTGGATGT TGGAATGACCCTAGATGCATGTTAAATAGCACGTTCATTAGTGGTACACGCCTATC ACTAACGCTATGGAAAAATAGAAGAAGCCAGAACAAGTAAACCTATGGTGACAAAT AATTACATAAGGAAATCCCTCATAATTAGAATACCATAAAACGTTAGTTGTACTAT CCGTAATCTACCTTCTAGCGTGGAATAGTTGAGTGTATTCTAGTCACGCCCCGTTC CATAACGATACATGTAAAATTTACAGCGACGTTTAGGAACCCTACAAGGGGAGCAG CAGCGAGGATAGCTGACTAGCCTTACAATAAGCACCCATACTTATGATTGACATGA TGGTCATGCGGCGTTACCACTCCGCTAGCGTTACTTCTTTCGTCTTGTACCGGTTT GGCAATGCGATGCAGCCCAGGTACCGTAGAGAAAGTAGCGATGTGTGAGGTCGAGT ACTTTGTCAGAAAGCAAGTCGGATTGCGGTCCCATTTACCGCGACGTGCATTTGTA CAGTATGACCGTTTTTTACCACTTACTGATGAGGCCAGACTAATAAACGATATTTG GTCACAGGACAATATTACGGCCAATTATGAAATAACTGACTGGCCTATTGAATGAC TAGGAATGTCAAGTCCAGACTCTAGCTATTTGGGAGGTTTATATGTTTGGACCGAC TTGTGGGAGTTTGACACTACGAGTAACAAGATTATCCCTTTTTATGCTGCGCTAGT TGACATGGATTGACGAGGTTATTAATATCCATGACTAACTCATCACAGCTTCCCGA GCCGAGACGGATTATTTTAATCTCGTTGATCGATATATTAGGTGACGTGAGAAGAA GATGTGTCGTAATCAGTAATAGTTAGGATCAAGAGGTTAAAAGAAGCGCCTTCTTC ACAGATTCTCAGTATCTACCAGCACAGAGTTCTCAGTTTCTAACGTGTTCCGTATG GATTTGCGCCACTTTCTGAATAAGTCTTATGAGATATACTTACCTGGTCCAGATGT AGCAGCGAGTTAAGATTATAACTGCGGTTTAGCACGCAGCGTTTAAATACAAATAC TCTTGACTGTTATAACGTTCAGGATTAGGAACAGGTTCCTCACGGATATAGAACCC AATTCACGTGCATGAGGTATTCTATCTTAGGGGGAGGAACTGCGCTGGAGCTTGAA ACTGACCCTCTAGGCGCTTGCTTTCACTGAGATCTATTCAAACTGACGTTTAGTAA GAAATCATAAGACTTATCTACGCCGCCTTATAATTTATGTTATTAAAACATGATCA TGCGATCAATTAGGTAAATTTCTTTGTGCCTTGCAATATG |
| 40 | 38.60% | CGAATATTTATTTTTCCTACGCACCTACACTATCGTGAAGTTCATGGTATCAATTA TATGTCACTAGAGCCACAAATACGTACTTAAATCATTTACCTCGACTGAAGGTTGT AGGCTTGGACATACTCTTGCCACCATTGTAACAAAGGTAGATCGGTTGGACCCGAA ATTTGGTACTTTTAATCTAGAATCAGCAATATCCTACGGAAAGGCCCAAGAGATGT CTCAATGGATGAGAGTGTAATTACCTAATTTCAGAAAAGAGAGTTTAACACAAATA AGAACAGACGAATATCAATAAAGTGCACGTCGGGCCTAAATGAGCCCACAGCCTGG ATAGATTAAGTGCGATACGTCGCTACCAACGAACAAAAGTATTTGGTATTATGACA TCGGCTCCGACGGTATAGGATAGGAATAACTCCCAAACAATATAATCTTGGATACG ATTAAGTTTGAGTTTGATTGATCCCATCAAACATTTGTTGGTATAAAGTTAATGTG TGATCCAGTTAGAATTATATGAACATAGTGTTGTCACGATTTTGAGACGACCGTTA AACATTATACTGCGGTGGCATAGCAAGTTCATCTCCTGACATTAGTCAGCATTTAA TAGTAAGCAGGAGTACTATTAACACGCTCCTATAATCGGTTGCCTGTTGGGGATAA TCAGAACATGAAAACTCCATATTAGAAAATTACATAATATAGATCACGTGTATGA AACCTAATACCGCGAATATAATTACATTATGATTGCAATACATAGGGTAGACTCCT AGTTAACGTAAACCAAATAACCGACTCGAGAAACACAGGACTAACAATTATAATTT ATAAACTAAGAGTGCTATACTAGTTACTGCCTGATACCTATGTTTATTTGCAAGTC AAAAGTTTCAAATAGCCCTTGGCAAGCTACATGATGGGTGATTGGAGGTGGGACTA GGAGTTCCGTCCTTAGTCTGAATAAAGAACATGATGTGCACCGATTTGTCGTCTAC TCGGACGTTGTGGCAAGAATAAAAGTGAGGTATAGTACCGCTAGCCGCAGAGATAC TGCCTTCATATGCGCCGATACTCTATTGTTCATAAACAGCAATGAGGCAGAGCACA TAATCTTAATTATTAATTTAGTTAACGGCTTCCCAATTTAGCAATGAATAAATTTT TTGAGGTGCATCTGTGATTAATTCACCCAGAAACGCTTTCGCGAATTACCTGTCAC TATAGATCCTTAATGAATTATCTTCGTCGTCGGAACAATTATCGGACTTTATTTTG CCTGTTTTATGTATCGAGTTAAATAACGGGAATCATAATTTTATATTACATCTGTT TTGTATAGCGGATCTCAGTAGGTTACATCACTGTCGTCGGATTCAACAGCAACAAC ACCGTTAATGAATATAGCTACACTGCATGAGTCCCAACAGCACTGGTCCACTAGAA ATATATAATTATACGAATACTTTGCTATGTTCATGACCTGTCAAAGGAGAAATCTA GTAAAGACCCACGGATATCGAAGAACATTGTAGTTCTGACTCGGTTTGAATGTCCG GTAACTGCAGGTTCCCGTTATACTGAGCGGTCCGAAAATGGCAGTCTAAGTCCCCC TACATGACGATTGCTATTTATTAGGTCTCAGAATATAACATTAGCACAAGAGCAC AATAGTCGGAGTATGCGTTATCGAGACCGTATATGAGTCAATCGAACGTAGATCGA TCATAGCTAACTAGGTGGTGTATCACTGACGACTTGACGATGTTTTATCGCTGATT AGTTTATGATCTTGTAAAGATTGGATGCTACATATTATGGTAATTTTGCTACTTCC CCCAACTATACCAAATGACTCACTGTTTATCAAAGGTGACTGGATAGGCGCTAGGT ATATCCCGGTGCGCAATTATTGCCCTGGCGAGCCGAACATCTCGAATATGTAAAGA CGAATACTCCCTAATTACCTTTTCGAGGTAACAATGAATA |

TABLE 2-continued

Exemplary 2.0 Kilobase Stuffer Sequences Having 40 ± 5% GC Content

| SEQ ID NO. | GC Content | Stuffer Sequence |
|---|---|---|
| 41 | 42.20% | ATCGAGTTGGTTTCTACGAGTAGCTGGCAAGCGCACATAGAACACACATTGCATGT GAGTGGAGCGATTGCGAGACGAAACAACCTTCCAAAAGCCCAACGATTACAGTGCT AGTTATCTATGGGAACTTATTCCCTTAGGGCCAAAGTCCCTAGGTTATTCTATACG ACTCACACCGAAGAGGCTGTAAATTAACCCGAATATAGATGATTAGTCCTTTGTTT GTCTTAGGGATGGCACCATAATAAAATTGTCAAATTAGGGTACAGGACTAGTTCGA TTTCTTCTATCCGTCGTCCTAGGTTTATATGTGGCCGTCACCACTGTATCACATGC CAGCTAGCAACAGTATGATGTATAGCGGCAAATCATTCGTCGGGGGCATGCAGAAC GTCAGTTAACTTTAAAGATGAGACTACGTTTTGGTCACAATACAATGACTTAGACT CATCTCTTAACTCAGACAATCACTTTTATACTTAGTGCAATGTGTCACAGCCACTT AATGGCCTAGCTAATCCTTATAGTCGGTAGCTAGCGAGTTATAGAATCTTGTTGTG GATAATCCTGCTCAACCTTGCCTGGAAGTCTAAGACCAGTACTAGAAGTTAGGCGT CGGAGTCTGTGATGCTAAAGTTGTTCGGCCAACTAATTAGGGGTGTACCTCCTTGT CTAATCCTCTTAGAAATTATTCGAGAAGGGTACAGTACCCCTCACAAAGAGAATCT AAGTTACCGTCTGAAGTCTGAGTGATCCGTTTTGAGGTAAACAGCTGTTATACATA CTTACAGCTTAGTCTACATGACCTACTAAGCGCTTCGTGCTCCTTACCGTCCCAGA ATACCCATGGCTCGCGTCTCCTGCCGTACAATACGTAGATTTAATACTCGTAATGT TTACAAAAAATGGCTCAGCGAATATGAATACGATATACAGTACCATATTTATGGAT ACAAAATTTGTGGCATCCGCCTAATAGGGCTTTCCTCAGGGCTTACTCCACATACT GTTCAACCTTCTAGGTTCAGTAAAAGTGGAGACCACGATGCAGTGTCCTTCTTAAT CTGGCCTTATTTGTCGATCCCTTATCTCGCTAAGATTAGTCACACGACAAAGAGGT CGTTAATGACGTATCTAGCCACAATGACAGTCTTCTGGCGAAGATATCTACAAGA GTCGTTGATTCGTCACTTTTAGCCTTGTAAAATTGCCCTTTGAATAGGTGACACCC GAATGGATTGGTACTTTCGTAATTAACCGAGACTTTGGAGAATTGTCTCCGGCGTT TCATGTGGCGAAGAATAGAGGTGACTTTGATGGCACCAGAATCTCACTGACAATTG CTATAGACCTAATATCGGATATTTCTGCAACTTCCTAATCGAAAAAATTTCTACAA ACCAGTCGCAGCCTTGAGTATTCGCCCTTGACATAGATTCACAAGATTGAGTCGCA AATGGTCCTATGATAATGGATGTGTTATTGCTGGAACTTTATCATGATGCAAAGAG GTTATAATATTTTGTGTTAGTAGCACACTTAATGCACGCAGAATCCTTAATCAATC ATTAGCTGCTAATGAGAATCAACCGACCGTGTTGGTGTTACTGGAATTATATTCAG TATCGCTCTGATCTTAAGGCCCTCAGCACCTGAGGTCTAACGAAAATTTTTTAAG CCCATTCTCGCAAGGCCACAACCATCAGTCTCTCGAGAACGACATTGGACCTCATA TCCAAGCCTCCGGTTATTCACCGATGTATTTCTTCGAGTATCTAAAATCTGCCAAT ACGATTCAAGAGAAGTTAGTATGCGGGATCATGTAGCGTACCTTTATATGAATAAA ACATACCTGGTAGATGGAAACTTGGTGACCCGGGAGTACGTCATTCGGTACTGAT ACTTGAGGGTGAACATGGTGCGTGATTCCAGTATAGCGGTGAACCTACGACAATAT GTGCATGGCATTGCTTATTTGGTGTATCGTTTTTTGAGAA |
| 42 | 37.60% | TAACTATATGGTGTCTGTTTACTACGATTGCATTAAGATTTCTAGCAATCTTCTCC AGTAACTGCACTTCCCCATATTGTAGAAGCGACTTATGGAGCTAATCTTTCACTTG GTTTAATGCTAACTGGGATTTGAGCACGTAAAACTTAACTCGGACCACTTTGTTGA CATAATTCCGCTGCTTATATACCCATATTCATGTCTACGATTATAAAGTTCTTCGT ATTTGGCTAAGCGTCTCTACCTAGGCTCAAGCCTTTTTAGCCAATCTGAACGCTAA ACGGGTGCTAGCCTAGTGATTATTTAATGACGATTTGAGTTCATGGACGAAATTAC ATTATTACTGTCTAACCGGACAACGGGCACGTCACAATAAGAAGGGTACAGTTGGG ATCGCAGTTTATTCATGCTGTATGCCAATTCTACTACCTCTCGTCATCTTAATTCA TATATAGCTGAAGGGCTAGCAAGTAGTGGATGACTATAATCGGGATTTAGAAGAGT TTTTTCCTCGAACATTAGCCTTATGTGTCTATTTTGTTAAAATTGACATGCTAAAC GATAGCTATTAGCTGGAGGAATAACATAATGTTGTAAAAGGTAACCAGCTCATCAC TTCAGGAATCTTACTTCCTACGATGGCTGTCTTTTAGTCGACGTAAAGAAACCCAA CCAAGGAATACTTAGACAGACAGGAGATCATCCTACAAAGATAGTCGATCTTTTAT TTAGTCCAACGCTTACCAATGAATAGGGCTGTCTGAGACTCAAAATATTGGACCAT GGGTTTCGCAAAGCGCAAACGGAGAACTATGATTTCTTGTTGTGGCAGCGTATGGT CCCCACGGGTGACTGTACAATCACGGAGACTTTTATCATATAACGATAGTACATTT ATCTGGATACCGGATCCTTCATTTCTCGGAACTCTATACTTACTTTAATTTAATGG CCCGAAATCTATTATCCTTAAATTACACCGCCGTGGACTCGGAATGAAGATGAGTC CGCAAGGCATACTGTTAGATCGGCTGAGATATTGCCTAGTGCAATCGATCTTTTGA TGGTATTTGTGTACATTCTAATTCGAGGCGAAACTGTCAATAAACTAATGGGAAAA GCAAGCATATCACGAGAAATATTCTAGGGGATAACATTACGTTTTCGGAACACAAC AGGTTCGACATAAATCTTTTATCATATTATTTGCTTACAATTATTTAGGGCTTCCG CCCATACTCAGTAGTTCAAATGATGCAAAGGATGTGGTGTCTAGTAGATCTCTTAA ATTTCTATCGAATGGCGTAGTTACATTGCAGTTATTTTTACATGGCAAAATGATCA AATTTGTACGCAATAGCAGTAACATATTCTCTGTAGTCTATATCTTTATGATTGGA GACTGTTAAAAGCTGATATGACTAATCAAGAAAATATCGAAATTTGATCTACGACT TAACATTTTAACTAAGCAGACATCATAACGTTTATTCTTCAACGGGCCGTTACTGC TAAACATTAATCTAACGTAAATCGGAACTCTGCAGAGTGCCCGTCTCTTATTTTGT CTGAATTTTAGAATTTACAAGGAGATGCTCAAGCCGAGTTAGAAGAAGAGAAATAT AATGAATCCACCGAGTGTATGTTTATACATAAAGAACTATCTTTAGGCGACGTGCT AGATCCCACTATGTTCATGTGTAACGCATTTATTGGTGGAACTCTCGCAAAATCTT ACATTATTTCGCCATTACGTCTATACAAAAGCTAGATCCGTGAAGGGTCATAACCT CCTTTAAAGGCATGAAAGAGGTTATCTAACTTATGATTCTATAACATCGTCACTGG TGGAGTAAAAACATCTGTGATAAATACTTGTGATACTCTCTAACATCCCTGTAATA TGATGATCATAACGCTTGCACCTATTAACTTAAAAGAAAGTTGTCTTATGGTGATT CTTAAATAAAAGTGCCTGAGCCACCTTGTGTAATTTTTAA |

TABLE 2-continued

Exemplary 2.0 Kilobase Stuffer Sequences Having 40 ± 5% GC Content

| SEQ ID NO. | GC Content | Stuffer Sequence |
|---|---|---|
| 43 | 40.20% | CACAATAGTATAGGGACGTCTATTATTGAAAATTATACCATGTGGACATATTCTGG ATTTGAATTTATTTTTTACGAACTTACTCGTCTCTTTGTCGAACTGATCGAACCAT GATAGGCGGTCCATACGTGTAGTGTGTGCTAGAAGCATCTGTACTTGTATTGAAAG GAACAAAGTCAACCATGCTGTTCACCAATTTGATACGAAGGAATGTCCTATCTAAC CGGGCTTATTTTACAGGCTAAGTAGGTGAATAATGACAGGAAAAATTCGAATAAAT CAGAAGAGTTTTAAGTAAGGCTCACTGGTCGAACGGTGATAATACTGGCGGCAAGT TCTATGTAGCTTATTAGATAACTCTTCGGGTGAGAGAAAGAGCTTATAAATGTGGC GCTGAAATCCGATGCCAGCTGTAGCCGAGTCGCGTCATCTCCTAACGGATCAGTTA ACATTATGCTTACTGGACGTAAAGTGGCTTGTCTAGCTCTCATGCGCCTTGTAAAG CTTTTTCTCACTGTGTTCGATTATAGTGCTCTCAGCCTACCGTTGCAAACAATGAC TAGCGACTGAGATGACAACACGCCACACATATCGAGTGGTACCGTATTGGGAGGGT AGTGGAGAGACCACCCGATATGGATAACACGTACAAGATGTGGTTAAAGAGCCAAT CACAAATTGAGCGGCGATCGTGTCGACAATTTTTCATTGTGTAAGCATGCATGTAT ACTAGAAATAGAGTAATACTTAGCATATACGATTAACTCTTGGTGAGATGAGATTC TAGCTTTAAAAGAGGGGATACCGATAGAGTAATACATGTTCTTTTGAGCAAATGGG TTGTTCGCCCTGATCCATGATAACGACTATTTCATAGCTCTAATTTAGATGCTTGA CCCAGTGTAAAGATCCGTTTTAACTAACTTAGATGATAATGAGAATAAAGTAATT GACTACTTAGTACACTTTAAATCCTCCAGTCGATGTGTATTGTCGCTATATCGCAA CCCGATGTTCACATACAGGGTCCTGACTTTGGGTATACCTTAGTACGTAACAATCT CACTCACAATCAATCCAAGCGCGGTTACTATGTTACGACGGGGAAGCAATACACAG CTAGGCGTGCAGTACTGCTCTTAGCTCTCCGAAATCTGATCTAGATGCCCAAATAA TTTTGTTTCCAAAGCTAGCGAGGTTTTACGACCAGTCATGACAGATTCTGCAGTTG AAGCATGTCACAGGTAAGCAAAAGCGTGGAACGGATGGAGCGAGTAATCAATAGAA CTTACTTTACGAGCGGTGTTACAAAATTGGGTATAATGCACTAGCCGACATCGATG GTGTAGTGAATTGGACTGGCACCCTCAAGGCCTCGCCCAACTCAGTCTCGCTAGTT TGCTACCTGCATCCTATGAAGCTGTTTTTAAAAATATCGATTTCTAGCGGTAGTTA AACTATTAGGAAGGGCTAAAACAAAGTTAATTATACTTATGTGAACTTACAATTTA TATATTAGAAAGTGAGTAAGCATATCTGAACAAGCATCATCGTAATGAGGTCGGTT CGAAGTATAAACTTAAGTTAACGACATCTTCCAATACCATCGAAGTCTACTAAGTA AGTTAGGTGCTTAATGATCATTCATAGTGTAGCAAGTCCCCGCAACTAGATAAAGT CAACGACTTAGGAGTTTAGATAGAATTGTGTACCACTAGCTCGCTACAATTGGTTT GTCTAGACTTAATCCCTTACCTGTTGAGACCGACTCTATTTCGGTAAAAATCGGCA AAATACGGTAACATTGTCTGCAGTCTGAACACAGACTAGCTTATATACATGGATCA ACCATCAGGTGTGACTATGTTTTATTATATGAACTGTTACCATGGCGCCTACGACA ATAGTATATTTCCATTTCGGTTACCAGTTTTTGTCTACTTTATCCATTAAGTGATA TATATACATGTGTCCAACGTTATATGGACAGCGTTGTGCA |
| 44 | 41.90% | TAAAAGAACGGACATGGCGCACAAAATGACTATGAGGCGGTTACTTCTGATGATCA CACCCTAGTTCTTACTCAGGCTATTGTACACCCTGCCCTCTCAATATACCCGGAAA TATGCATTTATACGGCAATCGATCTTGAATCCCAGTTCGAGTCTTTACAAATTCCA TCGTTTACTACGCAACGTCATGCTAAATAACACCTTCCCATATATGTAGCGTGGGC GGGACTATTAGAGTCACTTTGTGCTAAACAGCCGGTAAGTATAATAGTTTACTCCG GAAGGTGTCAATATGTTTAGCGACTGTATTTTGGTACTTTATCCCTAAACTTAGCT AATTTACACATATAGCAGCTGGAGGAGCAAGGTATCATTTAATCTTGCTTAAGACC CTAGTTTGTACCCCTGTCGCACACTAAACCCAAAATTGCGACATTGAGCCACTTAG GCCACATTCGTTAATCTGGTAGTTACAGCACAATGGCTATAATATACAGATACGTC TAGAAAAAAGTTATTTAATGCATAGCTTGCATAATCGATTCTTTAAAACAGGGTGG GGAGCTACGTATCTAGGATTTTATTCTACGTCATGATAACGAATCTTCCTGAACGT ACTAGATGGCGACTATCGGAGAATGATTTAGAACGCCGGGTGTGTCTTGATGATAT AACAATAAGTACCACGAAAAGAATGTAAATAACTTGATATCGACTGTCACAATTTG TTTGTATCATTGTTCGTATCATTATGCTCCTGCTCGTGTCGCAATTCCCCTTTCAC CTTTTGGTTCTTTATACACAATCATATTATAGACTTATACGGAATATTGGTTGTAA CTTAGAGTAATACCGATTGAACCCACATGTCGCTGACTGCGACGCTACGGCATCTT AAGCCGATATATCGTCGTGACGTAACTAGGAGTCCGTAAGCGAAGAGTAGCATAGC GATGATCGTTTCAGACTCGGAGTATTAGAGTTACCATGCTAGCCACATAGAACGGC CTTCCGTAACCGGTGGCACTCGTTCGCAGTGGGAAGCCCAAGTTAGAATAAATTGC TAAATCTGATTCTCCCGTCTGGACTTCGATCTTCGAGCTAGAGTGCCACTACGGGC ACTAACACATTCAACGAGTTTCGTCGGGTGGCTCGACTATCGGCACGAGTGTTGCT CTACGAGAATACCTGCCTTCCTTACTGCGATTTCTCTTTACGCTCTTCCACTGGTG CCAAGTGGCTGTATATTACTGGTCGAGTAGGGCTCGCTGATTGTCGTGATTCAAAA ACGCAACTCTAAAATCCATACCTTTGTTGAATACCTTTATTCTCGTTATCATAGAG GTGTTCGGGCCCTCACTATCGATGGCAGATATAGCTTCTCCGCTCGTACTTTCATA TAGATGTTCCCCAACAGCTTTAAAGTTAGAATGATCCACTTTCAGGGCATCCAGTA ACTCGAGCAATTATGTATGTAACCGATCTTTCGATGATAGGGGATAGTACACCTTA ACCCTTGTCCCCGGTGAATTGCGGCGACACCATGCGGTAGGCGTATGTACGGTGTG CCCTTAATTAACATCGCTACTGTACTACACGGTTAGGTCGTTTGAAAAGGCAGCCA TGAATGTTAAGATCTTATTTTAAAATTGATCATTTACATTTAGCTGCTTTGGGGGT AAATCTACTGATCCAGGTATTAATCTCTTTTGTATAATGTACCAATTGTAGTAGGT TCTCTATGTTCTTAAGTTTCATTGTCGATAATAAACTAATCGGCAAAGGAAGAAAA CTCAATAACTTGTATTGTACCAAAAAAGCGGGGGCTATAGTTAGATCGGTGACTCA CTTTCTTCGATATAAGGGAAACCCACCGTATAACGACGGTGATCTTAAGCCTTCTC CCAGGTTAACGTATAGCCTACAAATGAATGCATTCAAAATGTCGTAAGCCTTTTAC CTGGAAAGCACAAACGATAGCGCATTTCCTTAAAGTACCT |

TABLE 2-continued

Exemplary 2.0 Kilobase Stuffer Sequences Having 40 ± 5% GC Content

| SEQ ID NO. | GC Content | Stuffer Sequence |
|---|---|---|
| 45 | 38.90% | ACTTGCACAGAAATGACAAAGACGTCGATTCACGATAAGGCATTCCAATAAGTATA<br>ACATAATCGTGTTTCGGGGCGCACAAAATAGATACCCAAAAGAGTGTCCTTTCCAC<br>TCGACAGTAGAGCTCATAGTTCCGTGAGATTCTTGCCTCGTAACTAGTAGACTGTC<br>TATCGCAAGAATATCACACCCAATATTTAACAACGCTCTGACGTAGTAGTGGCTAC<br>TTGTGCGAATAATCTAGTTTCTCATATTTGCGATTCAACTTACGGCTAAACGGCCT<br>CATAGTTTTTCCCTATTTTGAACATAAGTCGCTGTTAAGCAGAGTGATACTTCCCT<br>TATTTAAGTGTAAGATGTTAAACACTAAGCTAGAACACAGTAAGCCCCCGTATCTT<br>AGACGTAATAGCCCTGTTAGATTAAAGGATTGCGATCGACATACCAACAGATGACA<br>TTAAAGCAAGTATAGCTTCAATTCCCGCCACGGTAAACACCTATCACGATACAAAG<br>GATAGACTTACCGAGTACCGTAGTTAGTAACCTCTAAGCTAGTAAATCAAAGTTTT<br>CGCTAGTTATTCATAAGAACAAAATTACAAAATGCGTATTTACAACTCATTTACAG<br>TGATGAGACCGATTCTAATCCAATCGGTGTTAGTTTTGCTTATCTGAAAATACTGT<br>TAGAAATGACGTGGCTGTTAATCAATGTATAACGTGCATGCGCTGAATATCAATCA<br>TCAGTATCGAGGAGTTGGCATACGCGGGGCTGTTGTTAAAAATTGATCCGAATCA<br>TCTGGTTTACTCCACTAATGGATTAAGCCTCCTCAAGGCAGCTGATGTGAAACCCA<br>AAGATGTCAATTTGATTTCGGTAATTAATTGAAATCCCTGTCCTGAGCAGACTATA<br>AACAGATAACCGTATGGAAATCTGATTCCTTAGACGTTTTCAAATCTATTCAAGTA<br>AATTTTTACGGGAATCTTAAACGATATCGTTCCGTGAAGTAATTCAAAAAACGGTC<br>TTGATCTTATAATTCACGTTTGATACTAATTTAGTCCTCCGCTCCCTAATGATTTT<br>TTACGAAATGGTCCAGTTTATTGTTTTTAAAACTCTTTGGAAAATTCGTGTATGAG<br>GATGATAAATTGTTCGATCAACGTTTGTATACTTAGATCTCAAGCAAGAACTGTCA<br>GCGACCTGTCGTTAGGTAGTTTGTTGCCTGCCACCTCGCGACCTTAGGAAAGGAAG<br>GTAATCTATTCCTTAATACGTACTATGTACAAGAGATGCAAGAAAAGGGCAACATG<br>AGAACGGTTAGTCTCTTTGACCCTCTTACTGGTTAGTGAATATTTTTACCAGCTGC<br>TACGATGCAGGATATCTGGCCCTTTGACTGTTCCATGGACACGAGCCCGAAGGATA<br>TTTATTTAATCGAGAGCTGTATTTAGTATCTTCATAGGACTTGAAATCGGATACCG<br>CTGTAATTGTGGAACCTCATGAGACCTCCTAACAAAACAAGTATCGACCTGCCCTA<br>TCTCCGACATTTACTCAACTCTACCCCCAGGTTGACAATTTAGGATGGTGTCTATG<br>GGAAATATGATTCGTAACGTGCTGCCTCAAGAATAGGTTATGAAAATATATATATA<br>AAATTCTATGATAGTTCCTTCGTCTCACTCAATACTAAGTCGTTAAGCCAACTAGC<br>TCGGGCGGGCTATTAGTTGCCATATGAGGATCCATGAATCAAACAAATAATGCAAT<br>TCTGCTAAAAAGTGTGTATATAGAGCGTACACACAAGAAACAAAACTGACCGATCC<br>GACTTAACCATTTCAATATAATGCTGCACCCTTGTCCTCAATAGCTTGCAGGGGGC<br>AATTACGTTTGGAGTCTGGTTGTGGTAATACTCGACTGTCCTCGGCGATATAGAAT<br>AATTATAGAGTGTATTATAGCACAAATTATTAATAGATTCCATAGCCTGGCGTTAC<br>ATGAATATTCTCAGTTAAAGCATTTGAACGATCAAGTGGT |
| 46 | 40.60% | AGGAACAATGTTAATATCAAGTCGGGTCCAAAAAGATGTGTAAAGTTTGCGAACCG<br>TTGCGATCTGTTTCTGTATCGTCTTACACTGTCAGGGCACTAGGACTCACTACGAC<br>TCATATGTACATTGTTTAGCTCACTCCGAGACGCTTAGTGAATCGTTAATAGGTTG<br>ATTTGTTATTGAAGCTGTCTGACTTATTATCTTCTTAAACGACTTTTTACGTATTG<br>GGAGTCATAGGCGTTTTACAGATATCCGCGTCAGTCCACGACGTGGTGCTCTATCG<br>GATAGGTACAATCAACAAGAATGATTATTGCTCATCTTAATTTACTATGTGCGCCG<br>TTTCACCCCAAATTCGCTCAAGCTCAGACCATTGAGGGCGGAATAGGATTGAGGGG<br>TAGTGAGGCGCTGCTGTATTAGGCAACCCCGGTGGTTCATTTGAAAAAACAATCGC<br>GGAAACAACTCTAGGCCTAAGGGGAACAATCGCTTTGACTATGAGCTTCTATACCT<br>TTGAATATACACTTTGCGTGGAGCTTGGCGCGACTCCTTTTGAGGTAATGCGATCC<br>TACCCATTTTGGGTTCCCTCTTAATTATATTATCGGCTTTTGTCACCATGATCTCA<br>TAATACTGATAAGTTACCCCTGATGTTACGACCCCGCAGCCGTTAGATATTTTATT<br>TAGGAGGACCTACCCAAGGCCTATGATCCTTTCTCTATATCACGAGGATTACAGAC<br>AAGAGATGTGTAATCCGCCCAAGTTACTCTACTCAAGGTTGCGCATATTAGGGGAG<br>GGCGTTTGACAGTTGCAGTATGCCATCTTGGAAGGCAACAATAAACGGTACACAAC<br>TTTACAAATATTCCATAATTGTTTCTACTTTTCATTCATTCATTATGTATCCCTCT<br>ATACTTATAAAACATGTACGACATGTCCTGTAGAGCGGGACCTGTTCCCGCTCATG<br>ACAGACGAGTTATTTGTCTCCGACGTATCATCCATCTTTAAATATTGAATAGCAGC<br>AGCATCAAGTGTGGATAAGTGCAAGCACTATTAAATCCGCGTGAACTTTCATATGA<br>CATGAGAATCGGACTGTCTGTTATCGTAAATAAACCCGAGATAATGTTAAAACTAT<br>TCTAATGACTTCATGAAGCAGGATCATCTAAAGTTATCACAAGAGGTGGTCTTGAG<br>TCTTGCAAACTTCAGAAAACATTTACAAACGATTCAAATTAGCCTAAACCACTTAC<br>TTAACCACTCATATTCCACAAGTTACGGTTCTTTAGAATATTAAGGTGTAATGACC<br>CATCGAGCCTTATAGCTCGAATCAAGATTAAAAGAATATTCTAAATGACCATACCG<br>GTTACATGTGTGGGCGGAGTCAAAAGTTTTTCTGACTATTAGGTGCACAAAGGTGT<br>TCAGAACTTAACCAAACTCTTAGCACATTTGATTAGCTAGTCAGATTAAGGTCTCC<br>ACTTTCTTTTCTGTGGTAGTTCGGTAAATTGATGGGCATTAACAAACTTAAGGTTG<br>ATTACAATGGGGGGTTATCGGATGGTTATTGTAATTGACCCGTCCATAGATTTGCT<br>TAAAAATCGCATTTTGAATACATATCCTAACTTCCAAGCATTACACAGCGCTGCAC<br>TATAGAGCTAGGATGACTGTACAACCTCGGATTATAGCTTCTACGTAAGGCGTGGC<br>CGTGGCTGGTATAATAGTGGGGTGGAGGGAGAATTGACAAAAAAAGTTTATCATTT<br>AAATATTAGTAATGGGGTTGTCGTTCTAGGACCGTATTTCGCGTACTAAGTCACAT<br>ACCCTTATATATTTTCCACAGCAAGTCTATCATTGCAAGCTGTTAACTTCATTCCG<br>GCGGCTGCTGAACCAGTATCAGTTGGTCCACAGAAGCTAAAGTTAGCAAAGTAATA<br>CACGCCAACCTACTTATATATGTATATCGTATAGCTTAATTGAGATGTCGTAGCCA<br>TTACATGCTGAGCCTTATTTTTGACCGAGACCAGGTACAC |

TABLE 2-continued

Exemplary 2.0 Kilobase Stuffer Sequences Having 40 ± 5% GC Content

| SEQ ID NO. | GC Content | Stuffer Sequence |
|---|---|---|
| 47 | 39.40% | TTGGACGTCGAAATTATTTTTGATATACGTGTAATGATAGACTAAAGGCAAAAAGA AGGAGTATAAGTCTAAGTTCGAAGAGGCGGATTTGGTTATACGTCCTGCACCTCTT GCCAGACATTCTTTTAATTCTTGTGACCTGGACTTGAAGTTCCTTTTTGCGACCAT TTGTGGGTTTAGTACGAAACCCCCATAAGCAGTTAGCATTAAACCATCAGGTTTGA CTCGCCACATTCGCTATCGCAAATGCTACTAATTCATCTTAATCTGACCCCCCCGG GAAGGAAGCCATTTAATAGATAATCTGAGTCGTTCCAGAGATGTACTTCTCAGATA AACCGTGAACACTATTACGACATATGCTGAATAACCAGTATGTATGGCTGTTGTCG ACTCTCATTCCTATAGTGGAGAGAACTGATACATACATATTCCCTACACGGATGTT AAAGAGTCGCAGGACCTGGTGAGGCACTGGATCAACAAGTTGCCAAACTGAGTGCC AGTGGAGCTAATCACACCTTCGGCTCTGCGTTACATGCGTTAGTGAAGGTCCTTGA GGTGTGCCAGCAAAGATTGTTAACATATAATCTAAGGGATTATATGGTGTATATGG GACTGAAAACCTAGAGGTCTGTGGGGAAAGACCGTACAGTCCCTGACCATCACAAT AAAAAATAGCCAAAATAGCGTGCCATTCTAAAATTTTAATTTTTAATCAATCGCGA CTCCTTTGGTTTCATGCTAGTTGATTCTATTTAAGAATCCAAGTGAGTTTTAATCT TAACCCTAATGATTTAAGGTTCCAGTAAGCAAATAAACGACTCGCCGTAAAGCGAA ATTGATCGATACGTTTCTTGCTTTATTTTTGGGTACAGCAATCCTTCGAAATGTTG GCTTCGTAATTCCCTCCAGTAACTTAAATCAGTTAATTTGCATTGTAAGAAAACAG CAAGTGAATCATGTCGCCGCTTCAGTAACTTACTGCAAAATGAAAGCCTAATAAAT AGTTACCCATCTATCTAAGTATAAACGACTTTTGCTTATGTCCACCCATGCTAGGC TGTGAATCCTCTTACGTATAACGTGCTTTGCGTGTACTTTCGAACTTTCTAAGTAT CAATCGCAAATCGAAGTAACTTACCACCGCTCGTAGGAATTGCATGTTAAAAAGGG TTAACTCCCTTCGCTTTGTCGTTTCCCAACCTGATGAAGGAAGGTGAAATACAACA TATGGAATGATATATATCACAAATACACACGACTCTGGACCAGTGCAAAGTAGTTA TAAACTCAAAACGCCCCCGACATACATTAATTCTACTTCGAAAAATATGTTGCCCT AACGAAATGGTTTGCCTAACAGCGGCAAAAGATATGTCGACTCGATTGTATTTAAA TCGATTATTAAGATTGGGATGAGGGCCACGTAGCCGAAACTGCAACATACCGAAAT GGGCGTTACAATGCATTAATTATAATTTATTGGCGCTCAGCCTTAATTAACAATCT AGGCGTGCTCATACTGTGTACTTTAAAGCACCATTTACATGTCATAACAGATTATT GATGTTACGTAAAATTCATAGTATACAGTATCACCTCGATCAAATTCATATGTTTT TATTTTAAACAAGAGTACTCCTGTGTCGTTCTGAATTACTATTAGTCAGGTGCGTT AAGCTCTGCAGAACGATACCGACTATCTGTGCATCTACCTGATTCGAAAATGAAGG CGATTGGGACTCTCCACTAGTTCTGAGTTGTCCTCCTCGATTTACAAAAGATAACT TCAGCTGGATGTTTATCGAACGCACAAATCTTAACAATGGTTTAAGTAGCCGAATC AGATTCGCCATTCAAATCTTTGCTCTAGTTTCATCAGTCCGAGTTACTCTCAAAAT AACAACCTAACTCGTCTTGCCTACACTGGTTCTGGGTTTTATATTTAGAGACATAA TCACGAAACTTCATGCACTATAGAAGGCACCATGCTGTTC |
| 48 | 41.40% | TGAGCTTCGCTTTTTCCAGAGTCGCTGACTAAAGTGAAGTGTCTAGTCGTTGTCCA TGCGATATCGGGGTCCATCAACTAGAATTCATTTACGGTACGCGTTGTCATGCCTT ATATTTAGCAATAAGACTAACGGAAGCTCCTCTGGAGGGAAAGTAAGAACGTCCCC CCGGGAACATACCTAAAATAAAGGTGCATGAACCATCACGGAGTGGAGACGCAAAA GATCAATTAGTACAAATCAGCAGGAGACATGCAAAGACCGCGCCCCTTTCTTTTTA TACCATCTTAATAGCCTTTACTGATCGTGTATGTTTTCATCGTGCACCTAATTATG GAAATTCTATGAAGCTTTTGCTCCTAATCGTTTAGTAATGCTCTCGGATGCCACGT TATCTTACTGAGAAGCCCGTGACCAAAGCATGGTGACAATAGAACCAATATATATG AAAATACCGGGTTCGTCTGAAGACTGTGTAGTAACAAAGGTATTCTTGTGAATTCA CGTTTTTAATCTCATCTACTATCGGATATGACAACAAACTCTGATTAGGGTAATAT AAAATTTACCGTTCGGCCTAATTAAAGGACAACCGGTATGTAAAACAGCAACATCA CCTAGCACGAAATTTACCTATGAGTGTGGAATTCGTTAGCGCTGTCGACGTGCATA ACCTACGGGTTGTTGCATACGGGTCAGTGGGATAATGTTGACTCGGTCCTTAGTAA AGACTAGCTCTTCTTATTCTTGCGCTTGTAACTGACAAGTCGAGTTCACGTGGGCG CAGTAAAGTCGGGAAGACGGTAATCGCAAAAGTTCGGTAAAACTAACAGTTTTTAA CGAGTCCGTAAGTTCAAGGGCCTAAATAGCTGGAGGATTTTAACGTCTAAACATTC GGGACACAGTGTATGACCCGCATAAAAGGTTCAAAGAAATAATACTTAGAGCCGTC GTTCGGATCTTATATGTTTGAATGAACCCTTAATCACCCTATAACATGAAGCTACG ACACATTAATCAGATCAAAACCTACTTAGAGCTCGTCCGATACTACAACTTGAAAT CTTCCACCAAAACTAAAGGGTCCATTATGTCAAAATACCATTTCTATTTATATTTT AACCATCAATTCGCCTATACCCCTAATCAGCATTAATCTCGCTTAAAGATGGTAGA GTTAAATACAACGCAGAGCTTTTATACTACCAGTGATGGATCACAGGATTGCGTTT CAAAAGGTGATAGCAATTACCAATGACCTTTGACAGTAATGTTACATCCTAACCGG ATTATTTGGAATACCCTCTATTTGCTTTCTGTTTAGCCGACGCCTGTAATTGTCTA CCTGCGTGCGTTGTGATGCCGGTCCGCTCGATTTAAGCACTCCGATATCTCATGTA GGTGTGGACTTTGGACAAGGGGAAATAACTCTCAATGACAATCGTACTGCTTATGT TAGGCAATGCTGGCATATGCAACTCTGAGGCTAACTAAGTTAGTCTTGTCCGTGAT CTCAGAACAGTAACTATTTAGTTGCTTGCGAGTATATTTCGGTAGAGACGTATCTT CTACTAAACACGGTTAAATATTTTTGGTTATCTCTCGCCCGGTCTAGTAGTGCCA TAACGTTTACGAGGTCATATAACTGTCATACATTGCAAGGCGCTTTATCTCAATTG TGAACAAGTAATTATAGCCATGATACAATTTTTGGACGGAACTTGTTTTATCTAAA TCGAAAGAACCTACATTGCCTCGGCATAGACCTCGGAAGCAGCTAGTTCACTAGCT GCTTCATGATGGTCCAAGCTTGTGAAAGATTCACATAAAATCAACCTCCGTGGGAG TCTCCGATGGACGAAGCTGTGTGACTGGATATTATCTCATGATTGCGTCACCCTTA ACATGTGTGAGGTAGAGCTAACTATAGAAATACCAGTCGAGTTAGCGACATAATGC GAATTGATCCGCCTGTCAATTCCTCCTTATACGCGCCGTT |

TABLE 2-continued

Exemplary 2.0 Kilobase Stuffer Sequences Having 40 ± 5% GC Content

| SEQ ID NO. | GC Content | Stuffer Sequence |
|---|---|---|
| 49 | 40.00% | ATTGTCCATTCTTGTATTTGAATCACTCCCTAATGAACCAAACTCTCTAAGCCCAT<br>TCTTGTAGTATTTAACACACATGACAACGGTCCAATTTTCATGTATAGTCGGAGTA<br>ACGCGATATACTGAATCTTCTGACTTATCAGACATATAAGATGTAAAAACAGCGGA<br>TCAAAAGTGTTCTCTGCTGGGTGAAAAATGACAATTAAGCGTGGTATTATCTCTGT<br>AAATAACACAGGGATTTATATGTAAGGATCGCGCCCTCATACATTCATTAATTCTC<br>ACTCAGACTTCCCTCCTTCGGGCTACGTTAGATTGAAATGAAAATAACATGTTGTA<br>ATCATTAAATAGTACATACTGAGTTTTTAAAGTCGAATACTACAAAAAATATCATA<br>CTTTTTTTACCAGTTCAGTATTGGAGTCGACACATGATCTAACATAACAGAAGACA<br>TAGCGATGGGGATTATCGACCTTTTTATGGGTAGTAACAGGTGGTTGCCGGATGCA<br>CTAGCATGATCAGGTCTCCTACTCACACAGTCCTTCTGACTGTTAGGTTGTCTTTG<br>CTTATAAAAATACTCGGATTATTGCGCCACAATTATTTGATCAACGAGCTTCTTGG<br>AGAGAATAAAAATATTACACTTCGGATAGATAATACAGGTTAGGTTCTCCTATGAA<br>TTTGAAGATCCCATGTTCGTTACCGTCCAAGAGCCACGGCTTGCTTGCTCGAAATT<br>AAAGTGGGCATTCGCGCGGGATGGGAAGTACCCTCAGTCTTGACAATTCCCATCGT<br>CAATATTAGAACGGTGGATTCGCCATCACCAGGAAACGTATTGCTGATGATGATTT<br>CAATACTGAAGTCGTACACTTCTCACCCGGAAACGTTAAAAGGACGATAATGACTT<br>AATTGAGATCATCGAGGTACGAGCCCATGCCTTAGGTCGCTTCGTAGGGGTCCTCC<br>TTAAAGGAGACTGTTTCTTACATGATTTGTTACTTCGTTGAAAATAAATCATGGAT<br>CGACGTCACCAATTACTGGGGTACCTGAGTATATAGCGTAGAACGTGAAAGTGATT<br>ACACCTGTATAGGAAATGATGAGCTCGGGGAACCATAATGAATTATAGTGTAAAGA<br>TAAAAAACTTGCCCCGTGCCACGAGAAGGAATGTAGCAGACAATCATGGGGACATT<br>GTAACTTACCCAGACTTTAATTTCGTTTTCACTATACCACTCAATTATGATGTGAC<br>ATTCTGGAATTGATAGCGTATGTTGCAGCCTTCTAAACTCAACACTGAGCTCCTTA<br>AGGGTTATTATGGTTATATTTGAGACTATAATATAATCCGAGTTCGGTCGAAGTGA<br>GTAATCTTTGGAGGGTTTAGGGGGGCAGAATTCACTATAAGCAGCAGAGATTTTCT<br>TAGAAAGAGCCGGGTCCCGTTCCAATAAGCCCTACCGGACGTTTATAATCATTGGT<br>GCATCAGTGAGGCCTTCTGTTCATCTTCTATTCTGCTGTACCCTTCTTGCACCAAC<br>GCGTTGGATCCTTGTATCGAGTCACTGCCAGGTTTGTGGATTTTTTGCAGCCCACC<br>CTACGTTATATCTTAACAATCGGATAATTAAACCAAGCTATCGAATGCTATGAGCT<br>ACCACAGATTATCATCGATTGTTTTCCCTATCATTACGATCCCTGACGGACTACTT<br>AGTATGTCCTTTTCTTAATATTCGTTAAGAACTGGAGTACAGGCTGATTACACAAC<br>CAGTAGGATTAGGATTAAATAGAGAAATGTATCCGGAAAAGCGGAGTTACTGTTTG<br>GGTCTTTAACCGCGAATCGCGGTTTTTTTCTAATATGCAGTGATCCTTTATTTGG<br>TTACTGTACATCTGCTGAACACGCTATGTGGATCTCCCACAGTTGCAAGTGCAAAA<br>TATTAATAAATTAATCACAATACAGTACAGCTAGATTTCATACTAAATGCTGATTT<br>TTGACCGCACCCTCGAGAGTAATTCAATGACGGCCATGTA |
| 50 | 38.90% | AATCAGAATGAGCAGATGTAAAACATATTTATGTAAGCAGGTTATCCCGTATGGCA<br>CTCGTTGCTCTAAGTAGATGTTTTTGTCTCGGGTAACTTATGTCCCCATCCTCAGA<br>GTGTATTTACTTTTATTTAACCCGACGGTGAGAACATACAACGGGTCAACAAGACA<br>ATACGACCATTATACTGCTAAACTCTCTTCCTCAGGTGCTATATGAGTTACGACAC<br>AATTTTTGATGTTAAAGTCGACCCTAGCTGCTAACTGAACTTCTGGGACTTAAAAC<br>TACCAGAAAGGATGAAGAATTAGTTTGGTCAATAACTATATACGAAACGCCCTGAA<br>GGAAGTCGTATTAAATTTGGAGTGCATAAGACATGGTGAGCGAAAACTAACACCTA<br>CCTCTTAGATACAGATTACTTTTAGTTATCTTCTGGTCTATCGTTGATCATTCTAA<br>GTTTATTCAGCACTAGAGACTTTTGGAATACGACTGCCAAAGCTAGTATAGGATTA<br>TCTAAAGATCATTATTATTAACGGATAATGCGAAATTTGCTAGATCGTATATACTA<br>TTAATGCAGCAACTTAACTAAAGATATATTTACAGTGGGGCTTATGCAACCGGTGA<br>GCCCTCGGTTCTTTATGATTCGTCAAGTAAAGTTGCACAACGTTCACGATTTAATC<br>TTATTCTTTGATCTTGGGCTGATGTATCCTCATTATTTATGATAGAAAATTGATTG<br>GTGCATTTGATTCGCCCGATACTAGACCCACAGCTGTTGTTCGATCCCGTATACAA<br>TGAGAGCATGTTCAGATCAACAGTAGGTGTAACATCTTATGTTCCGAGCCTTCTAG<br>TAACCAACGAACACCTGGCAAATGAATTTGCCATCTTTCCGCTGTACGAATAGGGG<br>TAATGTGCCCTTGATTTAAAATGTTATCGATAGGGGAACTACAGATACTGAGAACT<br>CCTGAAACGACGTTAACAAACCTCCTGCAAAACTTGCACTCTTTGAACGAGGTTGC<br>CTAGTTTCCAGAAGTAGGTTCTTGTCACTTGAATTTCGATGGAATTCTCCTTATCT<br>ATCCAGTGACGAGGAAGAAGAAATGGGTTTTTACAAGGACTAAGTGTTTAGACAGA<br>AAAACTAATCTTTCAGTAAAGGTGAGAAGTGATTTTGCAGAGGGAGATTGTGTTAC<br>GAGGATAGTACTGACGTTATATGAGAAATAGTTATCGATAATGTGCGTGTCTTTA<br>CCAAGGGACTGACCAACTGATGTGGAAATTTAACTCTTCATGATCACATAATTTCA<br>ATACGTTAACAGTTAGAAGCGGTGATCTTTACAAAGTAGACAATGAGTTATTGTCC<br>CATAGCAATGCCTAATGTCGAGCGTGCTTCAAACAATTGAATGGCGTTATTTTTTG<br>ATCCTTAGGAAACAAAAACCAGCAACGTAACTTATTCTTGTATCTTCATGTAATCA<br>CATTACCGGTATAGAGATGGTTTTACATATACGCACGTTACTTTGAGATAGCGAAG<br>CATACGAATATACACGATACAATGTCAGAAGGATAAAATCATATGGCCTCACTCG<br>GTGCATTTGATTTCAAAGGCTTAATGTAGCTCTGTTCGCACTCGTGGATATAGTTG<br>GAGCCAGATAGACTAGGAAGATGTTTGTTTAGATAGTATCCTCGTTCGTGCATAAT<br>ATCCTTGAGATAGTATAGGTCGAATCTCCACAGCAGCAAGATTCTCCGTGAGCATT<br>GCCACTCTTTCAGTAGTAAGCCTAAGTAATTCATTAAGCGTAATTAGAGACTTATT<br>TTCCATATCTGCGCGTCGAGTTTCTTCTGCAGCCCTAGTTAGGAGACATACGGGAC<br>GCTTGCGTTTTTATCGTAGATTCACTTAGTACAGGGAAGATAAACATGAGAGGAAA<br>TCCGACACCTAACAATACTTTCAAACTGAGGGGCTGGATTGTACTTACCTTCACAT<br>CATCGAAGTCAATTCTTCACCTTCACAAGCTCTTTCTTCG |

TABLE 2-continued

Exemplary 2.0 Kilobase Stuffer Sequences Having 40 ± 5% GC Content

| SEQ ID NO. | GC Content | Stuffer Sequence |
|---|---|---|
| 51 | 43.30% | ATTTACACCCATGCCGAACATAAATAAACAAACACAAAAGGATGAGAGGAATAATG GGTTAACTAAGGGGAGTCGAATCGTATTGATACTTATGAATGGCTATGTTACACTC AGGTTGTACTGGATTTCGTTTGCGCTACAGCTTAGACCTTTCGCTAAAGATACACG CCGCAGTGTCTGAAACAGACGCACATTTAAACCGCTGGGCTGTTAACGCTCATTCT CGCTGAACTAGTCTGTCATTTATCAGTGACATCAGCTTATCTCCAATCCTCATAAG ACCGTCGACAGGAACCCTCAATTCCACTCGTAACAGTCCCACGCTGGGTTGCGTAG TCTGTTGTAAGAATTCATTCATGGTTGAAATGGGGCTGATGACTATGAGGCGGCAT CTATTGGTATGGTTTAGTAGACGATCAGAGGAAGTCTGTATAGTCAGGGCTCAATA TGTATCCACGTAGTAATGTTGCCTGCTACCGACACGATTTAGACAACGTCAGCGTA ATTACGAACACGACCTCGGTTCCACGTGTCATCGTCTAGATGGTCCCTTTGTTCGT AGGCCTCCAAGACCTCAGTAATATCTAATTCGAGCTTCAAGTTTGCTAGACGTTGA CTTGACGTAGCAGATAAATCGCACTGTAATGGAATGATACCTGAATCCCGTTAACT TCCAGCATGGCACATACGATTTTTAAATTACGCTTAAGATAAAGAAGCAGTGCGGT CTAATCCAAAGTGCACAAGCATATCAAAACTCAGGTCTGGTTTGTACGATTATTTG GAGCAGATTTTCAAGATAGTTATGCCAATCTCTCCATAACCATATACAGTGACGGG GACCCTCTATGATACGTCATCTCCGGGACCTACTTTGACGCTGGAGTCTTACAGAT GGTGGGACCATTTGTGCTTAAGCTACTTTTAGTGCGGTAGGAGCCCTCCACAATAT GATTCAAACCTAAAGAAGCTAGGAGCCCTCTCGACCCTGGTACTTGGCATTGGCTT AAATTTCACGTATACGCCATAGCAGATTAGTTTAATCTCCGATTTTCAAAATACTA GATAGGGAGAGTTCTATACCACATTAACTCGCCCCGATGGGAGAACGCACAAGAGT TAGTTTTCGACGCCGCGTAAAACAATTCAACATGGCCCTCGAGTCTGCTACTGTAG TGCATGAAAGCTTTCCTAGTTGGGCTAGTAGCCCAAGATTCTGGAAAAATTCAAGT TAGTCGACAGATGTTTCCGCCTTACGAGTAATTTAAAGAGGTTACCCCGAGACCGC AAAGAGTTTAGTGCATCTTATGTGCATTGTGTTGTTCGTCAGGGGGCTTTGCACCT AAACGGTCTTACGTACAAGCTCAGTTCGTGGATACATGAAAGTCTTGGAGTCAAGA CCTACAAATCGACGCGATTCTAAGTCTAATGTATCCTTACTTCGGGCGTATTGTGA TAGTATCATAACGGTTAAGACAGTTTAGGATAAACCGCAGAGACAAAAAATCTCGT TCGTGTAACTGAGTATATAGTGTACACTTGTGCCCGCAAATGCATATTATTGATCG AGTAATTTAACGTGTGCCTCCTTGGTAGAGGGTTTCCCTAACATACTCCTTTTCCT GATTACCTCAGTCTCCTGCTTCAACCGGTCTCCATAAGTGAGAGGTTGTGTGTACC GCACTTTAGAAGAGTAGAGGTTTGGCAAATTTTGGGAGCATTAGACTAGTCGAATT TCATACTTCTTAGTCGTCTGGGAGAACGTAAGACCTGATTAAACGCATGATACACG AAGTCATTCAGTTCTTCAGTTAAGAGGTTGCATCAAATAGCACTAGCTTAAATGTA AATCGTCTTAAGTCCAACTATTATGCGGCACTTGATCACCATTTCACTCACCTCAT CACTACGCTTGATAGTATGATCTCATCGTGATGGTACCCAGTTGAGATCAGCGAGG ATCTCCTCATAAATTTACACATTGTTAAAAGGTCCCGCGC |
| 52 | 41.50% | TAGATCTGCTTTGTGAATGCCGAATTTCAGATTGACTGTCCGCGCGCTAGCTCATT ATGACCCGGCAGTTGAAATCGTATAGGGTTGGACCCAACTACTAACGGAACTCAAC CACTCGCCCTGTACGAGATCACAGGGAACGTCGGCTAAGGAGGTTATGGTGGCCTT ACCTTAGCACTATATAAAGTGCGTTCGAAACCTCAGTGATTCCCCGATAGTATGAT TTTTAAGTTCTAAGATTAAATTTGATACATCAGTTGGTCCTAGAGTTAGTGCTACT AAGCTTAAATCAACCAAAATTTTACCCGTTCTATTCAGAAGGAAACTATAGTGGTA GCAAGTGTGACAGTAGGTATAGACTTAAATAGTTACGGCGAAATAGAAAGATTACG ACGTTCAGCCTTGTGTATCGAATTTGTGACTTTAGAGGCACACAGAGTAATGGACC TATCATCTACGTCCTGTCAGAGTATCATGTGCATGATTCGACAGAAATCTCAATAA TAACCCAAATCGGGCTCTCTTGCATTGAATAATTCATCATCAACATGAGGTAATAG CAAAATGCCTTTACTTCAGTTGATTAGGGTGATGGCCGATCACCTATGTATTTGAA CATATATTGTATATCCGGTCGGAATATGGCATCCTTAGCCGTCGTGCGCCGGCTTT CGGAATTTGATCTGTCTCTGTTTAGACGCGTAACCTCAATTCGCCGCAAACTAGAT CACTATTCTAATAATCTCACTAGGAATCTATTCGACATGCGATCTTTGATTATAGG ATTCAGAATCTAAGAAATTGCTACGATGGGGTGTCATAGCGATGTCTATTTGAGTT TCTATAGTGAATTGGCCATTTGTTTTGGCATCATAGATCGCTGACACAATCATTGT GTCTTTCATCGATCTGGAGTACAGTTAGAAGAGAAGCGAGGGCTGGTAACATGCTT ATAGATTCTTATACTTACTACCTTAGGGTACACTAACAATATTTGACATTATAGGT CGACCAAAAGATTTCTCTATCAGGTTTAGAGACAAAGTCGTCGACATATTTCTGT TTGAACTCTTGAGGATGCACGAAAGTGTCTATCGGGGTATCAGTGAGAAGGCGTGG CAAGCATTCTCTAGGTGAATTCCACCCTTTTTAGTCCTCGTTAGTACCCCGTAGAC CGCGGAACATCGAGAAGTTATTCGTAAACGTGTCTATCTGTTCTATGTTAGGAGTA GGTCATTGAACAAATTGAGCTTTCAAATAGATTCTAGAATGTAGCGCGTAAGTATG TCCCGATAGCGGTTTTCAGTGTATTAGTTGCATCTAATGTAATTGAGATGAAGAAA ACCTTGGTCGAAGAGACATGCCTAAAGAAGAAGGCTAAGTGAAGGCCTTTATATCA CGTGGTTCATAGCCCATTATATAAAAATTTATATTGGAGATGTCCCATTGGTATTG ATAGATGGTTGGTAGCTGTCAGCAGTGCGCCCTAGGTAAACCAGAAGACTCCTTAA CAGATCGGTATAATTATTCGAGGTTTCCGGCTCTAGCATTCAGACATGGAAGGTTC TTTCTAAGCGGATATATTGCTCGAAGCCCGTGAACCTTTAGAATCAACCTTTATTA TCTCTAACCATCTTTTTTACGTTTCACCTTTAACTTACGCGAATCGATTCACGACT GCCGAAGTACAAACGATGACTCAGTGTTGGTTTTCGCTACAACATTGAGCTCAGCT CTATAGCGCGGACTACAAGTTCTGCGTAGATTTTGCCAAAAAAAGTTGCGGGTAGC CTTATTCATTTAACGTATGACTGGGAGGCGCTCAAATCTCTCACTGCACCTATTCG CAGACGCAAATTATGGCGTCGACCCCAAACTTTCAGGTAAATAGCTCACAAGATTG ACCATTGGCAAGTTTGAACTAGTGTCGTAACGTCCTGAACAAATGTTTTTCTAGCC GCTCCTGCTAACCTTATGGACATTTTCCTCTTCACCCCTG |

TABLE 2-continued

Exemplary 2.0 Kilobase Stuffer Sequences Having 40 ± 5% GC Content

| SEQ ID NO. | GC Content | Stuffer Sequence |
|---|---|---|
| 53 | 39.40% | AAACTACAGAAGAACCCAAAGGCTACTCACTCCCTTTGCTGTGTTCAGCTCGCTGG CTCGTCAAGATAACGGACTCATGTCTGTGGGCAAAGCAATTTATTACAGCTATACC TTTGTGGAAAAGTCTCCTTGTAAAATTGTTTAGCAATATTGTTTCGAGTTATATCGA ATTTAAGGTTTATTGTTATTCGTGACCATAAGGAGCTAACATGATGCGGTTTAATG CGTATGGAAAAGCGATAGTGTTTTTAGTGAGGGAATGTAGAAGACCTCGTTTCAAC CCTTACCATACCCGAGGGTGTCTTAATCTGTTATTAAATAAAGAGCAGCAAAATAA AAAAAAATGCAGTGTCTATCAAATTCCCAAATTTGGCTACGTCGTTCACTACCAA TTTTCAAAATAATAAGAAGAAGTATATGGATCCAGTCTGATTGTCTTTCCGATCAG CAATATAAAGCACCAACGTCTTATAAGAGCTAAATAGTGATGATTCCATGCAGTAT AATTCAATTCCCCTAAAGCTACTGTCGATAAACTTCATATAACATATGTACTTGGA CCGTTTGGTTTGGACTTGACAGGCTTTAAGCAGTCTGCATCATGAGCCTCCTTCTA GATGTGCAAGCATTCCCCAGAGGCGGTTCGCTTCAGCGTGGTAAGGAATGATCTCT GGGTCGGAGGTAGTGCAGAATGACCACTTATCCTATCTAGTGGTTTACTTTATCTA AAACAACAGGGGACTAGATCTTATTATACGGCCAAAACTGAAATGAAGATCATCTC ATGAATATTCTCTTAACATGAGAAATTTCCGTTGTCAATTTTTAAATGGATTAATG TCATAAAATCTGGGATATGGCGAGCTTAACACAATGCCCCTAGTTTACGTTAAGAA ACATTTGATACATCAACAAAACGTAGGATCCGCCCCGGTTTTTTGGAATCCACTTC TAGAAGCAGGAGCGGGTCGCTGTATTTAAGTCATAAAGGACGTCGTTTTACGAACA AGACCGTGTATGAATCTGGACTGTTACAACGGCCCATCCCCACCACTAGTTATACT AGTCACCGAATAATCTGAACTATTTTACTAGAAAGTCTAGAAATTCATCCTTTGAC ATAAATGGATTGGAATTAAAAAAAAGAATTTCAAATATAATCATATAAAAGTGGATG CACCAGAGCTCATGCGACGTCATTCTACGAGCGATTTATAGCTTATACCAATAAAC CCCGCGTGTATTAACGGTCCAGTCAAAAATACTATGATACCGAACAAGGTTTATCG ACTTGTCCCGTTGAAATCCTAGATGAAGTTTATAACCAAATGGCGCCCCTTTAGTG ACGCTGTAAACGCAGATTTATCAAACAGGAAACATTTCTGATTAACCAGAAGTATG CGTAGTGAAGGTATATCGCGCAGTAACATTCAGGTGCTTCGGGGATTCAAAAACGT GTTGCTGGTATAGCTCGCCTGTTTTATCGAATGTAGTCTCAAAATCTAGCCGAGTT TATCAACTGGTCGACGCTGGAAGTCTGCACTTGAACATCGTTCACATGTAAGCCAG AGATAATGGCCTCAGCATCGTCTTATTGCTAATCTCACGCTGCTTTGTCGCGACGT ACTCTCTGCATTACCAAATGGGATTAGTTTAATTTCGTTCTCTGGGTGACCTTGTG CACGCTATGTGGGTTTGTATTAGTTGATTAAAGAGTCCCTTTGAAGATGGCTTCAC TCACCACATGACTACACTTCCTATCGAGGTAAGGAAACGTTTTCTTGTGCAAACAC CCCAGACTTACCAAGTTTAAAGTTTTGTATAATATTAAGAATTTATCTAACACTGA GACACCATACACAGCTTCCGTACCCTATTGGTCCACAATATAAGACGTTAGATATT GCCAATAAATGCTTCATTCGGTTTTTGTTAGACAATTGGAAAATCTTATACATAA CATATAAACGTTTCGCATCCCTGGTTCCTTCCGATAGGTC |
| 54 | 40.50% | TCGTTTTATCACGTTTTAACATTGAATCTTTAGTGCAACCAAGAGCCACTTCTCCT GGGTTATAATCATCATCTATTTAGCATACCAACGCGTTTGGCTGCCTCGGTTTGTA TATAGTCGTAAAAGCCTCCGGTTTATGAGGTGATGGAAATTAGTTGGATACTTGAA TAGATAATATCCCATGCGGTATTCACCCACTGAATCACATCGCCTGATGATCCTTG CTGTTTGCGGGAGAGCTCTTCTAATGATTTTTGCAAATGCTGTGCATCCCTAATAG TCTTTTACAGGGCAAAGTACAGGGATTGACAGCCCCGAATGTCTACAGCCGACAA ACCGAAAGTCTTCTACCCCGAGGTAGCTGAAGGTGCATAGACGTAGACATGTTGAC TAATCTCATCTTGTCTACTATCTTGTACACAAAATCAAAATTACAATTATATGGAA GGCATGGGATGAGTGATCGTTAATTAGACAGGGGCGTCTTTGGCAATGCATTCTCT TATGATAAAAGGTTGACCAGATTACTGCTCATGACTTAGTGTCCACCGGCCCAACA ATTAATAATTAAGAGACTCAACCGACATACGTTAATACCCAATAATGCCCCAATAC CCAGACTTTTACAGGGTTATTCGTGAACATGAGTCCCTCGACATCTTCCCAGATTT TAATCCCCATATTACTAGTTTGTAACAGATTGGTTATGGGACTGATTAGAACAGGG AATTTCAGCTGGAAATCACTACTAACTTATTGCTAGTTTGCCGATCTAAGAAGAGT CTTTGCTAATTGATTTTAAAGAGATATTCTGAACACGTCAATATCCAAATTTTATC CGCACCATTCTGACGTAATGACGCCTAGAGAACGAGTTGGTGGCAGTCTATCGCTT CTGTTTATTTTAACCTTCAAAATATGATAAGGCCCCAGTTATAAACTATTTTTTAC GGCAACTTCGGATTAAGTGTTCTATACGCCAAAACTATTGATTTACTTAACATTTC ATCCCGAGAAGCTCCGTCTTATCAAGTACGAGATGATCCCCTATTAGAAAAACCAC GGCTAGTATCAACGACATGCGTTACACACACGCCTCAGTGGGGGCCGTCACACATA GTTCAAATATTGATACTGCTCGTCTCGATATGTGTTCAATGTCGGCAATCAAGCAG TGTCGGAACTGAACCCGCACTACGGGCTCGTAAACGACCCAAAATCCCCTAATCAA TCATTGTAGTAATGGTAGCAACTTGTATGTCCTGTCAACGCAACACCCTCCTGGTG AATTATTCTATTAGAACTACTAAAAAATAAACCCGAGGTCCAGCTCTATCGTACAC GACACGAAAACGTATCAAGGTACAGTTCGATAGCCGTACTTATTATGGTGACTAGC GCCATATACAAGGTCATAAGGGACCTTGTTAGCGGTGTGTTCACTTCATCGTCAGC GACTCGTTCGACTGTCATTTCAATGAAATCTTTAATGAGTTTAATAGAGTAGGAAG GGACAGTAAGATATTTTATGAATAATGTCGTACGTAGGATTTTTTTCAAATGATGA CTATCACAGTACGGCATACGGAAAATTCAGTAGGGAATTAGATCAAGTGTAAAATT ACTGGTATACTAGCGTATACCTAGTACGATGATAATTAACAATCACCCCCAGCATG ATGTGAGAATAGTAAAGTATCCATATTTACAACTAAAAAGCTCGGAAGCTGAAATC CCAAACCGCTTGAACAGCTCTCGAATAATACCGGTGTTTATCATCGGAAGGACAGC GCCTCAGGATTTTCGGCAAATCATAGCTCTTATCTTCGATCTAAGCGTTTGATGAA TATTAGAATCGGACTGAGATATAAAGAATAGTGATATATGTCGGAAAACGACGATG TCATTTTAGACTATGATCTTAAGACGGAGAAAGCTACCATCATAACACCGACTTGT CCTGCCATTGTATTACTGGCTTTCCATCGTGAGGGATAGC |

TABLE 2-continued

Exemplary 2.0 Kilobase Stuffer Sequences Having 40 ± 5% GC Content

| SEQ ID NO. | GC Content | Stuffer Sequence |
|---|---|---|
| 55 | 42.10% | ATTATGATCCCAGGCTTCGTTGAGTCTAATAGCTATCCGACTAATCAACTTCTCAG<br>GCATGTCTCGACTCCGATCCTGGTGGCCTTAAATTTCTTAGGTGCACGGAATTGTG<br>TGTACCTGGTATGTAGAGACTATAACGACTCACTTCTTGCCAATTAGGATTCAAAA<br>CTCCCTACTTGAGCAACGTGTTCCCCCGCATTATCCATATCACAACAGTTGAATTT<br>TTCTAACGTCTTCTCCTCAAACCGGAGGGAAGTGTGAATGTACTGTTGTCCGGCCA<br>TGCCTGAGGTATTTTGATTCTAGTTAGTAATTACATTAGGAACTCACTTCGTCAAC<br>TCAAACACGTTGACAAATGTGCAGTTGGGTAATACATGCCGTGCAAAGCATGTATG<br>ACCGTGGTCTACTAGATGGCTTCGCGATTTACTGTTTTGCGATATAGGCGTCGGAA<br>TAAACTTCAGCAGGTGCGGATGCTGATCTGGCGCCGTCATTTATAAAGATATGGCT<br>ACGACTTAGCTCGTGAGATCGAGACAAAATCAAGATCTTATCGTCTTCCACAAAAA<br>GTACCCTCAATCGGATATTCGGACCGTAAAAAAGAGCATGGCGCTTGATTATCGTA<br>GCTAGCGCCCAAGGAACAATTGTATTATTCAGATTAAACCCCGGATTGGACCTATT<br>TTCATCCTAGTAGAAACGGTGACGACGCGACTTCCGAAAACTCCAGGAACAGTGCG<br>GTCTACCCAGGTTGTAGTAGATGCCCGTTTTCTCAGGGCAACCAGGGCATCATACG<br>TTAACTTAATCGGTTTTAACCGCGAAGTTCGATACGGACTGATTTAATAATAAACG<br>CGAACAACCTAGTAATATCATAAATTGCGGCGTGTACTTCAGAAATGGTAACTAAA<br>TGTCAGACTTCTTGAAAAGGAACAAGCGCGCTTTCTCAAGTTTGTTGAGTCTCATC<br>ATAATGGGGGAACTCCGTACATGGTCCGATGGACTCGATATCCGAAGGCGATAATA<br>ATTATCCCCGTGTTCTACGCTATTTACGAACTATTAATAATGATCGGTCATGTCGG<br>TGGTTTATTCCATTCCTTTATCTCCGATAAGTACGTTACCATGGGATTACGCAACA<br>GCTAGATTTTCAAATGATCGGGTCGAATCCGGCCTAAACGAAACGTCGCTAGCGAT<br>TGAGAACGGATGTACAGATCTCTCGAATACATGAGATGCGCGTAATCATAGTGTAC<br>GATAGAACCTCATGTTATCAACAGGTGCTATCTTAGTAAAATACATAGTCATATTC<br>TTTACACGCGTAAAGATTCTTTGAGCCAGCGAACATGGAAATGGGCGTTGGTGTGT<br>TTCTCCCCGGCTTTCGTAATAGTCGCCACCATCCGCTTGGGTGCTGATTCGATCAG<br>TTCTAACCAAGGAGCCTGACAGTCTTCGATTTTTGTGTATTCCTGTAGAATATGGC<br>ACCATAATTCAGCGGGAAAAAATTGTCAACTCAGCAGTGTCTATTAAGAGATTACT<br>CTCGCTTTTGGACTGGTACAGCCTTTACCTAGTAATATAGACGGACAAAAATTTTG<br>TGAGTCAGACGGCATATCCTGAAAACAAATACAAGTGTAGTCTACGTTTTAGAATA<br>GACTGAGTGGCGTCGGTAGAAGTTACTGCTCGAGTTATTGTAAAATTCTTGCCAAG<br>AACGAAGTTACTCCATATGGAAAAGATGACTCAATCGAGTCTTACTAGATTATTTC<br>CGAAGTCTTAAACGTTTAGACCTAACTTAGTCGAAAGTTGAGCTCCAGAAGTCATC<br>TCTCCCAGTTTATCAATAGTGGGTGGAACAAATTCATCGGCTGTTGACCTTATTGC<br>ATCCACCTCGTTGGAGTTATCTTGCCATGTATCCTCAAGTGTTCCGACCTGGAAGT<br>ATGTAGAAACCCCTTTGAAATATCTATCACAAAGCAATATCTTATATTATCTTCGT<br>AGTTTTTAGAATTATATCTATTTAAGGGCACAAAGTCTAG |
| 56 | 41.70% | TTAACAATAAATGATTAGGTTGTGCTTGCCTCCTAATTTTGTTTAAAAAGTTGTTC<br>TTCTGCTGACTAGTTTGATTCTACTCATTTCTGTAGTACCGGTTCGGCGTACTTTT<br>TTTAGAGGAAAATACTAATGTGCGGAGGAGGGCTTAAGAAAACTGCAGATCACTGG<br>ATGAGCAGGAAAACCGAAGGACGTGCACGAAAATCGGACTTGCTGTTGTGACTATA<br>CGCAGGCTAGAATCAATACCGTCGGTGCTCGTGCCTCAGCCGTATCAGATATGATT<br>CTTGAGCGATGTTATCGTTGGATCAAATAGTTCTTTTCGTGGAAAGGTATGGTTAG<br>ATATCCGGGGCCTCTTAATATTGGTTTCGACTAGATCTGACAGAGTCGGGTCAAAG<br>CTAACGCTGTCGCTAATGATGACAGTGTCAATCGGTTAAGTATACTCTGGAGTTA<br>TTAGTCGATCTCTCTCAGTGTTTCTTAAGGTGTTCTCAGCTGGCCGGGTTGTGCGC<br>TTGTGAGGGAGCGATAGCAGTTTGTGCTCGGTCTACGCAGTAGATCGTTCACAACT<br>TAGTCAGACCAATTTATATTCCTATGCCTAAGAAATAGTAGATCATCTAAATGTAG<br>TTGCCGATCAACTCAAAAATCATGAGCAGTGATAAACGCTAGTACGGAGCTAGCAT<br>ATGCGCCTGCCGATAGATTGCATAGAACCACAGAATCTCTAAATTTCTGGCACTGA<br>CTTTACCTTACTTGTCTACTGATCATTTAGTTCTAAGGCGGGTCCCAGCATATACT<br>GAGTAAAGGAAATTGCAACGGTCCAACAAAGAATCAATAAGTAAATAGAACTCATC<br>AATCTCCATGGTTTTTTACCCTGTGGTATGAGAGCTTCGAGACAGTACAAATACAT<br>TCTACGAGTGCATTTATTAAACACACGGACCCTATACAAATTAATAGCATCACTAG<br>CTCGAAACCTATTACAGCCTGAACGTTTCGAACGCACTTCGGTATACAGTGTACTC<br>GCGCGCGTGTTGAACCGAAGGTGCTAGCCGAATTAGTTGGATTCGTATATATGTGG<br>GATCCCGATTTCCAAGTCCTTGCTGGTTTAACACACGGATATTAGTTGCTATTATT<br>AGCGTGTTTGAAAACCATGTCAGAGTTAACGACCGGCTAAAAAGCCGACTTATAAA<br>AGCCGAGTGGTTTGGCAACCTTCTACTGGTCTTGGAATTAACTTCTGAATAAATA<br>CAAACATGAAAAGAGTGAACTGCTAGACTGCACCTGTGGAATGATCCATAACAGTT<br>AAATTACTCCGCCGAGTCCATTTTGCTGACGGTGGATTATCCTAACTGAAGAGCGT<br>ACAGCGATTCTGTCCAACCGTTGAAATCAGTAATTTTCTATACCTACTATCGTTTG<br>ACCAAACTCAGGGAAGCATACCTAAATATCATCAAGGCGAGAAACTTTTAGACCCA<br>TAGTTGTATTATAGTCTAATTTCAATGCACATTCTGTTCAGGCACAGACTGATATT<br>GAAAGAGGCCCGCGACTTTGAAGGTGGGCTAAATTTATGCAATAATGGCACACCAA<br>TCAACACAGTCTAGAACTTACCAAACCAAGCCTAGATTCACCTATCTATTTTTGAT<br>CCGACTGTATAACGTATTGTAATACCTCAAGACATAAGACACTCATAACAATTTAA<br>CTTTCTCTTATTAGGAGGCTCCTCTATGGGATTCGTCGTCGAGTTAAATGATTTGA<br>GGTTTTATGTGGACTCCGAGCACGCCCGGTAAGAATTTCTAGGACTTAGGATACAA<br>TGCAACTCAGTGGAGTATGTTCCCCCGTGTGATCTATATGATAGCTGAGTACGACA<br>ATAGGCATGCGATTCAGACTATCCGCTTTTAATTACCAATGAATGTCACGACGGAG<br>AACGTTATGAAAGGTTTTCTCTAGCACGCCCTATCGCTCTTATATGCGAAATACAT<br>TCCTGCTTGTGAATGGCCGGGATTGCTTACACATTAGCCT |

TABLE 2-continued

Exemplary 2.0 Kilobase Stuffer Sequences Having 40 ± 5% GC Content

| SEQ ID NO. | GC Content | Stuffer Sequence |
|---|---|---|
| 57 | 38.40% | CTTAAGATTTCAGCTAGAATGGTTCTGGCGCGCCTAAGAAACTAGGTTAAGTCTTC TTTTGCGCGTTAAATAAAAATTTTGTCGGTAGTTCTTAAATGGTGCACGAAGTTGA CTGCATATATATATGAAGCACCTAAGAGCTCTATCCCCCCTTAAATGTCAAGATTG GCTAATATACCACCCCATACACATGATTAACCCGGTTACCTTCGACAGGTTTGGAT CTTTAAATACAATTAGTTGATCTTCGCTCTGGCAGAGCTCGGGTTCGTTCGTAGTG TATAAAATATCTCTACTTGCAATTATCGTTTAACCCCTGCAAGAGCGTCTATTGGT CTTGCTGTTTTCTTACAGTTGTATGCTCGCCATGTATAGGCAGGTAAACAGACTTT GACAAGGGTGGGCGAGTCGCGTAGAACCTTTCCATGAAGGCATTTATTTTTGATTA TCTCTGATACCTGGGTGTGTATAATTGGATGCAACGTCGCTTGCTAAGACATTCGA GCTCGAAATTCTAGGATTTTGTCTATACCCTTTAGAATCTTCACTTCTATAAATGA CTAAAAACATGGGAAATGACAAATTAGCAAGCGGCGCTTTTTTGAATCAATCACTA GATATATTTCTAAAACTTAGCAATGCTTTCATGAAAACCACTAATTTTAATTACAT ATTTGTAAATAACCCGCATCAAACGCAAGTTGATGTCGCATCATATATATCTCCAT AGTCATTTCTATTCAACTGGCATGTTCGGTTAATCAAACAAACCTGACAACATTAT TGGTCTCATCAAAATTTGCTCTATTGGCATCCAGAAGATTGAATTTTGAGTGACCA GTAATATTACCCTCTGGGACTACTTGTATCTTTTGTAAAAGACGTATAATTGTAGG GAAAATTTGAAGTTGTAAACTAGAACAATGAAATAAATCACAAGCCTCTTAAATTT CCGAGTGTGTTTAATAGCTGTCCGAAGAATAAATATCCAGGGAGGATCTGATCTCT AAAAAGGAAACTTTCCTAGGTGCAATTCATGGGACAATAGTCTTTACCATCATTTG GATCGGAATCTTTAAAGATTTAACGTAAAACTGTAGATGGGTGAAGCAACCACTGG TGTCAGGATTGTTGTAATAACCTACAATACGAAAACACATGGAAATATTTTTTCA CGAGCTATACACGTAGTTATACGTATGAAAACAAACAGGACTCAAATAATCTATAG AGGAATTTATAGGTTCTTCGTGAACGTTTCGAGAGCATAGACATGATTACAGGCTG CAGATGATTGCTCTAGGGACACTGGATACGTCTGTCTCAGTATATTAAGAGGCATT AACTTATAGAGCTGGTTTGAGTTCCTCATGAGAGAGAATATATATTTGCACAATGA TACTCAAAAACTTACCGCTCTGCACAATCCGCACATCGCGATCATACGCGCCGTTA AAGTTATCATCCAATATACTCATAAATGGTGTAACCTAGCTCCTACCACAAACTGA GTACCGGGATCGCTATCCACATCGCTGAAACAATGGGAAAAGAAAGGTTTCCTTCG AGTCACGCACTGACTAGATCTACAATACTTATGCTCTAGAACGCGTGATATTTCTA TGTAAAGTAAAGCATGCTACTAAGGTACATCTAATTTTACGAAACCGTATACTACT ACTCGCCATTGGTATACTTTAGACTTTGTAAGTAAAAAACGAGTAGGGCCTCAAGG ACATAGTCACTGCTTATACAGCGAAACGAAGCTGCTAACAAAGCTCAGACCGGTAT TGCTGTTAGTATATTCTTGTTAGAAGCGTACATCGGTTGGGCCGTATGGTCCGATT ACCTTAAGAATAGTTGACTAGGATCGTCTCTAAGGTCGTACTTACCCACCTAGCAG CTGATATCTTCGATGCCTATATCTGTATAGGTAGAGATTCATTCTCAGCGCATTGC CGCGGTAGATCCTATGTAGATTATTTAGCATAGTTAATTA |
| 58 | 39.10% | GAACCTTGGGTCCTTATCCTGAAATAAAAAGAAAGTGCACGTCTCCGTAATATATG GATGTCTCAGTGATATCCACGATTACATCAAGCTGAGTTATTTTTAATGATAGTTG ACTGTATTGCCTAAAACGTATCTGTAGTAATGAATACATAAAGGTACTGGTGATTG AGAAGTTCTCATTAAACGTTAAAATCCGCATCATCTGTAAAAGGTGGGTAATTGCA CTATAGAGGGTAGACCACGCCTGTAGCCCGCTTAGAACAATTCTTGTACTATCATT TTTAAGTCCTTCAATGTCTATCATAAGTATTGGACATTGCACGAGAAAACACGGGA CAAAATGCTCGTCGTTTGAGACTATGGATCGCTATTCGGGTCGAGCAATCTGAAAC AGATATTGTCATGTTTGGAAGGTGAGCCCATTAGTAGTAAGCGCTTTATACCACTA TTCAGGAGTAATAATTTAAGGAGTGTAACAGTATGATGTCTACCGGTACACGGAG ATTGTAATACAGTAGTAGCTCCTTATGGCTTGGGAATAAATTACAAACTGAACGCT TTCTTTAGAGCTCTAGTGTCCTGATTTATGGGTAAGGCGTATTATCTGCAAGTCTC AGTTCGGGATAGGTATTCCGTCATCTAATATTACCTCTAGGGTGTATACTACCATC CTTTGCAGACTATAAATACTATCTATCGTCGGCACTGATAGATGGAGGATTCCTTG CAAGACCTGATATCTCCGTCTCCATGTCTAGTTTATAGATTTGCCTTACAAGTTCA TTTATGCATGTGTAATAGAATGATTTATATGAACCGTCATAGTTCCATTTTAGCAT CCGAGCGTGTGTCCTCTCTCGTAATTAGGCGTACGTCGAATCATTTTGCTTTCACT GTAAATAGGCAAAGCAAAATGTAGCAAAGGAAGGAATGAAATGATCATTCTCATGC TACATGTGTCCTTATACATAAAAATATATACTTGATTAATTGCACATGAATCAC TTACATTCGATTATCATAATACATCCCCCACTCGGATTGCTCCACGACCAGATGGT TAAAAAGTTGAATCTGTGCTTTGATTTTTAAGTGAGCACTCACGTAGTATGAAACC GCTAGCTCAGGTTTTTTTTGGGGATCGTTCAGTATTCACGAAAGAAGAATGCGGCG GGGTGGTTCCACACCCATATCAACTAGTGTTTATAGTTGCTTATATAACGGCAACCG GCTAGTAAATGGTAACTTAACAGTAAAATGTCTAGGATTAGTAAACATATATTATG GAGGCGTTAAGGCTGTACGCCTTGATAGTACACACCTTTTTACAATCACAATCCTA GGTTGATCTAAAACCGTTGACGTCAAGTCCATTATAAAATCTTAATCGCCTGATTT CCCTGTCCTAAAATGAAGAGATTAAAGAAGTGAAATATATCCCTAAGCCAGAAGTG GGAGAATACCATTTGGATATATGCGAGCTTCTGCCAAATCTTAGAGATTTCTGGAC TTTTCAATTATCCAATATGAGGCTTGAGGATTACCAACTCTGGACTACATGACAGT TCCACAGAAACTATTTAGTTAGACGCAGAGCCAATTAGAACCTCGACAATTAGGTA AAGTAAAGTTTACAATACTGTTAAGTCGCGTAAAAAAGGTTGATTCAACTATGACG GGTATAGAGGAGGAAATAGAGGCTCTCGTTAGCTGTGTCGTTGGACATAGTAACTT TTTACAAAGAATGTTAGAGCTGTTGAATATTTACGCTTATACAAAGTATCTGCTGT ATCACGACGGATTTTATCCATGCAGGGCAGTAATCCATCAGGCTTTTGGAGAGGAC AGCCTTGGGAAGGATATCGTCACGAGGCGTTTCGCACTCAGACACCCGAAAAAATT ACGAGGAAATGATAATCGTAACGTGGCGCCTAGCGCTGGATAATTACCATAATTTA ACAGAGGCCACAACAGGTTTTCACCCTTCAATGAGTGTAA |

TABLE 2-continued

Exemplary 2.0 Kilobase Stuffer Sequences Having 40 ± 5% GC Content

| SEQ ID NO. | GC Content | Stuffer Sequence |
|---|---|---|
| 59 | 41.00% | GATTCTGTACAATTGTTTCAAAATATAGCTTAACACATTTGATGGAATAATAAGGG TTCCAACTAGATATAGTTAGTTAGGAGTTACGGGAGTGGTGCTCGGGTACACCGAA GCGTTTATGTCTAAGCTCTCTTCTGAGGGGGCTCAGACAGCTGGTACAATAATTCA TCCGAGCCGCGGTGAATGCGGCATCAGGCCCCTTCTATACTTATAAAAGAGCATAT CTAATTTATTGGCATATTCCTGCAGGCTACATAAAGTCACTCGGTCGAGGCATCCC TATTCGGGCTAAATTTCAACACGTCTGGTTTGAATAGCGACTGTTTTTTACAGATG GCTTGGATAACCAATCAACCTTCAAGAAGCACAGTTCTTATGTTAGGAACCGTATG CAACCGTAGACTCCTATTTTCACTTGCGTGAGCATTCAACGAAATTGGGAAGACAG ATGGACTTACATTAACGTATCGGACTACGATCGTAATATCCGTGATGTGAGTATTA TAGTATACAAGAGTGAGGAGATGGAAATCATGACGGTTATCCCACGTAGCAGCACA CGCAGATGCAGACCAGACAGATACGAATAAACTTTTTTGTACGGTTGCCCGGTAAA CTAGCCTGGGATCCCGCGAACAAATGTTAGAATAAAAACGCGAGAGACTTGCTTTA GTAGCTTTTCATCAGGATTCCTTGCAAAAAGTTAACACAAAGTAAGCGTGTTGTTA GTAATGTAATGTTTGTGAGGTAACACTGTGGGTTAAGTAGTACTAATGATCTTTCT TTGCTGTTTGACTTTCAAAATGCGTGGAGTTCAGTGGTGGCAAAGATTGTTTAAGT CTTACGTATTGGTAGTACTCGTTAAGCTTGAAAGTTTCGATTATCTCTTTTTATTC CGATCTGAAATGAGCTTGTTCTATCCGAAGCTGAGGTAGTCCACTTAGACCGATCT ATCGCTAACGAGAATAATACTTATTATTTAAATCCTTTCTCATGCCAATAGAGGAG ACTGTCATGGTAACCGGTATGCTTGTGTTCATATTAATTCTAAGATTTGCTACAGG ATTAAGTCTAGTTCAAGTCCTATTCCAAATACCACAATCTCTAAGGCCTCACACGC CTTAACAGAAAGGGGATTATACGCGTCGGTTGTTCGTTATGCCTTATAGTACTCAA CCCATAAATAGATCGCACATAAGAGTATGAATCGGTTGATGAAAAAGTACATAACT CACTACAGTGCCGGATGAGAGATTCCCGTGAATTAACTAGTGGCTACAAAACGTAA CGTGCCGAAGAGCAAAGGTGGCCGCGATATTACCTTTACTTTCGGTGCCTTAGTAAA AGAGGATAATGGCAAATGAACGTCCTGGGCAATCAGACCAGAGGGAATATGCTTA GCTATTGGCTTTGTAATTGTTGTAGTTTTTAATGGTTCTAAATATCAACAAATACC ATCATGATAGTTACCGATCAGATGAGCTTGAGCCGTTGAAAAGAATGCAAATACAA AATCTTGTTCATTAATCCGATGCAACGTGCCGGCTTGAAATTCATTTTCGAAGTAG TGCGTCCCGCGTATAGACGCTACAGTAGCTCCGAAGGTCTATTGTTAGAACAACA TTTTAGAAACGGGCCTAATAGGAGTTCCTCGGGAAAAAGAGGAAGGGACAAGTTGA TTGTCTATTAAGATAGATGATCCTATTATAGCGATGTCAATACTACGCCCAGTGAC ACCATCAAAATAGACTGGAAATGATGGTACGATTGGATGAGAAGATCATTAGCTGC CTTTACCTTCGACGACTTCGTCGTAGTGAGGGTTCTGACCAATGTCCATAGCAGTT GAAAGCGCGACATTACTCGAACAACGCTGTGGTCACTCTTTAATGATTCGTATAAT GAATCTTCCTCTGCAACAGTTGGACAGAAAAGTGGCTTCTTGCTTAGGACCTAGCT AGACTTTGTTGCCTTTCTATGTAATACGTACGCAAATTCC |
| 60 | 41.40% | CAGTAGATGAGGATAAGCCCAAGTATCGATTCCAGGAAGCCGCCATATGGAGATAT AGAGGTATCTCTGGCTTCGCGAACTCACAAAGGAGTGTCTCGATGGACCTCCATAG GTAACAAAGATCAAGGCCCCTTACCAACTCATGTTCTATAAACTGACATCTATGCA ATAAAGTTAACACCAGAAGGTGGGTCAGACCACAAACCACAACCCCGCTCAATTTT AGAACAAAGTCTACTAAGAGGTGCGAATCAAGCCGAAAACGGGAGTTTATTGTCCA TATGATGCTGGATCGGATTATTGTATTATAATAGCCTAAGATCGTGTCTCCGATCC AAATGCGTGTACGCATCAATCCTGAGAGATCCGGGATGGTTGCTGGGGTTAATAAC TTCTCCTTTATATCCGGATGACTGCTAATTCCTCAAATGCAATCATTCTGGAATTA TGAGGCCTATTAAACGAATTTAACAGTACCTAGTCGGTAGAAACAATTCTACCCCG CATCCTTAAGTCTACTTTCAGAGCTACTGGCGCCTTTGACGCATAGGTAAAACCGG CGACTAGAGGAATGTCGTATCAAGATAAGCCCTAATTTACTTATGCTAGCCTGTGT TCGATAAATAAGATGTCTGAATTGAATTCGCGCAGAAACCAGTGCTGCCACGGTGA AGAGTGATCGGGGCGGCTATCAACTACGCGGTGAACTACCCCAAAACATTTAGGAC ATGCGAATATATCAAAGAGAAATCAATTCCATTAGTTCGAAGATGAGCACGATCGT TACTAACTGCAGACAAAGAAGGCACTATTGATAGAACCGATTGACAACCCGAACGT GTACCGGAGTTTGGATCAGATCTTGAGACTGCGCTTAAAAGCAAGAACCCATCACA AAAAGGCAATAGCATTAGGAGGAATCGCGCACAAGTACAATAACTTTTTCCGTATT TTAATAATATTAATTGTCCTTCTCACCACGAGGCCGTTTCCTTCGTGGAACCAGTC GTCCTACTTTCTCTCCGTAATTTCATTTTATTTAGAATAAAGGTATATACGGACGA CTATCGTTCGGAACAACTAATAACAGTGCTTGGAGGTGAATAGAAGTAAGTTGAAC TGAGCTAAAGTGAACAACTACAATTCGTAGCCCTGATTTCATTGTCATTTTTTTTC TGACTCAACACCCCAAAGATCGCGCAAAGAATAAGGCCATAGCTCAAACCCGAAAA AATCTTCTAAGGCCTGATAACTTAGTTATTATATGAACACCGGTAATCCCTGCATG CAGCATATATGAAATAAAATGCCGTCGTTTTCATTGTTTCGTATAAGTAGGGAACG AGGTCCATGTGCTATTTTGCTCTTTTATGTGTGCCCAAGGGGTACTGGAATGTCGA GTAATACTCAGTCCTTCAATGCTCATCTTGTGACCAAATTCATTGGGGAACTCCAT TGGGAAAGGAATCTGTGAGAGTGAATCCAGACTAGGATCTACCCACATTGTAGTCT GAATTTTACCTTCTAGAAAGTACCGCTCAAGTTGACTATATTTTACACAATGTGGG CTGATGGCTGGTCTCCGGTTGAGGAAGGATCAATCATACTCATCATGCATACATGA AGATATACTAGTATGATTAACAATAGGTTTTCAAAACAGACACTCGACTTATTGAG CACCCTATTGGCTAAGCAACTGCATCTGCACTAGCAATGGATCTTAAGGCATCATA TAACCGGTTAGGTACTTTCTTGTTAGGTAGAACAACACGGTTGATCAGGCCAATCG CTACTGAAGTAATGAAATCAATAAACACTGAGTCTTATGAAGTACTATTACAATCT CCTAGGGTCGTATCAGACCTTTGTTATGTTTTAAGGACAATGCGGGATCTCTCATC CAAAAAGCGAAATTGATACCAGGCATTGGTAGTCAAGATTACCGAATTATTTTACG TAGGTCATTATATGCCTGCAATTTTGGCGCTTTACGCTCA |

TABLE 2-continued

Exemplary 2.0 Kilobase Stuffer Sequences Having 40 ± 5% GC Content

| SEQ ID NO. | GC Content | Stuffer Sequence |
|---|---|---|
| 61 | 38.90% | GTTTAATCTCCTTGACTAACAGGAGTCTCTTGCCAACGGATGTACGTAACCGTATG<br>TTAAGACATTATGAAGAGTTAATATTACATGCAACCATTCGATTTGCCATAAATGT<br>ACCGAACGCCGTTATATTTACTTACTGGATGAAAGATTCAAGAATCAATATAAGTT<br>AAAATCTTAAAAAGATCAATCATACGTATAAAGTCTATTTGCTATTAGAGACGACT<br>GTCTGATTTGATGATGCAGCGCGTTGTTATAAACCTCATAAATAAGAGGCGGTGGC<br>TTTCTTACTATTAGCACAAGTCTCACTGAGTAGTAGAATAACTCTTACTCTATATG<br>TTTCATCAGGTACGACCCCACGTGGCAAAATTACATTTTGCACACGAGGCACATTA<br>AGACCGAAGAGAACATTTGGCCGAGAGGTATGTCAAAGCCGGCTTAATGATATCGA<br>CACAACTCATAAATGGTGAAAGTTATAACCAGGTAATCTTATGGGATTCTGTGGAG<br>TAAAGCCCATTGGACTTCGGAATAAATAAGCAAGCTAATCAGTTATAATAGCATAT<br>ATGTTAATACCAAGCGTGGAATGAGCACATTTTGGCAGTTTAACACTAAGCTTGAT<br>AAAACTCGTAGAGTAGCGATTGGACACTACAAGACGCGTGTTTCGCTAGAGACGAA<br>CCACCTTGTGCCAACAGATTACTCTGAAGCTCGCCTATTTGTGGAAGTAAATATTA<br>CGTAACGGTTATAGCATTGTTAACGATGATTTTGTCGAGTAACGGTATGAATTTAT<br>GAAAAACGTCAAACAAGCGTGATCAGTTTCGCATGATCGAATTGAGTTTTTGCCCG<br>CGCAGGGTTCGCGTCAAAACACCTTAGAGTAAATACTTAAGAGGAATCGCTACGTC<br>TATTTGTAAAAGTCCGAGTACCCACCTTGGAATCCCCATTTTTTTTTTTCCAGTCA<br>GCTCAACGGTTGAATCCACGTGTCCGAAGAAGCTCTGAGCAAACTATGGTGTCGCC<br>GTTCTAAGCCCATTTCAAACGTTATGGAGCGTTGTGCCTCTTTGTTGGCACTTGTT<br>ATTCACCGCGGCGAAGTAACGCGCTCGTCAAGCGAATCATTTTATGCCTACTCGGG<br>CTATAGTTAACGGAGTTAAAATGCTTCAAGTGTAGGTCGACAAAAGATCAGGAATT<br>CGAGATAAACTCTCCATGTGAAATAGCAAGTTTACGTCCTCGTTTTTGATTATAGA<br>CTAAGATTACGAATTCTTTAGCGCTGGCTCATTTGAATCCAAAACCGTAGAATAAG<br>AACCCCAGACTTATGTCCTCGAAATTATCAGGTAAGAGAACAAATAATTCACGAGT<br>ACTGACAGTATAAGCGCTTATGTGAGACGACCACGTAACTACAATTTATAAACTTG<br>ACCGTTATTATGTAGTATTTAGTGGCTCATAAAACCAGCTTAGCTTAGATCTGTGA<br>GACTGACCAGCTGACCCACAAGACTTTTACATTGAAGTTGCAGCTATATGGAAACG<br>TACTTTATAATTTCTTAATGTAAGAATAAATTTGCTGTATCGCTTTGTTCGTTTGA<br>ACTCTTTTCTATGTAAAAGGCTGACTAACCCAGGAAGAGGGGAGCATATTTTACAA<br>ATTAGTAAGCGCTCTCTCATTCATTTAATGATCACCTTATACCGACTTCAGCCTAT<br>GGAAGATCTTGCGCTGTTGCGTACCTACAGCGGGTAAACGGATGTGTTAAACACGA<br>TAGTAATAGTAAGTTTCCGTTAGGCTGTAGTTTATAACAGTAACATAAGTGCTAAC<br>GAGATCAACACAATTCAAGTTGCGAAAGCAAGAAAATCTTGCTACATATATCTTAG<br>ATAAGTATGAAAACATAGATTGCGTTTTTACAAAAAGTACGAAAACATTATATTCT<br>CAAGCTCACGCTCCATGAACATGCCATGGATGCGAGAGCTACTTAATATTATCCGG<br>TAATTATTAAAGTAACTACCGGTTGCGCACAACGGCTTAA |
| 62 | 42.00% | GACTCTTCTTCTCAGTCCACGTTTGAAAATCAGACAACTACATATTCAATGGAAGC<br>GCTGAGTCGGAGTGGCTTTCCGATTGACTGCAGGTGTCTGGCGATAGATTATTAAA<br>ATAACCGAGGACCTCATCTGTGATTACTTATGTTAACACGTCGTTACAAGCAAAT<br>GTACAGATCGTGTGTGGGTTAGGGGTTCACTAGAATCGGTGGGCAAATTTGCCGC<br>AACCGATATCGTATCTGTCGCCATTTAGTGGGAGCTGGGCGTGCTATCAGAATTTA<br>TTTAAACGGTTTGGGGACAAAAGAGGACCTTATACTGGTAGTATACCTTCTTTAGT<br>CTTTGCTCCGATTGAATACACCGGAACCTAATTTGTAAAGAGGCCCAGATGTTGGA<br>CAGAGTGGTTATGAGTGCAGGTTTATAGTTCAAGCATCAGAATAGTATTAAGATAA<br>AACTGAGGGCTTTCAGGCCTTGATTTAAATGTGAGAGTATTGTCAGGCCATTTGGA<br>AATATCATAAAATCCTTTGTGCCAGATAGTTATGAAGCTGCTTAGATCCACTTGCC<br>TTCATTTGAGTCTGCTGACTGCCAATTAGAGTCCTCCTCGGTACGTATGAATAGAA<br>AACTTCAAATACGATTCTCCCCAATTTGCTCTGTGCAGCCTTGCCGATAGTCCTTT<br>ATGTCATACACTAGGTGTGAGCTCCAAGGGTCTTGGTTCCAGCCCCGCAATTCAGA<br>TAAACATAAGCCCCAGTAGCGGAGGAGATTTTGAATACCAAACTAACTTTATAACC<br>CGCGCATGGCCAGTGCCATAGCGAATGCGCGGGGAGAAGTCATTTTAGAAGCCTAT<br>CAGGCGATCCCGGATCATTACCCTCGTATAATAAATAGCCTTAGCTGCAAGTTCGT<br>GTCGCCGCAACGTATTCGGTATCAGACTCTGATGTCCTTTAATAGTGATTATGAC<br>GACTGTCATAAACTTTGTAGTAGTGTATATTATCGATTGCGTTTTATTCATCTTGA<br>TGATGGGATACATCTGCACTTTTGAGCTAATCTAAGATCAAATATCTATTTTCACG<br>ATCCCGCTACTACGGCTCGAGAAAGTTACTTTACCGGACCGGGCTTAACACAAGAC<br>TTACGACGTCCTGGATAGAATTTTAGGGGTTTCTAAATTGATCCGGTTTGAGAACT<br>TCTTACTTATATTCCAGTTTCGAGGACTAGGCATTTCTTCATTAAGACCGAGGCAT<br>GGGTTATTTTTATATTGTGATGCAAATCGGTTTGCCCCGCCGGAGAGACTACATGC<br>CAGTTGGTAACGTGACAAGGCATGTGCAACGTTCTTAGTGTCGCTACGGGATTCT<br>GAAGTCTACTGCTTACCTGATTATACCACGGTTCAACTTCGGTTACAAAGGATATT<br>CGCTATTGCACGGGATGGAAATTTATTCATGTCCCAAAAAACAAACTCGACAAAGG<br>TGCCCACATGCGGCCTCATTTTACAGTGCACTTATGAGCTATTGCGAGCTCCCTCC<br>AAATATTGGTGGGACAGTTAATAAAAACGATCTGATAAAAATAGTAGGTATCGAGA<br>CCTAAGATTGGAATGATCACATTCGCGTGTTATAAGATTGGAGATGTTCTAACTTG<br>GATGAAAATGTTAGTTACAATAACCATATCCTGGTTCGAAGAGTATTGAGATGGAC<br>TTTCGACATTATAATATGATTTCAGAAAGGTCGCACATGACTGATCCTTTCCTCTG<br>CAGGTGGTCCTGTCATCGGGTATGTTTTTTCCTCTAGATAAATGGATATTGTAAG<br>CAAATAGTAATTCCTGCATGCTGGATACCATACATGATGTGACCGCCATAAGCTAA<br>CCAGCTTCTAAAAAAATACACTCCTTGCTAGTATGGTGATTAGTTACGGTGCATGA<br>AAATAGTAGGAACGCTGATTCTCGTTCATTTTGTGTGCGTTCCACGACGAATTTCT<br>GTTCAAAGTCCTGCAGATCTTATTGAGACCTTTACAGCAC |

TABLE 2-continued

Exemplary 2.0 Kilobase Stuffer Sequences Having 40 ± 5% GC Content

| SEQ ID NO. | GC Content | Stuffer Sequence |
|---|---|---|
| 63 | 41.20% | TCGTAGGCTAATAGAAACAGAATTATCAATTCCTTATTTAATACATCACTGGACTG
AGTCATTCTCTCAGAGCAAAAGGTAATCGCTTCATTAAGGTATTGTCTATCCTGTA
AGAACACCCACGCCGTGGATATATCTCAACATGTAATTAGGGGGTACATGCAGTGT
CGCAAAATTCAAGCGCGAACTGGGGCATTTCTAGTTATGCTAGCTAATCTACTCTT
GTAAAGGAGCTTTCGACTAAAAACTGCCACTATAATCTGATTCAATGGTGGTAATA
AGCGGTAATCTTTAACCGTGTTTTTGCTGTCCGACTTAGTGAATTGATACGTTTAT
AGGGAAAAAATAGGTCGCTCAATATACCTTAAAGATAATATCACCGGCATGCGCCT
ATGAGGTATCGATCCTGTGTCTATGAGGTAAAAAACGAGACTAAAGTTTGACTGTA
TTAATAATTATGAAAGGGAACCTTGTAGTCAAAAGATTAAGAGCAAACCCGTCTTT
CAATGACAAGACATACATTGGATGCCTCGAAATTGATTATTAAGTAACCAGAACCA
ATGATTATACTAAGAGCTTATTCCTTTCTCCGCAGACTCTTAAGAAACAAGGACAA
CTGCCCCTGAGCAACCAGCCTGCTGATACGTCCAAACAACCCGTTATCATTAGCCT
GTATTGAGCTAAAAGCACGTTTATTACTTACATGGCAAGTATTATTTATTATGTGG
CTCGTATAGGTCGGGTATAGAAATGTTGCACATTACAAGAAAGTTCAATCATAAAG
CGAATCGTTTATGTTAGCAGACTTTTATCTACAGTTAACACGAGGCTAGCGAGATGT
GCTACTTTTCAAGTGTTTGGAATGCATCCGAGGTCACTATAGGCAATTCTTTACCG
CGATCAATTCGTATTTGAAACGCCCGGCTAGCCTCCCATAGATTCCCAGTCAAAGG
AATCAAGGCTGCGCCATTCTGTGATTTACTCCCTCTTTGGACAACCAACGTACTAG
CCTGCAGGATACGATGCCAACATTAATTTTTATAACCGTGAGATCAACGCGGTCAA
GGAAAAAGTTAGGCATAATATCGCGGACACCCTGGCGTGAACGATTAACATCTGCG
GGATATGAACATTTCTCGATTTACTTTAATGATACTTGGCTTCATAATAAACATAA
TACATCCCCCTGAGGTTGATAAACGTTAGAAACTTAGGCGAGTCCATAAGCGCTTT
AAAGGATCTTTTATCACACACGCGAAACATTACCATTCGATAAAACTCTTTATCACT
CATCCCGAAATGCCAGTTTCGCACATGCAAAAATAAGCCTTCGAGATTGGTCACGC
CCGATCAGTCGTCTTTCGCTACCTAACCTATGATAAAATAGTTCTTAGGAGTCAGG
CAATTGACTTGCCTGTGTCTCTTTGGAGGCTTCCAAGTTCGGATTTAAGGGTATAT
GCCTGTTGTAGTCGGACAAATAGATAGGATAAGCGCTTTCCAGGCGGACTACACTA
TTAGTAACTATCAGCGAATATAAATGTACTCGGCAGCTTAAGCGTAGACTTAGTAC
TCGCAGGACCTCTTGCTCGTTCTAGCATATATCCTGGTCGTTTTTAACATTTTAAG
CTCGAAAAAGTTGTCGGAAGATGACTCCATTAGATGGACGATTAACGAACAAAGGT
CTGTGAATGACATACACATCTGATCAGTATTGGCCGCATTCGCAGGATAGTACATC
GCGGGGCAGACGTATTAAATCAACCTCTCCACACCCGGGTTTCGTTTTGCCATTGT
TGCCCTCGACAGCAGCGTTTCATTAATAGGAGGCTTTATAATACGTCCAGAAGGTG
TCAGAGGCCTACGAGCTCACGAACGTATCCTCATAAACTTATTGTGTCACCAGTCA
AGTCGTATTTTATCTCCTAAAACGACTTACCCACACCTTATGGAGGCTTAGCGATC
GTGTATATATGCTTCTTATTATAGTGCACCCTGGGTTCTA |
| 64 | 41.20% | ATTGGGCATTTCGTCGGACACTAAATGAACATTAAAGGATTGATCTTAGAGTGCTA
TATTGAATCACTCAGCCCAGTCCTTCGGACTTCCTTGTATTTCACTGGGCGTATAC
TACATTCTCAAAATAATTTTGCGAGTCAATTAAACTAGATACCACCTATGGGGGGT
TTCGTCTTGGTTTCAAATTAGATGGTAGTAAGTTTACGTGAACACCGTTGAGACGT
AGACGGCTTTTATGGGTTGTCTGTGTTAGACTCATTGAGCTGCTCATCCGAATTAT
TCATTCAGTACTATTTAGCACTTGGACATCCCTGCTAGAGCTCTGCGAAATGCGGT
ATTAGGTCTGGGGTGACCTCCAGCTCAATTAATTTACACCGGTAGTAACCAAAGGT
TAGTTAAACTCACGAAAATGATACTCACTGTTTTGTGTATCCTTAGTTATATGTCG
GCGGATTCAACCTTCGGATAATAAGTAAATGGTCTCAGATCGTAGCTGCAAAAAAT
CGTAAAGCAACTGTTGTTAAGATTGGCTACTCCTAACAAATTCCGCCTCCCTCAAG
CAGGACACTTCGGAATACAATCCGGAAATATGGCGTGAACCCTCTATGATCGACTG
ATTCCAATCACGGTTCAGTCCACTCTATCTAATTAACTTATCGGGTAGATACTAGA
AACTCACTCAAACCGTATTCGTGAAATAATTATTCGGAGTCAGTAAGCAAAGCCCA
GTGTGTATTTTACACTTAATTGGCTCTCTGTCAACTTCTTGCAAATTAATCCATTA
CTTGATAATAATATATCGCGTTCAATGGCAAGAAATCCACCGCAGAATCGCAAATG
GACTCCCTCTCATCTAGGTTAAAGCAAAAATGTTGAGATTCCACCTAAAAGTGGAT
ATAGAAGACAAAATTATTTGTACCAACAGTAAACAGGGACGGAAGGTGCCTCTCAG
GTAGTTACTGAATACCTGTTAGACGGGTTCTGCCCGGCTTCTATGACTTGAGATTA
TGTGGTTCTACAGTATATCATCCGTCTAGGAGTGAACCTAATGAAAAATACTCTAG
GTTGGTACGTATTCATTCACATAAACGGATGCGATGAGTTGGCGGGTTGGAAGTTC
TGTTAATGTCGTAAGTACTTATAGGCTGACAAGAGGTAACTGTCATACGAAAGGAT
TCGGTCTCGACGGCCGAACTCTAAAAGGTCTCCTTTTCCGGAGAACACAAGACTCT
TCTGCTTCTGACCGTATTTGGATAGATCCATCGGCGGTACCTTTGTTTGTTGGATC
GTAACATCTCTTTTGATCCTACTATGTGCCAACTCAGTTAGTTCGCGCTGAATTAA
GATTCAAGATCCTGTTCATATCTTTTATAAAACATGTGGATGTCTTAAAACTCATC
TCTTCAAACGCCATTGCTCGTTTCTGGAGTGTTACGGGTTCGGAGTAGAGTGGTAT
TGGATGTCAATATGTGAATTTATCCACTCTGACATACACAACGAGTCCGAGAATTT
TAGATCGTGCCTCCAAACAGCGCTCAAATCTTACAAATATTAATGTAGAGCCATGG
CCCCATGCAGAGATGTTACATTCGCATGGATCAATCTAAGTTTGTACAAAAGAAAG
GCACTTCTTAATCTGAACTTCATATCGTGTTTCCCTAGCGATTACTATGATTCTAG
TGTAGCGTTAGTTGCTTATGCTCTTTATACACTCGAGGTATCATGTACCAACAACC
TAGCGAAACTGATACTGAGAGGTTGCAGATAGTCTTCGACGATTTAGCTACTGTCA
TTTAACATTCCTGCCTAAAATAGCTTCCGTCCACTCACGTACTGGATCTCATTCTC
CGCGAGCCTTATAGAGACTGGATTACGTATATTCAATAATAATCTACTCTAGACCA
CCGACCTCATCCCTTGTTTATTGATAGTGGTGTCCCTAGCTGACCAGTCTTGTTGG
GAAGAAGCATGTAACATTCCTATTAGCGCCAACAACGCGT |

TABLE 2-continued

Exemplary 2.0 Kilobase Stuffer Sequences Having 40 ± 5% GC Content

| SEQ ID NO. | GC Content | Stuffer Sequence |
|---|---|---|
| 65 | 40.70% | AGAGAACGTGTCACGTACTAAGTGCAAAAGAGGCTGGGTTTTTTTTGTTAGCTTAA<br>AACACCAATAGACACAAATCCATGGAGATTTAAATGCAATTATTAATCTTGATCGA<br>ATTGTCTTTTAGCCGACAACCTGTTGGTCCCGACAATAAATTTAACGATTGTTTTT<br>ATCCTAAGATCAACCGTTGACGAACAAATTAGGCGAAAGTTATATTAGTAGCCAGA<br>CGCGTTTGGAAACAGGCAAAAACTGCTAGAATACCCGTAGAAACCTACTGGAATAA<br>ATGAACCGATACGTTACCGTCTCAGGAACTACTTAGGTTTGATAGACAGTGGAATG<br>CCATATGTCTTTTAGCGTAACAACCCTAAAACCTTATTATTGGAAATTTACCAGGT<br>AGGATGTCATGTAACACGCCAATCCAATTCATGTCACAAAGTGATTAGGTATACTA<br>GCATTTATAACTTGGGTAAGTGCATCTCATGTAAGTACCGATGGGCGTACCTCTTC<br>GATGTATTAACCAGCACCCACTTCATACAAGTTCATCGGTAAGTGGTTTACAAGAA<br>ACATCATAAATAGAAATAACACCTCTTCAGTGATAAGCGGAACCCCGTGCCACTTG<br>AAACAATCTCTCGCAGATGACCCTTGGAACAGGGCTGACAGTTTGAAGTGACAGGG<br>TGAAGTCATTCCTTTACAATTTAAGCCGGGAAATTTATCAACACTAAACGTAAAAT<br>AAAATTGGCGTACTGCCTGGACATTGGTCGCAATGTAATCTTCTTTGTTCTCGTAA<br>ACCAAACAATAATATTTTGAATCGTATTATATTGCACAGGTAAGCCACTGCAATTA<br>AATTAGAGCCCATCACTTCCCGGGCTAATTGAGACTAAGTCAAATTATCCTTTCAG<br>ACTTCTTTAACCTAAACATGAAGAGGGTTTTGGAATTGTTAAAGACATTCCATGGG<br>GTACTGACGTAGTACCAGCCAGAGTTCGATTCTTACAATTCACACGTATAGGTAGA<br>GGGTCCCACAGCTACATATCCTATCCTGAGCCGAATTCTCGCCATTGTTAGCTTTA<br>AATATTTCGAGCCAGACCTGTGGAATTTAGTGAGTTGAAGACTATGGGAGCCATAC<br>CGAAGTTGCTAATAAAATTGTTTCTAATTACTCTTCGTACATCAGAGGCACGCCAT<br>GTGTGTGATTAATTCATCTTGTTTCCCGTACAAGCAATAGCAATATTGCTCGCATC<br>ACGTCCACCAAGTAATTATTGTATAGTTACTTTGAACTATATCTCTGTAGCATTTC<br>GAGTGGTGCTCAGAGGCGCGGATCTTGCCTGTCGGGGATTGTGAAAGTTGGTCAGA<br>AAGTTACAACGGTATGGTATTTTAGAAATCGCGAACCTGATTGCGTCCTAACGCGA<br>TGTTATTAGTATTCAACGGTTGGTCAGAGTTATATACCCCTAGAGAGGCCTATGGA<br>GATAGACAGTCTCGCGTATCTCATCATAACTCTTGATCAATCTAGTCAAGTAGTTC<br>ACGGGACTAGCCGTACACAATAAGGAACCTAAGTGCAAAACCACTCTTTAGATAAG<br>GATCCTGCGCCATGCTTTGAGCCGCAGCATTCTCTCGATGAGTCCAGCGTGGTTTG<br>CAACACTTAGTACATAAGATAGTTAAATACAGAGCGGTCCTATTTTGAAAAAGAAA<br>TCCTATGGACCGCACCAGCCGGAGGTTACCTAAGACTTCGGACGAACATCCTTGTT<br>TAAATGTATGACTGGATGACTGATTTTCAACAGAGCGAGGTCCAAGAAAAACTACA<br>AGCCACTTATTAAAGACATGAGTAAGGACGAGTTATTGAAACTAAGACATACGTGG<br>GATAGCTAGGTGGCATAATACAAGCAGATAACCCCGTACGATTCAAACGATCTTAA<br>CAAGTATTTTATTACAAACGGGCCTGGTTTTAAGAGAAAAACGTGCAGTACCCTCA<br>ATATGAGTAATAAGGGAAGTGACAGGGAGCACTCGGCGAT |
| 66 | 40.50% | AGGGCTTGCATATCCACAAAAATGAATTTATCTAGGTTCAATTACGTGTTATCCAC<br>TCCAGCGAAAACTTGACACTAGGATTATTGTCTTTTGTCGACACGTTAATACAGCA<br>ACGTCCAAGAGATCTCTTGCTTTGGCTTGAACTTGCAATATTCACGGGTTGTTTCC<br>ATTCTTACCTCGACTGGCTAGCTGAATGACCTTTCACCTGGGTTACGATGTACGCG<br>GGGCACTGTGGCATTAAACGAAGTCATTATCTGCACCAACCCTTGATAACAAAATA<br>AATATGGTCTGCGACACCTTGTGCTGGGAGACAAAAATCTTCTGTAATTGGTTCTG<br>TACGACAGGATTAGTTCCTCTTTATTTCTTACCATGTTTCCTCTTCCAGCATTAAG<br>ATGGTAAATTGAATGTATAGTGCGCGATACGGAGCACGTGTCAGTTGTCGCTCGGT<br>CGTCGCGATTATTGCTTGGAGGATCCTAATAAAGCTAAATGAGTGGAGTAGTAGTA<br>TGCGTGTGTGCCGGCCGTAATATCTCATTCACGTGCATCATAGCGCATATATTCGA<br>CACTTGTAATCCCGTCTTTCGAAGAATCTAGGTTAAATGGATACTACTTTTTACAC<br>ACGCATCCTGCCTCTCGGCGGGAAATATGTTATTAGAAACTTCTGAAGTTGTCTGG<br>ATTAAAGTACTCATCATGGCTAAAACACTCTATTTTTGGTGTGAATATAGCTCTAT<br>TTACTTCTATCGAGGCCTCGTTCTAGAGGTTATTAGTGACAGTCCGTCCGTAAATT<br>TTCCTGTATACTCGTCTTCCTTATTAGGGTTGAGGTGTACTGCATGTCTTATGCTA<br>TACAATCAGCGTACGATCAAGACTGTAATATGTGTATACGACCACATTATGAATGA<br>GGGTAAGGTGCGATAGTCAGTAGCTGCTTGCTATTATCCTTAAATCGAATAATGCA<br>GCGCTTCAACAATAGATCATATGTATTTCAAGCAACAATTAGGGGATTCAACTAGA<br>GATGCTAATGTAGGTTTGTGAATATTTTGGTCGTACATTGGTAGGGCATCTGATTG<br>CATGTATACAGTCATAATTCAGAGCGACGCTCTTTTTAACCTTGGGAAAGGCCGTG<br>AACGAATGCGATTAGGCCAATCTAGCGCATATAGTTAATTATTTTACTCTTTATCT<br>CTTGAGCAACAGCGGCAAGGAAACCTGGGAGTTGCTAGACACCGAGTAGAAATCCC<br>TTACTTCGCCAGCGGATCGATCTGTACTACATGCATCTTCTACTAATGGTTGAAAG<br>TGAAGCTAGTACTTATTTGCATGGTGCACCCATTCTTACAACCAGGTTGTTCTAAT<br>GTCTTTTCATCAATTCTTAGCGGAGTGGGCATAATGAAAGTATAAGAATGGAAGTG<br>TTCTATTTTGCAACCGGAGACCACATGAAAGGATGGACACAGAGATGCAAACAGTG<br>CATACATTCGATGTGGCATAGACCAACTCTTGTACGATTTAATGTGATCTCTGTCA<br>CAATTCGTTTAGGTGTCTATGGTAAAACCTCAGCCACAACATGTATAGTCTTACAG<br>GCATGGCTATCGTGATTTAACCGTGAATAACTTGTCGGTAACAGAAACTCTGGCAC<br>AGGTGAGCGTAATCAAATCAACTTCAGTAATGAGGACTTCTAAGATAGTTCCGAAT<br>CTGTTCACAGTATTAGCACGGTGATTGAGTTCTCTTCTAATATTCCTATCTTTACA<br>TTGCGTACTGTCACAGAATGCTGTTGCCTCTATGATTTTACAACGCAATCTAAAT<br>CGTCGTATCATATGTTCAGAATATTTAAATAGCTCAACTCCGTGTTGAGTCCTAAGA<br>TAAAGATAGAAACATTGACTATAAAATCTATCCATTGTAAACCAGACTAATCATGC<br>AAGCACAAATTAGAGGGCAGACCGCGGCCATTGGAATCATTTATATCTTTATCGTT<br>TAATTCACAAGAATGGCTAAATGCCGGATTTTGACCGGGC |

TABLE 2-continued

Exemplary 2.0 Kilobase Stuffer Sequences Having 40 ± 5% GC Content

| SEQ ID NO. | GC Content | Stuffer Sequence |
|---|---|---|
| 67 | 39.10% | TTACATAACGACTCCGTCGAAGCCGTCCCGGACATCGAGTCTGACACTTACAACCC<br>TGAGAGCCGCTTCCCTATATGTCTATAGATTGCGAGTGTATGCCACTGTCATTGCA<br>GATTTAGGGTCACCCCAAAAACACGAGTATTATTAGAGACTACGAATCATTTAGCA<br>AACAATTTCGCGAAGCCCTAATTGAAAAGGCAACCGATTCACCCCTGGATAGATAA<br>GCTAAAATAGTGTTATGCGGAGCAATGTTCTCATTTGGACCCATACACTCTATTCC<br>TTCTGAATGACCTTCGAAATACGAATAAGAACATGGCGTTCCCAATCATCCATATA<br>CCCGTTCAGGCTGAGTAGCCAACATTTCGTATTCAAAGATACAGTTGACAAGCTGA<br>CATTCATTGATGACTTAGGGGCTAACATATCAGGCCTTTTCTTAATGTTTAAATAC<br>TTGCCTATTATGTGGCCATGAGGAGTGCGATGATACCAATGTTATTGGAGTATCGT<br>TAAAAAAATTCGGTAGTGTTATAATTACGAACTATAGCTTACGGGTCATCTATTTT<br>AACATAGTGAGGGCTTCTTCACACTTCCAGTCGTCGGTCTGCATGAAACAAAAATG<br>AGTTACATTTAGAGGAATGCGGGGTAGGCACAACTAAACACAAGGATTAAATTCGT<br>CGCGACAGGAGTACACTAAACGTAATTAAAAAGCTACCAGGCGAAACTTCTATTTA<br>CGGGCAATTACGAATCCTATGACACTTCAAGGACCTCTCATTCTAAAATAGAGACA<br>GCCTCCACTCGAGCTCCGATTGAGCTCTGCTCTCTTCCAAACAAGAACCTCCGTGC<br>GAGCAGCATATAGCGAGCATTCTTCGGAAGGACCTATATAGATCGGTCAGTTGGGA<br>AATCTTACAAAACGTCGAGCATATATTATTTGCCGTCCGCAACCTATGCACAGGGG<br>CCTTTTAAATCAGTTTATTTAAAAAATCTAATTTCAAACAGTCTTGCAATAGGTTAG<br>GTGGGTATAGAGTATCAAAAATACGTGACTAAAAACAACAGAAGTTGATAAACAAC<br>AGTGATTTTCGGGATTTATGCTACACCTTAGCGAGAAACTTCTGTTAACATTGTCT<br>ATGCTTTGAAACTATGTAAAGGAATTCGTGATATGGTATACCTAATAGGCCCATAC<br>CATTAAACTGAATCATAGTGGACGAGAAGCTTTATCGCCCTCTAATGCGTAGTGAC<br>GAATGAAAATCAGACAACCATTATAGAAGTCCGAGTCAGCCACGGATGTTCGGAAT<br>TGCTATATATACGCATGACTTGCCAAAGTTGTGGTTTACTGTATATTTCGTATTCC<br>ACAATTACATATAGCTAAATCTACGATCGCGGCGCGGTATAAGATTTCAAACTCGG<br>TAAACTTGAATGATTTAAATCATCCAATTGTTTTATGGATCGTGGCCTGGAGTTTG<br>GCAATTAATTAAAGGATATTTAGCTGAATGTGTAAAATAATTTTTAACCCAAATGT<br>GTCTATAATATGTGCTCGGATAAAGCTCAGGCATAACCACAGATCTACGCGACCTT<br>GTGATCGTCCTTGTATGTGTATATAGAGCAACTACCAACAGTTGTTCAGACGCAAT<br>CAAACGATAGCTTTACGATAGGATGTTCATTTATTACCAAGTACTATTATTCACTC<br>TATAGGGTTATTATATCCTCTACTACTCCGGGGTGCGCAACTTTCCTTACGCCATT<br>ATTAACGGAATGAGCGGTAAGCGGCACCTTCTATATCATCGTCATAAGAGTGAGAT<br>GTAATGTTACTATGCCTTATGCTTGCCATGGTAAGCCGAAAATAAGAAGATCACAA<br>AATAGCACCATCTTTTCCATAGATTCTCATAAACATTGATGTTTGAGCAAAATAAC<br>AGCTATTACAATGATGTAAATTATTATAAATGTCTAATCATAAGCCAGTAATTTCG<br>TTAAGCAATCTAGAGAAGTATCTTAAGAGCGTTAAGAACC |
| 68 | 41.30% | CCTCACTGAGACCAATTATGACTTTTCTCTTGCAATTACACAATAGTGCGTTAAGT<br>ACTGAAAACCATCCTCAAGGCTAAATGTTATAAGATTTTTCATACGAGTGGCGAAA<br>ACCAAGTCAAACTGGTTAAATGATGTCTACTACAAGTTTGGGCTTGGCTGACAAAT<br>TTTTCTATGAGCTACTGTAATAATGCGTCTTCATACGAACGCACTCTGCCCATAAA<br>TAGGCGATGGACCTAATACGTCAAGCCCATCTTCAAATAGTTTTTCTTGTAAATTT<br>TTGTCTTGACAGACATGATACGTTAACGTTGTCTTTGACCATTATATCTTCGCGAT<br>AGGGTCGAGTTCGTATTTATTAAATTGATGAAATTGCGACACATATCACGTGACTT<br>AATCCCGAAAAATTAGAGTTCTTGCGCTTGTCATAGGCATGAAAAGCTCCCCTCAT<br>AATACGTTTGACCTTTAACGTATGTCTTTAACATATGTTCCTGGTAACCAGGATTT<br>AAAGTCATGGTCAGCCTTCGAAAAATGTGAGAAGATCGCGAATACATCACGAACTC<br>TCTCAGGCAAACATCTCATCCACCATTTATATAGTAGATGCGCTACCCACTGTTAA<br>CCTGTTTGAGATGTCGATTTAAACGTTAGAAGGTGGTTCCATCGCTGGATTGCAAC<br>CTTTACTTAAGGTCGATGATACGTACAATCGCTTTACTTTAAGCTAAGTTATTGGC<br>ATACTACTGAAATTCACTTCCTGGCAGACTTGCGTTGCTCTCGCAATCCCGCAGTC<br>CTTTATGATGTCTAGGCGTTTTACAAATCGACAGTCATTGTATTAAAGTCATTGGA<br>TTGTACGGTGTAAGTCGACAGGGAACGTGTTGAGTTAATAGTAAAAGGTTCAGATT<br>CTTGCAAGCGCGCTTTTCTATCGCCTGGTTTATCAAACTCATGGTGATTATATATT<br>TTGCAATTCATCAGCCCTCATATGTTGGTAAGACTCGGATTGGGTCGACGCCAGAC<br>TAACGTCATAAATGTTAGAATTATTAAAGACGCAATTGTTTATGATACTCACTAAT<br>GGGTCGTTAGATACTTATTGTTTTAAGGCACCAGCCTCCATTTGTCCGAGTCCAGG<br>CCCGAGCTTGGGCGCAAAACTTTTAGTATCTAACTGTGAGTGACAACCTTTAGAGT<br>TCTCTCGTATAGAAGGTCCGACGTCAGAGTATCATAACCTACTGGAATTGGCCGGG<br>TTCGCGTGCACTCTCACTTCCTGCCAGAACGCAATTAAGCATGCTGGTAGTCTCGA<br>CCCGGTACCTCACTCTATCAAATGAAACTATAGTATACCTATCGATCTTAAGATGT<br>GGGTTCTAGCTGTGACTGCCCGAAGAAATAGTATTTCAACGACCCGATCGTCTAGG<br>AGCGTTGTGGGAGGGTTCAATGCTCTCGTATCGATTCCCAAGACGTTGTGGACATA<br>CTAGCTGGCGAATAATACTATGTGTAGTGAAGTTTGCGGTAATCTGCGTAGTGGCT<br>AATTAAGAAACACCGAGCCGTGTCTTTTGCAAACTCATCGAGGCGTTGACTAAAAT<br>GTCTAACGGTTAGGGCGATATTTTATTTTTACCCGCGGTTTATTATCTATGAGTAC<br>TCCCCATTCCCATATAGCGTGCATAGTTTACTTTTCCATATGTTATTAGCAGGCTG<br>TCCGCCCAAACGTTGCGCTAGCCACCGTTAGATCACAGTCATATTATCATAACGAT<br>TACCAGGTTATAGTTTCACTGACTAAGGAGCCCATAAATGTTCATTTTCACTAGAC<br>ATGCTATGGGTTTGGCCCGACCAAGATTGATAAACTGCGGTAATGGCGATATGATT<br>AAACGATTAAACTTTTAACTACCATGGGGAGACAAGACTTCTTAACTAGTCGGTAT<br>GGATTGCTGCTTGTAAAGCTAAACAAGCTGAATGTAAGAACAGGCTGGCCGGTTCA<br>TAACACTATCACGAGTGGCTGACAGAGTTTTACTTATAGT |

TABLE 2-continued

Exemplary 2.0 Kilobase Stuffer Sequences Having 40 ± 5% GC Content

| SEQ ID NO. | GC Content | Stuffer Sequence |
|---|---|---|
| 69 | 40.30% | ATTCGCATTGTTTGAGTAGCCGAGCACTAGTGGGATCATTTACCTTCTCGCGGAAG AGTTACAAAAGTACTGAGGAAATATGTGAATTGTTATAGCTTTTAGGAAAGTAAAC ATGAAACAAGGTAGAACAGATGACGACGTGATACAATTATTTACACAACTGGAAAA TTCCGTCAAAGTTTTAAAGTATATTCCTTGAGTCCTATTATTGAATATTCGAAAGG TAGTCACCTGAGTTGTCCCGTAATAATTACATAAGTATCCGTATGGCAACAAATAT CTCCTAGATCCGGGCCGCGGATAGTTTTCGCTAAAGTATCTAAATCGAACTTCTTA GCATACGATTACTAGACTATCACCTTGAGTAGTCTATATCTCTGCGAGTGTAAAAT GCACACGCCGTTAAATCGCCTAAATGCCTTTCCGTGGCCATTATATGCCCCACTTG CTTTCAATTCATTCCATAAACTATGATCATGGACCCGGTTGCGAGATGTTACAGAT AAAGTCGAAACTTTCAAGAGCAGCTGACGACAGGTAAAATTACGATGCACTGCGGT GTAAGGAAATAATCTCCAGGTTGCAATAGACATTTAAATTGTAGAGGAATAGAGTT ACGCAAACCAAGCCCAAGGATCTACCGAACCCCTCTACCTTATACAAACTCGTCAG CCGAAATATACCAAATAGCACGTTGCCTAGAGGTTTACATTAATCATTTTACACGA TCCCTTTACTATTAATATATCGATTCCGATCTAAAAGGCGTTTCAAGGATAGCAAT AGTCCTATCAAAATCATTCAGTTACTGGCAATCCAACCAATTCGCTGTACACGACG GGGTGAGGTCGTAAAATATTATATGTCATAGATGCACTGTTTGCGACCATGTCTAG CATTTTTCAATAGCTCCACCCACGCGTTGGCGACCCATTGTTATTCAAAAATGGGC CGCATGAAGAGTTAATTCGTCTTGTTCTGACATAAGTGTTGACCATCAGACAATAG ACGTATACCGCTGGTTACCTCTAATCGAAGATCCAGAGCTCCTTATGCAACGTATA GTAAACCTGGCTCGGAAAGGGGTTACTCTTATTTTTAGCACCTACATTCGGGATCA AATCATATGCACTTTCAAGATGGTGCTCACTATAACACAATAACTTGGGTTTCCAG TTAGGATGAGGAATCCGCCAGGTTACTCTATGAAGTCAAGCTCTTCCGTAGTTTAG GCGACGCTTGACCCGCGTTCCTCACAAGTAACGCGACAGATTGGAGCAATAGCGAC TGCTTCACCATATAGGGACTTACATACAGATCGAATGATTTGCAGCTTTAACAACC CATAACGATCTGCACTAGATGCGATGAGATCTCTGTAAAACGAAACTTGGAATTAC CCAGAGCAGTTCTAATTAAGCTTTTTCGATAATATTACACAGCAACTAAATGAGCA CGTATGCTCAAGTGTCGCAAAATCCTTATTGTATAGGAATAGGTCGTTGTCACAAC ATAGGTCTGTCACCAAACTCAGACATTATAGTACTTTACGGAGCATGTTTAGACAT AATCTGCACAATGCTGATTAGTCTCAGTGTGGTCAAATTCTTTAACGTCTCTGTTC CAATCAAAGTGAGCAGACTGATTGCATCACAACTCCATCACTTAACCAATTATTAA TAGTCCACACAATTCATTCACTCTTCACTGTTCAGCACTCAGTCATGCTCTGGATA TTCCATATTTCCCCGCCACATATACTGAGTTTGGTCACTCATATGTTCGCTAAAAT CGATTTTTAAGCCATTCTTGCCTATTAACGACGGTCCTAATCGTTTCCCTTCACCA TGGATATACGGTACGGGCCCTATTATCTGCGTTACGCAATGTCAATAAAAGATATT CTAAGAAGAAAAAAGATAAGTTGCGTAAGCGTGCTGCAAGAGACACTCTCTCTTC GCAGTAAACTAATTTTTCCTTTAAGAATACAAAGCGAACA |
| 70 | 39.10% | GGATTAGATTGTGCCATAACGCAACAGGTAAAATTATTAGACCAGCAAAAGAATCC TAACGTATACAATTTTATCGTACATAACCCGTGAATCTTATTAAACCCAGCCAGGC CGCCTTACTTTGCTCCAAGTAGGAGCATAATGCATAGAAGTTTCAGTATCCTGTCT AAAGCTATTAAGTCGAAATGAGACAAAAGTGACGAGTTATTAACGATCAGAAACTA GTCTAAAGGGAACCCTCCTGCGGCCATTTCTTGAGGACTTACGTGCACCATATCAT GAGGTCCTACTGTGGGAAAGGAAATCCTCAGTTTACATGATTTGAAATACTGTAGT GACCTGTCAATTTACTGATTTCTATGCATAAAATGACAATCTCACCGAGTACGCAT AAATCAGCGCAGATCTCATATATTCATAATAATCTCCGGGACGTTATTAAATTAAT TTTTTTCTAGACAGATATTCAGAAGTCCGACGTTATACAAGTGCCCAGTAACATGT TCTGAGCAAATAGATTGTCGACAGCCCCAATTAACCACCTACTAGTCTTTAGGCAC TGTGTGAATGAAGCTATTAAGTACTAGACATAATGTCATTGCTGGCTCTAGCTGAA GAGTATACCTAGCTTTTTTTCCAGATTTTTGAGTACGGGATCTGTTCTTGTTGAAC AAATAATCTGGATGGCGCCATACAGGCGTCGCCTGGAGCGTCAAGCTCACATACCC TATCGTCAAAGTATGTTCCGTCAAAGGTGTCTCAGCACTTAAATACTTAAACAATC CGAGTTTCGAGTTCTAAATGGTTGCACAATATGCCTGGTAGATTGATATAATCTTG AAGCAACGATGGATGAACAAAAATTATTGATACTTACTTTTACCCACACAAACCGT CTGAGTGTCTTTTTAAGAGGGTTACGAATATATAAAAGCGGATCACGATATTCCAC CGGGAATAGCGCAATTAGTCATATGGAACATGGTGTGAAACCACAACTATGAAATC TATCCGTACACCAACCAAGAGACCTAAAAGTTTTACATAATCCGTTTGCTTTCGTA TTGCCCTCTATCTAATGAAAACCCATTGACAATTATAAAGAACAAAGGTTATCACA CGCTGCGTATTTAGAAGAGAGGACATGTGGGATCAATGTGGTCGCAAAAATTAT CACTTTAATCAACACCGATTCTAAGAAGAAATAAACGTCGTATTCAAGGGTACTGT ATAGGTACGTTAAGCGTTGTCGTACACTCAGCGATTTAACTAACAGCCGGGAGAAT GCATAATTATGATAAAGTGAATCCACTTAGCGTCTCGAATAGAGGCTATTTCGCTT GCAATCAAATGCTTAAGAGTATCCTAACCAATTTTAGACAAATATCAGTATGTTTA TCGATTAAGCTGGACAATTCCTCTACACAGATGTTTAAGCGAACTAGCATTTTCAT CCTCCCGACTCATAGGAGTCCTTCGTTGCACAGTAGATAGTCAGCGTGTGTTCTCT TCTCCAATTGATATGCTGAAAAACTATAGGTTACCCGTTTCGGTCGGATAAAGAAT TTGACTTAATTTTCTTGCCGATAGTAGGTATACTGTAAGGCAGCCAATATAACCGT TAGAGCTTGATTAGTATGATATTCGCTCCTTTTAATGTATCTACATCTAGCTCTGG AAAACCCGGTGTAGAAGTAATGTATTAAGTCTGCGAAGCGGGAATCTGCTTGTGAC AAAGATTCTGTCGCCCGCAAACGTCAAGTAATAAATCGCAGATACGGTCAGAAATT CCTTCTGCATTTCAAGATTAGTAATCTATTCGATTCCAAACATCCTGCTCCTAACA GAATGCGCACGGGACCTAATGAACTTTTCATATACGTTTCATCAAGCAGTAGTGTT CGGAAACGAGACATAACAGGGTACATGTGCATCAACCTTTAAAAACCAATCTCTAT TTGGTATAGTCGTATTCGAAATCCAGTAGTGAGGTGAAAA |

TABLE 2-continued

Exemplary 2.0 Kilobase Stuffer Sequences Having 40 ± 5% GC Content

| SEQ ID NO. | GC Content | Stuffer Sequence |
|---|---|---|
| 71 | 38.70% | AATTGGAGCCAACCATAAATTGGATGGTAGTTCCAAAATTTTATAACCTATTCTAG TGTCTGCAAGTATTTAGGAGATAGGTGAATTACACGTCGTACACATAAATATGATA ATGCGATCAAGAGTGAATGGGGTCTATAGTAATATGATGTAAAACTTAAGGATATT GTGGACTGATTTAACGTTACGTAGTCCTGACAAGAGTTTAGATGCCAGGTCGTAGA AGTTGTGTATCCCCCTATTCTCCCAATGGTAGATACCGTGATAAAAGATAAATTCC TGTTAAGGAAGTCGAGGATGTTCTGTGGAGTGCAGAGTTCTACATGTGATGAGATA ACCTAAGAGAAAAAGTAATTTATAGATTGCCCCCGTTAGGAGCTACACCCGACTAT TTGTTTCGTTAAGATATTTGTTCGTACCATGCTGTTATAACGACACTCCCTCGAAT CTTATTTTATGGCAATTAAAGATGTTACAGGTGGCGTTGGCAATTCTGGTAAACTC CGCACTTTACAAATTGTTGTTTGCAACTCTCTCATATTGTATGCAATCGACCCCAA ACCCTCATCCTCGACCCTATGAATGAAGGTTTTCTGTGCCAAAAGCCATTTTACTC AAAAATTAGCTTTTAATTTGGGGAGCTTAATAGCGAATTCCAGAATCGTTTCATGG GGATTAGGAGATATATTATAGGAGTCCACCAATAGTCTATTGACTTAGTGGTTTTG GCTCATGCACGGTGGACAAAACTTCAGGCGTGTTATCTAATTACAACCCGTATTCA TACATATCAGGGGTGTTGATTTCAGAGAATAGATTAGGAAACTACGAGCAATACCA ATTTTGAAGATATGGTCTACTAGTAGCTCACTTACTCAACATTGCTACTTTATTCG AAGGCCCATATTGAGGAATACTGTCTTGTTGAGTAAAACGATACCCGTAACTTTAA ACTATAAAGGCATACCAGAAAAGTGTCACCGCAGGAAAATATAAGAACGTCCATC AATATATGATGCAAACTAGAGAAAGAGCTTGATAAATTATCAAACTAGCACTTCTG GGAATACTCCGTGGTTGCAAGGTTACAGGGTTCAGTCAAAGAGTTATTAAATCGAT TGATATACTTATTCAAGTGATTGATTCTATATAGCTACGCATATCTGCTGACTTTT TCGAAACGTTGCCTGGTTGTCCAGAGCATGTTTTGGACGAGAAATTTCGCGCAGAT ATCATGATTACGATTGGCAACTAAGGATGACTAGCGTAATGAGAACCTGGCTAATT TTGTGTTTCTTATTCAAATTGTATAACTAGGTAAGGAACGACTCGTTCAGAATGAG TTCTAATCATAATCTTCTAAAATACTGACAGAAATAATAATATATATTATGACTAT TCAGAAAACCTATAAAAAGCACTCCGTAGAAGCTCTTCAATCTTAGAATCCTCACC TAGGAACCTGAAGATTATTGTATTGACTTATTTTGTAGTTATTAAAGAAATCCAAC GACGGGGACGACTGCTTGTATGTAATATTTCCGTTCCACAAGCCGGGAGTAATAAT AAGCAACCGTAGAGGAGCAATGGGTTTTTATCTCACGCACAGGATGTCGGAGTAGC GAGCCGTCTGAGTATGTTATCACCAAAGATATATGTAATATGGTTAATCAGCTGAT TTAAAGAGAACTTCATCCCAACCTCGACCGACGATCCGATTACTGTTTATCGTCAT ACCTTACGAGATGTCAGGTCCTCGCACAAACCGCCACAAATTCCTTGTCACTGCAA GAATAAGTTTGTCCGCAAACTGTCTACGCGCTAGGTCGTTGTATGTATTGATGAGC CCTATCCTTATGCACTCGGACTGCTAGCCTTCTGAGATTTACGACAGGCAGTCTA GTATTAAACCCTTACTACTTTTTGCTGTATATTGCATTGCAAGTTCCAACAAGTTA ATGAAACACAAACCGTGATCGCCTCACCCCACAAAAGGCT |
| 72 | 38.80% | GTAAGGGTCGAACCTCTGATCATATTCGATTACTAATAACTCCAGATATATAGAAT TGAGAAAGGCAAATGTATTTTAAACAGCAAGAAACTGTTTCAATTCGGCTTATCTG ATGTACATTTAATAAATAGAATGAAGATCGAGTATTAGAACTGATATGAAAGTTCG TAACATCAGGACGATTAGAGTTTATGCATGCTAACAGGAACTGACCTGCTGACATT ATATCATACAATTTCCTGCGTCCCGCTTATGGATGGCGTCAATAGGCTAGTAACCT AATTGCAGCTTAGAATAAGGAGAACCAAGTAACGACAACAAAATGAAAAGCAATAG ATGGCGGACTGCGCTTTAATTGCATTGAAATACTCTGGGCTTCAAGTGTTAGTTCA TTAAAGCTGTCTCGCGATACACAAACGCTGCGAAGTGGTTCCGGAGTAAATGTGAC CAATGTTAGACAGTGGGCCCGCCATGAATGTGAAGTTAGTTACTAGGAAGAGTATT CTCAGTTTGGTGTTTACTAGAGGTGTGCTTGGCGTTTATCTGGGATAATAATTGTA ACTCAATTCTATTCTTTTTCGTTTTTTCTGCTCATATCGAAGTTTTGCTCGCCTCA ATCAACGTTGTTTGTATAGCACTTAGGATCACTCTGCGCATAGGGAATGCTTAAAT CAGGGAGTTCATCGGTGTCCATCCTGCAGGGACATGAAAGCTGTCATACACGGACT CGTACCGGTCTGACAATCCGCTTTGCCTCATAGCAACTATTGAGCCGCATTCGCGT GGAGCTGAACTATCAGAATGGCTAGAAAGGATAAACCTGTGGTGGGTCCACGAGAT TGGTCTTCTTATGTTAATATTAGCTCACAAAGTCCAGAGTTAGTATCCATCTCTTC CAGTCACATGGAATTTTACTAATTATTGTGGTATCATTATTATAAAAATGACATTA TCTAGCATGACTCCCTACCACTAGTGCAGAGCTACTATGTACATAACTCGCTGTTT ATGCGATACTCCAACAAGTAGATACGGTAATTTCGATATAGGATGAAAAAACCTTC ATAACAGCTTAAGTTTAACTTCGAGGGTCCGTGTAATCGGACAACGCACATACGAA GTGGCACGACCTTTCATTTGGGCTCCCTTTTGCAGGCTAGTAAACCTAGTATACAT GAAAGCCGTCTTGCTTGTGCCTACGGCTTATTTCGTGAACGTACGTCTAATAGTG CCAAGGAACGAACACACGGCTAGATCATAATATTACTCCAGGTGATGGTTTCGGTA TTTGCAAAGTAAAGATAAGTTATCTGATTCACAACAATCGAGAATTTGTCCTGTTT GAACGCCGAAATATTATCTTACTATTGCTTTACTCAGATACCTCCAATAAATTATA AAATGGCTTGTTTGAATGTGTATCGAAACCGAAAGCTATATCTTTTGACCGAATTA ACCAAATGCTACGCGTTTGCTGTTTATTATGTCCATCATCGCTTTAGGTTAAGCTT AATAGGTTAGGGAAAACTACCAGCATTCACATAATATCCTATCTAGGAAGTTAAAT TCACCCATGTATACTATACTACTTAGTCTACAATATTTCTGCTTTATTCTTTATTT CCATTATCAAAGTATTTCGGCTCTTAAATGGGGCAATTACGAAAGATATGATTCTA GCTCATGCTCAATTGAGATGAATTTATGACTTTAATGGGGTGTACCATTTAATAAT GCAGCGCTAACATAACGTGCGACGCTAATATCATTTACTAATAGATTTTCATTCAC TATAATAATTAATAATCTTCTGGCCCCATGGCACAGGCAATTTTAAATCCGTACCC GTCAGCCCTAAAATGCCAAGATTAGTGAATCTGGTGTCATACAGGACTAACAGGTG CAAAAACCGGTTGCGTCATCAAAACGCAGGATTTACTCAGGATCTTAAGAAATCTA AATTTTCGCAGAATCGCTCATCGCCAAAATTTTAGGCGTC |

TABLE 2-continued

Exemplary 2.0 Kilobase Stuffer Sequences Having 40 ± 5% GC Content

| SEQ ID NO. | GC Content | Stuffer Sequence |
|---|---|---|
| 73 | 42.80% | CACGTGGTTTTCAGCGGTTAACGCAATCTGCATTATTGGTAGAATTTTACACTTAACAAAATATCACCACGCGGACAACTGATTTAGCAAATGCCGTCCGTGACGCGGGACCCGCAGCACATTATTAGACATAGTACATCAGCCTGTAACCGATCAGTCATCACATATCCCGGAAAGATTTCAATCCAGTTGTAATCAACGCGTAAAGTTATATAATCACTTCAATCACCTTACTAACTTCAGAATGGCAGCCTAAAAATCTGATGCTACGAACCGCATGGTGTTGAATAAATTCAATAGAATGGAGCTCCTGGATATTTCACGACGCCGGGACAGAAATAGTGTTATAGAGAAGAAGGCATGCCGTTTTACTCGATTCGTAAGTAGTTTGACGAAGCAAAAACTTGGGGAAGAACTTATGAGTTAGCCACGACAACTACCGGGAGGATTTGCTTTTCTTCCTCCATGCCAATCTTGGAGGGAGTACCTCAATCACACGATGAATCAGCCTTAATGGGCGCCCAAAACATTCTTGGTGCCAGAAAAGCGGATGCTTCCTCGAATGTGTAATCAGAAAAGTGGTAGATGAATCTCCGGCTCCATCATGGATAGAGCTGCAGGTATTGGTGCAGCAGGAACGAAGGTTCTACCAGTAAGTAAAGTTTGACGTTAGTTACGAGTCTAGAAGGCCCAAAGGGCAACCAAAACGTCGGCACCATAACATCTACAGGTGGTAGGCTAATGTAAAAGTGGTTATAATTGCTAGGCAGAAATAAGGCCGTTCATTGGGCATGTGTACACTCCATTGATGGAGCTTAATTCCTCTCAAAATAATTACATTCTGTTAACAAGAAATAACTTATTGGTCGATCTACGAGCTAGCAATAAATAATCATGACCAAAGAGCTGTGCTGTGATCAGAAGTTATGACGCTTATACAGAGAGCATTGTAAAGGGCAGGCCGAAGCAAATTCACAGAGTACCTGAAGCGAACAAAGGAAGAGACTTCTTTATAATTTACATCGCTTGGCAATTAAAGAAGCGAAACACAGTTGCTCGAATCACATCCTTACGTGTCGTCGACAATATCATAAGCATTACTAGTTTAGAGAGGTGAGATATCGGTAGTAGGTATTAGAACATTCTAATACCTAAAGCTCATTACTATTAGCACCTTTCCTCACCTTATTTGGATTTCCCGCACGCCGTTCGCACCGAGCTAAGTGCAATAAGCCATGGCGATGACTTAGATGTCACATTGCCCCATGAATTCACCCCAGTGAGTTGAGACGATTTGAAGTTTAATACGTCGTTCGTGGACAGCTTGAATGTTTCACACGTGGTAAGTTGCATATGAACATATAGGAGGGGCCACAAAGCTTATGCGTGAAGCAAATATGATTCCTCCCTCGATCCGTTAATTAGAGTTGCTGAAGGGCATAAACTTTAGCGAGTTTGTATTAACATAGTCATATGAAGTAACAGAGACCCGTCATAACGCTTGAAAACCTGAACTCAGAATGCGCTTTGTGTACCATAGGCATATACCCCACATTACGGAGATGATAATCGACAAATGCTCCAAGAAGTAGACCTCTAGCCATCATCACGTGTCTCTACTGTATTCTCCGAAGTTCCGGAGGCCAGTTCTTAAGTAGGCACAGAACACACGATGGATTTCCTAGGGACGTACGTATGTTCGACTTCTCGTCAGTAATCGCGACAGAAATGGGAAGGTGAGCTTAACCTAACCCACATTTTTGTCATGGGACTCTGTGAATGGTGTTTCTTATGAAGCTATCACGGTGTAAAGATATCTAGACACGCTATGTGCTACTCCGATAACCCTACGTTTAGGTTTACGAGATTGGAGAAATATACTTTATTAATTCTTCCCTGGAATCGTACCAACAAGTTCCAAAATGGCTCTGCGGTCTGTCAAAATATGAAGGGCTCAACTTGACAGGACGACTGACCGGAAATGATTTAAGTGAACCTCC |
| 74 | 38.00% | ATAATTATCGACATAGATGTGCTTCACTCGATTTGACAGCTGGATAGTAAGAATTAGTGTATAACCCAATACGTATGCTAATACAAACCCTGGACTGATTTGAATGTAATCCTATTCATAATATTTTAGCTACCGTAAATGTATTCTGCAATTGAATTTCGTGTGAATGTAAAAGGTTTAGAAGTTTCCTAAGTTATCGGGTGACGTTTTTAATGGGTCTTACCGTAGATTCAGACAATCTTTTGGAAACCAACTGAAGAAGGAAATCACACGACCTGGCGGATAAGGGTTTGTAATTCGCGTTAAAAAACTGACGTTTGCTATAAGAGACGTTAATGTAAATGTAACGCTTTAAATTCTCTGTGCGAGAGTTTTTTAAATGAGATCAAGGATTGTTAATTTCAGGAAGCTCCGTTATTGGATTTTGCCTTCTCATTCGTCACTATCCCTCTCCGATCAATCCGATTGAGTCCTAGTGTAGAAAGTTCACATAGAAAGCAGTTTTCCGATTAGTCTAGCGGGGTACTAAGTGAACACTAGTCAGTTGGTGATATACTATAGCTAGGCTGTGATAATGTTAATCGGTTTGTGCCTACTGGAATGCTTAATTTCATCTTGAGGACTTGCGCTAGGAATCGGTATGTCTTCGTTAAGTCCAAAGTGCCTTTTCGACAGATGTTGGATTGATGCACTCCTCCGAAAAGGAATCAAATTGGGTTTATAAATTTTGTCTTTGTGACACCTGCCGAATTTAGATCTCACCATTATCCACAATAACCCTATTATCTTTACCTACTTCCGTCGGAGCTTGATTATGAATATTGGCAGAATTATGTAATAGTCATTAATATGTTGAATAAAGATATCAATACATTCAGACAATTGAATTAATCCTGCGTAAAAACCTACTTAGGACGAGTTGCTGGTATTTGTTTTTATAATGGTAGACATGAGGGACATATTACGAACCTCTGTAAGCCTGTTCTGATGTGGCCGGCGATCACGTTACCTGATGAGATTTATAGATCTCAAGTCGGATGTCCTCTTTAATAAACTGAAAAATTGACGACTAAGTGGGCTAATTATGCCATCAGAAATAAGCTAACCAAACCTCTAAAGTCGACCCTGTAGTATAACTGGCAGTGCTAGATATCACAGGGTGTTTGTCTACTGAAATTTCGGCATTCTGGTCACACTTATTGCCGATAGGTTCTAGTAGCTAGTTTATCTAGACTCCAATTGAAAGCTTACTTCGGCCTATCAGGTTGAATGATAGACGGTCTGTCTTAAGAAACTACAGGACATATACTGCATCGAATGCGTTTAAATCCTAACGCAGAAGGGTTGTTATCTGATCATCAGTAAGCACCAATCTGCATGATTACAGACGTACCAACAACTGAATACATCCTGCCTCCTGAGAACTAGAACCTATTGTATTGCGGATGAGGGTAAGATAGGTAGAAACCTGCTGCCAACTTATCGATAATAATTATGAACCATGCGTGGGTGTTGATATAGACTTAATATGACCTCCTGTCTGGTTCATATACCAGTTTTCAATGCTTAAGAGAACTAGCTTGTACGGAGTTTTTTAATACAAGTGCTAAATTAACAATTGTTCAAAAACAGTTTATAGTAGTAAGGTATTGTACCAATCGTATAGCAATAAATCATACCTGTGTTTACTCCATACTTTCTTGATTATCGGGCACGAGAAGAGGACAACTCCCAAACATCAATGTAGCCATAGTGAATGAAAAAATCGGTTATGAATCGTTAGCTAAATCGTTTGCTCCAATTAACAAAACTATAACCTAAACTGGTGAACACATAGATAAATGCCAACTCGTTATCGTGTTATGCTATAGATCCGAATTTGGTGGTTCTCCGAGTCTGTATCGTTTTTAATCGAGATCTTACCTTATTCCTAACCACATTTCGTAAGCCTATTGAAACGGGTATTGCCGGTTCGCCCATCTGGTAGTACGTAAACGA |

TABLE 2-continued

Exemplary 2.0 Kilobase Stuffer Sequences Having 40 ± 5% GC Content

| SEQ ID NO. | GC Content | Stuffer Sequence |
|---|---|---|
| 75 | 38.20% | GAGGTTAGTGATCAAGCGCATTAGCTTTTTACTGCGGAACGCATACAGGATATTTA CGCTTAAAAAGGTGGATTTCGTATTTATTAAGTATTCTCTTTACTGAATTATTGTC CATCAGTAATCGCTGGCTTTATGAACTATCAACATTCGGTGTTGTGTTAAGTTATT AATGACACATGCTCGACGTTCCCCAATTCCCGTGCGTGATATATTATCATATGACC ATTAAATGATTAAAGGGGCATAATATTTTGAAATAACACTATTAATTTGAAACTTT TGTCCTTTTCGCACTACATGTTGGTAACATCGCACGCACTAAATACTGACATATCG TGCACCATGCTTTCTAATAGCACTCCGTTCCAGTCCATAGCTGAGACTGTCTTTTC GGACAACACAATAGATAAGAGTCTATCTCTCATCAAAACTGTAAGAAAAGCTCTAC CATAATTGGGGCCGAAACGTAATACGATTATTATGATATCGCTCCTGCCGAGGTCA AACACCATAGCACTCAAAAATGGTATCCAATTTAGAGGGGCTATGAGTAGTTAAAA AATAGGAATTAAGGTGGCAACAGGACAGAAGTCAATAGGTTCCCTTGAAGGCTAGA TTAACAGAACTGTAATGTGACTGCCTGTAAGCGCACTGGAGACATCAAGTATTGTA CGAGTATAATTGCACTTTGGAGGTACAACATCGCACTCGACTCTTTCATCGATATT TTTTCGTGGGTGAACTTGAGTTAAAGTTGATGGTCCCATTCACAACGAGCGGTTTT CGCGATGTAAACGCCGGCCAAAGACAACCTAACGCCGAATTATTCTACTTCATATG CCTAAGTAAGCCCGTTCTTTGGAGAAGTCTCATCCTCTATTATTATACATAGTTAT CATATTAGTCTAGTCGCCAAAGTGTGGTTTCTAATTGATAAATATAATAAGTTAAA AAATGAGAGCTCAAAGTTTTTCCTTACCGTGCCGCACAAGTAAGTAGTCTCAAAAG GACCGCGTAGGGAGGGAAAATTTAATGAGTTCTAATATAATATGCAGGCTTGTGAA AGCTGACATTGACTACTCTGGACTGGTCGGATAGTTGCTAGACATACCTATTGTGA CAAACTGACCCATTATCGAGTCTAGTAGAACCGGTCCGTACAATTACACATTCTTC GTAAACTAGTTCTATAAAGACTAAAAAAATCTATATCACTTGGAGAATTATGGAAG ATGAGTCAACTCCGAAGTGTGGTCAAAAATATTACAGATTGTATCAAATCGAATAG GCCGTAAACAAGGGGTATACGTTCACAGTACAAAATAAATCAAAGCCTTCAATTAT ATCGAGAGATTATTACACTACCGCTGCTCTTGACTAGTCAAACGTACCTCTCATTG ACAACATTCAGCATGATTATTGCTCCATGTCAAAGACTCCGTGTTCCCATTAGTTT TAAAGGCATAATTTATCTCTTTTCCTCTTGGATAACGAGAGATAATTAGACAATGC TAGTTTCACCAAGCCCGACTCGATAAGTGGCGGTTTTAGCCTACCCAATCGCCTAA ATATATCAAAAATGACTTGTACGCGATAATACTGCTCGGGTAGTTAACGGCCAAGT ACACGCTCACAGAACAACGGTTGTACCGCTTATCTAATTAGGGAATGTACGGCTCT CTCACTAATATGCGATTAATCTATTTTGATTTTTATGCAGAGCATCCTAAGTGAAA CTCTAGATGCCGCCAATTTTTGTTTATCATTTCGCCAACCGTGAATTCCAAGATGG CCCGCCAAAGGGCGTATAAATCGAGTATTTACGAAGTAATAAGTTAATTCTAAAAT TCTTTAAATATGAAGACAAACAATGAATTGATTATGATTTCCAGATATTTACTTTG GTACCGGATTAAACCCATTTGAACGTCATTCGATATCAAAGTCCGCTAATAAGGGT TTCAATTACAATTCTTCAGGAGAACACATCGGTAACCTTC |
| 76 | 38.30% | GCGCAAACCAGCAAATTAGGTTTGACCTTCAACAACTGTAACTCGATCTGCAGACG AGTGAGTAACAACAGCTACTGGTACAATTTTTTTGTACCGCAGCATTCAGGTATTA CCCCTTCACGCTCAGTACAGAGGTATCGGGCATCCGTATAAAAAATTGACTTCTTT TTACGATAGTCCAATAGACCGTTAGCTTCTACTTCATAGTACTAATAATAACCTAA TGCAATAGTCTGGATAACATTCACGGGACACTGATACTAGAATCAACTACGCTGAT GAGCATGTCCAGACTGACAATCGGTCGACATGAGAAGGAATAGAAAAAATCCTACC CTGTTAATTCTGGTCATGTTTGCTGGTCTCTTTCCTACTCGGTGCTTCTCAAATGC CACATATTCGAGCATAATACCTAGTTATAGGCATAAACTTATTGTTGCTGCCCATG TTGAGCATTTTTTATATTTAGGCCTTTTACGAATTTCTGTTTCTATTACTAAAGAT GTCAGAGTAATACCACCTTCAGACAGAATCACATGATTAAAACTATAGAATCGGCG GTACAAAGATGTATCTCACCTATAGAGTATGCTGATAAAATCATAGACCCTAGACA TACTATTCTTATCGCCCCTTAGAAATTATTGTAGGGGTTGCGATTACAACGCATAC GGTATTTGCTATATGAGCACTCATGGCTTATGTGTACAATTTATTGATATATATAT TTAGAGCTCCGGATCGGGTTACAGAATCACTTCACGACCCAGCAAATGCTAATGAT TTAAGCGTAGTATATTGGCTTTGTGTCCAGTTTTCACTACGGGTTCCTTTCTATGT CCTGATAATCTGTACAACCGACATACCCTGAATTCATGCCGCATATGTCGTGTTAA CAGTGATCTAGGGTCCAGTGATAGGGTCATTTTCGTATCGTCGCATCTGTATCGAT TGGAAAAGAATTATACAGTCCGATTATCACTTAGAACTACACGAGGGGACCTCTTA TCTGCCCTACCTATTGGAGTTAAAGTTCTAACTGCTCAATCTCAAGACGGCCGAAG ATGGTTTTAAAATGACGGTCCACACATTTACAGACAAATTGGAATGCTTAGATATA TCCTACTGTTGATTTTTGTCCAAAATTAGAGGCGATGTAACCCCACTGAAAGATTG AGCAGTACAGTAATTCTAACTTGAAAAAATAAATTTTTGGGTATGCTCAATCTTTA AGGTGACCTACTAACAATATCCTAGATCCCATACGGTAGTTCGACAGAGATCCAAT ACATTCTAATCGAACATTAGTAAGTTAAATAATATAGAGCTACATTTCTAAGTAAA TCGATGCTTGAAGATATTGGTAGTTCGCAGAATTTGCATCCATCACAAACACTAGT CTTTACGTTTGCCAATTGCTAGGTAGAGTAGATTACGAGTCAATCAGAAGACCAAA TTTTTTGACCCATAGGATACAACACGTAGTCATGACAATCGCATATCGCTAGTATG TTAGATCTAAGAAAATAGTCTACTTAACCGGGTCATACATCTCAGCTATTAACGAT ATTATGTTGCCTTATGTTAGACACGTCAATAAGTAGAGCATGCATTTCTGCCTCAA ATAACAAATTTGTTAATATGCAATGAATACCTGAGTTGAATGAACCCAAACTAAAC TCAGGGTCCTTCCATAGCGAGAGCGCTAGGCTAACATGAGATTCTGACGTCTTCGT GAGTTGACAGGATCTTGCCAACAAATTACATATTTGAATAGGCATGTACGATCCAT TATACTATGAGTGCCAGAGAAAACTCTGCTGGCCGACCGTTTTACGGGGGGAAAGT CAAATATGTAGTAAGTACGAATTTTCCTGGGAGACTATAGTTGCTGAACGTTCTTA TTCTCATTTTCTTGAAGTTAAGGATGGTAAAACATACTATACCTATGTAGATATTC TTTGGTAGTATAACTATTATAGTAGCGTAGACGTTATGTG |

TABLE 2-continued

Exemplary 2.0 Kilobase Stuffer Sequences Having 40 ± 5% GC Content

| SEQ ID NO. | GC Content | Stuffer Sequence |
|---|---|---|
| 77 | 39.50% | GCCTAAAGACCTCTATATTTTAAGCTAGCATAAAGGCAGGAGACGTTCTAACATCG CACCGAGTTCGACTATGAAGAGAGGTATTATCAACCCTGTCTCCCAGTTCACACCG GTTGCATTATCATGACGTTTTTGATTTGTTTTTTTTGAGTAACGGGTTCATTGTAC GTTCGATAGAGTACTCGATAAACGACTCATTCCACGCAAGCCTATTTTGTAACTTA TAACTAGACATTAGTCTATGGCTACTTTCACACCCGAACTTACGAACAACGAGTAT TTTTTTTTGGCAAAAACGTAACGTTCGTATGTGGCCTAAGTCATTAAAAGACAAA TATTGAAGAAAAACCCATGATTTAATACCGATAGGACATTACAAGGGTCATTAGAG ATAACAAATAAATTAGGCTTCTTCCAAGAGTTATCCGACTAGTTGTGCTCCAGATC TGCGATACTGATCGAATTTATACCTCATTAGACATTCGTAGTCATTGGTGTTGGAC TTGAAGTTCTGTACAATCCTCGGTGATCACTCTTGGACAACCTGCTGATAAAACAT GTCTATCGTCAGTCCAGTTTGTATAATAAACTAATGAGACAATATACAAAACAATC CGTGGCACTACATGTTGTATACCAACATAAATTCTGAAGACCTATGATTCTTGTGG CCGAATAGTCAACAGATTTTACGATCACTAATAACCATATATCTGTTACTTGTCTT CTCAGATAGGAGCGGACTAGAAATACTCACTTATGTTATTCTTACGTTACTGTGCC AGACGAGAGGTTTTTGCAGACTCTATGGTTTGCCGGATCTTGCTAGGAAAAGGGTA ACTGGTGCCTGATTGCATGAACTATGTGGTATGACTATAGATGAAGCATCCGTCAC TGAGCTCTTCGAAGTCTTTTATGAGACAAGAATATTCTTTGATAGAATCATCTATG TCTCAATTTAATCAAGGGAACGGTTGGGTACTAAATCGAGTTATCATGAGGTCCTA TCGGAATGCATTGTATTTGAGCAATATCTATAACTGTAGGTACTATGGCGGATATT TATTTTCCTTGCTGCGACTTCATGTAGCAAGTCGGCAATTCCCCGCGGTTTTACAT TTTCTGCTTCGAGGTATTAAGGCCCTAAAGTTGTATATATTATAAATTAAAGATCT GGATTATTAACTCAGTGCAGAGGGCGTAATCTGACGTGGCGACATGTAGATGAAGC TTGCCCAAAAGATATGAGATCTTAATATCTATAAGAAGTATGCCTACTGTTAATTT TGGGGAGAAATGCTACCCCGGACAATTATGCGATTGTCAAGCGAATATCTTGATTT TATCCTTGGAATAGGTATATTACTTCGGTTACACCAGATATGAACCTATCTATTAC TTCATATTTTACTCAGGCTTGGTCGGGACCTGTGTTACTTTAAAGGCATTAAAACA TACAGCGTCGACAATCCTCCTAATCAATATCCTCAGAAGGAATTTACTCGCAATAG CGAACTGAGTTTTTTGCCTGTACAACGGTCGTGCCTACTCAATCATTGCCGCATAC TAATCTCTATCATATTGCCTTTACGGGGCGACCAAGGAGGAATCCTATCTAATCCC AGGGCACCTGGAACACCTGCGGAACATGCTTCAATAATAACATCGTATAAGTCTAT GTCTGCGCTTGTGACGTCATAGTACTTCTTCTAGTGATATATTACGCCGTTGGATT GGGATCACGTTTAGAACGACACTGTGAACTTCTATATGTACTCTTTTCTCACGATA TGCCGTCGAGTTTTTTATCGATAATAGGCAGTGTTGGAGCGGGACGTGTCATTAGT AATAAGTTTTTCCTATCAATTTCCTGCGATACTTGACTCCTTTGGGGCAAACATAG ACGACGGTTGGAGTCAAGGTGAACCAAAATAGAAGTACCTGGGTAAATGCTTCATA GGCACTTGGACAAGACATTAAGTCGACACACTATGCCTTT |
| 78 | 38.10% | AATGTTCGGTCCCGGGTAAGCTATCATTCTATAAAAGTCCCACCCCGCTTATTTAA GATTCACAGCGCCGCAATGACGCGGAACAGGGTTGTCTATGATGACCTAACTACGG CACTTTAGGTATCATATATTGAGTTGAGCGAATGGATCTGCTAGGCTTCCCGTCTA TCGGATGCTTTAATGCAGGTTAATGGCCCGATTGAAGTTTATAGTATATATATACA CTGTGATGGTGTAACTACGTTACTTCGTTACTGATCAATTTTCAAATTATCTCATT TGTTAGGCTACAACTAGGACTAAAGCTCAAGTAACCGATGCGAAGAGGCCGAGATG GTATAATCAACGGGGGTGTAATCTAATATACGAATCATGCTAGGAGAGCAGCTTAT CGTCAAAACTCTGTTGGCCAGATTCTAATTACTCTTTATTGTATCTTTTTTCATGT AGATTAACCGTGAAGACAGTAGTTCATGTACGTTAGTCAATTATTGAGAACATTAG CTTGAATGGACGCGTGCTCAAATAATACCCCAGTAATCTAAACCATATTGTTAATC TTTTACAAGACCCACCAATGACCTAATGAGTTCACCTCCACATACCTGTCATTAGG TGACCTTATTTCCACATTTGTATTAAATACTAATAACTGACCATATTGTGCTGTGG TTCTGTACACTTGTATACCTGTTCGGCTAATACTAGTCAGTGATTTCATAGCGAAT ATAACATTTGACAAGACTGTAGCAACAAGTTTTTGGTATAGGGTTTGTTAAAGCAT ACCGCGCAGGACGACCGTCTCTTACATTAATTTACTCGTTTTAATCTATAATTATC CATATAATCAACTAGTCCTGAGCCAAATCTTCAATTTCCCCCGCGTTTGAGATTGC TTGATGAGGCGAAATAAGAGGCGAACGGAACTCCAAAAAAGAGCGATCTTTTATCA CGTCCCTCCATAACGCTTTATAAGTCATTAGTCGGCATCGTTACAAATTAATGATA GACCAGAAAGTACACAGACGTGTCTTTTATCCTGTAACGACCCTAATTCGGCACCG TCTACTAAATGCTTTGCCGTACGCTCTGATGATTCTATCCAGCGATTACGTATATG TTCCGGGGTAACTACCTAAATCTAATGCGGCCATAGGCCCATACTGATCCGCCGAT TTCGCGCACTGCTTTACTTATATACATCAGTACTACTCGGGCAACCGGTAAATAAT TTACAATAGAAGTTTAAGTGCAGTTACATGCTTAAGATATCGAGAGAACTTGTGAA ATACGTACACTAGGATTTTCTCAAATTCGTGACATTACAAGGTCTGGTTTCGCGAT TCTCTTGGACTGATATAATATGATTGAAAAATGTAGTAGATATGATCCTGGATAAC ATTTTTAAACAAGTCTTGGGTGAGCTCGGTACCTTAAATCCGATCATAGAATACAA CATGGCACCTACATTCATATTAAATAGTCTATTACATGATAAGACTCCTTCATGTC TGAAACATTGGTTAGACAATTCGCGGTTTCAGTGGGTAGCGTGTTCTATTGACTTC GAAATGAGAAAGTGTTTCGGCGCGTACGGTATATCTTCCCCCATGATTATACATAA CATCCTTCTAAAAATCGCGCCACTGCAGGGTCCTCTTTTCTTATATATTATTGAGG ATTTGGACCGATCAAACTTAATATTTAAATATGATTCTACATACAAAGGTAATGATG GCAATCTACTTGCGGGCTCGACTCGTAGTCGTTCAATGAAAAATACATTTCTCAA GAAATAATCTTCGAGCTATTTCACTCTGTAGTTAAAGTTTCAATCTTGTTACATAC TGCTTATACAAATTTAATTTAAAAGCATGTGTCAATTTAAGGCTAAATGCTCAGTG TAAATTGTATTGGTAAACTCCCTAAGACTAATGAATAACTTGATAATGTGGATAGA TTAAATCCGTGCAAGCCTATCCTAAAATCAATTTGAAGTG |

TABLE 2-continued

Exemplary 2.0 Kilobase Stuffer Sequences Having 40 ± 5% GC Content

| SEQ ID NO. | GC Content | Stuffer Sequence |
|---|---|---|
| 79 | 41.00% | TACAAATTGTCCACGGGCGTGAAAACAAGCCCATTCTTCTTCAATTGCAAGATTTG CGATACTTAAACCTTACTGATTTAATAATCGATTCAAAACGCAAGAGTCATGAACA GAACGAGACCCCGCCATATTTAAATGCACATTCGTGCAGCGATGGGTATATTGAGG CTGTGAGAGGCTCAATTAAACATTTTACCAGGAGATGGGCAAAATAATGCGTGGGG ATCGCGGGACTATAATCTAATCAGTCATACTCTAAAGTGAGCTTCGTGATATCTTG AGGATAAAAAAGGGCCTAAGCGCACAGGGTTATTGAGTTCCAGCTAATGATGCTCG ATAATAATCGGCCGTAACTTCAATGCGAAGAGAATATACGATTCTGAACAGTTACA GATAAGGCCTATTAGGCGCGAAAATAGTCGTCTAAAAGAGGAGAACTGCTGGTCGA GAATGAGTGGGGGTTATTCTAACAAAGGTAGCTAGGTGTGGTTATAAACGAGAAGG ACTACACCCAATTGATCTCGATAATAGGGCGGGATTGTTTATTGACAGTAGTGAGG TGTTCTAATAACAGAAATTTAGTTAAGGTGCGTATTCTTGGAGTAGAGCACAAAAC CCGCTAATGAGCATTGTATGAATCCGCGACAAAAGAGCAAAGATCACAGCAACGAA AGTCTAATTGAAATAGTCCTCGATTATGCCGGTGAGTTGAAAAAAGTTGTACGTTC GTTTATGCCGTTCTAGATAATTTACACATCACATTCCTCACGTAACTACATGATTT ACCTACTATCACTTCCAATCACCAACTCGGATTTAGGAATACTGTAACTTATTTCC GATTATCCGATTGAGACCTAAGCAGAAAAACATAAGATGCCCATCCGAATTGTGAT GTGGATACCAGTTGTGATAATTCGTCGGATTGAACTCAGCCTGCTTACCGCTTTTG ATCGCAGTCGCCGCGGGTAGATGTAGTTAGCCTCACCGGCTGGATACATATCTCCA GGAAATCGCGGAGTATCAATCTCTAGAGTAAATCCCCTGCCTTCCGTTGATCGTCT TGCTCACCTAAATGTCTGAACTAGGCTGAGAACACAACCATACTCCGGCCACGTAG ACGATGCTGAATATTACGCAGCTATACTCAAAGTTAAACTCTTCTCAGTGATTTAT GATGTAGCTTAGTGATCTTTACAGATTTGGTATCGATTGGGAATCCAGTTTAAAAC TGAAACGACATATAGAAATATGTACCAATCTACCAGCGCAAACCGAGTCGAAGTCA TATTATACGGTAAATCACCATCGTGTGATATATTGCAATTTGAACTGATTTTTAAT CCCTAGCTTAAATACTTCATTGATTTCTCGCCTTTAATTCTCTGAACGTTACAATT TTTCTGCCCAACGGTCCTCCTCTAGAATACCTCGAGAGCCGACACAAATACAGTTA GAGAATTTTTGGTGATTTGTGCGACTTATTAGAACCACGGGGTCATGACCTTAGCC CGAATAGGTAGTATCCGGATATCTGAAACTCCAGGCAGTAATAATACATTGCCGGA ACGACAATCGGATCTAGTGAATGCGACATAGACGGTAATATGTTAAGCACCTCATA GATGATTACTATCAGGAAATATCAATTTAAAGCTGCGATGAAAGGGTCAGGACCCA GCCCTTTCAAGTCTACGTAACTCCACTAGCCACATTGTCTAAGGGTGCCAATCATA GATCATGCATCAACACCGGCGATACGCTTGTTCAGGCATTCATATCTTATAGTTAT AAAAATTTGTTTATCGTGTGCAGGGGTCGATTTTTCTCACTTTCGGCAACCAGGAAA AGTAGTAATTACTATATAAAATGAAGGCGAATTTCGGATTACTCTGCAAAAAATCA TTAGAATACACATCTAGGATCCGGAGGTATCTGCCTCCATGAAGTTAACTCCATTG TGGATATGATGCGAGTAACATATTTAGGTCCGAAGAAAGG |
| 80 | 39.30% | ATCATCTACCTAAGACAGAGCTGACCGTATCCATTGTCAATAGAACAGCAACGATT TTTTCCATCGCTGGAAGAGTGATGCGCACTAGTTCATTTCGGACAAGTAACTTGGA CGCGATACAAGATACAATCGATGTCACAGCCTCTTTAGTACATACCATGGAATTAT GAATCGACTAAAAACGCAGACGTATAATTCAGCTGATCGAATGATTTCGATTATAT ACCGAAGTCAGTGACGAGAACCTTCACTTTGCGGGATACCGAACTCTGTCACAAGA AATAAGTATAGGTTAGAATCCAGAGAAAACATTGAATATTATGTTTTTTCGCACCA AAATAATCCAACGATGTTACGCTTAGTTAGTGGATATCATGACTTCACTAAACACT TGGATTGTTATCTAAAGTTTTTATCTTCCTGGCTGCGACATTGTTTATTTAAGACG TAGTTAAAAAAGTCGACCACGGAGGAGGAATTACATCGTCGCTGATGAGCCCATTT TCGCTAAATGCAGTCGACTACGAAGAGTTTTTCGCGTATCGTCAACATAAGTTGAT CTTTTTAGATAACAAACAAAACTCTTCGCATCGACGTAAAACATTTTTCATAGGCG CTTTTTACACCGAAGAATCTCAGCTTCAGAATTGTACGATGTCTTGTCACAGATAT CCTTTAAACAAATAACTAATAGCGTTGATTGTTTGACATCTACTCCTTATTGTTAT GAATGTATACCATATTGTTATATGCTATTAAATCCCACATATTGCGGTTCGCACTA AAATGAACATCTATATAACTTGACTGTTACTTGAATTAGTTATGGTCCAGCTAATT TTTCATTCTAGGCATTTAATCCTTTATGTTCCATAGTTTCCTTCGACGCCTTGAAC GATGGGTGCGAGTCCGACGGACTAACATTTATAAACACATTTGTGGGTTTGGGTTT GCTACAGATATCTGGACGCAGGATGTTTAGAGTAACATCTGTTGTCATTTGGCTAG CAAAATTTGAGTTACCTGATAGACCTTCCTCATTCCCTTAATATTAAACTGTCTTT CTCGAATACCGTTCGCACAGGGTCCAGGAAATGTGATGTTATGACGGCGTGCAATG GTTAGTCCTTATGCAGGAGTTTCTCCGCACCCATCAATGCCATTATTTTACAGTCA AAAAAACATAAACTTGTATGACGAATGCAGACCTTTGAACTTTTGTTAACCTACTT TTGTAAAACCAGCGAACCCTAACAGTTATGTAACGAGATCCGTTAACCAAAAGCGG TTATCCGAGGATAAGCTTCCTACGACGTCACATTTGTCATCTTCCTTACCGGTATG AATTGTATGCAGGTCCCTATTCGAAATGTGGTTATAACTGATGGGTATCAGCAGGT TATTTATAACGCGTACTTTATCCTTGTAGGTTAGTTGCTCAGTACGCCCAAATCAA AGAGGAGGCCGAGGTGCAGGAAGGACCTGACTGACAATCGTAACTAAATTATCCAA CAGGATTGTTAATTGACAATGTTTACACTGACTATGGCAAAAATTGTCTCCCAAAC GGCTGCGGACAGCGTTCTTTTTATCGATCTGAGGTAGCACTTGCATATGGATATAG CAATAAGAAATAGGGAGATACCAGCGAAGAACGGAGTAGATGCCTGTGACGTGTGC CGACCTGACATTGATTATCGAGCATGCGGATTAAAATTCAACAACTATTCCCGTGA AGAGTGCCAGCCTGTAGTCAATTATTGTGGATATTATCTAAGTTCAGATCATACCT CTCGTCGGTGAAAACAGATAGAGGCCAAAGGGCAAATCTATTGAATGATTGACAAT TTGATCATATACGTGTCTAAGAATTAATTGTAACGGATGCGAATTCGTTAATCTTC CTGGGGTACTCTTCTCCACGTCACGAGAGATAACAACAACATCAGGCTTCTGATAA ATAGCGTAACAACGTATTATCAAATGCATCCTGTCTGTAT |

TABLE 2-continued

Exemplary 2.0 Kilobase Stuffer Sequences Having 40 ± 5% GC Content

| SEQ ID NO. | GC Content | Stuffer Sequence |
|---|---|---|
| 81 | 38.10% | TTAATGACCCCTGCCTTACTGCATAAATCTCCTAATTGTGTAATCACTCCTCACTC<br>AGATAACGCTTTACGTATGGATTACCAAGTAAGTGAAATCACTATACAAGAGATTG<br>CCTAATTTTGCTAAGTTAGCGTTGTTCGTGTTTTATAATTTTATTGTGAGTCTTTC<br>ACCGAAGTAGAAGGAAGTAAACTCGCAGTTTCTTATAACCACTTCTAGGCGATGTA<br>GACGACATAGAAAATGGGGTAAGGAACTCATAATTTTTAAGTCAATGATACAGCCT<br>TAAAAGATAAAAATTAGATTACCGTTTAATGAGGGTACGTGACCATTAACAGTAAG<br>AAAGCCTGCAAGCATGGGACAGGTGCTATTGCAGAGCTCATAAACGAAATGTCGCT<br>TGGGCGTCCTGCACCAGATACTTAGTGGCGGATGTCAATAGCGAGGACGAATCATT<br>GGATGAATATTAGCTAGTGGATACGGAAAAACGTGACTACGATTGCGGCATCGAGT<br>TCTTAACCCTCTCATGGAGGCATCTCTCGACCTTACACAGTGAGAGTGCATTTTGT<br>TCGCCAGTCTACTATGACACATTAAGGCTCAAACACGCTCTGCTTATTCATTTGGC<br>CTTGGGGTTCTAGATCACACTACAATTGCCCTTTGCAAGAAAAACAAATGTCATTG<br>AAAAATTAACTGCTGTCTTATAAACCTAAACTACCAGATACTGTAATTGGTTTTAG<br>GTTTGAGCATCCACCAACACCAATAGCCAAGATTGTTAAACTCTAATAACTGTCTA<br>ATACACGTGCATATTCATAGTGAATCAGTGCGGTTCATTTTCTGAAGAGCTCCAAT<br>CTGAACGATACAAGGCGTCCTGCGCGTGGATTAAAAACAACTTAAGCGTTACGCAG<br>AGCAGTATTCCATTTTATAATATACCGTTTGCCGCAGGAGGTTATATTGTAGAAGA<br>TTAGTTCATTTTGTGGGGATTTACAGGCCAATATTTACCAAATTTTACGAGGTAG<br>TTGAACCTAGTGTTACTTCGTGAGGCTCGAACGGTCTTCCCGCTCCAACTGTACCT<br>TTAGATGGGGGCTTCTTTGGATGTAACGAAGTACCGGCTTAATATGAGACGTTTGT<br>ACGCGAGGCATTCTTATTTAACCCATACTTAATCAATTCAAAATTTATCTTGGTGA<br>GTAGCACTGGAGAATTTGGTATCCATAGCGGACCGATAGAAAGATTGTTATACCAA<br>AATTCATGAATGACGCTTAGTATTTTCTAGTTTGATAACATGGTTAAGACTACATT<br>CTATCCGAATTCTTATTAAAATTGAAATGACGCATTGCATGCTGTGATTCCAAAAC<br>CATGCCGACAGGAGGTCTTCTTAAAAATTCAGCGTGAGGTTACTACACCTTCAAAA<br>GTGCATAATTGGTGGACAACTAAAGGATAATTGGGTAAGATCTTTCTACATTCCAT<br>TAAAAAATTCTAACAAACCCTATCTCATGTTAAGTACTTATGTTGCCTCTTACTAC<br>ATTGACCCTACACTCAGATATGATAAATTGATGTTTAACCTAACTATTTAAAAGCT<br>CAATACCTTCCTTTTTACGCGCAATAAAAGGTTAGGCACTTTTAATGTGAAATTTC<br>AGCGAAATATTCGATCTTGATATAACTAAGTTTACAGTTCCTATTACTACTCATTA<br>TAATAGAATGTATGGGCTATGAATAATAAATGGACCCTTAGAAGGATAAATGCATT<br>GATTCGATGCTAGAGTAAACTGATGGCTCAGACAGAATCATGCCCATGGGGAAACA<br>TAACACCTAATCAGCATCAACTAAAAGTCACATGTACGAGAGCAGAATCAAATACA<br>AATCAATTATATAACGTGAACGTAGAATCCGGACCAGGGACGTTTCTACTCTGACT<br>ATATTACCGCCAGCTGCTATAGTAATCGCGTATGGAGCATGTATTTGCTGACTAAT<br>GCTAAAGTACAACATTACTGTGTAATTTAAAATGCTACCT |
| 82 | 40.40% | TGTACTTGTCTTCTTGTTTGTCACATACGGACCCTAAATGACCTTGTCTAGTTATC<br>CGATACACCTTGCTTAAGTAGCCTCCCCTAGGGGGAACTTATTACGGAATAACAGT<br>TTTACAGTATTAATCAAACTCTTATCCACGTTTTCCTGTGATCACAACGTATTGTT<br>TCCCTTGATTTGTTGAGAATCTCTATTGAGCCTTTTATCTATTAGAGTCTCCGTCG<br>CACATAATCCCGGTGCGTTGAACAGATACTGGCTAGACTCCTTACTTTTCTATCAG<br>TTGAACGGAGGATACGAGCTTCAAAATAATGATTTGTTTGTAGATGTCAGAGCATC<br>GTCGTGAGAGGAACCCGGATAGGGGGAATAACAGGTAGCGTTGCGGTTGCCTGACT<br>AAAACCCAGGACTCAAGTTTCATTATTAACATTATTTGCATGAATGACAGTGTCGC<br>AGATCTGGTATAATGACCAACGATCGTTTAGTAGATAAATTCCAATCTAACAAACA<br>CTAACCAGTATCTCAGCCCACATTGCATCTTGTTTTAGCAATCCTGCAGATATCAG<br>AACCCTCCTGCAGTGAATTGACTAGTGCACGACGGTAACATATCTCTTTAATAGCG<br>CACCGTCCTCAACGTAGATGTTACGTCTGGGGTTATATTGGGCCGGAATGTCCTGG<br>GCTTGGACTAATGAAGGCAAAGGCTATAAATGTGCTTATTATTTACTTCTGCGTAC<br>TTATTTGGAGAATGTCATATTAAAGATGTCGCGGTGGTCGGATTAATTGAATAATG<br>TGCGACTTGGATGCACCTCAATCTTCATTGTTTTGAAAAGTCTGGAGACGTGCAAT<br>TACACTCTATATGTCTTTGTATTAATCGTTATAAGCTCTAAAGGAGATAGCAAGCT<br>CGGGCAAATGGTAGATTAATGCTTCAAGAAAATACAAGCCTGGGGATTCACATTCC<br>GAATATACAACTAATGACGCTCTCATTCTCTTGCAAGTATAGTAATCGGCCCGCTA<br>CTCTATGGGGAGTATGGCATCAGGAGAGAGTATCATTGACATTCGAAGTTTGCATA<br>CTGAGCAATAAGCGGGTAATGCTTCAAAACAAAGTGCACTCACTTAATGTCGGACA<br>TTGTTTATAAGTGTTAGCGCTCAATTTTCCGCAATCACGCTCGAGCACTAATAGTT<br>GGAGTTCGCTTTAGTTTGATAATAACAAATATGACTTTGTCGCGAGATTGCCTATT<br>TGCATCCAGGACTATCGAACGCAACAAACTCGTGAAGAGGCCGCATTTTAACTGCA<br>GGATAGTAAGATCTAATTATGAAATACATAGTCCAGAAAATCATTCGAGACTACTT<br>AACAAATAGTTTCAGAGGTTCTAGACTTTCTCAAATGTATGTAGTTCGTGAATATG<br>TAGTTATACTCAATTACGACTTTGATTTTTATTTACCGCCTAAGAAACTTGATTGA<br>AATAATCTAGAAGCCTCAATCCTGCTCCATCACAAACATAATATACTGAAAGCTAG<br>AGGGCGTTACCACAGTGGTACGTCTAGATTCCAAAGCGTGCTAGGAGATTAGTGGT<br>CGAAACGCAGGTTCCGCGAGCAGTATCACCCTACAAAGTAGCTGGTTACAGTCAAC<br>ACCTAGCAGCAATTCTTCACTTTTGTTACGATACGTCCGTGGCATGATCGTCGTT<br>GCCTAATTCTACGACTTAAAGATACCGAAAAAGCAAAATCTAGAACCATGATAGA<br>GCTACAAAATCCCTCTACCCGTTCGTACGTGCTTCCTAATCAGATCAACTATGTGA<br>GCGACATAGTTTTAGCTAGTACTTGAGCGGGAGTTTTGTTCTCGTCTCTGAATATA<br>TAAAGTGTTTAATGAAGTGCTATGAGGGCCACTCATCTTTAGCATACTAAATCATC<br>AGACATAAAGGTCACCCGAAATAATCAAGCAGAAGACTAACAGAACATGCTAAGAG<br>AGGTCTTTCAACTACGCACTTGATAGATAACCGTTAGCTC |

TABLE 2-continued

Exemplary 2.0 Kilobase Stuffer Sequences Having 40 ± 5% GC Content

| SEQ ID NO. | GC Content | Stuffer Sequence |
|---|---|---|
| 83 | 40.40% | TCACGACGAGTGAGGTCTGAGACCGTCATCAAAGATCGTAACACTTTTTACCGGGC<br>TGCCATAACGTAAGATGCATGACTGCAAGAAAGTTCACGGTGGTAATTTCAATGAG<br>TCATTGTCATTCCCTGAAGGACGTATAATACTATGTTACGTAGATTATTAGGGATC<br>CTTATGCGTTGAGGAGATATCTTGCCTTGAGTGAAAGAAACTCATCTGTTTAGAAA<br>CATACCAAATATGTCAGACACGGTCGGCTTTGATAAGAGTCCCTAACTAATTGGCT<br>GCACATTACGATTCGCCGAAAATATATGTTGGGAGTAGTGTACACGATTTTAGACA<br>AATTCCCGAGATGATGACCGTGACATGTACAATCGCACTAAAAATCCCCGGTATTA<br>GACTTTGAAGTGGTTTTGGTATGTGATCTTAAGCATATTCACTATACTAGCATAAC<br>AATGGTGGTTGCTTTTGGACGCAAGTTCTGAGTATATGACTATGAAGCGGAATCGA<br>TTAATTATGTCTTCCAATAAAGCTTAGAAGTATGGTTCGTGAACAGCTTCCAGTAT<br>AATTTAGAGAGGCCGACAATATATAGGGTTTTATTTACTATTGGCCAAGAACAT<br>CCTCAGTCGATCTAAACTTCTTCCAAAGCACTAATTCTATCGCAAAATGGTATTAT<br>AACAACACTAATCTTGGAGTCAACTCATATACGCGCGTGTAGAGTCATGTAATACT<br>CAGCGGCTAACTACATGTATTATGTCAAGTCTTCCTTGCTATGAATACTGGTATTC<br>CTTTGTGGATTAAAACGTACCGTCATGTAATTTTGAGATAAAGATCTAGGACGGG<br>GAAGAAAATAGTAATACGGTATGTATGCGTTGAGTTGGGTCTGGATATTCAGTCAA<br>CTATGGGTAACTGAGGACTTTGACGCTGCATCCCTGCTGGTGCGTAGTCCTAAAA<br>AAAATTCTCTGGGACAATATGTCTTCACAAGATCCTTGTGAGAATCCCGCTTCCGG<br>TCCGGCTGGGCCATATAGACTCCTATTACTTTCAAACTTCGCACAGAATCTTAAAT<br>ATGAGATTGTAAGGAAACTATCAGATCTGCTCTAGACACCGACGGAGGAGCTCCCG<br>GAACGTTCCAAAGCTTTTTTTTCTAAGTGTTGCACTTGGCCGGTCGTACACGCAGA<br>GCGGTAGATAACCCAAATACAGTTCTTCTCTATGTCTACGCCCATTATGGGACGCG<br>TGGAGTCTCTGTGACGTTGACGGTTTATAGGTTAAGTATGCTTACGGATGAATATT<br>AATGAATCGTCGTAGTTATTGAAGACGGCCGATGTAGTATGCACCGTCAGCCGATT<br>CCAAACTAGTATCTTGCTCCTGAGTTACTCTGTTAGATTCCTGTCAGTTTATCCAT<br>TTTAGTGTAGAAATATCCTTGAATGGTTGTACCATGGCTCCTAGAACTAGACAAGA<br>TAAAATGTTATACCGTCTGGTGAACATTTAACCTCGTACTTATCCGGACTAATGGT<br>AATTGTCGACCGCCTCCTGAAAACTCGCATTGGTGTCGAAAAAAGCAATGAGCGCG<br>TATTTTTATGGAGATAGGTGCATGTATTAGTCTGTATTCTTAGATGCTCTGTCGAT<br>AACATGATGTAATGCGAATTGATTAGAACAATCTGAGAGGCTGAAATTGATTGCCT<br>GCCCAAACACGATACGGTTCGATAGCTAGCTGCCGATGCGCTTCGATATTAAACGT<br>AGGCAAAGACTTCCATTCTGTTGGTGGTAATCCTATCGATTCCTTAATGAACCCAC<br>GACATTGGATATTGATATCGTGCTTAGATATTTGCCACCATATGATGTATATAATT<br>AAAATACATATGCTTAAGGCGATAGTATTTACTCCCTGTACGCGCAGTTACCGTTG<br>GCATGTAACAATTTAATGGCCCAATGAAGCGACTACGAACCATATAATTTGCTACA<br>ATAGTACTATTAACATGCTATGAATTTATGCAAAAAAAAA |
| 84 | 38.80% | GAGTTGATTTTCCGCATTTCATGGAAATATAATAGGGTAACGTTTAGTTACGGAAC<br>GTATTCTTTTGAAAACTCTACTTAGTGTCGCAACTAAACTTCTCTGTTTTAGTACA<br>GTCAGGATTAGAGACTACTAAGAAATTCCTGATCTGCTCGCTACTGCCACACTTTA<br>CGCAGGAGGCTTGTTTTCGCAGTAACCGGTGAGTTAAGGTCCAACAGGGTCAGATG<br>TCCCTTTTGTCACCACGAATCACTGGCTCATTAGAAATTGATAGATTTGTTAAAAC<br>GAACCTCTATGTCAACAAATGCTTGGAACGTCATTATGACAGTGTTTTGATGTCAG<br>TTTATCCAGAAGGGCGAGAGGGTCATGGCGCGGTCAATTAGAGGTTCGCATATTAG<br>TACTTAGGTATTGTCAGATCACCGGAGTTTGGAAACCCTGCTTGTGTGATACCTAC<br>AACTTAACTTGGCCCAACATGAGAACGTTCCATGCTTCTGGTATCCGTGTTTAAGC<br>TCTCAGTGGAGAAATTCTTAAAATGATATTCGTAACTAAAGGCATGAAACAAAATG<br>TGAGGATCGGTTATAATGGACACAGTCCTGACCCCTTCGATTGACCTAAAATATTG<br>AAACTACATTCAAGTAGCGAGAATTTTTTAATTGTTCCTAAAGTTTTATTATTAGA<br>TAAGTGGTCGATGTGTAGGAAATAAGAGATGATAAGAAAACCAGACGTTATTTAAA<br>GGGAAATGTCCACCAGTGCCCAGCGTTATAACATGATAGCCAAGAATTTGGTTAT<br>ACGCAAAGTTCGATTGCGTGCTCGGTTACTGGAGATCAAATTAATGGAGCTTCAAT<br>AATAGTACTAAATCATGTTTTCAATTTCTTAGCACATCCCCACTAATAGTTTGTCT<br>CAGATATTATATGATATAGTTGATCGACCCTGTTATACGCCTAAAACCAATTCTCT<br>TTCGCTACCCGAGAGTGAAAACATATTCAAAGTTGTCAGCCTCGACGTTTAATCTT<br>CGTAATAATTTGTCGGTAACAGATTAAATACGGAAGACAAATATTATTATCTTCAA<br>CTGTCCAAATTCTCCGTCTCCATTTGAGACTTACTCATACTTCAGTGACCTTGGCA<br>CTATAGCTGATGTTTGGAGAGAATTAAACCGAGATACTTATAATAATGAGAGCTAA<br>TGAAATGGTAGTTCGTATATGCGGTTATAGACTGTAAGAACTATCCAACAGACTCT<br>GCCGCACTCTCAGATTTCATCTTAGGCTAGGTTATAATGTATGGGACGGCTCGGAT<br>ATTCTATTGAATTTAACAATTTCGTCCAACAACCCTTGGTAACTGAGTTTCCCGAT<br>TACATGACGATCCAGCTTACCGTAACCATAGAACTTGGCAATCCTCTCCTTAAGGC<br>GCATGACTAGATCATCAATCGCACTTCTTCAATCAAGTTCTCTATCTGGCGCGGAC<br>ATACTGTTTACGTCTCGTTTCATTGTAAAAACCCTTCTGTGTAATAAGAACACGC<br>GACTTTGATGGTTGCGATCCCTACGTAACGTGCACTTAACTACATATACTTGGTGA<br>GATTGTGCTCCATATTGAAAGTCGATGTTAATCAAGACGGAGTTGTGATTAATAAA<br>ATGGCATAATACACCTGTGTTTTTCCTATATAATCCAGAGAGGAAAATAACTGTTT<br>TCCGACCAAGTTTGTACTAGATTTATGATTTTCCGAATATGCATCTGCGTGAGTGT<br>GTACGTCTGTGTGCATACGTCATTCAGAAAGATCTTCCGTATGTGAGACCTTTTGG<br>ATCAGTTGTTCATTTTTGTACCTGCCTACTTTAGACCAGGTTCTAAAAGGCTCATT<br>TAACACATGATTATTATAGATCATATAACCATTACTCCTAATCAAATTTGTGCCAT<br>CGTTGCAACCGAAATCGTCTAGCAAGATGATCATCGAGCAATACCGACCCTTTATA<br>TAGGCTCAACCCTATATTCAGAGGAAAATCACGGTTTGTC |

TABLE 2-continued

Exemplary 2.0 Kilobase Stuffer Sequences Having 40 ± 5% GC Content

| SEQ ID NO. | GC Content | Stuffer Sequence |
|---|---|---|
| 85 | 38.90% | GTCCATCATTGACTCTGTTTTCTCGAGGAACTCTGCAAACCAGATAAGAGATTATT AGCATATATGTACCTAGAAGGACATATTATCGTGGACATCCCGGGTGTTTGCTATT TGAGATTTATTGATTGTTTTTTGGTAAAAGATCTGATTTACATGGCATTATAGCCG AGGCTCATGTTTACATTAGCATAGTAGGCTGGACTAGTTGCGAGAGATTTTGTTAC CCGGGATCAATTGCCATTACATCAAATCACGTGAAACGCTTTTCCAATACATGCAT ATCCCAGCCGATACTTAGTACGAGATGATAGTTGTACGACGGATATATAATTACGT CTATACGTTATAAATTGTCACCTGTCACCACTTTCTGAATTAAAAGCTGAGGGACG AGCCGTATTAATACTAAGAGCGTAAGAGCCTCCTAGGGTTATATAACTTCCGCACT CAGCTATTATTATTGAACCTGCGTACAAGTATCTACTTATTCAAGTTACTACGTAT GAATTAGTAAGCATCTTGTTTTACTTATGACCGCAATTTCATACGTTGCATGATAA GACAAGTTCAAGCACAATAACTACGGCAGTAGGAATTGTGGCTCGACAAGAGAGAG CTGTTTTCGCCGTTCTGGGGATGAGCATATTTAAAGTTGTTTAACACATCCTTTAA CGATAACAAAAGACATACACAGGATGAGGTATTTCTGTCAAGAGAATTGGTAGTTT GTGTTAAGAAGATCCCTGACCGTCCTTAGATGGAAGAATTAACGTCCATAGCTGGA GGTGTTGTCTTTATTCACGGAAGCATAAGAGACTCGTAGTACAGAATAAGACGGTC TCAGGGTATCCACCAGGATCAACGCCAGAAAGTGGGCAACAGATCGGAAGTGGAAT TCGGAACAAACTTCATATGTGAAAGAAAAGCTTTGATCGACTTCCATGCCTTGGT GATAGGTCAAATTTAGCTATTAGAAACTGCAATGGGAGATGTTCGTGCATGGGAAG TAAATGTATCGACCATAATCGCTCTGCGGGCTAGAGCTTGCGGACAGTTAGCGGTT CTTTAGACGGGCTGAACCCTATCGAGAACCGATACAGCAATGTAGTCCATTACGAC ATATGTGCTTCCTCGACTTTACTGGAGAACCTTAAGACGCGATGGATTATTTAACT AAATTTCCAGTTATCTGAACTGGCATAATTTACAACAAACCTAAACATTTTCCATA GAAACTCGTTATGAGCATTTCATGCAGTGCGTCCACTGTGATATCTGTAATGGTAA TCGGTCCTCATGCGATACGGCTCGGTAGTTTGTCTTGCGACTTAAGGCAATGATGT GTGGCATGCTGTCCAGAAGCAGATAGATCAGGGTCAAGTATTGCCCGCCCATTTAA TTACTAAAGAGAATAATGCACATAATAATCTCTATTGTTAATGATATAATTATTCT AGTGATTTATATCTTTATAAGGTAAGCGATTTCAACAAATTAAATTAAACGCCATA AATTTCTAGCAATTTAGATACTGTATGGGACTATTAGGGACTCCATAATTAACGTA TGACATACTACACTAATAACTAAACTCTATTTGACAGTTGCATTGCTTAAACACCC TTGTGTGTTAAACCATACAACCTTATGTCTGGCTATATTTGTACTTCAGGACCGGG ATTCATGATAAGTGCTTAGGAACCTAGACGATGAATCAAGATCAACGTCTTATTTA TAAAACGTTGACACAATATTAATCCTACAAGATCTAACTTTACCATTAAACAGAAC TTGCTAATCCCTAATGACCAACAGACTTCTGGCAACGAGAAAAAAATAATCATAAT TTGTGCGGTACACTTTAGCATTAATTTCTAGGATTCAGCTAGCTGGGCCTAGGGAA CACGAGCTTTACGTGGCGTCGTCCGAATCGTTAGAGAAACATTGTGAGATACTCGA TATTTTTATCGGTAGAATCCTCCCTCATTCTTACAATGTA |
| 86 | 38.70% | CTCAACAGCATTCTATAGCCACTAATCTTATCTCACAGGCGCATTGCTGCCATACC GTTAGAGGGTTTATGAGTGTGGTGCCAAATTTAATTTCCAGCTATTGCTGAGAAGT CATATAAGTTTAAGTGCCTCTATTCATGAATCTACGAAGACTACGCCGTCTGCGCA CTGGCTTTGCCGTCCCACTTAATTTAACGTTAATATGCAGGTCCGGGTTAATTCAT GAAATTTATACGAGGGGGTAGATTGTCGCATTATACGCTCACCTACAAATCTGCCT ATCAGCACAGCCATTATGACTAGATTTACCGGGGAATTTTCATATACACAAACCAC ACTCATTTTCCCACTTATAGGATTGAGTCTCAGATCACACTTGTGCTGCTTGCTGC AAATCCTTTTATCATTGTTCATGGTTACTTGTTTAACTAATATCATTCATTTAAGA TAGGGTATCTTTATACCTTGAGGCCAAGTTTTTTCACAGAATACTGAACATCGAAA CCTTTACTTCAAATAGATCAGGTAAGATTGTTTTTCATTTAAAGCGATTCGCTCAT ACAGCTTTCTGTTAATAGTGATATGGATTGGAAACTAAATTACCGAGATATATCGT CATCGTCGGCAAGCAGCTGCTTTATACTAGGATACAGAAGACGGCCGTTTCCAGTA AAAAAACCGCCGATTCGATCTTCGATTATTACCTTTTTACTTGCGGCACCAAATGT AGCTGAATTATGTTATGAGCTATGCGTAGTATACCCCCTTTGTCCTAGTGCTAGGC TCTATCATTTTATGAAATTTAACTCTTGCTCCAGGATACGTCGGATGTACTTTTAA CAAAATCTACTGAGAGGACAGGATTGACCACGTAATAGTAGAACTGATAGGCGGGA TGATAGGATCATGGGCAGTATTGCTGATTTTAGACCTTGGAGATAGCTGCTTAATG AGCTCCTCGACCTCACACTTACTGCAAGGTCAAGATAAGAAAATCTCCTAAAGATC AAACCATTCCAAATTCGTGTTTACATAAATTTTACTATTATACATCGTAATGTTAA GTGATTTAGCTACTGTGTGTCTAGGATCCAGGATAGTCGTCTAAGAAGCCGACCAA CGTGCTAAATAGGATTTGAACAGCGTTATAGTTTAGTTTATAAGGTTGTCTATTTT ATCAGTTACTGCACGACACATATACTCTCAGAGAATAGGGTATCACGGTATACATC GCTATCATATTGACTAACGATTGTTCACGGCTTATATTTTCACGAGCATTCCAATG TGGTAACCATTCGCAATCATCTGGGCTCTCAGTTGTTAATGTAGAATTTAACCAGG TTCCGTATTAGTCGAAATCGATGCTCTATGACCTCAACCTTCCTCTTGTCATGATA GGGTGACTAAAGAAGTTTCCGATACGCGACGTGAAGTCCGATTATTATCCAGATGG TAAAGTGAAGCTTAAAACATAAGAGATCATTCTCTCTGATGAGACATAATGATATC ATTTCAAAGTTCTGTTAATAATACAACTGCTAGTCAACGGAATCCTTTCCATCTAA AGGCGAACACTAACTAATTTGAATGAGAAAGATAACACTAAAACCGCCAACCTAGT AGTTACTTGAGCTAACACATATATTACTTAAGTAGCTTTATCTCTGGTCTAAGTCG GAGGTCACAATGACTTGGACTTCTTTTAGTTTTTCGAGTACAACTAGACAATGACC TCCCGACGTAGCATATAGAAAGTTAGAACATAGGATTACCGAGTGGTAATAGCCCA ATCAAATTATGGTGCGAAAAGATAGTACTGTACTCATTACTTCCGGTATGGGACAA AGCCGATCTATTTGTCGGAGCACGTTAATTTTATGACCGGCTACCCTACGTTTACT GAGTCTAAAAATTTGTAAATACAAAAATTTTTCCCGCGCTAAGTTAACCATAACTC TCAAGTTATACGGGGTAATGGATCTTAAGTTCCCGGAAAA |

TABLE 2-continued

Exemplary 2.0 Kilobase Stuffer Sequences Having 40 ± 5% GC Content

| SEQ ID NO. | GC Content | Stuffer Sequence |
|---|---|---|
| 87 | 39.70% | GTAAGACTGATTAAGAAATTACATAGGGACCTGGAACCGGTATCAGATTTCAAATT TTGGATAATAAACCGCCAGGTGTTAACCCATCAACATCTAGTATTGGCGTAGTGAG ATCTCTTGCATTTCAGACATCCTGGGACGGCAGGAGTTTCTATCCATTTTCCGCAA GTGTTATGCTCCAATTGACAGATATGTCGCCGAGGAACACCAATCTGGAGAATATT TAGTCGAGAGGCACAACTGGTGTTATAATCTTAGTGTTATCAAGATGACCTTTTGG AGTCCTTTGGATACATGAACCCATACAAATTATCAGCGCTCTACTCTTCTGTAACA CCTCGGAAATACACTGAAACAGATGTCAGAGATAACCATGAGTGGTGATTGCAATC GGTGACCATGTTCGTAGATCAGTCCTACGAGCGTCCATATGGCGACGAGGGAACTC CACCTTTCGAGCAATCATATTGGATTGAGCAAATGGTCATTCAAAAATATACTGTT CACTCTGCCAATATAAAAATAGCACTCGTTTTTTCTATTAGGACGATACTAAGTGG GCACTTTATCCCTAAATAACTTTCACAAACCCGATTATAGATCCCCCGTATCCAAC TGGTAGAAGGCGGCTCGGATCTATCAAGCATTTGCCGAATTTTGCGTGAAATTTTT CCACTGACTGCTAAGCATAAACCGATGAAGCCAATCTTGAATGGGTTATCTTGAAA ATATTTTGCTAGATTTCATAGAAACTTTGATTAACTATATACGATATACTTATGAA TAACGCGAATTACATATATAGACATGTTCTACGTTCCCTGACCTTGCGTCAACAAA AATCGGTTATGTCTTAATCAGAATTGTATTATAATACATACGTAGCCGTTTTTTAA CTACTGCTTATAAGAGAATATTTCTATACTTACTACACAGATGTTTGGACTATAAA TAGAATGACATGGGGGCAGGGGAATATGTATAAATGCCTGTGTGATCTCCAACTGC GCATTTTGCCGATGATATGTAGATAATACTTTGAGTCTTGGACGGCCAACGCGCAC AGACTACACACTACTATAGACAATGGATGATTTCAGACGCAATAAAATGCTAAAAT CCTACCGATTGTCATATTTTTAAGTCTATACCTCACCGTATATTGAATTCATGTCG TATCCGAGCGATTTTCGATTTGCCCTGAGACCATAGATAAAACTCACTGAGCTCTA ACGTAAGATTCAATTCAATCAATTATAAGAGCAAAAGTGTAACCCGTCGAAGTTAT TAAGCTGAAATAGTCGCAAAAACTGTCAGGTATTGCTGTCCAAGTTAGCGGGGCGC CATGAGAATGTGAATGACACGGCTCCTTGATATCACAGCGTCAATGTTTAGGTGGA TTAGAGCAGAGATATAACGAATGCTCATCCGATATGACGTATAAACAAATGAGTAA TGTTAACACTTTTATACTCCGGTACCTCAGTATTCCAGATCTGACGTCCGTGGACA CAGTCCTCAATTACGCTGTTATTGTATGGACTACCCATCGCTGCTTGACACGATCT TGAATTTATATAGCTACGAATGCAGAGGTTTTGCACCGCTTGGCACTACCGAGTAT AAGGATTATGTCAGTCGAGGCCTGAAGCGGGGACTGTGAAAAGCACTCCACACACA ACAGCCAATGTAGAGCCTTCGTGTTTGAAATTCTAGGTTTTCAACATAGTTTTTTG GCTGCTATTCTATTAACTACTAGCTTTACTTGTAATCTTCGGCTAAAGTAGGAATG TATTAATTCGCTCACCGAATATCGCCCATCCTTGACCACGATGTCCCGTCAATTTG TAAAAGGCATCTAGTATTCATCACGGTATGGTATCCCTTAAGTTGTGTATGGCTAC AAAAAAGTAATGGAATCTAACTAATTCCATCATGCGCGATTCATGAGCTCGTGTCT GTATGAAAGAATATACCATTCAATAGACACAACAATGATT |
| 88 | 39.50% | CAAGCTAGTCTAAACTAACAACAGCAGGAGGGCGAGAACGTTGGCCACAAGACATT AGGCGTTCTGTTTATCAAGCATCGACGTCTAATAATTTTAATACTAAAATTCGTCA CTATCTAGTTGTTCACCATGGATTTTTATGTAGGCGTATCAATTCAGTAAGGTAA CCCTAGTTCTCTGGGCTCATGTATGAAATCGGGAAGAAAGATATGAATGAAAAGAA CCTAACTACTGAAGGGTAGTCGACGAGAGGCAGCTAATAGGCAACCTTTGTCCCTT CGGACGGACTGGTTGCTGAAATTAATTTACATAAATTAATGAAACATCCCCAACGC CACCTTACCCATAGGGCGTCTCACGCTATACGGTCTATTTTAATGCCTAAGAATTT ACGATGAGCCTATAAATACCTTAGTTGTGAACGAAACGCAGCACACGACAATCGTA CAACCTCACTTTTAATGTTATATACGGGCGCGGCTTGGTAAATGCCGTAGCTCTAG TAACATAATGCATCCTCACCATACCAGCAAAGCTAAAAATCTTCAAATATTCGTAT AAAACTAACCAGTTTAACGTGTATGAGGCGGTCTTTTTACCAGTTTGGGAGCATAT TGCACGTACTATCTTCTTTTTAGCAGACCTGGGATCTGAGAACTTCCCCTGGGTAG TCTTACGATTATAGTTAGCCTAATAGATTATTTGTTCGTTAGGAAGAATTCATATA TACTAGGTTATCCTTCAGGTTGAAAATTAAGGACGTTACAGATTTTTCACAATTAT ACCGACTACCATAAGTGGGAGCGCGAATAGCATTTGAGTATTTGGATCAAGCATCT GCTGGGTTACACGTATTAATTAGACCCTTGCCGAGATCTAGGGAAACAAAATCCAG ACCCGCAGTACGTGGGTGGTATGACGCTTCTTAGGATAGGAGCGCAAGTCCATAGA CCTTTATATTACTACGTTTACCTGATCTAAATAATCTGATAGAAAATTAACCAGGA GTCCCATTAAGGTATTCAACCACGGAACAGAGTATAATCTGGTTGATAAAGTCGTT TTGATCTGTTAAAGATTTGTTAAACTAAACGAGACTTCTTTGGGTAACATCATACA AGTCTGATAAAGGATGATGCAGGGACTAGTCTAAAATGAGGGAGTCTTTGGGTATC CACCAAATAATTTCAGGAGTTAAGAGCACTTCCAACGATGCAGTCCTTTGGCCTTC TCGTGCGACAAGGCAAGAAAAGTTTATAACTCTACAGCTTGTGTAACTCGAAAGCT GACCTACTATATAATGTTATTGGAAATCAAACTCAGGGTTATCTTCAAACAGTTTG TTATTGGCTAGACAGCTATTACCTTTAATTGGTCCTTAATCTTGCCTATGGACATG CTCCACACATTAAACATACTTAATGGCATGCAATTATAGATTGTCCCGTTCATTCA CTATAGCTTCATAATGGTTGGGGTAGTACACGCAAAGTCTACTTATATGGGCAACG CGCCGGCCCGTCTTTCCTGTTAAGTTACGGGAGGTCGCTAATTACTATTTTACTGG GAATGCGCAATCAAATCTTGATTGAGACCAACGCCAGGCCCGAACTATTCTTATTG TTCCAGAGTCTTTACTTGAATGCATAGTATCGGGATGGGTGATGCCGGCCACCGG ATCACCATGGATATACGTCAGTTGGCCCACGTGTTAATTAATGTCATATTGTTATG GGCTAATACATTACTGTATTGTTTAAATACAATTCGTCATGCATTATCAGTACTGT GTAATTTATATAAGCGTTCATCATTGAACGTGTATTTTGTTGGTGCGTACTGAGTT AGATATTGGAGAAATTCCCTAACCAAGGAACAATGACTGGACTTGTTAGCGATGTA AGAGTAATGCAAAAGTTAATGAGACTGATATTGGAAACAGTATTGTTTAGGCTAGT CTAGAAATAAACTGCTCATAAAGAATCTTGCAGTTAATAT |

TABLE 2-continued

Exemplary 2.0 Kilobase Stuffer Sequences Having 40 ± 5% GC Content

| SEQ ID NO. | GC Content | Stuffer Sequence |
|---|---|---|
| 89 | 39.60% | TTCACTATTAAGTACACCTAGTCAGACGTGAAAGTTAGTTCTTTTCACGTCTCATA TAGTGCTATTTTCGACCACGTCTTGCAATCGTGATAGACAGAGCTGTCATTAACAA GATCAAGTTATAAAATTGTACGGGTTGTACCTGCTTATAGTTATATGTTGAAATTG CAAGGCCGCGTTGTGACCGGTTTGACGGAATCTGAAGGGATTAGAGGAGTTTATAT TTAATTTCTTTCATGTAGAGATAGAACCCAATAACCTCTCGCTACATAGAACTAAC GTTTTCGCAGTGATTTACCTTGTGAAGTGCACAGTACACTTCACTGCCTTTTACTC GCATATTGATACAGTAGCCAAAAGTATCATTATTAGTGCATAACCTTCACCTATTC CAACGGTTTTACGCATTCTGCGTACGTTCGATTGAAATAGAACAAATATAACTATA ATTGGTACCCATGATGTAACATTTTACCTCAGTAATATGTCGAAGATAGGCTAAGT CCCCAGCTAGCGTAACTAGCTAAGCCTTGATGCGTATTCCTTAATCTTGTTTAACG TCTCTGCTTACGCTAGTTTTTAGTAGAGCATAAGATAGCAATTTCAGGATGGAACG AGTTATAGAACAGACCACTCCTACAGTGAGTAGGGTCACATGTATTGTCCGACACT GTTTATTCAATTCCAATCTTTTAAGTGCGAATATAATAAGAAGCACCCTTTCAAAC AATTGTTATAATACGTTTTCATGACACCAACGATGTCGACTATGATGTGCTTCTCT TTTGGTTAGACATCTTTGCATTTCGACGACTCCTTTTCATTGAGCAGGTTTTAGTT AGCTAAGTGTTTCCTACATTGTAGCGCATTAGTCTAATAGAGAGTGAGCATTAGTC ACAATATAGTCCAATGGATCTGAGAAGCCTTATGAGGCGTGCTTAGGGAACAATTG CAGTTTAGGCAGAAAGAGTTACCCTTTAAGGGTGGTATTCTTATCTCATATCTATC TTATTGGTGCAAAGTTTGTCTTTGAACGACAGAGTAACTCCATTCGCAGCCTTGCT AAAAGTGGAGAGACGCAAAAGTGGAGGCACAGGTCGTTTCTTTTAGTCGTATATCC AGTTTATGAGCTTCACATTTAAGATCAAATCCCTTCTCGAAATAAAAAGGATTCCC ACTTTAAATAGGCGATTGATTGTGCGCACTATTTATTCGTAATCTATACGTAAAGA AACTGAACGCCACAGCCTAATACATGCTAGTATTTCATACATGTGAGCCGAAGACA CGCACTTCCTTTTTGATGCGAGAATTTAGGGCGACCAAGTCTGGTAACATTCTGTC CTAGTTGCCGAGTAACATAGATATAAGCCTTAGCAGGGCGCGGCTATACCTTGGTA GTAAGACGGGTGTTTGAGTAATATTAGTAGCTTAATTAACAGCGGTCAATCGCCAA ACGGAATTGTAACTGGAATGTCGTATAATCCCATTTATATCTCAGCACATAAATCA AAATGGCTGTGAGATTTAAAGAGGTTAGTAATTGTTCAGAAATCCGAAATCCTCAT AACCAAATAAAATTCGCATATGCATACTTGATCGGCGGAGCGATGAAAGAATTACA CTTTTAGTATCCAATTATAAACATCATTTGCGGCCTACTTTTCCCAGTAAATCAAT ACGTGGAGAACTGGCTCGTACTCTGCTCTACACTTATTGAATGAGTTAGCCAATGT AGAGCTGGATACTAAGCTCTAGAAGTTACTCCAGAACAATTACCACGTTAATAACT TCTATTATTCAGAGTCGTAACAGCCCTCAAGTCCTCTCTTGTTCGCCTGTCAGCAA TCTCCTACGGACCTACCCTGCCAGGTAGTTGCTGTCTAAGCCACTATTAGAGTTGC TAGATTTGTTAATTATAATGCTTCGCCATAGTCATCCACGGTCAGGCGGTACCTC GCAGCTTGTGTAAGGGATCCCTCGAGTAACTCTTGATGAT |
| 90 | 39.60% | CGTAGTATTTTGTGAGCTAGATGGAGTACTCCGATTCAAGGTATTATGAACGATAG ATACCGTGGCTATATCATAGGATTGCTACACTGTAGGTTCCAGACCTTAGCGAAGC GGATACCTTCCGTTCGGTTATCTGTTAAAAACTTTACATCTTCATGATAAAGTGTG CCTACCTTTGTATCACTGATGTACTTCCCTACAATAGATACTCTTTAAGACCTGAG TACGCCGAAAGAATCTGTTCGATCTAGCAACGACAAAACAGTTATCAGCATATCCG TATATTGTGGTGTAGCGTCTTCGTGTACTAATTTAGATTTCTGCATCTGTCTAGTT ACGTGTAGGGCCTATGACGGTCCCTTGCTTTTCCCGGGAAATATCAATTGCAGTTG TGAAAATTGTTTATAGGAAAACACAAATCTAAATAAATTACTCCAAGGATCTTCTC CCAGATGACTATTCTTAGATAATGAGAAAGGGAGACTCGATTAAGTAATATTGTCG AGCACCACAATCTGCCTATATTCTAACTTAGTAATAATTAATTAATTATGAGTCAA CCAAAGGGTCGTTTAGCTGATTCATATACATACTATATTTGATCACCACCTACGAG CAGTTGGCATAATTTCCTTGTTGACTAGTTTTGACCCACGTGATTCCCCTAAATTT TTTGTGCTCTATGACCGACAACCACAGTGTAATGTCTCAGGTAAAAATGAGTACAT ACTACTTTTCCAGATTGCATAAGTTATAGACTTCGGTATTTTCCAAATATTATTGC ATTGTACTACAAAACTAACGGGTATGAGTAGACACAAACGATCACGGGTTTCACTT ATGAATAACGTTGTAACGATAAGTGCGCCTCGCCTGCACCGCATCACTAACGCCTT TTTCGAGGTAATACCACGTTCCGAAGAATCTATTTAGTTCCTCGAATAAAACATTA TTGATAAGTAGTGAATCACCAGCCTCCCAAAAATACCAGAAGAGAGAAACAGGTCT TTCAATTGCTGGTACTATTTGATATCCTTTACACGTTTTCTATTCTCCAGTGTAAG TCTCGTTATGCAAGTTTGTCAATATCAGAACAATATGATATACAACACCTCGCAAG CTGCTAGCAGTTAGATGCGATCCGATGATGATCGATAAAAACTTATGTACTGGACC TGCTGGTTTAGCCTTTAAGAATAAGTTGATTCTTGACATACAGCTCGGGCGATAGG ATTGAAGAGTAAAAGCGATGTAAACCAGGTCTGTGTTCGATGCAGAGCAAGTTCCT GCATCGGATTTTCGGATATGCAGCTTAGATGGTTACTCAAATCCAATTCCGGGCT GTTGTCTGTACAATTTGGGAGGTTGACATTGCCACCTGGGCAAATGTTGTCCGAGA ATTCGCCCGATGAGAGAAGGGACTTGGTGGAGTCACAAGAATAGGCGATTTCGCCC CAAATTTAATATCCAAAGAAGGCGTTCTACTAACCGTAACGTTAGACATATTCGT ACAGTGAAGTTCGCACTATGTGTGCATTACTCAAGTATCTGTTGTATAGGATACCT TAGTGGTTCAGTATTAAACACGATTCTTTTATCTTGTATGTTGTAATAGCGATCGT TACTTATCAACAGAGTTAAACCATGGTACAAGTGCACAAGTCATTAAGCATCTAGA CTGCACTACATCGCTTCTATATTCACCATATGACGTTACAATCTCCCAAAGTAAGT ATGTGACAACTTCTCCGGCCAGCTACATCCGGTAGAATTGTGTTAACTAACAGTGT AATTATACTCCATCATACGATTTAACCGGTTGAATGACTAAAACTTAAGTAGTTCT CGCATGGGTCTCCGCCTCACTGGTAATATGTGACCGCTCTATTGAATTCGAGACCA GGATCAATTACATCCTCACCGGGTAAAGAGTAGATCAGGATTTTTAAGTGAGTAAC CTGGCGATGAATACAAGGTTGTACTGCAGTTTTACCCTGA |

TABLE 2-continued

Exemplary 2.0 Kilobase Stuffer Sequences Having 40 ± 5% GC Content

| SEQ ID NO. | GC Content | Stuffer Sequence |
|---|---|---|
| 91 | 39.20% | GATTTAAATGGTAATTAAAATCGAAGGTTTTAAAAGGTGAGAATTTTTTTATAAAA<br>TGCAATCTGTTACGCCCCTAATATTCGGTTTCATGATTTGCTTAATATTGTATCAA<br>CACAAGCATATTGTTAAACAGTCTCTGTACTTTCTTGATGACCAATAATGAACAGA<br>TGAAGTCTTCATATATTGAACTTCAATTGAATGCGTGCATGCCATTATTCGTCATC<br>GAGAATTAGGAAGAAAACAATTGCAGCCTTCTAGCGCCAATTGCGATTAGTAAGCT<br>TCGCCCTCACGTACTAAATTATATTAGACTGATCGGAGACATTAACAAGCTGCTTA<br>TTCCGTCTTGAAGACCGTATTTCTTACTGTTACGGTGTCCTTAGGCGTCATATATC<br>AACTAATATAAACCGGTACTTTATTCATAATAGCCGATATTCAGTGATTGTTTGCC<br>ATAGGCTACTTTCTTTCCCAAATCCCCGGTATCGCTATCCTATGATTTCTGCGTCA<br>GGGGTTAATTACGGCGACACCAGCCTAACCCAAGATCAGACTAGGATAATATTTCA<br>CTGGCAATACTCATCGATTAATTCAACTAGTATCTATTTTTTCACACTCCGCAAAA<br>AAGGGCAAAACAAAGTCGTCAAGCCGGGAATAAGGGTTATTCTTGCAGTCTTCGTA<br>ATAAAATTTGAACTCAGTTATTGCGAATTTACTCGTATAAAGCTTCTATTATCATT<br>CTCTGATTACTCAAAAACGCTCCATGAGGGTAGTAGCACATAAGTAGAATTGCTCA<br>TAGTGGCTTCTTTCTCTCAATCCCTTTGATACTCATTTTTATATTACTTACATGTA<br>ACGATTGTTGAAGGCCAGCAAACCATATAAGTGGACAGAACAGGGAACAAGAGAAA<br>ATAATACAGAAAGTAGTAACTAGTCAAGAAAGTCTAGATGAATCTATAAGTTGTAC<br>CTATCGAACTATGATCGTAGCATTTTCAGTCTACTTGAGGGAGAGGCTGTAAGGAA<br>TTTTAGCGGCCAGATATATATCGCTGGAACCAAGTTATCGCATGGAAACTTGATCA<br>CGTACAGAATGTGATGTACGCGCAAATTAGATCTGAAATCCCTCTGTCCTCATTTT<br>TTAATTAATACAATTAATATCAAAGGCCTTCTTTTCTGAATGTTATTAGACGGAAC<br>ACGGAACTGCGATTCATCATCCTAACTACACAACACGAACTGACCAGATTTGCGTG<br>TAATCGTCACGTGCCGTTGCTTACTCTAGTAAACCCCGGCGCAAGGGCGAATTGTG<br>AAAAAATGAGTCAATTCGCTACAGTGGCAAAAAACGAGCTCCTGGACGACACAACC<br>TCGTATAGCAAGGCGTAGCTCAATGCGCCAGATATTCAGGTATTGTAGCCCATGAC<br>AACAAGAAATAAAGCTATAGTAGGCATCATTATCGTTTCGTCCGGCAGCTTTTTTC<br>TGACTTCCACCTCATTGCGTCTTATGTCATTACTGCGTAGGGTCACCTATATGAGT<br>CTTCATCCCTGGGACACTGAAGGGAGTACGCCAGTATTTCATCTATGAATAAACCT<br>CGATTACTCCTTTATGAGAACAATACTTACACTCGACGGGTCTTGTGGTAGTGAT<br>CTTAAGATTATCTACCATTTGTTCACCCTTGAAAAAAGAGACTTACCTCTCGACTT<br>TTTTCTATACTGGGCCCCGACCGCTGACATGCAGAATATTGAGGAGATGCAGATTG<br>ATATTTACAAAAATTAAAGCAGATACTCAACGCATATTCTATGAAAATCAGGGACA<br>CCCAGGGTGGTGCTTTAGGATGATTTACATGAAACTTTAAAAGGACCGGGATAAAC<br>TGGCCGCCGGTCTTTCACTGCCACAGGGATCTTATTCATTCGGATATATTATTGCC<br>ACTCAAGATAAATTCTGTTAGTAAGTGTTAAAGTGTATCATTATTGCCCATTCTTC<br>AGACTCGAGAACTTCGAAGGCAAATGCTGGACGTGTGTAC |
| 92 | 38.70% | AGATCCACGGCCCTGAAATCGCCATCGCTGTTCTTCTTTGATGAATAATGCAAGGG<br>CTGAGTTCATCAGTGTATTCGAATGCTACTATATTTCAGTATTGTGAGTATCACAG<br>CTGTAATCTTCGGAAATACAAGGATGTTTGTCGACCTCGCTAACACTAGATTATTT<br>TGGCCCGTTACTATTTATATTTTTATGACTTCAAAATGCGCTTCAAGATTGTAACT<br>CTGGTTGATATAGGATGCAGGGACCGGCTCAGGGCCGCTCTGCACTACATTAATAC<br>CTCAGGGATCTCTATTTCGTTAGAGCACACGACTTAGTGACTAGAATAGCTTTAAA<br>TGTAAAACTTCATCATATATTCCTCCTGGCTAAGCCTTAATTTCATTCTTGGGGCT<br>GTTGCCAAGACTGCTCAAGAGTTAGTTTTTCTTTCTCCTTGTAGTACCCGTTCTCC<br>TAAGTGCAAATAATCTATACACACTTCATATTGGGTATACCATTCTTGGTTTATTG<br>TCACCTGTTATGTATTTTGCATCAAAATAATCATCGATGTATACGTTAACCCAGGA<br>GACAATCGACCGGCTAATTCCGGGAACGTAGATGTATGTAAAGTAACATGTATTTC<br>AATTTCTTCTGAAGTATGAGATTTCAGTTGCACAAAAGGTACTCAGCATGTCTTAT<br>CATCCATAGGGCCGCAATTATAGAGGATCTTGAGTGGAGGGTCCATACGAGGCCTT<br>AGGAAGCCGGCTTATCTCAGCGAAGGTTATCGAGATGCTAAATTTACGGATAAAGA<br>TCCGTTACTCTTCTTTAGAACTACCGTTCCAACTCGAACATAGAATCGGCTCCGAA<br>TTCTTGGGTACCTTGCAGAACTGAAAAATAGATATCTCGGTATCTAAAGGCAGAAA<br>TAGTTTTCGCTCTGGATTGGTTTCTAAAGTGAATCTCAAGTTCTAGGTAAGCATTC<br>AAGTCCATTGGGGACCATTAGGGGTTAATACGCACTGACGTCGGTCTTTCGATTGA<br>TAAAATACTTAACCTCGTTAGCAGTGAGGGTCAACAATCATTAATCTCCAGCTATAG<br>AGCGGGTTAGCCAGATTTTATATCGGCGTCATTCCTTTTATCTTTGAAATTTAGGC<br>CAAAAAGAAGGGAACTGGTTCTATTCGCGAATTGAACCGCATTTATGGTAATAGAT<br>CTGACCACGTGCTACTGCTCACTTACAATAGCTAGTTTTCGGCTCAAACTTTGTAT<br>AAGGCTCACTAGGCATATAACGAGTTAAAACTTTTCACATGATACGTGACTAGCTT<br>CGCCCGACATACTATATATAAGGTCTACCGTTGCGGGAAAAGATGAAGATGATATT<br>ATCAAGTCTTTGACTAATAAATTAACTTATGCTTACAAATTTCCAAAATAGATATT<br>CCAGTCGTCTATCCTTCTATTACAGAGAAAGGCAGACTTAATCCGTTCATTATATA<br>ATTTATTTAGATGTTAGTCTTTCTGGTGGGTCGATTGTTAGTCTTTACATAGAACT<br>CCTTTAATGTTCATAAGTTTCCATCAGTAGAAAGTGAGCTTATGGGTTATTCACCT<br>TTGATATTAAAAGATTTACTACTGCTATAATCTACCTAGCTCAGCTGAGAGGCAAG<br>AGGATCACATGTTATTGTTATAATGCTTTGATTGGTAAACTATAGTGTCAAGGCAA<br>TTCGAGTGTCGCCAAGTTACGTCGATTAGATCGATCATTAAAATCTAATAATGTTT<br>AGAGTTTGTTAGAGTAATGGTGTTGATCGGCACATAAGAGTCAGAACGCGGGAGTA<br>TTGATATTTTGCCGAATTGCAAATTTATCAACATCGGTTCTACGTATCGTTGATGT<br>CCTAAGGCCTTAGTTACGTAGCTTACATTTAATGCGCATAGGGTTGAAGCGTGTGT<br>TAATCGCTCTTTCAAATAAGTGTTAGGAAATATACGAAGTAACGAATATCAGCCTA<br>ATTCCAGCGACTAAAATGAAACAAGAGCATCCGGTGGTAG |

TABLE 2-continued

Exemplary 2.0 Kilobase Stuffer Sequences Having 40 ± 5% GC Content

| SEQ ID NO. | GC Content | Stuffer Sequence |
|---|---|---|
| 93 | 39.50% | TTGATAGTGTGATTAATTAGCTGGTCATTATCGGTATCGTTGACAACAGTAGGATG<br>ATGGCGATTGTCTGCAGATTTCGTCCATTAATATAAGTAATACTTGTTATGATGTC<br>CAACTTAGATATATTGGAGTTTTATTGCTCTATTTCCTGTACCCTTGTGACGAGTA<br>ACTGCTCCGTGATATAGGCAAGTTAAGTGTGTCGCAATATGGCAGTAGGCTGAATA<br>CCACACATACTGTCTTTCTAAATAACACTAGGCGACTACCTTTAACTTCATCTAAG<br>GACGTTATTTCACACTAAGCACTCCGTCCCGAGAACAGGGTCTATTGAGGCTACTG<br>ATTGCGTAAAGTAGTTGGACACGCATGGGTTCTAGATCCTCATCTCTGGTTTCTCA<br>ACATATTGAGTTATACTTTCTGTTAGTTGTTAAGCCGGGCGATCAAAGCATTTCTA<br>CTTCAGAAATGGAGGACTGTAGTTATATACTACATTCTGAAGCGGTACCATTAATG<br>CTTTCCGCATTGATGAATATCTATATTTACAGTTTGGTGAACACAATTAGGAGAGT<br>CGGACTGCGCAAACAGAATATTTAGTTACTTATAGTTAATATACACCTATACACGG<br>TAGAAGGTCAGTTCATATAGACTTCTGGGTGTGTACTTCATCAGAAGTCTCCTGTC<br>TGTTTAGCCAATCGCCACCTTCTCAGTCCCGTGGGAGTACCACTCGAATAGATCGT<br>TGTTTTCGTTGTTGATAAACGGACCCCGTCTTATTTTCGTTACCATTTAATACGAT<br>ATCATATAATTGAAATATTAGGAAACGGCATTTCAAATACGAACGATTTGAACTTC<br>ACCTACCTTTTGACATTTATATTACAATTTTATAGGGCAAAACGTAATGCACCTAA<br>ATTTACTGCACTTCAGATCTACCAATTGATTTGTCACACCAGCTATTTAACGAACA<br>ATATGACTAAATATTAGCTGGTATGCAATCTGAAAAGTCAACATGGTATTTCTGCT<br>TACACCGGTAGGGTTAATGGAAGTTCTGCGCCCATTCGAATTTTAGAACTGAACAA<br>TAATTCATGAAAATTTACGTTAGCAGTACCTTTTTGTCTTACTAGTTGTTGCAGAA<br>ATTTAAACATTACTTGGTAGCCTGCTGTGTATATAAAAGAGCGATCTCCGATAAGT<br>TGTTAATCTGTTGCTACCTAAGCGCTTACTGTGTGCCTTGGCTCGCGTATATGCCC<br>AGGTCAACATTTATTTGTCGCTCGACTCGAAATAATCTATATCATAAGATGGGAAC<br>GAGTATGCTCCATGAGGGAGCCGGACTAGGCATTCAATTTTGTTTGAGTCTTTAGT<br>AACCATACCTATTCATGCGTAGTTAACTTCGTAGTAAAGCAGCGTTTATACATAAA<br>CACCAAAAAATGTCCTAGGGGCATACCAAGAATCTAAGAAACAGCGCAGTAGTTCG<br>TTCGGTTTGGCAACCATACGAAAGTATCATTGCACACGACGCATACAGCATCCTAG<br>GAGTTTACTATGTCTTCGTTTTTTTGTAGGCCCCACACACATTAAATTCGATTTAT<br>TACACTCAGAGTACCTGTCCGCCAATTCACGTGAGTACCTTCGCGCAGCAGATAAT<br>ACATTGCTATGCGTTCAGACCATTGTAAGAAAACAGATCATGACTCTAGAAAAAGT<br>GGCCTTAGATCAATAAATGTTAAATCCGGTTCTCTCTAACCTCGCCGTACACAGTT<br>AAAATCAACGCGCATACATAAACATTGATCTTATGGGGGCTCACATAGTGAGACAA<br>TAGTAGTACCCAGTGTTATACCTAATCTAATATATAGGCTAAAAGGTAGATTAATT<br>GTCTGATCATAGATCTCAACCGATCATGGATAGCTGGGAATACGTTATAAAGGTAG<br>GTCTACGACCCGCGAAATCTCGAGGAACCACAACAGAAACCATTGTCTGTACGAGC<br>GACAGCGTATGTACTCCGTGGCTGGTCTACCTCGGTAATG |
| 94 | 39.40% | GGGTAGTTTTTTCTCCAAGGATCCCCTTAACTAGGGTGAAGATTGGGATTAAACCT<br>AAGATAAAGATATAACGGTCACTGGCGACAAGCTTACAAATTTGCGCTTTACAACA<br>GACCAAGGCGAAAGTAATCTTGGCCCTACTAAACCAAGGGAAATCAGTAGTAGTGT<br>TCTCCAAATAGGCAAGGCTAATATCTATACTGTCCCTGCATGATGTGTTAAGCCAT<br>AGGCGTGTAATGTTATTCCTTTTCCTAACCAGCTTTTAATGTATCCTTGTGTAGGA<br>AGAACTGCGAAGTTATGTTACTCCGAAGCCAACCAACATGTGTCCTCTTGGCACCA<br>TGATTCGAAGGTGATATTATAAGTTATTCGACCGTGAAGATTACATATTACTGGAT<br>GGTGTATAAATAGACCATACGTTCATTGAAGCGTGACTGAAGCCGACAACGGCTTA<br>CGTAATGATTCAAAATCGGTAATAAGGATAACGGTTATATATAGTAGAATTCGAGA<br>TGGAAAAACCAACTTGCTAATGACAATATTAAGGGTATATCACACTGTGGTTTGTA<br>AAGTAGTCACCTATTCGTGATGCCGTGTACTTCAACTTATAGTAAAAAGTATTGTT<br>TTCTAACCAGCGGTAACCTGTTGCAAAAAACCACGTTTAACCGATTGATAGCTTGT<br>GGTAAAGTGGCATAGAGTATACTTCCTCCATCTGTAGTACTTAATAGGTGTTCCAG<br>TTGCAGTATAAACCTTTCTTCGAGTATCATCACTAAGACCATTAGACATAGGATAT<br>ATACAATAAGAGCTGGAACTTGAATCTTCTAATGACAGACTTTACTAATTATAGTT<br>CAAGCGCAGTTTAACTATAAATACAATTGTCAATTCATCATATGGTAGGCAAGATT<br>CCTTTAGCCTGGCGTACAGTGGCCCGGAGGCCTTGACCAAAACATGGTTCTGTTAT<br>ATCACGAGATGGATTGACTATGCTCGTGAATCTGGAGAGGCACTAACTTGGTAACG<br>CCCGTACTCTACCGCAGCGGGACAGGTGATAGACTGTCTATGTAAATCGTCATCAA<br>TCTATATTTCAATACAACTATAAATCCAGACAAGTATCCTTGAGATAATAGTTAAT<br>CTATCCTAACTAATAAGAAGAAAAGAGACGATACGGTAGTAGATTAAGCTTTCGCG<br>GAAACAAGAGGAATCTACAGAAAACACCCTAAATAAGCTATTCCATGCCGCCTTTG<br>CTATGAACGAAGTACGGAAGCATGATGCTTATCAACGTCAGGAACCTAGCTCAAAT<br>CAAGGTCTTACCAGTGACGATAACATGGGTGCGGATGGTTATTTGTGGAGAGGCGT<br>AATACAATGTACTTGTTTTCAGGATATCAATTTAATTTCACTTAGAATACGAGACG<br>GCCGACAACTTTAACGAATACATTTGCATCCCACATTAATACCTGAGTGCCGCTCA<br>TATCGTCCTAGCACAATTTTTAACAGAAGTTTTGGTGGTGAGTAGAACAACAACAT<br>GTAGTCATCTTAAGCGTATGAAATCTGGCTCTCAAATTCATGTTTAATAGTGTTTA<br>ATCTTTTATGTATAAATCGTTTTATGGTTTAGACGAAGCACTCAAAAATATAGAC<br>TGATGCCTATGACCTGTGCTATCTTTATTTTCCAGGGCAAAGATGATCTTTCCGAG<br>TCCATATCTTGAATGACTTCCCGCCTGAACCAATACCTGGTCGGAAGGAGGACTCA<br>TTAATAAACATGCATAAATGGCAGATCTGAACTGGACGGCTGACTTATCTCACAAT<br>GTGTTCTAAAGTCCACACCGTTTCTGTACCAATGAAAGGACGAATTATACATGCAT<br>TGGTTTGGTTAAAACCAATACTTGGTAACGATCTGGACCGGGCGGTTAGAATGATG<br>AATTAATGCGCCGTATGTGGAATGAAGTCCTGTTAAAATGCAAAAGGTGGCTCTTC<br>GAGAGTTGTTGGGTTGAATGAGAGAAACGCCACCTTCACA |

TABLE 2-continued

Exemplary 2.0 Kilobase Stuffer Sequences Having 40 ± 5% GC Content

| SEQ ID NO. | GC Content | Stuffer Sequence |
|---|---|---|
| 95 | 40.00% | TAGTATCTAGTTTCAGGTGTGCACAGAATAGTTATCCTCCTTTGTCTGTGGCTATT TGGAGAACGTATTAGAGGAAGCATATGGCAAAATGGCCTGTACACGATAGATGGTA TCATGTTTGGAGGACGCTAGGCATTTCGCCCTAAACACCGCAACGATACCTAAAGA GCTCGTCAATGGGCTTGCCGATTAAATACGCAAGTTTTAGTCAGTCCAGACCACAT TTACCGGTAATTATGCACAGACAAGATATTATGCTGGTTTATAGCCCATATTTGTC TCCCCCTAAAGTGAGCTCTGATATTTGGTTAGGTCGAGTAGTACAGTTTGCTATCT ATGGATACGATGTAATTGTGCTTGAGATACGTGCATCACGAACATTGCTAAGCGGA TTCGCAATGTTCGTGATGCATGGAGTAGTCTAAGCAATCCAACAAGCGCCTGAATA TAATTTTGTCACAAGTAAACCTTCATATTGTCTAACATACAGAGCTGTTTTACCCC CTCATGATCTAAATCTTTCGCTTCTTCCCAAACTGCACGCCCTATTCGCCTGTTAG CGCATTCAACCCTAATACAGCTGTTGTGGGGATACTCTGATTGAAACAAAGTTCTC TATGGAAGCTTCATCATTAGGCCATACGAAATAGAATCCCCTGTTGTCCAGGTGCT TCTCGACTGCGTTGCGGTTCTTATTTTGGCTTTGCTAATAGGAACTTCTCTCTTCG AGCTCGGTCGAACGCCAGTTCGTCAACTATACCGCCTTCTTTTTGCGCAAGGTCAT CGAAACTGAGGTCCATCCTGGGACAAGAGATCAGTTAAGCCTACACTTGTGTGAGA CTCCGCAGAAAATCGGGACCAAAGCGTTAGGGCTTCCCAATTATGAGGATCTATGG TGTCATTGAAATTGATAATCCTTATAGGGCCATTTTTATCCCTGACCTGAATTCTA TTTGGTGAATAAAGTATTGGTCGCCTTTCGAGGGATACTACTATGTTATGGACCTA ATGGATGACCATCTGGAACATTAGCAACAGCAACTCTAATCTTATTTTATCATCTT CAGTGTAATATATCGTACATTTTAGGCTTTCCTTTATGTTAAATTGTTATTATGAA AGAGGTGTATTATAAGCTAGTTAAGCGCGTTAAAACACAAGTGGTCTGCTGTCATT CATATACCAAAGAAGGTCTTGATGGACAATGTCTTCACAAGACCATGCATAGATTC TAAATCGATATGACACCTAACAAATGCGGGCTAATATTCGATTTCTGACTCCCACA CTGTGAGCACGTTTATTGCGGAGACTTTTAAGCGAGATACTCTTACTCCCCATTGC CATATATGTAAATGGACTTCCAATTCTGCATATTTCAGTACATCCGGACTGCGTT ATAAGCATTGTCGTGGATGCATCACCATCCCATAGTTCCACTTCTTTTTTTTAGTT CAGATCCAAACTACACTATAGGGTGACTTATTGTCGATCAAAATTATTATATGTAA GTAATAGATCATACATCAACACCGAGGTCTTTGTCCAATAGAAATAGTATGTCCTG GAGTTTTATCAAATACCTGCCATGTGCAAGTTCACAGAATAGGACGCTTCTACAGA ATTCATAAAATCCCACATCCTTAGCGTAAGTTGTCAGATGAATTAATTATATTTTT GATACGGCCCCAGTTATTCTCGAAGTCCACTCTTAAAAAAAGTTATTGTACGAACT TGCATAAATCGATAACCTGTTACCAACATGCCCCGGCATAAATCAACAACGTGGTT CGGATACGACAATATCAATCAATCCGAAATTCAAAATAGAATATTCAACTTGACTT AATCGCAGTTCATTCGTGAATAGACACATATTAGCTCTCGCGCGCTTTCTTATCTT CACAGCTTCTTCTCGATACCTGAATAAGTACGGGACCATTTATGTTCATAAGCATT CAGTGAAACTGCAGTCTAAATACTATTGGCATATACTTAT |
| 96 | 40.20% | GATATGCCATCTATCGAGGCCTGTTAGCTTAGGACATTACATGACAGTGAGACCTA GATATATAGTTGCATGAGTAGATGTAACCGAAGGTACTCAGGGACAGAACTGACGG ATTGACGTTTTTCAGTATCGTAAAAGTTTGAGATCCAACAATGAAAGCTTGATGCG CCAGATGATGGAAATGCGCAAACTGTCGTGTGATAACACGGGAATTGGTGCTAAGC TGGAATGGTCTAATTCAAGTTCCAATCCATATCCATCTATGTGCGAGGAATTTGTA ACGGTAATTATATTGCCTTACAATTATTATCAACCAACACACTTGAACGATGTAAT TGGGGGTATATACCAATAATAGTACTGCCAACTACTGTTTTTTGCAAGAATTAATC GTAGTCCGAATTAAAAGAAAAGACGGTGTACGCAACCCAAGTAATTAAACGAATAA TCATACGGTCGATATGCTCATTCGATAAAACGCGAGATCTTTAAGTTCTCTCACCG GGGTAATGCATAATTGCCTTAATTGGAAATTGCTTTAGGTGAGAGTCAGTAAACCA TTGGTGAGATGTGGTTATACTGCACCTCACGCAAATTAATATTCTAACTTTAACCT GAATTATGGGTTCCCCTCATCGGGAAGTATATCTAGTGCCAACCTATCACAGTTGC GCACATATGTTTAGAAATGGTTAGTCGGTCAGGGGAACTCACGTAAGCGGTAGTAG TAGAATTTAATTTATGGTCTCCTAAAGCATCGACATAGTACACTGCGACCATTCTA ACACATACTAAACTTTGAACTTACTGATATCTTTTATGTTTGACTTCCTTGCTACG CAAGTCCAGGCCCAGACAGCTGAGTTGTCCTTACACGAGCTATTTGCTGATCATAT GGTTTAATCGGCACGCGAATTGCAAGTTTGATTAAGGTGAGCGCATACTTGAATA CAGCCAGGGAGCTCCCTACTCAGCGATCGTCTTCAGAGATTTCACGAAAATATAAG CATTCCCATCAGAAATTCTAATTAAACCTTACCGGAGGTGGGGATTACTCGCAGAG TTAAATAATGAGCCCACATTATGCGTTTGCTTCTGGAGATTATGGGTGGTTTTCC CGTACCGCCTAATATAGTATGCTTCGACTCAGCAACTTCACTCTAAACCCTAGAGA GCCTCTGTATGTACGCGCGTGGATGAAATCAAGAATGGTTGGAGTCAATGACTGGG GCACAAGTGTAATCTGGTTCGATTAATACATGGCACTAGGTGCTACGAGGACGAGT GAATGCAATATATGAGTCCTTGCTAATAAGCATCGAAGATACTCTCCGGTACTCCT TCATATTCGACTAATCGGTGCACTCAACTTTAGGGGGGCTCCTTATTATAAAATAC ATATAGGGTTTGTTTAAATGATTTGTTCTATTAATACGGGCAAAATTAATGCAATG TTCACCTAGGCACGTTGGTACTCGCCGCCAAACATTGGCATTAATGGGGATACTTA GAAACAACATAACATGAAAAATATCTAGGAACGCCAACATATACGCCGTGACCGTC TGTCTTAATAGACTCTTTTTGTTTAAAGGGTACTGAGTGATTAACTAATGCTTTCC AATCCTTTCCGTTAGAAGGCTATTACTACAAGTGTTTCCCACGTGCCGTTAAAAAT AGAATTATCTTTGTGGGTTTACGAGCGCGTACTGAAAACAGGTTTCTTGGATGGGA TAATATTATAGATAGCAATAAAGTAAACTGGAAAACAGTATTGGATAGCATGTGAT GGACCTTGACCCCCTTGTGGCATAAGATAATCTCAGCGTTTCGTTACACTTACATT CACTGTTAATGTCTATAGGCAAGTTACTATTTGGAGTATTTCAAAGTGAACGGAAG AAATAGAAGTGCTAACAAACTCCGTCATAGTAGGATCATATCTCCAGAGCGACCTC ATACATGCTAAAAACCTAGTAGACTTCGTACTATGGATTT |

TABLE 2-continued

Exemplary 2.0 Kilobase Stuffer Sequences Having 40 ± 5% GC Content

| SEQ ID NO. | GC Content | Stuffer Sequence |
|---|---|---|
| 97 | 40.60% | AAGACACTTTACCACATAAGTAAACCGTTGACATTATCGTGGCGGAGAGATACTGC TTGTACTGGGACACTCAGTATTTTGTGGAATATTGTACCTAGCGCCTCGTTCCGTG AAAGTGTGGCATGGATTTTCATAATTTTATGCTGTCCTCATTGCCTACAATTAATC CAGTAAGCACTAGAGAAATATCTGCTCCTATGCTGAGATTAGCCTTATGAGGTCTT TATATCTTTCTGTAAAGGCCATTGTTCTTTTGATCCTGGAGTCTCTGAATTTTGAT TTGTCCCTCAAAGCCTTATGTGTACCCGGTCCCGGAGCATGAAGACGTATATCTTG AAGTAATCCGAAAGTATTTAGGTGTCGTTGTCCAGTAGTAATCCCGGTTATGGGTT ATAATTAAGTGTTAACATCCGAGCTTGGTCTGTATAATAGTGTGTTTGAATAGTAA ATATCAGGACTCTACAGGGACCTATTCTACTTCGGGTTGTGTATCTTCCTTGGAAT AACTTTTGCTACGCAAAAAAGCTATAACAAGGTCTGGAGACGGATGTGATTTAGTA GGGCAAATAGATTTAGGTCTTCGATAGTACAGAATACTATGCTACAACCAATCTCT TCATGGCTTTATCAATACAATGTTCTTCCTTAACTCAGACGGGAGCAATTATAGTT AGCTGAAGGTTGCCTCACAATATGTGTCAGAGCTAGCGAAAAGCTCCTACCAATAT ACATCAGATAAGGAGTTCATACATCTGTGGCCGATCAAGCAAGCAAGGCCGTCCGG TTCACGACCTGGGTAGTCTGAGTTTGGAGGAGAAGCCATCGCCTCTCGCATTCTAC TAGAGAAAGATTTCACACTTACTGACAGAGCTACACTGGTACGACGAATCTACAAA ACTAAGCAAAGTCCTAGGGTGAGCAATGCATGGTAACTAGTACGATTGATCAGTGC GTGGTATACTATCCGGATAGTCCAGACGTCAAGACCTAATCATCGTACGTAATTAA ATAATAATGCATTCAACTCTTCGGATACGATATATACTTATATGCATTAACTATAC TTTCTCATGCATTGTATCTAACAAAATCTGTACGGCAGAATTAATTACTAAAGTCT TAATGATTCGAATATTAATATCAATTTTATTACGAAACAACCAAACTGACAACGTA GAGAGGCAACTACCCAGAGTCGCCAAGAATACTGTTTACGAATTGTAGAAAAGATG TAAGAATGTTCGGATGTCGGATTACTTAATTGCGAACGTTTGTCAAGTCGTTGCAG GATACCCTCATCTCCTCTTCCTAGTGAATTATCTGAAAGTACTATTATACAATCTA AATCGGATACATTCGTTTGTAACACCACATGGTTGGCTCAGCTGACCATTTACGCG CGATATTCTGTGCTATCCGAAGGCGTAAAAGGAATTCAAGTCAGTCTCCTCTTCGT TATGTAGAAAGGGAGGACTCCTCCGCCGTATATTCAGCTGGCTTTAACTAGGAACA TAGTTGCAGTTCAAACAGTAGAAAATCCTGGAAGACATTTCTTGATAGTCTATCTC AGAAAAAGGGGGGTGACGTTCATGTTTACTAAGACTTGAAATGTGGCTCCGTATCT GCACAACCAGGTTTGGGCGGATGCCGGCCGCCATGTAACACTGAACCTCGCAAGAA ATGCACAATTGAACAAATGAATACTCACATCTTATCGCTTAATGTTAAATTCAAGG CGAGACTGGCTCGAATTATTGGAGCCTATGAAGATGTATATTAATGCCAAGGCACC GCACATAGTAAAGACTATACTAACCAAGTGTGATATTCAATCGATCGTTGTGGGGA ATCAGGTACAGTTAGTGGCGAACAGCTTTGACATCCGTTTAACTTTGGCAGCACCA CAAACCCTTTGCGTACGTTTTTGTGTTATAACCAAGTTATGTTGCAACCTACTTTG ACCTCTTATTTCTTTGCCGCAAGACTGAATGTCGTATTAT |
| 98 | 41.50% | GAGCAACCTACGGATATACTATCGATTCTGGACATGGTAAGTGTGTTGCGTGGTTA ATAAAAAGATTTCGTGGTCGGGGGTAGATATACCTGTAAGGTTTCCAACAGACCGC TTTGTAGAAAGAGACTTAGTCCCTTTGCAAAATGAGGGGACCGACTAAGAAAGCGT TGAATTCAGGTAATACTTTTTGACGTTACCATAGTTGTTGCAGTCCCGGAGTTAAA CAGAGACACATCGTGGCGGAGTCCGTAGTATCGCATGCGTGGATTTATTGTTGTAA TCAGATGTTCAATATGGCGTCAATATACAAATAAACAGGTCAGATGGAGTTAGCCT TACTTAAAAAACGAAAACAATGTATGCCCTAAGCAAAAAAACTAGATAAGGACGAT CACCACAGTTTTAAGAGATCTATATGCCCCTTTGACATCCTTATTCTGACAATGGG CAGATCCAACTACAAGATGTCGTACCGCTAACACTTGACTAACTAACGTCAAGTAA AAAGTTCGTTAGTCATATTATCAAGTATGGACTTATTCATCGACAGGTTGTAATTA GCCCTCCCCTAGATTAGCTGGGCTGAACCCCTATTCCTACGCTCCCTTGTCACATG TATTCTCTACCTCAATAGGCCGGAAACTCGCAAGCCCAAGTATAGCGTACGGATTA AATTCGCGCAATCGCTCTTGACCATGTTAAATGCTTGCGCGTAACATCGAAAAGGA GGCAAGACATTTCAGAAGTAACATATCAGTTGACGGCTTACGGTGCTGAGGTTTAA AATCCGACTGATTGCTATCCTATCGCTGAGGAATGACTAACCTTGCAAATCCAAGT CTAGAACTGTCCTAGTTCTGTACCATGCCCAGCGTTCGGATGTCAGTACGTGTATG CAGCATTTAGGAGGTGATGTCTCCCAGTCGGTCAATAAGCTTTGCTTACCTCACGG ATAACTAAGTTCATCTCCAGTGTACGAAGATTCTCTAGCACTAACTATTCATTGTA ACTAATTGGTATCCGACTTTAAGCCATAGTGTGGCATGACGTAAGTTATGTCAGTT CTTTGGAACTTTTTGCGCAGCTGTGTTGACGAAACACAGGTTGCAGGTTGGTCTAG GTAAGGGATGCACTCACTGCGATGTGATCCTTTAATGGCCATTTAAATCTATCTCG AGTATAGCGTGTATACTTACTATGAAGCAAATTAGTATACATATAACAATGAATAT ACACATAGTGGGAGGTTGCCATTCATCCATGTAGGCATGTAATATGGCACCTCCTC TTTGGATACAGAGGCCCATGCCTCCGAATCACATATTTACTTAAACAGTTAACGGA ATTCAGGTATCCCGTTTCATTATTCGAAACGTCTCTGGGGTTACCTTACTTACGTT ATCTGCATGAGAATAGAGTCCATCGGCGTTTCTAACAATCAATCATGCTTGCAATT CAGCGAGTGTAGAGGAATTGTAAGAACGCCGGATGCTCCCTTTACCTTATCCGCAC AGGCCCCTACGATTGAACTATTGAAAGTTTTATTACAAATCTCATATATGGGGGAG CAGTTAAAGTTCTGCATAAGAAGGACCTAGGATAATGCCATAAAAGGTTGATATGG AAATACTATTGGAATAAGAAAGTATATGGTGTCTATAATGGATATATCAGTAAACG AAGGCATTTCTTACACTTTGATTTCATTAACTGTAATCTCTATTTGTGTTGGCGAA TCCGGTAAACAGAGGTTTATAACTGGTTTACCTTAGTCGAGTGTCTTAGATATACA TGTCGATTCAGATCAATCCTACTCATCCCAAACGCACATGTCACGATACGTACTTT ATACAGTAAGAGGCACAATGTGGGTGCCCTCTCTCGTCCGACTTATTGCGGACGGA GAAATAGTTAGTACGGACTGTCACAAGTCTGTAACCACTAAAGATCGGGCAGCTCA GACATTATTGAAGGTAGGCCAAAGTATCATTAATGCTTTG |

TABLE 2-continued

Exemplary 2.0 Kilobase Stuffer Sequences Having 40 ± 5% GC Content

| SEQ ID NO. | GC Content | Stuffer Sequence |
|---|---|---|
| 99 | 39.90% | ATTAATAAATGTCTAACGGTCTAGAAATGCACCTAATTTGCTACTGCTGAACTCCT GATTACTCCTCCTCGTTTATACTTGTTCATTAAGAATTTTTTCCGTCTAGATTAAG TACACGGTAATACACACGATTAAATACACCGCCACAGATCTTCGCTATCAATATTA CATTTTGTTCACTCATTACGATAAGCGTGGCTTGGCTGAGTTCTAGACTTATCGTG TTAACGTCAATGAAAACTTATGGATTTGAAGCTACGATGCTAATCTAACTTTACCT TAAGCAAGAAAGACCTTCGTTAATAGGACCCTTAAAGCCTGTGATGTCGGTTAAAC GGTTCTAGTTTGATAGTGACGTTAGGGACTCGGTATACATCTTAGCCGAACTGTCT AAATTACTTTAGAGAAACTTTTCCCTGGGGGAGGCACGTTCCGTTTATGGACCTCA TTTGAGACTCAATATGTACAACTAATAGTGTGATTAGATCCTGATTCCCATACGTA TCGGCTCGCCCTTAATCAATACAGATCCGTGCTATGTCCATACTGCGATTCCAAAG GTTGTCTAACAAGACAAACTTGAGAGAGGCTTCACAAAGCAACCCAGCACCCTTGT CCTCTTTTTTAGGGGTACGCTGACATCTGGATGCATTAAGAAATACGTATCTAGAA GGATCGCGATAAGTCGCACAAGTTTACCACCTTATATTCTGCAGGCTGCTATTGGA GGTAATACGTGCTCGCACACGCCCAAGTGAGGCATTCTTACAAGACTTACCTTACA GCCTATTAATAACGTCGAATTTTGCGCAGCAACCAATTCCAGGGCAAACTATAAGC CTTATTGAGGTTAATAGGGCGCAATATATTTACGATAGAAGGTAAATCTATAATAC TGTCACTTGTCAATGATGATGGTCTAACTAATTGATTCCCATGCAAGTGGCGAACC AGGCTTACTTTAGTTTAATAGCGATCAAGTATACTAAGCACACACTGAATGTATCA CATAAGATACGTAAAATAAATCAACTCATTAAATCAAAGACAGATTCACAAATGTT TCGTGTTTTAACAGATCTGAATATAAACTCTGCTGATGTGATCGTAGGACGTAAGA AGGTATAGTTGAAGAATAGCGTGAATATCTGATCTCTGTTAGCAAATACATCACGA TTATCACCAGGTTTACCACAACAATAAGATTGTGACTGACACTACTTTCTATATGA ATGTATTCTCATGAGGATGCGTAAGACGTATAGGATCATACTGAATTATAACTCCA TATTAGGGTCTATATCACATACATCTCCAAGTTAAAAAGTCTATTGGCGATTCCAC ACAACTCGCGCTAGTAGTACATTTTACCGGTACCGGTACAGTCTAAGTTATTGATC TAGGTTCAACTTCTAAAATACTGAAGTCTCAGGTATATAGAATTTATACTACTCGC GGGACGTAAAGCCCCTCTGTGGTTAGCGTCGCAGCGTCGAGTAAATTCCTTATAGA GCCTAAACCTTGATAATTTCGACGTACCGTTATAACGCAATTAATAGACTTCTCAT TTTCCTGCCGAGTCGGGTCTGGTATAGTCTAGGACGGGGGTAGATATGATCGTCGT CTTCTCTAATCTAATTTAATCTATAACCACAGCGTACAAGTAAGGTATGTAAGATA CAGAGATAAATTAGAGATTTGTGTTACTCCGCATGTTGAACTAAACCCAAAGGTTC ACGCCGTATGCCTTTCAAGTTCCTCCGCTCAAAAGGCTCCGGGTGTCCCCTACCCG ATATGGCGGAAATCGTTAATTCTCATAACGACCAACCTTACCTTGGACACACCTAA GCACTAAGTCGGTAAATGGAGTACACAATGTGGGAGTTGTGTTTAACATAATGAGG CTCGTTCAGACTATGTTCGAGGCGTATAACGATTTGTGACAGATTCCTCATCAACT CGGGTCAGATTTATAGCAATGGTAAATTCCCTATATCCTA |
| 100 | 39.60% | TATGGTGTGGCACATATGAATAAAACAAGGAGAAGCAGCCGACAATACTTAGAACG TGTCAGAACAATCAAGATGTCTGAAACGTTCAACAATCGAGTTATTCCGGGCTAAT TTATTCCCATCCTTATATACAGAGCCGCACAATACCAAGTAACGTGCTTTGGGCCA CGAACTCACTCTAGTCTTCCGGACCCTCCGGTACTACTCGGTATGGTGGATATTCA TGAGAATGGTTTTAGTCTTAAAAAAATGTGAACAAGAAAACATTTACGTCCAAGAA AGCGGTATTTGTTTGGGTCTAGGAAACAATCAGTCGTGGACCTGGGCGAGATCGG CTGTTTTCGACCGATTTTATGCTAAGCAGAAGGAAGTGACCGAGGTTGTGTTTAGA TCCAGTAAAAGTCGTCATACCCGAGGAGATTTCTGTGGTGCCTAGTGACTAGCGAT CCCGTGCAGCAGTTCAAATGCGCTGGATAGTTCGCTCCTGCACCACTAGTTCACAC CAGAAGTATGTCTTTTAAGAGACTGTCTAAGAAATATAGTCTCTAAACGTGACTAT CGTTCACTCCCTGTACAAATCTAGGACTAACGGGTATAGATTAAACGTATTAGAAT TCGGAGCATTAGAATTTTGTTGTTCTAAGTTAGGATGATTTCAAGTGTCCATGTA AATTGAGGTCAATATAGGACGATCTACATCCGAGATAGGCCAAGTACGATTCTGTG TTACATTTTGCGTTCGCACAAGCTAGGACGAGGGTATGAGCATTTTGTGCTAACCG AATGAGATGCAGCTTATTGTATCCTTACCCGCAACATAGGGCATGAAGGCGTGGTT CGAGAATCGCGCGAGATAAATACATGTTTCGATTTATGTCAACCACTGCAATGGTT TATAAATGTTATTCAAGCATCGATTCAATAACCTCTGGATGTAGTAATATCTGCGG GTGTGTAAGTGCGATATCCTAAGTCGGGAGATTTAACAATACCTTGGGATGCTCCG GACAATTTTCGACGTACGCAATTATGAACATGCATTGATTGACTAAACTTAAGAAA CATAATCAGTGTATAGTATTGTAACAATGGATTCTGAGTGTCTAATGTTTTCTCGC TCCATGTTATAACACATAATTATACTTATAATACCATCCCATCTTTAAGTACAAAA CCTTGTTGCGCTGCTTTATGGAGACTATTGAGCCCAACGGGTTGAGTGGTTATTAC TATTTGAAGTAAAAGCAGTATCTACTCAGATTCCTAGAGGTAAATATGAACTTGTT TTCTATCTGGTTATCTATTTTTAGTTTTATGGATATGGACGAAGTTAAAAGTTATA GACCTGACATTCTTCTCCCATAGGTATAGAAGTGGAGTTAAACAAGTTCTTAGTGG GGGAAATGACGTACAGACTACTATCTTGATGATAGCTTTTCGATCAAACAAGAGTT TCAACCGCTGTAAAGGTTTATATGCGATGTAGTGTGGTACGATAACGTACTTTGCC GATCATTCACTGATTCCATTAGGTACGACACTCTCAGTTACAAAGCGGTACTAACC TAGCAAAAAGTGAATATCGCCCTACAAACTATTACTGGAGTGCGGTGGCAGCTTTG GCGAAAATTGGCCGAACTCTTTGCTGTTTATATGGTAACTATTCTCACTATGCTAC TGATTGGAAAAGATATTTGCCAACTAATAGTCGTAATGTTAGTATTGATAGGGAT AATAGGCATTTAAAGTTCCCTGAAACATACGGTAAATAAGATCTCTTTTAACAACA CCAGGGGTGGCTCACTGGGGTAGCAAATACTTAACGATCCCTTTTTCATCAAGTGA GTTATCTGCTTTGGATTCTTACAACTAGATGTTATAAAGAAGAAGCTGCGCAGTT TGCATGACTAAAATTTATATGAAGTAGTAGTTATTAGTACTATCTCTTAGTAGGCT AGAATGTAAACCTGCAGACATCATGGAATGCACATACCCG |

TABLE 2-continued

Exemplary 2.0 Kilobase Stuffer Sequences Having 40 ± 5% GC Content

| SEQ ID NO. | GC Content | Stuffer Sequence |
|---|---|---|
| 101 | 38.40% | TCAATAGCCCAGTCGGTTTTGTTAGATACATTTTATCGAATCTGTAAAGATATTTT<br>ATAATAAGATAATATCAGCGCCTAGCTGCGGAATTCCACTCAGAGAATACCTCTCC<br>TGAATATCAGCCTTAGTGGCGTTATACGATATTTCACACTCTCAAAATCCCGAGTC<br>AGACTATACCCGCGCATGTTTAGTAAAGGTTGATTCTGAGATCTCGAGTCCAAAAA<br>AGATACCCACTACTTTAAAGATTTGCATTCAGTTGTTCCATCGGCCTGGGTAGTAA<br>AGGGGGTATGCTCGCTCCGAGTCGATGGAACTGTAAATGTTAGCCCTGATACGCGG<br>AACATATCAGTAACAATCTTTACCTAATATGGAGTGGGATTAAGCTTCATAGAGGA<br>TATGAAACGCTCGTAGTATGGCTTCCTACATAAGTAGAATTATTAGCAACTAAGAT<br>ATTACCACTGCCCAATAAAAGAGATTCCACTTAGATTCATAGGTAGTCCCAACAAT<br>CATGTCTGAATACTAAATTGATCAATTGGACTATGTCAAAATTATTTTGAAGAAGT<br>AATCATCAACTTAGGCGCTTTTTAGTGTTAAGAGCGCGTTATTGCCAACCGGGCTA<br>AACCTGTGTAACTCTTCAATATTGTATATAATTATAGGCAGAATAAGCTATGAGTG<br>CATTATGAGATAAACATAGATTTTTGTCCACTCGAAATATTTGAATTTCTTGATCC<br>TGGGCTAGTTCAGCCATAAGTTTTCACTAATAGTTAGGACTACCAATTACACTACA<br>TTCAGTTGCTGAAATTCACATCACTGCCGCAATATTTATGAAGCTATTATTGCATT<br>AAGACTTAGGAGATAAATACGAAGTTGATATATTTTTCAGAATCAGCGAAAAGACC<br>CCCTATTGACATTACGAATTCGAGTTTAACGAGCACATAAATCAAACACTACGAGG<br>TTACCAAGATTGTATCTTACATTAATGCTATCCAGCCAGCCGTCATGTTTAACTGG<br>ATAGTCATAATTAATATCCAATGATCGTTTCACGTAGCTGCATATCGAGGAAGTTG<br>TATAATTGAAAACCCACACATTAGAATGCATGGTGCATCGCTAGGGTTTATCTTAT<br>CTTGCTCGTGCCAAGAGTGTAGAAAGCCACATATTGATACGGAAGCTGCCTAGGAG<br>GTTGGTATATGTTGATTGTGCTCACCATCTCCCTTCCTAATCTCCTAGTGTTAAGT<br>CCAATCAGTGGGCTGGCTCTGGTTAAAAGTAATATACACGCTAGATCTCTCTACTA<br>TAATACAGGCTAAGCCTACGCGCTTTCAATGCACTGATTACCAACTTAGCTACGGC<br>CAGCCCCATTTAATGAATTATCTCAGATGAATTCAGACATTATTCTCTACAAGGAC<br>ACTTTAGAGTGTCCTGCGGAGGCATAATTATTATCTAAGATGGGGTAAGTCCGATG<br>GAAGACACAGATACATCGGACTATTCCTATTAGCCGAGAGTCAACCGTTAGAACTC<br>GGAAAAAGACATCGAAGCCGGTAACCTACGCACTATAAATTTCCGCAGAGACATAT<br>GTAAAGTTTTATTAGAACTGGTATCTTGATTACGATTCTTAACTCTCATACGCCGG<br>TCCGGAATTTGTGACTCGAGAAAATGTAATGACATGCTCCAATTGATTTCAAAATT<br>AGATTTAAGGTCAGCGAACTATGTTTATTCAACCGTTTACAACGCTATTATGCGCG<br>ATGGATGGGGCCTTGTATCTAGAAACCGAATAATAACATACCTGTTAAATGGCAAA<br>CTTAGATTATTGCGATTAATTCTCACTTCAGAGGGTTATCGTGCCGAATTCCTGAC<br>TTTGGAATAATAAAGTTGATATTGAGGTGCAATATCAACTACACTGGTTTAACCTT<br>TAAACACATGGAGTCAAGTTTTCGCTATGCCAGCCGGTTATGCAGCTAGGATTAAT<br>ATTAGAGCTCTTTTCTAATTCGTCCTAATAATCTCTTCAC |

In one embodiment, the first stuffer has a sequence comprising at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, at least 245, at least 250, at least 275, at least 300, at least 325, at least 350, at least 375, at least 400, at least 425, at least 450, at least 475, or at least 500 nucleotides of a sequence set forth in Table 2. In another embodiment, the second stuffer has a sequence comprising at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, at least 245, at least 250, at least 275, at least 300, at least 325, at least 350, at least 375, at least 400, at least 425, at least 450, at least 475, or at least 500 nucleotides of a sequence set forth in Table 2.

It is preferable that the stuffer sequence not interfere with the resolution of the cleavage site at the target nucleic acid. Thus, the stuffer sequence should have minimal sequence identity to the nucleic acid sequence at the cleavage site of the target nucleic acid. In some embodiments, the stuffer sequence is less than 80%, 70%, 60%, 55%, 50%, 45%, 40%, 35%, 30%, 25%, 20%, or 10% identical to any nucleic acid sequence within 500, 450, 400, 350, 300, 250, 200, 150, 100, 50 nucleotides from the cleavage site of the target nucleic acid. In some embodiments, the stuffer sequence is less than 80%, 70%, 60%, 55%, 50%, 45%, 40%, 35%, 30%, 25%, 20%, or 10% identical to any nucleic acid sequence within 500, 450, 400, 350, 300, 250, 200, 150, 100, 50 base pairs from the cleavage site of the target nucleic acid.

In order to avoid off-target molecular recombination events, it is preferable that the stuffer sequence have minimal homology to a nucleic acid sequence in the genome of the target cell. In some embodiments, the stuffer sequence has minimal sequence identity to a nucleic acid in the genome of the target cell. In some embodiments, the stuffer sequence is less than 80%, 70%, 60%, 55%, 50%, 45%, 40%, 35%, 30%, 25%, 20%, or 10% identical to any nucleic acid sequence of the same length (as measured in base pairs or nucleotides) in the genome of the target cell. In some embodiments, a 20 base pair stretch of the stuffer sequence is less than 80%, 70%, 60%, 55%, 50%, 45%, 40%, 35%, 30%, 25%, 20%, or 10% identical to any at least 20 base pair stretch of nucleic acid of the target cell genome. In some embodiments, a 20 nucleotide stretch of the stuffer sequence is less than 60%, 55%, 50%, 45%, 40%, 35%, 30%, 25%, 20%, or 10% identical to any at least 20 nucleotide stretch of nucleic acid of the target cell genome.

In some embodiments, the stuffer sequence has minimal sequence identity to a nucleic acid sequence in the donor template (e.g., the nucleic acid sequence of the cargo, or the nucleic acid sequence of a priming site present in the donor template). In some embodiments, the stuffer sequence is less than 80%, 70%, 60%, 55%, 50%, 45%, 40%, 35%, 30%, 25%, 20%, or 10% identical to any nucleic acid sequence of the same length (as measured in base pairs or nucleotides) in the donor template. In some embodiments, a 20 base pair stretch of the stuffer sequence is less than 80%, 70%, 60%, 55%, 50%, 45%, 40%, 35%, 30%, 25%, 20%, or 10% identical to any 20 base pair stretch of nucleic acid of the donor template. In some embodiments, a 20 nucleotide stretch of the stuffer sequence is less than 80%, 70%, 60%, 55%, 50%, 45%, 40%, 35%, 30%, 25%, 20%, or 10% identical to any 20 nucleotide stretch of nucleic acid of the donor template.

In some embodiments, the length of the first homology arm and its adjacent stuffer sequence (i.e., A1+S1) is approximately equal to the length of the second homology arm and its adjacent stuffer sequence (i.e., A2+S2). For example, in some embodiments the length of A1+S1 is the same as the length of A2+S2 (as determined in base pairs or nucleotides). In some embodiments, the length of A1+S1 differs from the length of A2+S2 by 25 nucleotides or less. In some embodiments, the length of A1+S1 differs from the length of A2+S2 by 24, 23, 22, 21, 20, 19 18, 17, 16, 15, 14, 13, 12, 11, 10, 9, 8, 7, 6, 5, 4, 3, or 2 nucleotides or less. In some embodiments, the length of A1+S1 differs from the length of A2+S2 by 25 base pairs or less. In some embodiments, the length of A1+S1 differs from the length of A2+S2 by 24, 23, 22, 21, 20, 19 18, 17, 16, 15, 14, 13, 12, 11, 10, 9, 8, 7, 6, 5, 4, 3, or 2 base pairs or less.

In some embodiments, the length of A1+H1 is 250 base pairs or less. In some embodiments, the length of A1+H1 is 200 base pairs or less. In some embodiments, the length of A1+H1 is 150 base pairs or less. In some embodiments, the length of A1+H1 is 100 base pairs or less. In some embodiments, the length of A1+H1 is 50 base pairs or less. In some embodiments, the length of A1+H1 is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 base pairs. In some embodiments, the length of A1+H1 is 40 base pairs. In some embodiments, the length of A2+H2 is 250 base pairs or less. In some embodiments, the length of A2+H2 is 200 base pairs or less. In some embodiments, the length of A2+H2 is 150 base pairs or less. In some embodiments, the length of A2+H2 is 100 base pairs or less. In some embodiments, the length of A2+H2 is 50 base pairs or less. In some embodiments, the length of A2+H2 is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 base pairs. In some embodiments, the length of A2+H2 is 40 base pairs.

In some embodiments, the length of A1+S1 is the same as the length of H1+X+H2 (as determined in nucleotides or base pairs). In some embodiments, the length of A1+S1 differs from the length of H1+X+H2 by less than 25 nucleotides. In some embodiments, the length of A1+S1 differs from the length of H1+X+H2 by 24, 23, 22, 21, 20, 19 18, 17, 16, 15, 14, 13, 12, 11, 10, 9, 8, 7, 6, 5, 4, 3, or 2 nucleotides. In some embodiments, the length of A1+S1 differs from the length of H1+X+H2 by less than 25 base pairs. In some embodiments, the length of A1+S1 differs from the length of H1+X+H2 by 24, 23, 22, 21, 20, 19 18, 17, 16, 15, 14, 13, 12, 11, 10, 9, 8, 7, 6, 5, 4, 3, or 2 base pairs.

In some embodiments, the length of A2+S2 is the same as the length of H1+X+H2 (as determined in nucleotides or base pairs). In some embodiments, the length of A2+S2 differs from the length of H1+X+H2 by less than 25 nucleotides. In some embodiments, the length of A2+S2 differs from the length of H1+X+H2 by 24, 23, 22, 21, 20, 19 18, 17, 16, 15, 14, 13, 12, 11, 10, 9, 8, 7, 6, 5, 4, 3, or 2 nucleotides. In some embodiments, the length of A2+S2 differs from the length of H1+X+H2 by less than 25 base pairs. In some embodiments, the length of A2+S2 differs from the length of H1+X+H2 by 24, 23, 22, 21, 20, 19 18, 17, 16, 15, 14, 13, 12, 11, 10, 9, 8, 7, 6, 5, 4, 3, or 2 base pairs.

Genome Editing Systems

The term "genome editing system" refers to any system having RNA-guided DNA editing activity. In addition to a donor template, described above, genome editing systems of the present disclosure include at least two components adapted from naturally occurring CRISPR systems: a guide RNA (gRNA) and an RNA-guided nuclease. These two components form a complex that is capable of associating with a specific nucleic acid sequence and editing the DNA in or around that nucleic acid sequence, for instance by making one or more of a single-strand break (an SSB or nick), a double-strand break (a DSB) and/or a point mutation. In certain embodiments, the genome editing system is a transiently active genome editing system. In certain embodiments, the genome editing system can alter both a cellular endogenous target gene and the RNA-guided-nuclease expression. In certain embodiments, the gRNA/RNA-guided nuclease complex can cleave both the nucleic acid encoding the RNA-guided nuclease and the nucleic acid encoding the cellular endogenous target gene.

Naturally occurring CRISPR systems are organized evolutionarily into two classes and five types (Makarova et al. Nat Rev Microbiol. 2011 June; 9(6): 467-477 (Makarova), incorporated by reference herein), and while genome editing systems of the present disclosure may adapt components of any type or class of naturally occurring CRISPR system, the embodiments presented herein are generally adapted from Class 2, and type II or V CRISPR systems. Class 2 systems, which encompass types II and V, are characterized by relatively large, multidomain RNA-guided nuclease proteins (e.g., Cas9 or Cpf1) and one or more guide RNAs (e.g., a crRNA and, optionally, a tracrRNA) that form ribonucleoprotein (RNP) complexes that associate with (i.e. target) and cleave specific loci complementary to a targeting (or spacer) sequence of the crRNA. Genome editing systems according to the present disclosure similarly target and edit cellular DNA sequences, but differ significantly from CRISPR systems occurring in nature. For example, the unimolecular guide RNAs described herein do not occur in nature, and both guide RNAs and RNA-guided nucleases according to this disclosure may incorporate any number of non-naturally occurring modifications.

Genome editing systems can be implemented (e.g., administered or delivered to a cell or a subject) in a variety of ways, and different implementations may be suitable for distinct applications. For instance, a genome editing system is implemented, in certain embodiments, as a protein/RNA complex (a ribonucleoprotein, or RNP), which can be included in a pharmaceutical composition that optionally includes a pharmaceutically acceptable carrier and/or an encapsulating agent, such as a lipid or polymer micro- or nano-particle, micelle, liposome, etc. In certain embodiments, a genome editing system is implemented as one or more nucleic acids encoding the RNA-guided nuclease and guide RNA components described above (optionally with one or more additional components); in certain embodiments, the genome editing system is implemented as one or more vectors comprising such nucleic acids, for instance a viral vector such as an adeno-associated virus; and in certain embodiments, the genome editing system is implemented as a combination of any of the foregoing. Additional or modified implementations that operate according to the principles set forth herein will be apparent to the skilled artisan and are within the scope of this disclosure.

It should be noted that the genome editing systems of the present disclosure can be targeted to a single specific nucleotide sequence, or may be targeted to—and capable of editing in parallel—two or more specific nucleotide sequences through the use of two or more guide RNAs. The use of multiple gRNAs is referred to as "multiplexing" throughout this disclosure, and can be employed to target multiple, unrelated target sequences of interest, or to form multiple SSBs or DSBs within a single target domain and, in some cases, to generate specific edits within such target domain. For example, International Patent Publication No. WO 2015/138510 by Maeder et al. (Maeder), which is incorporated by reference herein, describes a genome editing system for correcting a point mutation (C.2991+1655A to G) in the human CEP290 gene that results in the creation of a cryptic splice site, which in turn reduces or eliminates the function of the gene. The genome editing system of Maeder utilizes two guide RNAs targeted to sequences on either side of (i.e. flanking) the point mutation, and forms DSBs that flank the mutation. This, in turn, promotes deletion of the intervening sequence, including the mutation, thereby eliminating the cryptic splice site and restoring normal gene function.

As another example, WO 2016/073990 by Cotta-Ramusino, et al. ("Cotta-Ramusino"), incorporated by reference herein, describes a genome editing system that utilizes two gRNAs in combination with a Cas9 nickase (a Cas9 that makes a single strand nick such as S. pyogenes D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, WO 2015/070083 by Palestrant et al. ("Palestrant", incorporated by reference herein) describes a gRNA targeted to a nucleotide sequence encoding Cas9 (referred to as a "governing RNA"), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

Genome editing systems can, in some instances, form double strand breaks that are repaired by cellular DNA double-strand break mechanisms such as NHEJ or HDR. These mechanisms are described throughout the literature, for example by Davis & Maizels, PNAS, 111(10):E924-932, Mar. 11, 2014 (Davis) (describing Alt-HDR); Frit et al. DNA Repair 17(2014) 81-97 (Frit) (describing Alt-NHEJ); and Iyama and Wilson III, DNA Repair (Amst.) 2013-August; 12(8): 620-636 (Iyama) (describing canonical HDR and NHEJ pathways generally).

Where genome editing systems operate by forming DSBs, such systems optionally include one or more components that promote or facilitate a particular mode of double-strand break repair or a particular repair outcome. For instance, Cotta-Ramusino also describes genome editing systems in which a single-stranded oligonucleotide "donor template" is added; the donor template is incorporated into a target region of cellular DNA that is cleaved by the genome editing system, and can result in a change in the target sequence.

In certain embodiments, genome editing systems modify a target sequence, or modify expression of a gene in or near the target sequence, without causing single- or double-strand breaks. For example, a genome editing system may include an RNA-guided nuclease fused to a functional domain that acts on DNA, thereby modifying the target sequence or its expression. As one example, an RNA-guided nuclease can be connected to (e.g., fused to) a cytidine deaminase functional domain, and may operate by generating targeted C-to-A substitutions. Exemplary nuclease/deaminase fusions are described in Komor et al. Nature 533, 420-424 (19 May 2016) ("Komor"), which is incorporated by reference. Alternatively, a genome editing system may utilize a cleavage-inactivated (i.e. a "dead") nuclease, such as a dead Cas9 (dCas9), and may operate by forming stable complexes on one or more targeted regions of cellular DNA, thereby interfering with functions involving the targeted region(s) including, without limitation, mRNA transcription, chromatin remodeling, etc.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). gRNAs and their component parts are described throughout the literature, for instance in Briner et al. (Molecular Cell 56(2), 333-339, Oct. 23, 2014 (Briner), which is incorporated by reference), and in Cotta-Ramusino.

In bacteria and archaea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, for instance, but not by way of limitation, by means of a four nucleotide (e.g., GAAA) "tetraloop" or "linker" sequence bridging complementary regions of the crRNA (at its 3' end) and the tracrRNA (at its 5' end). (Mali et al. Science. 2013 Feb. 15; 339(6121): 823-826 ("Mali"); Jiang et al. Nat Biotechnol. 2013 March; 31(3): 233-239 ("Jiang"); and Jinek et al., 2012 Science August 17; 337(6096): 816-821 ("Jinek"), all of which are incorporated by reference herein.)

Guide RNAs, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu et al. et al., Nat Biotechnol. 2013 September; 31(9): 827-832, ("Hsu"), incorporated by reference herein), "complementarity regions" (Cotta-Ramusino), "spacers" (Briner) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes. (Nishimasu et al. et al., Cell 156, 935-949, Feb. 27, 2014 (Nishimasu 2014) and Nishimasu et al., Cell 162, 1113-1126, Aug. 27, 2015 (Nishimasu 2015), both incorporated by reference herein). It should be noted that the first and/or second complementarity domains may contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for instance through the use of A-G swaps as described in Briner, or A-U swaps. These and other similar modifications to the first and second complementarity domains are within the scope of the present disclosure.

Along with the first and second complementarity domains, Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain," (Cotta-Ramusino) "stem loop 1" (Nishimasu 2014 and 2015) and the "nexus" (Briner). One or more additional stem loop structures are generally present near the 3' end of the gRNA, with the number varying by species: S. pyogenes gRNAs typically include two 3' stem loops (for a total of four stem loop structures including the repeat:anti-repeat duplex), while s. aureus and other species have only one (for a total of three stem loop structures). A description of conserved stem loop structures (and gRNA structures more generally) organized by species is provided in Briner.

While the foregoing description has focused on gRNAs for use with Cas9, it should be appreciated that other RNA-guided nucleases have been (or may in the future be) discovered or invented which utilize gRNAs that differ in some ways from those described to this point. For instance, Cpf1 ("CRISPR from Prevotella and Franciscella 1") is a recently discovered RNA-guided nuclease that does not require a tracrRNA to function. (Zetsche et al., 2015, Cell 163, 759-771 Oct. 22, 2015 (Zetsche I), incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate, however, that although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or modular gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

gRNA design

Methods for selection and validation of target sequences as well as off-target analyses have been described previously, e.g., in Mali; Hsu; Fu et al., 2014 Nat. Biotechnol. 32(3): 279-84, Heigwer et al., 2014 Nat Methods 11(2):122-3; Bae et al. (2014) Bioinformatics 30(10): 1473-5; and Xiao A et al. (2014) Bioinformatics 30(8): 1180-1182. Each of these references is incorporated by reference herein. As a non-limiting example, gRNA design can involve the use of a software tool to optimize the choice of potential target sequences corresponding to a user's target sequence, e.g., to minimize total off-target activity across the genome. While off-target activity is not limited to cleavage, the cleavage efficiency at each off-target sequence can be predicted, e.g., using an experimentally-derived weighting scheme. These and other guide selection methods are described in detail in Maeder and Cotta-Ramusino.

gRNA Modifications

The activity, stability, or other characteristics of gRNAs can be altered through the incorporation of certain modifications. As one example, transiently expressed or delivered nucleic acids can be prone to degradation by, e.g., cellular nucleases. Accordingly, the gRNAs described herein can contain one or more modified nucleosides or nucleotides which introduce stability toward nucleases. While not wishing to be bound by theory it is also believed that certain modified gRNAs described herein can exhibit a reduced innate immune response when introduced into cells. Those of skill in the art will be aware of certain cellular responses commonly observed in cells, e.g., mammalian cells, in response to exogenous nucleic acids, particularly those of viral or bacterial origin. Such responses, which can include induction of cytokine expression and release and cell death, may be reduced or eliminated altogether by the modifications presented herein.

Certain exemplary modifications discussed in this section can be included at any position within a gRNA sequence including, without limitation at or near the 5' end (e.g., within 1-10, 1-5, or 1-2 nucleotides of the 5' end) and/or at or near the 3' end (e.g., within 1-10, 1-5, or 1-2 nucleotides of the 3' end). In some cases, modifications are positioned within functional motifs, such as the repeat-anti-repeat duplex of a Cas9 gRNA, a stem loop structure of a Cas9 or Cpf1 gRNA, and/or a targeting domain of a gRNA.

As one example, the 5' end of a gRNA can include a eukaryotic mRNA cap structure or cap analog (e.g., a G(5')ppp(5')G cap analog, a m7G(5')ppp(5')G cap analog, or a 3'-O-Me-m7G(5')ppp(5')G anti reverse cap analog (ARCA)), as shown below:

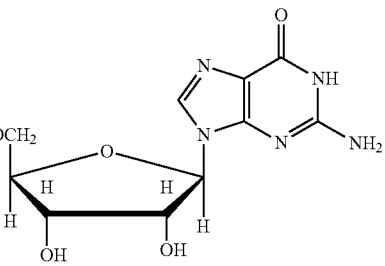

The cap or cap analog can be included during either chemical synthesis or in vitro transcription of the gRNA.

Along similar lines, the 5' end of the gRNA can lack a 5' triphosphate group. For instance, in vitro transcribed gRNAs can be phosphatase-treated (e.g., using calf intestinal alkaline phosphatase) to remove a 5' triphosphate group.

Another common modification involves the addition, at the 3' end of a gRNA, of a plurality (e.g., 1-10, 10-20, or 25-200) of adenine (A) residues referred to as a polyA tract. The polyA tract can be added to a gRNA during chemical synthesis, following in vitro transcription using a polyadenosine polymerase (e.g., E. coli Poly(A)Polymerase), or in vivo by means of a polyadenylation sequence, as described in Maeder.

It should be noted that the modifications described herein can be combined in any suitable manner, e.g., a gRNA, whether transcribed in vivo from a DNA vector, or in vitro transcribed gRNA, can include either or both of a 5' cap structure or cap analog and a 3' polyA tract.

Guide RNAs can be modified at a 3' terminal U ribose. For example, the two terminal hydroxyl groups of the U ribose can be oxidized to aldehyde groups and a concomitant opening of the ribose ring to afford a modified nucleoside as shown below:

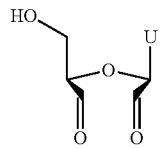

wherein "U" can be an unmodified or modified uridine.

The 3' terminal U ribose can be modified with a 2'3' cyclic phosphate as shown below:

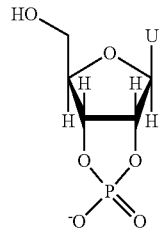

wherein "U" can be an unmodified or modified uridine.

Guide RNAs can contain 3' nucleotides which can be stabilized against degradation, e.g., by incorporating one or more of the modified nucleotides described herein. In certain embodiments, uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In certain embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., NH₂; alkylamino, dialkylamino, heterocyclyl, arylamino, diarylamino, heteroarylamino, diheteroarylamino, or amino acid); or cyano (—CN). In certain embodiments, the phosphate backbone can be modified as described herein, e.g., with a phosphothioate (PhTx) group. In certain embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

Guide RNAs can also include "locked" nucleic acids (LNA) in which the 2' OH-group can be connected, e.g., by a C1-6 alkylene or C1-6 heteroalkylene bridge, to the 4' carbon of the same ribose sugar. Any suitable moiety can be used to provide such bridges, include without limitation methylene, propylene, ether, or amino bridges; O-amino (wherein amino can be, e.g., NH₂; alkylamino, dialkylamino, heterocyclyl, arylamino, diarylamino, heteroarylamino, or diheteroarylamino, ethylenediamine, or polyamino) and aminoalkoxy or O(CH$_2$)$_n$-amino (wherein amino can be, e.g., NH$_2$; alkylamino, dialkylamino, heterocyclyl, arylamino, diarylamino, heteroarylamino, or diheteroarylamino, ethylenediamine, or polyamino).

In certain embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'→2')).

Generally, gRNAs include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a gRNA comprises a 4'-S, 4'-Se or a 4'-C-aminomethyl-2'-O-Me modification.

In certain embodiments, deaza nucleotides, e.g., 7-deaza-adenosine, can be incorporated into the gRNA. In certain embodiments, O- and N-alkylated nucleotides, e.g., N6-methyl adenosine, can be incorporated into the gRNA. In certain embodiments, one or more or all of the nucleotides in a gRNA are deoxynucleotides.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., S. pyogenes vs. S. aureus) or variation (e.g., full-length vs. truncated or split; naturally-occurring PAM specificity vs. engineered PAM specificity, etc.) of RNA-guided nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 3' of the protospacer as visualized relative to the top or complementary strand:

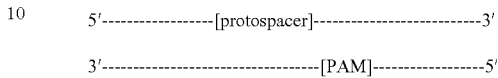

Cpf1, on the other hand, generally recognizes PAM sequences that are 5' of the protospacer:

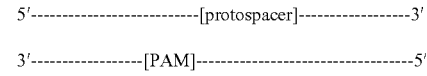

In addition to recognizing specific sequential orientations of PAMs and protospacers, RNA-guided nucleases can also recognize specific PAM sequences. S. aureus Cas9, for instance, recognizes a PAM sequence of NNGRRT or NNGRRV, wherein the N residues are immediately 3' of the region recognized by the gRNA targeting domain. S. pyogenes Cas9 recognizes NGG PAM sequences. And F. novicida Cpf1 recognizes a TTN PAM sequence. PAM sequences have been identified for a variety of RNA-guided nucleases, and a strategy for identifying novel PAM sequences has been described by Shmakov et al., 2015, Molecular Cell 60, 385-397, Nov. 5, 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., Cell 154(6), 1380-1389, Sep. 12, 2013 (Ran), incorporated by reference herein), or that do not cut at all.

Cas9

Crystal structures have been determined for S. pyogenes Cas9 (Jinek 2014), and for S. aureus Cas9 in complex with a unimolecular guide RNA and a target DNA (Nishimasu 2014; Anders 2014; and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g., a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e. bottom) strand of the target nucleic acid. It may be formed from two or more split RuvC motifs (such as RuvC I, RuvC II, and RuvC III in S. pyogenes and S. aureus). The HNH domain, meanwhile, is structurally similar to HNN endonuclease motifs, and cleaves the complementary (i.e. top) strand of the target nucleic acid. The PI domain, as its name suggests, contributes to PAM specificity.

While certain functions of Cas9 are linked to (but not necessarily fully determined by) the specific domains set forth above, these and other functions may be mediated or influenced by other Cas9 domains, or by multiple domains on either lobe. For instance, in S. pyogenes Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains).

Cpf1

The crystal structure of Acidaminococcus sp. Cpf1 in complex with crRNA and a double-stranded (ds) DNA target including a TTTN PAM sequence has been solved by Yamano et al. (Cell. 2016 May 5; 165(4): 949-962 (Yamano), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Modifications of RNA-Guided Nucleases

The RNA-guided nucleases described above have activities and properties that can be useful in a variety of applications, but the skilled artisan will appreciate that RNA-guided nucleases can also be modified in certain instances, to alter cleavage activity, PAM specificity, or other structural or functional features.

Turning first to modifications that alter cleavage activity, mutations that reduce or eliminate the activity of domains within the NUC lobe have been described above. Exemplary mutations that may be made in the RuvC domains, in the Cas9 HNH domain, or in the Cpf1 Nuc domain are described in Ran and Yamano, as well as in Cotta-Ramusino. In general, mutations that reduce or eliminate activity in one of the two nuclease domains result in RNA-guided nucleases with nickase activity, but it should be noted that the type of nickase activity varies depending on which domain is inactivated. As one example, inactivation of a RuvC domain of a Cas9 will result in a nickase that cleaves the complementary or top strand as shown below (where C denotes the site of cleavage):

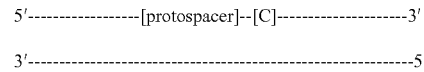

On the other hand, inactivation of a Cas9 HNH domain results in a nickase that cleaves the bottom or non-complementary strand:

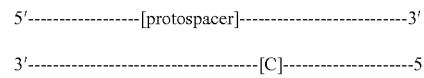

Modifications of PAM specificity relative to naturally occurring Cas9 reference molecules has been described by Kleinstiver et al. for both S. pyogenes (Kleinstiver et al., Nature. 2015 Jul. 23; 523(7561):481-5 (Kleinstiver I) and S. aureus (Kleinstiver et al., Nat Biotechnol. 2015 December; 33(12): 1293-1298 (Kleinstiver II)). Kleinstiver et al. have also described modifications that improve the targeting fidelity of Cas9 (Nature, 2016 January 28; 529, 490-495 (Kleinstiver III)). Each of these references is incorporated by reference herein.

RNA-guided nucleases have been split into two or more parts, as described by Zetsche et al. (Nat Biotechnol. 2015 February; 33(2):139-42 (Zetsche II), incorporated by reference), and by Fine et al. (Sci Rep. 2015 Jul. 1; 5:10777 (Fine), incorporated by reference).

RNA-guided nucleases can be, in certain embodiments, size-optimized or truncated, for instance via one or more deletions that reduce the size of the nuclease while still retaining gRNA association, target and PAM recognition, and cleavage activities. In certain embodiments, RNA guided nucleases are bound, covalently or non-covalently, to another polypeptide, nucleotide, or other structure, optionally by means of a linker. Exemplary bound nucleases and linkers are described by Guilinger et al., Nature Biotechnology 32, 577-582 (2014), which is incorporated by reference for all purposes herein.

RNA-guided nucleases also optionally include a tag, such as, but not limited to, a nuclear localization signal to facilitate movement of RNA-guided nuclease protein into the nucleus. In certain embodiments, the RNA-guided nuclease can incorporate C- and/or N-terminal nuclear localization signals. Nuclear localization sequences are known in the art and are described in Maeder and elsewhere.

The foregoing list of modifications is intended to be exemplary in nature, and the skilled artisan will appreciate, in view of the instant disclosure, that other modifications may be possible or desirable in certain applications. For brevity, therefore, exemplary systems, methods and compositions of the present disclosure are presented with reference to particular RNA-guided nucleases, but it should be understood that the RNA-guided nucleases used may be modified in ways that do not alter their operating principles. Such modifications are within the scope of the present disclosure.

Zinc Finger Nucleases (ZFNs) and Transcription Activator-Like Effector Nucleases (TALENs)

In addition to the CRISPR nucleases described above, there are several widely used systems to introduce targeted cuts into the genomes of cells, including Zinc Finger Nucleases (ZFNs) Transcription Activator-Like Effector Nucleases (TALENs), and Argonaute nuclease systems. See, e.g., Gaj et al., Trends in Biotechnology 31(7): 397-405 (2013); Gao et al., Nature Biotechnology, 34, 768-733 (2016); and Carlson et al., Molecular Therapy Nucleic Acids 1(1):e3 (2012). Accordingly, the methods and systems described herein can employ ZFNs and/or TALENs to cleave a target nucleic acid at a cut site. Once cleaved, the donor templates described herein may be integrated into the target nucleic acid at the cleavage site.

Accordingly, in some embodiments, the invention provides a method of altering a cell, comprising forming, in a target nucleic acid of the cell, a break, (e.g., a single-strand break or a double-strand break) at a cleavage site using a ZFN or TALEN, wherein the target nucleic acid comprises a first strand comprising wherein the target nucleic acid comprises a first strand comprising: a first homology arm 5' to the cleavage site, a first priming site either within the first homology arm or 5' to the first homology arm, a second homology arm 3' to the cleavage site, and a second priming site either within the second homology arm or 3' to the second homology arm, and recombining an exogenous oligonucleotide donor template with the target nucleic acid by homologous recombination to produce an altered nucleic acid, wherein a first strand of the exogenous oligonucleotide donor template comprises either: i) a cargo, a priming site that is substantially identical to the second priming site either within or 5' to the cargo, a first donor homology arm 5' to the cargo, and a second donor homology arm 3' to the cargo; or ii) a cargo, a first donor homology arm 5' to the cargo, a priming site that is substantially identical to the first priming site either within or 3' to the cargo, and a second donor homology arm 3' to the cargo, thereby altering the cell. Additional aspects of the invention set forth herein may likewise employ ZFNs and/or TALENs in place of CRISPR nucleases to generate a single- or double-stranded break at a cleavage site in a target nucleic acid.

Nucleic Acids Encoding RNA-Guided Nucleases

Nucleic acids encoding RNA-guided nucleases, e.g., Cas9, Cpf1 or functional fragments thereof, are provided herein. Exemplary nucleic acids encoding RNA-guided nucleases have been described previously (see, e.g., Cong 2013; Wang 2013; Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with 5-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in Cotta-Ramusino.

In addition, or alternatively, a nucleic acid encoding an RNA-guided nuclease may comprise a nuclear localization sequence (NLS). Nuclear localization sequences are known in the art.

Functional Analysis of Candidate Molecules

Candidate RNA-guided nucleases, gRNAs, and complexes thereof, can be evaluated by standard methods known in the art. See, e.g., Cotta-Ramusino. The stability of RNP complexes may be evaluated by differential scanning fluorimetry, as described below.

Differential Scanning Fluorimetry (DSF)

The thermostability of ribonucleoprotein (RNP) complexes comprising gRNAs and RNA-guided nucleases can be measured via DSF. The DSF technique measures the thermostability of a protein, which can increase under favorable conditions such as the addition of a binding RNA molecule, e.g., a gRNA.

A DSF assay can be performed according to any suitable protocol, and can be employed in any suitable setting, including without limitation (a) testing different conditions (e.g., different stoichiometric ratios of gRNA: RNA-guided nuclease protein, different buffer solutions, etc.) to identify optimal conditions for RNP formation; and (b) testing modifications (e.g., chemical modifications, alterations of sequence, etc.) of an RNA-guided nuclease and/or a gRNA to identify those modifications that improve RNP formation or stability. One readout of a DSF assay is a shift in melting temperature of the RNP complex; a relatively high shift suggests that the RNP complex is more stable (and may thus have greater activity or more favorable kinetics of formation, kinetics of degradation, or another functional characteristic) relative to a reference RNP complex characterized by a lower shift. When the DSF assay is deployed as a screening tool, a threshold melting temperature shift may be specified, so that the output is one or more RNPs having a melting temperature shift at or above the threshold. For instance, the threshold can be 5-10° C. (e.g., 5°, 6°, 7°, 8°, 9°, 10°) or more, and the output may be one or more RNPs characterized by a melting temperature shift greater than or equal to the threshold.

Two non-limiting examples of DSF assay conditions are set forth below:

To determine the best solution to form RNP complexes, a fixed concentration (e.g., 2 µM) of Cas9 in water+10× SYPRO Orange® (Life Technologies cat #S-6650) is dispensed into a 384 well plate. An equimolar amount of gRNA diluted in solutions with varied pH and salt is then added. After incubating at room temperature for 10' and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

The second assay consists of mixing various concentrations of gRNA with fixed concentration (e.g., 2 µM) Cas9 in optimal buffer from assay 1 above and incubating (e.g., at RT for 10') in a 384 well plate. An equal volume of optimal buffer+10×SYPRO Orange® (Life Technologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

Genome Editing Strategies

The genome editing systems described above are used, in various embodiments of the present disclosure, to generate edits in (i.e. to alter) targeted regions of DNA within or obtained from a cell. Various strategies are described herein to generate particular edits, and these strategies are generally described in terms of the desired repair outcome, the number and positioning of individual edits (e.g., SSBs or DSBs), and the target sites of such edits.

Genome editing strategies that involve the formation of SSBs or DSBs are characterized by repair outcomes including: (a) deletion of all or part of a targeted region; (b) insertion into or replacement of all or part of a targeted region; or (c) interruption of all or part of a targeted region. This grouping is not intended to be limiting, or to be binding to any particular theory or model, and is offered solely for economy of presentation. Skilled artisans will appreciate that the listed outcomes are not mutually exclusive and that some repairs may result in other outcomes. The description of a particular editing strategy or method should not be understood to require a particular repair outcome unless otherwise specified.

Replacement of a targeted region generally involves the replacement of all or part of the existing sequence within the targeted region with a homologous sequence, for instance through gene correction or gene conversion, two repair outcomes that are mediated by HDR pathways. HDR is promoted by the use of a donor template, which can be single-stranded or double-stranded, as described in greater detail below. Single- or double-stranded templates can be exogenous, in which case they will promote gene correction, or they can be endogenous (e.g., a homologous sequence within the cellular genome), to promote gene conversion. Exogenous templates can have asymmetric overhangs (i.e. the portion of the template that is complementary to the site of the DSB may be offset in a 3' or 5' direction, rather than being centered within the donor template), for instance as described by Richardson et al. (Nature Biotechnology 34, 339-344 (2016), (Richardson), incorporated by reference). In instances where the template is single-stranded, it can correspond to either the complementary (top) or non-complementary (bottom) strand of the targeted region.

Gene conversion and gene correction are facilitated, in some cases, by the formation of one or more nicks in or around the targeted region, as described in Ran and Cotta-Ramusino. In some cases, a dual-nickase strategy is used to form two offset SSBs that, in turn, form a single DSB having an overhang (e.g., a 5' overhang).

Interruption and/or deletion of all or part of a targeted sequence can be achieved by a variety of repair outcomes. As one example, a sequence can be deleted by simultaneously generating two or more DSBs that flank a targeted region, which is then excised when the DSBs are repaired, as is described in Maeder for the LCA10 mutation. As another example, a sequence can be interrupted by a deletion generated by formation of a double strand break with single-stranded overhangs, followed by exonucleolytic processing of the overhangs prior to repair.

One specific subset of target sequence interruptions is mediated by the formation of an indel within the targeted sequence, where the repair outcome is typically mediated by NHEJ pathways (including Alt-NHEJ). NHEJ is referred to as an "error prone" repair pathway because of its association with indel mutations. In some cases, however, a DSB is repaired by NHEJ without alteration of the sequence around it (a so-called "perfect" or "scarless" repair); this generally requires the two ends of the DSB to be perfectly ligated. Indels, meanwhile, are thought to arise from enzymatic processing of free DNA ends before they are ligated that adds and/or removes nucleotides from either or both strands of either or both free ends.

Because the enzymatic processing of free DSB ends may be stochastic in nature, indel mutations tend to be variable, occurring along a distribution, and can be influenced by a variety of factors, including the specific target site, the cell type used, the genome editing strategy used, etc. It is possible to draw limited generalizations about indel formation: deletions formed by repair of a single DSB are most commonly in the 1-50 bp range, but can reach greater than 100-200 bp. Insertions formed by repair of a single DSB tend to be shorter and often include short duplications of the sequence immediately surrounding the break site. However, it is possible to obtain large insertions, and in these cases, the inserted sequence has often been traced to other regions of the genome or to plasmid DNA present in the cells.

Indel mutations—and genome editing systems configured to produce indels—are useful for interrupting target sequences, for example, when the generation of a specific final sequence is not required and/or where a frameshift mutation would be tolerated. They can also be useful in settings where particular sequences are preferred, insofar as the certain sequences desired tend to occur preferentially from the repair of an SSB or DSB at a given site. Indel mutations are also a useful tool for evaluating or screening the activity of particular genome editing systems and their components. In these and other settings, indels can be characterized by (a) their relative and absolute frequencies in the genomes of cells contacted with genome editing systems and (b) the distribution of numerical differences relative to the unedited sequence, e.g., ±1, ±2, ±3, etc. As one example, in a lead-finding setting, multiple gRNAs can be screened to identify those gRNAs that most efficiently drive cutting at a target site based on an indel readout under controlled conditions. Guides that produce indels at or above a threshold frequency, or that produce a particular distribution of indels, can be selected for further study and development. Indel frequency and distribution can also be useful as a readout for evaluating different genome editing system implementations or formulations and delivery methods, for instance by keeping the gRNA constant and varying certain other reaction conditions or delivery methods.

Multiplex Strategies

While exemplary strategies discussed above have focused on repair outcomes mediated by single DSBs, genome editing systems according to this disclosure may also be employed to generate two or more DSBs, either in the same locus or in different loci. Strategies for editing that involve the formation of multiple DSBs, or SSBs, are described in, for instance, Cotta-Ramusino.

Target Cells

The systems and methods described herein provide a streamlined approach for the detection and quantitative measurement of all possible gene editing events at a particular cut site, including targeted integration events, insertions, and deletions. These systems and methods rely on the use of donor templates comprising a 5' homology arm, a cargo, one or more priming sites, a 3' homology arm, and optionally a stuffer sequence. Such systems and methods can be used to edit virtually any cell type, at any target locus amenable to genome editing.

Genome editing systems according to this disclosure can be used to manipulate or alter a cell, e.g., to edit or alter a target nucleic acid. The manipulating can occur, in various embodiments, in vivo or ex vivo. In one embodiment, genome editing systems described herein are used to alter a nucleic acid in a target cell in vitro. In another embodiment, genome editing systems described herein are used to alter a nucleic acid in a target cell ex vivo. In another embodiment, genome editing systems described herein are used to alter a nucleic acid in a target cell in vivo.

A variety of cell types can be manipulated or altered according to the embodiments of this disclosure, and in some cases, such as in vivo applications, a plurality of cell types are altered or manipulated, for example by delivering genome editing systems according to this disclosure to a plurality of cell types. In other cases, however, it may be desirable to limit manipulation or alteration to a particular cell type or types. For instance, it can be desirable in some instances to edit a cell with limited differentiation potential or a terminally differentiated cell, such as a photoreceptor cell in the case of Maeder, in which modification of a genotype is expected to result in a change in cell phenotype. In other cases, however, it may be desirable to edit a less differentiated, multipotent or pluripotent, stem or progenitor cell. By way of example, the cell may be an embryonic stem cell, induced pluripotent stem cell (iPSC), hematopoietic stem/progenitor cell (HSPC), or other stem or progenitor cell type that differentiates into a cell type of relevance to a given application or indication.

In certain embodiments, the cell being manipulated is a bacterial cell. In other embodiments, the cell is an archaeal cell. In certain embodiments, the cell being manipulated is a eukaryotic cell. In one embodiment, the cell is a eukaryotic single-cell organism, e.g., an algal cell. In one embodiment, the cell is an animal cell. In one embodiment, the cell is an invertebrate cell, e.g., a fly cell or a worm cell. In another embodiment, the cell is a vertebrate cell. For example, but not by way of limitation, the cell can be a mammalian cell, a rodent cell, a mouse cell, a rat cell, a goat cell, a pig cell, a bird cell, a chicken cell, a turkey cell, a cow cell, a horse cell, a sheep cell, a pig cell, a fish cell, or a frog cell. In one embodiment, the cell is a non-human primate cell. In one embodiment, the cell is a human cell. In certain embodiments, the cell being manipulated is a somatic cell, a germ cell, or a prenatal cell. In certain embodiments, the cell being manipulated is a zygotic cell, a blastocyst cell, an embryonic cell, a stem cell, a mitotically competent cell, or a meiotically competent cell. In certain embodiments, the cell being manipulated is not part of a human embryo. In certain embodiments, the cell being manipulated is a $CD8^+$ T cell, a $CD8^+$ naïve T cell, a $CD4^+$ central memory T cell, a $CD8^+$ central memory T cell, a $CD4^+$ effector memory T cell, a $CD4^+$ effector memory T cell, a $CD4^+$ T cell, a $CD4^+$ stem cell memory T cell, a $CD8^+$ stem cell memory T cell, a $CD4^+$ helper T cell, a regulatory T cell, a cytotoxic T cell, a natural killer T cell, a CD4+ naïve T cell, a TH17 $CD4^+$ cell, a TH1 $CD4^+$ T cell, a TH2 $CD4^+$ T cell, a TH9 $CD4^+$ T cell, a $CD4^+$ Foxp3$^+$ T cell, a $CD4^+CD25^+$ $CD127^-$ T cell, a $CD4^+CD25^+$ $CD127^-$ Foxp3$^+$ T cell. In certain embodiments, the cell being manipulated is a long term hematopoietic stem cell, a short term hematopoietic stem cell, a multipotent progenitor cell, a lineage restricted progenitor cell, a lymphoid progenitor cell, a myeloid progenitor cell, a common myeloid progenitor cell, an erythroid progenitor cell, a megakaryocyte erythroid progenitor cell, a retinal cell, a photoreceptor cell, a rod cell, a cone cell, a retinal pigmented epithelium cell, a trabecular meshwork cell, a cochlear hair cell, an outer hair cell, an inner hair cell, a pulmonary epithelial cell, a bronchial epithelial cell, an alveolar epithelial cell, a pulmonary epithelial progenitor cell, a striated muscle cell, a cardiac muscle cell, a muscle satellite cell, a neuron, a neuronal stem cell, a mesenchymal stem cell, an induced pluripotent stem (iPS) cell, an embryonic stem cell, a monocyte, a megakaryocyte, a neutrophil, an eosinophil, a basophil, a mast cell, a reticulocyte, a B cell, e.g., a progenitor B cell, a Pre B cell, a Pro B cell, a memory B cell, a plasma B cell, a gastrointestinal epithelial cell, a biliary epithelial cell, a pancreatic ductal epithelial cell, an intestinal stem cell, a hepatocyte, a liver stellate cell, a Kupffer cell, an osteoblast, an osteoclast, an adipocyte, a preadipocyte, a pancreatic islet cell (e.g., a beta cell, an alpha cell, a delta cell), a pancreatic exocrine cell, a Schwann cell, or an oligodendrocyte.

In certain embodiments, the target cell is a circulating blood cell, e.g., a reticulocyte, megakaryocyte erythroid progenitor (MEP) cell, myeloid progenitor cell (CMP/GMP), lymphoid progenitor (LP) cell, hematopoietic stem/progenitor cell (HSC), or endothelial cell (EC). In certain embodiments, the target cell is a bone marrow cell (e.g., a reticulocyte, an erythroid cell (e.g., erythroblast), an MEP cell, myeloid progenitor cell (CMP/GMP), LP cell, erythroid progenitor (EP) cell, HSC, multipotent progenitor (MPP) cell, endothelial cell (EC), hemogenic endothelial (HE) cell, or mesenchymal stem cell). In certain embodiments, the target cell is a myeloid progenitor cell (e.g., a common myeloid progenitor (CMP) cell or granulocyte macrophage progenitor (GMP) cell). In certain embodiments, the target cell is a lymphoid progenitor cell, e.g., a common lymphoid progenitor (CLP) cell. In certain embodiments, the target cell is an erythroid progenitor cell (e.g., an MEP cell). In certain embodiments, the target cell is a hematopoietic stem/progenitor cell (e.g., a long term HSC (LT-HSC), short term HSC (ST-HSC), MPP cell, or lineage restricted progenitor (LRP) cell). In certain embodiments, the target cell is a $CD34^+$ cell, $CD34^+CD90^+$ cell, $CD34^+CD38^-$ cell, $CD34^+CD90^+CD49f^+CD38^-CD45RA^-$ cell, $CD105^+$ cell, $CD31^+$, or $CD133^+$ cell, or a $CD34^+CD90^+$ $CD133^+$ cell. In certain embodiments, the target cell is an umbilical cord blood $CD34^+$ HSPC, umbilical cord venous endothelial cell, umbilical cord arterial endothelial cell, amniotic fluid $CD34^+$ cell, amniotic fluid endothelial cell, placental endothelial cell, or placental hematopoietic $CD34^+$ cell. In certain embodiments, the target cell is a mobilized peripheral blood hematopoietic $CD34^+$ cell (after the patient is treated with a mobilization agent, e.g., G-CSF or Plerixafor). In certain embodiments, the target cell is a peripheral blood endothelial cell.

In certain embodiments, the manipulated cell is a plant cell, e.g., a monocot or a dicot cell. In one embodiment, the plant cell is maize, wheat, rice, corn or *Setaria*. In another embodiment, the plant cell is potato, soybean, tomato, tobacco, or *Arabidopsis*. Accordingly, in some embodiments, the invention provides compositions and methods for gene targeting and/or gene editing in monocot species of plant, or in dicot species of plant. The compositions, systems, and methods described herein are applicable to any plant species, including for example various dicot and monocot crops, such as tomato, cotton, maize (*Zea mays*), wheat, *Arabidopsis thaliana, Medicago truncatula, Solanum lycopersicum, Glycine max, Brachypodium distachyon, Oryza sativa, Sorghum bicolor*, or *Solanum tuberosum*.

As a corollary, the cell being altered or manipulated is, variously, a dividing cell or a non-dividing cell, depending on the cell type(s) being targeted and/or the desired editing outcome.

When cells are manipulated or altered ex vivo, the cells can be used (e.g., administered to a subject) immediately, or they can be maintained or stored for later use. Those of skill in the art will appreciate that cells can be maintained in culture or stored (e.g., frozen in liquid nitrogen) using any suitable method known in the art.

Target Nucleic Acids

The donor templates, systems, and methods described herein can be used to edit virtually any target gene in a cell.

Specific target nucleic acids can be selected for a desired application based on the cell type to be edited and the effect to be achieved.

In some embodiments, the target gene is a mammalian gene. In some embodiments, the target gene is a disease gene, i.e., a gene associated with a disease or disorder. In some embodiments, the target gene is a rodent gene, e.g., a mouse gene or a rat gene. In some embodiments, the target gene is a primate gene, e.g., a human gene. Exemplary mammalian target genes which may be edited using the donor templates, systems, and methods described herein include, but are not limited to, a mammalian β globin gene (HBB), a gamma globin gene (HBG1), a T-cell receptor alpha (TRAC) gene, a T-cell receptor beta (TRBC) gene, a Kruppel-like factor 1 (KLF1) gene, a dystrophin gene (DMD), a CCR5 gene, a CXCR4 gene, a PPP1R12C (AAVS1) gene, a Cystic Fibrosis Transmembrane Conductance Regulator (CFTR) gene, a B-cell lymphoma/leukemia 11 A (BCL11 A) gene, an hypoxanthine phosphoribosyltransferase (HPRT) gene, an albumin gene, a Factor VIII gene, a Factor IX gene, a Leucine-rich repeat kinase 2 (LRRK2) gene, an alpha-1-antitrypsin (A1 AT) gene, a Hungtingin (Htt) gene, a Transporter associated with Antigen Processing (TAP) 1 gene, a TAP2 gene, a tapasin gene (TAPBP), a rhodopsin (RHO) gene, a surfactant protein B gene (SFTPB), a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a class II major histocompatibility complex transactivator (CUT A) gene, a glucocorticoid receptor gene (GR), an IL2RG gene and an RFX5 gene. Exemplary plant target genes which may be edited using the donor templates, systems, and methods described herein include, but are not limited to, a plant FAD2 gene, a plant FAD3 gene, a plant ZP15 gene, a plant KASII gene, a plant MDH gene, and a plant EPSPS gene.

Cells and Cell Populations

In one aspect, the invention provides a cell, or population of cells, which comprise a donor template comprising one or more priming sites, e.g., a donor template comprising a cargo, one or two homology arms, and one or more priming sites. Exemplary donor templates comprising one or more priming sites are provided herein.

In one aspect, the invention provides a cell, or population of cells, which comprise a donor template for recombination with a target nucleic acid in the cell, wherein: (a) a first strand of the target nucleic acid comprises, from 5' to 3', P1-H1-X-H2-P2, wherein P1 is a first priming site; H1 is a first homology arm; X is a cleavage site; H2 is a second homology arm; and P2 is a second priming site; and wherein (b) a first strand of the donor template comprises, from 5' to 3', A1-P2'-N-A2, or A1-N-P1'-A2, wherein A1 is a homology arm that is substantially identical to H1; P2' is a priming site that is substantially identical to P2; N is a cargo; P1' is a priming site that is substantially identical to P1; and A2 is a homology arm that is substantially identical to H2. In an exemplary embodiment, the first strand of the donor template comprises, from 5' to 3', A1-P2'-N-P1'-A2.

Additional features of the homology arms, the priming sites, and the cargo are provided above.

In one embodiment, the first strand of the donor template further comprises one or more stuffer sequences, e.g., one, two, three, four or more stuffer sequences. For example, the first strand of the donor template can contain, in some embodiments, a first strand comprising, from 5' to 3', A1-S1-P2'-N-A2, or A1-N-P1'-S2-A2, where S1 is a first stuffer, and S2 is a second stuffer. In an exemplary embodiment, the first strand of the donor template can comprise, from 5' to 3', from 5' to 3', A1-S1-P2'-N-P1'-S2-A2. Additional features of the stuffer sequences are described above. In an exemplary embodiment, the stuffer comprises a random or heterologous sequence having a GC content of approximately 40%.

In one embodiment of the foregoing aspects, the donor template is integrated into the genome of the cell, or population of cells.

In one aspect, the invention provides a cell, or population of cells, which comprise an altered nucleic acid, wherein a first strand of the altered nucleic acid comprises, from 5' to 3', a first priming site, a first donor homology arm, a cargo, a priming site that is substantially identical to the first priming site, a second donor homology arm, and a second priming site.

In another aspect, the invention provides a cell, or population of cells, which comprise an altered nucleic acid, wherein a first strand of the altered nucleic acid comprises, from 5' to 3', a first priming site, a first donor homology arm, a priming site that is substantially identical to a second priming site, a cargo, a second donor homology arm, and the second priming site.

In another aspect, the invention provides a cell, or population of cells, which comprise an altered nucleic acid, wherein a first strand of the altered nucleic acid comprises, from 5' to 3', a first priming site, a first donor homology arm, a priming site that is substantially identical to a second priming site, a cargo, a priming site that is substantially identical to the first priming site, a second donor homology arm, and the second priming site.

The altered nucleic acid can optionally comprise one or more stuffer sequences. For example, the altered nucleic acid can comprise a first strand comprising, from 5' to 3', a first priming site, a first donor homology arm, a cargo, a priming site that is substantially identical to the first priming site, a first stuffer, a second donor homology arm, and a second priming site. In another embodiment, the altered nucleic acid can comprise a first strand comprising, from 5' to 3', a first priming site, a first donor homology arm, a first stuffer, a priming site that is substantially identical to a second priming site, a cargo, a second donor homology arm, and the second priming site. In another embodiment, the altered nucleic acid can comprise a first strand comprising, from 5' to 3', a first priming site, a first donor homology arm, a first stuffer, a priming site that is substantially identical to a second priming site, a cargo, a priming site that is substantially identical to the first priming site, a second stuffer, a second donor homology arm, and the second priming site.

In one embodiment of the foregoing aspects, the cell is derived from a cell comprising a nucleic acid having a first strand which comprises, from 5' to 3', the first priming site, a first homology arm substantially identical to the first donor homology arm, a cleavage site, a second homology arm substantially identical to the second donor homology arm, and the second priming site.

In one aspect, the invention provides a cell, or population of cells, comprising an altered nucleic acid, wherein the cell, or population of cells is produced by any of the methods disclosed herein.

The cell, or population of cells, can be provided as a therapeutic composition. Accordingly, in one aspect, the invention provides a therapeutic composition comprising the cell, or population of cells, as disclosed herein. The therapeutic composition can further comprise a pharmaceutically acceptable carrier or excipient. This may include a buffer suitable for administration to a subject.

The cell, or population of cells, can be of any cell type, including but not limited to the target cells disclosed herein, for example, eukaryotic cells, mammalian cells, plant cells, etc. In exemplary embodiments, the cell is a mammalian cell, e.g., a mouse, rat, goat, pig, bird, chicken, turkey, cow, horse, sheep, pig, fish, frog, primate, or human cell. In one embodiment, the cell is a human cell.

Exemplary cell types include, but are not limited to, immune cells (e.g., a T cell, a B cell, a natural killer cell, a monocyte, a macrophage cell, or a dendritic cell), stem cells (e.g., an embryonic stem cell, an induced pluripotent stem cell (iPSC), or a hematopoietic stem/progenitor cell (HSPC)), epithelial cells, endothelial cells, and neurons.

In an exemplary embodiment, the cell is a modified T cell comprising an altered TRAC gene. In another exemplary embodiment, the cell is a modified hematopoietic cell, e.g., a modified hematopoietic stem/progenitor cell, comprising an altered HBB gene.

In other exemplary embodiments, the cell is a plant cell. For example, the cell can be a monocot (e.g., maize, wheat, rice, corn, or *Setaria*), or a dicot (e.g., potato, soybean, tomato, tobacco, or *Arabidopsis*).

Implementation of Genome Editing Systems: Delivery, Formulations, and Routes of Administration As discussed above, the genome editing systems of this disclosure can be implemented in any suitable manner, meaning that the components of such systems, including without limitation the RNA-guided nuclease, gRNA, and optional donor template nucleic acid, can be delivered, formulated, or administered in any suitable form or combination of forms that results in the transduction, expression or introduction of a genome editing system and/or causes a desired repair outcome in a cell, tissue or subject. Tables 3 and 4 set forth several, non-limiting examples of genome editing system implementations. Those of skill in the art will appreciate, however, that these listings are not comprehensive, and that other implementations are possible. With reference to Table 3 in particular, the table lists several exemplary implementations of a genome editing system comprising a single gRNA and an optional donor template. However, genome editing systems according to this disclosure can incorporate multiple gRNAs, multiple RNA-guided nucleases, and other components such as proteins, and a variety of implementations will be evident to the skilled artisan based on the principles illustrated in the table. In the table, [N/A] indicates that the genome editing system does not include the indicated component.

TABLE 3

Genome Editing System Components

| RNA-guided Nuclease | gRNA | Donor Template | Comments |
|---|---|---|---|
| Protein | RNA | [N/A] | An RNA-guided nuclease protein complexed with a gRNA molecule (an RNP complex) |
| Protein | RNA | DNA | An RNA complex as described above plus a single-stranded or double-stranded donor template. |
| Protein | DNA | [N/A] | An RNA-guided nuclease protein plus gRNA transcribed from DNA. |
| Protein | DNA | DNA | An RNA-guided nuclease protein plus gRNA-encoding DNA and a separate DNA donor template. |
| Protein | DNA | | An RNA-guided nuclease protein and a single DNA encoding both a gRNA and a donor template. |
| | DNA | | A DNA or DNA vector encoding an RNA-guided nuclease, a gRNA and a donor template. |
| DNA | DNA | [N/A] | Two separate DNAs, or two separate DNA vectors, encoding the RNA-guided nuclease and the gRNA, respectively. |
| DNA | DNA | DNA | Three separate DNAs, or three separate DNA vectors, encoding the RNA-guided nuclease, the gRNA and the donor template, respectively. |
| DNA | | [N/A] | A DNA or DNA vector encoding an RNA-guided nuclease and a gRNA |
| DNA | | DNA | A first DNA or DNA vector encoding an RNA-guided nuclease and a gRNA, and a second DNA or DNA vector encoding a donor template. |
| DNA | | DNA | A first DNA or DNA vector encoding an RNA-guided nuclease and second DNA or DNA vector encoding a gRNA and a donor template. |
| | DNA DNA | | A first DNA or DNA vector encoding an RNA-guided nuclease and a donor template, and a second DNA or DNA vector encoding a gRNA |
| | DNA RNA | | A DNA or DNA vector encoding an RNA-guided nuclease and a donor template, and a gRNA |
| RNA | | [N/A] | An RNA or RNA vector encoding an RNA-guided nuclease and comprising a gRNA |
| RNA | | DNA | An RNA or RNA vector encoding an RNA-guided nuclease and comprising a gRNA, and a DNA or DNA vector encoding a donor template. |

Table 3 summarizes various delivery methods for the components of genome editing systems, as described herein. Again, the listing is intended to be exemplary rather than limiting.

TABLE 3

| Delivery Vector/Mode | Delivery into Non-Dividing Cells | Duration of Expression | Genome Integration | Type of Molecule Delivered |
|---|---|---|---|---|
| Physical (e.g., electroporation, particle gun, Calcium Phosphate transfection, cell compression or squeezing) | YES | Transient | NO | Nucleic Acids and Proteins |

TABLE 3-continued

| Delivery Vector/Mode | | Delivery into Non-Dividing Cells | Duration of Expression | Genome Integration | Type of Molecule Delivered |
|---|---|---|---|---|---|
| Viral | Retrovirus | NO | Stable | YES | RNA |
|  | Lentivirus | YES | Stable | YES/NO with modifications | RNA |
|  | Adenovirus | YES | Transient | NO | DNA |
|  | Adeno-Associated Virus (AAV) | YES | Stable | NO | DNA |
|  | Vaccinia Virus | YES | Very Transient | NO | DNA |
|  | Herpes Simplex Virus | YES | Stable | NO | DNA |
| Non-Viral | Cationic Liposomes | YES | Transient | Depends on what is delivered | Nucleic Acids and Proteins |
|  | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
|  | Engineered Bacteriophages | YES | Transient | NO | Nucleic Acids |
|  | Mammalian Virus-like Particles | YES | Transient | NO | Nucleic Acids |
|  | Biological liposomes: Erythrocyte Ghosts and Exosomes | YES | Transient | NO | Nucleic Acids |

Nucleic Acid-Based Delivery of Genome Editing Systems

Nucleic acids encoding the various elements of a genome editing system according to the present disclosure can be administered to subjects or delivered into cells by art-known methods or as described herein. For example, RNA-guided nuclease-encoding and/or gRNA-encoding DNA, as well as donor template nucleic acids can be delivered by, e.g., vectors (e.g., viral or non-viral vectors), non-vector based methods (e.g., using naked DNA or DNA complexes), or a combination thereof.

Nucleic acids encoding genome editing systems or components thereof can be delivered directly to cells as naked DNA or RNA, for instance by means of transfection or electroporation, or can be conjugated to molecules (e.g., N-acetylgalactosamine) promoting uptake by the target cells (e.g., erythrocytes, HSCs). Nucleic acid vectors, such as the vectors summarized in Table 4, can also be used.

Nucleic acid vectors can comprise one or more sequences encoding genome editing system components, such as an RNA-guided nuclease, a gRNA and/or a donor template. A vector can also comprise a sequence encoding a signal peptide (e.g., for nuclear localization, nucleolar localization, or mitochondrial localization), associated with (e.g., inserted into or fused to) a sequence coding for a protein. As one example, a nucleic acid vectors can include a Cas9 coding sequence that includes one or more nuclear localization sequences (e.g., a nuclear localization sequence from SV40).

The nucleic acid vector can also include any suitable number of regulatory/control elements, e.g., promoters, enhancers, introns, polyadenylation signals, Kozak consensus sequences, or internal ribosome entry sites (IRES). These elements are well known in the art, and are described in Cotta-Ramusino.

Nucleic acid vectors according to this disclosure include recombinant viral vectors. Exemplary viral vectors are set forth in Table 4, and additional suitable viral vectors and their use and production are described in Cotta-Ramusino. Other viral vectors known in the art can also be used. In addition, viral particles can be used to deliver genome editing system components in nucleic acid and/or peptide form. For example, "empty" viral particles can be assembled to contain any suitable cargo. Viral vectors and viral particles can also be engineered to incorporate targeting ligands to alter target tissue specificity.

In addition to viral vectors, non-viral vectors can be used to deliver nucleic acids encoding genome editing systems according to the present disclosure. One important category of non-viral nucleic acid vectors are nanoparticles, which can be organic or inorganic. Nanoparticles are well known in the art, and are summarized in Cotta-Ramusino. Any suitable nanoparticle design can be used to deliver genome editing system components or nucleic acids encoding such components. For instance, organic (e.g., lipid and/or polymer) nanoparticles can be suitable for use as delivery vehicles in certain embodiments of this disclosure. Exemplary lipids for use in nanoparticle formulations, and/or gene transfer are shown in Table 5, and Table 6 lists exemplary polymers for use in gene transfer and/or nanoparticle formulations.

TABLE 5

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl]-imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

TABLE 6

Polymers Used for GeneTransfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

Non-viral vectors optionally include targeting modifications to improve uptake and/or selectively target certain cell types. These targeting modifications can include e.g., cell specific antigens, monoclonal antibodies, single chain antibodies, aptamers, polymers, sugars (e.g., N-acetylgalactosamine (GalNAc)), and cell penetrating peptides. Such vectors also optionally use fusogenic and endosome-destabilizing peptides/polymers, undergo acid-triggered conformational changes (e.g., to accelerate endosomal escape of the cargo), and/or incorporate a stimuli-cleavable polymer, e.g., for release in a cellular compartment. For example, disulfide-based cationic polymers that are cleaved in the reducing cellular environment can be used.

In certain embodiments, one or more nucleic acid molecules (e.g., DNA molecules) other than the components of a genome editing system, e.g., the RNA-guided nuclease component and/or the gRNA component described herein, are delivered. In certain embodiments, the nucleic acid molecule is delivered at the same time as one or more of the components of the Genome editing system. In certain embodiments, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Genome editing system are delivered. In certain embodiments, the nucleic acid molecule is delivered by a different means than one or more of the components of the genome editing system, e.g., the RNA-guided nuclease component and/or the gRNA component, are delivered. The nucleic acid molecule can be delivered by any of the delivery methods described herein. For example, the nucleic acid molecule can be delivered by a viral vector, e.g., an integration-deficient lentivirus, and the RNA-guided nuclease molecule component and/or the gRNA component can be delivered by electroporation, e.g., such that the toxicity caused by nucleic acids (e.g., DNAs) can be reduced. In certain embodiments, the nucleic acid molecule encodes a therapeutic protein, e.g., a protein described herein. In certain embodiments, the nucleic acid molecule encodes an RNA molecule, e.g., an RNA molecule described herein.

Delivery of RNPs and/or RNA Encoding Genome Editing System Components

RNPs (complexes of gRNAs and RNA-guided nucleases, i.e., ribonucleoprotein complexes) and/or RNAs encoding RNA-guided nucleases and/or gRNAs, can be delivered into cells or administered to subjects by art-known methods, some of which are described in Cotta-Ramusino. In vitro, RNA-guided nuclease-encoding and/or gRNA-encoding RNA can be delivered, e.g., by microinjection, electroporation, transient cell compression or squeezing (see, e.g., Lee 2012). Lipid-mediated transfection, peptide-mediated delivery, GalNAc- or other conjugate-mediated delivery, and combinations thereof, can also be used for delivery in vitro and in vivo.

In vitro, delivery via electroporation comprises mixing the cells with the RNA encoding RNA-guided nucleases and/or gRNAs, with or without donor template nucleic acid molecules, in a cartridge, chamber or cuvette and applying one or more electrical impulses of defined duration and amplitude. Systems and protocols for electroporation are known in the art, and any suitable electroporation tool and/or protocol can be used in connection with the various embodiments of this disclosure.

Route of Administration

Genome editing systems, or cells altered or manipulated using such systems, can be administered to subjects by any suitable mode or route, whether local or systemic. Systemic modes of administration include oral and parenteral routes. Parenteral routes include, by way of example, intravenous, intramarrow, intrarterial, intramuscular, intradermal, subcutaneous, intranasal, and intraperitoneal routes. Components administered systemically can be modified or formulated to target, e.g., HSCs, hematopoietic stem/progenitor cells, or erythroid progenitors or precursor cells.

Local modes of administration include, by way of example, intramarrow injection into the trabecular bone or intrafemoral injection into the marrow space, and infusion into the portal vein. In certain embodiments, significantly smaller amounts of the components (compared with systemic approaches) can exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration can be provided as a periodic bolus (for example, intravenously) or as continuous infusion from an internal reservoir or from an external reservoir (for example, from an intravenous bag or implantable pump). Components can be administered locally, for example, by continuous release from a sustained release drug delivery device.

In addition, components can be formulated to permit release over a prolonged period of time. A release system can include a matrix of a biodegradable material or a material which releases the incorporated components by diffusion. The components can be homogeneously or heterogeneously distributed within the release system. A variety of release systems can be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically the microspheres are composed of a polymer of lactic acid and glycolic acid, which are structured to form hollow spheres. The spheres can be approximately 15-30 microns in diameter and can be loaded with components described herein.

Multi-Modal or Differential Delivery of Components

Skilled artisans will appreciate, in view of the instant disclosure, that different components of genome editing systems disclosed herein can be delivered together or separately and simultaneously or nonsimultaneously. Separate and/or asynchronous delivery of genome editing system components can be particularly desirable to provide temporal or spatial control over the function of genome editing systems and to limit certain effects caused by their activity.

Different or differential modes as used herein refer to modes of delivery that confer different pharmacodynamic or pharmacokinetic properties on the subject component molecule, e.g., a RNA-guided nuclease molecule, gRNA, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., adenovirus, AAV, lentivirus, and integration-deficient lentivirus (IDLV), delivery.

By way of example, the components of a genome editing system, e.g., a RNA-guided nuclease and a gRNA, can be delivered by modes that differ in terms of resulting half-life or persistent of the delivered component the body, or in a particular compartment, tissue or organ. In certain embodiments, a gRNA can be delivered by such modes. The RNA-guided nuclease molecule component can be delivered by a mode which results in less persistence or less exposure to the body or a particular compartment or tissue or organ.

More generally, in certain embodiments, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or exposure.

In certain embodiments, the second mode of delivery is selected to optimize, e.g., maximize, a pharmacodynamic or pharmacokinetic property, e.g., distribution, persistence or exposure.

In certain embodiments, the first mode of delivery comprises the use of a relatively persistent element, e.g., a nucleic acid, e.g., a plasmid or viral vector, e.g., an AAV vector, an adenoviral vector, a lentiviral vector, or an integration-deficient lentiviral vector (IDLV). As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV vector, an adenoviral vector, a lentiviral vector, or an integration-deficient lentiviral vector (IDLV). Transcription of these genes would be of little physiological consequence because the genes do not encode for a protein product, and the gRNAs are incapable of acting in isolation.

The second component, a RNA-guided nuclease molecule, is delivered in a transient manner, for example as mRNA or as protein, ensuring that the full RNA-guided nuclease molecule/gRNA complex is only present and active for a short period of time.

Furthermore, the components can be delivered in different molecular form or with different delivery vectors that complement one another to enhance safety and tissue specificity.

Use of differential delivery modes can enhance performance, safety, and/or efficacy, e.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in certain embodiments, a first component, e.g., a gRNA is delivered by a first delivery mode that results in a first spatial, e.g., tissue, distribution. A second component, e.g., a RNA-guided nuclease molecule is delivered by a second delivery mode that results in a second spatial, e.g., tissue, distribution. In certain embodiments, the first mode comprises a first element selected from a liposome, nanoparticle, e.g., polymeric nanoparticle, and a nucleic acid, e.g., viral vector. The second mode comprises a second element selected from the group. In certain embodiments, the first mode of delivery comprises a first targeting element, e.g., a cell specific receptor or an antibody, and the second mode of delivery does not include that element. In certain embodiments, the second mode of delivery comprises a second targeting element, e.g., a second cell specific receptor or second antibody.

When the RNA-guided nuclease molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA and the RNA-guided nuclease molecule are packaged in separated delivery vehicles with distinct but overlapping tissue tropism, the fully functional complex is only be formed in the tissue that is targeted by both vectors.

Determination of Targeted Integration Frequency in a Cell Population

The genome editing systems and methods described herein may advantageously be used to analyze a component of genome editing system (e.g., a nuclease, a gRNA, or a donor template), or variants thereof, to determine the component's suitability for generating targeted integration outcomes. In some embodiments, a genome editing system described herein may be used to determining the frequency of targeted integration versus the frequency of non-targeted integration in a population of cells treated with the genome editing system.

For example, when the genome editing system is used to alter a population of cells, wherein each cell comprises a target nucleic acid comprising from 5' to 3', P1-H1-X-H2-P2, wherein P1 is a first priming site; H1 is a first homology arm; X is the cleavage site; H2 is a second homology arm; and P2 is a second priming site; and the donor template comprises from 5' to 3', A1-P2'-N-P1'-A2, wherein A1 is a homology arm that is substantially identical to H1; P2' is a priming site that is substantially identical to P2; N is a cargo;

P1' is a priming site that is substantially identical to P1; and A2 is a homology arm that is substantially identical to H2; then the overall targeted integration frequency may be calculated according to the following formula:

$$\text{Sequencing (Overall)} = \frac{\text{Average}(\text{Amp}Y + \text{Amp}Z)}{\text{Amp}X + \text{Average}(\text{Amp}Y + \text{Amp}Z)} \times 100$$

wherein AmpY is the amplicon generated from the amplification of the 5' junction at a targeted integration event, AmpZ is generated from the amplification of the 3' junction at a targeted integration event, and AmpX is generated from the amplification of a non-targeted integration event.

When the genome editing system is used to alter a population of cells, wherein each cell comprises a target nucleic acid comprising from 5' to 3', P1-H1-X-H2-P2, wherein P1 is a first priming site; H1 is a first homology arm; X is the cleavage site; H2 is a second homology arm; and P2 is a second priming site; and the donor template comprises from 5' to 3', A1-P2'-N-A2, wherein A1 is a homology arm that is substantially identical to H1; P2' is a priming site that is substantially identical to P2; N is a cargo; and A2 is a homology arm that is substantially identical to H2; then the overall targeted integration frequency may be calculated according to the following formula:

$$\text{Sequencing}(5') = \frac{\text{Amp}Y}{\text{Amp}X + \text{Amp}Y} \times 100$$

wherein AmpY is the amplicon generated from the amplification of the 5' junction at a targeted integration event, and AmpX is generated from the amplification of a non-targeted integration event.

When the genome editing system is used to alter a population of cells, wherein each cell comprises a target nucleic acid comprising from 5' to 3', P1-H1-X-H2-P2, wherein P1 is a first priming site; H1 is a first homology arm; X is the cleavage site; H2 is a second homology arm; and P2 is a second priming site; and the donor template comprises from 5' to 3', A1-N-P1'-A2, wherein A1 is a homology arm that is substantially identical to H1; N is a cargo; P1' is a priming site that is substantially identical to P1; and A2 is a homology arm that is substantially identical to H2; then the overall targeted integration frequency may be calculated according to the following formula:

$$\text{Sequencing}(3') = \frac{\text{Amp}Z}{\text{Amp}X + \text{Amp}Z} \times 100$$

wherein AmpZ is generated from the amplification of the 3' junction at a targeted integration event, and AmpX is generated from the amplification of a non-targeted integration event.

Other methods for detecting gene editing outcomes, e.g., targeted integration events, include Digital Droplet PCR (ddPCR) and UDITAS™.

ddPCR can be used to quantitatively detect targeted integration events. In this method, droplets are formed in a water/oil emulsion to partition template DNA molecules, and PCR amplification is carried out within each droplet. A fluorescent probe anneals to the amplified product, and is read by a droplet analyzer. ddPCR is capable of providing an absolute count of target DNA molecules in a given sample. To detect gene editing outcomes, a detection probe that anneals to the amplified product is designed to detect the predicted amplification products.

Figure 14:
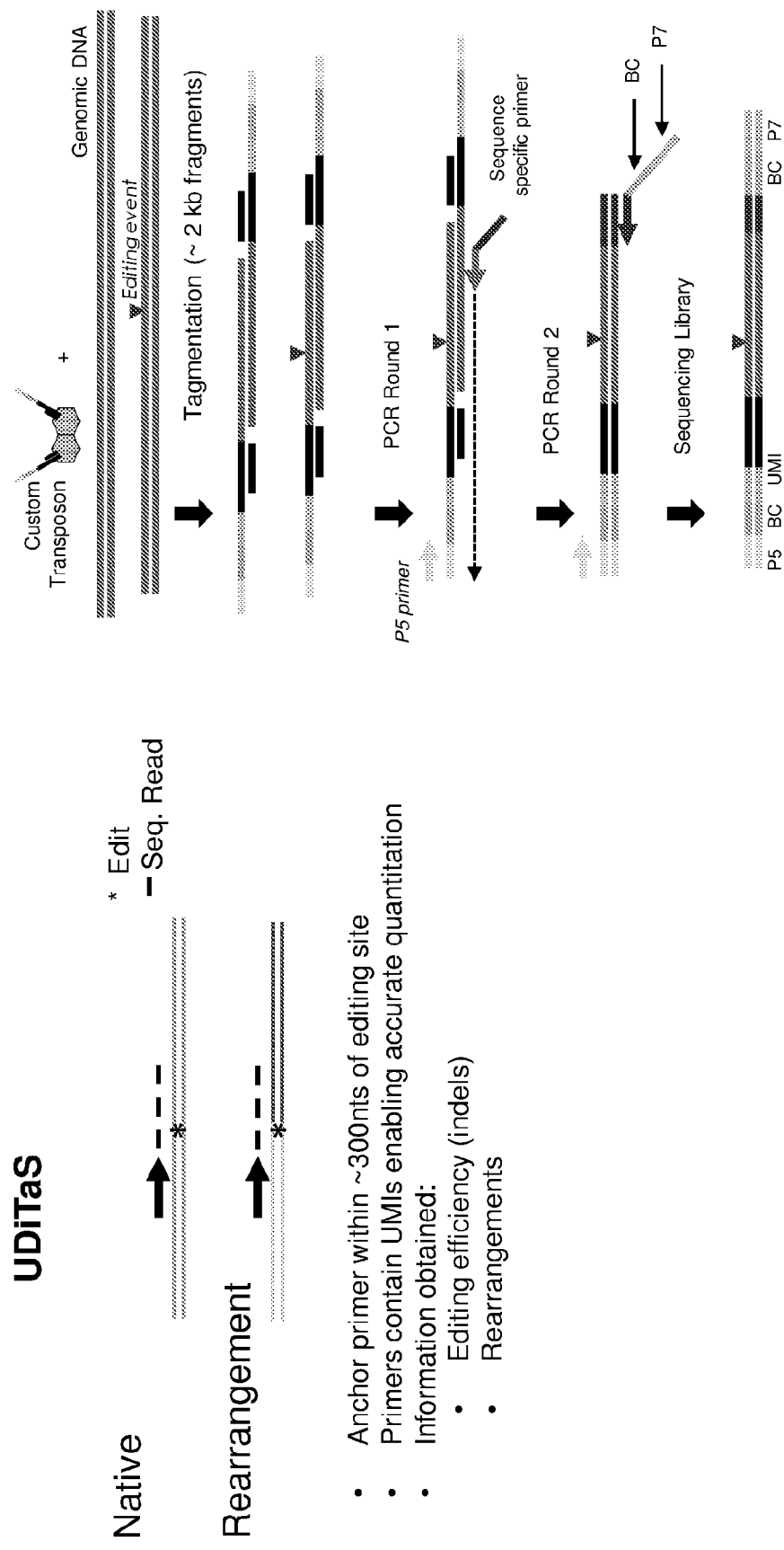
FIG. 14 graphically depicts the UDITAS™ method for detecting and measuring gene editing events.

Another PCR-based method, Uni-Directional Targeted Sequencing ("UDITAS™"), can detect the presence of genomic modifications, e.g., indels and targeted integration events, without specific knowledge regarding the nature of the alteration. In the UDITAS™ method, genomic DNA that has been cleaved, modified, and/or edited as described herein is contacted with a transposon under conditions (e.g., in the presence of a transposase) whereby the transposon is inserted into the nucleic acid template. Such transposition reactions and conditions are known in the art (see, e.g., U.S. Pat. Nos. 6,593,113 and 9,080,211). In some embodiments, transposition conditions are selected with the desired fragment size in mind. The transposition reaction results in fragmentation of the nucleic acid template into a plurality of tagmented double-stranded nucleic acid fragments, where the 3' end of the transferred strand of the transposon is attached to the 5' end of the nucleic acid fragments. The transferred strand of the transposon comprises a first detection sequence at the 5' end of the transferred strand. Following the transposition reaction, the tagmented nucleic acid fragments are amplified, e.g., using PCR, using a set of primers. A first primer can be a fixed primer, comprising a nucleotide sequence complementary to a predetermined location in the genomic DNA. A first primer can also be a fixed primer, comprising a nucleotide sequence complementary to at least a portion of a double-stranded oligonucleotide as described herein. The first primer also includes a second detection sequence at its 5' end. A second primer is a selective primer, comprising a nucleotide sequence complementary to at least a portion of the first detection sequence. The amplification forms amplified nucleic acid fragments, which include (in 5' to 3' orientation): the first detection sequence, the transferred strand of the transposon attached to the 5' end of the nucleic acid fragments, and the second detection sequence. The amplified nucleic acid fragments can then be sequenced. For example, the first and second detection sequences can include sequencing tags described herein to facilitate sequencing. In some embodiments, the method can include a size separation step after tagmentation and before PCR. This method is depicted in FIG. 14, and is described in PCT/US18/12652, incorporated herein by reference in its entirety.

EXAMPLES

The following Examples are merely illustrative and are not intended to limit the scope or content of the invention in any way.

Example 1: Targeted Integration at the HBB Locus

Previously, it was thought that longer homology arms provided more efficient homologous recombination, and typical homology arm lengths were between 500 and 2000 bases (Wang et al., NAR 2015; De Ravin, et al. NBT 2016; Genovese et al. Nature 2014). However, the methods described in the instant example can surprisingly be performed using donor templates having a shorter homology arm (HA) to achieve targeted integration.

To test whether shortening the homology arms negatively impacted targeted integration efficiency, two AAV6 donor templates to the HBB locus were designed (FIG. 2A). The first donor template contained symmetrical homology arms of 500 nt each, flanking a GFP expression cassette (hPGK promoter, GFP, and polyA sequence). The second donor template contained shorter homology arms (5': 225 bp, 3': 177 bp) in addition to stuffer DNA and the genomic priming sites, as described above, flanking an identical GFP cassette. A third donor template having 500 nt of DNA that was non-homologous to the human genome 5' and 3' of the same GFP cassette was used. The 5' and 3' stuffer sequences were derived from the master stuffer sequence and comprised different sequences in each construct to avoid intramolecular recombination.

Table 7 provides the sequences for the master stuffer and the three donor templates depicted in FIG. 2A. A "master stuffer sequence" consists of 2000 nucleotides. It contains roughly the same GC content as the genome as a whole, (e.g., ~40% for the whole genome). Depending on the target locus, the GC content may vary. Based on the design of the donor templates, certain portions of the "master stuffer sequence" (or the reverse compliment thereof) are selected as appropriate stuffers. The selection is based on the following three criteria:

1) the length
2) the homology, and
3) structure.

In the second exemplary donor template design depicted in FIG. 2A (HA+Stuffers), the stuffer 5' to the cargo is 177 nucleotides long while the stuffer 3' to the cargo is 225 nucleotides long. Therefore, the 5' stuffer (177nt) may be any consecutive 177 nucleotide sequence within the "master stuffer sequence" or the reverse compliment thereof. The 3' stuffer (225 nt) may be any consecutive 225 nucleotide sequence within the "master stuffer sequence", or the reverse compliment thereof.

For the homology requirement, neither the 5' stuffer nor the 3' stuffer have homology with any other sequence in the genome (e.g., no more than 20 nucleotide homology), nor to any other sequence in the donor template (i.e., primers, cargo, the other stuffer sequence, homology arms). It is preferable that the stuffer not contain a nucleic acid sequence that forms secondary structures.

TABLE 7

Nucleic Acid Sequences for the Master Stuffer and Donor Templates.

| DESCRIPTION | SEQUENCE | SEQ ID NO. |
|---|---|---|
| Master Stuffer | TACTCTTAATTCATTACATATTGTGCGGTCGAATTCAGGGAGC CGATAATGCGGTTACAATAATTCCTATACTTAAATATACAAAG ATTTAAAATTTCAAAAAATGGTTACCAGCATCGTTAGTGCGTA TACATCAAGAGGCACGTGCCCCGGAGACAGCAAGTAAGCTCT TTAAACATGCTTTGACATACGATTTTTAATAAAACATGAGCAT TTGAATAAAAACGACTTCCTCATACTGTAAACATCACGCATGC ACATTAGACAATAATCCAGTAACGAAACGGCTTCAGTCGTAAT CGCCCATATAGTTGGCTACAGAATGTTGGATAGAGAACTTAAG TACGCTAAGGCGGCGTATTTTCTTAATATTTAGGGGTATTGCC GCAGTCATTACAGATAACCGCCTATGCGGCCATGCCAGGATTA TAGATAACTTTTTAACATTAGCCGCAGAGGTGGGACTAGCACG TAATATCAGCACATAACGTGTCAGTCAGCATATTACGGAATAA TCCTATCGTTATCAGATCTCCCCTGTCATATCACAACATGTTTC GATGTTCCAAAACCGGGAACATTTTGGATCGGTTAAATGATTG TACATCATTTGTTGCAGACCTTAGGAACATCCATCATCCGCCG CCCTTCATCTCTCAAAGTTATCGCTTGTAAATGTATCACAACTA GTATGGTGTAAAATATAGTACCCGATAGACTCGATTTAGGCTG TGAGGTTAGTAACTCTAACTTGTGCTTTCGACACAGATCCTCGT TTCATGCAAATTTAATTTTGCTGGCTAGATATATCAATCGTTCG ATTATTCAGAGTTTTGGTGAGGAGCCCCCTCAGATGGGAGCAT TTTCACTACTTTAAAGAATAACGTATTTTTCGCCCTGTCCCTTA GTGACTTAAAAAGAATGGGGGCTAGTGCTTAGAGCTGGTAGG GCTTTTTGGTTCTATCTGTTAAGCGAATAAGCTGTCACCTAAGC AAATTAATGCTTTCATTGTACCCCGGAACTTTAAATCTATGAA CAATCGCAACAAATTGTCCAAAGGCAACAATACGACACAGTT AGAGGCCATCGGCGCAGGTACACTCTATCCACGCCTATCAGAA TGTCACCTGGTTAATGGTCAATTTAGGTGGCTGGAGGCACATG TGAAGCAATATGGTCTAGGGAAAGATATCGGTTTACTTAGATT TTATAGTTCCGGATCCAACTTAAATAATATAGGTATTAAAGAG CAGTATCAAGAGGGTTTCTTCCCAAGGAATCTTGCGATTTTCA TACACAGCTTTAACAAATTTCACTAGACGCACCTTCATTTTGTC GTCTCGTTGTATATGAGTCCGGGGTAAGAATTTTTTACCGTATT TAACATGATCAACGGGTACTAAAGCAATGTCATTTCTAAACAC AGTAGGTAAAGGACACGTCATCTTATTTTAAAGAATGTCAGAA ATCAGGGAGACTAGATCGATATTACGTGTTTTTTGAGTCAAAG ACGGCCGTAAAATAATCAAGCAGTCTTTCTACCTGTACTTGTC GCTACCTAGAATCTTTAATTTATCCATGTCAAGGAGGATGCCC ATCTGAAACAATACCTGTTGCTAGATCGTCTAACAACGGCATC TTGTCGTCCATGCGGGGTTGTTCTTGTACGTATCAGCGTCGGTT ATATGTAAAAATAATGTTTTACTACTATGCCATCTGTCCCGTAT TCTTAAGCATGACTAATATTAAAAGCCGCCTATATATCGAGAA CGACTACCATTGGAATTTAAAATTGCTTCCAAGCTATGATGAT GTGACCTCTCACATTGTGGTAGTATAAACTATGGTTAGCCACG ACTCGTTCGGACAAGTAGTAATATCTGTTGGTAATAGTCGGGT TACCGCGAAATATTTGAAATTGATATTAAGAAGCAATGATTTG TACATAAGTATACCTGTAATGAATTCCTGCGTTAGCAGCTTAG TATCCATTATTAGAG | 102 |

TABLE 7-continued

Nucleic Acid Sequences for the Master Stuffer and Donor Templates.

| DESCRIPTION | SEQUENCE | SEQ ID NO. |
| --- | --- | --- |
| Donor template design 1 (HA only) | TTATCCCCTTCCTATGACATGAACTTAACCATAGAAAAGAAGG GGAAAGAAAAACATCAAGCGTCCCATAGACTCACCCTGAAGTT CTCAGGATCCACGTGCAGCTTGTCACAGTGCAGCTCACTCAGT GTGGCAAAGGTGCCCTTGAGGTTGTCCAGGTGAGCCAGGCCAT CACTAAAGGCACCGAGCACTTTCTTGCCATGAGCCTTCACCTT AGGGTTGCCCATAACAGCATCAGGAGTGGACAGATCCCCAAA GGACTCAAAGAACCTCTGGGTCCAAGGGTAGACCACCAGCAG CCTAAGGGTGGGAAAATAGACCAATAGGCAGAGAGAGTCAGT GCCTATCAGAAACCCAAGAGTCTTCTCTGTCTCCACATGCCCA GTTTCTATTGGTCTCCTTAAACCTGTCTTGTAACCTTGATACCA ACCTGCCCAGGGCCTCACCACCAACTTCATCCACGTTCACCTT GCCCCACAGGGCAGTAACGGCAGACTTCTCAAGCTTCCATAGA GCCCACCGCATCCCCAGCATGCCTGCTATTGTCTTCCCAATCCT CCCCCTTGCTGTCCTGCCCCACCCCACCCCCCAGAATAGAATG ACACCTACTCAGACAATGCGATGCAATTTCCTCATTTTATTAG GAAAGGACAGTGGGAGTGGCACCTTCCAGGGTCAAGGAAGGC ACGGGGAGGGGCAAACAACAGATGGCTGGCAACTAGAAGGC ACAGTCGAGGCTGATCAGCGGGTTTAAACGGGCCCTCTAGACT CGACGCGGCCGCTTTACTTGTACAGCTCGTCCATGCCGAGAGT GATCCCGGCGGCGGTCACGAACTCCAGCAGGACCATGTGATC GCGCTTCTCGTTGGGGTCTTTGCTCAGGGCGGACTGGGTGCTC AGGTAGTGGTTGTCGGGCAGCAGCACGGGGCCGTCGCCGATG GGGGTGTTCTGCTGGTAGTGGTCGGCGAGCTGCACGCTGCCGT CCTCGATGTTGTGGCGGATCTTGAAGTTCACCTTGATGCCGTTC TTCTGCTTGTCGGCCATGATATAGACGTTGTGGCTGTTGTAGTT GTACTCCAGCTTGTGCCCCAGGATGTTGCCGTCCTCCTTGAAGT CGATGCCCTTCAGCTCGATGCGGTTCACCAGGGTGTCGCCCTC GAACTTCACCTCGGCGCGGGTCTTGTAGTTGCCGTCGTCCTTG AAGAAGATGGTGCGCTCCTGGACGTAGCCTTCGGGCATGGCG GACTTGAAGAAGTCGTGCTGCTTCATGTGGTCGGGGTAGCGGC TGAAGCACTGCACGCCGTAGGTCAGGGTGGTCACGAGGGTGG GCCAGGGCACGGGCAGCTTGCCGGTGGTGCAGATGAACTTCA GGGTCAGCTTGCCGTAGGTGGCATCGCCCTCGCCCTCGCCGGA CACGCTGAACTTGTGGCCGTTTACGTCGCCGTCCAGCTCGACC AGGATGGGCACCACCCCGGTGAACAGCTCCTCGCCCTTGCTCA CCATGGTGGCGACCGGTGGGGAGAGAGGTCGGTGATTCGGTC AACGAGGGAGCCGACTGCCGACGTGCGCTCCGGAGGCTTGCA GAATGCGGAACACCGCGCGGGCAGGAACAGGGCCCACACTAC CGCCCCACACCCCGCCTCCCGCACCGCCCCTTCCCGGCCGCTG CTCTCGGCGCGCCCTGCTGAGCAGCCGCTATTGGCCACAGCCC ATCGCGGTCGGCGCGCTGCCATTGCTCCCTGGCGCTGTCCGTC TGCGAGGGTACTAGTGAGACGTGCGGCTTCCGTTTGTCACGTC CGGCACGCCGCGAACCGCAAGGAACCTTCCCGACTTAGGGGC GGAGCAGGAAGCGTCGCCGGGGGGCCCACAAGGGTAGCGGCG AAGATCCGGGTGACGCTGCGAACGGACGTGAAGAATGTGCGA GACCCAGGGTCGGCGCCGCTGCGTTTCCCGGAACCACGCCCAG AGCAGCCGCGTCCCTGCGCAAACCCAGGGCTGCCTTGGAAAA GGCGCAACCCCAACCCCGTGGAAGCTCTCAGGAGTCAGATGC ACCATGGTGTCTGTTTGAGGTTGCTAGTGAACACAGTTGTGTC AGAAGCAAATGTAAGCAATAGATGGCTCTGCCCTGACTTTTAT GCCCAGCCCTGGCTCCTGCCCTCCCTGCTCCTGGGAGTAGATT GGCCAACCCTAGGGTGTGGCTCCACAGGGTGAGGTCTAAGTG ATGACAGCCGTACCTGTCCTTGGCTCTTCTGGCACTGGCTTAG GAGTTGGACTTCAAACCCTCAGCCCTCCCTCTAAGATATATCT CTTGGCCCCATACCATCAGTACAAATTGCTACTAAAAACATCC TCCTTTGCAAGTGTATTTACGTAATATTTGGAATCACAGCTTGG TAAGCATATTGAAGATCGTTTTCCCAATTTTCTTATTACACAAA TAAGAAGTTGATGCACTAAAAGTGGAAGAGTTTTGTCTACCAT AATTCAGCTTTGGGATATGTAGATGGATCTCTTCCTGCGTCTCC AGAATATGC | 103 |
| Donor template design 2 (HA + Stuffers) | GTCCAAGGGTAGACCACCAGCAGCCTAAGGGTGGGAAAATAG ACCAATAGGCAGAGAGAGTCAGTGCCTATCAGAAACCCAAGA GTCTTCTCTGTCTCCACATGCCCAGTTTCTATTGGTCTCCTTAA ACCTGTCTTGTAACCTTGATACCAACCTGCCCAGGGCCTCACC ACCAACTTCATCCACGTTCACCTTGCCCCACAGGGCAGTAACG GCAGACTTCTCTACTCTTAATTCATTACATATTGTGCGGTCGAA TTCAGGGAGCCGATAATGCGGTTACAATAATTCCTATACTTAA ATATACAAAGATTTAAAATTTCAAAAAATGGTTACCAGCATCG TTAGTGCGTATACATCAAGAGGCACGTGCCCCGGAGACAGCA AGTAAGCTCTTTAAACGGTCTAAGTGATGACAGCCGTAAGCTT CCATAGAGCCCACCGCATCCCCAGCATGCCTGCTATTGTCTTC CCAATCCTCCCCCTTGCTGTCCTGCCCCACCCCACCCCCCAGAA TAGAATGACACCTACTCAGACAATGCGATGCAATTTCCTCATT | 104 |

TABLE 7-continued

Nucleic Acid Sequences for the Master Stuffer and Donor Templates.

| DESCRIPTION | SEQUENCE | SEQ ID NO. |
|---|---|---|
| | TTATTAGGAAAGGACAGTGGGAGTGGCACCTTCCAGGGTCAA<br>GGAAGGCACGGGGGAGGGGCAAACAACAGATGGCTGGCAACT<br>AGAAGGCACAGTCGAGGCTGATCAGCGGGTTTAAACGGGCCC<br>TCTAGACTCGACGCGGCCGCTTTACTTGTACAGCTCGTCCATG<br>CCGAGAGTGATCCCGGCGGCGGTCACGAACTCCAGCAGGACC<br>ATGTGATCGCGCTTCTCGTTGGGGTCTTTGCTCAGGGCGGACT<br>GGGTGCTCAGGTAGTGGTTGTCGGGCAGCAGCACGGGGCCGT<br>CGCCGATGGGGGTGTTCTGCTGGTAGTGGTCGGCGAGCTGCAC<br>GCTGCCGTCCTCGATGTTGTGGCGGATCTTGAAGTTCACCTTG<br>ATGCCGTTCTTCTGCTTGTCGGCCATGATATAGACGTTGTGGCT<br>GTTGTAGTTGTACTCCAGCTTGTGCCCCAGGATGTTGCCGTCCT<br>CCTTGAAGTCGATGCCCTTCAGCTCGATGCGGTTCACCAGGGT<br>GTCGCCCTCGAACTTCACCTCGGCGCGGGTCTTGTAGTTGCCG<br>TCGTCCTTGAAGAAGATGGTGCGCTCCTGGACGTAGCCTTCGG<br>GCATGGCGGACTTGAAGAAGTCGTGCTGCTTCATGTGGTCGGG<br>GTAGCGGCTGAAGCACTGCACGCCGTAGGTCAGGGTGGTCAC<br>GAGGGTGGGCCAGGGCACGGGCAGCTTGCCGGTGGTGCAGAT<br>GAACTTCAGGGTCAGCTTGCCGTAGGTGGCATCGCCCTCGCCC<br>TCGCCGGACACGCTGAACTTGTGGCCGTTTACGTCGCCGTCCA<br>GCTCGACCAGGATGGGCACCACCCCGGTGAACAGCTCCTCGCC<br>CTTGCTCACCATGGTGGCGACCGGTGGGGAGAGAGGTCGGTG<br>ATTCGGTCAACGAGGGAGCCGACTGCCGACGTGCGCTCCGGA<br>GGCTTGCAGAATGCGGAACACCGCGGGCAGGAACAGGGCC<br>CACACTACCGCCCCACACCCCGCCTCCCGCACCGCCCCTTCCC<br>GGCCGCTGCTCTCGGCGCGCCCTGCTGAGCAGCCGCTATTGGC<br>CACAGCCCATCGCGGTCGGCGCGCTGCCATTGCTCCCTGGCGC<br>TGTCCGTCTGCGAGGGTACTAGTGAGACGTGCGGCTTCCGTTT<br>GTCACGTCCGGCACGCCGCGAACCGCAAGGAACCTTCCCGACT<br>TAGGGGCGGAGCAGGAAGCGTCGCCGGGGGGCCCACAAGGGT<br>AGCGGCGAAGATCCGGGTGACGCTGCGAACGGACGTGAAGAA<br>TGTGCGAGACCCAGGGTCGGCGCCGCTGCGTTTCCCGGAACCA<br>CGCCCAGAGCAGCCGCGTCCCTGCGCAAACCCAGGGCTGCCTT<br>GGAAAAGGCGCAACCCCAACCCCGTGGAAGCTCCAAAGGACT<br>CAAAGAACCTCTGGATGCTTTGACATACGATTTTTAATAAAAC<br>ATGAGCATTTGAATAAAAACGACTTCCTCATACTGTAAACATC<br>ACGCATGCACATTAGACAATAATCCAGTAACGAAACGGCTTCA<br>GTCGTAATCGCCCATATAGTTGGCTACAGAATGTTGGATAGAG<br>AACTTAAGTACGCTAAGGCGGCGTATTTTCTTAATATTTAGGG<br>GTATTGCCGCAGTCATTACAGATACTCAGGAGTCAGATGCACC<br>ATGGTGTCTGTTTGAGGTTGCTAGTGAACACAGTTGTGTCAGA<br>AGCAAATGTAAGCAATAGATGGCTCTGCCCTGACTTTTATGCC<br>CAGCCCTGGCTCCTGCCCTCCCTGCTCCTGGGAGTAGATTGGC<br>CAACCCTAGGGTGTGGCTCCACAGGGTGA | |
| Donor template design 3 (no HA) | TACTCTTAATTCATTACATATTGTGCGGTCGAATTCAGGGAGC<br>CGATAATGCGGTTACAATAATTCCTATACTTAAATATACAAAG<br>ATTTAAAATTTCAAAAAATGGTTACCAGCATCGTTAGTGCGTA<br>TACATCAAGAGGCACGTGCCCGGAGACAGCAAGTAAGCTCT<br>TTAAACATGCTTTGACATACGATTTTTAATAAAACATGAGCAT<br>TTGAATAAAAACGACTTCCTCATACTGTAAACATCACGCATGC<br>ACATTAGACAATAATCCAGTAACGAAACGGCTTCAGTCGTAAT<br>CGCCCATATAGTTGGCTACAGAATGTTGGATAGAGAACTTAAG<br>TACGCTAAGGCGGCGTATTTTCTTAATATTTAGGGGTATTGCC<br>GCAGTCATTACAGATAACCGCCTATGCGGCCATGCCAGGATTA<br>TAGATAACTTTTTAACATTAGCCGCAGAGGTGGGACTAGCACG<br>TAATATCAGCACATAACGTGTCAGTCAGGTCATCGACCTCGTC<br>GGACTCCGGGTGCGAGGTCGTGAAGCTGGAATACGAGTGAGG<br>CCGCCGAGGACGTCAGGGGGGTGTAAAGCTTCCATAGAGCCC<br>ACCGCATCCCCAGCATGCCTGCTATTGTCTTCCCAATCCTCCCC<br>CTTGCTGTCCTGCCCCACCCCACCCCCCAGAATAGAATGACAC<br>CTACTCAGACAATGCGATGCAATTTCCTCATTTTATTAGGAAA<br>GGACAGTGGGAGTGGCACCTTCCAGGGTCAAGGAAGGCACGG<br>GGGAGGGGCAAACAACAGATGGCTGGCAACTAGAAGGCACAG<br>TCGAGGCTGATCAGCGGGTTTAAACGGGCCCTCTAGACTCGAC<br>GCGGCCGCTTTACTTGTACAGCTCGTCCATGCCGAGAGTGATC<br>CCGGCGGCGGTCACGAACTCCAGCAGGACCATGTGATCGCGCT<br>TCTCGTTGGGGTCTTTGCTCAGGGCGGACTGGGTGCTCAGGTA<br>GTGGTTGTCGGGCAGCAGCACGGGGCCGTCGCCGATGGGGGT<br>GTTCTGCTGGTAGTGGTCGGCGAGCTGCACGCTGCCGTCCTCG<br>ATGTTGTGGCGGATCTTGAAGTTCACCTTGATGCCGTTCTTCTG<br>CTTGTCGGCCATGATATAGACGTTGTGGCTGTTGTAGTTGTACT<br>CCAGCTTGTGCCCCAGGATGTTGCCGTCCTCCTTGAAGTCGAT<br>GCCCTTCAGCTCGATGCGGTTCACCAGGGTGTCGCCCTCGAAC<br>TTCACCTCGGCGCGGGTCTTGTAGTTGCCGTCGTCCTTGAAGA | 105 |

TABLE 7-continued

Nucleic Acid Sequences for the Master Stuffer and Donor Templates.

| DESCRIPTION | SEQUENCE | SEQ ID NO. |
|---|---|---|
| | AGATGGTGCGCTCCTGGACGTAGCCTTCGGGCATGGCGGACTT<br>GAAGAAGTCGTGCTGCTTCATGTGGTCGGGGTAGCGGCTGAAG<br>CACTGCACGCCGTAGGTCAGGGTGGTCACGAGGGTGGGCCAG<br>GGCACGGGCAGCTTGCCGGTGGTGCAGATGAACTTCAGGGTC<br>AGCTTGCCGTAGGTGGCATCGCCCTCGCCCTCGCCGGACACGC<br>TGAACTTGTGGCCGTTTACGTCGCCGTCCAGCTCGACCAGGAT<br>GGGCACCACCCCGGTGAACAGCTCCTCGCCCTTGCTCACCATG<br>GTGGCGACCGGTGGGGAGAGAGGTCGGTGATTCGGTCAACGA<br>GGGAGCCGACTGCCGACGTGCGCTCCGGAGGCTTGCAGAATG<br>CGGAACACCGCGCGGGCAGGAACAGGGCCCACACTACCGCCC<br>CACACCCCGCCTCCCGCACCGCCCCTTCCCGGCCGCTGCTCTC<br>GGCGCGCCCTGCTGAGCAGCCGCTATTGGCCACAGCCCATCGC<br>GGTCGGCGCGCTGCCATTGCTCCCTGGCGCTGTCCGTCTGCGA<br>GGGTACTAGTGAGACGTGCGGCTTCCGTTTGTCACGTCCGGCA<br>CGCCGCGAACCGCAAGGAACCTTCCCGACTTAGGGGCGGAGC<br>AGGAAGCGTCGCCGGGGGGCCCACAAGGGTAGCGGCGAAGAT<br>CCGGGTGACGCTGCGAACGGACGTGAAGAATGTGCGAGACCC<br>AGGGTCGGCGCCGCTGCGTTTCCCGGAACCACGCCCAGAGCA<br>GCCGCGTCCCTGCGCAAACCCAGGGCTGCCTTGGAAAAGGCG<br>CAACCCCAACCCCGTGGAAGCTTGCGACCTGGAATCGGACAG<br>CAGCGGGGAGTGTACGGCCCCGAGTTCGTGACCGGGTATGCTT<br>TCATTGTACCCCGGAACTTTAAATCTATGAACAATCGCAACAA<br>ATTGTCCAAAGGCAACAATACGACACAGTTAGAGGCCATCGG<br>CGCAGGTACACTCTATCCACGCCTATCAGAATGTCACCTGGTT<br>AATGGTCAATTTAGGTGGCTGGAGGCACATGTGAAGCAATATG<br>GTCTAGGGAAAGATATCGGTTTACTTAGATTTTATAGTTCCGG<br>ATCCAACTTAAATAATATAGGTATTAAAGAGCAGTATCAAGAG<br>GGTTTCTTCCCAAGGAATCTTGCGATTTTCATACACAGCTTTAA<br>CAAATTTCACTAGACGCACCTTCATTTTGTCGTCTCGTTGTATA<br>TGAGTCCGGGGTAAGAATTTTTTACCGTATTTAACATGATCAA<br>CGGGTACTAAAGCAATGTCATTTCTAAACACAGTAGGTAAAGG<br>ACACGTCATCTTATTTTAAAGAATGTCAGAAATCAGGGAGACT<br>AGATCGATATTACGTGTTTT | 35 |

Targeted integration experiments were conducted in primary CD4+ T cells with wild-type *S. pyogenes* ribonucleoprotein (RNP) targeted to the HBB locus. AAV6 was added at different multiplicities of infection (MOI) after nucleofection of 50 pmol of RNP. GFP fluorescence was measured 7 days after the experiment and showed that targeted integration frequency with the shorter homology arms was as efficient as when the longer homology arms were used (FIG. 2B). Assessment of targeted integration by digital droplet PCR (ddPCR) to either the 5' or 3' integration junction showed that (1) HA length did not affect targeted integration and (2) phenotypic assessment of targeted integration by GFP expression dramatically underestimated actual genomic targeted integration.

Figure 3:
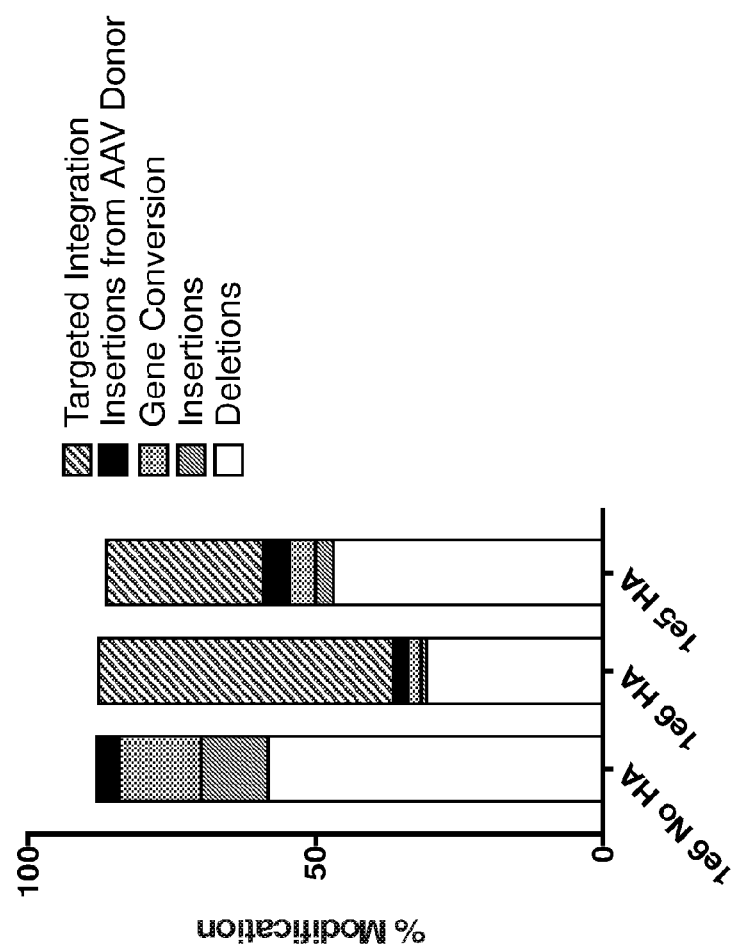
FIG. 3 depicts the quantitative assessment of on-target editing events from sequencing at HBB locus as determined using Sanger sequencing.

The genomic DNA from the cells that received the 177 nt HA donor (1e6 or 1e5 MOI) or no HA donor (1e6 MOI) was amplified with the 5' and 3' primers (P1 and P2), the PCR fragment was subcloned into a Topo Blunt Vector, and the resulting plasmids were Sanger sequenced. All high quality reads mapped one of the three expected PCR amplicons and the total number of reads were: 1e6 No HA—77 reads, 1e6 HA Donor—422 reads, 1e5 HA Donor—332 reads. The analysis allowed for the determination of on-target editing events at the HBB locus, including insertions, deletions, gene conversion from the highly homologous HBD gene, insertions from fragmented AAV donors, and targeted integration (FIG. 3A). To calculate targeted integration, the following formulas were used, taking into account the total number of reads from the $1^{st}$ Amplicon (AmpX), $2^{nd}$ Amplicon (AmpY), and $3^{rd}$ Amplicon (AmpZ). The results are summarized in Table 8 below.

$$\text{Sequencing (Overall)} = \frac{\text{Average(AmpY + AmpZ)}}{\text{AmpX + Average(AmpY + AmpZ)}} \times 100$$

$$\text{Sequencing}(5') = \frac{\text{AmpY}}{\text{AmpX + AmpY}} \times 100$$

$$\text{Sequencing}(3') = \frac{\text{AmpZ}}{\text{AmpX + AmpZ}} \times 100$$

TABLE 8

Comparison of Targeted Integration Frequency at HBB locus Using Different Methods of Calculation.

| | Assay | % Integration |
|---|---|---|
| 1e6 MOI | GFP | 9.6% |
| | 5' ddPCR | 70% |
| | 3' ddPCR | 62% |
| | Sequencing (Overall) | 51% |
| | Sequencing (5' Junction) | 57% |
| | Sequencing (3' Junction) | 43.9% |
| 1e5 MOI | GFP | 4.3% |
| | 5' ddPCR | 21.9% |
| | 3' ddPCR | 20% |
| | Sequencing (Overall) | 27.2% |
| | Sequencing (5' Junction) | 31.9% |

TABLE 8-continued

Comparison of Targeted Integration
Frequency at HBB locus Using
Different Methods of Calculation.

| Assay | % Integration |
|---|---|
| Sequencing (3' Junction) | 21.8% |

The sequencing (overall) formula described above provided an estimate for the targeted integration taking into consideration reads from both the $2^{nd}$ amplicon (AmpY) and 3rd amplicon (AmpZ). When either the $2^{nd}$ amplicon (AmpY) or 3rd amplicon (AmpZ) was used alone to calculate targeted integration, the output was similar, showing that this method can be used with only 1 integrated priming site (either P1' or P2'). The sequencing read-out matched the ddPCR analysis from either the 5' or 3' junction, indicating no PCR biases in the amplification, and that this method can be used to determine all on-target editing events.

Figure 4:
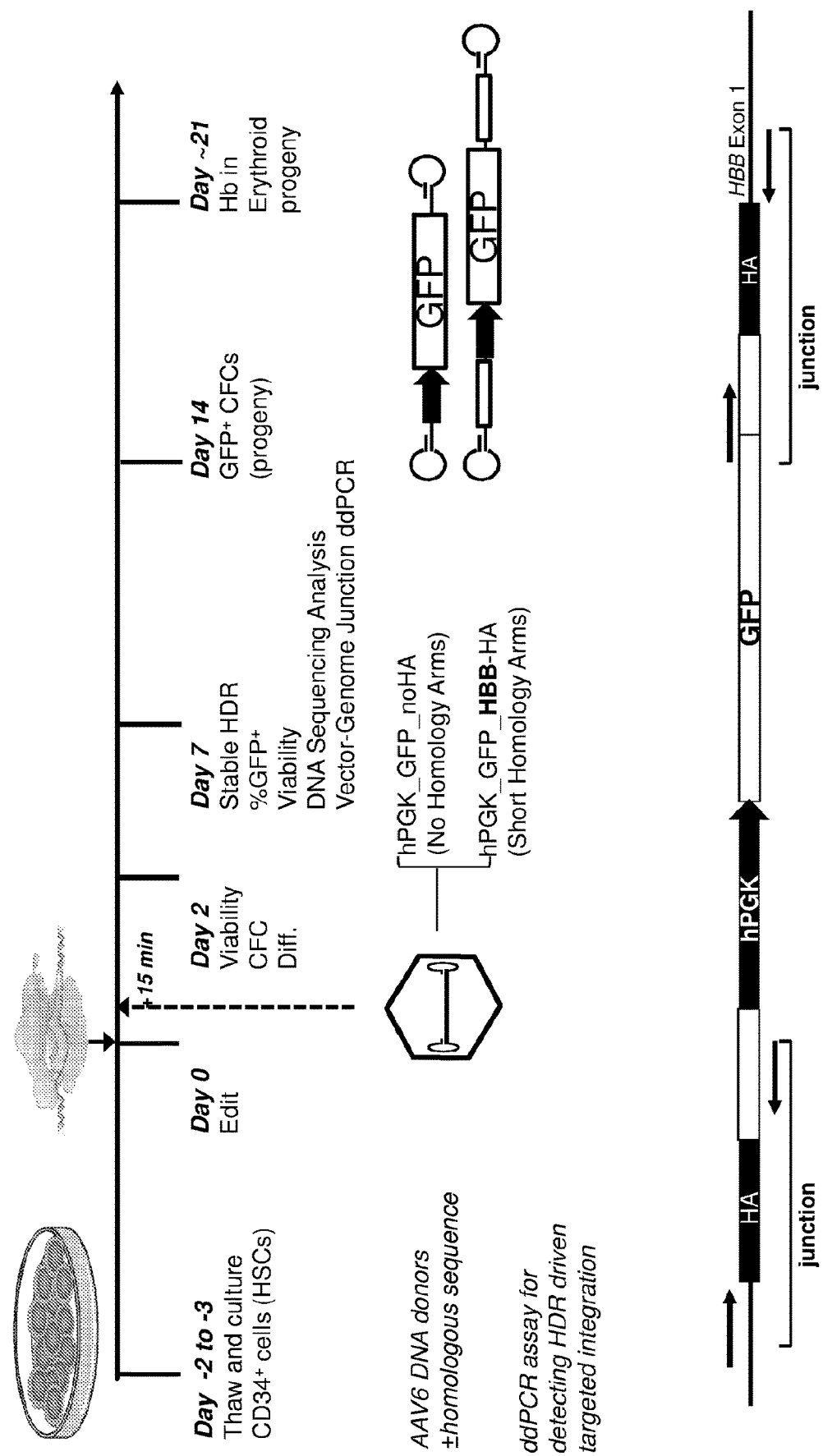
FIG. 4 depicts the experimental schematic for evaluation of HDR and targeted integration in CD34+ cells.

Example 2: Targeted Integration at the HBB Locus in Adult Mobilized Peripheral Blood Human CD34+ Cells In order to determine the baseline level of targeted integration at the HBB locus in hematopoietic stem/progenitor cells, the population of cells which would be targeted clinically for gene correction or cDNA replacement for the treatment of b-hemoglobinopathies, the donor as described in Example 1 and depicted in FIG. 2A and Table 7, were used to deliver the PGK-GFP transgene expression cassette flanked by short homology arms (HA). The experimental schematic, timing and readouts for targeted integration are depicted in FIG. 4. Targeted integration experiments were conducted in human mobilized peripheral blood (mPB) CD34+ cells with wild-type S. pyogenes ribonucleoprotein (RNP) targeted to the HBB locus. Cells were cultured for 3 days in StemSpan-SFEM supplemented with human cytokines (SCF, TPO, FL, IL6) and dmPGE2. Cells were electroporated with the Maxcyte System and AAV6 ±HA (vector dose: $5×10^4$ vg/cell) was added to the cells 15-30 minutes after electroporation of the cells with 2.5 µM RNP (CAGACUUCUCCACAGGAGUC). Two days after electroporation, CD34+ cell viability was assessed, and cells were plated into Methocult to evaluate ex vivo hematopoietic differentiation potential and expression of GFP in their erythroid and myeloid progeny. On day 7 after electroporation, GFP fluorescence was evaluated by flow cytometry analysis in the viable CD34+ cell fraction. In addition, assessment of targeted integration was also analyzed by digital droplet PCR (ddPCR) to both the 5' or 3' integration junction. ddPCR analysis and Sanger sequencing analysis were done as described in Example 1.

Figure 5A:
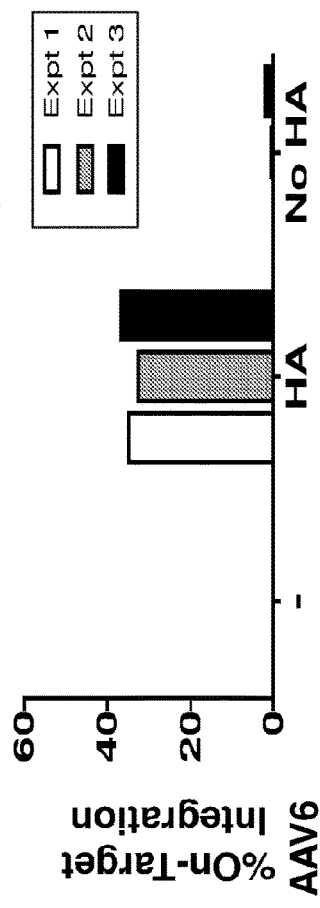
FIGS. 5A-5C depict the on-target integration as detected by ddPCR analysis of (FIG. 5A) the 5' and (FIG. 5B) the 3' vector-genomic DNA junctions on day 7 in gDNA from CD34+ cells that were untreated (−) or treated with RNP+AAV6+/−homology arms (HA).
Figure 5B:
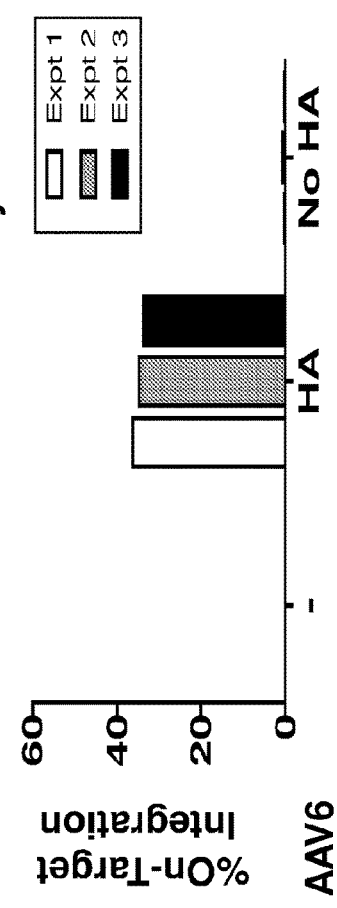
Figure 5C:
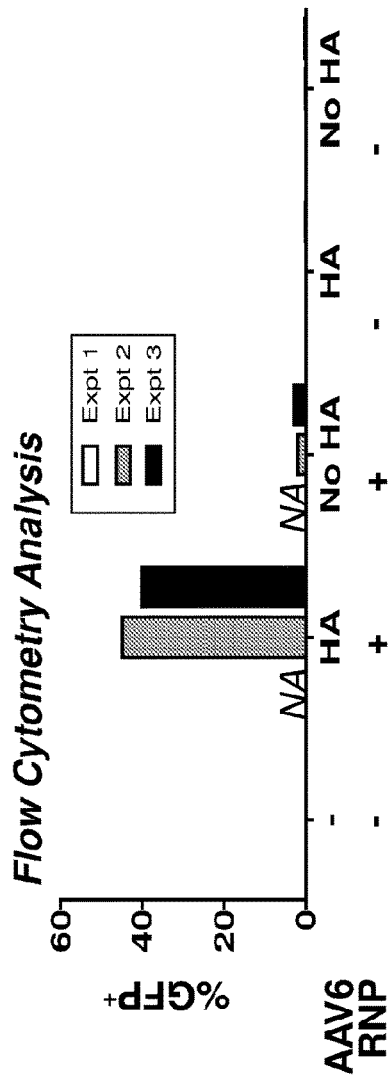
Figure 6:
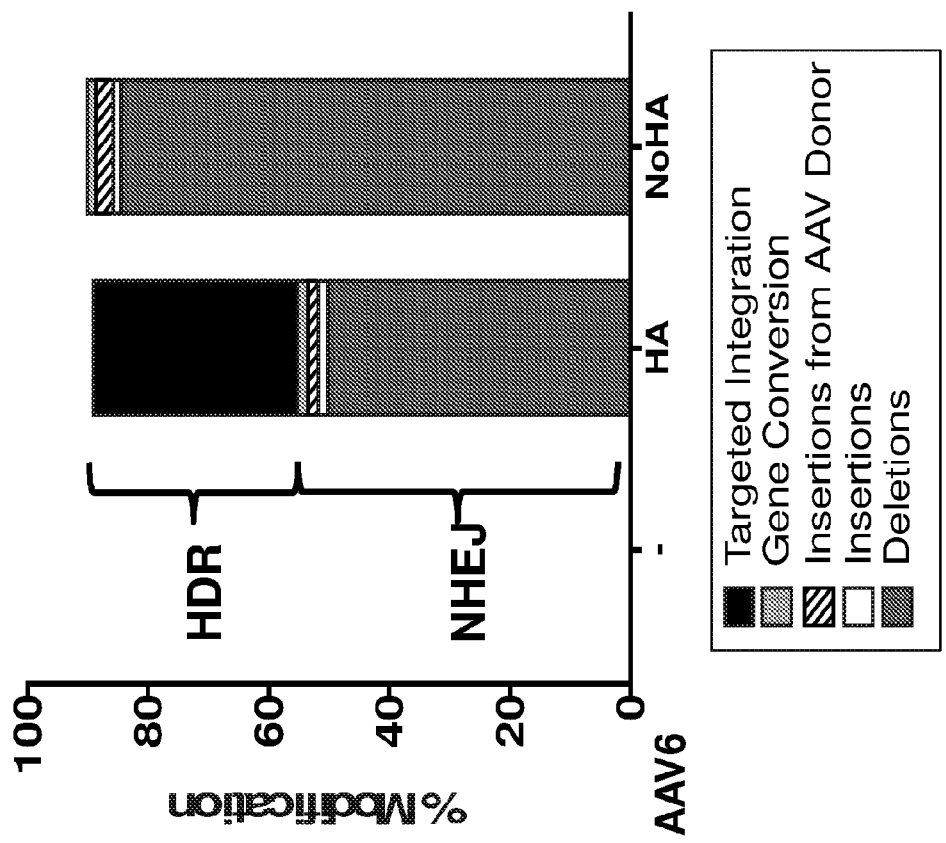
FIG. 6 depicts the DNA sequencing results for the cells treated with RNP+AAV6+/−HA with % gene modification comprised of HDR (targeted integration events and gene conversion) and NHEJ (Insertions, Deletions, Insertions from AAV6 donor).

Three separate experiments were conducted and the day 7 targeted integration results are depicted in FIG. 5. Targeted integration as determined by 5' and 3' ddPCR analysis was ~35% (FIG. 5A, 5B). Expression of the integration GFP transgene in CD34+ cells 7 days after electroporation was consistent with the ddPCR data, indicating that the integrated transgene was expressed. DNA sequencing analysis confirmed these results, with 35% HDR and 55% NHEJ detected in gDNA of CD34+ cells treated with RNP and AAV6 with HA (FIG. 6, total editing 90%). In contrast, CD34+ cells treated with RNP and AAV6 without HA, no targeted integration was detected, the only HDR observed was 1.7% gene conversion (that is gene conversion between HBB and HBD), while total editing frequency was the same (90%).

Figure 7:
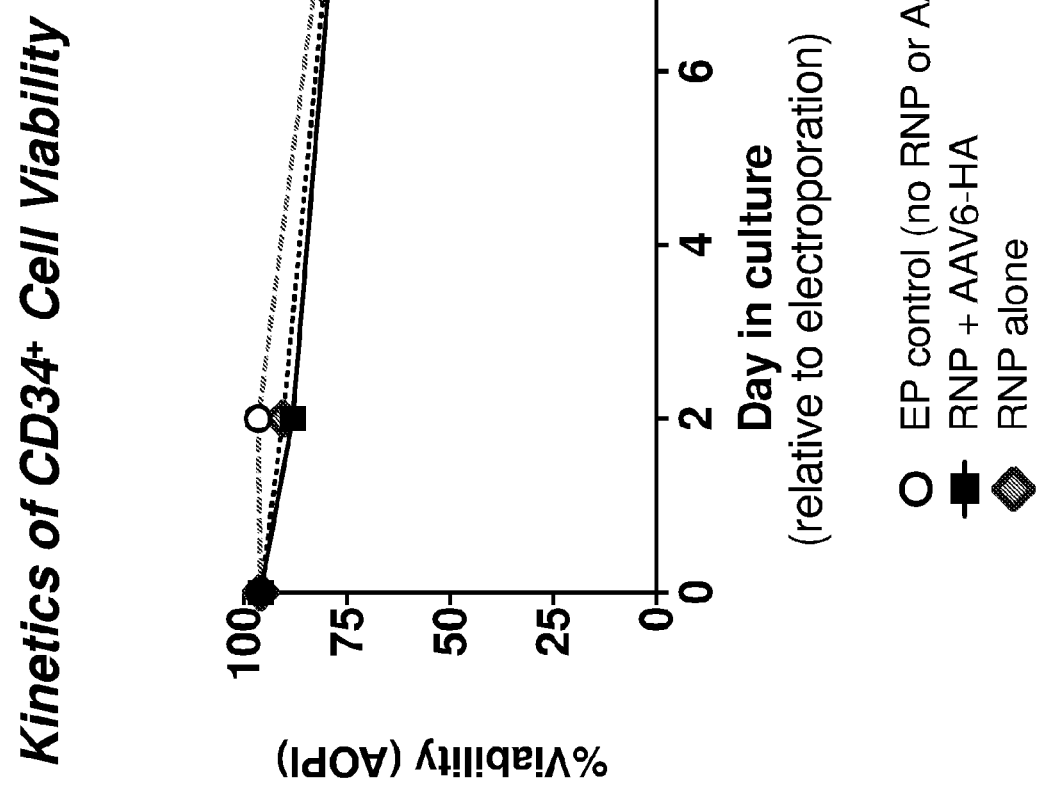
FIG. 7 depicts the kinetics of CD34+ cell viability up to 7 days after treatment with electroporation alone (EP control), or electroporation with RNP or RNP+AAV6. Viability was measured by AOPI.

Importantly, between days 0 and 7 after electroporation there was no substantial difference in the viability (as determined by AOPI) of cells treated with RNP+AAV or untreated (EP electroporation control) (FIG. 7). This suggests that the RNP and AAV6 combination is well-tolerated by CD34+ cells.

Figure 8:
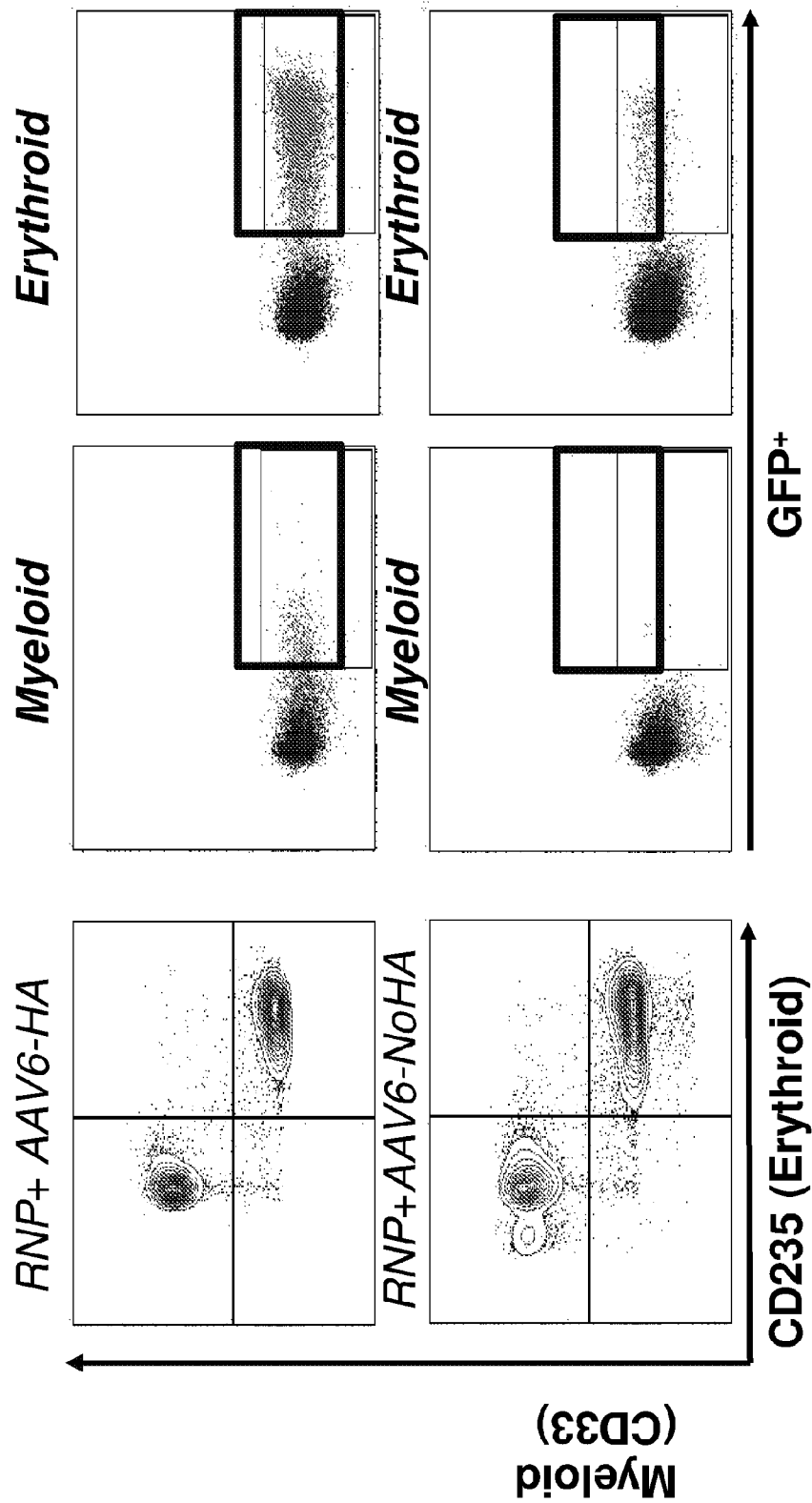
FIG. 8 depicts flow cytometry results which show GFP expression in erythroid and myeloid progeny of edited cells. The boxed gate calls out the events that were positive for erythroid (CD235) or myeloid (CD33) surface antigen (quadrant gates). GFP+ events were scored within the myeloid and erythroid cell populations (boxed gates).

To determine whether the cells containing the targeted integration maintain differentiation potential, CD34+ cells on day 2 were plated into Methocult to evaluate ex vivo hematopoietic activity. On day 14 after plating CD34+ cells into Methocult, GFP+ colonies were scored by fluorescence microscopy For the CD34+ cells treated with RNP with AAV6-HA and RNP with AAV6 with no HA the percentages of GFP+ colonies were 32% and 2%, respectively. Pooled colonies were collected, pooled, immunostained with anti-human CD235 antibody (detecting Glycophorin A, erythroid specific cell surface antigen) and anti-human CD33 antibody (detected a myeloid specific cell surface antigen) and the analyzed by flow cytometry analysis. GFP expression was higher in the CD235+ erythroid vs. CD33+ myeloid cell fraction for progeny of cells treated with AAV6 (FIG. 8). This suggests that although the human PGK promoter is regulating transgene expression, higher expression occurs in the erythroid progeny, consistent with the integration of this gene into erythroid specific location (HBB gene). These data also show that integration is maintained in differentiated progeny of HDR-edited CD34+ cells.

Example 3: Detection of Targeted Integration at the TRAC Locus

Figure 9A:
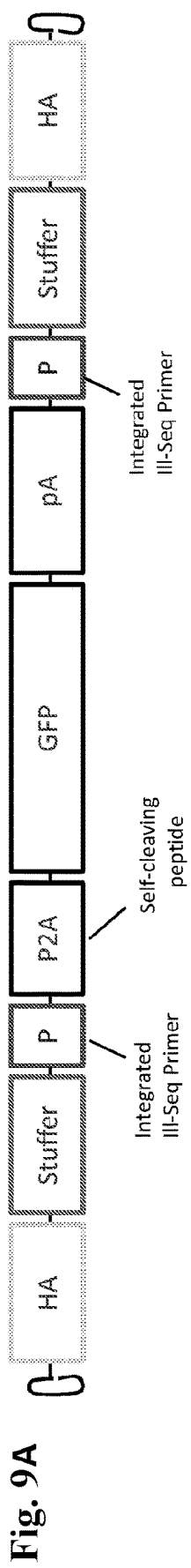
FIG. 9A-9C provide a comparison of various methods for targeted integration assessment.

Exemplary DNA donor templates were designed for use with three different gRNAs targeting the T cell receptor alpha constant (TRAC) locus (TRAC1, TRAC4, and TRAC13), as shown in FIG. 9A. Each donor contained the same cargo (P2A-GFP-polyA sequence), but with different homology arm sequences designed to start immediately 5' and 3' of the predicted cut site. The integrated primer sequences were unique to the donors, and the homology arms extend from the cut site to the beginning of the primer binding site in the genome. The homology arm length used for each donor is provided in Table 9. Primer sequences and homology arm sequences for each donor are provided in Table 10. Targeted integration experiments were conducted in primary CD4+ T cells using wild-type S. pyogenes ribonucleoprotein with the appropriate gRNA and associated donor template. Cells were expanded after the experiment until Day 7, when flow cytometry was conducted to check the rate of targeted integration by GFP expression. The P2A self-cleaving peptide must be joined in-frame with the endogenous TRAC locus to obtain expression of GFP. Since the donor templates each contain a P2A-GFP cassette, GFP is not expressed from the donor template alone, as the P2A-GFP cassette requires a promoter to initiate expression and also must be in frame with the preceding transcription. Accordingly, only accurate HDR-driven targeted integration results in GFP expression.

Figure 9B:
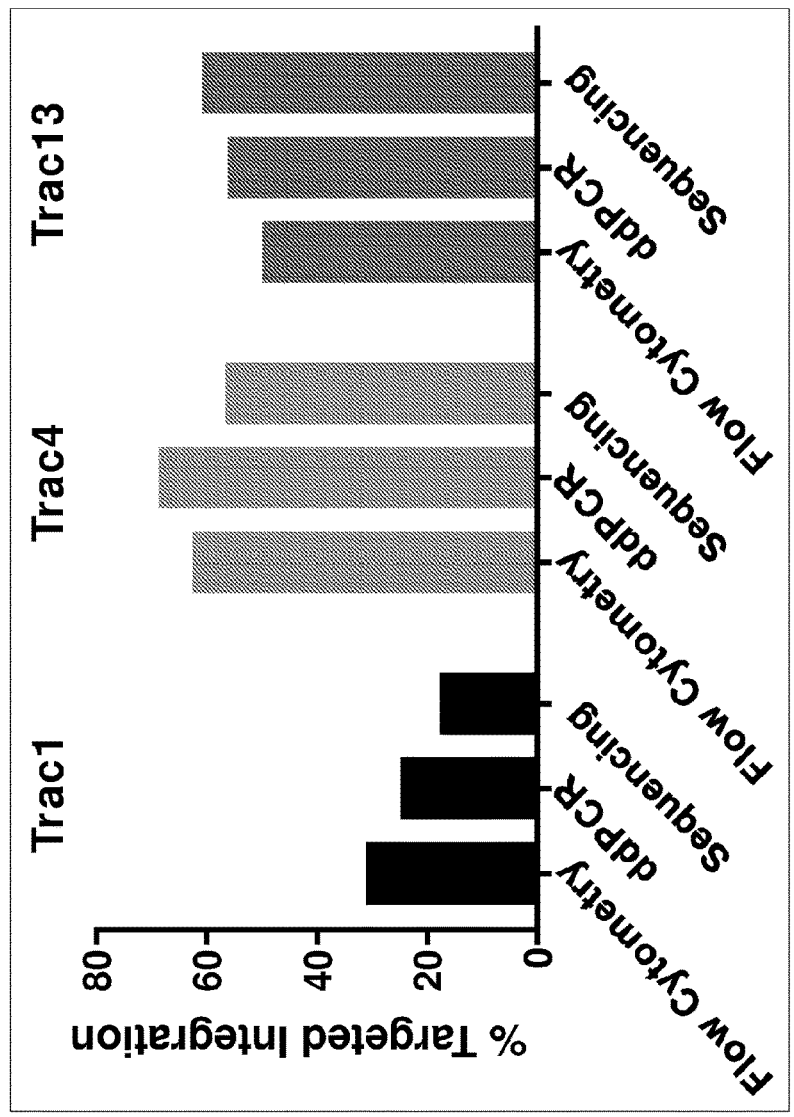
Figure 9C:
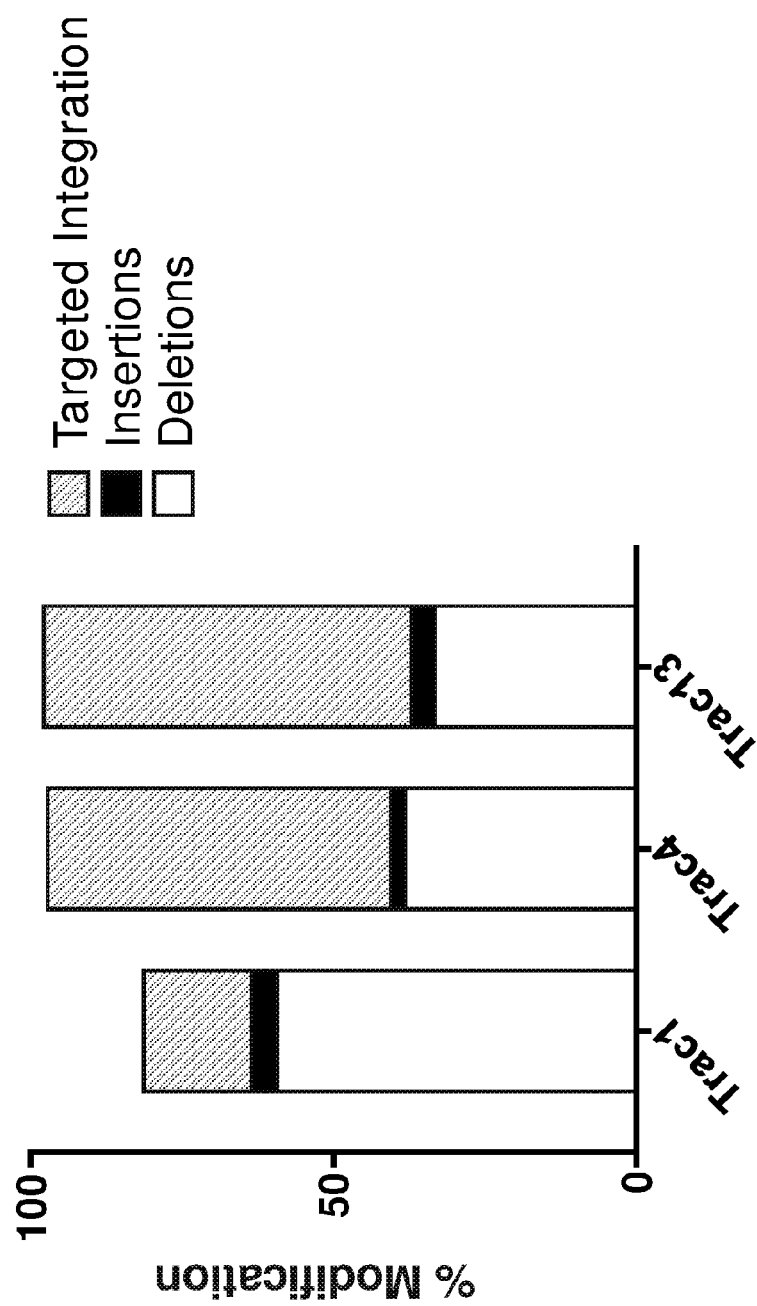

After flow cytometry was conducted, cells were collected, gDNA was isolated, and targeted integration was assessed by ddPCR and sequencing of amplicons generated from amplification of the 5' and 3' junctions of the targeted integration event using the integrated priming sites with 5' and 3' primers (P1 and P2), as described herein. The results from the three analyses (fluorescent flow cytometry, ddPCR, and sequencing) at the three gRNA sites is shown in FIG. 9B. Importantly, all three methods of analysis showed consistent results. Sequencing using the integrated priming sites advantageously provides a complete picture of all editing events at the cut site, as shown in FIG. 9C. This figure depicts all editing events that took place during targeted integration experiments after cuts were introduced using TRAC1, TRAC4, and TRAC13, including insertions, deletions and targeted integration. This analysis was completed by using the integrated primers to amplify gDNA, followed by Sanger sequencing and alignment to one of the three expected amplicons.

TABLE 9

Homology Arm Length in donor templates for targeted integration at the TRAC locus

|  | 5' HA Length | 3' HA Length |
|---|---|---|
| TRAC1 | 281 bp | 140 bp |
| TRAC4 | 142 bp | 311 bp |
| TRAC13 | 188 bp | 259 bp |

TABLE 10

Primer Sequences and Homology Arm Sequences for TRAC donor templates

| | Primer Sequences | HA Sequences |
|---|---|---|
| TRAC1 | P1 (SEQ ID NO: 106):<br>GCATTTCAGGTTTCCTT<br>GAGTGG<br>P2 (SEQ ID NO: 107):<br>GCACTGTTGCTCTTGAA<br>GTCC | 5' (SEQ ID NO: 108):<br>CAGGCCAGGCCTGGCGTGAACGTTCACTGAAAT<br>CATGGCCTCTTGGCCAAGATTGATAGCTTGTGCC<br>TGTCCCTGAGTCCCAGTCCATCACGAGCAGCTGG<br>TTTCTAAGATGCTATTTCCCGTATAAAGCATGAG<br>ACCGTGACTTGCCAGCCCCACAGAGCCCCGCCC<br>TTGTCCATCACTGGCATCTGGACTCCAGCCTGGG<br>TTGGGGCAAAGAGGGAAATGAGATCATGTCCTA<br>ACCCTGATCCTCTTGTCCCACAGATATCCAGAAC<br>CCTGACCCTGCC<br>3' (SEQ ID NO: 109):<br>GTGTACCAGCTGAGAGACTCTAAATCCAGTGAC<br>AAGTCTGTCTGCCTATTCACCGATTTTGATTCTC<br>AAACAAATGTGTCACAAAGTAAGGATTCTGATG<br>TGTATATCACAGACAAAACTGTGCTAGACATGA<br>GGTCTAT |
| TRAC4 | P1 (SEQ ID NO: 110):<br>CTTGTCCATCACTGGCA<br>TCTGG<br>P2 (SEQ ID NO: 111):<br>TTTGGTGGCAATGGATA<br>AGGC | 5' (SEQ ID NO: 112):<br>ACTCCAGCCTGGGTTGGGGCAAAGAGGGAAATG<br>AGATCATGTCCTAACCCTGATCCTCTTGTCCCAC<br>AGATATCCAGAACCCTGACCCTGCCGTGTACCA<br>GCTGAGAGACTCTAAATCCAGTGACAAGTCTGT<br>CTGCCTATT<br>3' (SEQ ID NO: 113):<br>CACCGATTTTGATTCTCAAACAAATGTGTCACAA<br>AGTAAGGATTCTGATGTGTATATCACAGACAAA<br>ACTGTGCTAGACATGAGGTCTATGGACTTCAAG<br>AGCAACAGTGCTGTGGCCTGGAGCAACAAATCT<br>GACTTTGCATGTGCAAACGCCTTCAACAACAGC<br>ATTATTCCAGAAGACACCTTCTTCCCCAGCCCAG<br>GTAAGGGCAGCTTTGGTGCCTTCGCAGGCTGTTT<br>CCTTGCTTCAGGAATGGCCAGGTTCTGCCCAGAG<br>CTCTGGTCAATGATGTCTAAAACTCCTCTGATTG<br>GTGGTCTCG |
| TRAC13 | P1 (SEQ ID NO: 114):<br>TCCTAACCCTGATCCTC<br>TTGTCC<br>P2 (SEQ ID NO: 115):<br>CCGTGTCATTCTCTGGA<br>CTGC | 5' (SEQ ID NO: 116):<br>CACAGATATCCAGAACCCTGACCCTGCCGTGTA<br>CCAGCTGAGAGACTCTAAATCCAGTGACAAGTC<br>TGTCTGCCTATTCACCGATTTTGATTCTCAAACA<br>AATGTGTCACAAAGTAAGGATTCTGATGTGTAT<br>ATCACAGACAAAACTGTGCTAGACATGAGGTCT<br>ATGGACTTCAAGAGCAACAGTG<br>3' (SEQ ID NO: 117):<br>CTGTGGCCTGGAGCAACAAATCTGACTTTGCATG<br>TGCAAACGCCTTCAACAACAGCATTATTCCAGA<br>AGACACCTTCTTCCCCAGCCCAGGTAAGGGCAG<br>CTTTGGTGCCTTCGCAGGCTGTTTCCTTGCTTCA<br>GGAATGGCCAGGTTCTGCCCAGAGCTCTGGTCA<br>ATGATGTCTAAAACTCCTCTGATTGGTGGTCTCG<br>GCCTTATCCATTGCCACCAAAACCCTCTTTTTAC<br>TAAGAAACAGTGAGCCTTGTTCTG |

Figure 10:
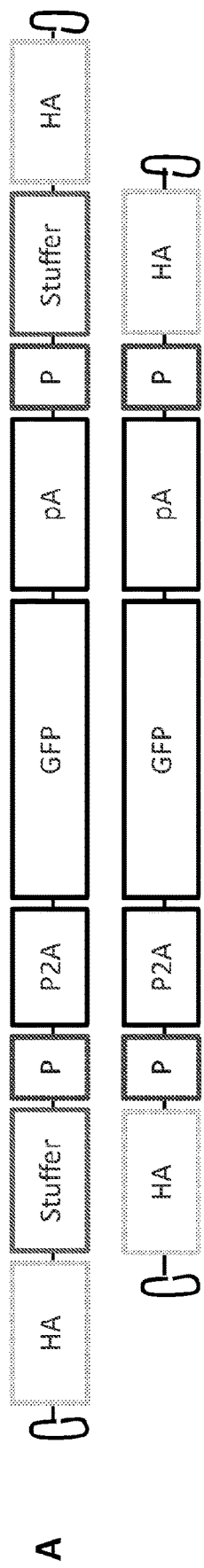
FIG. 10A-10B provide a comparison of various methods for targeted integration assessment, using donor templates that lack a stuffer sequence.
Figure 10:
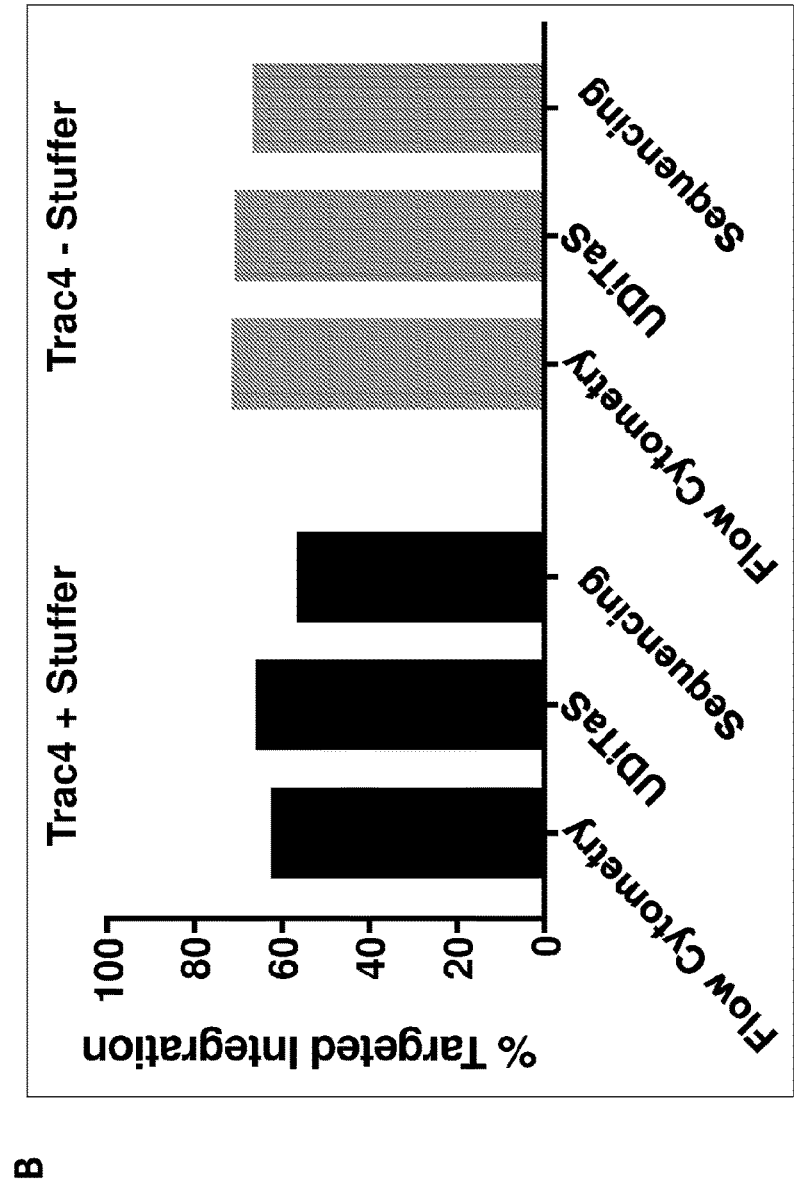

DNA donor templates for targeted integration at the TRAC4 cut site were designed with and without stuffer sequence, as shown in FIG. 10A. Targeted integration experiments were conducted in primary CD4+ T cells using wild-type *S. pyogenes* ribonucleoprotein with the TRAC4 gRNA and either AAV-donor. Cells were expanded after the experiment until Day 7 when flow cytometry was conducted to check the rate of targeted integration by GFP expression. After flow cytometry was conducted, cells were collected, gDNA was isolated, and targeted integration was assessed by sequencing using the integrated priming sites, as described above, and UDITAS™, a unidirectional sequencing method described herein. The results from all three methods of assessing targeted integration efficiency are shown in FIG. 10B. The three methods of assessing targeted integration efficiency demonstrated consistent results, with or without the use of stuffer sequence in the donor template, indicating that targeted integration is not dependent on the presence of the stuffer sequence.

Additional donor templates for targeted integration at the TRAC locus were prepared as described in Table 11. Briefly, donors contain long or short homology arms (HA) flaking the cut site of gRNAs TRAC1, TRAC4, or TRAC13. Constructs containing short homology arms additionally contain primer sequences P1 and P2 flanking the cargo, as described above (see Table 9 and Table 10). Constructs were prepared with and without stuffer sequence, and with P2A or Promoter cargo, as indicated. Additional donor templates lacking homology arms were prepared as a negative control.

TABLE 11

Donors for targeted integration at the TRAC locus

| | gRNA | HA Length | Stuffer | Cargo |
|---|---|---|---|---|
| 1. | TRAC-1 | Short | Yes | P2A + GFP |
| 2. | TRAC-4 | Short | Yes | Promoter + GFP |
| 3. | TRAC-4 | Short | Yes | P2A + GFP |
| 4. | TRAC-4 | Short | No | P2A + GFP |
| 5. | TRAC-4 | Long (500 bp) | No | P2A + GFP |
| 6. | TRAC-13 | Short | Yes | P2A + GFP |
| 7. | No HA | n/a | N/A | P2A + GFP |
| 8. | No HA | n/a | N/A | PGK + GFP |

Targeted integration experiments were conducted in primary CD4+ T cells using wild-type *S. pyogenes* ribonucleoprotein with TRAC1, TRAC4, or TRAC13 gRNA, and the appropriate AAV-donor as shown in Table 11.

Figure 11:
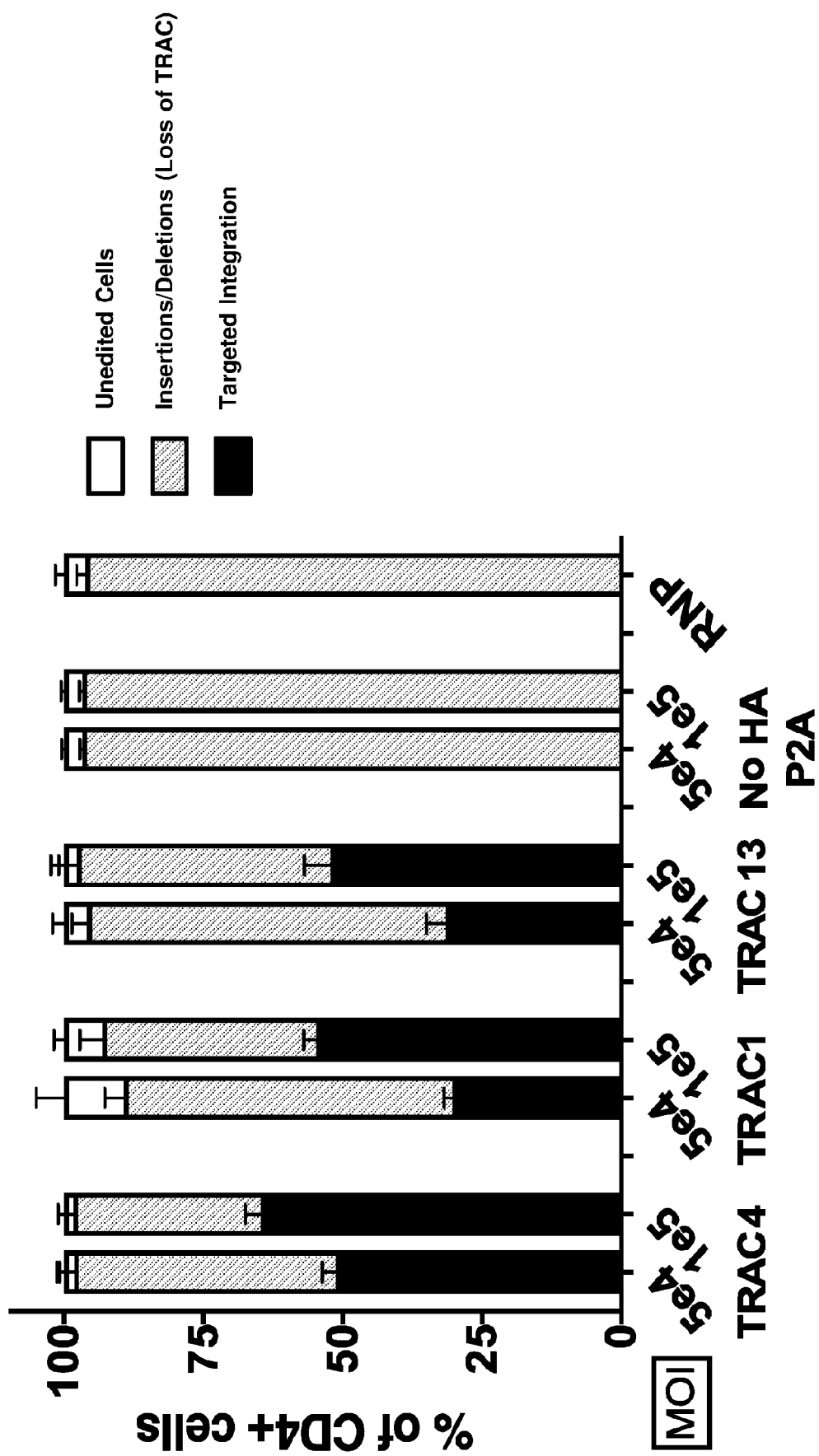
FIG. 11 depicts the editing outcome and targeted integration frequency in CD4+ T cells at the TRAC4, TRAC1, and TRAC13 locus, following exposure to AAV donors targeting each cut site.

Cells were expanded after the experiment until Day 7 when flow cytometry was conducted to check the rate of targeted integration by GFP expression. Editing outcomes were assessed using flow cytometry. Targeted integration efficiency at the TRAC locus is shown in FIG. 11 (from left to right, Donor 3, Donor 1, Donor 6, Donor 7; RNP=without donor). The rate of each editing outcome was validated by sequencing amplification products generated using primers P1 and P2, as described herein, and by ddPCR, as shown in Table 12. A high rate of targeted integration was observed at three gRNA cut sites in Exon 1 of TRAC, using comparable donors at two concentrations. Rates of targeted integration are shown in Table 12. Levels of targeted integration at the TRAC1 site were reduced slightly due to contamination with TRAC13.

TABLE 12

Targeted integration frequency at three gRNA sites in Exon 1 of TRAC using comparable donors

| | Flow Cytometry (GFP) | ddPCR | Sequencing Amplification Products from Integrated Priming sites |
|---|---|---|---|
| Trac1 | 28% | 24% | 18% |
| Trac4 | 61% | 67% | 57% |
| Trac13 | 49% | 56% | 60% |

Figure 12:
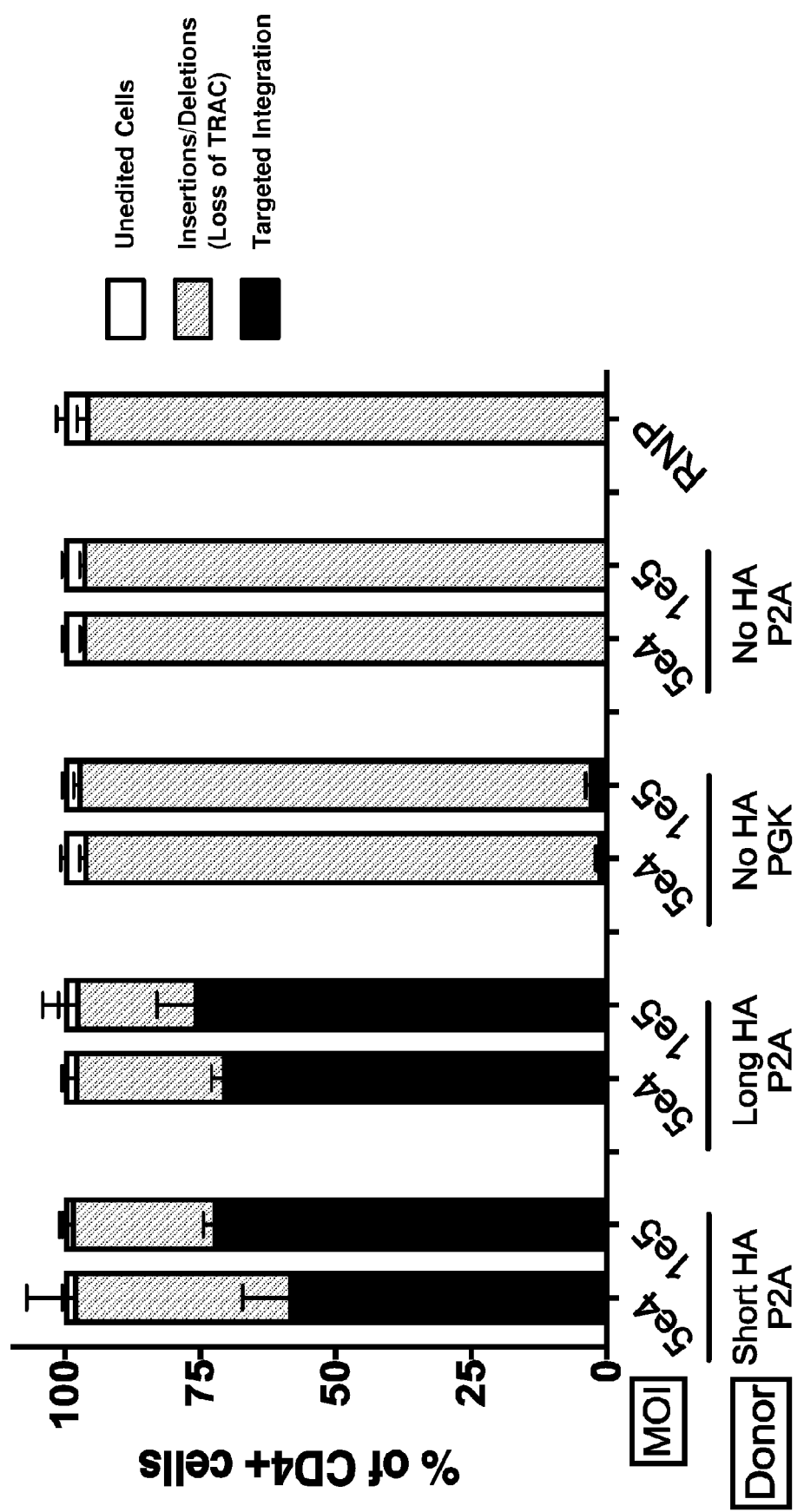
FIG. 12 depicts the editing outcome and targeted integration frequency in CD4+ T cells at the TRAC4 locus, following exposure to AAV donors containing short or long homology arms.
Figure 13:
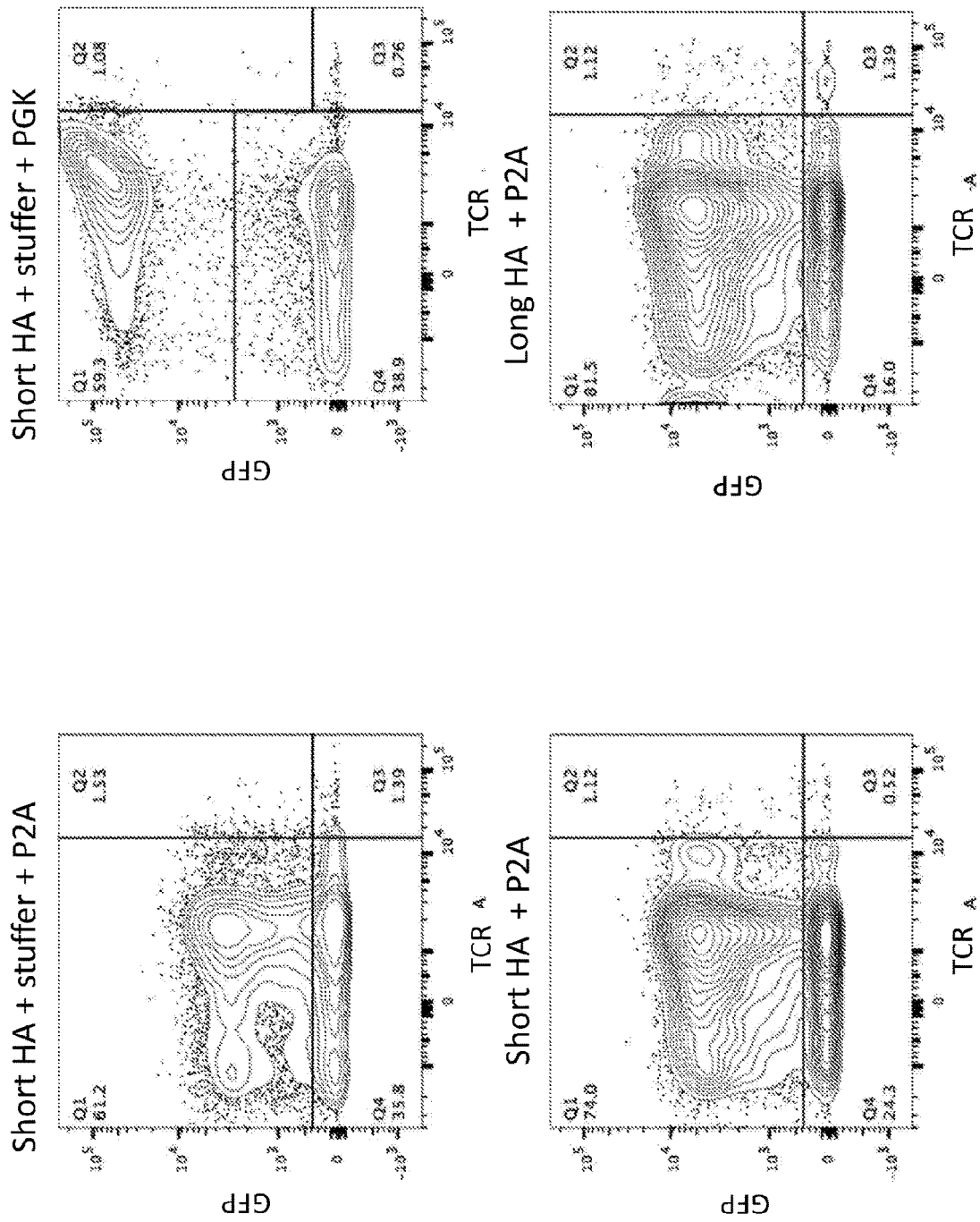
FIG. 13 depicts representative flow cytometry plots of targeted integration and knock out with donors targeting the TRAC4 cut site. GFP expression (indicative of targeted integration) is shown in the Y axis, expression of T cell receptor (TCR) is shown on the X axis. Q1, +GFP/−TCR; Q2, +GFP/+TCR; Q3, −GFP/+TCR; Q4, −GFP/−TCR.

The foregoing experiment was repeated with multiple donors targeting the TRAC4 locus. Results are shown in FIG. 12 (from left to right, Donor 4, Donor 5, Donor 8, Donor 7, RNP only (no donor). Flow cytometry measuring GFP and TRAC expression in edited cells is shown in FIG. 13. Consistently high rates of targeted integration were observed at the TRAC4 locus, across multiple AAV donors, preparations, and MOIs tested. Donors containing long homology arms (500 bp) had higher levels of targeted integration than donors containing shorter homology arms.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

The invention claimed is:

1. An isolated nucleic acid for homologous recombination with a target nucleic acid having a cleavage site, wherein:
   (a) a first strand of the target nucleic acid comprises, from 5' to 3', P1-H1-X-H2-P2, wherein
   P1 is a first priming site;
   H1 is a first homology arm;
   X is the cleavage site;
   H2 is a second homology arm; and
   P2 is a second priming site; and
   (b) a first strand of the isolated nucleic acid comprises, from 5' to 3', A1-S1-P2'-N-P1'-S2-A2, wherein
   A1 is a homology arm that is substantially identical to H1;
   P2' is a priming site that is substantially identical to P2;
   N is a cargo;
   P1' is a priming site that is substantially identical to P1;
   A2 is a homology arm that is substantially identical to H2;
   wherein S1 is a first stuffer, wherein S2 is a second stuffer, and wherein each of S1 and S2 comprise a random or heterologous sequence having a GC content of approximately 40%.

2. The isolated nucleic acid of claim 1, wherein:
   (i) the first stuffer has a sequence having less than 50% sequence identity to any nucleic acid sequence within 500 base pairs of the cleavage site, and wherein the second stuffer has a sequence having less than 50% sequence identity to any nucleic acid sequence within 500 base pairs of the cleavage site;
   (ii) the first stuffer has a sequence comprising at least 10 consecutive nucleotides of a sequence selected from the group consisting of SEQ ID NOs: 1-101, and wherein the second stuffer has a sequence comprising at least 10 consecutive nucleotides of a sequence selected from the group consisting of SEQ ID NOs: 1-101; or
   (iii) the first stuffer has a sequence that is not the same as the sequence of the second stuff.

3. The isolated nucleic acid of claim 1, wherein:
   (i) Al has a sequence that is at least 40 nucleotides in length, and A2 has a sequence that is at least 40 nucleotides in length;
   (ii) Al has a sequence that is identical to, or differs by no more than 1, 2, 3, 4, 5, 6, 7, 8, 9, 10, 15, 20, 25, or 30 nucleotides from a sequence of H1;
   (iii) A2 has a sequence that is identical to, or differs by no more than 1, 2, 3, 4, 5, 6, 7, 8, 9, 10, 15, 20, 25, or 30 nucleotides from a sequence of H2;
   (iv) N comprises an exon of a gene sequence, an intron of a gene sequence, a cDNA sequence, or a transcriptional regulatory element; a reverse complement of any of the foregoing or a portion of any of the foregoing; or (v) N comprises a promoter sequence.

4. A composition comprising the isolated nucleic acid of claim 1 and a pharmaceutically acceptable carrier.

5. A vector comprising the isolated nucleic acid of claim 1.

6. A genome editing system comprising the isolated nucleic acid of claim 1.

7. A method for determining the outcome of a gene editing event at a cleavage site in a target nucleic acid in a cell using an exogenous oligonucleotide donor template, wherein the target nucleic acid comprises a first strand comprising: a first homology arm 5' to a cleavage site, a first priming site either within the first homology arm or 5' to the first homology arm, a second homology arm 3' to the cleavage site, and a second priming site either within the second homology arm or 3' to the second homology arm, and wherein a first strand of the exogenous oligonucleotide donor template comprises from 5' to 3', a first donor homology arm, a first stuffer, a priming site that is substantially identical to the second priming site, a cargo, a priming site that is substantially identical to the first priming site, a second stuffer, and a second donor homology arm, wherein the first stuffer and the second stuffer each comprise a random or heterologous sequence having a GC content of approximately 40%, the method comprising:

i) forming at least one single- or double-strand break at or near the cleavage site in the target nucleic acid;

ii) recombining the exogenous oligonucleotide donor template with the target nucleic acid via homologous recombination to produce an altered nucleic acid; and iii) amplifying the altered nucleic acid using a first primer which binds to the first priming site and/or the priming site that is substantially identical to the first priming site; and/or a second primer which binds to the second priming site and/or the priming site that is substantially identical to the second priming site;

thereby determining the outcome of the gene editing event in the cell.

8. The method of claim 7, wherein the step of forming the at least one single- or double-strand break comprises contacting the cell with an RNA-guided nuclease.

9. The method of claim 7, wherein:

(i) the first stuffer has a sequence having less than 50% sequence identity to any nucleic acid sequence within 500 base pairs of the cleavage site, and wherein the second stuffer has a sequence having less than 50% sequence identity to any nucleic acid sequence within 500 base pairs of the cleavage site;

(ii) the first stuffer has a sequence comprising at least 10 consecutive nucleotides of a sequence selected from the group consisting of SEQ ID NOs: 1-101, and wherein the second stuffer has a sequence comprising at least 10 consecutive nucleotides of a sequence selected from the group consisting of SEQ ID NOs: 1-101;

(iii) the first stuffer has a sequence that is not the same as the sequence of the second stuffer;

(iv) when the altered nucleic acid comprises a targeted integration genome editing event at the cleavage site, amplifying the altered nucleic acid using the first primer and the second primer produces a first amplicon, wherein the first amplicon has a sequence that is substantially identical to a sequence consisting of either (a) the first donor homology arm and the first stuffer, or (b) the second stuffer and the second donor homology arm;

(v) the cell is a population of cells, and wherein, when the altered nucleic acid in all the cells within the population of cells comprises a targeted integration genome editing event at the cleavage site, amplifying the altered nucleic acid using the first primer and the second primer produces a first amplicon, wherein the first amplicon has a sequence that is substantially identical to a sequence consisting of either i) the first donor homology arm and the first stuffer, or ii) the second stuffer and the second donor homology arm; or (vi) when the cell is a population of cells, wherein, when the altered nucleic acid in a first cell within the population of cells comprises a non-targeted integration genome editing event at the cleavage site, amplifying the altered nucleic acid using the first primer and the second primer produces a first amplicon, wherein the first amplicon has a sequence that comprises an indel as compared to a sequence of the target nucleic acid; and wherein, when the altered nucleic acid in a second cell within the population of cells comprises a targeted integration genome editing event at the cleavage site, amplifying the altered nucleic acid in the second cell using the first primer and the second primer produces a second amplicon, wherein the second amplicon has a sequence that is substantially identical to a sequence consisting of either (a) the first donor homology arm and the first stuffer, or (b) the second stuffer and the second donor homology arm.

10. The method of claim 9, wherein, when the altered nucleic acid in a first cell within the population of cells comprises a non-targeted integration genome editing event at the cleavage site, amplifying the altered nucleic acid using the first primer and the second primer produces a first amplicon, wherein the first amplicon has a sequence that comprises an indel as compared to a sequence of the target nucleic acid.

11. The method of claim 9, wherein the cell is a population of cells, and wherein, when the altered nucleic acid in all cells within the population of cells comprises a non-targeted integration genome editing event at the cleavage site, amplifying the altered nucleic acid using the first primer and the second primer produces a first amplicon, wherein the first amplicon has a sequence that comprises an indel as compared to a sequence of the target nucleic acid.

12. The method of claim 7, wherein the altered nucleic acid comprises, from 5' to 3', i) the first priming site, the first donor homology arm, the first stuffer, the priming site that is substantially identical to the second priming site, the cargo, the second donor homology arm, and the second priming site; and/or ii) the first priming site, the first donor homology arm, the cargo, the priming site that is substantially identical to the first priming site, the second stuffer, the second donor homology arm, and the second priming site.

* * * * *